US007858621B2

(12) United States Patent
Kim et al.

(10) Patent No.: US 7,858,621 B2
(45) Date of Patent: Dec. 28, 2010

(54) COMPOUNDS, ISOMER THEREOF, OR PHARMACEUTICALLY ACCEPTABLE SALTS THEREOF AS VANILLOID RECEPTOR ANTAGONIST; AND PHARMACEUTICAL COMPOSITIONS CONTAINING THE SAME

(75) Inventors: Sun-Young Kim, Seoul (KR); Jin Kwan Kim, Suwon-si (KR); Ki-Wha Lee, Seoul (KR); Byoung Young Woo, Yongin-si (KR); Song Seok Shin, Yongin-si (KR); Joo-Hyun Moh, Seoul (KR); Sung-Il Kim, Yangju-si (KR); Yeon Su Jeong, Yongin-si (KR); Kyung Min Lim, Suwon-si (KR); Jin Kyu Choi, Suwon-si (KR); Jun Yong Ha, Seoul (KR); Hyun-Ju Koh, Gunpo-si (KR); Young-Ho Park, Seoul (KR); Young-Ger Suh, Seoul (KR); Hee-Doo Kim, Seoul (KR); Hyeung-Geun Park, Seoul (KR); Uh Taek Oh, Seoul (KR)

(73) Assignee: Amorepacific Corporation, Seoul (KR)

( * ) Notice: Subject to any disclaimer, the term of this patent is extended or adjusted under 35 U.S.C. 154(b) by 583 days.

(21) Appl. No.: 11/829,531

(22) Filed: Jul. 27, 2007

(65) Prior Publication Data
US 2008/0312234 A1 Dec. 18, 2008

Related U.S. Application Data

(60) Provisional application No. 60/893,974, filed on Mar. 9, 2007.

(30) Foreign Application Priority Data

| Jul. 27, 2006 | (EP) | ................................. 06015724 |
| Sep. 29, 2006 | (EP) | ................................. 06020620 |
| Feb. 28, 2007 | (EP) | ................................. 07004194 |

(51) Int. Cl.
*C07D 401/04* (2006.01)
*C07D 213/56* (2006.01)
*A61K 31/44* (2006.01)

(52) U.S. Cl. ............................. 514/235.5; 514/253.01; 514/318; 514/343; 514/351; 514/352; 514/357; 544/131; 544/360; 546/194; 546/278.4; 546/300; 546/309; 546/337

(58) Field of Classification Search .................. None
See application file for complete search history.

(56) References Cited

FOREIGN PATENT DOCUMENTS

| WO | 02/16318 | 2/2002 |
| WO | 03/049702 | 6/2003 |
| WO | 2005/003084 | 1/2005 |
| WO | 2006/051378 | 5/2006 |
| WO | 2006-095263 | 9/2006 |
| WO | 2006-097817 | 9/2006 |
| WO | 2006-098554 | 9/2006 |
| WO | 2006-101318 | 9/2006 |
| WO | 2006-101321 | 9/2006 |

OTHER PUBLICATIONS

Mezey et al., "Distribution of mRNA for vanilloid receptor subtype 1 (VR1), and VR1-like immunoreactivity, in the central nervous system of the rat and human", PNAS, Mar. 28, 2000, vol. 97(7), 3655-3660.
Cortright et al., "The Tissue Distribution and Functional Characterization of Human VR1", Biochemical and Biophysical Research Communications, vol. 281(5), 2001, 1183-1189.
Nagy et al., "The role of the vanilloid (capsaicin) receptor (TRPV1) in physiology and pathology", European Journal of Pharmacology 500 (2004), 351-369.
Petersen et al., "Capsaicin evoked pain and allodynia in post-herpetic neuralgia", Pain 88 (2000) 125-133.
Walker et al., "The VR1 Antagonist Capsazepine Reverses Mechanical Hyperalgesia in Models of Inflammatory and Neuropathic Pain", The Journal of Pharmacology and Experimental Therapeutics, vol. 304(1), 2003, 56-62.
Akerman et al., "Anandamide acts as a vasodilator of dural blood vessels in vivo by activating TRPV1 receptors", British Journal of Pharmacology (2004) 142(8), 1354-1360.
Kim et al., "Transient Receptor Potential Vanilloid Subtype 1 Mediates Cell Death of Mesencephalic Dopaminergic Neurons In Vivo and In Vitro", The Journal of Neuroscience, Jan. 19, 2005, vol. 25(3), 662-671.
Kamei et al., "Role of vanilloid VR1 receptor in thermal allodynia and hyperalgesia in diabetic mice", European Journal of Pharmacology 422 (2001), 83-86.
Chan et al., "Sensory fibres expressing capsaicin receptor TRPV1 in patients with rectal hypersensitivity and faecal urgency", The Lancet, vol. 361, Feb. 1, 2003, 385-391.
Yiangou et al., "Vanilloid receptor 1 immunoreactivity in inflamed human bowel", The Lancet, vol. 357, Apr. 28, 2001, 1338-1339.
Holzer, Peter, "TRPV1 and the gut: from a tasty receptor for a painful vanilloid to a key player in hyperalgesia", European Journal of Pharmacology 500 (2004) 231-241.
Hwang et al., "Hot channels in airways: pharmacology of the vanilloid receptor", Current Opinion in Pharmacology 2002, vol. 2, 235-242.
Geppetti et al., "The transient receptor potential vanilloid 1: Role in airway inflammation and disease", European Journal of Pharmacology 533 (2006) 207-214.

(Continued)

*Primary Examiner*—Zinna N Davis
(74) *Attorney, Agent, or Firm*—Heslin Rothenberg Farley & Mesiti PC

(57) ABSTRACT

This present invention relates to novel compounds, isomer thereof or pharmaceutically acceptable salts thereof as vanilloid receptor (Vanilloid Receptor 1; VR1; TRPV1) antagonist; and a pharmaceutical composition containing the same.

The present invention provides a pharmaceutical composition for preventing or treating a disease such as pain, migraine, arthralgia, neuralgia, neuropathies, nerve injury, skin disorder, urinary bladder hypersensitiveness, irritable bowel syndrome, fecal urgency, a respiratory disorder, irritation of skin, eye or mucous membrane, stomach-duodenal ulcer, inflammatory diseases, ear disease, heart disease and so on.

45 Claims, No Drawings

OTHER PUBLICATIONS

Birder et al., "Altered urinary bladder function in mice lacking the vanilloid receptor TRPV1", Nature Neuroscience, vol. 5(9), Sep. 2002, 856-860.

Birder et al., "Vanilloid receptor expression suggests a sensory role for urinary bladder epithelial cells", PNAS, Nov. 6, 2001, vol. 98(23), 13396-13401.

Southall et al., "Activation of Epidermal Vanilloid Receptor-1 Induces Release of Proinflammatory Mediators in Human Keratinocytes", The Journal of Pharmacology and Experimental Therapeutics, vol. 304(1), 217-222, 2003.

Tominaga et al., "The Cloned Capsaicin Receptor Integrates Multiple Pain-Producing Stimuli", Neuron, vol. 21, Sep. 1998, 531-543.

Balaban et al., "Type 1 vanilloid receptor expression by mammalian inner ear ganglion cells", Hearing Research 175 (2003), 165-170.

Scotland et al., "Vanilloid Receptor TRPV1, Sensory C-Fibers, and Vascular Autoregulation", Circulation Research, Nov. 12, 2004, vol. 95, 1027-1034.

Bodo et al., "A Hot New Twist to Hair Biology, Involvement of Vanilloid Receptor-1 (VR1/TRPV1) Signaling in Human Hair Growth Control", American Journal of Pathology, vol. 166(4), Apr. 2005, 985-998.

Biro et al., "Hair Cycle Control by Vanilloid Receptor-1 (TRPV1): Evidence from TRPV1 Knockout Mice", Journal of Investigative Dermatology (2006), vol. 126, 1909-1912.

Dinis et al., "Anandamide-Evoked Activation of Vanilloid Receptor 1 Contributes to the Development of Bladder Hyperreflexia and Nociceptive Transmission to Spinal Dorsal Horn Neurons in Cystitis", The Journal of Neuroscience, Dec. 15, 2004, vol. 24(50), 11253-11263.

Sculptoreanu et al., "Protein kinase C contributes to abnormal capsaicin responses in DRG neurons from cats with feline interstitial cystitis", Neuroscience Letters 381 (2005), 42-46.

ND PHARMACEUTICAL
COMPOUNDS, ISOMER THEREOF, OR PHARMACEUTICALLY ACCEPTABLE SALTS THEREOF AS VANILLOID RECEPTOR ANTAGONIST; AND PHARMACEUTICAL COMPOSITIONS CONTAINING THE SAME

CROSS-REFERENCE TO RELATED APPLICATIONS

This application is a non-provisional application which claims the priority of U.S. provisional application Ser. No. 60/893,974 filed Mar. 9, 2007; European application serial no. 07004194.2 filed Feb. 28, 2007; European application serial no. 06020620.8 filed Sep. 29, 2006 and European application serial no. 06015724.5 filed Jul. 27, 2006.

The present invention relates to novel compounds, isomer thereof or pharmaceutically acceptable salts thereof as TRPV1 antagonist; and a pharmaceutical composition containing the same.

BACKGROUND ART

The vanilloid receptor-1 (VR1, or transient receptor potential vanilloid-1, TRPV1) is the receptor for capsaicin (8-methyl-N-vanillyl-6-nonenamide), a pungent ingredient in hot peppers. The molecular cloning of TRPV1 was reported in 1997 (Caterina et al., 1997, Nature, 389, pp 816-824), which belongs to the TRP channel family of non-selective cation channel. TRPV1 is activated or sensitized by stimuli such as capsaicin, resiniferatoxin, heat, acid, anandamide, lipid metabolites or the like thus it plays a crucial role as a molecular integrator of noxious stimuli in mammals (Tominaga et al., 1998, Neuron, 21 pp 531-543; Hwang et al., 2000, PNAS, 97, pp 6155-6160). The TRPV1 is highly expressed in primary afferent sensory neurons, and also reportedly expressed in various organs and tissues such as bladder, kidney, lung, intestine, skin, central nervous system (CNS), and non-neuronal tissues (Mezey et al., 2000, PNAS, 97, pp 3655-3660; Stander et al., 2004, Exp. Dermatol. 13, pp 129-139; Cortright et al., 2001, BBRC, 281, pp 1183-1189), and besides TRPV1 protein is upregulated in painful disease conditions. Activation of the TRPV1 by endogenous/exogenous stimuli leads to not only transmission of noxious stimuli, but also liberation of neuropeptides such as substance P, CGRP (Calcitonin Gene-Related Peptide) in the neurons, thereby causing neurogenic inflammation. TRPV1 knock-out mice show normal responses in a wide range of behavioural tests including noxious mechanical and acute thermal stimuli, but exhibit little thermal hypersensitivity in inflammation states. (Caterina et al., 2000, Science, 288, pp 306-313; Davis et al., 2000, Nature, 405, pp 183-187; Karai et al., 2004, J. Clin. Invest., 113, pp 1344-1352).

As mentioned above, the TRPV1 knock-out mice exhibit reduced responses to thermal or noxious stimuli, which has been supported by the effects of TRPV1 antagonists in various animal models of pain (Immke et al., 2006, Semin. Cell. Dev. Biol., 17(5), pp 582-91; Ma et al., 2007, Expert Opin. Ther. Targets, 11(3), pp 307-20). The well-known TRPV1 antagonist, capsazepine, decreases hyperalgesia caused by physical stimuli in several models of inflammatory and neuropathic pain (Walker et al., 2003, JPET, 304, pp 56-62; Garcia-Martinez et al., 2002, PNAS, 99, 2374-2379). In addition, treatment of the primary culture of afferent sensory neurons with the TRPV1 agonist, capsaicin etc., results in damage to nerve functions and furthermore death of nerve cells. The TRPV1 antagonist exerts defense actions against such damage to nerve functions and nerve cell death (Holzer P., 1991, Pharmacological Reviews, 43, pp 143-201, Mezey et al., 2000, PNAS, 97, 3655-3660). The TRPV1 is expressed on sensory neurons distributed in all regions of the gastrointestinal tract and is highly expressed in inflammatory disorders such as irritable bowel syndrome and inflammatory bowel disease (Chan et al., 2003, Lancet, 361, pp 385-391 Yiangou et al., 2001, Lancet, 357, pp 1338-1339). In addition, activation of the TRPV1 stimulates sensory nerves, which in turn causes release of neuropeptides which are known to play a critical role in pathogenesis of gastrointestinal disorders such as gastro-esophageal reflux disease (GERD) and stomach duodenal ulcer (Holzer P., 2004, Eur. J. Pharmacol. 500, pp 231-241, Geppetti et al., 2004, Br. J. Pharmacol., 141, pp 1313-1320).

The TRPV1-expressing afferent nerves are abundantly distributed in airway mucosa, and bronchial hypersensitivity is very similar mechanism to hyperalgesia. Protons and lipoxygenase products, known as endogenous ligands for the TRPV1, are well known as crucial factors responsible for development of asthma and chronic obstructive pulmonary diseases (Hwang et al., 2002, Curr. Opin. Pharmacol. pp 235-242; Spina et al., 2002, Curr. Opin. Pharmacol. pp 264-272). Moreover, it has been reported that air-polluting substances which are a kind of asthma-causing substances, i.e., particulate matter specifically acts on the TRPV1 and such action is inhibited by capsazepine (Veronesi et al., 2001, Neuro Toxicology, 22, pp 795-810). Urinary bladder hypersensitiveness and urinary incontinence are caused by various central/peripheral nerve disorders or injury, and TRPV1 expressed in afferent nerves and urothelial cells play an important role in bladder inflammation. (Birder et al., 2001, PNAS, 98, pp 13396-13401). Further, TRPV1 knock-out mice are anatomically normal but have higher frequency of low-amplitude, non-voiding bladder contractions and reduced reflex voiding during bladder filling as compared to wild type mice, which is thus indicating that the TRPV1 affects functions of the bladder (Birder et al., 2002, Nat. Neuroscience, 5, pp 856-860). The TRPV1 is distributed in human epidermal keratinocytes as well as in primary afferent sensory nerves (Denda et al., 2001, Biochem. Biophys. Res. Commun., 285, pp 1250-1252; Inoue et al., 2002, Biochem. Biophys. Res. Commun., 291, pp 124-129), and it is then involved in transmission of various noxious stimuli and pains such as skin irritation and pruritus, thereby having close correlation with etiology of dermatological diseases and disorders, such as skin inflammation, due to neurogenic/non-neurogenic factors. This is supported by the report that the TRPV1 antagonist capsazepine inhibits inflammatory mediators in human skin cells (Southall et al., 2003, J. Pharmacol. Exp. Ther., 304, pp 217-222). Over recent years, evidence has been accumulation on other roles of TRPV1. TRPV1 might be involved in the blood flow/pressure regulation via sensory vasoactive neuropeptide release and in the regulation of plasma glucose levels or in the pathogenesis of type 1 diabetes (Inoue et al., Cir. Res., 2006, 99, pp 119-31; Razavi et al., 2006, Cell, 127, pp 1123-35; Gram et al., 2007, Eur. J. Neurosci., 25, pp 213-23). Further, it is reported that TRPV1 knock-out mice show less anxiety-related behavior than their wild type littermates with no differences in locomotion (Marsch et al., 2007, J. Neurosci., 27(4), pp 832-9).

Based on the above-mentioned information, development of various TRPV1 antagonists is under way, and some patents and patent applications relating to TRPV1 antagonists under development were published. (Szallasi et al., 2007, Nat. Rev. Drug Discov., 6, pp 357-72; Appendino et al., 2006, Progress in Medicinal Chemistry, 44, pp 145-180; Rami et al., 2004, Drug Discovery Today: Therapeutic Strategies, 1, pp 97-104

Correll et al., 2006, Expert Opin. Ther. Patents, 16, pp 783-795; Kyle et al., 2006, Expert Opin. Ther. Patents, 16, pp 977-996)

Compounds of the present invention, are useful for prophylaxis and treatment of diseases associated with the activity of TRPV1 (Nagy et al., 2004, Eur. J. Pharmacol. 500, 351-369) including but not limited to, pain such as acute pain, chronic pain, neuropathic pain post-operative pain, rheumatic arthritic pain, osteoarthritic pain, postherpetic neuralgia, neuralgia, headache, dental pain, pelvic pain, migraine, bone cancer pain, mastalgia and visceral pain (Petersen et al., 2000, Pain 88, pp 125-133; Walker et al., 2003, J. Pharmacol. Exp. Ther., 304, pp 56-62; Morgan et al., 2005, J. Orofac. Pain, 19, pp 248-60; Dinis et al., 2005, Eur. Urol., 48, pp 162-7; Akerman et al., 2004, Br. J. Pharmcol., 142, pp 1354-1360; Ghilardi et al., 2005, J. Neurosci., 25, 3126-31; Gopinath et al., 2005, BMC Womens Health, 5, 2-9), nerve-related diseases such as neuropathies, HIV-related neuropathy, nerve injury, neurodegeneration, and stroke (Park et al., 1999, Arch. Pharm. Res. 22, pp 432-434; Kim et al., 2005, J. Neurosci. 25(3), pp 662-671); diabetic neuropathy (Kamei et al., 2001, Eur. J. Pharmacol. 422, pp 83-86); fecal urgency; irritable bowel syndrome (Chan et al., 2003, Lancet, 361, pp 385-391); inflammatory bowel disease (Yiangou et al., 2001, Lancet 357, pp 1338-1339); gastrointestinal disorders such as gastro-esophageal reflux disease (GERD), stomach duodenal ulcer and Crohn's disease (Holzer P, 2004, Eur. J. Pharm., 500, pp 231-241, Geppetti et al., 2004, Br. J. Pharmacol., 141, pp 1313-1320); respiratory diseases such as asthma, chronic obstructive pulmonary disease, cough (Hwang et al., 2002, Curr. Opin. Pharmacol. pp 235-242; Spina et al., 2002, Curr. Opin. Pharmacol. pp 264-272; Geppetti et al., 2006, Eur. J. Pharmacol., 533, pp 207-214 McLeod et al., 2006, Cough, 2, 10); urinary incontinence (Birder et al., 2002, Nat. Neuroscience 5, pp 856-860); urinary bladder hypersensitiveness (Birder et al., 2001, PNAS, 98, pp 13396-13401); neurotic/allergic/inflammatory skin diseases such as psoriasis, pruritus, prurigo and dermatitis (Southall et al., 2003, J. Pharmacol. Exp. Ther., 304, pp 217-222); irritation of skin, eye or mucous membrane (Tominaga et al., 1998, Neuron 21 pp 531-543); hyperacusis; tinnitus; vestibular hypersensitiveness (Balaban et al., 2003, Hear Res. 175, pp 165-70); cardiac diseases such as myocardial ischemia (Scotland et al., 2004, Circ. Res. 95, pp 1027-1034; Pan et al., 2004, Circulation 110, pp 1826-1831); haemorrhagic shock (Akabori et al., 2007, Ann. Surg., 245(6), pp 964-70); hair growth-related disorders such as hirsutism, effluvium, alopecia (Bodò et al., 2005, Am. J. Patho. 166, pp 985-998; Birò et al., 2006, J. Invest. Dermatol. pp 1-4); rhinitis (Seki et al., 2006, Rhinology, 44, pp 128-34), pancreatitis (Hutter et al., 2005, Pancreas, 30, pp 260-5); cystitis (Dinis et al., 2004, J. Neurosci., 24, pp 11253-63; Sculptoreanu et al., 2005, Neurosci. Lett. 381, pp 42-6); vulvodynia (Tympanidis et al., 2004, Eur. J. Pain, 8, pp 12-33); psychiatric disorders such as anxiety or fear (Marsch et al., 2007, J. Neurosci., 27(4), pp 832-9).

Compounds that are related to VR1 activities are discussed e.g. in WO 02/61317, WO 02/090326, WO 02/16318, WO 02/16319, WO 03/053945, WO 03/099284, WO 03/049702, WO 03/049702, WO 03/029199, WO 03/70247, WO 04/07495, WO 04/72068, WO 04/035549, WO 04/014871, WO 04/024154, WO 04/024710, WO 04/029031, WO 04/089877, WO 04/089881, WO 04/072069, WO 04/111009, WO 05/03084, WO 05/073193, WO 05/051390, WO 05/049613, WO 05/049601, WO 05/047280, WO 05/047279, WO 05/044802, WO 05/044786, WO 06/097817, WO 06/098554, WO 06/100520, WO 06/101321, WO 06/102645, WO 06/103503, WO 06/111346, WO 06/101321, WO 06/101318, WO 06/1113769, WO 06/116563, WO 06/120481, WO 06/122250, WO 06/122799, WO 06/129164, WO 06/51378, WO 06/95263, WO 07/42906, WO 07/45462, WO 07/50732, WO 07/54474, WO 07/54480, WO 07/63925. WO 07/65663, WO 07/65888, WO 07/67619, WO 07/67710, WO 07/67711, WO 07/67756, WO 07/67757, WO07/63925, WO07/65662, WO07/65663, WO07/65888, WO07/69773, US20070149517, or US20070149513.

More specifically, WO 06/101321 and WO 06/101318 relate to VR1 modulators with a biphenyl partial structure. As a result of extensive and intensive studies, the present inventors have consequently synthesized novel compounds having VR1 antagonistic activity by the replacement of one phenyl ring with a substituted heterocyclic ring. Furthermore, the present inventors have also surprisingly identified that the replacement of one phenyl ring as mentioned above provided the improvement of their physicochemical characteristics, such as metabolic stability or pharmacokinetic profiles.

Therefore, it is an object of the present invention to provide novel compounds useful as a potent antagonist for a TRPV1, isomer thereof and pharmaceutically acceptable salts thereof; and a pharmaceutical composition comprising the same.

DISCLOSURE OF THE INVENTION

The present invention provides a novel compound of the following formula (I), an isomer, or a pharmaceutically acceptable salt thereof:

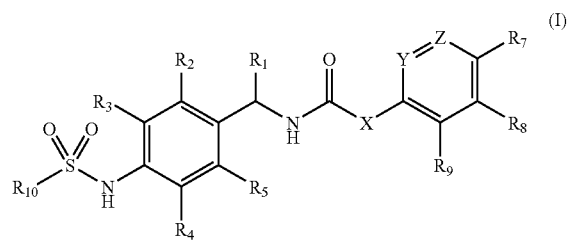

wherein,

X is $CR_{11}$=$CR_{12}$, $CHR_{11}CHR_{12}$,

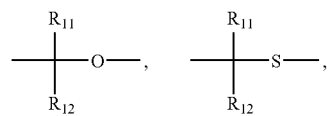

or C≡C, wherein, $R_{11}$ and $R_{12}$, if present, are independently hydrogen, halogen, or C1-C10 alkyl;

Y and Z are independently CH, $CR_6$, or N, such that at least one of Y and Z is N;

$R_1$ is hydrogen, halogen, or alkyl (preferably C1-C10 alkyl);

$R_2$, $R_3$, $R_4$, and $R_5$ are independently hydrogen, halogen, nitro, cyano, alkyl (preferably C1-C10 alkyl), alkoxy (preferably C1-C10 alkoxy), haloalkyl (preferably halo (C1-C10) alkyl), alkenyl (preferably C2-C10 alkenyl), alkynyl (preferably C2-C10 alkynyl), carboxy, alkoxycarbonyl (preferably C1-C10 alkoxycarbonyl), or alkylthio (preferably C1-C10 alkylthio);

$R_6$, $R_7$, $R_8$, and $R_9$ are independently hydrogen, hydroxy, halogen, nitro, carboxy, alkyl (preferably C1-C10 alkyl), alkoxy (preferably C1-C10 alkoxy), alkenyl (preferably C2-C10 alkenyl), alkynyl (preferably C2-C10 alkynyl), alkylthio (preferably C1-C10 alkylthio), alkylsulfonyl (preferably C1-C10 alkylsulfonyl), alkylcarbonyl (preferably C1-C10 alkylcarbonyl), alkoxycarbonyl (preferably C1-C10 alkoxycarbonyl), alkenyloxy (preferably C2-C10 alkenyloxy), alkoxyalkoxy (preferably C1-C10 alkoxy (C1-C10) alkoxy), alkoxyalkoxyalkyl (preferably C1-C10 alkoxy (C1-C10) alkoxy (C1-C10) alkyl), piperidyl, piperazinyl, alkoxyalkylamino (preferably C1-C10 alkoxy (C1-C10) alkylamino), alkylamino (preferably C1-C10 alkylamino), dialkylamino (preferably di(C1-C10 alkyl) amino), cycloalkyl (preferably C3-C8 cycloalkyl), cycloalkylamino (preferably C3-C8 cycloalkylamino), cycloalkoxy (preferably C3-C8 cycloalkoxy), oxacycloalkyloxy (preferably C3-C8 oxacycloalkyloxy), N-alkoxyalkyl-N-alkylamino (preferably N—(C1-C10) alkoxy (C1-C10) alkyl-N—(C1-C10) alkylamino), N-cycloalkyl-N-alkylamino (preferably N—(C3-C8) cycloalkyl-N—(C1-C10) alkylamino), N-aryl-N-alkylamino (preferably N-aryl-N—(C1-C10) alkylamino, more preferably N-phenyl-N—(C1-C10)alkylamino), aryl preferably phenyl, arylamino preferably phenylamino, arylthio preferably phenylthio, heteroaryl preferably pyridinyl or thienyl, heteroarylamino, aryloxy preferably phenoxy, heteroaryloxy preferably pyridinyloxy, pyrrolidinyl, or morpholinyl, wherein, each alkyl, alkenyl and alkynyl, also as a part of a group such as in alkoxy, alkylsulfonyl, alkylcarbonyl, alkylamino, or alkenyloxy may be independently unsubstituted or substituted with one or more substituents selected from among halogen, hydroxyl, unsubstituted or halo-substituted (C1-C5) alkoxy, (C3-C8), cycloalkyl which may be unsubstituted or substituted with one or two halogen radicals and/or methyl groups, unsubstituted or halo-substituted (C1-C5) alkylamino, phenyl which may be unsubstituted or substituted with one or more substituents selected from halogen, unsubstituted C1-C3 alkyl, or halo (C1-C3) alkyl, or unsubstituted or halo-substituted di(C1-C5) alkylamino, each aryl or heteroaryl, also a part of a group such as in arylamino, aryloxy, heteroarylamino, or heteroaryloxy, may be independently unsubstituted or substituted with one or more substituents selected from halogen, unsubstituted C1-C5 alkyl, unsubstituted C1-C5 alkoxy, or halo (C1-C5) alkyl, each cycloalkyl, also as a part of a group such as in cycloalkoxy or cycloalkylamino may be unsubstituted or substituted with one or more unsubstituted or halo-substituted C1-C3 alkyl groups, hydroxymethyl, hydroxy, methoxy, or amino, and each piperazinyl, piperidyl, morpholinyl, and pyrrolidinyl may be unsubstituted or substituted with one or more unsubstituted or halo-substituted C1-C3 alkyl groups, hydroxy(C1-C3)alkyl, C1-C3 alkoxy, (C1-C3)alkoxycarbonyl, or hydroxyl;

and $R_{10}$ is alkyl (preferably C1-C10 alkyl), haloalkyl (preferably halo (C1-C10) alkyl), or alkenyl (preferably C2-C10 alkenyl)

The present invention provides a novel compound of the following formula (I), an isomer, or a pharmaceutically acceptable salt thereof:

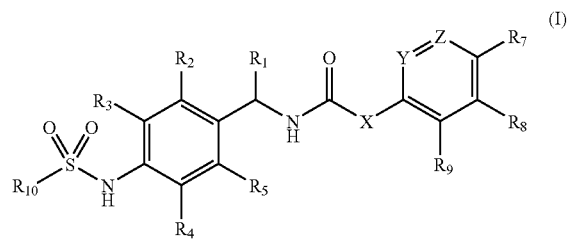

wherein,

X is $CR_{11}=CR_{12}$, $CHR_{11}CHR_{12}$, or $C\equiv C$, wherein, $R_{11}$ and $R_{12}$, if present, are independently hydrogen, halogen, or C1-C5 alkyl;

Y and Z are independently CH, $CR_6$, or N, such that at least one of Y and Z is N, $R_1$ is hydrogen, halogen, or C1-C5 alkyl;

$R_2$, $R_3$, $R_4$, and $R_5$ are independently hydrogen, halogen, nitro, cyano, C1-C5 alkyl, C1-C5 alkoxy, halo (C1-C5) alkyl, C2-C5 alkenyl, C2-C5 alkynyl, carboxy, C1-C5 alkoxycarbonyl, or C1-C5 alkylthio;

$R_6$, $R_7$, $R_8$, and $R_9$ are independently hydrogen, hydroxy, halogen, nitro, carboxy, C1-C10 alkyl, C1-C10 alkoxy, C2-C10 alkenyl, C2-C10 alkynyl, C1-C10 alkylthio, C1-C10 alkylsulfonyl, C1-C10 alkylcarbonyl, C1-C10 alkoxycarbonyl, C2-C10 alkenyloxy, C1-C5 alkoxy (C1-C5) alkoxy, C1-C5 alkoxy (C1-C5) alkoxy (C1-C5) alkyl, piperidyl, piperazinyl, C1-C5 alkoxy (C1-C5) alkylamino, C1-C10 alkylamino, di(C1-C10 alkyl)amino, C3-C8 cycloalkyl, C3-C8 cycloalkylamino, C3-C8 cycloalkoxy, C3-C8 oxacycloalkyloxy, N—(C1-C-5) alkoxy (C1-C5) alkyl-N—(C1-C5) alkylamino, N—(C3-C8) cycloalkyl-N—(C1-C5) alkylamino, N-aryl-N—(C1-C5) alkylamino preferably N-phenyl-N—(C1-C5)alkylamino, aryl preferably phenyl, arylamino preferably phenylamino, arylthio preferably phenylthio, heteroaryl preferably pyridinyl or thienyl, heteroarylamino, aryloxy preferably phenoxy, heteroaryloxy preferably pyridinyloxy, pyrrolidinyl, or morpholinyl, wherein, each alkyl, alkenyl and alkynyl, also as a part of a group such as in alkoxy, alkylsulfonyl, alkylcarbonyl, alkylamino, or alkenyloxy may be independently unsubstituted or substituted with one or more substituents selected from among halogen, hydroxyl, unsubstituted or halo-substituted (C1-C5) alkoxy, (C3-C8), cycloalkyl which may be unsubstituted or substituted with one or two halogen radicals and/or methyl groups, unsubstituted or halo-substituted (C1-C5) alkylamino, phenyl which may be unsubstituted or substituted with one or more substituents selected from halogen, unsubstituted C1-C3 alkyl, or halo (C1-C3) alkyl, or unsubstituted or halo-substituted di(C1-C5) alkylamino, each aryl or heteroaryl, also a part of a group such as in arylamino, aryloxy, heteroarylamino, or heteroaryloxy, may be independently unsubstituted or substituted with one or more substituents selected from halogen, unsubstituted C1-C5 alkyl, unsubstituted C1-C5 alkoxy, or halo (C1-C5) alkyl, each cycloalkyl, also as a part of a group such as in cycloalkoxy or cycloalkylamino may be unsubstituted or substituted with one or more unsubstituted or halo-substituted C1-C3 alkyl groups, hydroxymethyl, hydroxy, methoxy, or amino, and each piperazinyl, piperidyl, morpholinyl, and pyrrolidinyl may be unsubstituted or substituted with one or more unsubstituted or halo-substituted C1-C3 alkyl groups, hydroxy(C1-C3)alkyl, C1-C3 alkoxy, (C1-C3)alkoxycarbonyl, or hydroxyl;

and $R_{10}$ is C1-C5 alkyl, halo (C1-C5) alkyl, or C2-C5 alkenyl, and wherein, in one embodiment, preferably, Z is N, Y is $CR_6$, and $R_7$ is C3-C6 alkyl or halo(C1-C5 alkyl), e.g. trifluoromethyl, and wherein, in another embodiment, in said compounds of formula I, preferably X is $CR_{11}$=$CR_{12}$ or C≡C, Z is N, Y is $CR_6$, $R_6$ is different from hydrogen, and $R_7$ is halo(C1-C5 alkyl), particularly preferably trifluoromethyl.

The present invention provides a novel compound of the following formula (I), an isomer thereof, or a pharmaceutically acceptable salt thereof;

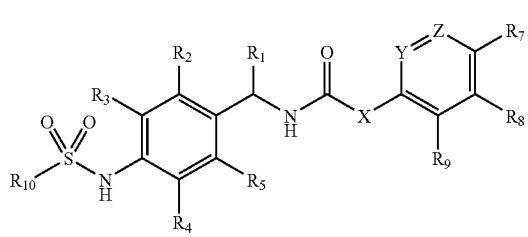

wherein,
X is $CR_{11}$=$CR_{12}$, $CHR_{11}CHR_{12}$,

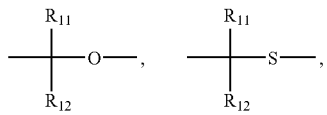

or C≡C, wherein, $R_{11}$ and $R_{12}$, if present, are independently hydrogen, halogen, or C1-C5 alkyl;
Y and Z are independently CH, $CR_6$, or N, such that at least one of Y and Z is N;
$R_1$ is hydrogen or C1-C5 alkyl;
$R_2$, $R_3$, $R_4$, and $R_5$ are independently hydrogen, halogen, nitro, cyano, C1-C5 alkyl, C1-C5 alkoxy, halo (C1-C5) alkyl, C2-C5 alkenyl, C2-C5 alkynyl, carboxy, C1-C5 alkoxycarbonyl, or C1-C5 alkylthio;
$R_6$, $R_7$, $R_8$, and $R_9$ are independently hydrogen, hydroxy, halogen, nitro, carboxy, C1-C10 alkyl, C1-C10 alkoxy, C2-C10 alkenyl, C2-C10 alkynyl, C1-C10 alkylthio, C1-C10 alkylsulfonyl, C1-C10 alkylcarbonyl, C1-C10 alkoxycarbonyl, C2-C10 alkenyloxy, C1-C5 alkoxy (C1-C5) alkoxy, C1-C5 alkoxy (C1-C5) alkoxy (C1-C5) alkyl, piperidyl, piperazinyl, C1-C5 alkoxy (C1-C5) alkylamino, C1-C10 alkylamino, di(C1-C10 alkyl)amino, C3-C8 cycloalkyl, C3-C8 cycloalkylamino, C3-C8 cycloalkoxy, C3-C8 oxacycloalkyloxy, N—(C1-C5) alkoxy (C1-C5) alkyl-N—(C1-C5) alkylamino, N—(C3-C8) cycloalkyl-N—(C1-C5) alkylamino, N-aryl-N—(C1-C5) alkylamino, aryl preferably phenyl, arylamino preferably phenylamino, heteroarylamino, aryloxy preferably phenoxy, heteroaryloxy preferably pyridinyloxy, pyrrolidinyl, or morpholinyl, wherein,
each alkyl, alkenyl and alkynyl, also as a part of a group such as in alkoxy, alkylsulfonyl, alkylcarbonyl, alkylamino, or alkenyloxy may be independently unsubstituted or substituted with one or more substituents selected from among halogen, hydroxyl, unsubstituted or halo-substituted (C1-C5) alkoxy, (C3-C8), cycloalkyl which may be unsubstituted or substituted with one or two halogen radicals and/or methyl groups, unsubstituted or halo-substituted (C1-C5) alkylamino, or unsubstituted or halo-substituted di(C1-C5) alkylamino,
each aryl or heteroaryl, also a part of a group such as in arylamino, aryloxy, heteroarylamino, or heteroaryloxy, may be independently unsubstituted or substituted with one or more substituents selected from halogen, unsubstituted C1-C5 alkyl, or halo (C1-C5) alkyl,
each cycloalkyl, also as a part of a group such as in cycloalkoxy or cycloalkylamino may be unsubstituted or substituted with one or more unsubstituted or halo-substituted C1-C3 alkyl groups, hydroxymethyl, hydroxy, methoxy, or amino, and
each piperazinyl, piperidyl, morpholinyl, and pyrrolidinyl may be unsubstituted or substituted with one or more unsubstituted or halo-substituted C1-C3 alkyl groups, hydroxymethyl, or hydroxyl;

and $R_{10}$ is C1-C5 alkyl, halo (C1-C5) alkyl, or C2-C5 alkenyl.

The present invention also provides a novel compound of the following formula (I), an isomer thereof, or a pharmaceutically acceptable salt thereof; and a pharmaceutical composition containing the same;

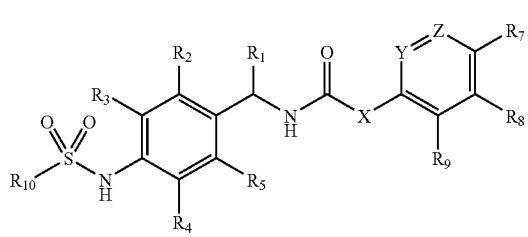

wherein,
X is $CR_{11}$=$CR_{12}$, $CHR_{11}CHR_{12}$,

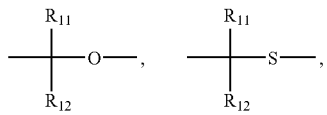

or C≡C, wherein, $R_{11}$ and $R_{12}$, if present, are independently hydrogen, halogen, or C1-C5 alkyl;
Y and Z are independently CH, $CR_6$, or N, such that at least one of Y and Z is N;
$R_1$ is hydrogen or C1-C5 alkyl;
$R_2$, $R_3$, $R_4$, and $R_5$ are independently hydrogen, halogen, nitro, cyano, C1-C5 alkyl, C1-C5 alkoxy, halo (C1-C5) alkyl, C2-C5 alkenyl, C2-C5 alkynyl, carboxy, C1-C5 alkoxycarbonyl, or C1-C5 alkylthio;
$R_6$, $R_7$, $R_8$, and $R_9$ are independently hydrogen, hydroxy, halogen, nitro, carboxy, C1-C5 alkyl, C1-C5 alkoxy, hydroxy (C1-C5) alkyl, C2-C5 alkenyl, C2-C5 alkynyl, halo (C1-C5) alkyl, halo (C1-C5) alkoxy, C1-C5 alkylthio, C1-C5 alkylsulfonyl, C1-C5 alkylcarbonyl, C1-C5 alkoxycarbonyl, C2-C5 alkenyloxy, C1-C5 alkoxy (C1-

C5) alkoxy, C1-C5 alkoxy (C1-C5) alkoxy (C1-C5) alkyl, C1-C3 alkylpiperazinyl, piperidyl, C1-C5 alkoxy (C1-C5) alkylamino, C1-C7 alkylamino, di(C1-C5 alkyl)amino, C3-C6 cycloalkyl which may be unsubstituted or substituted with one or more C1-C3 alkyl groups, pyrrolidinyl, phenyl, or morpholinyl, wherein the phenyl may be unsubstituted or substituted with one or more substituents selected from halogen, C1-C5 alkyl, and halo (C1-C5) alkyl; and $R_{10}$ is C1-C5 alkyl, halo (C1-C5) alkyl, or C2-C5 alkenyl.

Another aspect of the present invention is a compound according to the above formula (I), an isomer, or a pharmaceutically acceptable salt thereof;

wherein,

X is $CR_{11}$=$CR_{12}$, wherein, $R_{11}$ and $R_{12}$, are independently hydrogen, halogen, or C1-C3 alkyl;

$R_1$ is hydrogen or C1-C3 alkyl;

$R_2$, $R_3$, $R_4$, and $R_5$ are independently hydrogen, halogen, nitro, cyano, methyl, ethyl, ethenyl, ethynyl, trifluoromethyl, methoxy, ethoxy, or methoxycarbonyl;

$R_6$, $R_7$, $R_8$, and $R_9$ are independently hydrogen, hydroxy, halogen, nitro, carboxy, C1-C5 alkyl, C1-C5 alkoxy, hydroxy (C1-C5) alkyl, C2-C5 alkenyl, C2-C5 alkynyl, halo (C1-C5) alkyl, halo (C1-C5) alkoxy, C1-C5 alkylthio, C1-C5 alkylsulfonyl, C1-C5 alkylcarbonyl, C1-C5 alkoxycarbonyl, C2-C5 alkenyloxy, C1-C5 alkoxy (C1-C5) alkoxy, C1-C5 alkoxy (C1-C5) alkoxy (C1-C5) alkyl, C1-C3 alkylpiperazinyl, piperidyl, C1-C5 alkoxy (C1-C5) alkylamino, C1-C7 alkylamino, di(C1-C3 alkyl)amino, C3-C6 cycloalkyl which may be unsubstituted or substituted with one or more methyl groups, pyrrolidinyl, phenyl, or morpholinyl, wherein the phenyl may be unsubstituted or substituted with one or more substituents selected from halogen, C1-C5 alkyl, and halo (C1-C5) alkyl; and $R_{10}$ is C1-C3 alkyl or C2-C3 alkenyl.

According to one embodiment of the present invention, in the compounds of formula I as further described herein, $R_6$ is different from hydrogen, and $R_7$ is halo (C1-C5)alkyl, preferably halo (C1-C4) alkyl, more preferably halo (C1-C2) alkyl such as $CF_2Cl$ or $CF_2CF_3$, particularly preferably $R_7$ is $CF_3$.

According to another embodiment of the present invention, in the compounds of formula (I) as further described herein, —Z is N;

—Y is $CR_6$;

—X is $CR_{11}$=$CR_{12}$, $CHR_{11}CHR_{12}$, or C≡C;

$R_7$ is C3-C6 alkyl or halo(C1-C5) alkyl; and $R_7$ is even more preferably tert-butyl, isopropyl, isobutyl, or trifluoromethyl;

and $R_6$ is not pyridynyl, pyridinyloxy, piperazinyl, a hydroxyl-substituted alkylamino, or a substituted pyrrolidine. In some embodiments $R_6$ is also not hydrogen. In another embodiment, $R_6$ is not hydrogen and also not phenylthio.

Accordingly, one embodiment of the present invention is a compound of the formula (I), an isomer, or a pharmaceutically acceptable salt thereof:

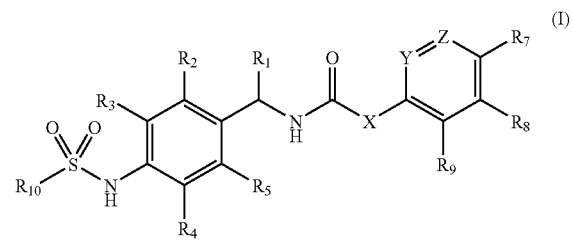

wherein,

—X is $CR_{11}$=$CR_{12}$ or C≡C; wherein, $R_{11}$ and $R_{12}$, if present, are independently hydrogen, halogen, or C1-C5 alkyl;

—Z is N;

—Y is $CR_6$;

$R_1$ is hydrogen, halogen, or C1-C5 alkyl;

$R_2$, $R_3$, $R_4$, and $R_5$ are independently hydrogen, halogen, nitro, cyano, C1-C5 alkyl, C1-C5 alkoxy, halo (C1-C5) alkyl, C2-C5 alkenyl, C2-C5 alkynyl, carboxy, C1-C5 alkoxycarbonyl, or C1-C5 alkylthio;

$R_6$ is hydroxy, halogen, nitro, carboxy, C1-C10 alkyl, C1-C10 alkoxy, C2-C10 alkenyl, C2-C10 alkynyl, C1-C10 alkylthio, C1-C10 alkylsulfonyl, C1-C10 alkylcarbonyl, C1-C10 alkoxycarbonyl, C2-C10 alkenyloxy, C1-C5 alkoxy (C1-C5) alkoxy, C1-C5 alkoxy (C1-C5) alkoxy (C1-C5) alkyl, piperidyl, C1-C5 alkoxy (C1-C5) alkylamino, C1-C10 alkylamino, di(C1-C10 alkyl)amino, C3-C8 cycloalkyl, C3-C8 cycloalkylamino, C3-C8 cycloalkoxy, C3-C8 oxacycloalkyloxy, N—(C1-C5) alkoxy (C1-C5) alkyl-N—(C1-C5) alkylamino, N—(C3-C8) cycloalkyl-N—(C1-C5) alkylamino, N-aryl-N—(C1-C5) alkylamino preferably N-phenyl-N—(C1-C5)alkylamino, aryl preferably phenyl, arylamino preferably phenylamino, thienyl, heteroarylamino, aryloxy preferably phenoxy, pyrrolidinyl, or morpholinyl, provided that R6 is not a hydroxyl-substituted alkylamino;

$R_8$ and $R_9$ are independently hydrogen, hydroxy, halogen, nitro, carboxy, C1-C10 alkyl, C1-C10 alkoxy, C2-C10 alkenyl, C2-C10 alkynyl, C1-C10 alkylthio, C1-C10 alkylsulfonyl, C1-C10 alkylcarbonyl, C1-C10 alkoxycarbonyl, C2-C10 alkenyloxy, C1-C5 alkoxy (C1-C5) alkoxy, C1-C5 alkoxy (C1-C5) alkoxy (C1-C5) alkyl, piperidyl, piperazinyl, C1-C5 alkoxy (C1-C5) alkylamino, C1-C10 alkylamino, di(C1-C10 alkyl)amino, C3-C8 cycloalkyl, C3-C8 cycloalkylamino, C3-C8 cycloalkoxy, C3-C8 oxacycloalkyloxy, N—(C1-C5) alkoxy (C1-C5) alkyl-N—(C1-C5) alkylamino, N—(C3-C8) cycloalkyl-N—(C1-C5) alkylamino, N-aryl-N—(C1-C5) alkylamino preferably N-phenyl-N—(C1-C5)alkylamino, aryl preferably phenyl, arylamino preferably phenylamino, arylthio preferably phenylthio, heteroaryl preferably pyridinyl or thienyl, heteroarylamino, aryloxy preferably phenoxy, heteroaryloxy preferably pyridinyloxy, pyrrolidinyl, or morpholinyl, wherein, each alkyl, alkenyl and alkynyl, also as a part of a group such as in alkoxy, alkylsulfonyl, alkylcarbonyl, alkylamino, or alkenyloxy may be independently unsubstituted or substituted with one or more substituents selected from among halogen, hydroxyl, unsubstituted or halo-substituted (C1-C5) alkoxy, (C3-C8), cycloalkyl which may be unsubstituted or substituted with one or two halogen radicals and/or methyl groups, unsubstituted or halo-substituted (C1-C5) alkylamino, phenyl which may be unsubstituted or substituted with one or more substituents selected from halogen, unsubstituted C1-C3 alkyl, or halo (C1-C3) alkyl, or unsubstituted or halo-substituted di(C1-C5) alkylamino, each aryl or heteroaryl, also a part of a group such as in arylamino, aryloxy, heteroarylamino, or heteroaryloxy, may be independently unsubstituted or substituted with one or more substituents selected from halogen, unsubstituted C1-C5 alkyl, unsubstituted C1-C5 alkoxy, or halo (C1-C5) alkyl, each cycloalkyl, also as a part of a group such as in cycloalkoxy or cycloalkylamino may be unsubstituted or substituted with one or more unsubstituted or halo-substituted C1-C3 alkyl groups, hydroxymethyl, hydroxy, methoxy, or amino, and each piperidyl and morpholinyl, may be unsubstituted or substituted with one or more unsubstituted or halo-substituted C1-C3 alkyl groups, hydroxy(C1-C3)alkyl, C1-C3 alkoxy, (C1-C3)alkoxycarbonyl, or hydroxyl;

$R_7$ is halo(C1-C5)alkyl;

and $R_{10}$ is C1-C5 alkyl halo (C1-C5) alkyl or C2-C5 alkenyl.

In another embodiment, in the compounds of formula I as described herein,

X is —CH═CH—, —C(CH$_3$)═CH—, —CH═C(CH$_3$)—, —C(CH$_3$)═C(CH$_3$)—, —C(C$_2$H$_5$)═CH—, —CH═C(C$_2$H$_5$)—, —CF═CH—, —CH═CF—, or C≡C;

$R_1$ is hydrogen, fluoro, methyl, or ethyl;

$R_2$, $R_3$, $R_4$, and $R_5$ are independently hydrogen, fluoro, chloro, bromo, nitro, cyano, methyl, ethyl, ethenyl, ethynyl, trifluoromethyl, methoxy, ethoxy, or methoxycarbonyl;

$R_6$ is hydroxy, fluoro, bromo, chloro, hydroxymethyl, C1-C6 alkyl, C1-C6 alkoxy, C2-C6 alkenyl, C2-C6 alkynyl, halo (C1-C6) alkyl, halo (C1-C6) alkoxy, C2-C6 alkenyloxy, C1-C5 alkoxy (C1-C5) alkoxy, C1-C5 alkoxy (C1-C5) alkoxy (C1-C5) alkyl, di(C1-C6 alkyl)amino, C1-C6 alkylamino, C1-C3 alkoxy (C1-C5) alkylamino, C3-C6 cycloalkyl which may be unsubstituted or substituted with one or more methyl groups, C3-C6 cycloalkylamino which may be unsubstituted or substituted with one or more methyl groups, C3-C6 cycloalkoxy, C3-C6 oxacycloalkoxy, N—(C1-C2) alkoxy (C1-C3) alkyl-N—(C1-C3) alkylamino, N—(C3-C6) cycloalkyl-N—(C1-C3) alkylamino, C1-C3 alkylpiperazinyl, piperidyl, pyrrolidinyl, halophenyl, phenyl, phenoxy, phenylamino, halophenoxy, morpholinyl; C1-C2 alkoxy (C1-C3) alkyl, phenyl (C1-C3)alkyl, phenyl(C2-C3)alkenyl, C1-C3 alkoxyalkynyl, di(C1-C3)alkylaminoalkynyl, (C1-C3) alkoxyphenyl, thienyl, (C3-C6) cycloalkyl (C1-C3) alkoxy, phenyl (C1-C3) alkoxy, C1-C5 alkylthio, phenyl (C1-C3) alkylamino, arylamino, N-phenyl-N—(C1-C3) alkylamino, (C1-C3)alkoxycarbonyl, or piperidyl;

$R_7$ is halo (C1-C5) alkyl, such as CF$_2$Cl, CF$_2$CF$_3$ or, particularly preferably, CF$_3$;

$R_8$ and $R_9$ are independently hydrogen, halogen, or trifluoromethyl; and $R_{10}$ is C1-C5 alkyl, halo (C1-C5) alkyl, or C2-C5 alkenyl.

The present invention also provides a novel compound of the following formula (II), an isomer, or a pharmaceutically acceptable salt thereof;

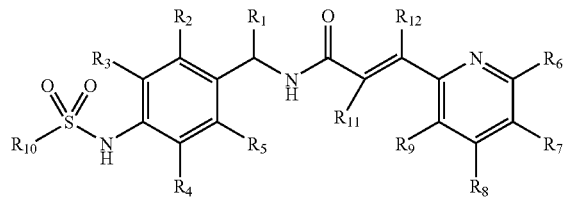

wherein, $R_1$ is hydrogen or C1-C5 alkyl;

$R_2$, $R_3$, $R_4$, and $R_5$ are independently hydrogen, halogen, nitro, cyano, C1-C5 alkyl, C1-C5 alkoxy, halo (C1-C5) alkyl, C2-C5 alkenyl, C2-C5 alkynyl, carboxy, C1-C5 alkoxycarbonyl, or C1-C5 alkylthio;

$R_6$, $R_7$, $R_8$, and $R_9$ are independently hydrogen, hydroxy, halogen, nitro, carboxy, C1-C5 alkyl, C1-C5 alkoxy, C2-C5 alkenyl, C2-C5 alkynyl, halo (C1-C5) alkyl, halo (C1-C5) alkoxy, hydroxy (C1-C5) alkyl, C1-C5 alkylthio, C1-C5 alkylsulfonyl, C1-C5 alkylcarbonyl, C1-C5 alkoxycarbonyl, C2-C5 alkenyloxy, C1-C5 alkoxy (C1-C5) alkoxy, C1-C5 alkoxy (C1-C5) alkoxy (C1-C5) alkyl, C1-C3 alkylpiperazinyl, piperidyl, C1-C5 alkoxy (C1-C5) alkylamino, C1-C7 alkylamino, di(C1-C5 alkyl)amino, C3-C6 cycloalkyl which may be unsubstituted or substituted with one or more C1-C3 alkyl groups, pyrrolidinyl, phenyl, or morpholinyl, wherein the phenyl may be unsubstituted or substituted with one or more substituents selected from halogen, C1-C5 alkyl, and halo (C1-C5) alkyl;

$R_{10}$ is C1-C5 alkyl, halo (C1-C5) alkyl, or C2-C5 alkenyl; and $R_{11}$ and $R_{12}$ are independently hydrogen, C1-C5 alkyl, or halogen.

One preferred aspect of the present invention is a compound of the formula (III), an isomer, or a pharmaceutically acceptable salt thereof;

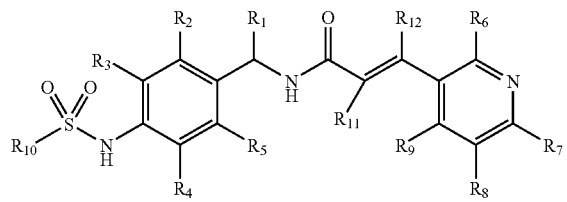

wherein, $R_1$ is hydrogen, halogen or C1-C10 alkyl;

$R_2$, $R_3$, $R_4$, and $R_5$ are independently hydrogen, halogen, nitro, cyano, alkyl (preferably C1-C10 alkyl), alkoxy (preferably C1-C10 alkoxy), haloalkyl (preferably halo (C1-C10) alkyl), alkenyl (preferably C2-C10 alkenyl), alkynyl (C2-C10 alkynyl), carboxy, alkoxycarbonyl (preferably C1-C10 alkoxycarbonyl), or alkylthio (preferably C1-C10 alkylthio);

$R_6$, $R_7$, $R_8$, and $R_9$ are independently hydrogen, hydroxy, halogen, nitro, carboxy, alkyl (preferably C1-C10 alkyl), alkoxy (preferably C1-C10 alkoxy), alkenyl (preferably C2-C10 alkenyl), alkynyl (preferably C2-C10 alkynyl), alkylthio (preferably C1-C10 alkylthio), alkylsulfonyl (preferably C1-C10 alkylsulfonyl), alkylcarbonyl (preferably C1-C10 alkylcarbonyl), alkoxycarbonyl (preferably C1-C10 alkoxycarbonyl), alkenyloxy (preferably C2-C10 alkenyloxy), alkoxyalkoxy (preferably C1-C5 alkoxy (C1-C10) alkoxy), alkoxyalkoxyalkyl (preferably C1-C5 alkoxy (C1-C10) alkoxy (C1-C10) alkyl), piperidyl, piperazinyl, alkoxyalkylamino (preferably C1-C10 alkoxy (C1-C10) alkylamino), alkylamino (preferably C1-C10 alkylamino), dialkylamino (preferably di(C1-C10 alkyl) amino), cycloalkyl (preferably C3-C8 cycloalkyl), cycloalkylamino (preferably C3-C8 cycloalkylamino), cycloalkoxy (preferably C3-C8 cycloalkoxy), oxacycloalkyloxy (preferably C3-C8 oxacycloalkyl-oxy), N-alkoxyalkyl-N-alkylamino (preferably N—(C1-C10) alkoxy (C1-C10) alkyl-N—(C1-C10) alkylamino), N-cycloalkyl-N-alkylamino (preferably N—(C3-C8)cycloalkyl-N—(C1-C10) alkylamino), N-aryl-N-alkylamino (preferably N-aryl-N—(C1-C5) alkylamino, more preferably N-phenyl-N—(C1-C5)alkylamino), aryl preferably phenyl, arylamino preferably phenylamino, arylthio preferably phenylthio, heteroaryl preferably pyridinyl or thienyl, heteroarylamino, aryloxy preferably phenoxy, heteroaryloxy preferably pyridinyloxy, pyrrolidinyl, or morpholinyl, wherein, each alkyl, alkenyl and alkynyl, also as a part of a group such as in alkoxy, alkylsulfonyl, alkylcarbonyl, alkylamino, or alkenyloxy may be independently unsubstituted or substituted with one or more substituents selected from among halogen, hydroxyl, unsubstituted or halo-substituted (C1-C5) alkoxy, (C3-C8) cycloalkyl which may be unsubstituted or substituted with one or two halogen radicals and/or methyl groups, unsubstituted or halo-substituted (C1-C5) alkylamino, phenyl which may be unsubstituted or substituted with one or more substituents selected from halogen, unsubstituted C1-C3 alkyl, or halo (C1-C3) alkyl, or unsubstituted or halo-substituted di(C1-C5) alkylamino, each aryl or heteroaryl, also a part of a group such as in arylamino, aryloxy, heteroaryloxy, or heteroarylamino, may be independently unsubstituted or substituted with one or more substituents selected from halogen, unsubstituted C1-C5 alkyl, unsubstituted C1-C5 alkoxy, or halo (C1-C5) alkyl, each cycloalkyl, also as a part of a group such as in cycloalkoxy or cycloalkylamino may be unsubstituted or substituted with one or more unsubstituted or halo-substituted C1-C3 alkyl groups, hydroxymethyl, hydroxy, methoxy, or amino, and each piperazinyl, piperidyl, morpholinyl and pyrrolidinyl may be unsubstituted or substituted with one or more unsubstituted or halo-substituted C1-C3 alkyl groups, hydroxy(C1-C3)alkyl, C1-C3 alkoxy, (C1-C3)alkoxycarbonyl, or hydroxyl;

$R_{10}$ is alkyl (preferably C1-C10 alkyl), haloalkyl (preferably halo (C1-C10) alkyl), or alkenyl (preferably C2-C10 alkenyl); and $R_{11}$ and $R_{12}$ are independently hydrogen, C1-C5 alkyl, or halogen.

A compound of the formula (III), an isomer, or a pharmaceutically acceptable salt thereof;

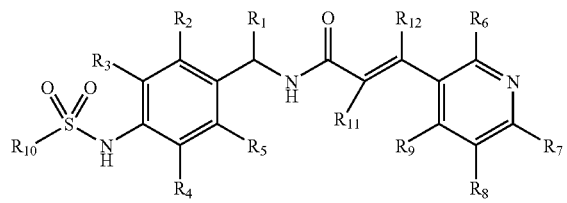

(III)

wherein, $R_1$ is hydrogen, halogen or C1-C5 alkyl;

$R_2$, $R_3$, $R_4$, and $R_5$ are independently hydrogen, halogen, nitro, cyano, C1-C5 alkyl, C1-C5 alkoxy, halo (C1-C5) alkyl, C2-C5 alkenyl, C2-C5 alkynyl, carboxy, C1-C5 alkoxycarbonyl, or C1-C5 alkylthio;

$R_6$, $R_7$, $R_8$, and $R_9$ are independently hydrogen, hydroxy, halogen, nitro, carboxy, C1-C10 alkyl, C1-C10 alkoxy, C2-C10 alkenyl, C2-C10 alkynyl, C1-C10 alkylthio, C1-C10 alkylsulfonyl, C1-C10 alkylcarbonyl, C1-C10 alkoxycarbonyl, C2-C10 alkenyloxy, C1-C5 alkoxy (C1-C5) alkoxy, C1-C5 alkoxy (C1-C5) alkoxy (C1-C5) alkyl, piperidyl, piperazinyl, C1-C5 alkoxy (C1-C5) alkylamino, C1-C10 alkylamino, di(C1-C10 alkyl)amino, C3-C8 cycloalkyl, C3-C8 cycloalkylamino, C3-C8 cycloalkoxy, C3-C8 oxacycloalkyl-oxy, N—(C1-C5)alkoxy (C1-C5) alkyl-N—(C1-C5) alkylamino, N—(C3-C8)cycloalkyl-N—(C1-C5) alkylamino, N-aryl-N—(C1-C5) alkylamino, preferably N-phenyl-N—(C1-C5)alkylamino, aryl preferably phenyl, arylamino preferably phenylamino, arylthio preferably phenylthio, heteroaryl preferably pyridinyl or thienyl, heteroarylamino, aryloxy preferably phenoxy, heteroaryloxy preferably pyridinyloxy, pyrrolidinyl, or morpholinyl, wherein, each alkyl, alkenyl and alkynyl, also as a part of a group such as in alkoxy, alkylsulfonyl, alkylcarbonyl, alkylamino, or alkenyloxy may be independently unsubstituted or substituted with one or more substituents selected from among halogen, hydroxyl, unsubstituted or halo-substituted (C1-C5) alkoxy, (C3-C8) cycloalkyl which may be unsubstituted or substituted with one or two halogen radicals and/or methyl groups, unsubstituted or halo-substituted (C1-C5) alkylamino, phenyl which may be unsubstituted or substituted with one or more substituents selected from halogen, unsubstituted C1-C3 alkyl, or halo (C1-C3) alkyl, or unsubstituted or halo-substituted di(C1-C5) alkylamino, each aryl or heteroaryl, also a part of a group such as in arylamino, aryloxy, heteroaryloxy, or heteroarylamino, may be independently unsubstituted or substituted with one or more substituents selected from halogen, unsubstituted C1-C5 alkyl, unsubstituted C1-C5 alkoxy, or halo (C1-C5) alkyl, each cycloalkyl, also as a part of a group such as in cycloalkoxy or cycloalkylamino may be unsubstituted or substituted with one or more unsubstituted or halo-substituted C1-C3 alkyl groups, hydroxymethyl, hydroxy, methoxy, or amino, and each piperazinyl, piperidyl, morpholinyl and pyrrolidinyl may be unsubstituted or substituted with one or more unsubstituted or halo-substituted C1-C3 alkyl groups, hydroxy(C1-C3)alkyl, C1-C3 alkoxy, (C1-C3)alkoxycarbonyl, or hydroxyl;

$R_{10}$ is C1-C5 alkyl, halo (C1-C5) alkyl, or C2-C5 alkenyl; and
$R_{11}$ and $R_{12}$ are independently hydrogen, C1-C5 alkyl, or halogen, wherein m one embodiment $R_6$ is preferably different from hydrogen, and $R_7$ is halo (C1-C5) alkyl.

One preferred aspect of the present invention is a compound of the formula (III), an isomer, or a pharmaceutically acceptable salt thereof;

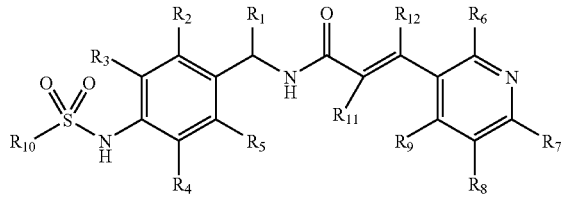

(III)

wherein,
$R_1$ is hydrogen or C1-C5 alkyl;
$R_2$, $R_3$, $R_4$, and $R_5$ are independently hydrogen, halogen, nitro, cyano, C1-C5 alkyl, C1-C5 alkoxy, halo (C1-C5) alkyl, C2-C5 alkenyl, C2-C5 alkynyl, carboxy, C1-C5 alkoxycarbonyl, or C1-C5 alkylthio;
$R_6$, $R_7$, $R_8$, and $R_9$ are independently hydrogen, hydroxy, halogen, nitro, carboxy, C1-C10 alkyl, C1-C10 alkoxy, C2-C10 alkenyl, C2-C10 alkynyl, C1-C10 alkylthio, C1-C10 alkylsulfonyl, C1-C10 alkylcarbonyl, C1-C10 alkoxycarbonyl, C2-C10 alkenyloxy, C1-C5 alkoxy (C1-C5) alkoxy, C1-C5 alkoxy (C1-C5) alkoxy (C1-C5) alkyl, piperidyl, piperazinyl, C1-C5 alkoxy (C1-C5) alkylamino, C1-C10 alkylamino, di(C1-C10 alkyl)amino, C3-C8 cycloalkyl, C3-C8 cycloalkylamino, C3-C8 cycloalkoxy, C3-C8 oxacycloalkyl-oxy, N—(C1-C5)alkoxy (C1-C5) alkyl-N—(C1-C5) alkylamino, N—(C3-C8)cycloalkyl-N—(C1-C5) alkylamino, N-aryl-N—(C1-C5) alkylamino, aryl preferably phenyl, arylamino preferably phenylamino, heteroarylamino, aryloxy preferably phenoxy, heteroaryloxy preferably pyridinyloxy, pyrrolidinyl, or morpholinyl,
wherein,
each alkyl, alkenyl and alkynyl, also as a part of a group such as in alkoxy, alkylsulfonyl, alkylcarbonyl, alkylamino, or alkenyloxy may be independently unsubstituted or substituted with one or more substituents selected from among halogen, hydroxyl, unsubstituted or halo-substituted (C1-C5) alkoxy, (C3-C8) cycloalkyl which may be unsubstituted or substituted with one or two halogen radicals and/or methyl groups, unsubstituted or halo-substituted (C1-C5) alkylamino, or unsubstituted or halo-substituted di(C1-C5) alkylamino,
each aryl or heteroaryl, also a part of a group such as in arylamino, aryloxy or heteroaryloxy, may be independently unsubstituted or substituted with one or more substituents selected from halogen, unsubstituted C1-C5 alkyl, or halo (C1-C5) alkyl,
each cycloalkyl, also as a part of a group such as in cycloalkoxy or cycloalkylamino may be unsubstituted or substituted with one or more unsubstituted or halo-substituted C1-C3 alkyl groups, hydroxymethyl, hydroxy, methoxy, or amino, and
each piperazinyl, piperidyl, morpholinyl and pyrrolidinyl may be unsubstituted or substituted with one or more unsubstituted or halo-substituted C1-C3 alkyl groups, hydroxymethyl, or hydroxyl;

$R_{10}$ is C1-C5 alkyl halo (C1-C5) alkyl or C2-C5 alkenyl; and
$R_{11}$ and $R_{12}$ are independently hydrogen, C1-C5 alkyl, or halogen.

One preferred aspect of the present invention is a compound of the formula (I) or (III), an isomer, or a pharmaceutically acceptable salt thereof;

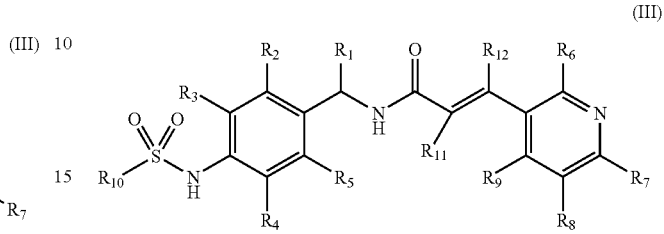

(III)

wherein,
$R_1$ is hydrogen or C1-C5 alkyl;
$R_2$, $R_3$, $R_4$, and $R_5$ are independently hydrogen, halogen, nitro, cyano, C1-C5 alkyl, C1-C5 alkoxy, halo (C1-C5) alkyl, C2-C5 alkenyl, C2-C5 alkynyl, carboxy, C1-C5 alkoxycarbonyl, or C1-C5 alkylthio;
$R_6$, $R_7$, $R_8$, and $R_9$ are independently hydrogen, hydroxy, halogen, nitro, carboxy, C1-C5 alkyl, C1-C5 alkoxy, C2-C5 alkenyl, C2-C5 alkynyl, halo (C1-C5) alkyl, halo (C1-C5) alkoxy, hydroxy (C1-C5) alkyl, C1-C5 alkylthio, C1-C5 alkylsulfonyl, C1-C5 alkylcarbonyl, C1-C5 alkoxycarbonyl, C2-C5 alkenyloxy, C1-C5 alkoxy (C1-C5) alkoxy, C1-C5 alkoxy (C1-C5) alkoxy (C1-C5) alkyl, C1-C3 alkylpiperazinyl, piperidyl, C1-C5 alkoxy (C1-C5) alkylamino, C1-C7 alkylamino, di(C1-C5 alkyl)amino, C3-C6 cycloalkyl which may be unsubstituted or substituted with one or more C1-C3 alkyl groups, pyrrolidinyl, phenyl, or morpholinyl, wherein the phenyl may be unsubstituted or substituted with one or more substituents selected from halogen, C1-C5 alkyl, and halo (C1-C5) alkyl;
$R_{10}$ is C1-C5 alkyl, halo (C1-C5) alkyl, or C2-C5 alkenyl; and
$R_{11}$ and $R_{12}$ are independently hydrogen, C1-C5 alkyl, or halogen.

One preferred aspect of the present invention is a compound of the formula (I), (II), or (III), an isomer, or a pharmaceutically acceptable salt thereof as defined further herein, wherein X is $CR_{11}=CR_{12}$ or $C\equiv C$, particularly preferably $CR_{11}=CR_{12}$, wherein $R_{11}$ and $R_{12}$ are preferably hydrogen, halogen or C1-C3 alkyl, and even more preferably hydrogen or methyl.

Accordingly, one preferred aspect of the present invention is a compound of the formula (I), (II), or (III), an isomer, or a pharmaceutically acceptable salt thereof as defined further above, wherein X is selected from among —CH=CH—, —C(CH$_3$)=CH—, —CH=C(CH$_3$)—, —C(CH$_3$)=C(CH$_3$)—, —C(C$_2$H$_5$)=CH—, —CH=C(C$_2$H$_5$)—, —CF=CH—, —CH=CF—, or C≡C, even more preferably —CH=CH—, —C(CH$_3$)=CH—, or —CH=C(CH$_3$)—, and particularly preferably —CH=CH—.

One aspect of the present invention is a compound of the formula (I), (II), or (III), an isomer, or a pharmaceutically acceptable salt thereof as defined further above, wherein $R_7$ is a C3-C6 cycloalkyl group which may be unsubstituted or substituted with one or more methyl groups, or a C1-C5 alkyl group that is optionally halogenated with one or more radicals selected from chloro, bromo, or, preferably, fluoro. Examples are methylcyclopropyl, CF$_3$, isopropyl, t-butyl and isobutyl.

In one preferred embodiment of the present invention, in the compounds of formula (III) as further described herein, $R_7$ is C3-C6 alkyl or halo(C1-C5 alkyl), and $R_7$ is even more preferably tert-butyl, isopropyl, isobutyl, or trifluoromethyl. In one preferred embodiment of the present invention, in the compounds of formula (III) as further described herein, $R_7$ is halo (C1-C5) alkyl, or halo(C1-C4) alkyl, such as $CF_2Cl$, $CF_2CF_3$ or, particularly preferably, $CF_3$.

In another embodiment of the present invention, in the compounds of formula (III), $R_6$ is not pyridinyloxy, phenylthio, or a substituted pyrrolidine. In another preferred aspect of the present disclosure, $R_6$ is different from hydrogen.

In another embodiment, in the compounds of formula (III) as further described herein $R_7$ is C3-C6 alkyl or halo(C1-C5 alkyl), and $R_7$ is even more preferably tert-butyl, isopropyl, isobutyl, or trifluoromethyl;

and $R_6$ is not pyridynyl, pyridinyloxy, piperazinyl, a hydroxyl-substituted alkylamino, or a substituted pyrrolidine. In some embodiments $R_6$ is also not hydrogen and/or phenylthio.

Another aspect of the present invention is a compound of the formula (I) or (III), an isomer, or a pharmaceutically acceptable salt thereof as defined further above, wherein $R_6$ is selected from hydrogen, bromo, chloro, n-butyl, methoxy, isobutyloxy, sec-butyloxy, methoxyethoxy, diethylamino, N-pyrrolidinyl, N-piperidyl, N-morpholinyl, cyclopentylamino, n-butylamino, phenoxy, n-butyloxy, and methoxyethylamino.

Another aspect of the present invention is a compound of the formula (I), (II), or (III), an isomer, or a pharmaceutically acceptable salt thereof as defined further above, wherein $R_3$ is selected from hydrogen, fluoro, bromo, chloro, methyl, ethyl, trifluoromethyl, ethenyl, ethynyl, and cyano.

Another aspect of the present invention is a compound of the formula (I), (II), or (III), an isomer, or a pharmaceutically acceptable salt thereof as defined further above, wherein $R_{10}$ is methyl.

Another aspect of the present invention is a compound of the formula (I), (II), or (III), an isomer, or a pharmaceutically acceptable salt thereof as defined further above, wherein $R_{11}$ and $R_{12}$, if present, are both hydrogen. In another embodiment, one of $R_{11}$ and $R_{12}$ is hydrogen and the other one is selected from methyl, ethyl and propyl. In one embodiment, $R_{11}$ may be hydrogen, and $R_{12}$ may be hydrogen, methyl, ethyl or propyl, preferably hydrogen.

Another aspect of the present invention is a compound of the formula (I), (II), or (III), an isomer, or a pharmaceutically acceptable salt thereof as defined further above, wherein $R_4$ is hydrogen, fluoro, chloro, bromo, methyl, ethyl, cyano, or trifluoromethyl.

Another aspect of the present invention is a compound of the formula (I), (II), or (III), an isomer, or a pharmaceutically acceptable salt thereof as defined further above, wherein $R_1$ and $R_2$ are both hydrogen.

Another aspect of the present invention is a compound of the formula (I), (II), or (III), an isomer, or a pharmaceutically acceptable salt thereof as defined further above, wherein $R_1$, $R_2$, and $R_{11}$ and $R_{12}$, if present, are all hydrogen.

Another aspect of the present invention is a compound of the formula (I), (II), or (III), an isomer, or a pharmaceutically acceptable salt thereof as defined further above, wherein $R_1$, $R_2$, and $R_{11}$ and $R_{12}$, if present, are all hydrogen, $R_{10}$ is methyl, and $R_3$ is selected from hydrogen, fluoro, bromo, chloro, methyl, ethyl, trifluoromethyl, ethenyl, ethynyl, and cyano.

Another aspect of the present invention is a compound of the formula (I), (II), or (III), an isomer, or a pharmaceutically acceptable salt thereof as defined further above, wherein $R_{11}$ and $R_{12}$, if present, are both hydrogen, $R_{10}$ is methyl or ethyl, $R_3$ is selected from hydrogen, fluoro, bromo, chloro, methyl, ethyl, trifluoromethyl, ethenyl, ethynyl, and cyano, and $R_4$ is selected from hydrogen, fluoro, chloro, bromo, methyl, cyano, or trifluoromethyl.

Another aspect of the present invention is a compound of the formula (I), (II), or (III), an isomer, or a pharmaceutically acceptable salt thereof as defined further above, wherein $R_{11}$ and $R_{12}$, if present, are both hydrogen, $R_{10}$ is methyl or ethyl, $R_3$ is selected from hydrogen, fluoro, bromo, chloro, methyl, ethyl, trifluoromethyl, ethenyl, ethynyl, and cyano, and $R_7$ is cyclopropylmethyl or a C1-C5 alkyl that is optionally halogenated with one or more radicals selected from chloro, bromo, or, preferably, fluoro.

Another aspect of the present invention is a compound of the formula (I), (II), or (III), an isomer, or a pharmaceutically acceptable salt thereof as defined further above, wherein $R_{11}$ and $R_{12}$, if present, are both hydrogen, $R_{10}$ is methyl or ethyl, $R_2$, $R_5$ and $R_8$ are hydrogen, $R_3$ is selected from hydrogen, fluoro, bromo, chloro, methyl, ethyl, trifluoromethyl, ethenyl, ethynyl, and cyano, and $R_7$ is a C1-C5 alkyl that is optionally halogenated with one or more radicals selected from chloro, bromo, or, preferably, fluoro.

One preferred aspect of the present invention is a compound of the formula (I), (II), or (III), an isomer, or a pharmaceutically acceptable salt thereof;

wherein, $R_1$ is hydrogen, methyl, or ethyl;

$R_2$, $R_3$, $R_4$, and $R_5$ are independently hydrogen, fluoro, chloro, bromo, nitro, cyano, methyl, ethyl, ethenyl, ethynyl, trifluoromethyl, methoxy, ethoxy, or methoxycarbonyl;

$R_6$, if present, is hydrogen, hydroxy, fluoro, bromo, chloro, hydroxymethyl, C1-C5 alkyl, C1-C5 alkoxy, C2-C5 alkenyl, C2-C5 alkynyl, halo (C1-C5) alkyl, halo (C1-C5) alkoxy, C2-C5 alkenyloxy, C1-C5 alkoxy (C1-C5) alkoxy, C1-C5 alkoxy (C1-C5) alkoxy (C1-C5) alkyl, di(C1-C3 alkyl)amino, C1-C3 alkylpiperazinyl, piperidyl, pyrrolidinyl, halophenyl, phenyl, or morpholinyl, wherein $R_6$ is preferably different from hydrogen;

$R_7$ is C1-C5 alkyl, halo (C1-C4) alkyl, halogen, piperidyl, morpholinyl, pyrrolidinyl, C3-C6 cycloalkyl which may be unsubstituted or substituted with one or more methyl groups, C2-C5 alkenyl, wherein $R_7$ is preferably halo (C1-C4) alkyl;

$R_8$ and $R_9$ are independently hydrogen, halogen, or trifluoromethyl;

$R_{10}$ is C1-C5 alkyl, halo (C1-C5) alkyl, or C2-C5 alkenyl; and $R_{11}$ and $R_{12}$, if present, are independently hydrogen, or methyl.

Another preferred embodiment of the invention is a compound of the formula (I), (II), or (III), an isomer, or a pharmaceutically acceptable salt thereof;

wherein, $R_1$, $R_2$, and $R_5$ are hydrogen;

$R_3$ is hydrogen, fluoro, chloro, cyano, methyl, ethenyl, ethynyl, or trifluoromethyl;

$R_4$ is hydrogen, fluoro, chloro, cyano, methyl, ethyl, or trifluoromethyl;

$R_6$, if present is hydrogen, hydroxy, fluoro, bromo, chloro, methyl, hydroxymethyl, methoxy, trifluoromethyl, diethylamino, piperidyl, pyrrolidinyl, trifluorophenyl, phenyl, or morpholinyl, wherein $R_6$ is preferably different from hydrogen;

$R_7$ is methyl, isopropyl, t-butyl, trifluoromethyl, chloro, bromo, cyclopropyl, methylcyclopropyl, piperidyl, pyrrolidinyl, or morpholinyl, and $R_7$ is preferably trifluoromethyl;

$R_9$ is hydrogen;

$R_{11}$, and $R_{12}$, if present, are hydrogen;

$R_9$ is hydrogen or trifluoromethyl; and $R_{10}$ is methyl.

Another preferred embodiment of the invention is a compound of the formula (I), (II), or (III), an isomer, or a pharmaceutically acceptable salt thereof;

wherein, $R_1$ is hydrogen or methyl;

$R_2$ is hydrogen;

$R_3$ is hydrogen, fluoro, chloro, bromo, cyano, methyl, ethyl, ethenyl, ethynyl, or trifluoromethyl;

$R_4$ and $R_5$ are independently hydrogen, fluoro, chloro, cyano, methyl, ethyl, or trifluoromethyl;

$R_6$, if present is hydrogen, fluoro, chloro, bromo, methyl, methoxy, piperidyl, or morpholinyl;

$R_7$ is isopropyl, t-butyl, or, preferably, trifluoromethyl, $R_8$ is hydrogen;

$R_{11}$ and $R_{12}$, if present, are hydrogen;

$R_9$ is hydrogen or trifluoromethyl; and $R_{10}$ is methyl.

Another preferred embodiment of the invention is a compound of the formula (I) or (III), an isomer, or a pharmaceutically acceptable salt thereof;

wherein,

X is —CH═CH—, —C(CH$_3$)═CH—, —CH═C(CH$_3$)—, —C(CH$_3$)═C(CH$_3$)—, —C(C$_2$H$_5$)═CH—, —CH═C(C$_2$H$_5$)—, —CF═CH—, —CH═CF—, or C≡C;

$R_1$ is hydrogen, fluoro, methyl, or ethyl;

$R_2$, $R_3$, $R_4$, and $R_5$ are independently hydrogen, fluoro, chloro, bromo, nitro, cyano, methyl, ethyl, ethenyl, ethynyl, trifluoromethyl, methoxy, ethoxy, or methoxycarbonyl;

$R_6$ is hydrogen, hydroxy, fluoro, bromo, chloro, hydroxymethyl, C1-C6 alkyl, C1-C6 alkoxy, C2-C6 alkenyl, C2-C6 alkynyl, halo (C1-C6) alkyl, halo (C1-C6) alkoxy, C2-C6 alkenyloxy, C1-C5 alkoxy (C1-C5) alkoxy, C1-C5 alkoxy (C1-C5) alkoxy (C1-C5) alkyl, di(C1-C6 alkyl)amino, C1-C6 alkylamino, C1-C3 alkoxy (C1-C5) alkylamino, C3-C6 cycloalkyl which may be unsubstituted or substituted with one or more methyl groups, C3-C6 cycloalkylamino which may be unsubstituted or substituted with one or more methyl groups, C3-C6 cycloalkoxy, C3-C6 oxacycloalkoxy, N—(C1-C2) alkoxy (C1-C3) alkyl-N—(C1-C3) alkylamino, N—(C3-C6) cycloalkyl-N—(C1-C3) alkylamino, C1-C3 alkylpiperazinyl, piperidyl, pyrrolidinyl, halophenyl, phenyl, phenoxy, pyridinyloxy, phenylamino, halophenoxy, or morpholinyl;

$R_7$ is C1-C5 alkyl, halo (C1-C4) alkyl, halogen, piperidyl, morpholinyl, pyrrolidinyl, C3-C6 cycloalkyl which may be unsubstituted or substituted with one or more methyl groups, C2-C5 alkenyl;

$R_8$ and $R_9$ are independently hydrogen, halogen, or trifluoromethyl; and $R_{10}$ is C1-C5 alkyl, halo (C1-C5) alkyl, or C2-C5 alkenyl.

Another preferred embodiment of the invention is a compound of the formula (III), an isomer, or a pharmaceutically acceptable salt thereof;

wherein, $R_1$, $R_2$, and $R_5$ are hydrogen;

$R_3$ is hydrogen, fluoro, chloro, cyano, methyl, ethenyl, ethynyl, or trifluoromethyl;

$R_4$ is hydrogen, fluoro, chloro, cyano, methyl, ethyl, or trifluoromethyl;

$R_6$ is hydrogen, hydroxy, fluoro, bromo, chloro, methyl, propyl, butyl, pentyl, hydroxymethyl, methoxy, ethoxy, propoxy, butoxy, pentoxy, methoxymethoxy, methoxyethoxy, methoxypropoxy, trifluoromethyl, diethylamino, methoxymethylamino, methoxyethylamino, methoxypropylamino, cyclobutylamino, cyclopentylamino, cyclohexylamino, ethylamino, propylamino, butylamino, pentylamino, N,N-dimethylamino, N-methyl-N-ethylamino N,N-diethylamino, N-methyl-N-propylamino, N-ethyl-N-propylamino, N,N-dipropylamino, N-methyl-N-butylamino, N-ethyl-N-butylamino, N-methyl-N-methoxymethylamino, N-methyl-N-methoxyethylamino, N-methyl-N-methoxypropylamino, N-methyl-N-cyclobutylamino, N-methyl-N-cyclopentylamino, N-methyl-N-cyclohexylamino, phenoxy, halophenoxy, piperidyl, pyrrolidinyl, trifluorophenyl, phenyl, or morpholinyl, wherein R6 is preferably different from hydrogen;

$R_7$ is methyl, isopropyl, t-butyl, trifluoromethyl, chloro, bromo, cyclopropyl, methylcyclopropyl, piperidyl, pyrrolidinyl, or morpholinyl, and is preferably trifluoromethyl;

$R_8$ is hydrogen;

$R_{11}$ and $R_{12}$ are hydrogen;

$R_9$ is hydrogen or trifluoromethyl; and $R_{10}$ is methyl.

Another preferred embodiment of the invention is a compound of the formula (III), an isomer, or a pharmaceutically acceptable salt thereof;

wherein, $R_1$ is hydrogen or methyl;

$R_2$ is hydrogen;

$R_3$ is hydrogen, fluoro, chloro, bromo, cyano, methyl, ethyl, ethenyl, ethynyl, or trifluoromethyl;

$R_4$ and $R_5$ are independently hydrogen, fluoro, chloro, cyano, methyl, ethyl, or trifluoromethyl;

$R_6$ is hydrogen, fluoro, chloro, bromo, methyl, n-butyl, methoxy, n-butyloxy, isobutyloxy, sec-butyloxy, methoxyethoxy, methoxyethylamino, diethylamino, n-butylamino, cyclopentylamino, phenoxy, N-pyrrolidinyl, N-piperidyl, or N-morpholinyl, wherein in one aspect $R_6$ is different from hydrogen;

$R_7$ is isopropyl, t-butyl, or, preferably, trifluoromethyl, $R_8$ is hydrogen;

$R_{11}$ and $R_{12}$ are hydrogen;

$R_9$ is hydrogen or trifluoromethyl; and $R_{10}$ is methyl.

Another preferred embodiment of the invention is a compound of the formula (III), an isomer, or a pharmaceutically acceptable salt thereof;

wherein, $R_1$ is hydrogen or methyl;

$R_2$ is hydrogen;

$R_3$ is hydrogen, ethenyl, or ethynyl;

$R_4$ is hydrogen or fluoro;

$R_5$ is hydrogen;

$R_6$, is hydrogen, hydroxy, fluoro, bromo, chloro, methyl, propyl, butyl, pentyl, hydroxymethyl, methoxy, ethoxy, propoxy, butoxy, pentoxy, methoxymethoxy, methoxyethoxy, methoxypropoxy, ethoxyethoxy, trifluoromethyl, N,N-dimethylamino, N-methyl-N-ethylamino N,N-diethylamino, N-methyl-N-propylamino, N-ethyl-N-propylamino, N,N-dipropylamino, N-methyl-N-butylamino, N-ethyl-N-butylamino, methoxymethylamino, methoxyethylamino, methoxypropylamino, N-methyl-N-methoxymethylamino, N-methyl-N-methoxyethylamino, N-methyl-N-methoxypropylamino, cyclobutylamino, cyclopentylamino, cyclohexylamino, N-methyl-N-cyclobutylamino, N-methyl-N-cyclopentylamino, N-methyl-N-cyclohexylamino, ethylamino, propylamino, butylamino, pentylamino, phenoxy, halophenoxy, N-piperidyl, N-pyrrolidinyl, trifluorophenyl, phenyl, or N-morpholinyl wherein $R_6$ in one aspect is different from hydrogen;

$R_7$ is isopropyl, t-butyl, or, preferably, trifluoromethyl, $R_8$ is hydrogen;

$R_9$ is hydrogen or trifluoromethyl;

$R_{10}$ is methyl; and $R_{11}$ and $R_{12}$ are hydrogen.

Another preferred embodiment of the invention is a compound of the formula (III), an isomer, or a pharmaceutically acceptable salt thereof;

wherein, $R_1$ is hydrogen;

$R_2$ is hydrogen;

$R_3$ is hydrogen, ethenyl, or ethynyl;

$R_4$ is hydrogen or fluoro;

$R_5$ is hydrogen;

$R_6$ is hydrogen, bromo, chloro, n-butyl, methoxy, isobutyloxy, sec-butyloxy, methoxyethoxy, diethylamino, N-pyrrolidinyl, N-piperidyl, N-morpholinyl, cyclopentylamino, n-butylamino, phenoxy, n-butyloxy, methoxyethylamino, wherein $R_6$ in one aspect is different from hydrogen;

$R_7$ is isopropyl, t-butyl, or, preferably, trifluoromethyl;

$R_8$ is hydrogen;

$R_9$ is hydrogen or trifluoromethyl;

$R_{10}$ is methyl; and $R_{11}$ and $R_{12}$ are hydrogen.

Another aspect of the present invention is a compound of the formula (III) as further described herein, an isomer, or a pharmaceutically acceptable salt thereof, wherein, $R_1$ is hydrogen or methyl, wherein, if $R_1$ is methyl, then the compound may be a pure enantiomer or may be a mixture of the (R) and (S)-enantiomer; and then, the C-atom to which $R_1$ is attached is preferably in the (R)-configuration;

one of $R_2$ and $R_5$ is hydrogen, and the other one is hydrogen, methyl, or halogen, preferably fluoro;

$R_3$ is selected from hydrogen, fluoro, bromo, chloro, methyl, ethyl, trifluoromethyl, ethenyl, ethynyl, and cyano, preferably hydrogen, fluoro, chloro, methyl, ethyl, ethenyl, ethynyl, and cyano;

$R_4$ is hydrogen, fluoro, chloro, cyano, methyl, or ethyl;

$R_6$ is as further described in various embodiments throughout this application;

$R_7$ is a C1-C5 alkyl, or more preferably a C1-C4 alkyl or a C1-C3 alkyl, that is halogenated with one or more radicals selected from chloro, bromo, or, preferably, fluoro, wherein $R_7$ is particularly preferably $CF_3$;

one of $R_8$ and $R_9$ is hydrogen, and the other one is halogen, $CF_3$, or, preferably, hydrogen;

$R_{10}$ is methyl, ethyl, or vinyl, and is preferably methyl, $R_{11}$ is hydrogen;

$R_{12}$ is hydrogen, methyl, ethyl or propyl, and is preferably hydrogen.

Another aspect of the present disclosure are compounds of the formula (III) as further described herein, an isomer, or a pharmaceutically acceptable salt thereof wherein, $R_6$ is halogen, nitro, carboxy, C1-C10 alkyl, C1-C10 alkoxy, C2-C10 alkenyl, C2-C10 alkynyl, C1-C10 alkylthio, C1-C10 alkylsulfonyl, C1-C10 alkylcarbonyl, C1-C10 alkoxycarbonyl, C2-C10 alkenyloxy, C1-C5 alkoxy (C1-C5) alkoxy, C1-C5 alkoxy (C1-C5) alkoxy (C1-C5) alkyl, piperidyl, C1-C5 alkoxy (C1-C5) alkylamino, C1-C10 alkylamino, di(C1-C10 alkyl)amino, C3-C8 cycloalkyl, C3-C8 cycloalkylamino, C3-C8 cycloalkoxy, C3-C8 oxacycloalkyl-oxy, N—(C1-C5) alkoxy (C1-C5) alkyl-N—(C1-C5) alkylamino, N—(C3-C8)cyclo alkyl-N—(C1-C5) alkylamino, N-aryl-N—(C1-C5) alkylamino, preferably N-phenyl-N—(C1-C5)alkylamino, aryl preferably phenyl, arylamino preferably phenylamino, arylthio preferably phenylthio, thienyl, heteroarylamino, aryloxy preferably phenoxy, pyrrolidinyl, or morpholinyl, provided that $R_6$ is not a hydroxyl-substituted alkylamino, wherein preferably, $R_6$ is chloro, bromo, methyl, ethyl, propyl, butyl, pentyl, trifluoromethyl, ethoxymethyl, methoxypropyl, phenylethyl, phenylethenyl, ethynyl, methoxypropynyl, diethylaminopropynyl, phenyl, halophenyl, methoxyphenyl, thienyl, methoxy, ethoxy, propoxy, butoxy, pentoxy, trifluoroethoxy, cyclopentoxy, cyclopropylmethoxy, methoxyethoxy, tetrahydropyranyloxy, phenoxy, halophenoxy, benzyloxy, ethylthio, propylthio, butylthio, pentylthio, methylamino, ethylamino, propylamino, butylamino, pentylamino, methoxyethylamino, ethoxyethylamino, methoxypropylamino, cyclobutylamino, cyclopentylamino, cyclohexylamino, benzylamino, phenylamino, N,N-dimethylamino, N-methyl-N-propylamino, N-ethyl-N-propylamino, N,N-dipropylamino, N-methyl-N-butylamino, N-ethyl-N-butylamino, N-ethyl-N-phenylamino, N-methyl-N-phenylamino, N-pyrrolidinyl, N-piperidyl, ethoxycarbonyl N-piperidyl, or N-morpholinyl, wherein preferably, $R_6$ is ethyl, n-propyl, isopropyl, n-butyl, isobutyl, sec-butyl, 1-methylbutyl, 2-methylbutyl, 3-methylbutyl, n-pentyl, ethoxymethyl, 2-phenylethyl, phenylethenyl, phenyl, fluorophenyl, thienyl, n-propoxy, isopropoxy, n-butoxy, isobutoxy, sec-butoxy, 3-methylbutoxy, 2,2,2-trifluoroethoxy, cyclopentoxy, cyclopropylmethoxy, phenoxy, ethylthio, propylthio, isopropylthio, methylamino, ethylamino, n-propylamino isopropylamino, n-butylamino, isobutylamino, sec-butylamino, methoxymethylamino, methoxyethylamino, ethoxyethylamino, cyclopentylamino, benzylamino, phenylamino, N-methyl-N-phenylamino, N-methyl-N-propylamino, N-pyrrolidinyl, N-piperidyl, or ethoxycarbonyl N-piperidyl, wherein more preferably, $R_6$ is ethyl, n-propyl, isopropyl, n-butyl, isobutyl, sec-butyl, 2-methylbutyl, 3-methylbutyl, n-pentyl, 2-phenylethyl, n-butoxy, isobutoxy, sec-butoxy, methylamino, ethylamino, n-propylamino, isopropylamino, n-butylamino, isobutylamino, sec-butylamino, methoxyethylamino, ethoxyethylamino, benzylamino, or N-methyl-N-phenylamino, wherein more preferably, $R_6$ is n-propyl, isopropyl, n-butyl, isobutyl, sec-butyl, 2-methylbutyl, 3-methylbutyl, n-pentyl, 2-phenylethyl, n-butoxy, isobutoxy, sec-butoxy, ethylamino, n-propylamino, Isopropylamino, n-butylamino, isobutylamino, sec-butylamino, methoxyethylamino, benzylamino, or N-methyl-N-phenylamino, wherein even more preferably, $R_6$ is C2-C5 alkyl, C1-C4 alkylamino, or methoxyethylamino, wherein particularly preferably, $R_6$ is C3-C5 alkyl, or C2-C4 alkylamino; wherein particularly preferably, $R_6$ is C2-C4 alkyl, or C1-C3 alkylamino; wherein particularly preferably, $R_6$ is linear or branched C3 alkyl, linear C4 alkyl, or linear (C2-C3) alkylamino.

Preferred examples of compounds according to the invention are selected from the group consisting of;

3-(2-Diethylamino-6-trifluoromethyl-pyridin-3-yl)-N-(3-ethynyl-5-fluoro-4-methanesulfonylamino-benzyl)-acrylamide, 3-(6-tert-Butyl-pyridin-3-yl)-N-(3,5-difluoro-4-methanesulfonylamino-benzyl)-acrylamide, 3-(2-Chloro-6-trifluoromethyl-pyridin-3-yl)-N-(3-ethynyl-5-fluoro-4-methanesulfonylamino-benzyl)-acrylamide, N-(3-Ethynyl-5-fluoro-4-methanesulfonylamino-benzyl)-3-(6-methoxy-4-trifluoromethyl-pyridin-3-yl)-acrylamide, N-(3-Ethynyl-5-fluoro-4-methanesulfonylamino-benzyl)-3-(2-methoxy-6-trifluoromethyl-pyridin-3-yl)-acrylamide, N-(3-Fluoro-4-methanesulfonylamino-benzyl)-3-[2-(2-methoxy-ethylamino)-6-trifluoromethyl-pyridin-3-yl]-acrylamide, 3-(2-Diethylamino-6-trifluoromethyl-pyridin-3-yl)-N-(3-fluoro-4-methanesulfonylamino-benzyl)-acrylamide, 3-(6-tert-Butyl-2-chloro-pyridin-3-yl)-N-(3-ethynyl-5-fluoro-4-methanesulfonylamino-benzyl)-acrylamide, 3-(6-Chloro-4-trifluoromethyl-pyridin-3-yl)-N-(3-ethynyl-5-fluoro-4-methanesulfonylamino-benzyl)-acrylamide, N-(3-Fluoro-4-methanesulfonylamino-benzyl)-3-(2-pyrrolidin-1-yl-6-trifluoromethyl-pyridin-3-yl)-acrylamide, 3-(6-tert-Butyl-2-morpholin-4-yl-pyridin-3-yl)-N-(3-ethynyl-5-fluoro-4-methanesulfonylamino-benzyl)-acrylamide, N-(3-Fluoro-4-methanesulfonylamino-benzyl)-3-(2-methoxy-6-trifluoromethyl-pyridin-3-yl)-acrylamide, N-(3-Fluoro-4-methanesulfonylamino-benzyl)-3-[2-(2-hydroxy-ethylamino)-6-trifluoromethyl-pyridin-3-yl]-acrylamide, N-(3-Ethynyl-5-fluoro-4-methanesulfonylamino-benzyl)-3-(2-pyrrolidin-1-yl-6-trifluoromethyl-pyridin-3-yl)-acrylamide, 3-(2-Butoxy-6-trifluoromethyl-pyridin-3-yl)-N-(3-fluoro-4-methanesulfonylamino-benzyl)-acrylamide, N-(3-Ethynyl-5-fluoro-4-methanesulfonylamino-benzyl)-3-[2-(2-methoxy-ethylamino)-6-trifluoromethyl-pyridin-3-yl]-acrylamide, 3-(2-Butoxy-6-trifluoromethyl-pyridin-3-yl)-N-(3-ethynyl-5-fluoro-4-methanesulfonylamino-benzyl)-acrylamide, N-(3-Ethynyl-5-fluoro-4-methanesulfonylamino-benzyl)-3-(2-methyl-6-trifluoromethyl-pyridin-3-yl)-acrylamide, N-(3-Fluoro-4-methanesulfonylamino-benzyl)-3-(2-methyl-6-trifluoromethyl-pyridin-3-yl)-acrylamide, 3-(2-Butylamino-6-trifluoromethyl-pyridin-3-yl)-N-(3-ethynyl-5-fluoro-4-methanesulfonylamino-benzyl)-acrylamide, 3-(2-Cyclopentylamino-6-trifluoromethyl-pyridin-3-yl)-N-(3-ethynyl-5-fluoro-4-methanesulfonylamino-benzyl)-acrylamide, N-(3-Ethynyl-5-fluoro-4-methanesulfonylamino-benzyl)-3-[2-(2-methoxy-ethoxy)-6-trifluoromethyl-pyridin-3-yl]-acrylamide, 3-(2-Butyl-5-chloro-6-trifluoromethyl-pyridin-3-yl)-N-(3-ethynyl-5-fluoro-4-methanesulfonylamino-benzyl)-acrylamide, 3-(2-sec-Butoxy-6-trifluoromethyl-pyridin-3-yl)-N-(3-ethynyl-5-fluoro-4-methanesulfonylamino-benzyl)-acrylamide N-(3-Ethynyl-5-fluoro-4-methanesulfonylamino-benzyl)-3-(2-phenoxy-6-trifluoromethyl-pyridin-3-yl)-acrylamide, 3-(2-Isopropyloxy-6-trifluoromethyl-pyridin-3-yl)-N-(3-ethynyl-5-fluoro-4-methanesulfonylamino-benzyl)-acrylamide, N-(3-Ethynyl-5-fluoro-4-methanesulfonylamino-benzyl)-3-(2-isobutoxy-6-trifluoromethyl-pyridin-3-yl)-acrylamide, 3-[2-(tetrahydro-furan-3-yloxy)-6-trifluoromethyl-pyridin-3-yl]-N-(3-ethynyl-5-fluoro-4-methanesulfonylamino-benzyl)-acrylamide, N-(3-Fluoro-4-methanesulfonylamino-benzyl)-3-[2-(pyridin-3-yloxy)-6-trifluoromethyl-pyridin-3-yl]-acrylamide, and N-(3-Ethynyl-5-fluoro-4-methanesulfonylamino-benzyl)-3-[2-(4-fluoro-phenoxy)-6-trifluoromethyl-pyridin-3-yl]-acrylamide.

Preferred examples of compounds according to the invention are selected from the group consisting of;

3-(6-tert-Butyl-pyridin-3-yl)-N-(3-chloro-4-methanesulfonylamino-benzyl)-acrylamide, 3-(6-tert-Butyl-pyridin-3-yl)-N-(3-fluoro-4-methanesulfonylamino-benzyl)-acrylamide, 3-(6-tert-Butyl-pyridin-3-yl)-N-(3-ethynyl-5-fluoro-4-methanesulfonylamino-benzyl)-acrylamide, 3-(6-tert-Butyl-pyridin-3-yl)-N-(4-methanesulfonylamino-3-vinyl-benzyl)-acrylamide, N-(3-Fluoro-4-methanesulfonylamino-benzyl)-3-(2-morpholin-4-yl-6-trifluoromethyl-pyridin-3-yl)-acrylamide, N-(4-Methanesulfonylamino-3-vinyl-benzyl)-3-(2-morpholin-4-yl-6-trifluoromethyl-pyridin-3-yl)-acrylamide, N-(3-Chloro-4-methanesulfonylamino-benzyl)-3-(2-morpholin-4-yl-6-trifluoromethyl-pyridin-3-yl)-acrylamide, N-(3-Fluoro-4-methanesulfonylamino-5-methyl-benzyl)-3-(2-morpholin-4-yl-6-trifluoromethyl-pyridin-3-yl)-acrylamide, 3-(6-tert-Butyl-2-methoxy-pyridin-3-yl)-N-(3-fluoro-4-methanesulfonylamino-benzyl)-acrylamide, 3-(6-tert-Butyl-pyridin-3-yl)-N-(3-fluoro-4-methanesulfonylamino-5-vinyl-benzyl)-acrylamide, 3-(6-tert-Butyl-2-methoxy-pyridin-3-yl)-N-(3-ethynyl-5-fluoro-4-methanesulfonylamino-benzyl)-acrylamide, N-(3-Ethynyl-5-fluoro-4-methanesulfonylamino-benzyl)-3-(2-morpholin-4-yl-6-trifluoromethyl-pyridin-3-yl)-acrylamide, 3-(6-tert-Butyl-4-trifluoromethyl-pyridin-3-yl)-N-(3-fluoro-4-methanesulfonylamino-benzyl)-acrylamide, 3-(6-tert-Butyl-4-trifluoromethyl-pyridin-3-yl)-N-(3-ethynyl-5-fluoro-4-methanesulfonylamino-benzyl)-acrylamide, N-(3,5-Difluoro-4-methanesulfonylamino-benzyl)-3-(2-morpholin-4-yl-6-trifluoromethyl-pyridin-3-yl)-acrylamide, N-(3-Ethynyl-5-fluoro-4-methanesulfonylamino-benzyl)-3-(6'-trifluoromethyl-3,4,5,6-tetrahydro-2H-[1,2']bipyridinyl-3'-yl)-acrylamide, 3-(2-Bromo-6-tert-butyl-pyridin-3-yl)-N-(3-fluoro-4-methanesulfonylamino-benzyl)-acrylamide, 3-(2-Bromo-6-tert-butyl-pyridin-3-yl)-N-(3-ethynyl-5-fluoro-4-methanesulfonylamino-benzyl)-acrylamide, and N-(3-Fluoro-4-methanesulfonylamino-benzyl)-3-(6'-trifluoromethyl-3,4,5,6-tetrahydro-2H-[1,2']bipyridinyl-3'-yl)-acrylamide.

Particularly preferred compounds according to the present invention are 3-(2-Diethylamino-6-trifluoromethyl-pyridin-3-yl)-N-(3-ethynyl-5-fluoro-4-methanesulfonylamino-benzyl)-acrylamide, N-(3-Ethynyl-5-fluoro-4-methanesulfonylamino-benzyl)-3-(2-methoxy-6-trifluoromethyl-pyridin-3-yl)-acrylamide, N-(3-Fluoro-4-methanesulfonylamino-benzyl)-3-[2-(2-methoxy-ethylamino)-6-trifluoromethyl-pyridin-3-yl]-acrylamide, 3-(2-Diethylamino-6-trifluoromethyl-pyridin-3-yl)-N-(3-fluoro-4-methanesulfonylamino-benzyl)-acrylamide, 3-(6-tert-Butyl-2-chloro-pyridin-3-yl)-N-(3-ethynyl-5-fluoro-4-methanesulfonylamino-benzyl)-acrylamide, 3-(6-tert-Butyl-2-morpholin-4-yl-pyridin-3-yl)-N-(3-ethynyl-5-fluoro-4-methanesulfonylamino-benzyl)-acrylamide, N-(3-Ethynyl-5-fluoro-4-methanesulfonylamino-benzyl)-3-(2-pyrrolidin-1-yl-6-trifluoromethyl-pyridin-3-yl)-acrylamide, 3-(2-Butoxy-6-trifluoromethyl-pyridin-3-yl)-N-(3-fluoro-4-methanesulfonylamino-benzyl)-acrylamide, N-(3-Ethynyl-5-fluoro-4-methanesulfonylamino-benzyl)-3-[2-(2-methoxy-ethylamino)-6-trifluoromethyl-pyridin-3-yl]-acrylamide, 3-(2-Butoxy-6-trifluoromethyl-pyridin-3-yl)-N-(3-ethynyl-5-fluoro-4-methanesulfonylamino-benzyl)-acrylamide, 3-(2-Butylamino-6-trifluoromethyl-pyridin-3-yl)-N-(3-ethynyl-5-fluoro-4-methanesulfonylamino-benzyl)-acrylamide, 3-(2-Cyclopentylamino-6-trifluoromethyl-pyridin-3-yl)-N-(3-ethynyl-5-fluoro-4-methanesulfonylamino-benzyl)-acrylamide, N-(3-Ethynyl-5-fluoro-4-methanesulfonylamino-benzyl)-3-[2-(2-methoxy-ethoxy)-6-trifluoromethyl-pyridin-3-yl]-acrylamide, 3-(2-Butyl-5-chloro-6-trifluoromethyl-pyridin-3-yl)-N-(3-ethynyl-5-fluoro-4-methanesulfonylamino-benzyl)-acrylamide, 3-(2-sec-Butoxy-6-trifluoromethyl-pyridin-3-yl)-N-(3-ethynyl-5-fluoro-4-methanesulfonylamino-benzyl)-acrylamide, N-(3-Ethynyl-5-fluoro-4-methanesulfonylamino-benzyl)-3-(2-phenoxy-6-trifluoromethyl-pyridin-3-yl)-acrylamide, 3-(2-Isopropyloxy-6-trifluoromethyl-pyridin-3-yl)-N-(3-ethynyl-5-fluoro-4-methanesulfonylamino-benzyl)-acrylamide, N-(3-Ethynyl-5-fluoro-4-methanesulfonylamino-benzyl)-3-(2-isobutoxy-6-trifluoromethyl-pyridin-3-yl)-acrylamide, 3-[2-(tetrahydro-furan-3-yloxy)-6-trifluoromethyl-pyridin-3-yl]-N-(3-ethynyl-5-fluoro-4-methanesulfonylamino-benzyl)-acrylamide, and N-(3-Ethynyl-5-fluoro-4-methanesulfonylamino-benzyl)-3-[2-(4-fluoro-phenoxy)-6-trifluoromethyl-pyridin-3-yl]-acrylamide.

Particularly preferred compounds according to the present invention are 3-(6-tert-Butyl-pyridin-3-yl)-N-(3-ethynyl-5-fluoro-4-methanesulfonylamino-benzyl)-acrylamide, 3-(6-tert-Butyl-pyridin-3-yl)-N-(4-methane sulfonylamino-3-vinyl-benzyl)-acrylamide, N-(4-Methanesulfonylamino-3-vinyl-benzyl)-3-(2-morpholin-4-yl-6-trifluoromethyl-pyridin-3-yl)-acrylamide, N-(3-Fluoro-4-methanesulfonylamino-5-methyl-benzyl)-3-(2-morpholin-4-yl-6-trifluoromethyl-pyridin-3-yl)-acrylamide, 3-(6-tert-Butyl-2-methoxy-pyridin-3-yl)-N-(3-fluoro-4-methanesulfonylamino-benzyl)-acrylamide, 3-(6-tert-Butyl-pyridin-3-yl)-N-(3-fluoro-4-methanesulfonylamino-5-vinyl-benzyl)-acrylamide, 3-(6-tert-Butyl-2-methoxy-pyridin-3-yl)-N-(3-ethynyl-5-fluoro-4-methanesulfonylamino-benzyl)-acrylamide, N-(3-Ethynyl-5-fluoro-4-methanesulfonylamino-benzyl)-3-(2-morpholin-4-yl-6-trifluoromethyl-pyridin-3-yl)-acrylamide, 3-(6-tert-Butyl-4-trifluoromethyl-pyridin-3-yl)-N-(3-fluoro-4-methanesulfonylamino-benzyl)-acrylamide, 3-(6-tert-Butyl-4-trifluoromethyl-pyridin-3-yl)-N-(3-ethynyl-5-fluoro-4-methanesulfonylamino-benzyl)-acrylamide, N-(3-Ethynyl-5-fluoro-4-methanesulfonylamino-benzyl)-3-(6'-trifluoromethyl-3,4,5,6-tetrahydro-2H-[1,2']bipyridinyl-3'-yl)-acrylamide, 3-(2-Bromo-6-tert-butyl-pyridin-3-yl)-N-(3-fluoro-4-methanesulfonylamino-benzyl)-acrylamide, and 3-(2-Bromo-6-tert-butyl-pyridin-3-yl)-N-(3-ethynyl-5-fluoro-4-methanesulfonylamino-benzyl)-acrylamide.

Another preferred embodiment of the invention is a compound of the formula (I) or (III), an isomer, or a pharmaceutically acceptable salt thereof;

wherein,

X is —CH═CH—, —C(CH$_3$)═CH—, —CH═C(CH$_3$)—, —C(CH$_3$)═C(CH$_3$)—, —C(C$_2$H$_5$)═CH—, CH═C(C$_2$H$_5$)—, —CF═CH—, —CH═CF—, or C≡C;

R$_1$ is hydrogen, fluoro, methyl, or ethyl;

R$_2$, R$_3$, R$_4$, and R$_5$ are independently hydrogen, fluoro, chloro, bromo, nitro, cyano, methyl, ethyl, ethenyl, ethynyl, trifluoromethyl, methoxy, ethoxy, or methoxycarbonyl;

R$_6$ is C1-C2 alkoxy (C1-C3) alkyl, phenyl(C1-C3)alkyl, phenyl(C2-C3)alkenyl, C1-C3 alkoxyalkynyl, di(C1-C3)alkylaminoalkynyl, (C1-C3)alkoxyphenyl, thienyl, pyridinyl, halopyridinyl, (C3-C6) cycloalkyl (C1-C3) alkoxy, phenyl (C1-C3) alkoxy, C1-C5 alkylthio, phenylthio, phenyl (C1-C3) alkylamino, arylamino, N-phenyl-N—(C1-C3) alkylamino, hydroxy(C1-C3)alkyl N-pyrrolidinyl, C1-C2 alkoxy N-pyrrolidinyl, (C1-C3)alkoxycarbonyl piperidyl, piperazinyl, or C1-C3 alkylpiperazinyl, wherein R$_6$ in one embodiment is different from hydrogen;

R$_7$ is C1-C5 alkyl, halo (C1-C4) alkyl, halogen, piperidyl, morpholinyl, pyrrolidinyl, C3-C6 cycloalkyl which may be unsubstituted or substituted with one or more methyl groups, C2-C5 alkenyl, wherein R$_7$ preferably is halo (C1-C4) alkyl;

R$_8$ and R$_9$ are independently hydrogen, halogen, or trifluoromethyl; and

R$_{10}$ is C1-C5 alkyl, halo (C1-C5) alkyl, or C2-C5 alkenyl.

Another preferred embodiment of the invention is a compound of the formula (III), an isomer, or a pharmaceutically acceptable salt thereof;

wherein,

R$_1$ is hydrogen or methyl;

R$_2$ is hydrogen;

R$_3$ is hydrogen, fluoro, methyl, ethyl, cyano, ethenyl, ethynyl, or trifluoromethyl;

R$_4$ is hydrogen, fluoro, chloro, or methyl;

R$_5$ is hydrogen;

R$_6$ is fluoro, chloro, bromo, methyl, ethyl, propyl, butyl, pentyl, trifluoromethyl, ethoxymethyl, methoxypropyl, phenylethyl, phenylethenyl, ethynyl, methoxypropynyl, diethylaminopropynyl, phenyl, halophenyl, methoxyphenyl, thienyl, pyridinyl, halopyridinyl, methoxy, ethoxy, propoxy, butoxy, pentoxy, trifluoroethoxy, cyclopentoxy, cyclopropylmethoxy, methoxyethoxy, tetrahydropyranyloxy, phenoxy, halophenoxy, benzyloxy, pyridinyloxy, ethylthio, propylthio, butylthio, pentylthio, phenylthio, ethylamino, propylamino, butylamino, pentylamino, methoxyethylamino, ethoxyethylamino, methoxypropylamino, cyclobutylamino, cyclopentylamino, cyclohexylamino, benzylamino, phenylamino, N,N-dimethylamino, N-methyl-N-propylamino, N-ethyl-N-propylamino, N,N-dipropylamino, N-methyl-N-butylamino, N-ethyl-N-butylamino, N-ethyl-N-phenylamino, N-methyl-N-phenylamino, N-pyrrolidinyl, methoxy N-pyrrolidinyl, hydroxymethyl N-pyrrolidinyl, N-piperidyl, ethoxycarbonyl N-piperidyl, piperazinyl, or N-morpholinyl;

$R_7$ is isopropyl, t-butyl, or trifluoromethyl;
$R_8$ is hydrogen;
$R_9$ is hydrogen or trifluoromethyl;
$R_{10}$ is methyl; and
$R_{11}$ and $R_{12}$ are hydrogen.

Another preferred embodiment of the invention is a compound of the formula (III), an isomer, or a pharmaceutically acceptable salt thereof;

wherein,
$R_1$ is hydrogen or methyl;
$R_2$ is hydrogen;
$R_3$ is hydrogen, fluoro, chloro, bromo, cyano, methyl, ethyl, ethenyl, ethynyl, or trifluoromethyl;
$R_4$ and $R_5$ are independently hydrogen, fluoro, chloro, cyano, methyl, or ethyl;
$R_6$ is n-propyl, isopropyl, n-butyl, isobutyl, sec-butyl, 2-methylbutyl, 3-methylbutyl, n-pentyl, 2-phenylethyl, n-butoxy, isobutoxy, sec-butoxy, ethylamino, n-propylamino, isopropylamino, n-butylamino, isobutylamino, sec-butylamino, methoxyethylamino, ethoxyethylamino, benzylamino, phenylamino, N-ethyl-N-phenylamino, or N-methyl-N-phenylamino;
$R_7$ is isopropyl, t-butyl, or trifluoromethyl;
$R_8$ is hydrogen or chloro;
$R_9$ is hydrogen or trifluoromethyl;
$R_{10}$ is methyl; and
$R_{11}$ and $R_{12}$ are hydrogen.

Another preferred embodiment of the invention is a compound of the formula (III), an isomer, or a pharmaceutically acceptable salt thereof;

wherein,
$R_1$ is hydrogen or methyl;
$R_2$ is hydrogen;
$R_4$ is hydrogen, fluoro, chloro, or methyl;
$R_3$ is hydrogen, fluoro, methyl, cyano, ethenyl, ethynyl, or trifluoromethyl;
$R_5$ is hydrogen;
$R_6$ is ethyl, n-propyl, isopropyl, n-butyl, isobutyl, sec-butyl, 2-methylbutyl, 3-methylbutyl, n-pentyl, ethoxymethyl, 2-phenylethyl, phenylethenyl, phenyl, fluorophenyl, thienyl, n-propoxy, isopropoxy, n-butoxy, isobutoxy, sec-butoxy, 3-methylbutoxy, 2,2,2-trifluoroethoxy, cyclopentoxy, cyclopropylmethoxy, phenoxy, ethylthio, propylthio, isopropylthio, phenylthio, ethylamino, n-propylamino isopropylamino, n-butylamino, isobutylamino, sec-butylamino, methoxymethylamino, methoxyethylamino, ethoxyethylamino, cyclopentylamino, benzylamino, phenylamino, N-ethyl-N-phenylamino, N-methyl-N-phenylamino, N-methyl-N-propylamino, N-pyrrolidinyl, methoxy N-pyrrolidinyl, N-piperidyl, or ethoxycarbonyl N-piperidyl;

$R_7$ is isopropyl, t-butyl, or trifluoromethyl;
$R_8$ is hydrogen or chloro;
$R_9$ is hydrogen or trifluoromethyl;
$R_{10}$ is methyl; and
$R_{11}$ and $R_{12}$ are hydrogen.

Another preferred embodiment of the invention is a compound of the formula (III), an isomer, or a pharmaceutically acceptable salt thereof;

wherein,
$R_1$ is hydrogen or methyl;
$R_2$ is hydrogen;
$R_3$ is hydrogen, fluoro, methyl, cyano, ethenyl, or ethynyl;
$R_4$ is hydrogen, fluoro, or methyl;
$R_5$ is hydrogen;
$R_6$ is n-propyl, isopropyl, n-butyl, isobutyl, sec-butyl, 2-methylbutyl, 3-methylbutyl, n-pentyl, 2-phenylethyl, n-butoxy, isobutoxy, sec-butoxy, ethylamino, n-propylamino, isopropylamino, n-butylamino, isobutylamino, sec-butylamino, methoxyethylamino, ethoxyethylamino, benzylamino, N-ethyl-N-phenylamino, or N-methyl-N-phenylamino;
$R_7$ is isopropyl, t-butyl, or trifluoromethyl;
$R_8$ and $R_9$ are hydrogen;
$R_{10}$ is methyl; and
$R_{11}$ and $R_{12}$ are hydrogen.

Another preferred embodiment of the invention is a compound of the formula (III), an isomer, or a pharmaceutically acceptable salt thereof;

wherein,
$R_1$ is hydrogen or methyl;
$R_2$ is hydrogen;
when $R_4$ is fluoro, $R_3$ is hydrogen, fluoro, methyl, or ethynyl, or when $R_4$ is hydrogen, $R_3$ is methyl;
$R_5$ is hydrogen;
$R_6$ is n-propyl, isopropyl, n-butyl, isobutyl, sec-butyl, 2-methylbutyl, 3-methylbutyl, n-pentyl, 2-phenylethyl, n-butoxy, isobutoxy, sec-butoxy, ethylamino, n-propylamino, isopropylamino, n-butylamino, isobutylamino, sec-butylamino, methoxyethylamino, ethoxyethylamino, benzylamino, N-ethyl-N-phenylamino, or N-methyl-N-phenylamino;
$R_7$ is isopropyl, t-butyl, or trifluoromethyl;
$R_8$ and $R_9$ are hydrogen;
$R_{10}$ is methyl; and
$R_{11}$ and $R_{12}$ are hydrogen.

In a preferred aspect of the present invention, in the compounds of formula III, as described herein, $R_7$ is a $CF_3$ group. Another embodiment of the present disclosure are compounds having formula III, as described herein, wherein $R_7$ is $CF_2C_1$ or $CF_2CF_3$.

Preferred examples of compounds according to the invention are selected from the group consisting of, N-(3-Ethynyl-5-fluoro-4-methanesulfonylamino-benzyl)-3-[2-(2,2,2-trifluoro-ethoxy)-6-trifluoromethyl-pyridin-3-yl]-acrylamide, N-(3-Ethynyl-5-fluoro-4-methanesulfonylamino-benzyl)-3-[2-(3-methoxy-pyrrolidin-1-yl)-6-trifluoromethyl-pyridin-3-yl]-acrylamide, 3-(2-Butylamino-6-trifluoromethyl-pyridin-3-yl)-N-(3-fluoro-4-methanesulfonylamino-benzyl)-acrylamide, 3-(2-Cyclopentylamino-6-trifluoromethyl-pyridin-3-yl)-N-(3-fluoro-4-methanesulfonylamino-benzyl)-acrylamide, N-(3-Fluoro-4-methanesulfonylamino-benzyl)-3-[2-(3-methoxy-pyrrolidin-1-yl)-6-trifluoromethyl-pyridin-3-yl]-acrylamide,
3-(2-Cyclopropylmethoxy-6-trifluoromethyl-pyridin-3-yl)-N-(3-ethynyl-5-fluoro-4-methanesulfonylamino-benzyl)-acrylamide,
N-(3-Cyano-5-fluoro-4-methanesulfonylamino-benzyl)-3-(2-pyrrolidin-1-yl-6-trifluoromethyl-pyridin-3-yl)-acrylamide,
3-(2-Butoxy-6-trifluoromethyl-pyridin-3-yl)-N-(3-cyano-5-fluoro-4-methanesulfonylamino-benzyl)-acrylamide,
N-(3-Ethynyl-5-fluoro-4-methanesulfonylamino-benzyl)-3-(2-isopropylamino-6-trifluoromethyl-pyridin-3-yl)-acrylamide,
3-(2-sec-Butoxy-6-trifluoromethyl-pyridin-3-yl)-N-(3-cyano-5-fluoro-4-methanesulfonylamino-benzyl)-acrylamide,
N-(3-Ethynyl-5-fluoro-4-methanesulfonylamino-benzyl)-3-(2-phenyl-6-trifluoromethyl-pyridin-3-yl)-acrylamide,
N-(3-Cyano-5-fluoro-4-methanesulfonylamino-benzyl)-3-(2-isopropoxy-6-trifluoromethyl-pyridin-3-yl)-acrylamide,
N-(3-Ethynyl-5-fluoro-4-methanesulfonylamino-benzyl)-3-(2-phenylamino-6-trifluoromethyl-pyridin-3-yl)-acrylamide,
N-(3-Ethynyl-5-fluoro-4-methansulfonylamino-benzyl)-3-[2-(3-ethoxycarbony-piperid-1-yl)-6-trifluoromethyl-pyridin-3-yl]-acrylamide,
N-(3-Cyano-5-fluoro-4-methansulfonylamino-benzyl)-3-[2-(3-ethoxycarbony-piperid-1-yl)-6-trifluoromethyl-pyridin-3-yl]-acrylamide,
3-(2-sec-Butylamino-6-trifluoromethyl-pyridin-3-yl)-N-(3-ethynyl-5-fluoro-4-methanesulfonylamino-benzyl)-acrylamide,
N-(3-Cyano-5-fluoro-4-methanesulfonylamino-benzyl)-3-[2-(3-methyl-butoxy)-6-trifluoromethyl-pyridin-3-yl]-acrylamide,
N-(3-Ethynyl-5-fluoro-4-methanesulfonylamino-benzyl)-3-(2-thien-3-yl-6-trifluoromethyl-pyridin-3-yl)-acrylamide,
N-(3-Ethynyl-5-fluoro-4-methanesulfonylamino-benzyl)-3-[2-(3-fluoro-phenyl)-6-trifluoromethyl-pyridin-3-yl]-acrylamide,
N-(3-Fluoro-4-methanesulfonylamino-benzyl)-3-(2-isopropylamino-6-trifluoromethyl-pyridin-3-yl)-acrylamide,
N-(3-Cyano-5-fluoro-4-methanesulfonylamino-benzyl)-3-(2-isopropylamino-6-trifluoromethyl-pyridin-3-yl)-acrylamide,
3-(2-sec-Butylamino-6-trifluoromethyl-pyridin-3-yl)-N-(3-fluoro-4-methanesulfonylamino-benzyl)-acrylamide,
3-(2-sec-Butylamino-6-trifluoromethyl-pyridin-3-yl)-N-(3-cyano-5-fluoro-4-methanesulfonylamino-benzyl)-acrylamide,
N-(3-Fluoro-4-methanesulfonylamino-benzyl)-3-(2-phenylamino-6-trifluoromethyl-pyridin-3-yl)-acrylamide,
3-(2-sec-Butylamino-6-trifluoromethyl-pyridin-3-yl)-N-(3,5-difluoro-4-methanesulfonylamino-benzyl)-acrylamide,
3-(2-sec-Butylamino-6-trifluoromethyl-pyridin-3-yl)-N-(3-fluoro-4-methanesulfonylamino-5-methyl-benzyl)-acrylamide,
N-(3-Fluoro-4-methanesulfonylamino-5-vinyl-benzyl)-3-(2-phenoxy-6-trifluoromethyl-pyridin-3-yl)-acrylamide,
N-(3-Ethynyl-5-fluoro-4-methanesulfonylamino-benzyl)-3-(2-phenylthio-6-trifluoromethyl-pyridin-3-yl)-acrylamide,
N-(3-Fluoro-4-methanesulfonylamino-benzyl)-3-(2-phenethyl-6-trifluoromethyl-pyridin-3-yl)-acrylamide,
N-(3-Ethynyl-5-fluoro-4-methanesulfonylamino-benzyl)-3-(2-phenethyl-6-trifluoromethyl-pyridin-3-yl)-acrylamide,
3-(2-Butyl-6-trifluoromethyl-pyridin-3-yl)-N-(3-fluoro-4-methanesulfonylamino-benzyl)-acrylamide,
3-(2-Butyl-6-trifluoromethyl-pyridin-3-yl)-N-(3-ethynyl-5-fluoro-4-methanesulfonylamino-benzyl)-acrylamide,
N-(3-Fluoro-4-methanesulfonylamino-benzyl)-3-(2-isobutyl-6-trifluoromethyl-pyridin-3-yl)-acrylamide,
N-(3-Ethynyl-5-fluoro-4-methanesulfonylamino-benzyl)-3-(2-isobutyl-6-trifluoromethyl-pyridin-3-yl)-acrylamide,
(R)—N-[1-(3-Fluoro-4-methanesulfonylamino-phenyl)-ethyl]-3-(2-phenylamino-6-trifluoromethyl-pyridin-3-yl)-acrylamide,
3-(2-Ethyl-6-trifluoromethyl-pyridin-3-yl)-N-(3-ethynyl-5-fluoro-4-methanesulfonylamino-benzyl)-acrylamide,
N-(3-Fluoro-4-methanesulfonylamino-benzyl)-3-[2-(2-methyl-butyl)-6-trifluoromethyl-pyridin-3-yl]-acrylamide,
N-(3-Ethynyl-5-fluoro-4-methanesulfonylamino-benzyl)-3-[2-(2-methyl-butyl)-6-trifluoromethyl-pyridin-3-yl]-acrylamide,
N-(3-Ethynyl-5-fluoro-4-methanesulfonylamino-benzyl)-3-(2-styryl-6-trifluoromethyl-pyridin-3-yl)-acrylamide,
N-(3-Fluoro-4-methanesulfonylamino-benzyl)-3-[2-(methyl-propyl-amino)-6-trifluoromethyl-pyridin-3-yl]-acrylamide,
N-(3-Ethynyl-5-fluoro-4-methanesulfonylamino-benzyl)-3-[2-(methyl-propyl-amino)-6-trifluoromethyl-pyridin-3-yl]-acrylamide,
3-(2-sec-Butoxy-6-trifluoromethyl-pyridin-3-yl)-N-(4-methanesulfonylamino-3-methyl-benzyl)-acrylamide,
N-(3-Cyano-5-fluoro-4-methanesulfonylamino-benzyl)-3-(2-isobutyl-6-trifluoromethyl-pyridin-3-yl)-acrylamide,
N-(3-Fluoro-4-methanesulfonylamino-5-methyl-benzyl)-3-(2-isobutyl-6-trifluoromethyl-pyridin-3-yl)-acrylamide,
(R)—N-[1-(3-Fluoro-4-methanesulfonylamino-phenyl)-ethyl]-3-[2-(methyl-phenyl-amino)-6-trifluoromethyl-pyridin-3-yl]-acrylamide,
N-(3-Ethynyl-5-fluoro-4-methanesulfonylamino-benzyl)-3-[2-(methyl-phenyl-amino)-6-trifluoromethyl-pyridin-3-yl]-acrylamide,
N-(4-Methanesulfonylamino-3-methyl-benzyl)-3-[2-(methyl-phenyl-amino)-6-trifluoromethyl-pyridin-3-yl]-acrylamide,
(R)-3-(2-Butoxy-6-trifluoromethyl-pyridin-3-yl)-N-[1-(3-fluoro-4-methanesulfonylamino-phenyl)-ethyl]-acrylamide,
3-(2-Butoxy-6-trifluoromethyl-pyridin-3-yl)-N-(4-methanesulfonylamino-3-methyl-benzyl)-acrylamide,
3-(2-Ethylthio-6-trifluoromethyl-pyridin-3-yl)-N-(3-ethynyl-5-fluoro-4-methanesulfonylamino-benzyl)-acrylamide,
N-(4-Methanesulfonylamino-3-methyl-benzyl)-3-(2-phenethyl-6-trifluoromethyl-pyridin-3-yl)-acrylamide,
N-(3-Fluoro-4-methanesulfonylamino-5-methyl-benzyl)-3-(2-phenethyl-6-trifluoromethyl-pyridin-3-yl)-acrylamide,
3-(2-Isobutyl-6-trifluoromethyl-pyridin-3-yl)-N-(4-methanesulfonylamino-3-methyl-benzyl)-acrylamide,
(R)—N-[1-(3-Fluoro-4-methanesulfonylamino-phenyl)-ethyl]-3-(2-isobutyl-6-trifluoromethyl-pyridin-3-yl)-acrylamide,
3-(2-sec-Butylamino-6-trifluoromethyl-pyridin-3-yl)-N-(4-methanesulfonylamino-3-methyl-benzyl)-acrylamide,
N-(3-Ethynyl-5-fluoro-4-methanesulfonylamino-benzyl)-3-(2-isopropylthio-6-trifluoromethyl-pyridin-3-yl)-acrylamide, N-(3-Fluoro-4-methanesulfonylamino-5-methyl-benzyl)-3-[2-(3-fluoro-phenyl)-6-trifluoromethyl-pyridin-3-yl]-acrylamide,
(R)—N-[1-(3-Fluoro-4-methanesulfonylamino-phenyl)-ethyl]-3-[2-(3-fluoro-phenyl)-6-trifluoromethyl-pyridin-3-yl]-acrylamide,
3-[2-(3-Fluoro-phenyl)-6-trifluoromethyl-pyridin-3-yl]-N-(4-methane sulfonylamino-3-methyl-benzyl)-acrylamide,
(R)—N-[1-(3-Fluoro-4-methanesulfonylamino-phenyl)-ethyl]-3-[2-piperid-1-yl-6-trifluoromethyl-pyridin-3-yl]-acrylamide,
N-(4-Methanesulfonylamino-3-methyl-benzyl)-3-[2-piperid-1-yl-6-trifluoromethyl-pyridin-3-yl]-acrylamide,
N-(3-Ethynyl-5-fluoro-4-methanesulfonylamino-benzyl)-3-(2-propylthio-6-trifluoromethyl-pyridin-3-yl)-acrylamide,
N-(4-Methanesulfonylamino-3-methyl-benzyl)-3-(2-propylthio-6-trifluoromethyl-pyridin-3-yl)-acrylamide,
3-(2-Butylamino-6-trifluoromethyl-pyridin-3-yl)-N-(4-methanesulfonylamino-3-methyl-benzyl)-acrylamide,
3-(2-Butylamino-6-trifluoromethyl-pyridin-3-yl)-N-(3-fluoro-4-methanesulfonylamino-5-methyl-benzyl)-acrylamide,
N-(3-Fluoro-4-methanesulfonylamino-5-trifluoromethyl-benzyl)-3-(2-phenethyl-6-trifluoromethyl-pyridin-3-yl)-acrylamide,
3-(2-Benzylamino-6-trifluoromethyl-pyridin-3-yl)-N-(4-methanesulfonylamino-3-methyl-benzyl)-acrylamide,
3-(2-Butyl-6-trifluoromethyl-pyridin-3-yl)-N-(3-fluoro-4-methanesulfonylamino-5-methyl-benzyl)-acrylamide,
(R)-3-(2-Butyl-6-trifluoromethyl-pyridin-3-yl)-N-[1-(3-fluoro-4-methanesulfonylamino-phenyl)-ethyl]-acrylamide,
(R)-3-(2-Butyl-6-trifluoromethyl-pyridin-3-yl)-N-(4-methanesulfonylamino-3-methyl-benzyl)-acrylamide,
(R)-3-(2-Benzylamino-6-trifluoromethyl-pyridin-3-yl)-N-[1-(3-fluoro-4-methanesulfonylamino-phenyl)-ethyl]-acrylamide,
3-(2-Benzylamino-6-trifluoromethyl-pyridin-3-yl)-N-(3-ethynyl-5-fluoro-4-methanesulfonylamino-benzyl)-acrylamide,
N-(3-Ethynyl-5-fluoro-4-methanesulfonylamino-benzyl)-3-(2-pentyl-6-trifluoromethyl-pyridin-3-yl)-acrylamide,
N-(4-Methanesulfonylamino-3-methyl-benzyl)-3-(2-pentyl-6-trifluoromethyl-pyridin-3-yl)-acrylamide,
N-(3,5-Difluoro-4-methanesulfonylamino-benzyl)-3-(2-pentyl-6-trifluoromethyl-pyridin-3-yl)-acrylamide,
N-(3,5-Difluoro-4-methanesulfonylamino-benzyl)-3-[2-(3-fluoro-phenyl)-6-trifluoromethyl-pyridin-3-yl]-acrylamide,
3-(2-Butylamino-6-trifluoromethyl-pyridin-3-yl)-N-(3,5-difluoro-4-methanesulfonylamino-benzyl)-acrylamide,
N-(3,5-Difluoro-4-methanesulfonylamino-benzyl)-3-(2-phenethyl-6-trifluoromethyl-pyridin-3-yl)-acrylamide,
N-(3,5-Difluoro-4-methanesulfonylamino-benzyl)-3-[2-(2-methoxy-ethylamino)-6-trifluoromethyl-pyridin-3-yl]-acrylamide,
3-(2-Butyl-6-trifluoromethyl-pyridin-3-yl)-N-(3,5-difluoro-4-methanesulfonylamino-benzyl)-acrylamide,
N-(3-Ethynyl-5-fluoro-4-methanesulfonylamino-benzyl)-3-(2-propyl-6-trifluoromethyl-pyridin-3-yl)-acrylamide,
N-(3,5-Difluoro-4-methanesulfonylamino-benzyl)-3-(2-propyl-6-trifluoromethyl-pyridin-3-yl)-acrylamide,
N-(4-Methanesulfonylamino-3-methyl-benzyl)-3-(2-propyl-6-trifluoromethyl-pyridin-3-yl)-acrylamide,
(R)—N-[1-(3-Fluoro-4-methanesulfonylamino-phenyl)-ethyl]-3-(2-propyl-6-trifluoromethyl-pyridin-3-yl)-acrylamide,
(R)-3-(2-sec-Butylamino-6-trifluoromethyl-pyridin-3-yl)-N-[1-(3-fluoro-4-methanesulfonylamino-phenyl)-ethyl]-acrylamide,
(R)—N-[1-(3-Fluoro-4-methanesulfonylamino-phenyl)-ethyl]-3-[2-(2-methyl-butyl)-6-trifluoromethyl-pyridin-3-yl]-acrylamide,
(R)—N-[1-(3-Fluoro-4-methanesulfonylamino-phenyl)-ethyl]-3-[2-(2-methoxy-ethylamino)-6-trifluoromethyl-pyridin-3-yl]-acrylamide,
(R)-3-(2-Butylamino-6-trifluoromethyl-pyridin-3-yl)-N-[1-(3-fluoro-4-methanesulfonylamino-phenyl)-ethyl]-acrylamide,
N-(3-Fluoro-4-methanesulfonylamino-5-methyl-benzyl)-3-(2-pentyl-6-trifluoromethyl-pyridin-3-yl)-acrylamide,
(R)—N-[1-(3-Fluoro-4-methanesulfonylamino-phenyl)-ethyl]-3-(2-pentyl-6-trifluoromethyl-pyridin-3-yl)-acrylamide,
N-(3,5-Difluoro-4-methanesulfonylamino-benzyl)-3-(2-isopropylamino-6-trifluoromethyl-pyridin-3-yl)-acrylamide,
(R)—N-[1-(3-Fluoro-4-methanesulfonylamino-phenyl)-ethyl]-3-(2-isopropylamino-6-trifluoromethyl-pyridin-3-yl)-acrylamide,
3-(2-Isopropylamino-6-trifluoromethyl-pyridin-3-yl)-N-(4-methanesulfonylamino-3-methyl-benzyl)-acrylamide,
N-(3-Fluoro-4-methanesulfonylamino-5-methyl-benzyl)-3-(2-isopropylamino-6-trifluoromethyl-pyridin-3-yl)-acrylamide,
N-(3-Ethynyl-5-fluoro-4-methanesulfonylamino-benzyl)-3-(2-propylamino-6-trifluoromethyl-pyridin-3-yl)-acrylamide,
N-(3,5-Difluoro-4-methanesulfonylamino-benzyl)-3-(2-propylamino-6-trifluoromethyl-pyridin-3-yl)-acrylamide,
N-(3-Fluoro-4-methanesulfonylamino-5-methyl-benzyl)-3-(2-propylamino-6-trifluoromethyl-pyridin-3-yl)-acrylamide,
(R)—N-[1-(3-Fluoro-4-methanesulfonylamino-phenyl)-ethyl]-3-(2-propylamino-6-trifluoromethyl-pyridin-3-yl)-acrylamide,
N-(4-Methanesulfonylamino-3-methyl-benzyl)-3-(2-propylamino-6-trifluoromethyl-pyridin-3-yl)-acrylamide,
N-(3,5-Difluoro-4-methanesulfonylamino-benzyl)-3-(2-isobutyl-6-trifluoromethyl-pyridin-3-yl)-acrylamide,
(R)—N-[1-(3,5-Difluoro-4-methane sulfonylamino-phenyl)-ethyl]-3-(2-isopropylamino-6-trifluoromethyl-pyridin-3-yl)-acrylamide,
(R)-3-(2-Butyl-6-trifluoromethyl-pyridin-3-yl)-N-[1-(3,5-difluoro-4-methanesulfonylamino-phenyl)-ethyl]-acrylamide,
(R)—N-[1-(3,5-Difluoro-4-methane sulfonylamino-phenyl)-ethyl]-3-(2-propylamino-6-trifluoromethyl-pyridin-3-yl)-acrylamide,
(R)—N-[1-(3,5-Difluoro-4-methane sulfonylamino-phenyl)-ethyl]-3-(2-propyl-6-trifluoromethyl-pyridin-3-yl)-acrylamide,
N-(3-Ethynyl-5-fluoro-4-methanesulfonylamino-benzyl)-3-(2-isopropyl-6-trifluoromethyl-pyridin-3-yl)-acrylamide,
N-(3,5-Difluoro-4-methanesulfonylamino-benzyl)-3-(2-isopropyl-6-trifluoromethyl-pyridin-3-yl)-acrylamide,
3-(2-Isopropyl-6-trifluoromethyl-pyridin-3-yl)-N-(4-methanesulfonylamino-3-methyl-benzyl)-acrylamide,
(R)—N-[1-(3-Fluoro-4-methanesulfonylamino-phenyl)-ethyl]-3-(2-isopropyl-6-trifluoromethyl-pyridin-3-yl)-acrylamide, 3-(2-sec-Butyl-6-trifluoromethyl-pyridin-3-yl)-N-(3,5-difluoro-4-methanesulfonylamino-benzyl)-acrylamide,
(R)—N-[1-(3,5-Difluoro-4-methane sulfonylamino-phenyl)-ethyl]-3-(2-phenethyl-6-trifluoromethyl-pyridin-3-yl)-acrylamide,
(R)—N-[1-(3-Fluoro-4-methanesulfonylamino-phenyl)-ethyl]-3-(2-phenethyl-6-trifluoromethyl-pyridin-3-yl)-acrylamide,
(R)-3-(2-Butylamino-6-trifluoromethyl-pyridin-3-yl)-N-[1-(3,5-difluoro-4-methanesulfonylamino-phenyl)-ethyl]-acrylamide,
N-[1-(3,5-Difluoro-4-methanesulfonylamino-phenyl)-ethyl]-3-(2-piperid-1-yl-6-trifluoromethyl-pyridin-3-yl)-acrylamide, and
(S)-3-(2-Butylamino-6-trifluoromethyl-pyridin-3-yl)-N-[1-(3,5-difluoro-4-methanesulfonylamino-phenyl)-ethyl]-acrylamide, including isomers, racemic mixtures and pharmaceutically acceptable salts thereof.

Preferred examples of compounds according to the invention are selected from the group consisting of;
N-(3-Ethynyl-5-fluoro-4-methanesulfonylamino-benzyl)-3-(2-isopropylamino-6-trifluoromethyl-pyridin-3-yl)-acrylamide,
3-(2-sec-Butoxy-6-trifluoromethyl-pyridin-3-yl)-N-(3-cyano-5-fluoro-4-methanesulfonylamino-benzyl)-acrylamide,
3-(2-sec-Butylamino-6-trifluoromethyl-pyridin-3-yl)-N-(3-ethynyl-5-fluoro-4-methanesulfonylamino-benzyl)-acrylamide,
N-(3-Cyano-5-fluoro-4-methanesulfonylamino-benzyl)-3-(2-isopropylamino-6-trifluoromethyl-pyridin-3-yl)-acrylamide,
3-(2-sec-Butylamino-6-trifluoromethyl-pyridin-3-yl)-N-(3-fluoro-4-methanesulfonylamino-benzyl)-acrylamide,
3-(2-sec-Butylamino-6-trifluoromethyl-pyridin-3-yl)-N-(3-cyano-5-fluoro-4-methanesulfonylamino-benzyl)-acrylamide,
3-(2-sec-Butylamino-6-trifluoromethyl-pyridin-3-yl)-N-(3,5-difluoro-4-methanesulfonylamino-benzyl)-acrylamide,
3-(2-sec-Butylamino-6-trifluoromethyl-pyridin-3-yl)-N-(3-fluoro-4-methanesulfonylamino-5-methyl-benzyl)-acrylamide,
N-(3-Ethynyl-5-fluoro-4-methanesulfonylamino-benzyl)-3-(2-phenethyl-6-trifluoromethyl-pyridin-3-yl)-acrylamide,
3-(2-Butyl-6-trifluoromethyl-pyridin-3-yl)-N-(3-ethynyl-5-fluoro-4-methanesulfonylamino-benzyl)-acrylamide,
N-(3-Ethynyl-5-fluoro-4-methanesulfonylamino-benzyl)-3-(2-isobutyl-6-trifluoromethyl-pyridin-3-yl)-acrylamide,
N-(3-Ethynyl-5-fluoro-4-methanesulfonylamino-benzyl)-3-[2-(2-methyl-butyl)-6-trifluoromethyl-pyridin-3-yl]-acrylamide,
N-(3-Fluoro-4-methanesulfonylamino-5-methyl-benzyl)-3-(2-isobutyl-6-trifluoromethyl-pyridin-3-yl)-acrylamide,
N-(3-Ethynyl-5-fluoro-4-methanesulfonylamino-benzyl)-3-[2-(methyl-phenyl-amino)-6-trifluoromethyl-pyridin-3-yl]-acrylamide,
N-(4-Methanesulfonylamino-3-methyl-benzyl)-3-(2-phenethyl-6-trifluoromethyl-pyridin-3-yl)-acrylamide,
3-(2-Isobutyl-6-trifluoromethyl-pyridin-3-yl)-N-(4-methanesulfonylamino-3-methyl-benzyl)-acrylamide,
(R)—N-[1-(3-Fluoro-4-methanesulfonylamino-phenyl)-ethyl]-3-(2-isobutyl-6-trifluoromethyl-pyridin-3-yl)-acrylamide,
3-(2-sec-Butylamino-6-trifluoromethyl-pyridin-3-yl)-N-(4-methanesulfonylamino-3-methyl-benzyl)-acrylamide,
3-(2-Butylamino-6-trifluoromethyl-pyridin-3-yl)-N-(4-methanesulfonylamino-3-methyl-benzyl)-acrylamide,
3-(2-Butylamino-6-trifluoromethyl-pyridin-3-yl)-N-(3-fluoro-4-methanesulfonylamino-5-methyl-benzyl)-acrylamide,
3-(2-Butyl-6-trifluoromethyl-pyridin-3-yl)-N-(3-fluoro-4-methanesulfonylamino-5-methyl-benzyl)-acrylamide,
(R)-3-(2-Butyl-6-trifluoromethyl-pyridin-3-yl)-N-[1-(3-fluoro-4-methanesulfonylamino-phenyl)-ethyl]-acrylamide,
3-(2-Butyl-6-trifluoromethyl-pyridin-3-yl)-N-(4-methanesulfonylamino-3-methyl-benzyl)-acrylamide,
(R)-3-(2-Benzylamino-6-trifluoromethyl-pyridin-3-yl)-N-[1-(3-fluoro-4-methanesulfonylamino-phenyl)-ethyl]-acrylamide,
3-(2-Benzylamino-6-trifluoromethyl-pyridin-3-yl)-N-(3-ethynyl-5-fluoro-4-methanesulfonylamino-benzyl)-acrylamide,
N-(3-Ethynyl-5-fluoro-4-methanesulfonylamino-benzyl)-3-(2-pentyl-6-trifluoromethyl-pyridin-3-yl)-acrylamide,
N-(4-Methanesulfonylamino-3-methyl-benzyl)-3-(2-pentyl-6-trifluoromethyl-pyridin-3-yl)-acrylamide,
N-(3,5-Difluoro-4-methanesulfonylamino-benzyl)-3-(2-pentyl-6-trifluoromethyl-pyridin-3-yl)-acrylamide,
3-(2-Butylamino-6-trifluoromethyl-pyridin-3-yl)-N-(3,5-difluoro-4-methanesulfonylamino-benzyl)-acrylamide,
N-(3,5-Difluoro-4-methanesulfonylamino-benzyl)-3-(2-phenethyl-6-trifluoromethyl-pyridin-3-yl)-acrylamide,
N-(3,5-Difluoro-4-methanesulfonylamino-benzyl)-3-[2-(2-methoxy-ethylamino)-6-trifluoromethyl-pyridin-3-yl]-acrylamide,
3-(2-Butyl-6-trifluoromethyl-pyridin-3-yl)-N-(3,5-difluoro-4-methanesulfonylamino-benzyl)-acrylamide,
N-(3-Ethynyl-5-fluoro-4-methanesulfonylamino-benzyl)-3-(2-propyl-6-trifluoromethyl-pyridin-3-yl)-acrylamide,
N-(3,5-Difluoro-4-methanesulfonylamino-benzyl)-3-(2-propyl-6-trifluoromethyl-pyridin-3-yl)-acrylamide,
N-(4-Methanesulfonylamino-3-methyl-benzyl)-3-(2-propyl-6-trifluoromethyl-pyridin-3-yl)-acrylamide,
(R)—N-[1-(3-Fluoro-4-methanesulfonylamino-phenyl)-ethyl]-3-(2-propyl-6-trifluoromethyl-pyridin-3-yl)-acrylamide,
(R)-3-(2-sec-Butylamino-6-trifluoromethyl-pyridin-3-yl)-N-[1-(3-fluoro-4-methanesulfonylamino-phenyl)-ethyl]-acrylamide,
(R)—N-[1-(3-Fluoro-4-methanesulfonylamino-phenyl)-ethyl]-3-[2-(2-methyl-butyl)-6-trifluoromethyl-pyridin-3-yl]-acrylamide,
(R)-3-(2-Butylamino-6-trifluoromethyl-pyridin-3-yl)-N-[1-(3-fluoro-4-methanesulfonylamino-phenyl)-ethyl]-acrylamide,
N-(3-Fluoro-4-methanesulfonylamino-5-methyl-benzyl)-3-(2-pentyl-6-trifluoromethyl-pyridin-3-yl)-acrylamide,
(R)—N-[1-(3-Fluoro-4-methanesulfonylamino-phenyl)-ethyl]-3-(2-pentyl-6-trifluoromethyl-pyridin-3-yl)-acrylamide,
(R)—N-[1-(3-Fluoro-4-methanesulfonylamino-phenyl)-ethyl]-3-(2-isopropylamino-6-trifluoromethyl-pyridin-3-yl)-acrylamide,
3-(2-Isopropylamino-6-trifluoromethyl-pyridin-3-yl)-N-(4-methanesulfonylamino-3-methyl-benzyl)-acrylamide,
N-(3-Fluoro-4-methanesulfonylamino-5-methyl-benzyl)-3-(2-isopropylamino-6-trifluoromethyl-pyridin-3-yl)-acrylamide,
N-(3-Ethynyl-5-fluoro-4-methanesulfonylamino-benzyl)-3-(2-propylamino-6-trifluoromethyl-pyridin-3-yl)-acrylamide, N-(3,5-Difluoro-4-methanesulfonylamino-benzyl)-3-(2-propylamino-6-trifluoromethyl-pyridin-3-yl)-acrylamide,
N-(3-Fluoro-4-methanesulfonylamino-5-methyl-benzyl)-3-(2-propylamino-6-trifluoromethyl-pyridin-3-yl)-acrylamide,
(R)—N-[1-(3-Fluoro-4-methanesulfonylamino-phenyl)-ethyl]-3-(2-propylamino-6-trifluoromethyl-pyridin-3-yl)-acrylamide,
N-(4-Methanesulfonylamino-3-methyl-benzyl)-3-(2-propylamino-6-trifluoromethyl-pyridin-3-yl)-acrylamide,
(R)—N-[1-(3,5-Difluoro-4-methane sulfonylamino-phenyl)-ethyl]-3-(2-isopropylamino-6-trifluoromethyl-pyridin-3-yl)-acrylamide,
(R)-3-(2-Butyl-6-trifluoromethyl-pyridin-3-yl)-N-[1-(3,5-difluoro-4-methanesulfonylamino-phenyl)-ethyl]-acrylamide,
(R)—N-[1-(3,5-Difluoro-4-methane sulfonylamino-phenyl)-ethyl]-3-(2-propylamino-6-trifluoromethyl-pyridin-3-yl)-acrylamide,
(R)—N-[1-(3,5-Difluoro-4-methane sulfonylamino-phenyl)-ethyl]-3-(2-propyl-6-trifluoromethyl-pyridin-3-yl)-acrylamide,
N-(3-Ethynyl-5-fluoro-4-methanesulfonylamino-benzyl)-3-(2-isopropyl-6-trifluoromethyl-pyridin-3-yl)-acrylamide,
3-(2-Isopropyl-6-trifluoromethyl-pyridin-3-yl)-N-(4-methanesulfonylamino-3-methyl-benzyl)-acrylamide,
(R)—N-[1-(3-Fluoro-4-methanesulfonylamino-phenyl)-ethyl]-3-(2-isopropyl-6-trifluoromethyl-pyridin-3-yl)-acrylamide,
(R)—N-[1-(3,5-Difluoro-4-methane sulfonylamino-phenyl)-ethyl]-3-(2-phenethyl-6-trifluoromethyl-pyridin-3-yl)-acrylamide, and
(R)-3-(2-Butylamino-6-trifluoromethyl-pyridin-3-yl)-N-[1-(3,5-difluoro-4-methanesulfonylamino-phenyl)-ethyl]-acrylamide, including isomers, racemic mixtures and pharmaceutically acceptable salts thereof.

Preferred examples of compounds according to the invention are selected from the group consisting of,
(R)—N-[1-(3,5-Difluoro-4-methanesulfonylamino-phenyl)-ethyl]-3-(2-isobutyl-6-trifluoromethyl-pyridin-3-yl)-acrylamide,
(R)-3-(2-Ethylamino-6-trifluoromethyl-pyridin-3-yl)-N-[1-(3-fluoro-4-methanesulfonylamino-phenyl)-ethyl]-acrylamide,
3-(2-Ethylamino-6-trifluoromethyl-pyridin-3-yl)-N-1-(4-methanesulfonylamino-3-methyl-benzyl)-acrylamide,
N-(2,5-Difluoro-4-methanesulfonylamino-benzyl)-3-(2-propylamino-6-trifluoromethyl-pyridin-3-yl)-acrylamide,
3-(2-Ethylamino-6-trifluoromethyl-pyridin-3-yl)-N-(3-ethynyl-5-fluoro-4-methanesulfonylamino-benzyl)-acrylamide,
3-(2-Ethylamino-6-trifluoromethyl-pyridin-3-yl)-N-(3-ethenyl-5-fluoro-4-methanesulfonylamino-benzyl)-acrylamide,
N-(4-Methanesulfonylamino-benzyl)-3-(2-propyl-6-trifluoromethyl-pyridin-3-yl)-acrylamide,
N-(3-Chloro-4-methanesulfonylamino-benzyl)-3-(2-propyl-6-trifluoromethyl-pyridin-3-yl)-acrylamide,
N-(3-Chloro-4-methanesulfonylamino-benzyl)-3-(2-propylamino-6-trifluoromethyl-pyridin-3-yl)-acrylamide,
N-(2,5-Difluoro-4-methanesulfonylamino-benzyl)-3-(2-ethylamino-6-trifluoromethyl-pyridin-3-yl)-acrylamide,
N-(3-Fluoro-4-methanesulfonylamino-benzyl)-3-(2-ethylamino-6-trifluoromethyl-pyridin-3-yl)-acrylamide,
N-(3,5-Difluoro-4-methanesulfonylamino-benzyl)-3-(2-ethylamino-6-trifluoromethyl-pyridin-3-yl)-acrylamide,
N-(3-Fluoro-4-methanesulfonylamino-5-methyl-benzyl)-3-(2-ethylamino-6-trifluoromethyl-pyridin-3-yl)-acrylamide,
N-(3-Cano-5-fluoro-4-methanesulfonylamino-benzyl)-3-(2-ethylamino-6-trifluoromethyl-pyridin-3-yl)-acrylamide,
3-(2-Butyl-6-trifluoromethyl-pyridin-3-yl)-propynoic acid 3,5-difluoro-4-methanesulfonylamino-benzylamide,
3-(2-Butyl-6-trifluoromethyl-pyridin-3-yl)-propynoic acid [1-(3,5-difluoro-4-methanesulfonylamino-phenyl)-ethyl]-amide,
N-(4-Methanesulfonylamino-benzyl)-3-(2-phenethyl-6-trifluoromethyl-pyridin-3-yl)-acrylamide,
N-(4-Ethenesulfonylamino-benzyl)-3-(2-isopropylamino-6-trifluoromethyl-pyridin-3-yl)-acrylamide,
(Z)-3-(2-propyl-6-trifluoromethyl-pyridin-3-yl)-hex-2-enoic acid 3-ethynyl-5-fluoro-4-methanesulfonylamino-benzylamide,
(E)-3-(2-propyl-6-trifluoromethyl-pyridin-3-yl)-hex-2-enoic acid 3-ethynyl-5-fluoro-4-methanesulfonylamino-benzylamide,
(Z)-3-(2-propyl-6-trifluoromethyl-pyridin-3-yl)-hex-2-enoic acid [1-(3,5-difluoro-4-methanesulfonylamino-phenyl)-ethyl]-amide,
(E)-3-(2-propyl-6-trifluoromethyl-pyridin-3-yl)-hex-2-enoic acid [1-(3,5-difluoro-4-methanesulfonylamino-phenyl)-ethyl]-amide, and
N-(3-Ethenyl-5-fluoro-4-methanesulfonylamino-benzyl)-3-(2-morpholin-1-yl-6-trifluoromethyl-pyridin-3-yl)-acrylamide, including isomers, racemic mixtures and pharmaceutically acceptable salts thereof.

Another aspect of the present invention relates to compounds of formula III, an isomer or a pharmaceutically acceptable salt thereof, wherein,
$R_1$ is hydrogen or methyl;
$R_2$ is hydrogen;
$R_3$ is hydrogen, fluoro, chloro, methyl, cyano, ethenyl, or ethynyl;
$R_4$ is hydrogen
$R_5$ is fluoro, chloro, or methyl, preferably fluoro;
$R_6$ is ethyl, n-propyl, isopropyl, n-butyl, isobutyl, sec-butyl, 2-methylbutyl, 3-methylbutyl, n-pentyl, ethoxymethyl, 2-phenylethyl, phenylethenyl, phenyl, fluorophenyl, thienyl, n-propoxy, isopropoxy, n-butoxy, isobutoxy, sec-butoxy, 3-methylbutoxy, 2,2,2-trifluoroethoxy, cyclopentoxy, cyclopropylmethoxy, phenoxy, ethylthio, propylthio, isopropylthio, ethylamino, n-propylamino isopropylamino, n-butylamino, isobutylamino, sec-butylamino, methoxymethylamino, methoxyethylamino, ethoxyethylamino, cyclopentylamino, benzylamino, phenylamino, N-ethyl-N-phenylamino, N-methyl-N-phenylamino, N-methyl-N-propylamino, N-pyrrolidinyl, N-piperidyl, or ethoxycarbonyl N-piperidyl, and wherein $R_6$ preferably is n-propyl, isopropyl, n-butyl, isobutyl, sec-butyl, 2-methylbutyl, 3-methylbutyl, n-pentyl, 2-phenylethyl, n-butoxy, isobutoxy, sec-butoxy, ethylamino, n-propylamino, isopropylamino, n-butylamino, isobutylamino, sec-butylamino, methoxyethylamino, ethoxyethylamino, benzylamino, N-ethyl-N-phenylamino, or N-methyl-N-phenylamino;
$R_7$ is halo(C1-C3)alkyl, preferably $CF_3$;
$R_8$ and $R_9$ are independently hydrogen, halogen or trifluoromethyl, wherein $R_9$ preferably represents hydrogen or chloro, and $R_9$ is hydrogen;

$R_{10}$ is methyl; and
$R_{11}$ and $R_{12}$ are hydrogen.

Another aspect of the present invention is a compound having the formula IV, an isomer, or a pharmaceutically acceptable salt thereof,

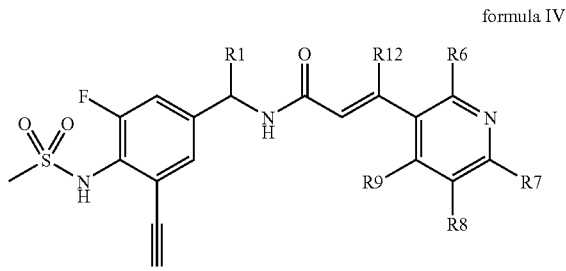

formula IV wherein,
$R_1$ is hydrogen, methyl, or ethyl;
$R_{12}$ is hydrogen or C1-C3 alkyl preferably hydrogen or propyl;
$R_6$ is C2-C6 alkyl, di (C1-C6 alkyl)amino, C1-C6 alkoxy, 2,2,2-trifluoro(C1-C3)alkoxy, C1-C3 alkoxy (C1-C5) alkylamino, C1-C6 alkylamino, C3-C6 cycloalkylamino, phenoxy, phenylamino, phenyl(C1-C3)alkylamino, phenyl(C1-C3)alkyl, N-phenyl-N—(C1-C5)alkylamino, methoxy-N-pyrrolidinyl, or C1-C6 alkylthio;
$R_7$ is $CF_3$, $CF_2Cl$, or $CF_2CF_3$;
and
$R_8$ and $R_9$ are independently hydrogen, CF3, or halogen.

In a particular aspect of the present disclosure, the compound of formula IV, is as described above, wherein,
$R_1$ is hydrogen or methyl;
$R_6$ is C2-C5 alkyl, C1-C4 alkylamino, methoxy, or methoxyethylamino;
$R_7$ is $CF_3$;
$R_8$ and $R_9$ are all hydrogen; and
$R_{12}$ is hydrogen.

Another aspect of the present invention is a compound having the formula V, an isomer, or a pharmaceutically acceptable salt thereof,

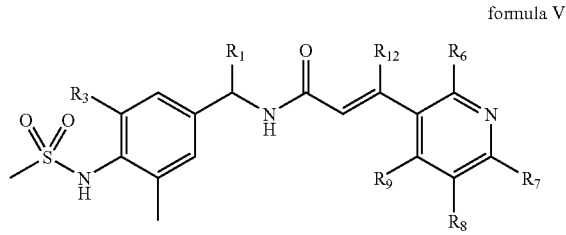

formula V wherein,
$R_1$ is hydrogen, methyl, or ethyl;
$R_3$ is hydrogen, fluoro, or chloro;
$R_6$ is C2-C6 alkyl, di (C1-C6 alkyl)amino, C1-C6 alkoxy, 2,2,2-trifluoro(C1-C3)alkoxy, C1-C3 alkoxy (C1-C5) alkylamino, C1-C6 alkylamino, C3-C6 cycloalkylamino, phenoxy, phenylamino, phenyl(C1-C3)alkylamino, phenyl(C1-C3)alkyl, or N-phenyl-N—(C1-C5)alkylamino;
$R_7$ is $CF_3$, $CF_2Cl$, or $CF_2CF_3$;
$R_8$ and $R_9$ are independently hydrogen, CF3 or halogen; and
$R_{12}$ is hydrogen or C1-C3 alkyl preferably hydrogen or propyl.

In one specific aspect of the invention, the compound of formula V, is as described above, wherein,
$R_1$ is hydrogen or methyl;
$R_3$ is hydrogen or fluoro;
$R_6$ is C2-C5 alkyl, C1-C4 alkylamino, methoxy, or methoxyethylamino;
$R_7$ is $CF_3$;
$R_8$ and $R_9$ are both hydrogen; and
$R_{12}$ is hydrogen.

Another aspect of the present invention relates to a compound having the formula VI, an isomer or a pharmaceutically acceptable salt thereof

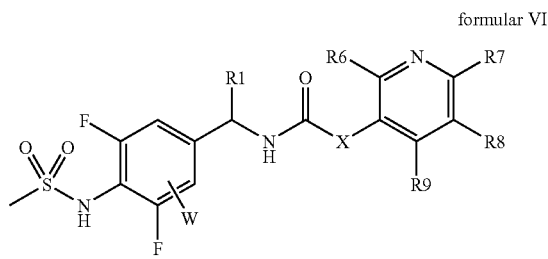

formular VI wherein,
W is hydrogen or fluoro;
X is —$CR_{11}$=$CR_{12}$— or —C≡C—;
$R_1$ is selected from hydrogen and C1-C3 alkyl;
$R_6$ is hydroxy, halogen, nitro, carboxy, C1-C10 alkyl, C1-C10 alkoxy, C2-C10 alkenyl, C2-C10 alkynyl, C1-C10 alkylthio, C1-C10 alkylsulfonyl, C1-C10 alkylcarbonyl, C1-C10 alkoxycarbonyl, C2-C10 alkenyloxy, C1-C5 alkoxy (C1-C5) alkoxy, C1-C5 alkoxy (C1-C5) alkoxy (C1-C5) alkyl, piperidyl, C1-C5 alkoxy (C1-C5) alkylamino, C1-C10 alkylamino, di(C1-C10 alkyl) amino, C3-C8 cycloalkyl, C3-C8 cycloalkylamino, C3-C8 cycloalkoxy, C3-C8 oxacycloalkyl-oxy, N—(C1-C5)alkoxy (C1-C5) alkyl-N—(C1-C5) alkylamino, N—(C3-C8)cycloalkyl-N—(C1-C5) alkylamino, N-aryl-N—(C1-C5) alkylamino, preferably N-phenyl-N—(C1-C5)alkylamino, aryl preferably phenyl, arylamino preferably phenylamino, heteroaryl preferably thienyl, heteroarylamino, aryloxy preferably phenoxy, pyrrolidinyl, or morpholinyl;
$R_{11}$ and $R_{12}$, if present, are independently selected from hydrogen and C1-C3 alkyl, preferably hydrogen or propyl;
$R_7$ is $CF_2CF_3$, $CF_2Cl$ or, preferably, $CF_3$;
$R_8$ and $R_9$ are independently selected from hydrogen, halogen or $CF_3$;
wherein,
each alkyl, alkenyl and alkynyl, also as a part of a group such as in alkoxy, alkylsulfonyl, alkylcarbonyl, alkylamino, or alkenyloxy may be independently unsubstituted or substituted with one or more substituents selected from among halogen, hydroxyl, unsubstituted or halo-substituted (C1-C5) alkoxy, (C3-C8) cycloalkyl which may be unsubstituted or substituted with one or two halogen radicals and/or methyl groups, unsubstituted or halo-substituted (C1-C5) alkylamino, phenyl which may be unsubstituted or substituted with one or more substituents selected from halogen, unsubstituted C1-C3 alkyl, or halo (C1-C3) alkyl, or unsubstituted or halo-substituted di(C1-C5) alkylamino, each aryl or heteroaryl, also a part of a group such as in arylamino, aryloxy, heteroaryloxy, or heteroarylamino, may be independently unsubstituted or substituted with one or more substituents selected from halogen, unsubstituted C1-C5 alkyl, unsubstituted C1-C5 alkoxy, or halo (C1-C5) alkyl, each cycloalkyl, also as a part of a group such as in cycloalkoxy or cycloalkylamino may be unsubstituted or substituted with one or more unsubstituted or halo-substituted C1-C3 alkyl groups, hydroxymethyl, hydroxy, methoxy, or amino, and each piperidyl, or morpholinyl may be unsubstituted or substituted with one or more unsubstituted or halo-substituted C1-C3 alkyl groups, hydroxy(C1-C3)alkyl, C1-C3 alkoxy, (C1-C3)alkoxycarbonyl, or hydroxyl.

One aspect of the present inventions are compounds of the general formula VI, as described above wherein $R_8$ and $R_9$ are both hydrogen, and/or X is —CH=CH—, and/or X is —CH=CH—, and W, $R_8$ and $R_9$ are both hydrogen, and/or $R_1$ is hydrogen or methyl, and/or $R_6$ is selected from C2-C6 alkyl, di (C1-C6 alkyl)amino, 2,2,2-trifluoro(C1-C3)alkoxy, C1-C3 alkoxy(C1-C5) alkylamino, C1-C6 alkylamino, C3-C6 cycloalkylamino, phenyl, phenylamino, phenyl(C1-C3)alkylamino, phenyl(C1-C3)alkyl, or N-phenyl-N—(C1-C5) alkylamino, wherein each phenyl can be substituted with one or more halogens; and/or $R_7$ is $CF_3$.

Another aspect of the present inventions are compounds of the general formula VI, as described herein wherein $R_1$ is hydrogen or methyl; and/or $R_6$ is selected from C2-C5 alkyl, C1-C4 alkylamino, or methoxyethylamino; preferably $R_6$ is —NH—(C1-C4) alkyl, or linear or branched C2-C5 alkyl; and/or $R_7$ is $CF_3$; and/or $R_{12}$ is hydrogen.

Another preferred embodiment of the invention is a compound of formula VI, as described above, wherein W, $R_8$, and $R_9$ are all hydrogen;

X is —CH=CH—;

$R_6$ is selected from C2-C5 alkyl, C1-C4 alkylamino, or methoxyethylamino; preferably $R_6$ is —NH—(C1-C4) alkyl, or linear or branched C2-C5 alkyl;

$R_1$ is hydrogen, or methyl; and $R_7$ is $CF_3$.

Another aspect of the present invention relates to Compounds of formula I, III, IV, V, or VI as described herein, wherein $R_1$ is hydrogen, methyl or ethyl, preferably hydrogen or methyl. In more specific embodiments, wherein if $R_1$ is methyl or ethyl, then the atom to which $R_1$ is attached is preferably in (R)-configuration.

The compounds of the formula (I), (II), (III), (IV), (V), and (VI) of the present invention can chemically be synthesized by the following reaction schemes. However, these are given only for illustration of the invention and not intended to limit to them.

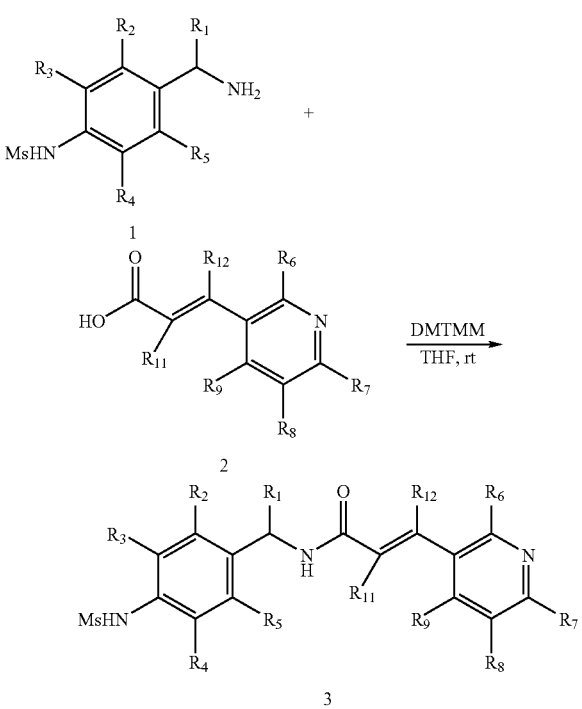

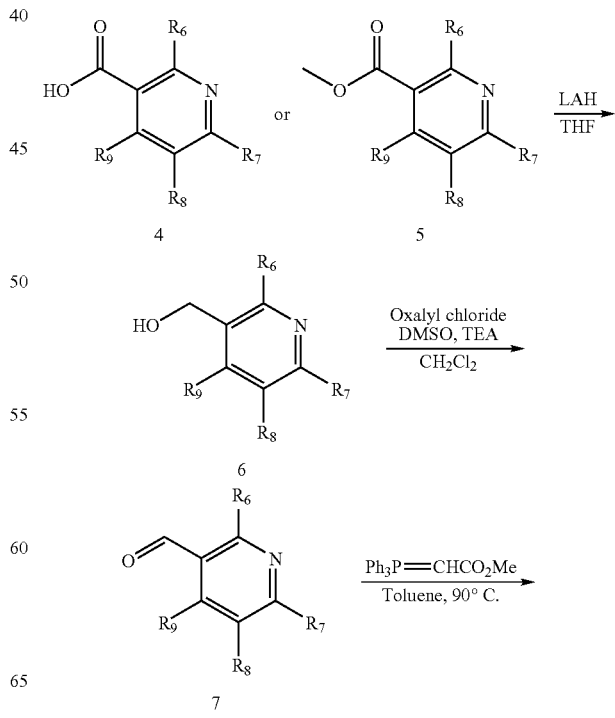

The Scheme 1 shows a proposed process for synthesizing acrylamide compound with various substituents. Substituted benzylamine (1) is reacted with pyridinyl acrylic acid (2) to yield benzyl pyridinyl acrylamide (3) using DMTMM {4-(4,6-dimethoxy-1,3,5-triazin-2-yl)-4-methylmorpholinium chloride} (Tetrahedron Lett., 1999, 40, 5327).

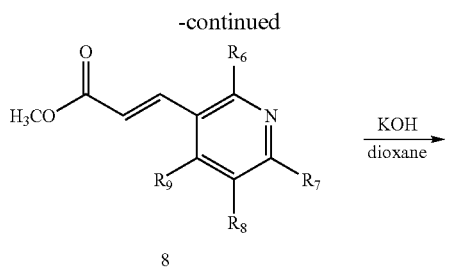

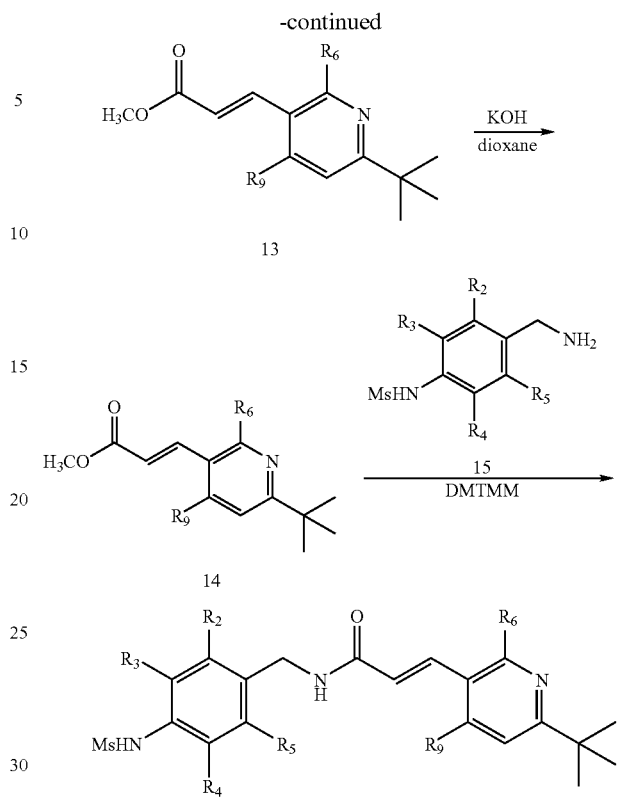

The Scheme 2 shows a proposed process for synthesizing pyridinyl acrylic acid (9) with various substituents. Substituted pyridinecarboxaldehyde (7) is prepared by known methods. Substituted nicotinic acid (4) or nicotinic ester (5) is converted to corresponding pyridinecarboxaldehyde (7) via pyridinyl methyl alcohol (6). Pyridinyl methyl alcohol is converted to pyridinecarboxaldehyde (7) via Swern oxidation. Pyridinecarboxaldehyde (7) is converted to methyl pyridinyl acrylic ester (8) by Wittig reaction. Methyl pyridinyl acrylic ester (8) is hydrolyzed with potassium hydroxide to yield pyridinyl acrylic acid (9).

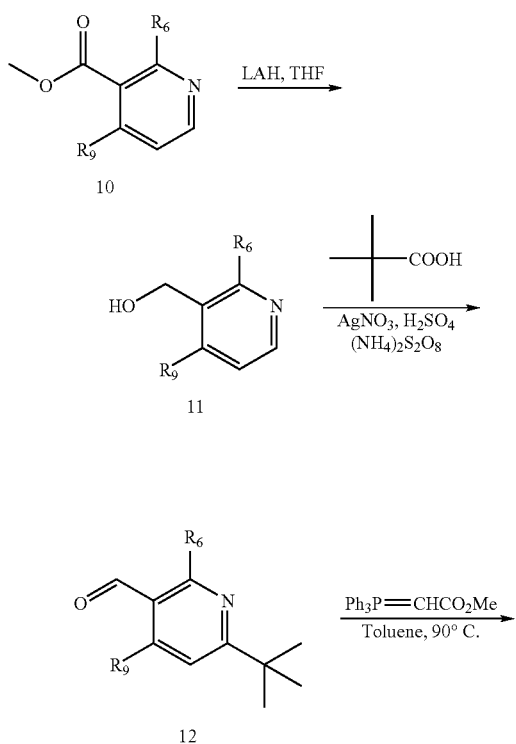

The Scheme 3 shows a proposed process for synthesizing pyridinyl acrylic amide (16) with t-butyl group. Substituted pyridinecarboxaldehyde with t-butyl group (12) is prepared by reduction followed by radical substitution method (J. Heterocyclic Chem., 1989, 25, 45-48). Substituted nicotinic ester (10) is converted to corresponding pyridine-3-methanol (11). Pyridinyl-3-methanol is reacted with pivalic acid and silver nitrate to give pyridinecarboxaldehyde (12) via Tada's radical substitution. Compound (14) is synthesized from compound (12) with similar method of scheme 2. 4-t-Butylpyridinyl acrylic acid (14) is reacted with compound (15) to yield compound (16).

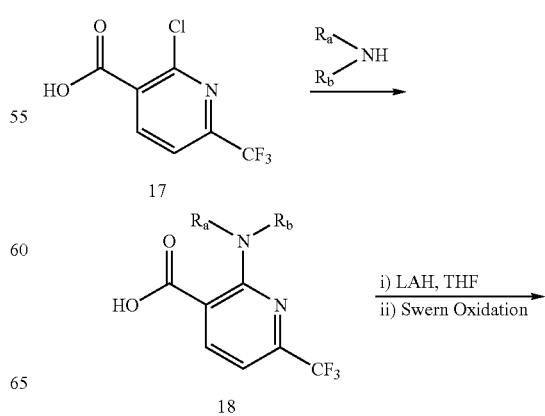

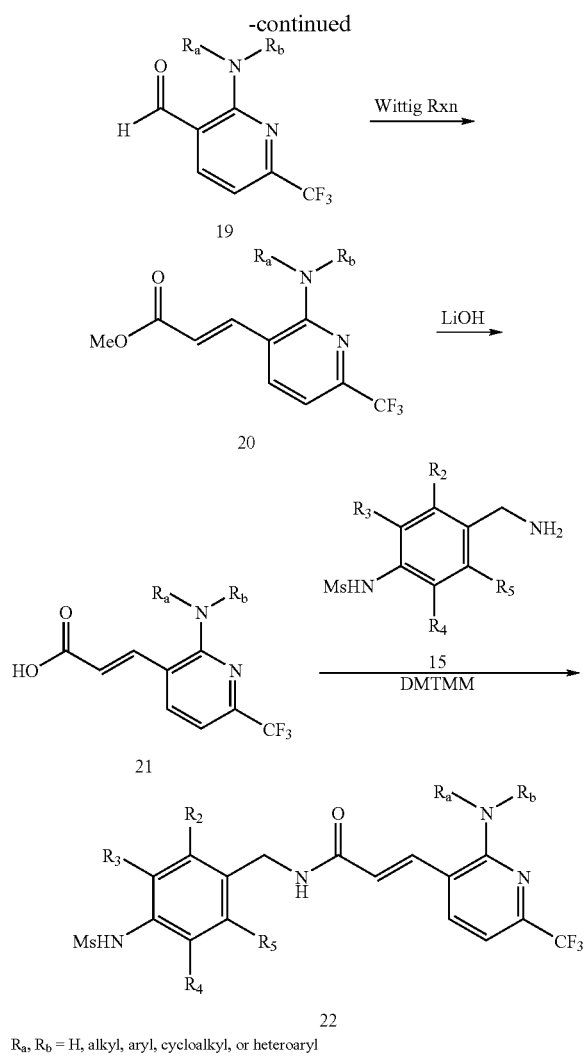

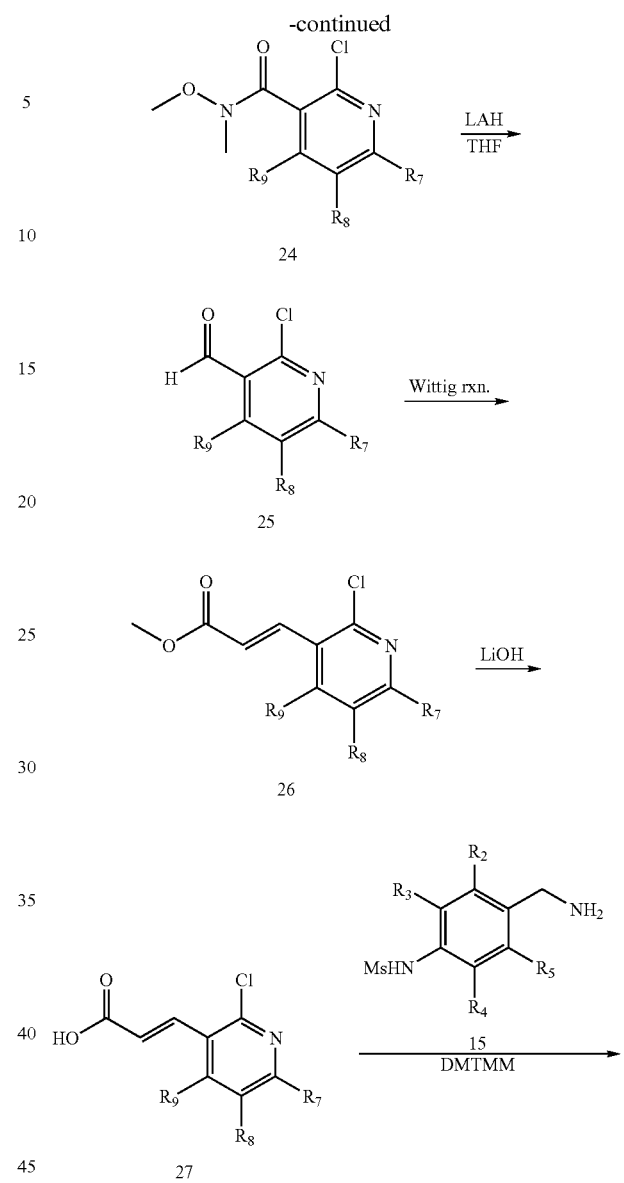

The Scheme 4 shows a proposed process for synthesizing pyridinyl acrylicamide (22) with trifluoromethyl group on pyridine. 2-Chloro-6-trifluoromethyl-nicotinic ester (17) is reacted with cyclic secondary amine to give compound (18). Compound (18) is converted to compound (21) following similar reaction of scheme 2. Compound (21) is reacted with compound (15) to give compound (22).

Scheme 5

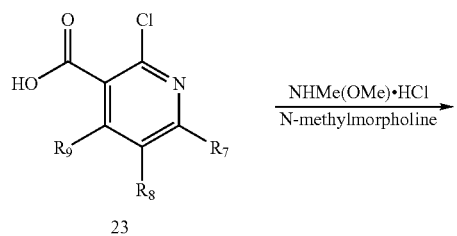

The Scheme 5 shows a proposed process for synthesizing pyridinyl acrylamide (28). 2-Chloro-nicotinic acid compound (23) is reacted with N,O-dimethylhydroxylamine hydrochloride to give compound (24). Compound (24) is reduced with LAH to afford compound (25), which is converted to methyl pyridinyl acrylic ester (26) by Wittig reaction. Compound (26) is hydrolyzed using LiOH to give pyridinyl acrylic acid (27), which is then reacted with compound (15) to give compound (28).

Scheme 6

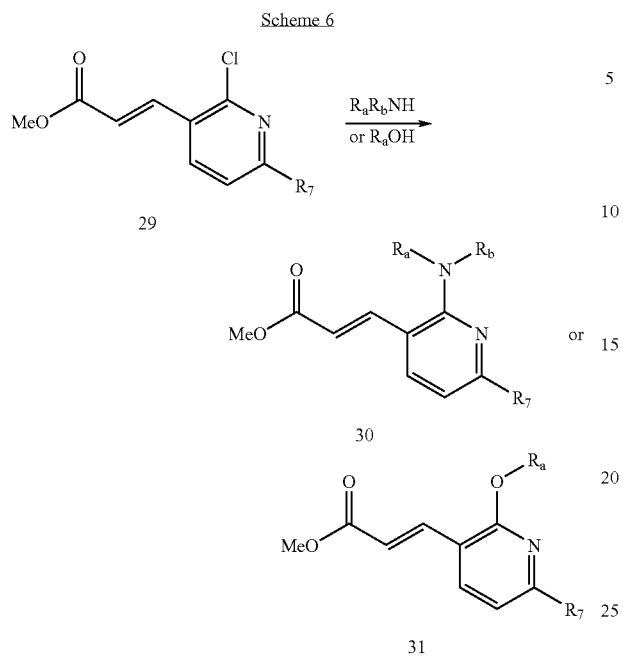

The Scheme 6 shows a proposed process for synthesizing pyridinyl acrylic ester or pyridinyl acrylic acid (30) or (31) with 2-alkylamino group or 2-alkoxy group on pyridine, respectively. Compound (29) is reacted with various amine or alcohol to give compound (30) or compound (31) with or without using a base such as $K_2CO_3$ or NaH.

Scheme 7

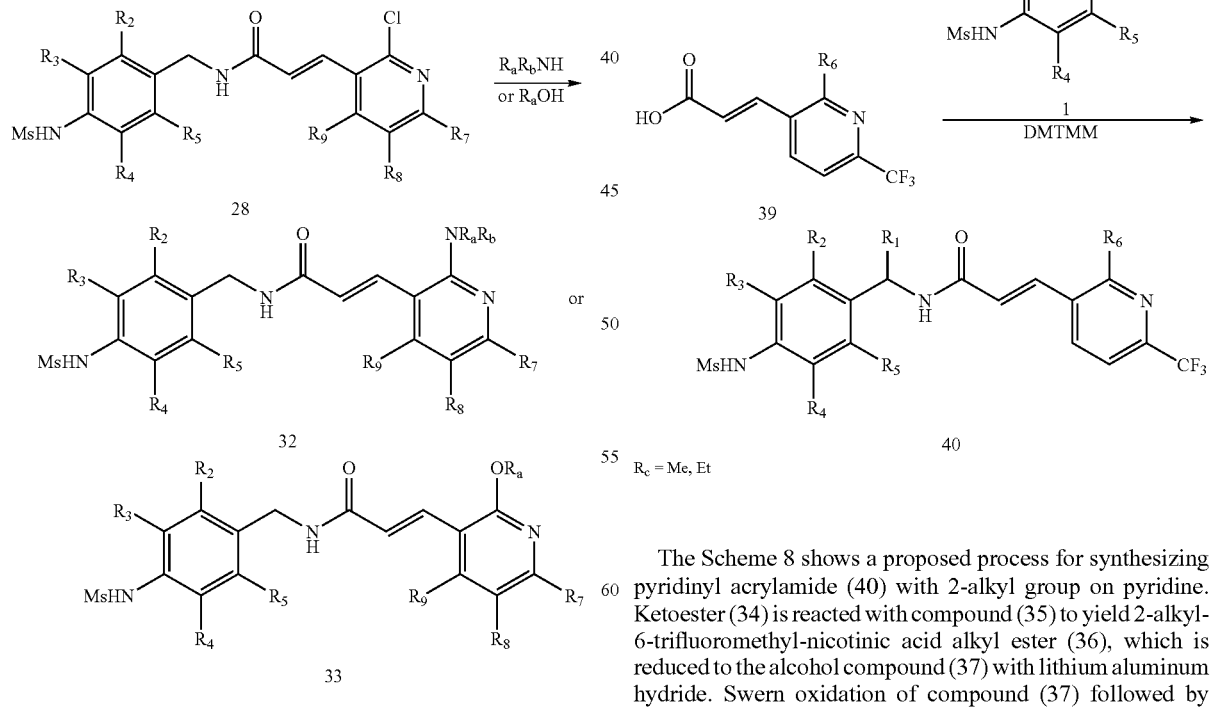

The Scheme 7 shows a proposed process for synthesizing pyridinyl acrylamide (32) or (33) with alkylamino (or arylamino) group or alkoxy group on pyridine, respectively. Compound (28) is reacted with various amine or alcohol to give compound (32) or compound (33) with or without using a base such as $K_2CO_3$ or NaH.

Scheme 8

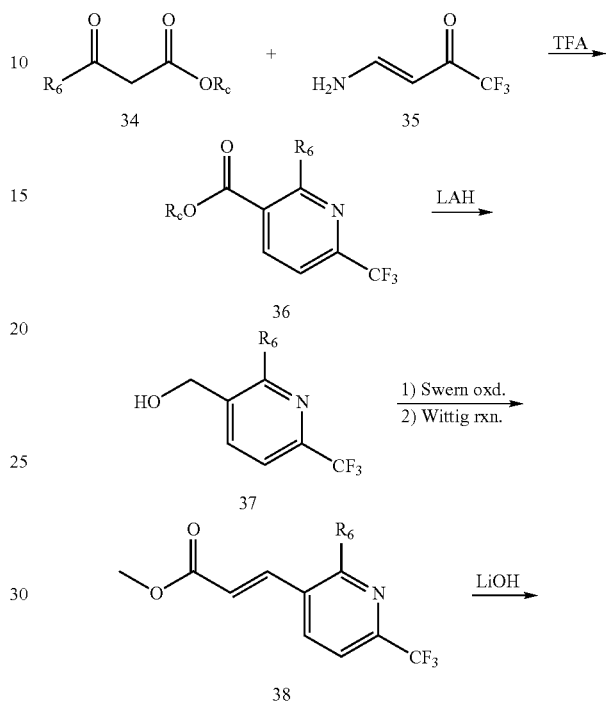

$R_c$ = Me, Et

The Scheme 8 shows a proposed process for synthesizing pyridinyl acrylamide (40) with 2-alkyl group on pyridine. Ketoester (34) is reacted with compound (35) to yield 2-alkyl-6-trifluoromethyl-nicotinic acid alkyl ester (36), which is reduced to the alcohol compound (37) with lithium aluminum hydride. Swern oxidation of compound (37) followed by Wittig reaction affords 3-(2-alkyl-6-trifluoromethyl-pyridin-3-yl)-acrylic acid methyl ester (38). 3-(2-Alkyl-6-trifluoromethyl-pyridin-3-yl)-acrylic acid (39) obtained by hydrolyzing the compound (38) with LiOH is reacted with the amine compound (1) to yield pyridinyl acrylamide (40) with 2-alkyl group on pyridine.

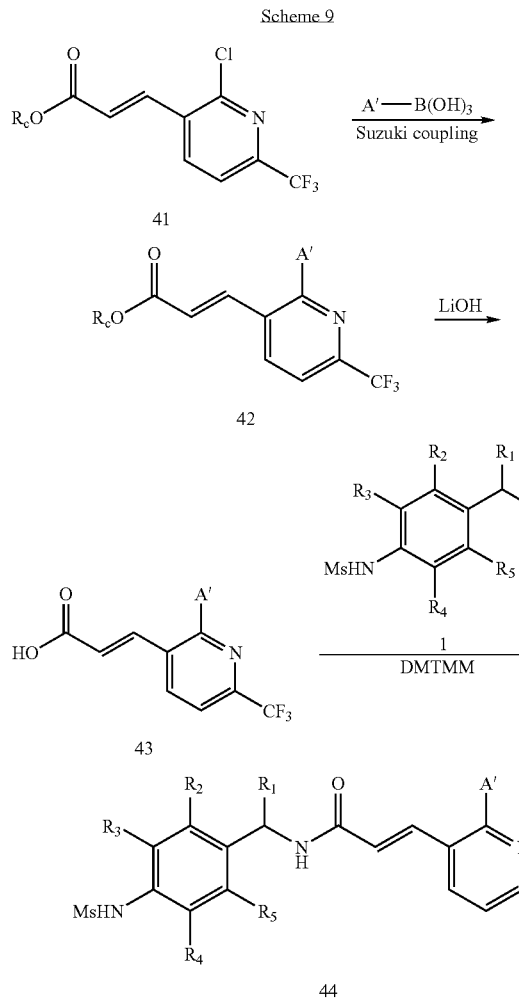

A' = aryl or heteroaryl

The Scheme 9 shows a proposed process for synthesizing pyridinyl acrylamide (44) with 2-aryl or 2-heteroaryl on pyridine. Compound (42) obtained by Suzuki coupling of compound (41) with various boronic acids using microwave irradiation is hydrolyzed with LiOH to yield acrylic acid (43). Acrylic acid (43) is then reacted with the compound (1) to give pyridinyl acrylamide (44) with 2-aryl or 2-heteroaryl group on pyridine.

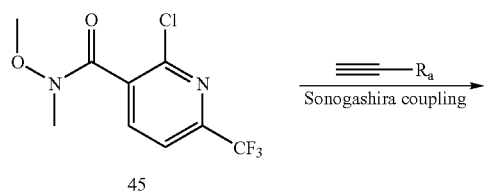

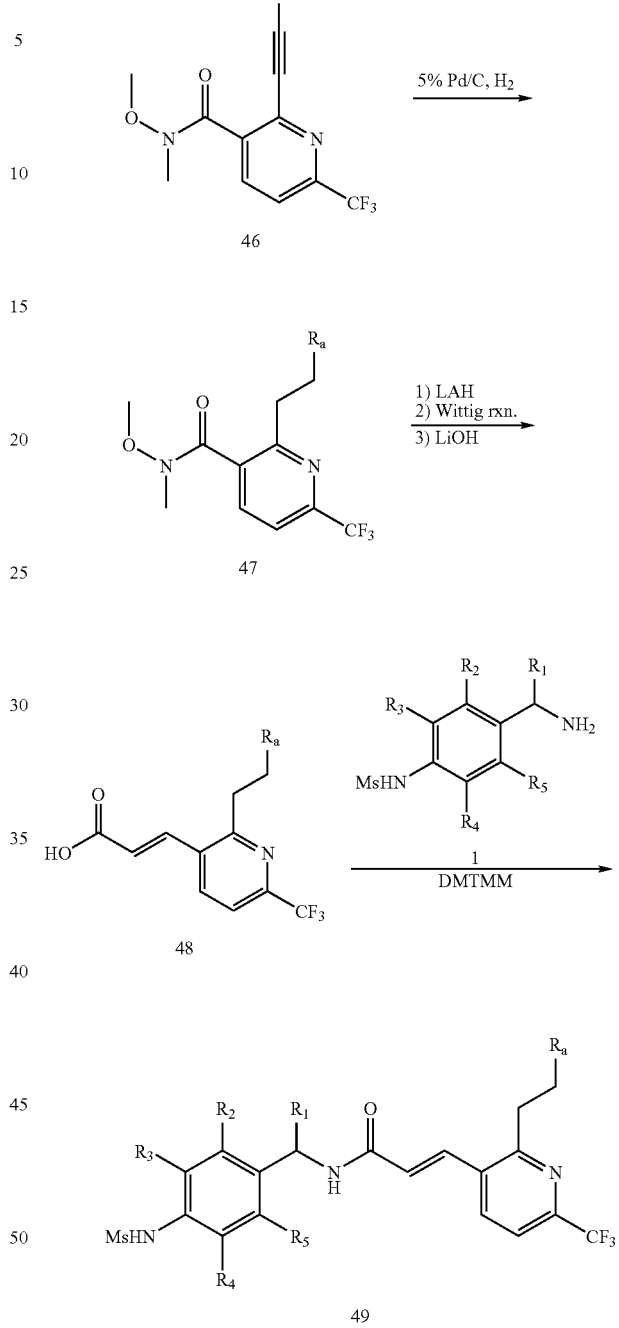

The Scheme 10 shows another proposed process for synthesizing pyridinyl acrylamide (49) with 2-alkyl group on pyridine. Compound (46) obtained by Sonogashira coupling of compound (45) with various alkynes using microwave irradiation is reduced by hydrogenation to yield Weireb amide (47). The amide (47) is reduced to aldehyde, and the resulting aldehyde is subjected to Wittig reaction followed by hydrolysis with LiOH to afford acrylic acid (48). Acrylic acid (48) is then reacted with the compound (1) to give pyridinyl acrylamide (49) with 2-alkyl group on pyridine.

Scheme 11

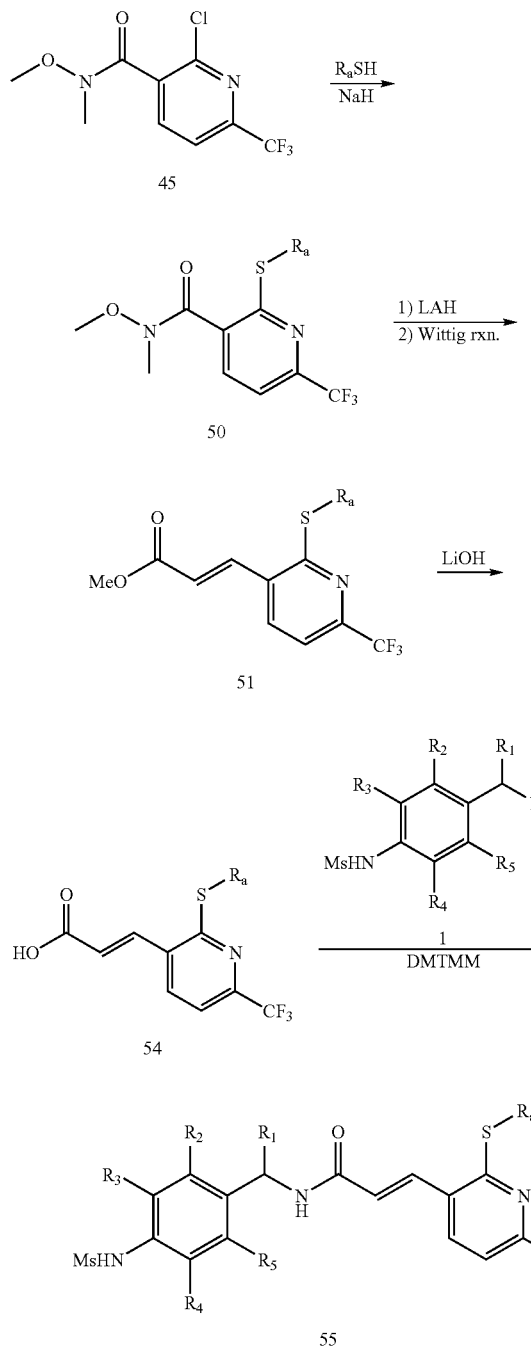

The Scheme 11 shows a proposed process for synthesizing pyridinyl acrylamide (53) with 2-alkylsulfinyl or 2-arylsufinyl group on pyridine. Compound (50) obtained by the reaction of compound (45) with various alkylthiols or arylthiols using NaH is reduced with lithium aluminum hydride to give an aldehyde, and the resulting aldehyde is subjected to Wittig reaction to give the compound (51). Compound (51) is hydrolyzed with LiOH to afford acrylic acid (54). Acrylic acid (54) is then reacted with the compound (1) to give pyridinyl acrylamide (55) with 2-alkylthio or 2-arylthio group on pyridine.

Scheme 12

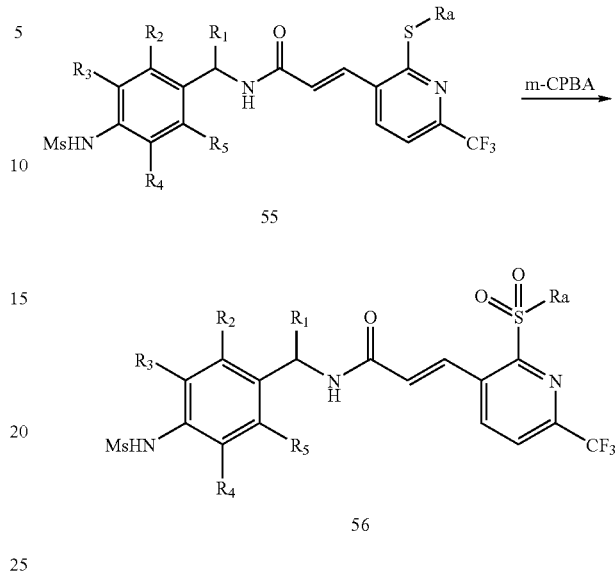

The Scheme 12 shows a proposed process for synthesizing pyridinyl acrylamide (56) with 2-alkylsulfonyl or 2-arylsulfonyl group on pyridine. Compound (55) is oxidized with mCPBA to give pyridinyl acrylamide (56) with 2-alkylsulfonyl or 2-arylsulfonyl group on pyridine.

Scheme 13

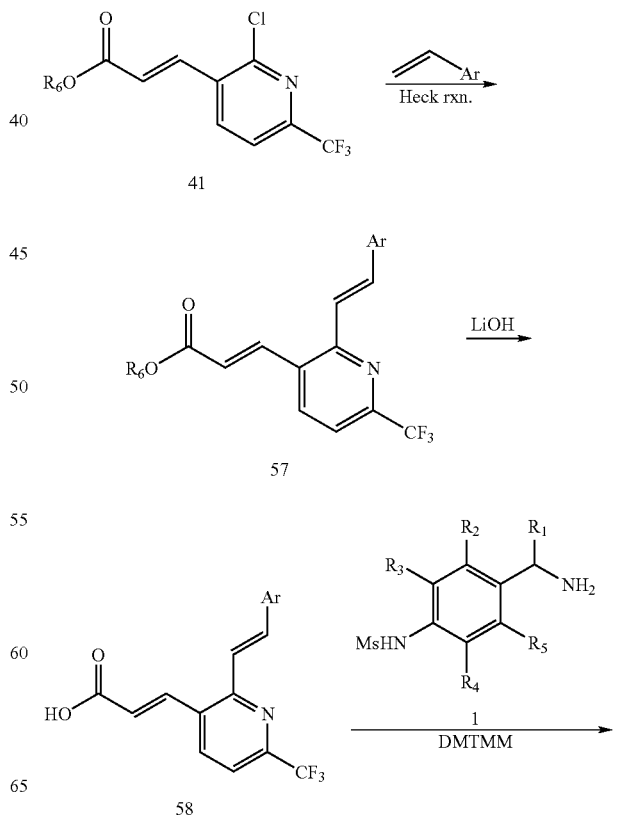

-continued

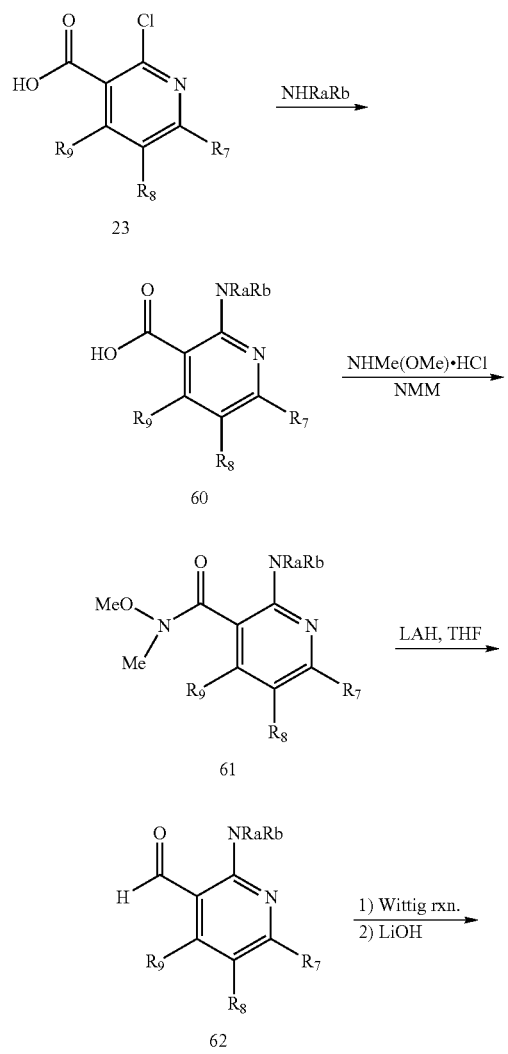

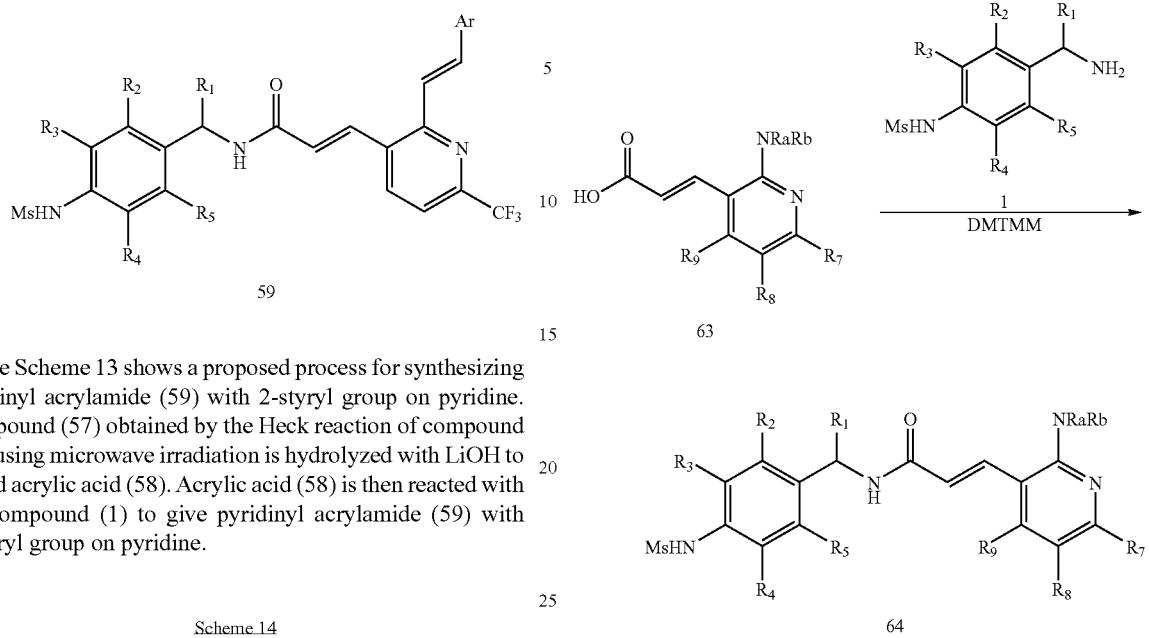

The Scheme 13 shows a proposed process for synthesizing pyridinyl acrylamide (59) with 2-styryl group on pyridine. Compound (57) obtained by the Heck reaction of compound (41) using microwave irradiation is hydrolyzed with LiOH to afford acrylic acid (58). Acrylic acid (58) is then reacted with the compound (1) to give pyridinyl acrylamide (59) with 2-styryl group on pyridine.

The Scheme 14 shows a proposed process for synthesizing pyridinyl acrylamide (64). 2-Chloro-nicotinic acid compound (23) is reacted with various amines to yield nicotinic acid compound (60) with 2-alkylamino, 2-dialkylamino, 2-arylamino, or 2-N-alkyl-N-aryl-amino group, which undergoes similar reactions to scheme 5 to give pyridinyl acrylic acid (63). Pyridinyl acrylamide (64) is then obtained by the reaction of pyridinyl acrylic acid (63) with the amine compound (1).

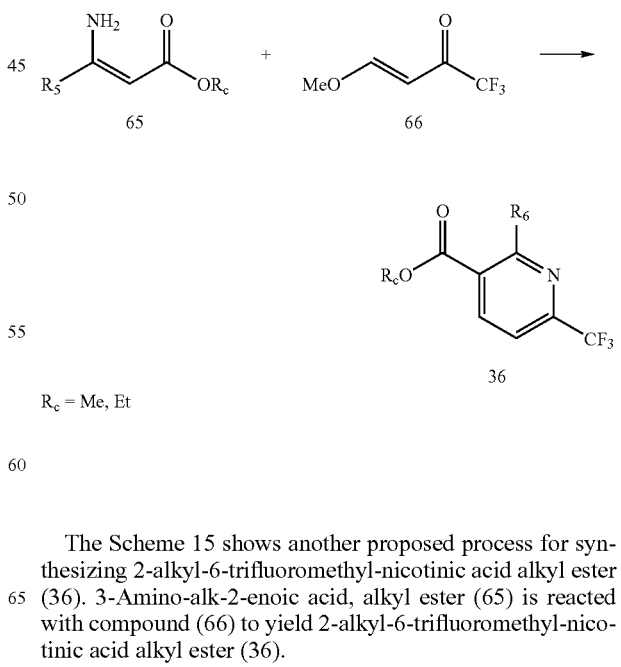

$R_c$ = Me, Et

The Scheme 15 shows another proposed process for synthesizing 2-alkyl-6-trifluoromethyl-nicotinic acid alkyl ester (36). 3-Amino-alk-2-enoic acid, alkyl ester (65) is reacted with compound (66) to yield 2-alkyl-6-trifluoromethyl-nicotinic acid alkyl ester (36).

Scheme 16

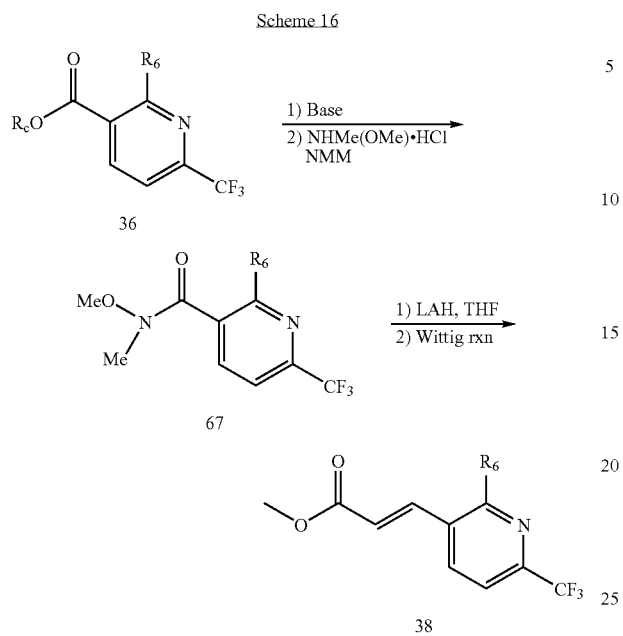

The Scheme 16 shows another proposed process for synthesizing 3-(2-alkyl-6-trifluoromethyl-pyridin-3-yl)-acrylic acid methyl ester (38). 2-alkyl-6-trifluoromethyl-nicotinic acid alkyl ester (36) is treated with a base such as LiOH to yield the corresponding acid, which was reacted with N,O-dimethylhydroxylamine hydrochloride to give the amide compound (67). The compound (67) is reduced with LAH to yield the corresponding aldehyde, which is converted to 3-(2-alkyl-6-trifluoromethyl-pyridin-3-yl)-acrylic acid methyl ester (38) by Wittig reaction.

Scheme 17

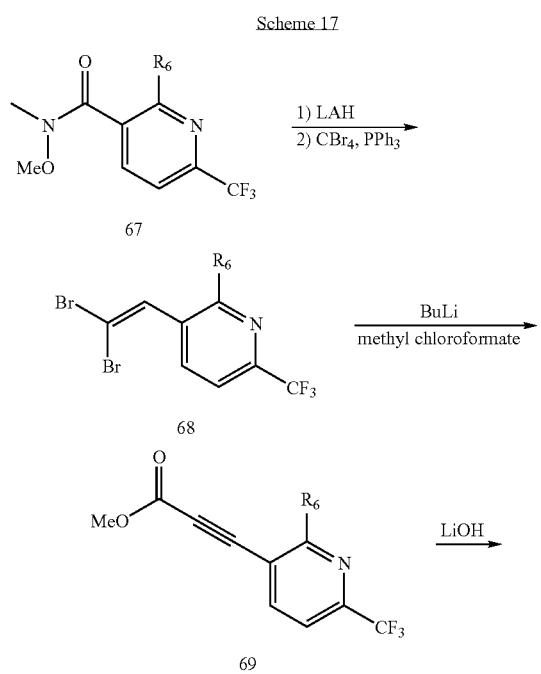

The Scheme 17 shows a proposed process for synthesizing 3-pyridin-3-yl-propynoic acid, benzylamide (71). The Weinreb amide (67) is reduced with LAH to yield the corresponding aldehyde, which is convered to the dibromide compound (68). The compound (68) is treated with BuLi followed by methyl chloroformate to yield 3-pyridin-3-yl-propynoic acid, methyl ester (69), which is then converted to 3-pyridin-3-yl-propynoic acid (70) using LiOH. 3-Pyridin-3-yl-propynoic acid, benzylamide (71) is obtained by reacting the propynoic acid (70) with the amine compound (1).

Scheme 18

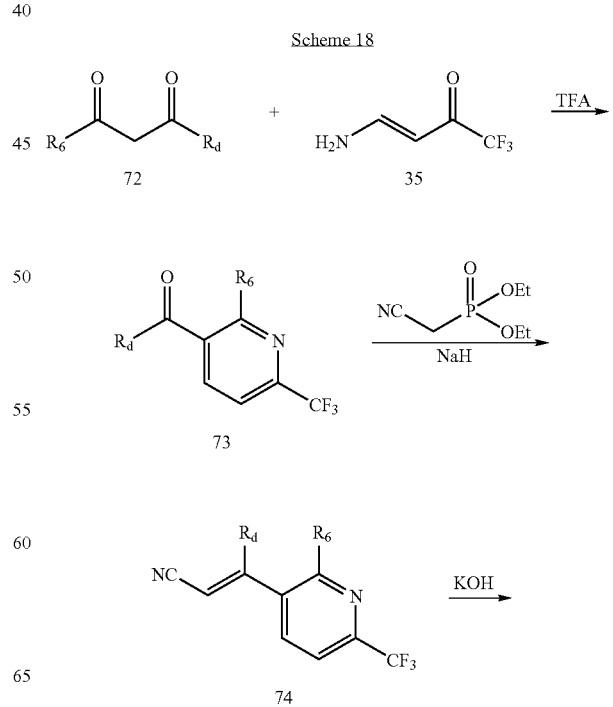

-continued

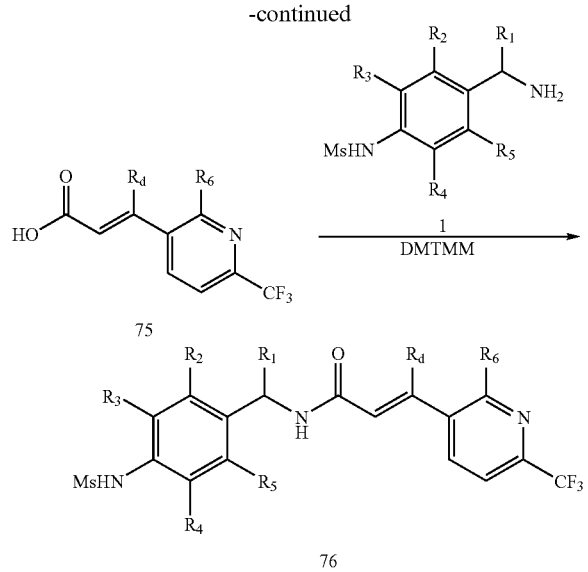

The Scheme 18 shows a proposed process for synthesizing pyridinyl acrylamide (76). Diketone (72) is reacted with compound (35) to yield pyridinyl ketone compound (73), which is transformed to the pyridinyl acrylonitrile compound (74) by reacting with cyanomethylphosphonic acid diethyl ester and NaH. 3-(2-Alkyl-6-trifluoromethyl-pyridin-3-yl)-acrylic acid (75) obtained by hydrolyzing the pyridinyl acrylonitrile compound (74) with KOH is reacted with the amine compound (1) to yield pyridinyl acrylamide (76).

Scheme 19

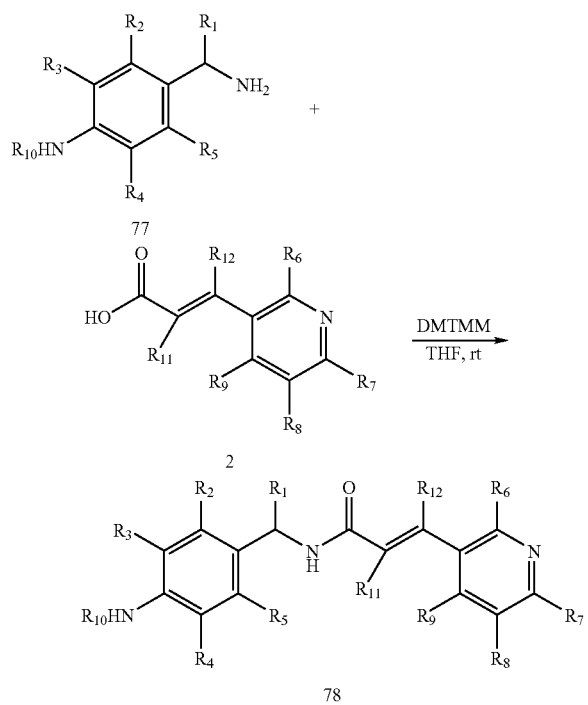

The Scheme 19 shows a proposed process for synthesizing acrylamide compound with various substituents. Substituted benzylamine (77) is reacted with pyridinyl acrylic acid (2) to yield benzyl pyridinyl acrylamide (78) using DMTMM.

The present invention also provides a compound of formula (I), (II), (III), (IV), (V), or (VI), an isomer thereof, or a pharmaceutically acceptable salt thereof for preventing or treating a disease associated with the pathological stimulation and/or aberrant expression of vanilloid receptor, wherein said composition comprises the compound of formula (I), (II), (III), (IV), (V), or (VI), an isomer thereof or a pharmaceutically acceptable salt thereof; and pharmaceutically acceptable carrier.

In one preferred aspect, the present invention provides a compound of formula (I), (II), (III), (IV), (V), or (VI), an isomer thereof, or a pharmaceutically acceptable salt thereof for treating a condition selected from the group consisting of pain, inflammatory disease of the joints, neuropathies, HIV-related neuropathy, nerve injury, neurodegeneration, stroke, urinary bladder hypersensitivity including urinary incontinence, cystitis, stomach duodenal ulcer, irritable bowel syndrome (IBS) and inflammatory bowel disease (IBD), fecal urgency, gastro-esophageal reflux disease (GERD), Crohn's disease, asthma, chronic obstructive pulmonary disease, cough, neurotic/allergic/inflammatory skin disease, psoriasis, pruritus, prurigo, irritation of skin, eye or mucous membrane, hyperacusis, tinnitus, vestibular hypersensitivity, episodic vertigo, cardiac diseases such as myocardial ischemia, hair growth-related disorders such as effluvium, alopecia, rhinitis, pancreatitis, vulvodynia, haemorrhagic shock, and psychiatric disorders such as anxiety or fear.

In a particularly preferred aspect, the present invention relates to a compound of formula (I), (II), (III), (IV), (V), or (VI), an isomer thereof, or a pharmaceutically acceptable salt thereof, wherein the pain is or is associated with a condition selected from the group consisting of osteoarthritis, rheumatoid arthritis, ankylosing spondylitis, diabetic neuropathic pain, post-operative pain, dental pain, non-inflammatory musculoskeletal pain (including fibromyalgia, myofascial pain syndrome and back pain), migraine, other types of headaches, bone cancer pain, mastalgia and visceral pain.

The present invention also provides a pharmaceutical composition comprising a compound of formula (I), (II), (III), (IV), (V), or (VI), an isomer thereof, or a pharmaceutically acceptable salt thereof as an active ingredient together with a pharmaceutically acceptable carrier.

The present invention also provides a pharmaceutical composition for preventing or treating a disease associated with the pathological stimulation and/or aberrant expression of vanilloid receptor, wherein said composition comprises the compound of formula (I), (II), (III), (IV), (V), or (VI), an isomer thereof or a pharmaceutically acceptable salt thereof, and pharmaceutically acceptable carrier.

In one preferred aspect, the present invention provides a pharmaceutical composition comprising a compound of formula (I), (II), (III), (IV), (V), or (VI), an isomer thereof, or a pharmaceutically acceptable salt thereof, for treating a condition selected from the group consisting of pain, inflammatory disease of the joints, neuropathies, HIV-related neuropathy, nerve injury, neurodegeneration, stroke, urinary bladder hypersensitivity including urinary incontinence, cystitis, stomach duodenal ulcer, irritable bowel syndrome (IBS) and inflammatory bowel disease (IBD), fecal urgency, gastro-esophageal reflux disease (GERD), Crohn's disease, asthma, chronic obstructive pulmonary disease, cough, neurotic/allergic/inflammatory skin disease, psoriasis, pruritus, prurigo, irritation of skin, eye or mucous membrane, hyperacusis, tinnitus, vestibular hypersensitivity, episodic vertigo, cardiac diseases such as myocardial ischemia, hair growth-related disorders such as effluvium, alopecia, rhinitis, pancreatitis, vulvodynia, haemorrhagic shock, and psychiatric disorders such as anxiety or fear.

In a particularly preferred aspect, the present invention relates to the pharmaceutical composition comprising a compound of formula (I), (II), (III), (IV), (V), or (VI), an isomer thereof, or a pharmaceutically acceptable salt thereof for treating pain as described above, wherein the pain is or is associated with a condition selected from the group consisting of osteoarthritis, rheumatoid arthritis, ankylosing spondylitis, diabetic neuropathic pain, post-operative pain, dental pain, non-inflammatory musculoskeletal pain (including fibromyalgia, myofascial pain syndrome and back pain), migraine, other types of headaches, bone cancer pain, mastalgia, and visceral pain.

The present invention also provides a pharmaceutical composition comprising a compound of formula (I), (II), (III), (IV), (V), or (VI), an isomer thereof, or a pharmaceutically acceptable salt thereof, which is characterized in that it is adapted for oral administration.

In another aspect, the present invention relates to a method for inhibiting vanilloid ligand from binding to vanilloid receptor in a patient, comprising contacting cells expressing vanilloid receptor in the patient with the compound of formula (I), (II), (III), (IV), (V), or (VI), an isomer thereof, or a pharmaceutically acceptable salt thereof.

In another aspect, the present invention also provides a method for preventing or treating a condition selected from the group consisting of pain, inflammatory disease of the joints, neuropathies, HIV-related neuropathy, nerve injury, neurodegeneration, stroke, urinary bladder hypersensitivity including urinary incontinence, cystitis, stomach duodenal ulcer, irritable bowel syndrome (IBS) and inflammatory bowel disease (IBD), fecal urgency, gastro-esophageal reflux disease (GERD), Crohn's disease, asthma, chronic obstructive pulmonary disease, cough, neurotic/allergic/inflammatory skin disease, psoriasis, pruritus, prurigo, irritation of skin, eye or mucous membrane, hyperacusis, tinnitus, vestibular hypersensitivity, episodic vertigo, cardiac diseases such as myocardial ischemia, hair growth-related disorders such as effluvium, alopecia, rhinitis, pancreatitis, vulvodynia, haemorrhagic shock, and psychiatric disorders such as anxiety or fear, which comprises administering to a mammal including a person in need thereof a therapeutically effective amount of the compound of formula (I), (II), (III), (IV), (V), or (VI), an isomer thereof, or a pharmaceutically acceptable salt thereof.

In a particularly preferred aspect, the present invention relates to the method of treating pain by administering a compound of formula (I), (II), (III), (IV), (V), or (VI), an isomer thereof, or a pharmaceutically acceptable salt thereof as described above, wherein the pain is or is associated with a condition selected from the group consisting of osteoarthritis, rheumatoid arthritis, ankylosing spondylitis, diabetic neuropathic pain, post-operative pain, dental pain, non-inflammatory musculoskeletal pain (including fibromyalgia, myofascial pain syndrome and back pain), migraine, other types of headaches, bone cancer pain, mastalgia, and visceral pain.

In another aspect, the present invention relates to the use of a compound of formula (I), (II), (III), (IV), (V), or (VI), an isomer thereof, or a pharmaceutically acceptable salt thereof for the preparation of a medicament for the prevention or treatment of a condition that is associated with the aberrant expression and/or aberrant activation of a vanilloid receptor.

In another aspect, the present invention relates to the use of a compound of formula (I), (II), (III), (IV), (V), or (VI), an isomer thereof, or a pharmaceutically acceptable salt thereof, in preparation of a medicament for the prevention or treatment of a condition that is selected from the group consisting of pain, inflammatory disease of the joints, neuropathies, HIV-related neuropathy, nerve injury, neurodegeneration, stroke, urinary bladder hypersensitivity including urinary incontinence, cystitis, stomach duodenal ulcer, irritable bowel syndrome (IBS) and inflammatory bowel disease (IBD), fecal urgency, gastro-esophageal reflux disease (GERD), Crohn's disease, asthma, chronic obstructive pulmonary disease, cough, neurotic/allergic/inflammatory skin disease, psoriasis, pruritus, prurigo, irritation of skin, eye or mucous membrane, hyperacusis, tinnitus, vestibular hypersensitivity, episodic vertigo, cardiac diseases such as myocardial ischemia, hair growth-related disorders such as effluvium, alopecia, rhinitis, pancreatitis, vulvodynia, haemorrhagic shock, and psychiatric disorders such as anxiety or fear.

In a particularly preferred aspect the present invention relates to the use of the compound of formula (I), (II), (III), (IV), (V), or (VI), an isomer thereof, for preparing a medicament for preventing or treating pain as described above, wherein the condition is pain or which is or which is associated with a condition selected from the group consisting of osteoarthritis, rheumatoid arthritis, ankylosing spondylitis, diabetic neuropathic pain, post-operative pain, dental pain, non-inflammatory musculoskeletal pain (including fibromyalgia, myofascial pain syndrome and back pain), migraine, other types of headaches, bone cancer pain, mastalgia, and visceral pain.

The present invention also provides a process for preparing a compound represented by the formula (III)

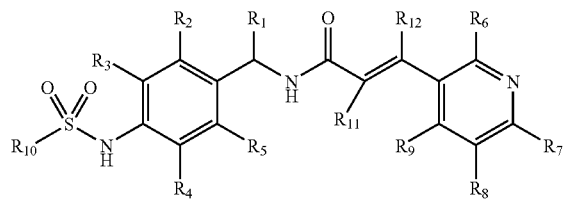

(III)

which comprises reacting a compound represented by the formula (IIIa);

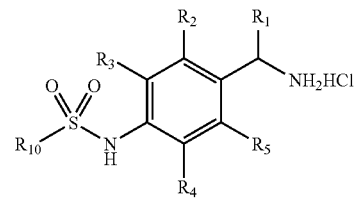

(IIIa)

with a compound represented by the formula (IIIb);

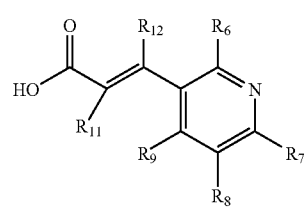

(IIIb)

wherein, $R_1, R_2, R_3, R_4, R_5, R_6, R_7, R_8, R_9, R_{10}, R_{11}$, and $R_{12}$ are as described in any of the preceding embodiments.

One preferred aspect of the present invention is the process for preparing a compound of formula (III), wherein, the reaction is conducted in the presence of a coupling agent.

Another preferred aspect of the present invention is the process for preparing a compound of formula (III), wherein the coupling agent is selected from the group consisting of DCC(N,N-dicyclohexylcarbodidimide), EDCI {1-(3-dimethylaminopropyl)-3-ethylcarbodidimide hydrochloride (EDCI)}, and DMTMM {4-(4,6-dimethoxy-1,3,5-triazin-2-yl)-4-methylmorpholinium chloride}.

The present invention also provides a process for preparing a compound of formula (IIIc),

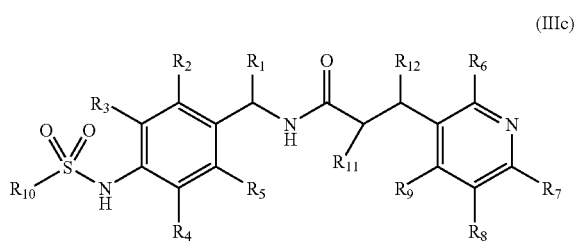

(IIIc)

which comprises a reducing step of the compound of the formula (III).

One preferred aspect of the present invention is the process for preparing a compound of formula (IIIc), wherein the reducing step is conducted in the presence of hydrogen gas and palladium on carbon.

Another preferred aspect of the present invention is the process for preparing a compound of formula (III) or (IIIc), wherein $R_1$, $R_{11}$, and $R_{12}$ are hydrogen.

Another preferred aspect of the present invention is the process for preparing a compound of formula (III) or (IIIc), wherein, $R_1$, $R_2$, $R_8$, $R_{11}$, and $R_{12}$ are hydrogen; $R_3$ is hydrogen, fluoro, chloro, bromo, cyano, methyl, ethyl, ethenyl, ethynyl, or trifluoromethyl; $R_4$ and $R_5$ are independently hydrogen, fluoro, chloro, cyano, methyl, ethyl, or trifluoromethyl; $R_6$ is hydrogen, fluoro, chloro, bromo, methyl, methoxy, diethylamino, pyrrolidinyl, piperidyl, or morpholinyl; $R_7$ is isopropyl, t-butyl, or trifluoromethyl; $R_9$ is hydrogen or trifluoromethyl; and $R_{10}$ is methyl.

The present invention also provides a novel compound of formula (IIId)

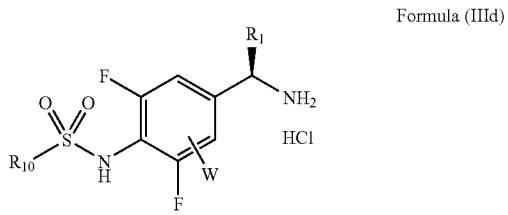

Formula (IIId)

wherein,
W is hydrogen or fluoro;
$R_1$ is hydrogen or C1-C3 alkyl, preferably methyl; and
$R_{10}$ is C1-C3 alkyl, C2-C3 alkenyl, or halo C1-C3 alkyl, preferably methyl;

provided that if $R_1$ is hydrogen and $R_{10}$ is methyl, then W is fluoro.

Specific examples of compounds of formula (IIId) are:

(R)—N-[4-(1-amino-ethyl)-2,6-difluoro-phenyl]-methanesulfonamide, HCl salt, (R)—N-[4-(1-amino-propyl)-2,6-difluoro-phenyl]-methanesulfonamide, HCl salt, N-(4-aminomethyl-2,3,6-trifluoro-phenyl)-methanesulfonamide, HCl salt, (R)—N-[4-(1-amino-ethyl)-2,3,6-trifluoro-phenyl]-methanesulfonamide, HCl salt, (R)—N-[4-(1-amino-propyl)-2,3,6-trifluoro-phenyl]-methanesulfonamide, HCl salt, N-(4-aminomethyl-2,6-difluoro-phenyl)-ethnesulfonamide, HCl salt, (R)—N-[4-(1-amino-ethyl)-2,6-difluoro-phenyl]-ethenesulfonamide, HCl salt, (R)—N-[4-(1-amino-propyl)-2,6-difluoro-phenyl]-ethenesulfonamide, HCl salt, N-(4-aminomethyl-2,3,6-trifluoro-phenyl)-ethnesulfonamide, HCl salt, (R)—N-[4-(1-amino-ethyl)-2,3,6-trifluoro-phenyl]-ethenesulfonamide, HCl salt, or (R)—N-[4-(1-amino-propyl)-2,3,6-trifluoro-phenyl]-ethenesulfonamide, HCl salt.

Another aspect of the present invention is the use of the compound of formula (IIId) as described above as an intermediate in the production of a compound of a VR1 ligand, preferably of the general formula I, III or most preferably VI, as described in this application, wherein W is hydrogen or fluoro.

Another embodiment of the present invention is a process for preparing a compound of formula (IIId), wherein $R_1$ is C1-C3 alkyl, preferably methyl, said process comprising:

(a) reacting a compound of Formula (IIIe)

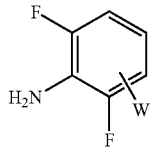

Formula (IIIe)

wherein, W is as defined as above,
with a compound of Formula (IIIf)

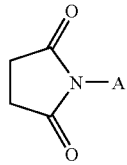

Formula (IIIf)

wherein, A is I or Br, in the presence of an acid in a solvent to afford a compound of Formula (IIIg)

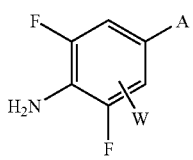

Formula (IIIg)

wherein, W and A are as defined above;

(b) reacting a compound of Formula (IIIg) with a compound of Formula (IIIh)

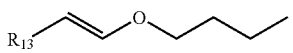

Formula (IIIh)

wherein, $R_{13}$ is hydrogen or C1-C2 alkyl, preferably hydrogen, in the presence of a catalyst and a ligand in a solvent to afford a compound of Formula (IIIi);

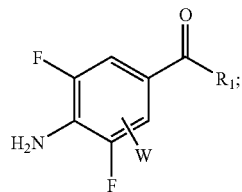

Formula (IIIi)

wherein W and $R_1$ are as defined above;

(c) reacting a compound of Formula (IIIi) with a compound of Formula (IIIj)

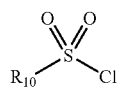

Formula (IIIj)

wherein, $R_{10}$ is as defined above, in the presence of a base in a solvent followed by NaOH in a solvent to afford a compound of Formula (IIIk)

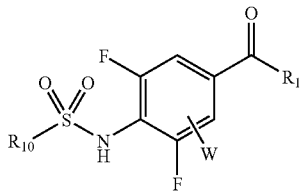

Formula (IIIk)

wherein, W, $R_1$ and $R_{10}$ are as defined above;

(d) reacting a compound of Formula (IIIk) with (R)-(+)-2-methyl-2-propanesulfinamide in the presence of an acid in a solvent followed by NaBH$_4$ in a solvent and then HCl in a solvent to afford a compound of Formula (IIId), wherein W and $R_{10}$ are as defined above, and $R_1$ is C1-C3 alkyl, preferably methyl.

Another embodiment of the present invention is a process for preparing a compound of formula (IIId), wherein $R_1$ is hydrogen, said process comprising:

(a) reacting a compound of Formula (IIIg)

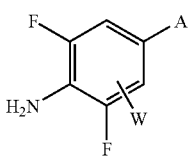

Formula (IIIg)

wherein, W and A are as defined above with CuCN in a solvent to afford a compound of Formula (IIIm)

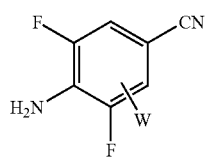

Formula (IIIm)

wherein, W is as defined above;

(b) reacting a compound of Formula (IIIm) with a compound of Formula (IIIj)

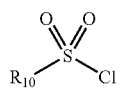

Formula (IIIj)

wherein, $R_{10}$ is as defined above, in the presence of a base in a solvent followed by NaOH in a solvent to afford a compound of Formula (IIIn)

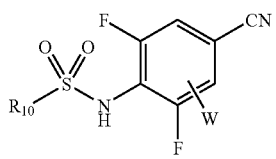

Formula (IIIn)

wherein, W and $R_{10}$ are as defined above;

c) reacting a compound of Formula (IIIn) with hydrogen in the presence of a catalyst and an acid in a solvent to afford a compound of Formula (IIId)

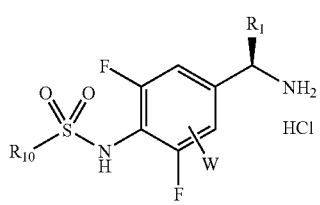

Formula (IIId)

wherein, W and $R_{10}$ are as defined above, and $R_1$ is hydrogen.

Hereinafter, the formulating methods and kinds of excipients will be described, but the present invention is not limited to them.

A compound of formula (I), (II), (III), (IV), (V), or (VI), an isomer thereof or a pharmaceutically acceptable salt thereof according to the present invention can be prepared as a pharmaceutical composition containing pharmaceutically acceptable carriers, adjuvants, diluents and the like. For instance, the compounds of the present invention can be dissolved in oils, propylene glycol or other solvents which are commonly used to produce an injection. Suitable examples of the carriers include, but not limited to, physiological saline, polyethylene glycol, ethanol, vegetable oils, isopropyl myristate, etc. For topical administration, the compounds of the present invention can be formulated in the form of ointment or cream.

The compound according to the present invention may also be used in the forms of pharmaceutically acceptable salts thereof, and may be used either alone or in combination or in admixture with other pharmaceutically active compounds.

The compounds of the present invention may be formulated into injections by dissolving, suspending or emulsifying m water-soluble solvent such as saline and 5% dextrose, or in water-insoluble solvents such as vegetable oils, synthetic fatty acid glyceride, higher fatty acid esters and propylene glycol. The formulations of the invention may include any of conventional additives such as dissolving agents, isotonic agents, suspending agents, emulsifiers, stabilizers and preservatives.

The preferable dose level of the compounds according to the present invention depends upon a variety of factors including the condition and body weight of the patient severity of the particular disease, dosage form, and route and period of administration, but may appropriately be chosen by those skilled m the art. The compounds of the present invention are preferably administered in an amount ranging from 0.001 to 100 mg/kg of body weight per day, and more preferably from 0.01 to 30 mg/kg of body weight per day. Doses may be administered once a day, or several times a day with each divided portions. The compounds of the present invention are used in a pharmaceutical composition in an amount of 0.0001-10% by weight, and preferably 0.001-1% by weight, based on the total amount of the composition.

The pharmaceutical composition of the present invention can be administered to a mammalian subject such as rat, mouse, domestic animals, human being and the like via various routes. The methods of administration which may easily be expected include oral and rectal administration; intravenous, intramuscular, subcutaneous, intrauterine, duramatral and intracerebroventricular injections.

DETAILED DESCRIPTION OF THE INVENTION
DEFINITIONS

When describing the compounds, pharmaceutical compositions containing such compounds, methods of using such compounds and compositions, and use of such compounds and compositions, all terms used in the present application shall have the meaning usually employed by a relevant person skilled in the art, e.g. by a medicinal chemists, pharmacist or physician. By the way of example some definitions of specific groups are given below:

"Alkyl" includes monovalent saturated aliphatic hydrocarbyl groups. The hydrocarbon chain may be either straight-chained or branched. "Alkyl" has preferably 1-15 carbon atoms ("C1-C15 alkyl"), more preferably 1-10 carbon atoms ("C1-C10 alkyl"), even more preferably 1-8 carbon atoms ("C1-C8 alkyl") or 1-6 carbon atoms ("C1-C6 alkyl"), and in some instances even more preferably 1-5 carbon atoms ("C1-C5 alkyl"), 1-4 carbon atoms ("C1-C4 alkyl"), or only 1-3 carbon atoms ("C1-C3 alkyl"). This term is exemplified by groups such as methyl, ethyl, n-propyl, isopropyl, n-butyl, iso-butyl, tert-butyl, t-amyl, and the like.

"Alkoxy" includes the group —OR wherein R is "alkyl" as defined further above. Particular alkoxy groups include, by way of example, methoxy, ethoxy, n-propoxy, isopropoxy, n-butoxy, tert-butoxy, sec-butoxy, n-pentoxy, 1,2-dimethylbutoxy, and the like.

"Alkoxyalkoxy" refers to the group —OROR', wherein R and R' are the same or different "alkyl" groups as defined further above.

"Alkoxyalkoxyalkyl" refers to the group —ROR'OR", wherein R, R' and R" are the same or different "alkyl" groups as defined further above.

"Alkoxyalkyamino" refers to the group —NH(ROR'), wherein R and R' are the same or different "alkyl" groups as defined further above.

"N-Alkoxyalky-N-alkylamino" refers to the group —NR(R'OR"), wherein R, R' and R" are the same or different "alkyl" groups as defined further above.

"Alkoxyalkynyl" refers to the group —C≡C—(CH$_2$)$_n$OR, wherein n is an integer from 0 to 8 and R is an "alkyl" group as defined further above.

"Dialkylaminoalkynyl" refers to the group —C≡C—(CH$_2$)$_n$NRR', wherein n is an integer from 0 to 8 and R and R' are the same or different "alkyl" groups as defined further above.

"Alkoxycarbonyl" refer to the radical —C(=O)—O—R, wherein R is an alkyl group as defined herein.

"Alkenyl" includes monovalent olefinically unsaturated hydrocarbyl groups being straight-chained or branched and having at least 1 double bond.

"Alkenyl" has preferably 2-15 carbon atoms ("C2-C15 alkenyl"), more preferably 2-10 carbon atoms ("C2-C10 alkenyl"), even more preferably 2-8 carbon atoms ("C2-C8 alkenyl") or 2-6 carbon atoms ("C2-C6 alkenyl"), and in some instances even more preferably 2-5 carbon atoms ("C1-C5 alkenyl"), 2-4 carbon atoms ("C2-C4 alkenyl"), or only 2-3 carbon atoms ("C2-C3 alkenyl"). Particular alkenyl groups include ethenyl (—CH=CH$_2$), n-propenyl (—CH$_2$CH=CH$_2$), isopropenyl (C(CH$_3$)=CH$_2$), and the like. A preferred "alkenyl" group is ethenyl (vinyl).

"Alkynyl" includes acetylenically unsaturated hydrocarbyl groups being straight-chained or branched and having at least 1 triple bond. "Alkynyl" has preferably 2-15 carbon atoms ("C2-C15 alkynyl"), more preferably 2-10 carbon atoms ("C2-C10 alkynyl"), even more preferably 2-8 carbon atoms ("C2-C8 alkynyl") or 2-6 carbon atoms ("C2-C6 alkynyl"), and in some instances even more preferably 2-5 carbon atoms ("C1-C5 alkynyl"), 2-4 carbon atoms ("C2-C4 alkynyl"), or only 2-3 carbon atoms ("C2-C3 alkynyl"). A preferred alkynyl group is ethynyl(acetylenyl).

"Alkylamino" includes the group —NHR', wherein R' is alkyl group as defined herein.

"Dialkylamino" includes the group —NR'R", wherein R' and R" are alkyl group as defined herein.

"Alkylsulfonyl" includes a radical-S(O)$_2$R, wherein R is an alkyl group as defined herein. Representative examples include, but are not limited to, methanesulfonyl, ethylsulfonyl, propylsulfonyl, butylsulfonyl and the like.

"Alkylthio" includes a radical-S—R wherein R is an alkyl group as defined herein that may be optionally substituted as defined herein. Representative examples include, but are not limited to, methylthio, ethylthio, propylthio, butylthio, and the like.

"Amino" refers to the radical -NH$_2$.

"Aryl" refers to an aromatic hydrocarbyl radical. Examples of "aryl" radicals are phenyl, naphthyl, indenyl, azulenyl, fluorine or anthracene, wherein phenyl is preferred.

"Arylamino" refers to the group —NHAr, wherein Ar is an "aryl" group as defined above.

"Aryloxy" refers to the group —OAr, wherein Ar is an "aryl" group as defined above.

"Carboxy" refers to the radical —C(=O)OH.

"Cycloalkyl" refers to cyclic saturated aliphatic hydrocarbyl groups. The numbers of C-atoms referenced in connection with a given cycloalkyl group corresponds to the number of ring forming carbon atoms, e.g. "C3-C6 cycloalkyl" refers to a cycloalkyl with between three and six ring-forming C atoms. Examples of "cycloalkyl" are cyclopropyl, cyclobutyl, cyclopentyl, cyclohexyl etc. If indicated, a "cycloalkyl" group may be unsubstituted or substituted with one or more alkyl groups, e.g. with C1-C6 alkyl groups, preferably with C1-C3 alkyl groups, particularly preferably with methyl groups. If a "cycloalkyl" carries more than one alkyl substituent these substituents may be attached to the same or to different ring-forming carbon atoms.

"Cycloalkoxy" refers to the group —OR, wherein R is "cycloalkyl" group as defined further above.

"Cycloalkylamino" refers to the group —NHR, wherein R is "cycloalkyl" group as defined further above.

"N-Cycloalkylamino-N-alkylamino" refers to the group —NRR', wherein R is the same or different "alkyl" group as defined further above and R' is "cycloalkyl" group as defined further above.

"N-aryl-N-alkylamino" refers to the group —NRAr, wherein Ar is an "aryl" group as defined above and R is an "alkyl" group as defined further above.

"Oxacycloalkyl" refers to cyclic saturated aliphatic hydrocarbyl groups with one oxygen atom at any position in the ring. The numbers of C-atoms referenced in connection with a given oxacycloalkyl group corresponds to the number of ring forming carbon atoms, e.g. "C3-C6 oxacycloalkyl" refers to a oxacycloalkyl with between three and six ring-forming C atoms and one O atom. Examples of "oxacycloalkyl" are oxiranyl, oxetanyl, tetrahydrofuranyl, tetrahydropyranyl etc. If indicated, a "oxacycloalkyl" group may be unsubstituted or substituted with one or more alkyl groups, e.g. with C1-C6 alkyl groups, preferably with C1-C3 alkyl groups, particularly preferably with methyl groups. If a "oxacycloalkyl" carries more than one alkyl substituent these substituents may be attached to the same or to different ring-forming carbon atoms.

"Oxacycloalkyl-oxy" refers to the group —OR, wherein R is "oxacycloalkyl" group as defined further above.

"Cyano" refers to the radical —C≡N.

"Ethenyl" refers to —CH=CH$_2$ which is also designated "vinyl" in the present application.

"Ethynyl" refers to —C≡CH.

"Halo" or "halogen" refers to fluoro, chloro, bromo and iodo. Preferred halo groups are either fluoro or chloro.

"Haloalkyl" includes an "alkyl" group as defined further above which is substituted with one or more halogens which may be the same, e.g. in trifluoromethyl or pentafluoroethyl, or which may be different.

"Heteroaryl" refers to aromatic ring system containing at least one heteroatom such as O, S or N. Examples of heteroaryl radicals are furanyl, thienyl, pyrollyl, thiazolyl, oxazolyl, imidazolyl, pyrazolyl, isoxazolyl, isothiazolyl, triazolyl, oxadiazolyl, thiadiazolyl, pyranyl, pyridinyl, pyridazinyl, pyrimidinyl, pyrazinyl, triazinyl, tetrazinyl, indolinyl, indolyl, isoindolyl, benzofuranyl, benzothiophenyl, benzoimidazolyl, benzthiazolyl, purinyl, quinazolinyl, quinolinyl, isoquinolinyl, quinolizinyl, pteridinyl, carbazolyl, wherein one ring systems, and in particular pyridinyl and imidazolyl are preferred.

"Heteroarylamino" refers to the group —NHAr', wherein Ar' is a "heteroaryl" group as defined above.

"Heteroaryloxy" refers to the group —OAr', wherein Ar' is a "heteroaryl" group as defined above.

"Hydroxy" refers to the radical -OH.

"Hydroxyalkyl" includes an "alkyl" group as defined further above which is substituted with one or more hydroxy groups.

"Nitro" refers to the radical -NO$_2$.

"Alkylpiperazinyl" refers to a piperazine ring that carries an "alkyl" as substituent, wherein the piperazinyl ring is preferably bound both to the "alkyl" as well as to the second attachment position via its nitrogen atoms.

"Piperazinyl" comprises a piperazinyl ring that can be bound by any C-atom as well as by a nitrogen atom, wherein bondage via one of its nitrogen atoms is preferred.

"Pyrrolidinyl" comprises a pyrrolidine ring that can be bound by any C-atom as well as by its nitrogen atom, wherein bondage via its nitrogen atom is preferred.

"Morpholinyl" comprises a morpholine ring that can be bound by any C-atom as well as by its nitrogen atom, wherein bondage via its nitrogen atom is preferred.

"Pyridinyl" comprises a pyridine ring that can be bound by any C-atom as well as by its nitrogen atom.

Any "alkyl", "alkenyl", "alkynyl", "aryl", "heteroaryl", "cycloalkyl", "piperazinyl", "piperidyl", "morpholinyl", or pyrrolidinyl", also as parts of larger groups such as "alkoxy", "alkylsulfonyl", "alkenyloxy", "aryloxy", "heteroaryloxy", "cycloalkylamino" etc. may be unsubstituted or substituted by one or more groups. Suitable substituents are e.g. halogen, hydroxyl, unsubstituted or halo-substituted C1-C5 alkoxy, unsubstituted or one or more times with methyl and/or with halogen substituted C3-C8 cycloalkyl, C1-C5 alkyl, halo (C1-C5) alkyl, amino, cyano, or nitro. Unless expressly specified otherwise, any "alkyl", "alkenyl", "alkynyl", "aryl", "heteroaryl", "cycloalkyl", "piperazinyl", "piperidyl", "morpholinyl", or pyrrolidinyl", (also as parts of a larger group) is preferably unsubstituted.

"Isomer" includes especially optical isomers (for example essentially pure enantiomers, essentially pure diastereomers, and mixtures thereof) as well as conformation isomers (i.e. isomers that differ only in their angles of at least one chemical bond), position isomers (particularly tautomers), and geometric isomers (e.g. cis-trans isomers).

"Essentially pure", e.g. in connection with enantiomers or diastereomers means at least about 90%, preferably at least about 95%, more preferably at least about 97 or at least about 98%, even more preferably at least about 99%, and particularly preferably at least about 99.5% (w/w) of a specified compound, e.g. a particular enantiomer or diastereomer.

"Pharmaceutically acceptable" means being devoid of substantial toxic effects when used in doses usually employed in a medicinal dosage, and thereby being approvable or preferably being approved by a regulatory agency of the Federal or a state government or being listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2naphthalenesulfonic acid, 4-toluenesulfonic acid, camphorsulfonic acid, 4methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced.

"Pharmaceutically acceptable carrier" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

MODE FOR CARRYING OUT INVENTION

The present invention is more specifically explained by following examples and experimental examples. However, it should be understood that the extent of the present invention is not limited to the following examples and experimental examples

EXAMPLE 1

3-(6-tert-Butyl-pyridin-3-yl)-N-(3-fluoro-4-methane sulfonylamino-benzyl)-acrylamide

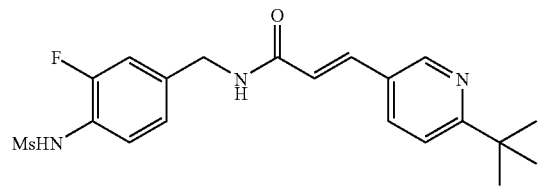

Step 1: Synthesis of 3-(6-tert-butyl-pyridin-3-yl)-acrylic acid

To a solution of 6-tert-butyl-pyridine-3-carboxaldehyde (1.34 g, 8.75 mmol) prepared by known procedure in toluene was added methyl(triphenylphosphoranylidene)acetate (2.93 g), and the resulting was heated at 90° C. for 3 hrs. The reaction mixture was diluted with EtOAc, and washed with water and brine. The organic layer was dried over anhydrous MgSO$_4$ and concentrated under reduced pressure. The resulting residue was purified by column chromatography (Hex/EtOAc=4/1) to give ester product (1.56 g, 81%). The resulting ester was dissolved in 1,4-dioxane, treated with water and KOH, stirred and heated at reflux for 18 hrs. The reaction mixture was cooled to room temperature, diluted with water, and then washed with ether. The aqueous phase was acidified with 1N HCl, and then extracted with CHCl$_3$, and the combined organic phase was washed with brine, dried over anhydrous MgSO$_4$ and concentrated under reduced pressure to give 3-(6-tert-butyl-pyridin-3-yl)-acrylic acid (1.00 g, 68%).

$^1$H NMR (300 MHz, CDCl$_3$): δ 8.78 (d, 1H, J=2.1 Hz), 7.84 (dd, 1H, J=2.1 and 8.4 Hz), 7.78 (d, 1H, J=16.2 Hz), 7.42 (d, 1H, J=8.4 Hz), 6.53 (d, 1H, J=16.2 Hz), 1.40 (s, 9H)

Step 2: Synthesis of 3-(6-tert-butyl-pyridin-3-yl)-N-(3-fluoro-4-methanesulfonylamino-benzyl)-acrylamide N-(4-Aminomethyl-2-fluoro-phenyl)-methanesulfonamide, HCl salt (50 mg, 0.20 mmol) was reacted with 3-(6-tert-butyl-pyridin-3-yl)-acrylic acid (40 mg) to give 3-(6-tert-butyl-pyridin-3-yl)-N-(3-fluoro-4-methanesulfonylamino-benzyl)-acrylamide (75 mg, 92%) after purification by column chromatography (Hex/EtOAc=1/2).

$^1$H NMR (300 MHz, CDCl$_3$): δ 8.70 (d, 1H, J=2.1 Hz), 7.77 (dd, 1H, J=2.1 and 8.1 Hz), 7.64 (d, 1H, J=15.6 Hz), 7.48 (m, 1H), 7.38 (d, 1H, J=8.4 Hz), 7.13 (m, 2H), 6.77 (s, 1H), 6.51 (d, 1H, J=15.6 Hz), 6.43 (t, 1H), 4.54 (d, 2H, J=6.0 Hz), 3.02 (s, 3H), 1.38 (s, 9H)

ESI [M+H]$^+$: 406.2.

EXAMPLE 2

3-(6-tert-Butyl-pyridin-3-yl)-N-(3-chloro-4-methane sulfonylamino-benzyl)-acrylamide

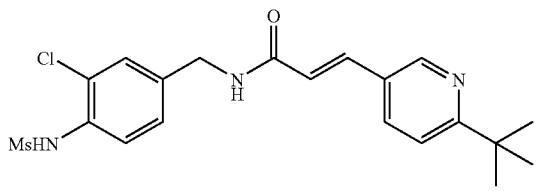

N-(4-Aminomethyl-2-chloro-phenyl)-methane sulfonamide, HCl salt (100 mg, 0.35 mmol) was reacted with 3-(6-tert-butyl-pyridin-3-yl)-acrylic acid (70 mg) to give 3-(6-tert-butyl-pyridin-3-yl)-N-(3-chloro-4-methanesulfonylamino-benzyl)-acrylamide (110 mg, 74%) after purification by column chromatography (Hex/EtOAc=1/2).

$^1$H NMR (300 MHz, CDCl$_3$): δ 8.66 (d, 1H, J=2.1 Hz), 7.74 (dd, 1H, J=2.1 and 8.1 Hz), 7.64 (d, 1H, J=15.6 Hz), 7.57 (d, 1H, J=8.7 Hz), 7.41 (d, 1H, J=2.1 Hz), 7.36 (d, 1H, J=8.1 Hz), 7.24 (dd, 1H, J=2.1 and 8.7 Hz), 6.82 (s, 1H), 6.48 (d, 1H, J=15.6 Hz), 6.42 (t, 1H), 4.53 (d, 2H, J=6.0 Hz), 3.00 (s, 3H), 1.37 (s, 9H)

ESI [M+H]$^+$: 422.2.

EXAMPLE 3

3-(6-tert-Butyl-pyridin-3-yl)-N-(3-ethynyl-5-fluoro-4-methane sulfonylamino-benzyl)-acrylamide

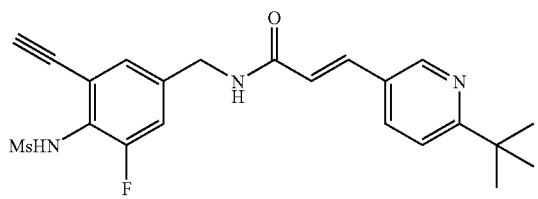

N-(4-Aminomethyl-2-ethynyl-6-fluoro-phenyl)-methanesulfonamide, HCl salt (70 mg, 0.25 mmol) was reacted with 3-(6-tert-butyl-pyridin-3-yl)-acrylic acid (52 mg) to give 3-(6-tert-butyl-pyridin-3-yl)-N-(3-ethynyl-5-fluoro-4-methanesulfonylamino-benzyl)-acrylamide (63 mg, 64%) after purification by column chromatography (Hex/EtOAc=1/2).

$^1$H NMR (300 MHz CDCl$_3$): δ 8.71 (d, 1H, J=2.4 Hz), 7.76 (dd, 1H, J=2.4 and 8.4 Hz), 7.63 (d, 1H, J=16.0 Hz), 7.39 (d, 1H, J=8.4 Hz), 7.28 (s, 1H), 7.16 (dd, 1H, J=2.1 and 11.0 Hz), 6.64 (s, 1H), 6.52 (d, 1H, J=16.0 Hz), 6.47 (t, 1H), 4.51 (d, 2H, J=6.0 Hz), 3.45 (s, 1H), 3.24 (s, 3H), 1.38 (s, 9H)

ESI [M+H]$^+$: 430.1.

EXAMPLE 4

3-(6-tert-Butyl-pyridin-3-yl)-N-(4-methanesulfonylamino-3-vinyl-benzyl)-acrylamide

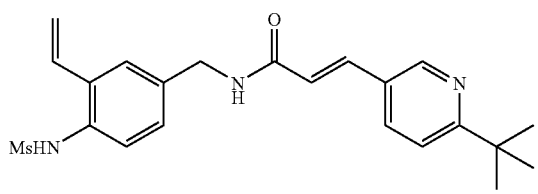

N-(4-Aminomethyl-2-vinyl-phenyl)-methanesulfonamide, HCl salt (70 mg, 0.28 mmol) was reacted with 3-(6-tert-butyl-pyridin-3-yl)-acrylic acid (52 mg) to give 3-(6-tert-butyl-pyridin-3-yl)-N-(4-methanesulfonylamino-3-vinyl-benzyl)-acrylamide (62 mg, 54%) after purification by column chromatography (Hex EtOAc=1/2).

$^1$H NMR (300 MHz, CDCl$_3$): δ 8.66 (d, 1H, J=1.8 Hz), 7.74 (dd, 1H, J=2.1 and 8.4 Hz), 7.63 (d, 1H, J=16.0 Hz), 7.44 (d, 1H, J=2.1 Hz), 7.36 (m, 2H), 7.23 (m, 2H), 6.90 (dd, 1H, J=11.0 and 17.0 Hz), 6.70 (s, 1H), 6.48 (d, 1H, J=16.0 Hz), 6.40 (t, 1H), 5.70 (d, 1H, J=17.0 Hz), 5.43 (d, 1H, J=11.0 Hz), 4.54 (d, 2H, J=5.7 Hz), 2.98 (s, 3H), 1.37 (s, 9H)

ESI [M+H]$^+$: 414.2.

EXAMPLE 5

N-(3-Fluoro-4-methanesulfonylamino-benzyl)-3-(2-morpholin-4-yl-6-trifluoromethyl-pyridin-3-yl)-acrylamide

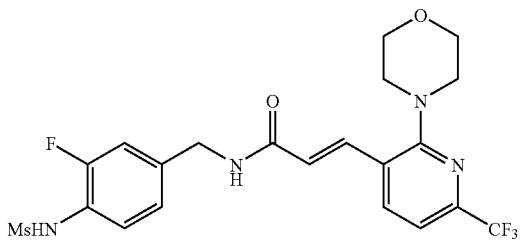

N-(4-Aminomethyl-2-fluoro-phenyl)-methanesulfonamide, HCl salt (100 mg, 0.40 mmol) was reacted with 3-(2-morpholin-4-yl-6-trifluoromethyl-pyridin-3-yl)-acrylic acid (121 mg) prepared by known procedure to give N-(3-fluoro-4-methanesulfonylamino-benzyl)-3-(2-morpholin-4-yl-6-trifluoromethyl-pyridin-3-yl)-acrylamide (118 mg, 66%) after purification by column chromatography (CH$_2$Cl$_2$/MeOH=20/1).

$^1$H NMR (300 MHz, CDCl$_3$+DMSO-d$_6$): δ 9.13 (s, 1H), 8.32 (t, 1H), 7.96 (d, 1H, J=7.8 Hz), 7.79 (d, 1H, J=15.9 Hz), 7.56 (t, 1H, J=8.4 Hz), 7.38 (d, 1H, J=7.8 Hz), 7.26 (m, 2H), 6.80 (d, 1H, J=15.9 Hz), 4.63 (d, 2H, J=5.7 Hz), 3.98 (m, 4H), 3.46 (m, 4H), 3.13 (s, 3H)

ESI [M+H]$^+$: 503.1.

EXAMPLE 6

N-(4-Methanesulfonylamino-3-vinyl-benzyl)-3-(2-morpholin-4-yl-6-trifluoromethyl-pyridin-3-yl)-acrylamide

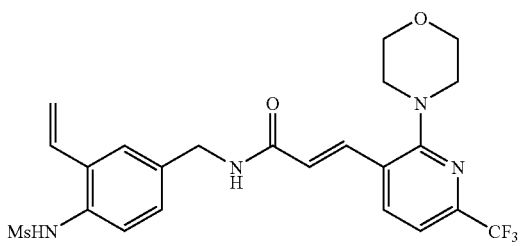

N-(4-Aminomethyl-2-vinyl-phenyl)-methanesulfonamide, HCl salt (70 mg, 0.27 mmol) was reacted with 3-(2-morpholin-4-yl-6-trifluoromethyl-pyridin-3-yl)-acrylic acid (81 mg) to give N-(4-methanesulfonylamino-3-vinyl-benzyl)-3-(2-morpholin-4-yl-6-trifluoromethyl-pyridin-3-yl)-acrylamide (55 mg, 45%) after purification by column chromatography (CH$_2$Cl$_2$/MeOH=20/1).

$^1$H NMR (300 MHz, CDCl$_3$+DMSO-d$_6$): δ 8.92 (s, 1H), 8.18 (s, 1H), 7.97 (d, 1H, J=7.8 Hz), 7.83 (d, 1H, J=16.0 Hz), 7.73 (s, 1H), 7.44 (m, 3H), 7.33 (dd, 1H, J=11.0 and 17.0 Hz), 6.83 (d, 1H, J=16.0 Hz), 5.93 (d, 1H, J=17.0 Hz), 6.55 (d, 1H, J=11.0 Hz), 4.69 (d, 2H, J=5.1 Hz), 4.01 (m, 4H), 3.50 (m, 4H), 3.09 (s, 3H)

ESI [M+H]$^+$: 511.1.

EXAMPLE 7

N-(3-Chloro-4-methanesulfonylamino-benzyl)-3-(2-morpholin-4-yl-6-trifluoromethyl-pyridin-3-yl)-acrylamide

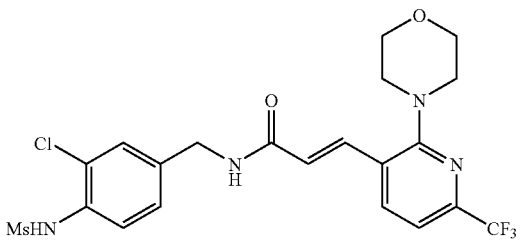

N-(4-Aminomethyl-2-chloro-phenyl)-methanesulfonamide, HCl salt (62 mg, 0.22 mmol) was reacted with 3-(2-morpholin-4-yl-6-trifluoromethyl-pyridin-3-yl)-acrylic acid (67 mg) to give N-(3-chloro-4-methanesulfonylamino-benzyl)-3-(2-morpholin-4-yl-6-trifluoromethyl-pyridin-3-yl)-acrylamide (93 mg, 91%) after purification by column chromatography ($CH_2Cl_2$/MeOH=20/1).

$^1$H NMR (300 MHz, $CDCl_3$+DMSO-$d_6$): δ 8.37 (s, 1H), 8.27 (t, 1H), 7.99 (d, 1H, J=7.8 Hz), 7.86 (d, 1H, J=15.9 Hz), 7.72 (d, 1H, J=8.4 Hz), 7.62 (m, 1H), 7.44 (m, 2H), 6.84 (d, 1H, J=15.9 Hz), 4.68 (d, 2H, J=5.7 Hz), 4.04 (m, 4H), 3.52 (m, 4H), 3.19 (s, 3H)

ESI [M+H]$^+$: 519.1.

EXAMPLE 8

N-(3-Fluoro-4-methanesulfonylamino-5-methyl-benzyl)-3-(2-morpholin-4-yl-6-trifluoromethyl-pyridin-3-yl)-acrylamide

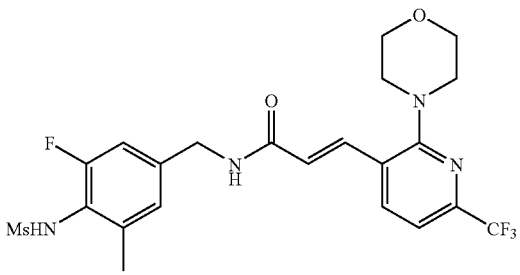

N-(4-Aminomethyl-2-fluoro-6-methyl-phenyl)-methanesulfonamide, HCl salt (100 mg, 0.35 mmol) was reacted with 3-(2-morpholin-4-yl-6-trifluoromethyl-pyridin-3-yl)-acrylic acid (116 mg) to give N-(3-fluoro-4-methanesulfonylamino-5-methyl-benzyl)-3-(2-morpholin-4-yl-6-trifluoromethyl-pyridin-3-yl)-acrylamide (120 mg, 74%) after purification by column chromatography (Hex EtOAc=1/2).

$^1$H NMR (300 MHz, $CDCl_3$): δ 7.76 (d, 1H, J=7.8 Hz), 7.71 (d, 1H, J=15.6 Hz), 7.24 (m, 3H), 6.42 (d, 1H, J=15.6 Hz), 6.32 (s, 1H), 6.06 (t, 1H), 4.59 (d, 2H, J=6.3 Hz), 3.85 (m, 4H), 3.34 (m, 4H), 3.05 (s, 3H), 2.25 (d, 3H, J=2.1 Hz)

ESI [M+H]$^+$: 517.1.

EXAMPLE 9

3-(6-tert-Butyl-2-methoxy-pyridin-3-yl)-N-(3-fluoro-4-methane sulfonylamino-benzyl)-acrylamide

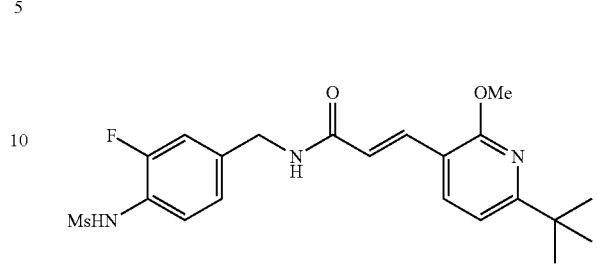

3-fluoro-4-methanesulfonylaminobenzylamine hydrochloride (17.8 mg, 0.052 mmol) was reacted with 3-(6-tert-butyl-2-methoxy-pyridin-3-yl)-acrylic acid (12 mg) DMTMM (1.1 eq, 16 mg) and NMP (1.2 eq, 90 μl) in THF to give the title compound (14 mg, 61.8%) after purification by column chromatography (Hex EtOAc=3/2).

$^1$H NMR (300 MHz, $CDCl_3$): δ 7.70 (d, 1H, J=15.6 Hz) 7.61 (d, 1H, J=9.3 Hz) 7.51 (m, 1H) 7.13 (m, 2H) 6.90 (d, 1H, J=7.8 Hz) 6.84 (d, 1H, J=15.6 Hz) 6.61 (bs, 1H) 6.10 (bs, 1H) 4.54 (d, 2H, J=6 Hz) 4.01 (s, 3H) 3.02 (s, 3H) 1.33 (s, 9H)

ESI [M+H]$^+$: 436.1.

EXAMPLE 10

3-(6-tert-Butyl-pyridin-3-yl)-N-(3-fluoro-4-methane sulfonylamino-5-vinyl-benzyl)-acrylamide

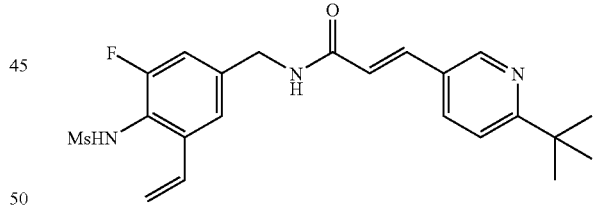

N-(4-Aminomethyl-2-fluoro-6-vinyl-phenyl)-methanesulfonamide, HCl salt (84 mg, 0.30 mmol) was reacted with 3-(6-tert-butyl-pyridin-3-yl)-acrylic acid (62 mg) to give 3-(6-tert-butyl-pyridin-3-yl)-N-(3-fluoro-4-methanesulfonylamino-5-vinyl-benzyl)-acrylamide (34 mg, 26%) after purification by column chromatography (Hex/EtOAc=1/2).

$^1$H NMR (300 MHz, $CDCl_3$+DMSO-$d_6$): δ 8.68 (d, 1H, J=2.4 Hz), 8.09 (s, 1H), 7.78 (dd, 1H, J=2.1 and 8.4 Hz), 7.61 (s, 1H), 7.56 (d, 1H, J=15.9 Hz), 7.35 (d, 1H, J=8.4 Hz), 7.33 (s, 1H), 7.12 (dd, 1H, J=14.8 and 18.0 Hz), 7.01 (dd, 1H, J=1.8 and 10.2 Hz), 6.60 (d, 1H, J=15.9 Hz), 5.73 (d, 1H, J=18.0 Hz), 5.33 (d, 1H, J=11.4 Hz), 4.46 (d, 2H, J=6.0 Hz), 2.97 (d, 3H, J=0.9 Hz), 1.34 (s, 9H)

ESI [M+H]$^+$: 432.2.

EXAMPLE 11

3-(6-tert-Butyl-2-methoxy-pyridin-3-yl)-N-(3-ethynyl-5-fluoro-4-methanesulfonylamino-benzyl)-acrylamide

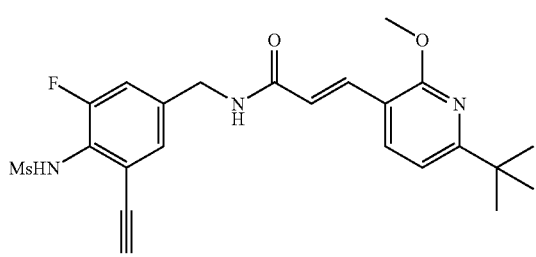

N-(4-Aminomethyl-2-ethynyl-6-fluoro-phenyl)-methanesulfonamide, HCl salt (82.4 mg, 0.30 mmol) was reacted with 3-(6-tert-butyl-2-methoxy-pyridin-3-yl)-acrylic acid (66 mg), DMTMM (1.1 eq, 90 mg) and NMP (1.2 eq, 40 μl) in THF to give the title compound (51.2 mg, 37.6%) after purification by column chromatography (Hex/EtOAc=1/1).

$^1$H NMR (300 MHz, CDCl$_3$): δ 7.70 (d, 1H, J=15.9 Hz) 7.62 (d, 1H, J=8.4 Hz) 7.30 (s, 1H) 7.17 (m, 1H) 6.91 (d, 1H, J=7.8 Hz) 6.69 (d, 1H, J=15.6 Hz) 6.41 (s, 1H) 6.02 (bs, 1H) 4.53 (d, 2H, J=6 Hz) 4.02 (s, 3H) 3.47 (s, 1H) 3.26 (s, 3H) 1.34 (s, 9H)

ESI [M+H]$^+$: 460.1.

EXAMPLE 12

N-(3-Ethynyl-5-fluoro-4-methanesulfonylaminobenzyl)-3-(2-morpholin-4-yl-6-trifluoromethyl-pyridin-3-yl)-acrylamide

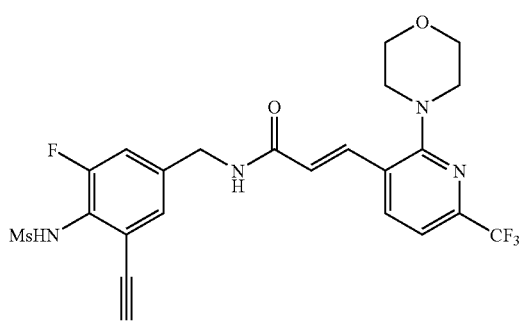

N-(4-Aminomethyl-2-ethynyl-6-fluoro-phenyl)-methanesulfonamide, HCl salt (100 mg, 0.22 mmol) was reacted with 3-(2-morpholin-4-yl-6-trifluoromethyl-pyridin-3-yl)-acrylic acid (108 mg) to give N-(3-ethynyl-5-fluoro-4-methanesulfonylamino-benzyl)-3-(2-morpholin-4-yl-6-trifluoromethyl-pyridin-3-yl)-acrylamide (190 mg, 100%) after purification by column chromatography (Hex EtOAc=1/2).

$^1$H NMR (300 MHz, CDCl$_3$+DMSO-d$_6$): δ 9.31 (s, 1H), 8.73 (t, 1H), 7.92 (d, 1H, J=7.8 Hz), 7.49 (d, 1H, J=15.6 Hz), 7.31 (d, 1H, J=7.8 Hz), 7.25 (s, 1H), 7.18 (d, 1H, J=10.8 Hz), 6.71 (d, 1H, J=15.6 Hz), 4.38 (d, 2H, J=5.7 Hz), 4.14 (s, 1H), 3.76 (m, 4H), 3.22 (m, 4H), 3.04 (s, 3H)

ESI [M+H]$^+$: 527.2.

EXAMPLE 13

2-(2-piperid-1-yl-6-chloro-pyridinyl-3-yloxy)-N-(3-fluoro-4-methanesulfonylamino-benzyl)-acetamide

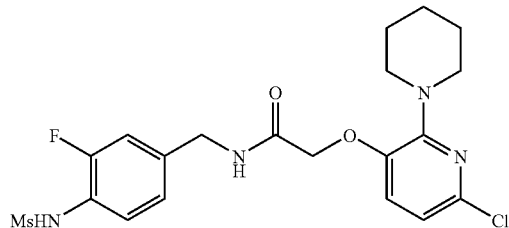

N-(4-Aminomethyl-3-fluoro-phenyl)-methanesulfonamide HCl salt (32 mg, 0.12 mmol) and NMP (0.05 ml) were added in 20 ml of THF. The mixture was stirred for 10 mins. DMTMM (51 mg, 0.18 mmol) and 2-(2-piperid-1-yl-6-chloro-pyridin-3-yloxy)-acetic acid (20 mg, 0.092 mmol) were added into the mixture. The reaction mixture was stirred overnight. The reaction solvent was removed in vacuo. The residue was extracted with ethylacetate (30 ml×3) and H$_2$O (30 ml). A combined organic layer was washed with sat. NaHCO$_3$ (30 ml), and with brine (30 ml), dried with MgSO$_4$, and concentrated in vacuo. The residue was purified with column chromatography to yield a white solid (11 mg).

$^1$H NMR (CDCl$_3$, 300 MHz) δ 7.87 (d, J=15.9 Hz, 1H), 7.62 (d, J=9.0 Hz, 1H), 7.51 (t, j=7.8 Hz, 1H), 7.12 (m, 2H), 6.39 (br, 1H), 6.51 (d, J=9.0 Hz, 1H), 6.20 (d, J=15.6 Hz), 6.00 (br, 1H), 5.53 (d, J=6.3 Hz, 2H), 3.60 (m, 4H), 3.01 (s, 3H), 1.65 (m, 6H)

ESI [M+H]$^+$: 467.1.

EXAMPLE 14

3-(6-Chloro-pyridin-3-yl)-N-(3-ethynyl-5-fluoro-4-methane sulfonylamino-benzyl)-acrylamide

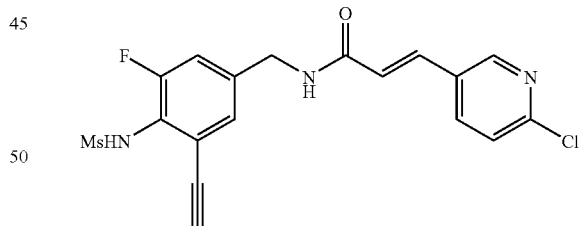

Step 1: 3-(6-Chloro-pyridin-3-yl)-acrylic acid methyl ester

To 6-chloro-pyridine-3-carboxaldehyde (300 mg, 2.12 mmol) in toluene was added methyl(triphenylphosphoranylidene)acetate (708 mg, 2.12 mmol) and the solution was refluxed for 6 hrs. The reaction mixture was diluted with EtOAc and then washed three times with H$_2$O, brine, dried. Na$_2$SO$_4$, filtered and concentrated under reduced pressure. The obtained residue was column-chromatographed to yield 3-(6-chloro-pyridin-3-yl)-acrylic acid methyl ester (380 mg, 90%).

$^1$H NMR (300 MHz, CDCl$_3$): δ 8.51 (d, 1H, J=2.7 Hz), 7.80 (dd, 1H, J=8.1, 2.4 Hz), 7.65 (d, 1H, J=15.9 Hz), 7.36 (d, 1H, J=8.4 Hz), 6.48 (d, 1H, J=15.9 Hz), 3.83 (s, 3H).

Step 2: 3-(6-Chloro-pyridin-3-yl)-acrylic acid 3-(6-Chloro-pyridin-3-yl)-acrylic acid methyl ester (107 mg, 0.541 mmol) in THF was added to a solution of 0.5 N-LiOH (2 eq) and the mixture was stirred for 3 hrs at room temperature. The resulting residue was dissolved in H$_2$O and then washed three times with Et$_2$O, neutralized with 1N HCl to pH 5~7. The resulting solid filtered and washed with H$_2$O and then dried in vacuo to give 3-(6-chloro-pyridin-3-yl)-acrylic acid (80 mg, 80%).

$^1$H NMR (300 MHz, DMSO-d$^6$): δ 8.64 (s, 1H), 8.16 (d, 1H, J=8.1 Hz), 7.54 (d, 1H, J=16.8 Hz), 7.50 (d, 1H, J=9.9 Hz), 6.63 (d, 1H, J=15.9 Hz).

Step 3: 3-(6-Chloro-pyridin-3-yl)-N-(3-ethynyl-5-fluoro-4-methane sulfonylamino-benzyl)-acrylamide N-(4-Aminomethyl-2-ethynyl-6-fluoro-phenyl)-methanesulfonamide HCl salt (78.3 mg, 0.272 mmol) was suspended in THF and treated with triethylamine (30 mg, 0.299 mmol) and then the resulting mixture was stirred for 10 mins. 3-(6-chloro-pyridin-3-yl)-acrylic acid (50 mg, 0.272 mmol) was added to the reaction mixture followed by DMTMM (82 mg, 0.299 mmol) after 10 mins. The resulting mixture was stirred overnight at ambient temperature and then diluted with EtOAc. The resulting solution was washed successively with water, sat'd NaHCO$_3$ (×2), brine, and then dried over anhyd. Na$_2$SO$_4$, filtered and concentrated under reduced pressure. The crude residue was recrystallized (CH$_2$Cl) to yield the title compound (26 mg, 23%).

$^1$H NMR (300 MHz, DMSO-d$^6$): δ 9.54 (s, 1H), 8.74 (t, 1H, J=6.0 Hz), 8.61 (d, 1H, J=2.4 Hz), 8.07 (dd, 1H, J=8.4, 2.4 Hz), 7.56 (d, 1H, J=8.4 Hz), 7.51 (d, 1H, J=15.9 Hz), 7.34 (t, 1H, J=8.1 Hz), 7.19 (d, 1H, J=12.0 Hz), 7.12 (d, 1H, J=8.4 Hz), 6.79 (d, 1H, J=15.9 Hz), 4.39 (d, 2H, J=5.7 Hz), 3.00 (s, 3H).

ESI [M+H]$^+$; 408.0.

EXAMPLE 15

3-(6-Bromo-pyridin-3-yl)-N-(3-ethynyl-5-fluoro-4-methane sulfonylamino-benzyl)-acrylamide

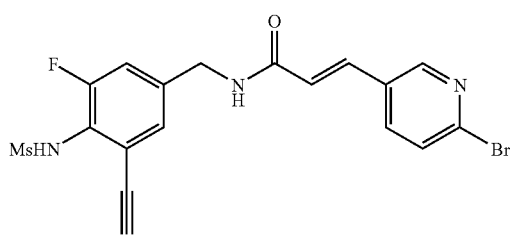

Step 1: 3-(6-Bromo-pyridin-3-yl)-acrylic acid methyl ester

To 6-bromo-pyridine-3-carboxaldehyde (300 mg, 1.61 mmol) in toluene was added methyl(triphenylphosphoranylidene)acetate (647 mg, 1.94 mmol) and the solution was refluxed for 6 hrs. The reaction mixture was diluted with EtOAc and then washed three times with H$_2$O, brine, dried. Na$_2$SO$_4$, filtered and concentrated under reduced pressure. The obtained residue was column-chromatographed to yield 3-(6-bromo-pyridin-3-yl)-acrylic acid methyl ester (380 mg, 97%).

$^1$H NMR (300 MHz, CDCl$_3$): δ 8.47 (d, 1H, J=2.4 Hz), 7.68 (dd, 1H, J=8.4, 2.4 Hz), 7.60 (d, 1H, J=15.9 Hz), 7.51 (d, 1H, J=8.4 Hz), 6.49 (d, 1H, J=15.9 Hz), 3.81 (s, 3H).

Step 2: 3-(6-Bromo-pyridin-3-yl)-acrylic acid

To 3-(6-bromo-pyridin-3-yl)-acrylic acid methyl ester (120 mg, 0.495 mmol) in THF was added a solution of 0.5 N-LiOH (2 eq) and the mixture was stirred for 3 hrs at room temperature. The resulting residue was dissolved in H$_2$O, then washed three times with Et$_2$O, and neutralized with 1N HCl to pH 5~7. The resulting solid filtered and washed with H$_2$O and then dried in vacuo to give 3-(6-bromo-pyridin-3-yl)-acrylic acid (100 mg, 88%).

$^1$H NMR (300 MHz, DMSO-d$^6$): δ 8.67 (d, 1H, J=2.1 Hz), 8.11 (dd, 1H, J=8.4, 2.1 Hz), 7.69 (d, 1H, J=8.4 Hz), 7.59 (d, 1H, J=15.9 Hz), 6.71 (d, 1H, J=15.9 Hz).

Step 3: 3-(6-Bromo-pyridin-3-yl)-N-(3-ethynyl-5-fluoro-4-methanesulfonylamino-benzyl)-acrylamide N-(4-Aminomethyl-2-ethynyl-6-fluoro-phenyl)-methanesulfonamide HCl salt (63 mg, 0.219 mmol) was suspended in THF and treated with triethylamine (25 mg, 0.241 mmol) and then the resulting mixture was stirred for 10 mins. 3-(6-bromo-pyridin-3-yl)-acrylic acid (50 mg, 0.219 mmol) was added to the reaction mixture followed by DMTMM (66 mg, 0.241 mmol) after 10 mins. The resulting mixture was stirred overnight at ambient temperature and then diluted with EtOAc. The resulting solution was washed successively with water, sat'd NaHCO$_3$ (×2), and brine, and then dried over anhyd. Na$_2$SO$_4$, filtered and concentrated under reduced pressure. The crude residue was recrystallized (EtOAc/n-Hexane) to yield the title compound (71 mg, 72%).

$^1$H NMR (300 MHz, DMSO-d$^6$): δ 9.42 (s, 1H), 8.77 (t, 1H, J=6.0 Hz), 8.60 (d, 1H, J=2.4 Hz), 7.96 (dd, 1H, J=8.1, 1.8 Hz), 7.70 (d, 1H, J=8.1 Hz), 7.48 (d, 1H, J=15.9 Hz), 7.28 (s, 1H), 7.27 (d, 1H, J=8.7 Hz), 6.81 (d, 1H, J=15.9 Hz), 4.50 (s, 1H), 4.39 (d, 2H, J=5.7 Hz), 3.06 (s, 3H).

ESI [M+H]$^+$; 452.0.

EXAMPLE 16

3-(6-Chloro-pyridin-3-yl)-N-(3-fluoro-4-methane sulfonylamino-benzyl)-acrylamide

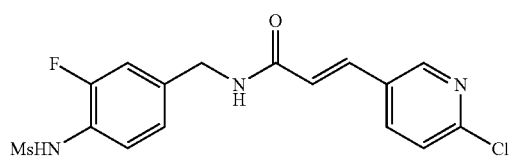

3-Fluoro-4-methanesulfonylaminobenzylamine hydrochloride (51 mg, 0.201 mmol) was suspended in THF and treated with triethylamine (23 mg, 0.22 mmol) and then the resulting mixture was stirred for 10 mins. 3-(6-chloro-pyridin-3-yl)-acrylic acid (37 mg, 0.201 mmol) was added to the reaction mixture followed by DMTMM (61 mg, 0.22 mmol) after 10 mins. The resulting mixture was stirred overnight at ambient temperature and then diluted with EtOAc. The resulting solution was washed successively with water, sat'd NaHCO$_3$ (×2), brine, and then dried over anhyd. Na$_2$SO$_4$, filtered and concentrated under reduced pressure. The crude residue was column-chromatographed to yield the title compound (74 mg, 96%).

$^1$H NMR (300 MHz, DMSO-d$^6$): δ 9.54 (s, 1H), 8.74 (t, 1H, J=6.0 Hz), 8.62 (d, 1H, J=2.4 Hz), 8.07 (dd, 1H, J=6.0, 2.4 Hz), 7.57 (d, 1H, J=8.4 Hz), 7.51 (d, 1H, J=15.9 Hz), 7.34 (t, 1H, J=8.1 Hz), 7.19 (d, 1H, J=12.0 Hz), 7.12 (d, 1H, J=8.4 Hz), 6.79 (d, 1H, J=15.9 Hz), 4.39 (d, 2H, J=5.7 Hz), 3.00 (s, 3H).

ESI [M+H]$^+$; 384.0.

EXAMPLE 17

3-(6-tert-Butyl-4-trifluoromethyl-pyridin-3-yl)-N-(3-fluoro-4-methanesulfonylamino-benzyl)-acrylamide

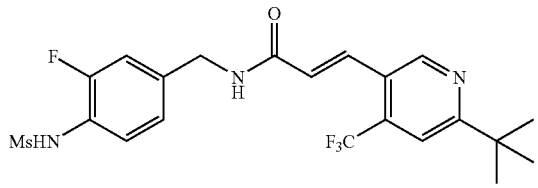

3-Fluoro-4-methanesulfonylaminobenzylamine hydrochloride (41.2 mg, 0.162 mmol) was reacted with 3-(6-tert-butyl-4-trifluoromethyl-pyridin-3-yl)-acrylic acid (1.0 eq, 44.2 mg) DMTMM (1.0 eq, 44.8 mg) and NMP (1.2 eq, 22 μl) in THF to give the title compound (48 mg, 62.6%) after purification by column chromatography (Hex/EtOAc=1/1).

$^1$H NMR (300 MHz, CDCl$_3$): δ 8.84 (s, 1H) 7.93 (d, 1H, J=15.3 Hz) 7.57 (s, 1H) 7.52 (t, 1H) 7.14 (m, 1H) 6.60 (bs, 1H) 6.45 (d, 1H, J=15.6 Hz) 6.24 (bs, 1H) 6.50 (bs, 1H) 4.54 (d, 2H, J=6.0 Hz) 3.03 (s, 3H) 1.39 (s, 9H)

ESI [M+H]$^+$: 474.2.

EXAMPLE 18

3-(6-tert-Butyl-4-trifluoromethyl-pyridin-3-yl)-N-(3-ethynyl-5-fluoro-4-methanesulfonylamino-benzyl)-acrylamide

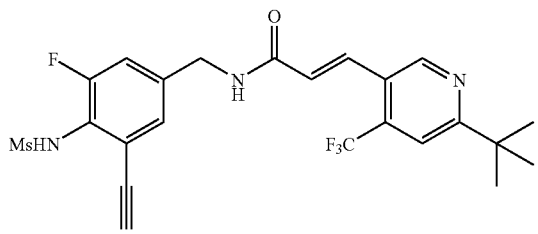

N-(4-Aminomethyl-2-ethynyl-6-fluoro-phenyl)-methanesulfonamide HCl salt (11.2 mg, 0.04 mmol) was reacted with 3-(6-tert-butyl-4-trifluoromethyl-pyridin-3-yl)-acrylic acid (1.0 eq, 11.0 mg) DMTMM (1.0 eq, 11.1 mg) and NMP (1.2 eq, 6 μl) in THF to give the title compound (6 mg, 30.2%) after purification by column chromatography (Hex/EtOAc=3/2).

$^1$H NMR (300 MHz, CDCl$_3$): δ 8.85 (s, 1H) 7.95 (d, 1H, J=13.5 Hz) 7.58 (s, 1H) 7.32 (bs, 1H) 7.20 (d, 1H, J=12.6 Hz) 6.05 (bs, 1H) 4.54 (d, 1H, J=6.0 Hz) 3.49 (s, 1H) 3.27 (s, 3H) 1.40 (s, 9H)

ESI [M+H]$^+$: 498.2

EXAMPLE 19

N-(3-Fluoro-4-methanesulfonylamino-benzyl)-3-(6-piperid-1-yl-pyridinyl-3-yl)-acrylamide

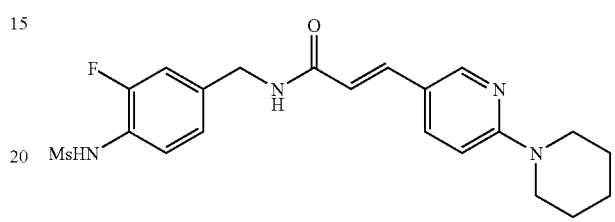

Step 1: 3-(6-piperid-1-yl-pyridinyl-3-yl)-acrylic acid methyl ester 3-(6-Bromo-pyridin-3-yl)-acrylic acid methyl ester (180 mg, 0.74 mmol) was added to piperidine (1 ml) and the mixture was stirred for 1.5 hrs at room temperature. The reaction mixture was diluted with EtOAc and then washed three times with H$_2$O, brine, dried. Na$_2$SO$_4$, filtered and concentrated under reduced pressure. The obtained residue was column-chromatographed to yield 3-(6-piperid-1-yl-pyridinyl-3-yl)-acrylic acid methyl ester (60 mg, 33%).

$^1$H NMR (300 MHz, CDCl$_3$): δ 8.25 (d, 1H, J=2.1 Hz), 7.63 (dd, 1H, J=6.0, 2.4 Hz), 7.58 (d, 1H, J=15.9 Hz), 6.62 (d, 1H, J=9.3 Hz), 6.21 (d, 1H, J=15.9 Hz), 3.78 (s, 3H), 3.64-3.61 (m, 4H), 1.66-1.60 (m, 6H).

Step 2: N-(3-Fluoro-4-methanesulfonylamino-benzyl)-3-(6-piperid-1-yl-pyridinyl-3-yl)-acrylamide 3-Fluoro-4-methanesulfonylaminobenzylamine hydrochloride (25.2 mg, 0.099 mmol) was suspended in THF and treated with triethylamine (11 mg, 0.108 mmol) and then the resulting mixture was stirred for 10 mins. 3-(6-piperid-1-yl-pyridinyl-3-yl)-acrylic acid (23 mg, 0.099 mmol) was added to the reaction mixture followed by DMTMM (30 mg, 0.108 mmol) after 10 mins. The resulting mixture was stirred overnight at ambient temperature and then diluted with EtOAc. The resulting solution was washed successively with water, sat'd NaHCO$_3$ (×2), brine, and then dried over anhyd. Na$_2$SO$_4$, filtered and concentrated under reduced pressure. The crude residue was recrystallized (CH$_2$Cl$_2$) to yield the title compound (15 mg, 35%).

$^1$H NMR (300 MHz, CDCl$_3$): δ 8.25 (d, 1H, J=2.7 Hz), 7.59 (dd, 1H, J=6.0, 2.7 Hz), 7.52 (d, 1H, J=15.9 Hz), 7.15 (t, 1H, J=6.0 Hz), 6.62 (d, 1H, J=9.0 Hz), 6.21 (d, 1H, J=15.3 Hz), 6.01 (s, 1H, br), 4.53 (d, 2H, J=6.0 Hz), 3.62-3.59 (m, 4H), 3.01 (s, 3H), 1.65-1.64 (m, 6H).

ESI [M+H]$^+$: 433.2.

EXAMPLE 20

3-(6-Bromo-pyridin-3-yl)-N-(3-fluoro-4-methane sulfonylamino-benzyl)-acrylamide

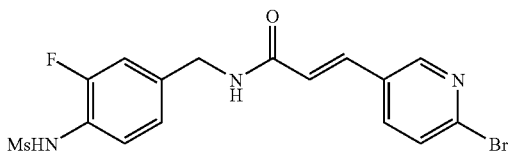

3-Fluoro-4-methanesulfonylaminobenzylamine hydrochloride (183 mg, 0.719 mmol) was suspended in THF and treated with triethylamine (80 mg, 0.791 mmol) and then the resulting mixture was stirred for 10 mins. (6-Chloro-pyridin-3-yloxy)-acetic acid (164 mg, 0.719 mmol) was added to the reaction mixture followed by DMTMM (218 mg, 0.791 mmol) after 10 mins. The resulting mixture was stirred overnight at ambient temperature and then diluted with EtOAc. The resulting solution was washed successively with water, sat'd NaHCO$_3$ (×2), brine, and then dried over anhyd. Na$_2$SO$_4$, filtered and concentrated under reduced pressure. The crude residue was recrystallized (CH$_2$Cl$_2$) to yield the title compound (225 mg, 65%).

$^1$H NMR (300 MHz, DMSO-d$^6$): δ 9.54 (s, 1H), 8.75 (t, 1H, J=6.0 Hz), 8.59 (d, 1H, J=2.1 Hz), 7.95 (dd, 1H, J=8.4, 2.4 Hz), 7.71 (d, 1H, J=8.4 Hz), 7.49 (d, 1H, J=15.9 Hz), 7.34 (t, 1H, J=8.1 Hz), 7.19 (d, 1H, J=12.0 Hz), 7.12 (d, 1H, J=8.4 Hz), 6.79 (d, 1H, J=15.9 Hz), 4.39 (d, 2H, J=5.7 Hz), 3.00 (s, 3H).

ESI [M+H]$^+$: 428.0.

EXAMPLE 21

N-(3,5-Difluoro-4-methanesulfonylamino-benzyl)-3-(2-morpholin-4-yl-6-trifluoromethyl-pyridin-3-yl)-acrylamide

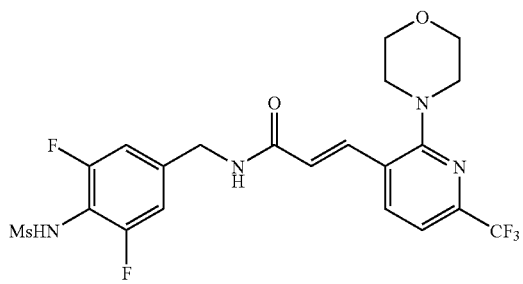

N-(4-Aminomethyl-2,6-difluoro-phenyl)-methane-sulfonamide, HCl salt (50 mg, 0.22 mmol) was reacted with 3-(2-morpholin-4-yl-6-trifluoromethyl-pyridin-3-yl)-acrylic acid (55 mg) to give N-(3,5-difluoro-4-methanesulfonylamino-benzyl)-3-(2-morpholin-4-yl-6-trifluoromethyl-pyridin-3-yl)-acrylamide (37 mg, 39%) after purification by column chromatography (Hex/EtOAc=1/2).

$^1$H NMR (300 MHz, CDCl$_3$): δ 7.78 (d, 1H, J=8.11 Hz), 7.75 (d, 1H, J=15.3 Hz), 7.25 (d, 1H, J=8.1 Hz), 6.98 (d, 2H, J=8.4 Hz), 6.46 (d, 1H, J=15.3 Hz), 6.15 (s, 1H), 6.10 (t, 1H), 4.38 (d, 2H, J=6.6 Hz), 3.85 (m, 4H), 3.35 (m, 4H), 3.21 (s, 3H)

ESI [M+H]$^+$: 521.1.

EXAMPLE 22

N-(3-Fluoro-4-methanesulfonylamino-5-trifluoromethyl-benzyl)-3-(2-morpholin-4-yl-6-trifluoromethyl-pyridin-3-yl)-acrylamide

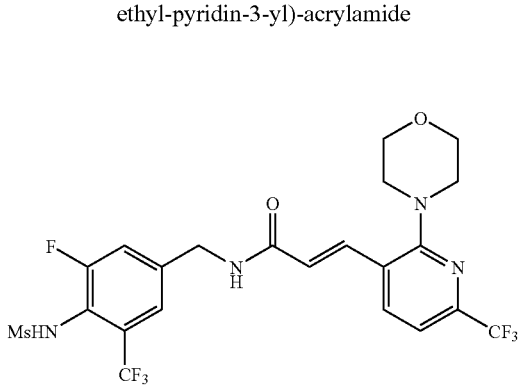

N-(4-Aminomethyl-2-fluoro-6-trifluoromethyl-phenyl)-methanesulfonamide, HCl salt (80 mg, 0.25 mmol) was reacted with 3-(2-morpholin-4-yl-6-trifluoromethyl-pyridin-3-yl)-acrylic acid (76 mg) to give N-(3-fluoro-4-methanesulfonylamino-5-trifluoromethyl-benzyl)-3-(2-morpholin-4-yl-6-trifluoromethyl-pyridin-3-yl)-acrylamide (56 mg, 39%) after purification by column chromatography (Hex/EtOAc=1/2).

$^1$H NMR (300 MHz, CDCl$_3$): δ 8.71 (s, 1H), 8.21 (t, 1H), 7.65 (d, 1H, J=7.8 Hz), 7.49 (d, 1H, J=15.6 Hz), 7.29 (s, 1H), 7.22 (d, 1H, J=9.9 Hz), 7.07 (d, 1H, J=7.8 Hz), 6.48 (d, 1H, J=15.6 Hz), 4.36 (d, 2H, J=6.0 Hz), 3.67 (m, 4H), 3.18 (m, 4H), 3.02 (s, 3H)

ESI [M+H]$^+$: 571.

EXAMPLE 23

N-(3-Ethynyl-5-fluoro-4-methanesulfonylamino-benzyl)-3-(6-morpholin-4-yl-pyridin-3-yl)-acrylamide

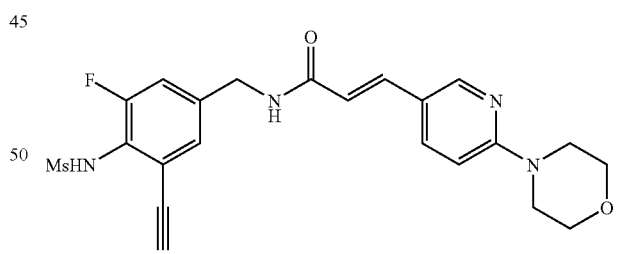

Step 1: 3-(6-Morpholin-4-yl-pyridin-3-yl)-acrylic acid methyl ester 3-(6-Bromo-pyridin-3-yl)-acrylic acid methyl ester (100 mg, 0.413 mmol) was added to piperidine (1 ml) and the mixture was stirred for 1.5 hrs at room temperature. The reaction mixture was diluted with EtOAc and then washed three times with H$_2$O, brine, dried. Na$_2$SO$_4$, filtered and concentrated under reduced pressure. The obtained residue was column-chromatographed to yield 3-(6-Morpholin-4-yl-pyridin-3-yl)-acrylic acid methyl ester (40 mg, 21%).

¹H NMR (300 MHz, CDCl₃): δ 8.27 (d, 1H, J=2.4 Hz), 7.68 (dd, 1H, J=6.0, 2.4 Hz), 7.59 (d, 1H, J=15.9 Hz), 6.62 (d, 1H, J=9.3 Hz), 6.25 (d, 1H, J=15.3 Hz), 3.82-3.78 (m, 7H), 3.61-3.57 (m, 4H).

Step 2: N-(3-Ethynyl-5-fluoro-4-methanesulfonylamino-benzyl)-3-(6-morpholin-4-yl-pyridin-3-yl)-acrylamide N-(4-Aminomethyl-2-ethynyl-6-fluoro-phenyl)-methanesulfonamide HCl salt (20 mg, 0.072 mmol) was suspended in THF and treated with triethylamine (11 mg, 0.108 mmol) and then the resulting mixture was stirred for 10 mins. 3-(6-morpholin-4-yl-pyridin-3-yl)-acrylic acid (17 mg, 0.072 mmol) was added to the reaction mixture followed by DMTMM (22 mg, 0.08 mmol) after 10 mins. The resulting mixture was stirred overnight at ambient temperature and then diluted with EtOAc. The resulting solution was washed successively with water, sat'd NaHCO₃ (×2), brine, and then dried over anh. Na₂SO₄, filtered and concentrated under reduced pressure. The crude residue was recrystallized (CH₂Cl) to yield the title compound (8 mg, 24%).

¹H NMR (300 MHz, DMSO-d⁶): δ 9.39 (s, 1H), 8.52 (t, 1H, J=5.4 Hz), 8.24 (s, 1H), 7.74 (d, 1H, J=8.7 Hz), 7.34 (d, 1H, J=15.9 Hz), 7.22-7.19 (m, 2H), 6.84 (d, 1H, J=9.3 Hz), 6.45 (d, 1H, J=15.9 Hz), 4.46 (s, 1H), 4.31 (d, 2H, J=5.7 Hz), 3.63-3.62 (m, 4H), 3.48-3.47 (m, 4H), 3.01 (s, 3H).

ESI [M+H]⁺: 459.

EXAMPLE 24

N-(3-Ethynyl-5-fluoro-4-methanesulfonylamino-benzyl)-3-(2-piperid-1-yl-6-trifluoromethyl-pyridinyl-3-yl)-acrylamide

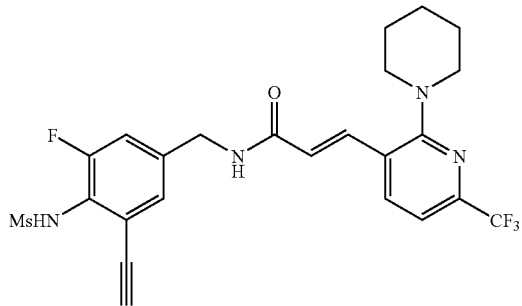

Step 1: Synthesis of 3-(2-piperid-1-yl-6-trifluoromethyl-pyridinyl-3-yl)-acrylic acid 3-(2-Piperid-1-yl-6-trifluoromethyl-pyridinyl-3-yl)-acrylic acid (720 mg) was prepared by similar procedure as described in the previous from 2-chloro-6-trifluoromethylnicotinic acid in an overall yield of 54%.

¹H NMR (300 MHz, CDCl₃): δ 7.81 (m, 2H), 7.18 (d, 1H, J=7.5 Hz), 6.45 (d, 1H, J=16.2 Hz), 3.31 (m, 4H), 1.72 (m, 6H)

Step 2: Synthesis of N-(3-ethynyl-5-fluoro-4-methanesulfonylamino-benzyl)-3-(2-piperid-1-yl-6-trifluoromethyl-pyridinyl-3-yl)-acrylamide N-(4-Aminomethyl-2-ethynyl-6-fluoro-phenyl)-methanesulfonamide HCl salt (139 mg, 0.50 mmol) was reacted with 3-(2-piperid-1-yl-6-trifluoromethyl-pyridinyl-3-yl)-acrylic acid (150 mg) to give N-(3-Ethynyl-5-fluoro-4-methanesulfonylamino-benzyl)-3-(2-piperid-1-yl-6-trifluoromethyl-pyridinyl-3-yl)-acrylamide (132 mg, 50%) after purification by column chromatography (Hex/EtOAc=1/1).

¹H NMR (300 MHz, CDCl₃): δ 7.72 (m, 2H), 7.30 (s, 1H), 7.16 (m, 2H), 6.44 (s, 1H), 6.43 (d, 1H, J=15.6 Hz), 6.10 (s, 1H), 4.53 (d, 2H, J=6.0 Hz), 3.48 (s, 1H), 3.30 (m, 4H), 3.26 (s, 3H), 1.65 (m, 6H)

ESI [M+H]⁺: 525.

EXAMPLE 25

N-(3-Fluoro-4-methanesulfonylamino-benzyl)-3-(6-pyrrolidin-1-yl-pyridin-3-yl)-acrylamide

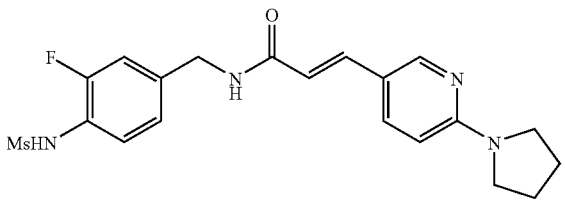

3-(6-Chloro-pyridin-3-yl)-N-(3-fluoro-4-methanesulfonylamino-benzyl)-acrylamide (15 mg, 0.413 mmol) was added to pyrrolidine (0.5 ml) and the mixture was stirred for 12 hrs at 90° C. The resulting residue was dissolved in EtOAc, then washed three times with H₂O, and neutralized with 1N HCl to pH 5~7. The resulting solution was washed with brine, and then dried over anhyd. Na₂SO₄, filtered and concentrated under reduced pressure. The crude residue was recrystallized (CH₂Cl₂) to yield the title compound (4 mg, 24%).

¹H NMR (300 MHz, DMSO-d⁶): 6, 8.41 (t, 1H, J=6.0 Hz), 8.15 (s, 1H), 7.65 (d, 1H, J=8.7 Hz), 7.29 (d, 1H, J=16.8 Hz), 7.26 (d, 1H, J=16.5 Hz), 7.10 (d, 1H, J=11.7 Hz), 7.02 (d, 1H, J=7.5 Hz), 6.43 (d, 1H, J=9.3 Hz), 6.36 (d, 1H, J=15.6 Hz), 4.29 (d, 2H, J=5.7 Hz), 3.85-3.75 (m, 4H), 2.92 (s, 3H), 3.48-3.47 (m, 4H).

ESI [M+H]⁺: 419.

EXAMPLE 26

N-(3-Fluoro-4-methanesulfonylamino-benzyl)-3-(2-piperid-1-yl-6-trifluoromethyl-pyridinyl-3-yl)-acrylamide

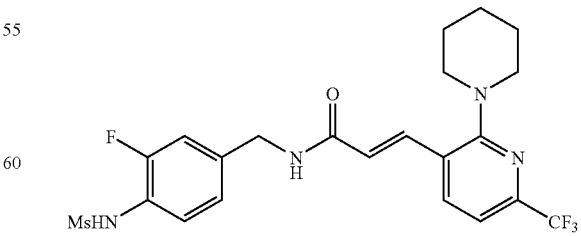

N-(4-Aminomethyl-2-fluoro-phenyl)-methanesulfonamide, HCl salt (127 mg, 0.50 mmol) was reacted with 3-(2-piperid-1-yl-6-trifluoromethyl-pyridinyl-3-yl)-acrylic acid (150 mg) to give N-(3-fluoro-4-methanesulfonylamino-benzyl)-3-(2-piperid-1-yl-6-trifluoromethyl-pyridinyl-3-yl)-acrylamide (175 mg, 70%) after purification by column chromatography (Hex EtOAc=1/1).

¹H NMR (300 MHz, CDCl₃): δ 7.70 (m, 2H), 7.50 (t, 1H, J=8.1 Hz), 7.12 (m, 3H), 6.65 (s, 1H), 6.45 (d, 1H, J=15.6 Hz), 6.14 (t, 1H), 4.54 (d, 2H, J=6.0 Hz), 3.29 (m, 4H), 3.02 (s, 3H), 1.70 (m, 6H)

ESI [M+H]⁺: 501.

EXAMPLE 27

N-(3-Fluoro-4-methanesulfonylamino-5-methyl-benzyl)-3-(2-morpholin-4-yl-6-trifluoromethyl-pyridin-3-yl)-propionamide

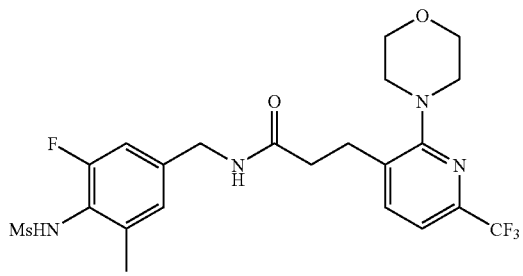

A suspension of N-(3-fluoro-4-methanesulfonylamino-5-methyl-benzyl)-3-(2-morpholin-4-yl-6-trifluoromethyl-pyridin-3-yl)-acrylamide (32 mg, 0.069 mmol) and 10% Pd/C (3 mg) in MeOH was reacted under hydrogen of 40 psi pressure. The reaction mixture was filtered through celite and then concentrated under reduced pressure to give N-(3-fluoro-4-methanesulfonylamino-5-methyl-benzyl)-3-(2-morpholin-4-yl-6-trifluoromethyl-pyridin-3-yl)-propionamide (22 mg, 69%).

¹H NMR (300 MHz, CDCl₃): δ 7.61 (d, 1H, J=6.9 Hz), 7.27 (d, 1H, J=8.4 Hz), 7.10 (m, 2H), 6.51 (s, 1H), 6.21 (s, 1H), 4.42 (d, 2H, J=5.1 Hz), 3.86 (m, 4H), 3.20 (m, 4H), 3.07 (m, 2H), 3.03 (s, 3H), 2.63 (m, 2H), 2.22 (d, 3H, J=2.4 Hz)

ESI [M+H]⁺: 519.

EXAMPLE 28

2-(2-Bromo-6-tert-butyl-pyridin-3-yloxy)-N-(3-fluoro-4-methane sulfonylamino-benzyl)-acetamide

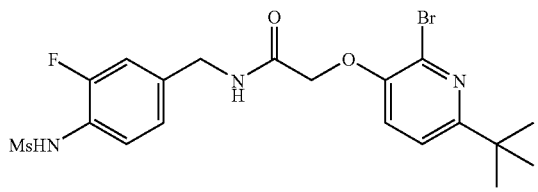

3-Fluoro-4-methanesulfonylaminobenzylamine hydrochloride (72 mg, 0.25 mmol) was reacted with (2-bromo-6-tert-butyl-pyridin-3-yloxy)-acetic acid (64 mg), DMTMM (1.2 eq, 83 mg) and NEt₃ (2.5 eq, 90 µl) in THF to give the title compound (71 mg, 58.2%) after purification by column chromatography (Hex/EtOAc=1/1).

¹H NMR (300 MHz, CDCl₃): δ 7.56 (m, 1H) 7.24 (m, 2H) 7.11 (m, 3H) 6.48 (bs, 1H) 4.58 (s, 2H) 4.55 (d, 2H, J=6 Hz) 3.03 (s, 3H) 1.33 (s, 9H)

ESI [M+H]⁺: 488.

EXAMPLE 29

2-(6-tert-Butyl-pyridin-3-yloxy)-N-(3-fluoro-4-methane sulfonylamino-benzyl)-acetamide

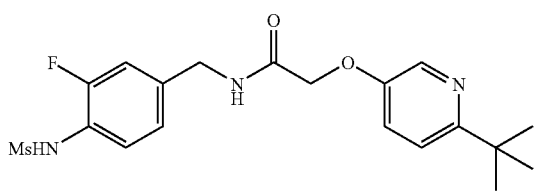

3-Fluoro-4-methanesulfonylaminobenzylamine hydrochloride (158 mg, 0.62 mmol) was reacted with (6-tert-butyl-pyridin-3-yloxy)-acetic acid (130 mg) DMTMM (1.2 eq, 206 mg) and NEt₃(2.5 eq, 220 µl) in THF to give the title compound (165 mg, 65%) after purification by column chromatography (Hex/EtOAc=1/3).

¹H NMR (300 MHz, CDCl₃) δ 8.33 (d, 1H, J=0.6 Hz) 7.38 (m, 1H) 7.21 (bs, 1H) 6.96 (m, 2H) 6.88 (m, 2H) 4.71 (s, 2H) 4.52 (d, 2H, J=6 Hz) 2.99 (s, 3H) 1.47 (s, 9H)

ESI [M+H]⁺: 409.

EXAMPLE 30

2-(6-tert-Butyl-2-chloro-pyridin-3-yloxy)-N-(3-fluoro-4-methane sulfonylamino-benzyl)-acetamide

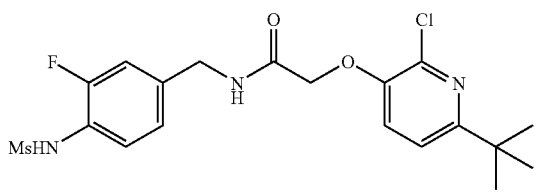

3-Fluoro-4-methanesulfonylaminobenzylamine hydrochloride (21 mg, 0.08 mmol) was reacted with (6-tert-butyl-2-chloro-pyridin-3-yloxy)-acetic acid (1.0 eq, 20 mg) DMTMM (1.2 eq, 27 mg) and NMM (1.5 eq, 14 µl) in THF to give the title compound (10 mg, 28.2%) after purification by column chromatography (Hex/EtOAc=1/1).

¹H NMR (300 MHz, CDCl₃): δ 7.55 (m, 1H) 7.23 (s, 1H) 7.16 (s, 1H) 7.13 (m, 2H) 7.10 (bs, 1H) 6.50 (bs, 1H) 4.59 (s, 2H) 4.54 (d, 2H, J=6.3 Hz) 3.03 (s, 3H) 1.33 (s, 9H)

ESI [M+H]⁺: 444.

EXAMPLE 31

N-(3-Fluoro-4-methanesulfonylamino-benzyl)-2-(2-hydroxymethyl-6-methyl-pyridin-3-yloxy)-acetamide

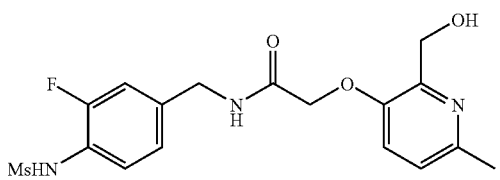

Step 1: Synthesis of (2-hydroxymethyl-6-methyl-pyridin-3-yloxy)-acetic acid (2-Hydroxymethyl-6-methyl-pyridin-3-yloxy)-acetic acid (200 mg) was prepared by similar procedure as described above from 2,6-lutidine-$\alpha^2$,3-diol in an overall yield of 51%.
$^1$H NMR (300 MHz, DMSO-$d_6$): δ 7.24 (d, 1H, J=8.1 Hz), 7.10 (d, 1H, J=8.1 Hz), 4.73 (s, 2H), 4.54 (s, 2H), 2.40 (s, 3H)

Step 2: Synthesis of N-(3-fluoro-4-methanesulfonylamino-benzyl)-2-(2-hydroxymethyl-6-methyl-pyridin-3-yloxy)-acetamide N-(4-Aminomethyl-2-fluoro-phenyl)-methanesulfonamide HCl salt (270 mg, 1.00 mmol) was reacted with (2-hydroxymethyl-6-methyl-pyridin-3-yloxy)-acetic acid (200 mg) to give N-(3-fluoro-4-methanesulfonylamino-benzyl)-2-(2-hydroxymethyl-6-methyl-pyridin-3-yloxy)-acetamide (350 mg, 88%) after purification by column chromatography (Hex/EtOAc=10/1).
$^1$H NMR (300 MHz DMSO-$d_6$): δ 8.69 (t, 1H), 7.29 (m, 2H), 7.09 (m, 3H), 5.10 (t, 1H), 4.66 (s, 2H), 4.60 (d, 2H, J=5.4 Hz), 4.31 (d, 2H, J=6.3 Hz), 2.99 (s, 3H), 2.40 (s, 3H)
ESI [M+H]$^+$: 398.

EXAMPLE 32

N-(3-Fluoro-4-methanesulfonylamino-benzyl)-2-(6-trifluoromethyl-pyridin-3-yloxy)-acetamide

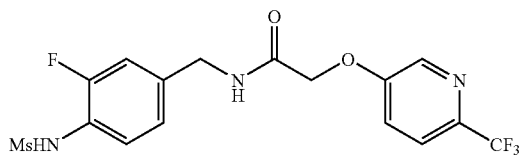

Step 1: Synthesis of (6-trifluoromethyl-pyridin-3-yloxy)-acetic acid (6-Trifluoromethyl-pyridin-3-yloxy)-acetic acid (410 mg) was prepared by similar procedure as described above from 2-trifluoromethyl-5-hydroxypyridine in an overall yield of 93%
$^1$H NMR (300 MHz, DMSO-$d_6$): δ 8.29 (d, 1H, J=2.7 Hz), 7.75 (d, 1H, J=8.7 Hz), 7.34 (dd, 1H, J=2.7 and 8.7 Hz), 4.33 (s, 2H)

Step 2: Synthesis of N-(3-fluoro-4-methanesulfonylamino-benzyl)-2-(6-trifluoromethyl-pyridin-3-yloxy)-acetamide N-(4-Aminomethyl-2-fluoro-phenyl)-methanesulfonamide HCl salt (270 mg, 1.00 mmol) was reacted with (6-trifluoromethyl-pyridin-3-yloxy)-acetic acid (221 mg) to give N-(3-fluoro-4-methanesulfonylamino-benzyl)-2-(6-trifluoromethyl-pyridin-3-yloxy)-acetamide (54 mg, 88%) after recrystallization from Hex/EtOAc.
$^1$H NMR (300 MHz DMSO-$d_6$): δ 9.52 (s, 1H), 8.80 (t, 1H), 8.49 (d, 1H, J=2.7 Hz), 7.87 (d, 1H, J=9.0 Hz), 7.60 (dd, 1H, J=2.7 and 9.0 Hz), 7.32 (m, 1H), 7.11 (m, 2H), 4.80 (s, 2H), 4.33 (d, 2H, J=6.3 Hz), 2.99 (s, 3H)
ESI [M+H]$^+$: 422.

EXAMPLE 33

2-(6-tert-Butyl-5-chloro-pyridin-3-yloxy)-N-(3-fluoro-4-methane sulfonylamino-benzyl)-acetamide

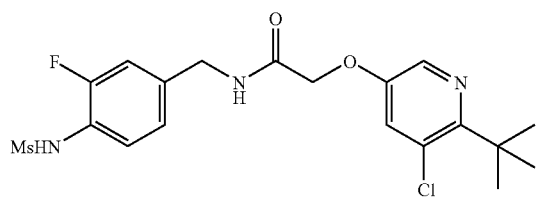

3-Fluoro-4-methanesulfonylaminobenzylamine hydrochloride (192 mg, 0.751 mmol) was reacted with (6-tert-butyl-5-chloro-pyridin-3-yloxy)-acetic acid (183 mg) DMTMM (1.1 eq, 229 mg) and NMM (1.2 eq, 100 μl) in THF to give the title compound (102 mg, 30.6%) after purification by column chromatography (Hex/EtOAc=1/1).
$^1$H NMR (300 MHz, CDCl$_3$): δ 8.18 (d, 1H, J=1.8 Hz) 7.56 (t, 1H) 7.10 (m, 2H) 7.07 (m, 1H) 6.71 (bs, H) 6.50 (bs, 1H) 4.60 (s, 2H) 4.54 (d, 2H, J=6 Hz) 3.03 (s, 3H) 1.38 (s, 9H)
ESI [M+H]$^+$: 444.

EXAMPLE 34

2-(6-tert-Butyl-pyridin-3-yloxy)-N-(3-ethynyl-5-fluoro-4-methane sulfonylamino-benzyl)-acetamide

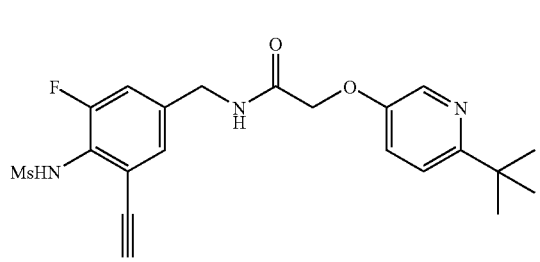

N-(4-Aminomethyl-2-ethynyl-6-fluoro-phenyl)-methanesulfonamide HCl salt (120 mg, 0.43 mmol) was reacted with (6-tert-butyl-pyridin-3-yloxy)-acetic acid (90 mg) DMTMM (1.1 eq, 131 mg) and NMP (1.2 eq, 60 μl) in THF to give the title compound (62 mg, 33.3%) after purification by column chromatography (Hex EtOAc=2/3).

¹H NMR (300 MHz, CDCl₃): δ 8.36 (d, 1H, J=1.8 Hz) 7.22 (bs, 1H) 7.18 (m, 1H) 7.06 (m, 1H) 6.89 (ts, 1H) 6.64 (s, 1H) 4.68 (s, 2H) 4.51 (d, 2H, J=6 Hz) 3.46 (s, 1H) 3.23 (s, 3H) 1.47 (s, 9H)

ESI [M+H]⁺: 434.

EXAMPLE 35

2-(6-Chloro-pyridin-3-yloxy)-N-(3-ethynyl-5-fluoro-4-methane sulfonylamino-benzyl)-acetamide

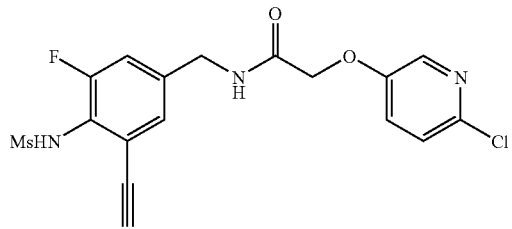

Step 1: (6-Chloro-pyridin-3-yloxy)-acetic acid ethyl ester

To a suspension of 6-chloro-pyridin-3-ol (1000 mg, 7.72 mmol) and bromoethyl acetate (1933 mg, 11.57 mmol) in CH₃CN was added Cs₂CO₃ (3772 mg, 11.57 mmol). The mixture was stirred for overnight at room temperature. The reaction mixture was diluted with EtOAc, then washed three times with H₂O and brine, and then dried. MgSO₄, filtered and concentrated under reduced pressure. The obtained residue was column-chromatographed to yield the (6-chloro-pyridin-3-yloxy)-acetic acid ethyl ester (1.5 g, 90%).

¹H-NMR (300 MHz, CDCl₃): δ 8.07 (dd, 1H, J=2.7, 0.9 Hz), 7.27-7.23 (m, 2H), 4.65 (s, 2H), 4.28 (q, 2H, J=7.2 Hz), 1.30 (t, 3H, J=7.2 Hz).

Step 2: (6-Chloro-pyridin-3-yloxy)-acetic acid (6-Chloro-pyridin-3-yloxy)-acetic acid ethyl ester (800 mg, 3.71 mmol) in THF was added to a solution of 0.5 N-LiOH (2 eq) and the mixture was stirred for 1.5 hrs at room temperature. The resulting residue was dissolved in H₂O, then washed three times with Et₂O, and neutralized with 1N HCl to pH 5~7. The solution was extracted three times with methylene chloride and then dried over anhyd. Na₂SO₄ and concentrated in vacuo to give (6-chloro-pyridin-3-yloxy)-acetic acid (300 mg, 36%).

¹H-NMR (300 MHz, CDCl₃): δ 8.05 (d, 1H, J=3.3 Hz), 7.43-7.35 (m, 2H), 4.74 (s, 2H).

Step 3: 2-(6-Chloro-pyridin-3-yloxy)-N-(3-ethynyl-5-fluoro-4-methanesulfonylamino-benzyl)-acetamide N-(4-Aminomethyl-2-ethynyl-6-fluoro-phenyl)-methanesulfonamide (74.3 mg, 0.266 mmol) was suspended in THF and treated with triethylamine (27 mg, 0.266 mmol) and then the resulting mixture was stirred for 10 mins. (6-chloro-pyridin-3-yloxy)-acetic acid (50 mg, 0.266 mmol) was added to the reaction mixture followed by DMTMM (62.5 mg, 0.266 mmol) after 10 mins. The resulting mixture was stirred overnight at ambient temperature and then diluted with EtOAc. The resulting solution was washed successively with water, sat'd NaHCO₃ (×3), and brine, and then dried over anh. MgSO₄, filtered and concentrated under reduced pressure. The crude residue was recrystallized (CH₂Cl₂) to yield the title compound (25 mg, 25%).

¹H NMR (300 MHz, CDCl₃): δ 8.13 (dd, 1H, J=3.0, 0.9 Hz), 7.34-7.24 (m, 3H), 7.14 (dd, 1H, J=10.5, 2.1 Hz), 6.90 (s, 1H, br), 6.44 (s, 1H), 4.58 (s, 2H), 4.53 (s, 1H), 4.50 (d, 2H, J=6.3 Hz), 3.26 (s, 3H).

ESI [M+H]⁺: 412.

EXAMPLE 36

3-(2-Bromo-6-tert-butyl-pyridin-3-yl)-N-(3-fluoro-4-methane sulfonylamino-benzyl)-acrylamide

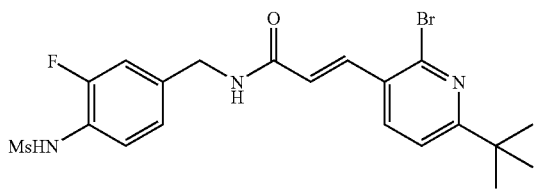

3-Fluoro-4-methanesulfonylaminobenzylamine hydrochloride (116 mg, 0.454 mmol) was reacted with 3-(2-bromo-6-tert-butyl-pyridin-3-yl)-acrylic acid (1.0 eq, 129 mg) DMTMM (1.0 eq, 126 mg) and NMP (1.2 eq, 60 μl) in THF to give the title compound (72 mg, 32.8%) after purification by column chromatography (Hex/EtOAc=1/1).

¹H NMR (300 MHz, CDCl₃): δ 7.89 (d, 1H, J=12.9 Hz), 7.72 (d, 1H, J=7.8 Hz) 7.56 (m, 1H) 7.29 (d, 1H, J=8.4 Hz) 7.15 (m, 2H) 6.46 (bs, 1H) 6.36 (d, 1H, J=15.3 Hz) 6.01 (bs, 1H) 4.56 (d, 2H, J=6.3 Hz) 3.03 (s, 3H) 1.35 (s, 9H)

EXAMPLE 37

3-(2-Bromo-6-tert-butyl-pyridin-3-yl)-N-(3-ethynyl-5-fluoro-4-methanesulfonylamino-benzyl)-acrylamide

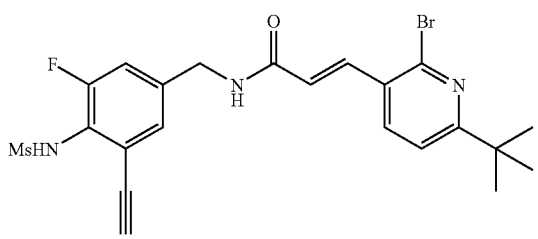

N-(4-Aminomethyl-2-ethynyl-6-fluoro-phenyl)-methanesulfonamide HCl salt (41.2 mg, 0.148 mmol) was reacted with 3-(2-bromo-6-tert-butyl-pyridin-3-yl)-acrylic acid (1.0 eq, 42 mg), DMTMM (1.0 eq, 41 mg) and NMP (1.2 eq, 20 μl) in THF to give the title compound (42 mg, 55.8%) after purification by column chromatography (Hex/EtOAc=3/2).

¹H NMR (300 MHz, CDCl₃): δ 7.90 (d, 1H, J=15.9 Hz), 7.73 (d, 1H, J=7.5 Hz) 7.31 (m, 1H) 7.28 (s, 1H) 7.17 (dd, 1H,

J=2.1 Hz and 1.5 Hz) 6.41 (s, 1H), 6.37 (d, 1H, J=15.7 Hz) 6.09 (bs, 1H), 4.53 (d, 2H, J=6.0 Hz), 3.48 (s, 1H), 3.27 (s, 3H) 1.35 (s, 9H)

EXAMPLE 38

3-(2-Diethylamino-6-trifluoromethyl-pyridin-3-yl)-N-(3-ethynyl-5-fluoro-4-methanesulfonylamino-benzyl)-acrylamide

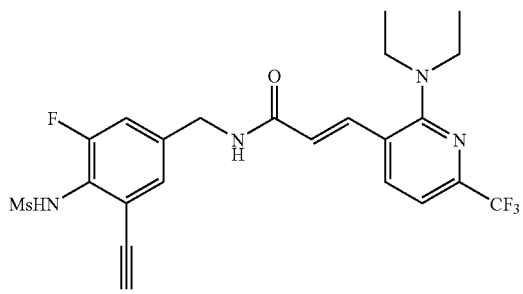

Step 1: 2-Chloro-N-methoxy-N-methyl-6-trifluoromethyl-nicotinamide

To a suspension of 2-chloro-6-trifluoromethyl-nicotinic acid (200 mg, 0.88 mmol) and N,O-dimethylhydroxylamine hydrochloride (95 mg, 0.97 mmol) in $CH_2Cl_2$ (3 mL) was added N-methylmorpholine (0.106 ml, 0.97 mmol). The mixture was stirred for 5 minutes, to which was added N-(3-dimethylaminopropyl)-N'-ethylcarbodiimide hydrochloride (185 mg, 0.97 mmol). The mixture was stirred for 3 hours at room temperature, and then diluted with EtOAc and water. The organic layer was washed with 1N HCl, saturated sodium bicarbonate and brine, dried over anhydrous magnesium sulfate, filtered and concentrated under reduced pressure. The product was vacuum dried to yield the 2-chloro-N-methoxy-N-methyl-6-trifluoromethyl-nicotinamide (220 mg, 92%).

$^1$H NMR (300 MHz, $CDCl_3$): δ 7.86 (d, 1H, J=7.8 Hz), 7.69 (d, 1H, J=7.8 Hz), 3.52 (s, 3H), 3.42 (s, 3H).

Step 2: 2-Diethylamino-N-methoxy-N-methyl-6-trifluoromethyl-nicotinamide

To a suspension of 2-chloro-N-methoxy-N-methyl-6-trifluoromethyl-nicotinamide (400 mg, 1.489 mmol) and diethylamine (0.773 ml, 7.44 mmol) in DMF (4 ml) was added $K_2CO_3$ (1.02 g, 7.44 mmol). The mixture was stirred for 4 hours at 110° C. The reaction mixture was diluted with EtOAc (30 ml) and then washed two times with 1N-HCl (30 ml) and brine, dried over $MgSO_4$, filtered and concentrated under reduced pressure. The crude residue was chromatographed to yield the 2-diethylamino-N-methoxy-N-methyl-6-trifluoromethyl-nicotinamide (400 mg, 88%).

$^1$H NMR (300 MHz, $CDCl_3$): δ 7.50 (d, 1H, J=7.5 Hz), 6.90 (d, 1H, J=7.5 Hz), 3.54-3.41 (m, 7H), 3.29 (s, 3H), 1.71 (t, 6H, J=7.2 Hz).

Step 3: 2-Diethylamino-6-trifluoromethyl-pyridine-3-carbaldehyde

To a suspension of 2-diethylamino-N-methoxy-N-methyl-6-trifluoromethyl-nicotinamide (66 mg, 0.216 mmol) in THF (2 mL) was added dropwise 1.0M $LiAlH_4$ (0.108 ml, 0.108 mmol) at −78° C. The mixture was warmed up to −20° C. for 30 min. The reaction mixture was diluted with $Et_2O$ and washed two times with 1N $KHSO_4$ and brine, dried over anhyd. $MgSO_4$, filtered and concentrated under reduced pressure. The product was vacuum dried to yield the 2-diethylamino-6-trifluoromethyl-pyridin-3-yl-carbaldehyde (43 mg, 75%).

$^1$H NMR (300 MHz, $CDCl_3$): δ 9.98 (s, 1H), 8.07 (d, 1H, J=7.5 Hz), 7.05 (d, 1H, J=7.5 Hz), 3.54 (q, 4H, J=7.2 Hz), 1.27 (t, 6H, J=7.2 Hz).

Step 4: 3-(2-Diethylamino-6-trifluoromethyl-pyridin-3-yl)-acrylic acid methyl ester To a solution of 2-diethylamino-6-trifluoromethyl-pyridin-3-yl-carbaldehyde (39 mg, 0.147 mmol) in toluene was added methyl(triphenylphosphoranylidene)acetate (73.8 mg, 0.221 mmol), and the resulting mixture was heated at 90° C. for 3 hrs. The reaction mixture was diluted with EtOAc, and washed with water and brine. The organic layer was dried over anhydrous $MgSO_4$ and concentrated under reduced pressure. The resulting residue was purified by column chromatography (Hex EtOAc=10/1) to give 3-(2-diethylamino-6-trifluoromethyl-pyridin-3-yl)-acrylic acid methyl ester (40 mg, 90%).

$^1$H NMR (300 MHz, $CDCl_3$): δ 7.73 (d, 1H, J=16.2 Hz), 7.72 (d, 1H, J=8.1 Hz), 6.36 (d, 1H, J=16.2 Hz), 3.82 (s, 3H), 3.38 (q, 4H, J=7.2 Hz), 1.78 (t 6H, J=7.2 Hz).

Step 5: 3-(2-Diethylamino-6-trifluoromethyl-pyridin-3-yl)-acrylic acid

To a suspension of 3-(2-diethylamino-6-trifluoromethyl-pyridin-3-yl)-acrylic acid methyl ester (40 mg, 0.132 mmol) in THF (1 ml) was added a solution of 0.5 N-LiOH (0.3 ml), and the mixture was stirred for 3 hours at room temperature. The resulting residue was dissolved in $H_2O$ and then washed three times with EtOAc, acidified with 1N HCl to pH 1~2. The solution was extracted three times with methylene chloride and then dried over anhyd. $Na_2SO_4$ and concentrated in vacuo to give 3-(2-diethylamino-6-trifluoromethyl-pyridin-3-yl)-acrylic acid (33 mg, 87%).

$^1$H NMR (300 MHz, $CDCl_3$): δ 7.79 (d, 1H, J=18.0 Hz), 7.74 (d, 1H, J=8.1 Hz), 7.09 (d, 1H, J=7.5 Hz), 6.37 (d, 1H, J=15.6 Hz), 3.38 (q, 4H, J=7.2 Hz), 1.22 (t, 6H, J=7.2 Hz).

Step 6: 3-(2-Diethylamino-6-trifluoromethyl-pyridin-3-yl)-N-(3-ethynyl-5-fluoro-4-methanesulfonylamino-benzyl)-acrylamide To a suspension of N-(4-aminomethyl-2-ethynyl-6-fluorophenyl)-methanesulfonamide HCl salt (476 mg, 1.66 mmol) in THF (5 mL) was added N-methylmorpholine (0.365 ml, 3.32 mmol). The mixture was stirred for 5 minutes, to which were added 3-(2-diethylamino-6-trifluoromethyl-pyridin-3-yl)-acrylic acid (434 mg, 1.51 mmol) and 4-(4,6-dimethoxy[1,3,5]triazin-2-yl)-4-methylmorpholinium chloride hydrate (DMTMM, 459 mg, 1.66 mmol). The mixture was stirred overnight at room temperature and was concentrated under reduced pressure. The residue was diluted with EtOAc and water. The organic layer was washed with saturated sodium bicarbonate, 1N HCl and brine, dried over anhydrous magnesium sulfate, filtered, and concentrated under reduced pressure. The crude residue was purified by recrystallization from $CH_2Cl_2$ to give the title compound (645 mg, 83%).

$^1$H NMR (300 MHz, $CDCl_3$): δ 7.73 (d, 1H, J=16.5 Hz), 7.69 (d, 1H, J=8.4 Hz), 7.28 (d, 1H, J=7.8 Hz), 7.16 (d, 1H,

J=11.1 Hz), 7.07 (d, 1H, J=7.8 Hz), 6.44 (s, 1H), 6.35 (d, 1H, J=15.3 Hz), 6.10 (s, 1H), 4.51 (d, 2H, J=5.7 Hz), 3.47 (s, 1H), 3.38 (q, 4H, J=7.2 Hz), 3.26 (s, 1H), 1.19 (t, 6H, J=7.2 Hz)

ESI [M+H]+: 513

EXAMPLE 39

3-(6-tert-Butyl-pyridin-3-yl)-N-(3,5-difluoro-4-methane sulfonylamino-benzyl)-acrylamide

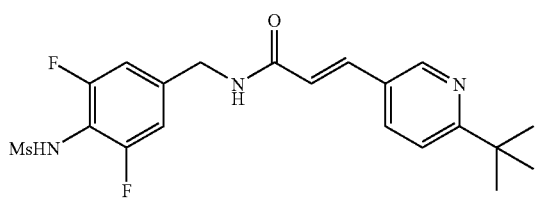

Step 1: 3-(6-tert-Butyl-pyridin-3-yl)-acrylic acid

To a solution of 6-tert-butyl-pyridin-3-yl-carbaldehyde (1.34 g, 8.75 mmol), prepared by known procedure, in toluene was added methyl(triphenylphosphoranylidene)acetate (2.93 g), and the resulting mixture was heated at 90° C. for 3 hrs. The reaction mixture was diluted with EtOAc, and washed with water and brine. The organic layer was dried over anhydrous MgSO4 and concentrated under reduced pressure. The resulting residue was purified by column chromatography (Hex/EtOAc=4/1) to give ester product (1.56 g, 81%). The resulting ester was dissolved in 1,4-dioxane, treated with water and KOH, stirred and heated at reflux for 18 hrs. The reaction mixture was cooled to room temperature, diluted with water, and then washed with ether. The aqueous phase was acidified with 1N HCl, and then extracted with CHCl3, and the combined organic phase was washed with brine, dried over anhydrous MgSO4 and concentrated under reduced pressure to give 3-(6-tert-butyl-pyridin-3-yl)-acrylic acid (1.00 g, 68%).

1H NMR (300 MHz, CDCl3): δ 8.78 (d, 1H, J=2.1 Hz), 7.84 (dd, 1H, J=2.1 and 8.4 Hz), 7.78 (d, 1H, J=16.2 Hz), 7.42 (d, 1H, J=8.4 Hz), 6.53 (d, 1H, J=16.2 Hz), 1.40 (s, 9H)

Step 2: 3-(6-tert-Butyl-pyridin-3-yl)-N-(3,5-difluoro-4-methane sulfonylamino-benzyl)-acrylamide N-(4-Aminomethyl-2,6-difluoro-phenyl)-methanesulfonamide HCl salt (50 mg, 0.18 mmol) was reacted with 3-(6-tert-butyl-pyridin-3-yl)-acrylic acid (37 mg) to give the title compound (60 mg, 79%) after purification by column chromatography (Hex/EtOAc=1/2).

1H NMR (300 MHz, CDCl3+DMSO-d6): δ 8.69 (d, 1H, J=2.4 Hz), 7.98 (7, 1H, J=6.0 Hz), 7.76 (dd, 1H, J=2.4 and 8.4 Hz), 7.63 (d, 1H, J=15.6 Hz), 7.37 (d, 1H, J=8.4 Hz), 6.99 (d, 2H, J=8.1 Hz), 6.63 (d, 1H, J=15.6 Hz), 4.50 (d, 2H, J=6.0 Hz), 3.11 (s, 3H), 1.37 (s, 9H)

ESI [M+H]+: 424

EXAMPLE 40

3-(2-Chloro-6-trifluoromethyl-pyridin-3-yl)-N-(3-ethynyl-5-fluoro-4-methanesulfonylamino-benzyl)-acrylamide

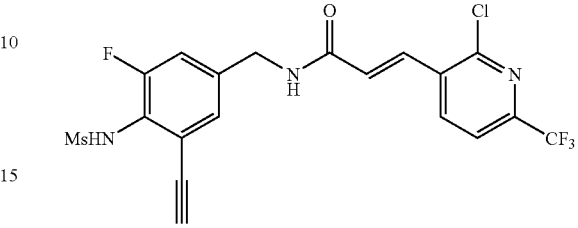

Step 1: 2-Chloro-6-trifluoromethyl-pyridin-3-yl-carbaldehyde

The title compound was obtained according to the general procedure described in example 38 (step 3).

2-Chloro-N-methoxy-N-methyl-6-trifluoromethyl-nicotinamide (1.109 mg, 4.128 mmol) was reacted with 1.0M LiAlH4 (0.5 eq) to give 2-chloro-6-trifluoromethyl-pyridin-3-yl-carbaldehyde (844 mg, 97%).

1H NMR (300 MHz, CDCl3): δ 10.49 (s, 1H), 8.41 (d, 1H, J=7.8 Hz), 7.79 (d, 1H, J=7.8 Hz).

Step 2: 3-(2-Chloro-6-trifluoromethyl-pyridin-3-yl)-acrylic acid methyl ester

The title compound was obtained according to the general procedure described in example 38 (step 4).

2-Chloro-6-trifluoromethyl-pyridin-3-yl-carbaldehyde (844 mg, 4.027 mmol) was reacted with methyl(triphenylphosphoranylidene)acetate (1.62 g, 4.83 mmol) to give 3-(2-chloro-6-trifluoromethyl-pyridin-3-yl)-acrylic acid methyl ester (900 mg, 84%).

1H NMR (300 MHz, CDCl3): δ 8.08 (d, 1H, J=8.1 Hz), 7.99 (d, 1H, J=15.9 Hz), 7.67 (d, 1H, J=8.1 Hz), 6.53 (d, 1H, J=15.9 Hz), 3.86 (s, 3H).

Step 3: 3-(2-Chloro-6-trifluoromethyl-pyridin-3-yl)-acrylic acid

The title compound was obtained according to the general procedure described in example 38 (step 5).

3-(2-Chloro-6-trifluoromethyl-pyridin-3-yl)-acrylic acid methyl ester (200 mg, 0.753 mmol) was reacted with 0.5N-LiOH (2 eq) to give 3-(2-chloro-6-trifluoromethyl-pyridin-3-yl)-acrylic acid (189 mg, 99%).

1H NMR (300 MHz, DMSO-d6): δ 8.56 (d, 1H, J=8.1 Hz), 7.93 (d, 1H, J=8.1 Hz), 7.68 (d, 1H, J=15.9 Hz), 6.77 (d, 1H, J=15.9 Hz).

Step 4: 3-(2-Chloro-6-trifluoromethyl-pyridin-3-yl)-N-(3-ethynyl-5-fluoro-4-methanesulfonylamino-benzyl)-acrylamide The title compound was obtained according to the general procedure described in example 38 (step 6).

N-(4-Aminomethyl-2-ethynyl-6-fluoro-phenyl)-methanesulfonamide HCl salt (228 mg, 0.795 mmol) was reacted with 3-(2-chloro-6-trifluoromethyl-pyridin-3-yl)-acrylic acid (200 mg, 0.795 mmol) to give the title compound (340 mg, 90%).

$^1$H NMR (300 MHz, DMSO-d$^6$): δ 9.47 (s, 1H), 8.96 (t, 1H, J=6.0 Hz), 8.43 (d, 1H, J=7.8 Hz), 8.02 (d, 1H, J=8.1 Hz), 7.67 (d, 1H, J=15.6 Hz), 7.31-7.27 (m, 2H), 6.90 (d, 1H, J=15.6 Hz), 4.52 (s, 1H), 4.41 (d, 2H, J=5.7 Hz), 3.07 (s, 3H)
ESI [M+H]$^+$: 476

EXAMPLE 41

N-(3-Ethynyl-5-fluoro-4-methanesulfonylaminobenzyl)-3-(6-methoxy-4-trifluoromethylpyridin-3-yl)acrylamide

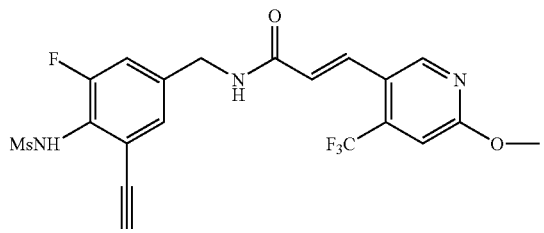

Step 1: Synthesis of methyl 6-methoxy-4-trifluoromethylnicotinate

To a solution of 6-hydroxy-4-trifluoromethylnicotinic acid (400 mg, 1.93 mmol) in chloroform (25 mL) were added silver carbonate (1.06 g, 3.84 mmol) and methyl iodide (2.4 mL, 3.84 mmol). The mixture was stirred in the dark at room temperature overnight, filtered through a pad of celite, and concentrated under reduced pressure. The residue was purified by column chromatography (EtOAc/hexanes=1/10 to 1/1) to give methyl 6-methoxy-4-trifluoromethylnicotinate (300 mg, 69.9%) as a solid.

$^1$H NMR (300 MHz, CDCl$_3$): δ 8.79 (s, 1H), 7.08 (m, 1H), 4.04 (s, 3H), 3.93 (s, 3H)

Step 2: Synthesis of 6-methoxy-4-trifluoromethyl-3-pyridinemethanol

To a cooled (−78° C.) solution of methyl 6-methoxy-4-trifluoromethylnicotinate (300 mg, 1.35 mmol) in toluene (10 mL) was added diisobutylaluminum hydride (DIBAL, 1 M/toluene, 1.35 mL). The mixture was warmed slowly to room temperature and stirred for 2 days. Additional DIBAL (1 M/toluene, 2 mL) was added to complete the reaction. After stirring for 4 hours, the mixture was quenched with saturated aqueous ammonium chloride solution (1 mL), dried over anhydrous magnesium sulfate, filtered through a pad of celite, and concentrated under reduced pressure to give 6-methoxy-4-trifluoromethyl-3-pyridinemethanol (220 mg, 78.6%). The crude product was used directly in the following Swern oxidation.

$^1$H NMR (300 MHz, CDCl$_3$): δ 8.41 (s, 1H), 7.00 (s, 1H), 4.80 (s, 2H), 3.98 (s, 3H)

Step 3: Synthesis of 6-methoxy-4-trifluoromethyl-3-pyridinecarboxaldehyde

To a cooled (−78° C.) solution of DMSO (0.15 mL, 2.13 mmol) in dichloromethane (2 mL) was added oxalyl chloride (0.14 mL, 1.60 mmol), and the mixture was stirred for 10 minutes. 6-Methoxy-4-trifluoromethyl-3-pyridinemethanol (220 mg, 1.06 mmol) in dichloromethane (4 mL) was added to the reaction mixture. After stirring at −40° C. for 50 minutes, the mixture was treated with triethylamine (0.44 mL, 3.16 mmol), stirred for 90 minutes while warming to room temperature, and quenched with water. The organic layer was washed with brine, dried over anhydrous magnesium sulfate, filtered, and concentrated under reduced pressure to give 6-methoxy-4-trifluoromethyl-3-pyridinecarboxaldehyde (162 mg, 74.4%) as a solid. The crude product was used directly in the following Swern oxidation.

$^1$H NMR (300 MHz, CDCl$_3$): δ 10.25~10.23 (m, 1H), 8.91 (s, 1H), 7.07 (s, 1H), 4.08 (s, 3H)

Step 4: Synthesis of 3-(6-methoxy-4-trifluoromethylpyridin-3-yl)-acrylic acid methyl ester To a solution of 6-methoxy-4-trifluoromethyl-3-pyridinecarboxaldehyde (150 mg, 0.73 mmol) in toluene (8 mL) was added methyl(triphenylphosphoranylidene)acetate (270 mg, 0.81 mmol). The mixture was heated at 110° C. for overnight, cooled to room temperature, and diluted with EtOAc and water. The organic layer was dried over anhydrous magnesium sulfate, filtered, and concentrated under reduced pressure. The residue was purified by column chromatography (EtOAc/hexanes=1/4) to give 3-(6-methoxy-4-trifluoromethylpyridin-3-yl)-acrylic acid methyl ester (140 mg, 73.3%) as a mixture of cis- and trans-isomers (cis-/trans-=1/10). The trans-isomer was then isolated by recrystallization from hexanes to give 60 mg as a solid.

$^1$H NMR (300 MHz, CDCl$_3$): δ 8.52 (s, 1H), 7.90~7.84 (m, 1H), 7.03 (s, 1H), 6.38 (d, 1H, J=15.9 Hz), 4.01 (s, 3H), 3.83 (s, 3H)

Step 5: Synthesis of 3-(6-methoxy-4-trifluoromethylpyridin-3-yl)-acrylic acid

To a solution of 3-(6-methoxy-4-trifluoromethylpyridin-3-yl)-acrylic acid methyl ester (trans isomer, 59 mg, 0.23 mmol) in THF (2 mL) was added 1 N LiOH (2 mL). The mixture was stirred at room temperature for 2 hours, acidified to pH 5 with 3 N HCl, and extracted with EtOAc. The organic layer was dried over anhydrous magnesium sulfate and concentrated under reduced pressure to yield 3-(6-methoxy-4-trifluoromethylpyridin-3-yl)acrylic acid (50 mg, 89.6%) as a solid.

$^1$H NMR (300 MHz, CDCl$_3$): δ 8.57 (s, 1H), 7.80~7.94 (m, 1H), 7.05 (s, 1H), 6.41 (d, 1H, J=15.9 Hz), 4.02 (s, 3H)

Step 6: Synthesis of N-(3-ethynyl-5-fluoro-4-methanesulfonylaminobenzyl)-3-(6-methoxy-4-trifluoromethylpyridin-3-yl)acrylamide To a suspension of 3-ethynyl-5-fluoro-4-methansulfonylaminobenzylamine hydrochloride (67 mg, 0.24 mmol) m THF (2 mL) was added N-methylmorpholine (40 μL, 0.36 mmol). After stirring for 5 minutes, 3-(6-methoxy-4-trifluoromethylpyridin-3-yl)acrylic acid (50 mg, 0.20 mmol) dissolved in THF (3 mL) and 4-(4,6-dimethoxy[1,3,5]triazin-2-yl)-4-methylmorpholinium chloride hydrate (DMTMM, 67 mg, 0.24 mmol) were added. The mixture was stirred at room temperature overnight and concentrated under reduced pressure. The residue was diluted with EtOAc and water. The organic layer was dried over anhydrous magnesium sulfate, filtered, and concentrated under reduced pressure. The crude product was purified by recrystallization from EtOAc/hexane to give N-(3-ethynyl-5-fluoro-4-methanesulfonylaminobenzyl)-3-(6-methoxy-4-trifluoromethylpyridin-3-yl)acrylamide (75 mg, 66.2%) as a solid.

¹H NMR (300 MHz, DMSO-d₆): δ 8.83 (t, 1H, J=6 Hz), 8.70 (d, 1H, J=0.6 Hz), 7.59~7.54 (m, 1H), 7.28~7.24 (m, 3H), 6.71 (d, 1H, J=15.6 Hz), 4.49 (s, 1H), 4.38 (d, 2H, J=5.7 Hz), 3.96 (s, 3H), 3.05 (s, 3H)

ESI [M+H]⁺: 472

EXAMPLE 42

N-(3-Ethynyl-5-fluoro-4-methanesulfonylaminobenzyl)-3-(2-methoxy-6-trifluoromethyl-pyridin-3-yl)-acrylamide

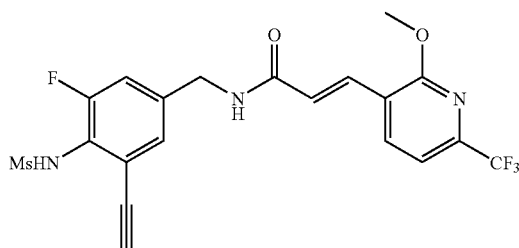

To a suspension of 3-(2-chloro-6-trifluoromethyl-pyridin-3-yl)-N-(3-ethynyl-5-fluoro-4-methanesulfonylamino-benzyl)-acrylamide (50 mg, 0.105 mmol) in CH₃OH (1 mL) was added dropwise 30% NaOCH₃ in CH₃OH (3 eq) at 0° C. The mixture was stirred for 12 hours at room temperature. The reaction was diluted with EtOAc and washed two times with 1N HCl and brine, dried over anhyd. MgSO₄, filtered and concentrated under reduced pressure. The resulting residue was purified by column chromatography to give the title compound (10 mg, 20%).

¹H NMR (300 MHz, DMSO-d⁶): δ 9.45 (s, 1H), 8.86 (s, 1H, br), 8.19 (d, 1H, J=7.5 Hz), 7.60-7.54 (m, 2H), 7.29-7.26 (m, 2H), 6.96 (d, 1H, J=15.9 Hz), 4.51 (s, 1H), 4.40 (d, 2H, J=5.7 MHz), 4.01 (s, 3H), 3.07 (s, 3H)

ESI [M+H]⁺: 472

EXAMPLE 43

N-(3-Fluoro-4-methanesulfonylaminobenzyl)-3-(6-methoxy-4-trifluoromethylpyridin-3-yl)acrylamide

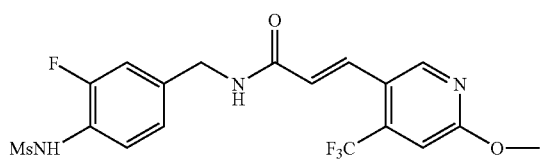

To a suspension of 3-fluoro-4-methansulfonylaminobenzylamine hydrochloride (40 mg, 0.16 mmol) in THF (4 mL) was added N-methylmorpholine (26 μL, 0.24 mmol). After stirring for 5 minutes, 3-[6-methoxy-4-(trifluoromethyl)pyridin-3-yl]acrylic acid (32 mg, 0.13 mmol) dissolved in THF (3 mL) and 4-(4,6-dimethoxy[1,3,5]triazin-2-yl)-4-methylmorpholinium chloride hydrate (DMTMM, 43 mg, 0.16 mmol) were added. The mixture was stirred at room temperature overnight and concentrated under reduced pressure. The residue was diluted with EtOAc and water. The organic layer was dried over anhydrous magnesium sulfate, filtered, and concentrated under reduced pressure. The crude product was purified by recrystallization from EtOAc/hexane to give N-(3-fluoro-4-methanesulfonylaminobenzyl)-3-(6-methoxy-4-trifluoromethylpyridin-3-yl)acrylamide (30 mg, 42.7%) as a solid.

¹H NMR (300 MHz, DMSO-d₆): δ 8.80 (t, 1H, J=5.7 Hz), 8.68 (s, 1H), 7.59~7.53 (m, 1H), 7.35 (t, 1H, J=8.4 Hz), 7.24 (s, 1H), 7.22~7.18 (m, 1H), 7.14~7.11 (m, 1H), 6.70 (d, 1H, J=15.6 Hz), 4.38 (d, 2H, J=5.7 Hz), 3.96 (s, 3H), 3.00 (s, 3H)

ESI [M+H]⁺: 448

EXAMPLE 44

3-(2-Chloro-6-trifluoromethyl-pyridin-3-yl)-N-(3-fluoro-4-methane sulfonylamino-benzyl)-acrylamide

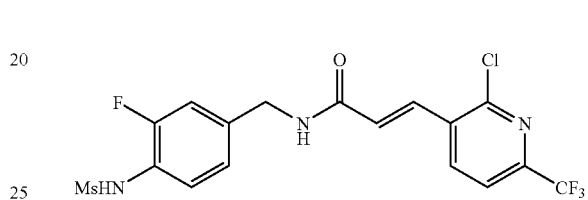

The title compound was obtained according to the general procedure described in example 38 (step 6).

N-(4-Aminomethyl-2-fluoro-phenyl)-methanesulfonamide HCl salt (467 mg, 1.84 mmol) was reacted with 3-(2-chloro-6-trifluoromethyl-pyridin-3-yl)-acrylic acid (420 mg, 1.67 mmol) to give the title compound (737 mg, 98%).

¹H NMR (300 MHz, DMSO-d⁶): δ 9.55 (s, 1H), 8.92 (t, 1H, J=5.7 Hz), 8.41 (d, 1H, J=8.1 Hz), 8.02 (d, 1H, J=8.1 Hz), 7.67 (d, 1H, J=15.9 Hz), 7.34 (t 1H, J=8.1 Hz), 7.20 (d, 1H, J=11.4 Hz), 7.13 (d, 1H, J=8.1 Hz), 6.89 (d, 1H, J=15.9 Hz), 4.40 (d, 2H, J=5.4 Hz), 3.00 (s, 3H).

ESI [M+H]⁺: 452

EXAMPLE 45

N-(3-Fluoro-4-methanesulfonylamino-benzyl)-3-[2-(2-methoxy-ethylamino)-6-trifluoromethyl-pyridin-3-yl]-acrylamide

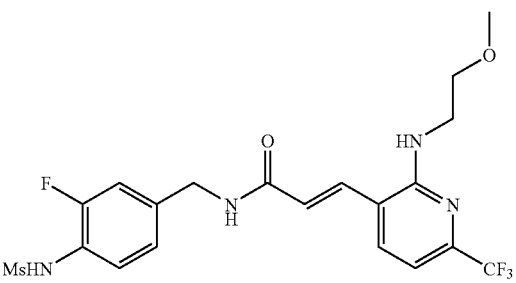

To a suspension of 3-(2-chloro-6-trifluoromethyl-pyridin-3-yl)-N-(3-fluoro-4-methanesulfonylamino-benzyl)-acrylamide (35 mg, 0.077 mmol) and methoxyethylamine (5 eq) in DMF (0.5 ml) was added K₂CO₃ (5 eq). The mixture was stirred for 12 hours at 110° C. The reaction mixture was diluted with EtOAc and then washed two times with 1N-HCl and brine, dried over MgSO₄, filtered and concentrated under reduced pressure. The crude residue was column-chromatographed to yield the title compound (10 mg, 26%).

¹H NMR (300 MHz, CDCl₃): δ 7.67 (m, 3H), 7.13 (t, 2H, J=9.3 Hz), 6.92 (d, 1H, J=7.8 Hz), 6.57 (s, 1H), 6.37 (d, 1H, J=15.3 Hz), 6.11 (s, 1H, br), 5.25 (s, 1H, br), 4.55 (d, 2H, J=6.0 Hz), 3.74-3.69 (m, 2H), 3.65-3.58 (m, 2H), 3.38 (s, 3H), 3.01 (s, 3H)

ESI [M+H]⁺: 491

EXAMPLE 46

Missing

EXAMPLE 47

3-(2-Diethylamino-6-trifluoromethyl-pyridin-3-yl)-N-(3-fluoro-4-methanesulfonylamino-benzyl)-acrylamide

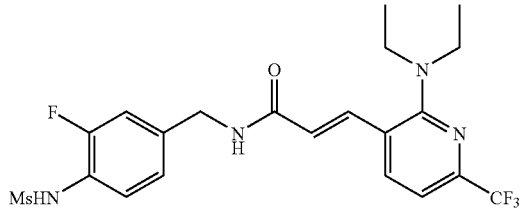

The title compound was obtained according to the general procedure described in example 45 (step 1).

3-(2-Chloro-6-trifluoromethyl-pyridin-3-yl)-N-(3-fluoro-4-methane sulfonylamino-benzyl)-acrylamide (27 mg, 0.06 mmol) was reacted with diethylamine (5 eq) to give the title compound (14 mg, 48%).

¹H NMR (300 MHz, CDCl₃): δ 7.75 (d, 1H, J=15.9 Hz), 7.68 (d, 1H, J=7.8 Hz), 7.52 (t, 1H, J=7.8 Hz), 7.17-7.11 (m, 2H), 7.06 (d, 1H, J=7.8 Hz), 6.57 (s, 1H), 6.35 (d, 1H, J=15.3 Hz), 6.04 (t, 1H, J=5.7 Hz), 4.55 (d, 2H, J=6.0 Hz), 3.38 (q, 4H, J=7.2 Hz), 3.02 (s, 3H), 1.19 (t 6H, J=7.2 Hz)

ESI [M+H]⁺: 489

EXAMPLE 48

Missing

EXAMPLE 49

N-(3-Ethynyl-5-fluoro-4-methanesulfonylamino-benzyl)-3-(2-morpholin-4-yl-pyridin-3-yl)-acrylamide

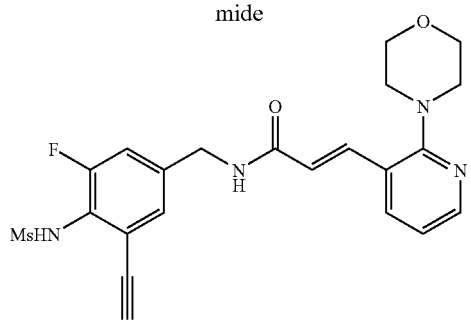

Step 1: Synthesis of 2-morpholin-4-yl-pyridine-3-carbaldehyde

To a solution of 2-chloro-pyridin-3-yl-carbaldehyde (0.5 g, 3.53 mmol) in DMF was added morpholine (0.37 ml, 1.2 eq) and the reaction mixture was stirred at 90° C. for 6 hrs. The reaction mixture was diluted with EtOAc, and washed with water and brine. The organic layer was dried over anhydrous MgSO₄ and concentrated under reduced pressure. The resulting residue was purified by column chromatography (Hex/EtOAc=4/1) to give the product (0.38 g, 56.1%)

¹H NMR (300 MHz, CDCl₃): δ 10.04 (s, 1H), 8.40 (m, 1H), 8.01 (m, 1H), 6.96 (m, 1H), 3.88 (m, 4H), 3.47 (m, 4H)

Step 2: Synthesis of 3-(2-morpholin-4-yl-pyridin-3-yl)-acrylic acid

To a solution of 2-morpholin-4-yl-pyridin-3-yl-carbaldehyde (0.38 g, 1.98 mmol) m toluene was added methyl(triphenylphosphoranylidene)acetate (0.793 g, 1.2 eq), and the resulting mixture was heated at 90° C. for 4 hrs. The reaction mixture was diluted with EtOAc, and washed with water and brine. The organic layer was dried over anhydrous MgSO₄ and concentrated under reduced pressure. The resulting residue was purified by column chromatography (Hex/EtOAc=4/1) to give ester product (0.35 g, 71.2%). The resulting ester was dissolved in 1,4-dioxane, treated with water and KOH, stirred and heated at reflux for 18 hrs. The reaction mixture was cooled to room temperature, diluted with water, and then washed with ether. The aqueous phase was acidified with 1N HCl, and then extracted with EtOAc, and the combined organic phase was washed with brine, dried over anhydrous MgSO₄ and concentrated under reduced pressure to give 3-(6-tert-butyl-pyridin-3-yl)-acrylic acid (0.25 g, 75.7%).

¹H NMR (300 MHz, CDCl₃): δ 8.33 (m, 1H), 7.90 (d, 1H, J=15.9 Hz), 7.77 (m, 1H), 6.97 (m, 1H), 6.42 (d, 1H, J=15.9 Hz), 3.86 (m, 4H), 3.27 (m, 4H)

Step 3: Synthesis of N-(3-ethynyl-5-fluoro-4-methanesulfonylamino-benzyl)-3-(2-morpholin-4-yl-pyridin-3-yl)-acrylamide N-(4-Aminomethyl-5-ethynyl-2-fluoro-phenyl)-methanesulfonamide HCl salt (96 mg, 0.35 mmol) was reacted with 3-(2-morpholin-4-yl-pyridin-3-yl)-acrylic acid (81 mg, 1.0 eq) to give N-(3-ethynyl-5-fluoro-4-methanesulfonylamino-benzyl)-3-(2-morpholin-4-yl-pyridin-3-yl)-acrylamide (105 mg, 63.6%) after purification by column chromatography (Hex/EtOAc=1/10).

¹H NMR (300 MHz, CDCl₃): δ 8.29 (m, 1H), 7.80 (d, 1H, J=15.3 Hz), 7.30 (bs, 1H), 7.18 (m, 1H), 6.94 (m, 1H), 6.43 (bs, 1H), 6.40 (d, 1H, J=15.3 Hz), 5.99 (bs, 1H), 4.54 (d, 1H, J=6.0 Hz), 3.88 (m, 4H), 3.49 (s, 1H), 3.27 (s, 3H), 3.26 (m, 4H)

ESI [M+H]⁺: 459

EXAMPLE 50

N-(5-fluoro-4-methanesulfonylamino-benzyl)-3-(2-morpholin-4-yl-pyridin-3-yl)-acrylamide

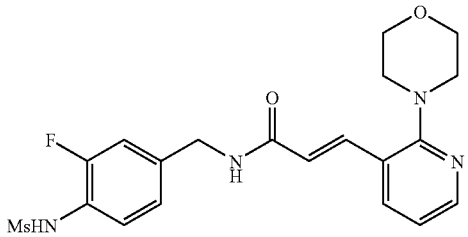

N-(4-Aminomethyl-2-fluoro-phenyl)-methanesulfonamide HCl salt (57 mg, 0.22 mmol) was reacted with 3-(2-morpholin-4-yl-pyridin-3-yl)-acrylic acid (52 mg, 1.0 eq) to give N-(5-fluoro-4-methanesulfonylamino-benzyl)-3-(2-morpholin-4-yl-pyridin-3-yl)-acrylamide (67 mg, 69.5%) after purification by column chromatography (Hex/EtOAc=1/7).

$^1$H NMR (300 MHz, CDCl$_3$): δ 8.29 (m, 1H), 7.81 (d, 1H, J=15.6 Hz), 7.69 (m, 1H), 7.55 (m, 1H), 7.17 (m, 1H), 6.93 (m, 1H), 6.46 (bs, 1H), 6.40 (d, 1H, J=15.6 Hz), 5.92 (bs, 1H), 4.56 (d, 1H, J=6.0 Hz), 3.88 (m, 4H), 3.26 (m, 4H), 3.03 (s, 3H)

ESI [M+H]$^+$: 435

EXAMPLE 51

3-(6-tert-Butyl-2-chloro-pyridin-3-yl)-N-(3-ethynyl-5-fluoro-4-methanesulfonylamino-benzyl)-acrylamide

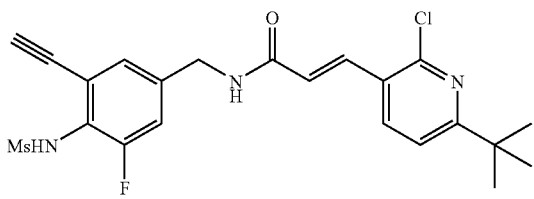

N-(4-Aminomethyl-5-ethynyl-2-fluoro-phenyl)-methanesulfonamide, HCl salt (30 mg, 0.11 mmol) was reacted with 3-(6-tert-butyl-2-chloro-pyridin-3-yl)-acrylic acid (30 mg, 1.0 eq) to give 3-(6-tert-butyl-2-chloro-pyridin-3-yl)-N-(3-ethynyl-5-fluoro-4-methanesulfonylamino-benzyl)-acrylamide (19 mg, 37.9%) after purification by column chromatography (Hex/EtOAc=2/3).

$^1$H NMR (300 MHz, CDCl$_3$): δ 7.93 (d, 1H, J=15.6 Hz), 7.23 (m, 3H), 7.00 (m, 1H), 6.42 (bs, 1H), 6.41 (d, 1H, J=15.6 Hz), 6.08 (bs, 1H), 4.53 (d, 2H, J=6.0 Hz), 3.48 (s, 1H), 3.26 (s, 3H), 1.36 (s, 9H)

ESI [M+H]$^+$: 464

EXAMPLE 52

3-(6-Chloro-4-trifluoromethyl-pyridin-3-yl)-N-(3-ethynyl-5-fluoro-4-methanesulfonylamino-benzyl)-acrylamide

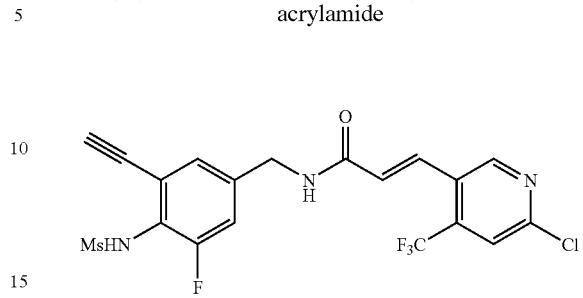

Step 1: Synthesis of N-(6-chloro-4-trifluoromethyl-pyridin-3-yl)-O,N-dimethyl-hydroxylamine To a solution of 6-chloro-4-trifluoromethyl-nicotinic acid (0.9 g, 3.99 mmol) in methylene chloride were added N,O-dimethylhydroxylamine HCl (0.39 g, 1.0 eq), NMM (0.44 ml), and EDC (0.768 g) at 0° C. and the reaction mixture was stirred at 0° C. for 2 hrs. The reaction mixture was extracted with methylene chloride, and washed with water and brine. The organic layer was dried over anhydrous MgSO$_4$ and concentrated under reduced pressure. The resulting residue was purified by column chromatography (Hex/EtOAc=4/1) to give the product (0.824 g, 76.9%).

$^1$H NMR (300 MHz, CDCl$_3$): δ 8.53 (s, 1H), 7.63 (s, 1H), 3.47 (s, 3H), 3.38 (s, H)

Step 2: Synthesis of 3-(6-chloro-4-trifluoromethyl-pyridin-3-yl)-acrylic acid

N-(6-Chloro-4-trifluoromethyl-pyridin-3-yl)-O,N-dimethyl-hydroxylamine (0.824 g, 3.07 mmol) was dissolved in anhydrous THF and cooled to −78° C. and 1.0M LAH (1.54 ml) was added in syringe and then the resulting mixture was stirred for 30 minutes. 1M NaOH (2 ml) and H$_2$O (2 ml) were added carefully to the reaction mixture, and then the resulting solution was stirred for 30 minutes. The mixture was dried with anhydrous MgSO$_4$, filtered, and concentrated in vacuo to give 6-chloro-4-trifluoromethyl-pyridin-3-yl-carbaldehyde as pale yellow oil (0.643 g, 100%). To a solution of 6-chloro-4-trifluoromethyl-pyridin-3-yl-carbaldehyde (0.643 g, 3.07 mmol) in toluene was added methyl (triphenylphosphoranylidene)acetate (1.13 g, 1.1 eq), and the resulting mixture was heated at 90° C. for 4 hrs. The reaction mixture was diluted with EtOAc, and washed with water and brine. The organic layer was dried over anhydrous MgSO$_4$ and concentrated under reduced pressure. The resulting residue was purified by column chromatography (Hex/EtOAc=8/1) to give ester product (0.56 g, 68.4%). The resulting ester was dissolved in 1,4-dioxane, treated with water and KOH, stirred and heated at reflux for 18 hrs. The reaction mixture was cooled to room temperature, diluted with water, and then washed with ether. The aqueous phase was acidified with 1N HCl, and then extracted with EtOAc, and the combined organic phase was washed with brine, dried over anhydrous MgSO$_4$ and concentrated under reduced pressure to give 3-(6-chloro-4-trifluoromethyl-pyridin-3-yl)-acrylic acid (0.43 g, 81.4%).

$^1$H NMR (300 MHz, CDCl$_3$): δ 8.77 (s, 1H), 7.97 (m, 1H), 7.65 (s, 1H), 6.52 (d, 1H, J=15.9 Hz)

Step 3: Synthesis of 3-(6-chloro-4-trifluoromethyl-pyridin-3-yl)-N-(3-ethynyl-5-fluoro-4-methanesulfonylamino-benzyl)-acrylamide N-(4-Aminomethyl-5-ethynyl-2-fluoro-phenyl)-methanesulfonamide HCl salt (123 mg, 0.40 mmol) was reacted with 3-(6-chloro-4-trifluoromethyl-pyridin-3-yl)-acrylic acid (105 mg, 1.0 eq) to give 3-(6-chloro-4-trifluoromethyl-pyridin-3-yl)-N-(3-ethynyl-5-fluoro-4-methanesulfonylamino-benzyl)-acrylamide (136 mg, 73.3%) after purification by column chromatography (Hex/EtOAc=3/2).

$^1$H NMR (300 MHz, CDCl$_3$): δ 8.70 (s, 1H), 7.90 (m, 1H), 7.62 (s, 1H), 7.30 (s, 1H), 7.18 (m, 1H), 6.46 (d, 1H, J=15.3 Hz), 6.14 (bs, 1H), 4.54 (d, 2H, J=6.0 Hz), 3.49 (s, 1H), 3.27 (s, 3H)

ESI [M+H]$^+$: 476

EXAMPLE 53

3-(6-Chloro-4-trifluoromethyl-pyridin-3-yl)-N-(3-fluoro-4-methane sulfonylamino-benzyl)-acrylamide

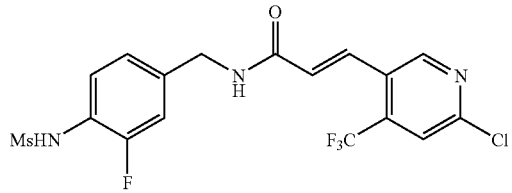

N-(4-Aminomethyl-2-fluoro-phenyl)-methanesulfonamide HCl salt (56 mg, 0.22 mmol) was reacted with 3-(6-chloro-4-trifluoromethyl-pyridin-3-yl)-acrylic acid (54 mg, 1.0 eq) to give 3-(6-chloro-4-trifluoromethyl-pyridin-3-yl)-N-(5-fluoro-4-methanesulfonylamino-benzyl)-acrylamide (66 mg, 65.7%) after purification by column chromatography (Hex EtOAc=3/2).

$^1$H NMR (300 MHz, CDCl$_3$): δ 8.69 (s, 1H), 7.89 (m, 1H), 7.57 (d, 1H, J=15.3 Hz), 7.54 (m, 1H), 7.15 (m, 2H), 6.53 (bs, 1H), 6.46 (d, 1H, J=15.3 Hz), 6.13 (bs, 1H), 4.56 (d, 2H, J=5.7 Hz), 3.03 (s, 3H)

ESI [M+H]+: 452

EXAMPLE 54

Missing

EXAMPLE 55

N-(3-Fluoro-4-methanesulfonylamino-benzyl)-3-(2-pyrrolidin-1-yl-6-trifluoromethyl-pyridin-3-yl)-acrylamide

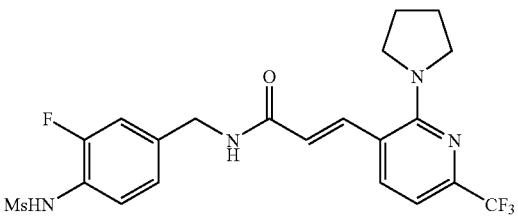

To a suspension of 3-(2-chloro-6-trifluoromethyl-pyridin-3-yl)-N-(3-fluoro-4-methanesulfonylamino-benzyl)-acrylamide (40 mg, 0.088 mmol) in pyrrolidine (0.4 ml) was added DMF (0.5 ml). The mixture was stirred for 12 hours at 110° C. The reaction mixture was diluted with EtOAc and then washed two times with 1N-HCl and brine, dried over MgSO$_4$, filtered and concentrated under reduced pressure. The crude residue was column-chromatographed to yield the title compound (40 mg, 93%).

$^1$H NMR (300 MHz, DMSO-d$^6$): δ 9.95 (s, 1H), 8.72 (t, 1H, J=6.0 Hz), 7.80 (d, 1H, J=7.5 Hz), 7.69 (d, 1H, J=15.3 Hz), 7.34 (t, 1H, J=8.1 Hz), 7.19 (d, 1H, J=11.4 Hz), 7.13-7.08 (m, 2H), 6.43 (d, 1H, J=15.3 Hz), 4.37 (d, 1H, J=6.0 Hz), 3.48-3.41 (m, 4H), 3.00 (s, 3H), 1.88-1.86 (m, 4H)

ESI [M+H]+: 487

EXAMPLE 56

N-(3-Fluoro-4-methanesulfonylamino-benzyl)-3-[2-(3-hydroxy-pyrrolidin-1-yl)-6-trifluoromethyl-pyridin-3-yl]-acrylamide

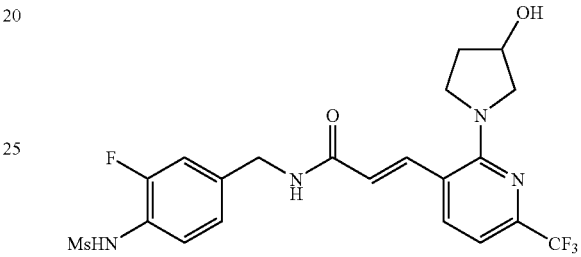

To a suspension of 3-(2-chloro-6-trifluoromethyl-pyridin-3-yl)-N-(3-fluoro-4-methanesulfonylamino-benzyl)-acrylamide (40 mg, 0.088 mmol) in pyrrolidin-3-ol (0.4 ml) was added DMF (0.5 ml). The mixture was stirred for 12 hours at 110° C. The reaction mixture was diluted with EtOAc and then washed two times with 1N-HCl and brine, dried over MgSO$_4$, filtered and concentrated under reduced pressure. The crude residue was column-chromatographed to yield the title compound (40 mg, 91%).

$^1$H NMR (300 MHz, DMSO-d$^6$): δ 8.72 (t, 1H, J=5.7 Hz), 7.80 (d, 1H, J=7.5 Hz), 7.68 (d, 1H, J=15.3 Hz), 7.34 (t, 1H, J=8.1 Hz), 7.19 (d, 1H, J=11.1 Hz), 7.12-7.08 (m, 2H), 4.98 (d, 1H, J=2.7 Hz), 4.37 (d, 2H, J=6.0 Hz), 4.31 (s, 1H, br), 3.74-3.64 (m, 4H), 3.00 (s, 3H), 1.98-1.84 (m, 2H)

ESI [M+H]$^+$: 503

EXAMPLE 57

N-(3-Ethynyl-5-fluoro-4-methanesulfonylamino-benzyl)-3-(6-trifluoromethyl-pyridin-3-yl)-acrylamide

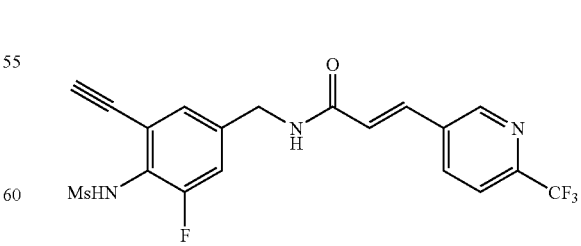

N-(4-Aminomethyl-5-ethynyl-2-fluoro-phenyl)-methanesulfonamide HCl salt (137 mg, 0.49 mmol) was reacted with 3-(6-trifluoromethyl-pyridin-3-yl)-acrylic acid (107 mg, 1.0 eq) to give N-(3-ethynyl-5-fluoro-4-methanesulfonylaminobenzyl)-3-(6-trifluoromethyl-pyridin-3-yl)-acrylamide (105 mg, 48.5%) after purification by column chromatography (Hex/EtOAc=2/3).

$^1$H NMR (300 MHz, DMSO-d$_6$): δ 9.44 (bs, 1H), 8.97 (s, 1H), 8.84 (m, 1H), 8.28 (m, 1H), 7.96 (m, 1H), 7.60 (d, 1H, J=16.2 Hz), 7.25 (m, 2H), 6.92 (d, 1H, J=15.9 Hz), 4.39 (d, 2H, J=6.0 Hz), 3.33 (s, 1H), 3.02 (s, 3H)

ESI [M+H]+: 442

EXAMPLE 58

N-(3-Fluoro-4-methanesulfonylamino-benzyl)-3-(6-trifluoromethyl-pyridin-3-yl)-acrylamide

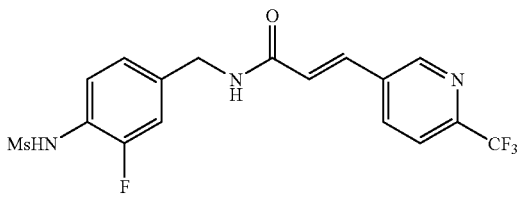

N-(4-Aminomethyl-2-fluoro-phenyl)-methanesulfonamide HCl salt (59 mg, 0.23 mmol) was reacted with 3-(6-chloro-4-trifluoromethyl-pyridin-3-yl)-acrylic acid (50 mg, 1.0 eq) to give 3-(6-chloro-4-trifluoromethyl-pyridin-3-yl)-N-(3-fluoro-4-methanesulfonylamino-benzyl)-acrylamide (47 mg, 49.0%) after purification by column chromatography (Hex/EtOAc=4/5).

$^1$H NMR (300 MHz, DMSO-d$_6$): δ 9.55 (bs, 1H), 8.97 (s, 1H), 8.83 (m, 1H), 8.28 (m, 1H), 7.96 (m, 1H), 7.60 (d, 1H, J=15.9 Hz), 7.35 (m, 1H), 7.17 (m, 2H), 6.92 (d, 1H, J=16.2 Hz), 4.41 (d, 2H, J=6.0 Hz), 3.00 (s, 3H)

ESI [M+H]+: 418

EXAMPLE 59

3-(6-tert-Butyl-2-morpholin-4-yl-pyridin-3-yl)-N-(3-ethynyl-5-fluoro-4-methanesulfonylamino-benzyl)-acrylamide

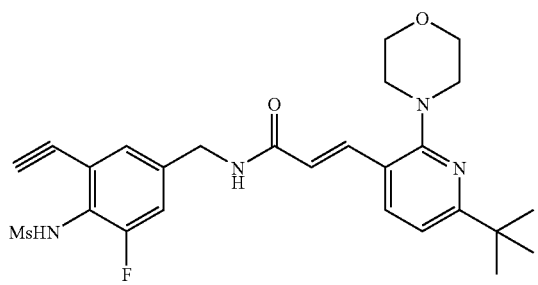

Step 1: Synthesis of 3-(6-tert-butyl-2-morpholin-4-yl-pyridin-3-yl)-acrylic acid 3-(6-tert-Butyl-2-chloro-pyridin-3-yl)-acrylic acid, methyl ester (0.28 μg, 1.11 mmol) was dissolved in DMF, and morpholine (0.15 ml), NEt$_3$ (0.31 ml) and palladium reagent (48 mg) were added stepwise and then the reaction mixture was stirred at 80° C. for 18 hours. The resulting mixture was extracted with EtOAc, and the organic phase was dried over anhydrous MgSO$_4$ and concentrated under reduced pressure. The resulting residue was purified by column chromatography (Hex/EtOAc=8/1) to give 3-(6-tert-butyl-2-morpholin-4-yl-pyridin-3-yl)-acrylic acid methyl ester (76 mg, 0.25 mmol, 22.5%). The methyl ester was dissolved in 1,4-dioxane, treated with water and KOH, stirred and heated at reflux for 18 hrs. The reaction mixture was cooled to room temperature, diluted with water, and then washed with ether. The aqueous phase was acidified with 1N HCl, and then extracted with EtOAc, and the combined organic phase was washed with brine, dried over anhydrous MgSO$_4$ and concentrated under reduced pressure to give 3-(6-tert-butyl-2-morpholin-4-yl-pyridin-3-yl)-acrylic acid (67 mg, 92%).

$^1$H NMR (300 MHz, CDCl$_3$): δ 7.88 (d, 1H, J=15.9 Hz), 7.68 (d, 1H, J=8.1 Hz), 6.97 (d, 1H, J=8.1 Hz), 6.38 (d, 1H, J=15.9 Hz), 3.87 (m, 4H), 3.30 (m, 4H), 1.33 (s, 9H)

Step 2: Synthesis of 3-(6-tert-butyl-2-morpholin-4-yl-pyridin-3-yl)-N-(3-ethynyl-5-fluoro-4-methanesulfonylamino-benzyl)-acrylamide N-(4-Aminomethyl-5-ethynyl-2-fluoro-phenyl)-methanesulfonamide HCl salt (59 mg, 0.23 mmol) was reacted with 3-(6-tert-butyl-2-morpholin-4-yl-pyridin-3-yl)-acrylic acid (67 mg) to give 3-(6-tert-butyl-2-morpholin-4-yl-pyridin-3-yl)-N-(3-ethynyl-5-fluoro-4-methanesulfonylamino-benzyl)-acrylamide (60 mg, 92%) after purification by column chromatography (Hex/EtOAc=3/2).

$^1$H NMR (300 MHz, CDCl$_3$): δ 7.78 (d, 1H, J=15.9 Hz), 7.61 (m, 1H), 7.25 (m, 2H), 6.93 (m, 1H), 6.41 (bs, 1H), 6.35 (d, 1H, J=15.9 Hz), 5.91 (bs, 1H), 4.53 (d, 2H, J=6.3 Hz), 3.86 (m, 4H), 3.48 (s, 1H), 3.29 (m, 4H), 3.26 (s, 3H), 1.32 (s, 9H)

ESI [M+H]+: 515

EXAMPLE 60

N-(3-Fluoro-4-methanesulfonylamino-benzyl)-3-(2-methoxy-6-trifluoromethyl-pyridin-3-yl)-acrylamide

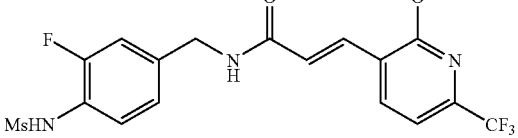

The title compound was obtained according to the general procedure described in example 42 (step 1).

3-(2-Chloro-6-trifluoromethyl-pyridin-3-yl)-N-(3-fluoro-4-methane sulfonylamino-benzyl)-acrylamide (40 mg, 0.088 mmol) was reacted with 30% NaOCH$_3$ in CH$_3$OH to give the title compound (39 mg, 98%).

$^1$H NMR (300 MHz, DMSO-d$^6$): δ 9.55 (s, 1H), 8.82 (s, 1H, br), 8.17 (d, 1H, J=7.5 Hz), 7.59-7.54 (m, 2H), 7.34 (t, 1H, J=7.8 Hz), 7.19 (d, 1H, J=11.4 Hz), 7.12 (d, 1H, J=7.8 Hz), 6.95 (d, 1H, J=15.9 Hz), 4.39 (d, 2H, J=5.4 Hz), 4.00 (s, 3H), 3.00 (s, 3H)

ESI [M+H]+: 448

EXAMPLE 61

N-(3-Fluoro-4-methanesulfonylamino-benzyl)-3-[2-(2-hydroxy-ethylamino)-6-trifluoromethyl-pyridin-3-yl]-acrylamide

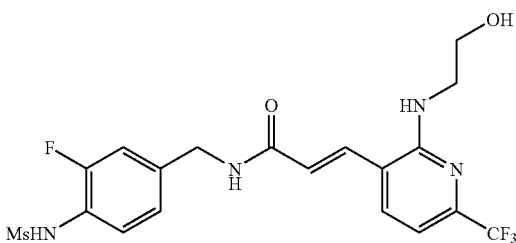

The title compound was obtained according to the general procedure described in example 56 (step 1).

3-(2-Chloro-6-trifluoromethyl-pyridin-3-yl)-N-(3-fluoro-4-methane sulfonylamino-benzyl)-acrylamide (40 mg, 0.088 mmol) was reacted with 2-aminoethanol (excess) to give the title compound (10 mg, 24%).

$^1$H NMR (300 MHz, DMSO-d$^6$): δ 9.55 (s, 1H), 8.72 (s, 1H), 7.78 (d, 1H, J=7.5 Hz), 7.60 (d, 1H, J=15.0 Hz), 7.34 (t, 1H, J=7.5 Hz), 7.19 (d, 1H, J=10.8 Hz), 7.13 (d, 1H, J=8.1 Hz), 7.04 (s, 1H), 6.98 (d, 1H, J=7.2 Hz), 6.63 (d, 1H, J=15.3 Hz), 4.68 (s, 1H), 4.40 (d, 2H, J=4.5 Hz), 3.55-3.54 (m, 2H), 3.42-3.40 (m, 2H), 3.00 (s, 3H).

ESI [M+H]+: 477

EXAMPLE 62

N-(3-Ethynyl-5-fluoro-4-methanesulfonylamino-benzyl)-3-(2-pyrrolidin-1-yl-6-trifluoromethyl-pyridin-3-yl)-acrylamide

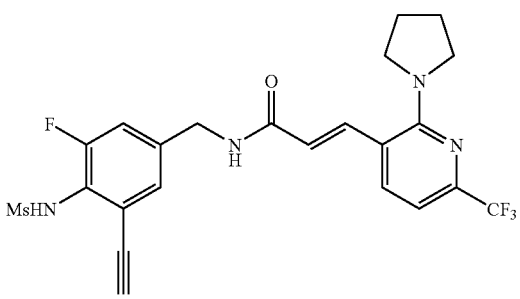

Step 1: 3-(2-Pyrrolidin-1-yl-6-trifluoromethyl-pyridin-3-yl)-acrylic acid

To a suspension of 3-(2-chloro-6-trifluoromethyl-pyridin-3-yl)-acrylic acid (100 mg, 0.397 mmol) in pyrrolidine (1.0 ml) was added DMF (1.0 ml). The mixture was stirred for 12 hours at room temperature. The reaction mixture was diluted with EtOAc and then washed two times with 1N-HCl and brine, dried over MgSO$_4$, filtered and concentrated under reduced pressure. The crude residue was column-chromatographed to yield the 3-(2-pyrrolidin-1-yl-6-trifluoromethyl-pyridin-3-yl)-acrylic acid (100 mg, 91%).

$^1$H NMR (300 MHz, CDCl$_3$): δ 8.05 (d, 1H, J=15.9 Hz), 7.69 (d, 1H, J=10.8 Hz), 6.97 (d, 1H, J=10.8 Hz), 6.21 (d, 1H, J=15.9 Hz), 3.64-3.60 (m, 4H), 1.96-1.92 (m, 4H).

Step 2: N-(3-Ethynyl-5-fluoro-4-methanesulfonylamino-benzyl)-3-(2-pyrrolidin-1-yl-6-trifluoromethyl-pyridin-3-yl)-acrylamide The title compound was obtained according to the general procedure described in example 38 (step 6).

N-(4-Aminomethyl-2-ethynyl-6-fluoro-phenyl)-methanesulfonamide HCl salt (94 mg, 0.327 mmol) was reacted with 3-(2-pyrrolidin-1-yl-6-trifluoromethyl-pyridin-3-yl)-acrylic acid (78 mg, 0.272 mmol) to give the title compound (110 mg, 80%).

$^1$H NMR (300 MHz, DMSO-d$^6$): δ 9.44 (s, 1H), 8.73 (t, 1H, J=9.0 Hz), 7.82 (d, 1H, J=7.5 Hz), 7.69 (d, 1H, J=15.3 Hz), 7.29-7.26 (m, 2H), 7.10 (d, 1H, J=7.8 Hz), 6.43 (d, 1H, J=15.9 Hz), 4.52 (s, 1H), 4.38 (d, 2H, J=5.7 Hz), 3.51-3.47 (m, 4H), 3.07 (s, 3H), 1.88-1.86 (m, 4H).

ESI [M+H]+: 511

EXAMPLE 63

3-(2-Butoxy-6-trifluoromethyl-pyridin-3-yl)-N-(3-fluoro-4-methane sulfonyl amino-benzyl)-acrylamide

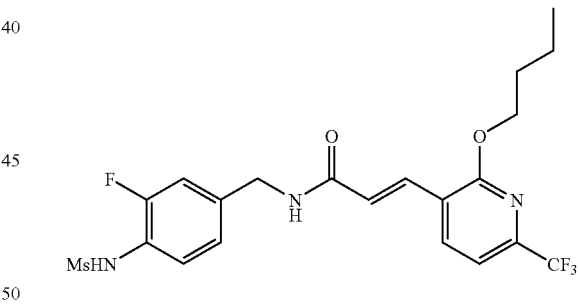

To a suspension of 3-(2-chloro-6-trifluoromethyl-pyridin-3-yl)-N-(3-fluoro-4-methanesulfonylamino-benzyl)-acrylamide (40 mg, 0.088 mmol) in 1-butanol (0.5 ml) was added K$_2$CO$_3$ (5 eq). The mixture was stirred for 12 hours at 110° C. The reaction mixture was diluted with EtOAc and then washed two times with 1N-HCl and brine, dried over MgSO$_4$, filtered and concentrated under reduced pressure. The crude residue was recrystallized from CH$_2$Cl$_2$/n-hexane to give the title compound (40 mg, 93%).

$^1$H NMR (300 MHz, DMSO-d$^6$): δ 9.54 (s, 1H), 8.83 (t, 1H, J=5.7 Hz), 8.16 (d, 1H, J=7.8 Hz), 7.58 (d, 1H, J=15.9 Hz), 7.52 (d, 1H, J=7.5 Hz), 7.35 (t, 1H, J=8.1 Hz), 7.19 (d, 1H, J=11.4 Hz), 7.12 (d, 1H, J=8.1 Hz), 6.92 (d, 1H, J=15.9 Hz), 4.42-4.38 (m, 4H), 3.00 (s, 3H), 1.83-1.73 (m, 2H), 1.47-1.40 (m, 2H), 0.94 (d, 3H, J=7.5 Hz).

ESI [M+H]+: 490

EXAMPLE 64

N-(3-Ethynyl-5-fluoro-4-methanesulfonylamino-benzyl)-3-[2-(4-methyl-piperazin-1-yl)-6-trifluoromethyl-pyridin-3-yl]-acrylamide

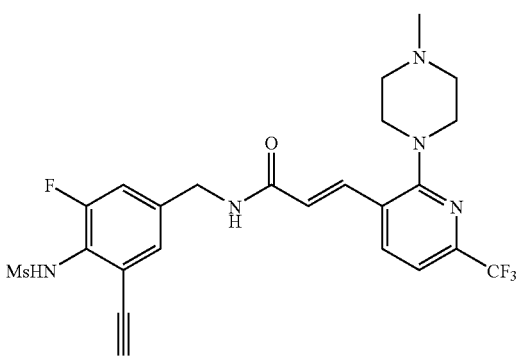

3-(2-Chloro-6-trifluoromethyl-pyridin-3-yl)-N-(3-ethynyl-5-fluoro-4-methanesulfonylamino-benzyl)-acrylamide (70 mg, 0.057 mmol) was reacted with N-methylpiperazine (30 μl) as in example 46 to give the title compound (13 mg, 15%) after recrystallization with Hex/EtOAc.

$^1$H NMR (300 MHz, CDCl$_3$): δ 7.75 (d, 1H, J=7.2 Hz), 7.72 (d, 1H, J=15.3 Hz), 7.29 (s, 1H), 7.18 (m, 2H), 6.44 (d, 1H, J=15.3 Hz), 6.12 (t, 1H), 4.53 (d, 2H, J=6.0 Hz), 3.48 (s, 1H), 3.39 (m, 4H), 3.26 (s, 3H), 2.59 (m, 4H), 2.35 (s, 3H).

ESI [M+H]+: 540

EXAMPLE 65

N-(3-Ethynyl-5-fluoro-4-methanesulfonylamino-benzyl)-3-[2-(2-methoxy-ethylamino)-6-trifluoromethyl-pyridin-3-yl]-acrylamide

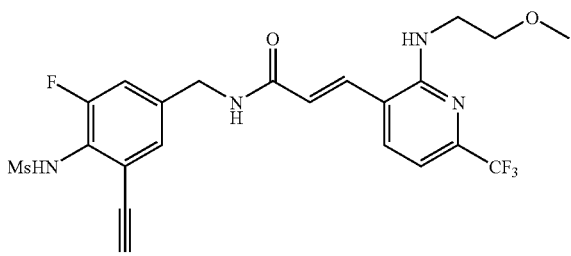

A mixture of 3-(2-chloro-6-trifluoromethyl-pyridin-3-yl)-N-(3-ethynyl-5-fluoro-4-methanesulfonylamino-benzyl)-acrylamide (30 mg, 0.28 mmol) and 2-methoxyethylamine (100 μl) was stirred at ambient temperature for 48 hrs. The reaction mixture was diluted with water and then acidified with 2N HCl solution. The aqueous phase was extracted with EtOAc and the combined organic phase was washed with brine, dried over anhydrous MgSO$_4$ and concentrated under reduced pressure. The resulting residue was purified by column chromatography (Hex/EtOAc=2/3) to give the title compound (4.0 mg, 12%).

$^1$H NMR (300 MHz, CDCl$_3$): δ 7.65 (d, 1H, J=15.6 Hz), 7.59 (d, 1H, J=7.2 Hz), 7.21 (s, 1H), 7.11 (d, 1H, J=10.5 Hz), 6.92 (d, 1H, J=7.2 Hz), 6.33 (d, 1H, J=15.6 Hz), 6.33 (t, 1H), 5.40 (s, 1H), 4.47 (d, 2H, J=5.7 Hz), 3.71 (m, 2H), 3.61 (m, 2H), 3.44 (s, 1H), 3.37 (s, 3H), 3.28 (s, 3H).

ESI [M+H]+: 515

EXAMPLE 66

3-(2-Butoxy-6-trifluoromethyl-pyridin-3-yl)-N-(3-ethynyl-5-fluoro-4-methanesulfonylamino-benzyl)-acrylamide

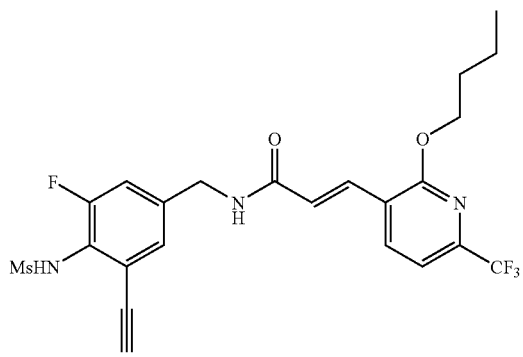

Step 1: 3-(2-Butoxy-6-trifluoromethyl-pyridin-3-yl)-acrylic acid

To a suspension of 3-(2-chloro-6-trifluoromethyl-pyridin-3-yl)-acrylic acid (40 mg, 0.158 mmol) and 1-butanol (0.029 ml, 0.316 mmol) in DMF (2 mL) was added NaH (19 mg, 0.47 mmol) at 0° C. The mixture was stirred for 12 hours at room temperature. The residue was diluted with EtOAc and water. The organic layer was washed with 1N HCl, saturated sodium bicarbonate and brine, dried over anhydrous magnesium sulfate, filtered and concentrated under reduced pressure. The crude residue was column-chromatographed to give 3-(2-butoxy-6-trifluoromethyl-pyridin-3-yl)-acrylic acid (21 mg, 92%).

$^1$H NMR (300 MHz, CDCl$_3$): δ 7.88 (d, 1H, J=16.2 Hz), 7.88 (d, 1H, J=7.8 Hz), 7.28 (d, 1H, J=7.8 Hz), 6.73 (d, 1H, J=16.2 Hz), 4.49 (t, 2H, J=6.6 Hz), 1.86-1.79 (m, 2H), 1.53-1.47 (m, 2H), 1.00 (t 3H, J=7.5 Hz),

Step 2: 3-(2-Butoxy-6-trifluoromethyl-pyridin-3-yl)-N-(3-ethynyl-5-fluoro-4-methanesulfonylamino-benzyl)-acrylamide The title compound was obtained according to the general procedure described in example 38 (step 6).

N-(4-Aminomethyl-2-ethynyl-6-fluoro-phenyl)-methanesulfonamide HCl salt (25 mg, 0.087 mmol) was reacted with 3-(2-butoxy-6-trifluoromethyl-pyridin-3-yl)-acrylic acid (21 mg, 0.73 mmol) to give the title compound (24 mg, 54%).

$^1$H NMR (300 MHz, DMSO-d$^6$): δ 9.44 (s, 1H), 8.85 (t, 1H, J=6.0 Hz), 8.18 (d, 1H, J=7.5 Hz), 7.58 (d, 1H, J=15.9 Hz), 7.52 (d, 1H, J=7.5 Hz), 7.29-7.25 (m, 2H), 6.93 (d, 1H, J=15.9 Hz), 4.50 (s, 1H), 4.42-4.37 (m, 2H), 3.06 (s, 3H), 1.83-1.73 (m, 2H), 1.50-1.42 (m, 2H), 0.94 (d, 3H, J=7.5 Hz).

ESI [M+H]+: 514

EXAMPLE 67

N-(3-Fluoro-4-methanesulfonylamino-benzyl)-3-[2-(2-methoxy-ethoxy)-6-trifluoromethyl-pyridin-3-yl]-acrylamide

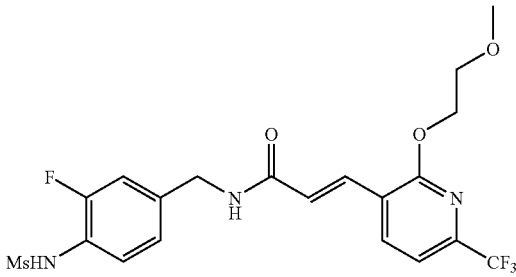

The title compound was obtained according to the general procedure described in example 63 (step 1).

3-(2-Chloro-6-trifluoromethyl-pyridin-3-yl)-N-(3-fluoro-4-methane sulfonylamino-benzyl)-acrylamide (70 mg, 0.155 mmol) was reacted with methoxyethanol to give the title compound (50 mg, 66%).

$^1$H NMR (300 MHz, DMSO-d$^6$): δ 9.54 (s, 1H), 8.82 (t, 1H, J=5.7 Hz), 8.19 (d, 1H, J=7.5 Hz), 7.61-7.53 (m, 2H), 7.34 (t, 1H, J=8.4 Hz), 7.21 (d, 1H, J=11.4 Hz), 7.12 (d, 1H, J=8.4 Hz), 6.92 (d, 1H, J=15.9 Hz), 4.52 (t, 2H, J=4.5 Hz), 4.40 (d, 2H, J=5.7 Hz), 3.74 (t, 2H, J=4.5 Hz), 3.31 (s, 3H), 3.00 (s, 3H).

ESI [M+H]+: 492

EXAMPLE 68

N-(3-Ethynyl-5-fluoro-4-methanesulfonylaminobenzyl)-3-(2-methyl-6-trifluoromethylpyridin-3-yl)acrylamide

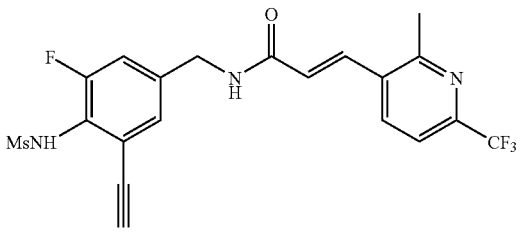

Step 1: Synthesis of N-methoxy-N-methyl-2-methyl-6-trifluoromethyl-3-pyridinecarboxamide To a solution of 2-methyl-6-trifluoromethylnicotinic acid (500 mg, 2.44 mmol) and N,O-dimethylhydroxylamine hydrochloride (285 mg, 2.92 mmol) in dichloromethane (10 mL) were added N-methylmorpholine (0.32 mL, 2.92 mmol) and N-(3-dimethylaminopropyl-N'-ethylcarbodiimide hydrochloride (EDC, 560 mg, 2.92 mmol). The mixture was stirred at room temperature for 2 hours and washed with 1 N HCl and water. The organic layer was dried over anhydrous magnesium sulfate, filtered, and concentrated under reduced pressure to give N-methoxy-N-methyl-2-methyl-6-trifluoromethyl-3-pyridinecarboxamide quantitatively as oil. The crude product was used directly in the following reaction.

$^1$H NMR (300 MHz, CDCl$_3$): δ 7.77 (d, 1H, J=7.5 Hz), 7.56 (d, 1H, J=7.8 Hz), 3.44 (br s, 3H), 3.39 (br s, 1H), 2.63 (s, 3H)

Step 2: Synthesis of 2-methyl-6-trifluoromethyl-3-pyridinecarboxaldehyde

To a cooled (−78° C.) solution of N-methoxy-N-methyl-2-methyl-6-trifluoromethyl-3-pyridinecarboxamide (615 mg, 2.48 mmol) in THF (10 mL) was added lithium aluminum hydride (LAH, 1 N/THF, 1.23 mL). The mixture was stirred for 15 minutes, and then warmed to −10° C. After additional stirring for 30 minutes, the mixture was quenched with saturated potassium hydrogen sulfate solution (1 mL) and extracted with diethyl ether. The organic layer was dried over anhydrous magnesium sulfate, filtered, and concentrated under reduced pressure to give 2-methyl-6-trifluoromethyl-3-pyridinecarboxaldehyde quantitatively as oil. The crude product was used directly in the following reaction.

$^1$H NMR (300 MHz, CDCl$_3$): δ 10.40 (s, 1H), 8.29 (d, 1H, J=8.1 Hz), 7.71 (d, 1H, J=8.1 Hz), 2.61 (s, 3H)

Step 3: Synthesis of 3-(2-methyl-6-trifluoromethylpyridin-3-yl)acrylic acid

To a solution of 2-methyl-6-trifluoromethyl-3-pyridinecarboxaldehyde (440 mg, 2.32 mmol) in toluene (10 mL) was added methyl(triphenylphosphoranylidene)acetate (855 mg, 2.56 mmol). The mixture was heated at 110° C. for overnight, cooled to room temperature, and diluted with EtOAc and water. The organic layer was dried over anhydrous magnesium sulfate, filtered, and concentrated under reduced pressure. The crude residue was purified by column chromatography (EtOAc/hexanes=1/4) to 3-(2-methyl-6-trifluoromethylpyridin-3-yl)acrylic acid methyl ester (376 mg, 65.9%) as a mixture of cis- and trans-isomers (cis-/trans-=1/10). To a solution of the ester (376 mg, 1.53 mmol) in THF (5 mL) was added 1 N LiOH (2.5 mL). The mixture was stirred at room temperature for 1 hour and concentrated under reduced pressure. The residue was diluted with EtOAc and water. The aqueous layer was then separated, acidified to pH 4 with 3 N HCl, and extracted with EtOAc. The organic layer was dried over anhydrous magnesium sulfate and concentrated under reduced pressure. The crude product was purified by recrystallization from EtOAc/hexanes to give 3-(2-methyl-6-trifluoromethylpyridin-3-yl)acrylic acid (trans-isomer, 200 mg, 56.4%) as solid.

$^1$H NMR (300 MHz, CDCl$_3$): δ 8.05~7.97 (m, 2H), 7.58 (d, 1H, J=8.1 Hz), 6.47 (d, 1H, J=15.9 Hz), 2.75 (s, 3H).

Step 5: Synthesis of N-(3-ethynyl-5-fluoro-4-methane sulfonylaminobenzyl)-3-(2-methyl-6-trifluoromethylpyridin-3-yl)acrylamide To a suspension of 3-ethynyl-5-fluoro-4-methansulfonylaminobenzylamine hydrochloride (73 mg, 0.26 mmol) in THF (5 mL) was added N-methylmorpholine (43 μL, 0.39 mmol). After stirring for 5 minutes, 3-(2-methyl-6-trifluoromethylpyridin-3-yl)acrylic acid (60 mg, 0.26 mmol) and 4-(4,6-dimethoxy[1,3,5]triazin-2-yl)-4-methylmorpholinium chloride hydrate (DMTMM, 73 mg, 0.26 mmol) were added. The mixture was stirred at room temperature overnight, concentrated under reduced pressure, and diluted with EtOAc and water. The organic layer was dried over anhydrous magnesium sulfate, filtered, and concentrated under reduced pressure. The crude product was purified by recrystallization from EtOAc/hexane to give N-(3-ethynyl-5-fluoro-4-methanesulfonylaminobenzyl)-3-(2-methyl-6-trifluoromethylpyridin-3-yl)acrylamide (89 mg, 75.5%) as solid.

¹H NMR (300 MHz, CDCl₃+DMSO-d₆): δ 8.22 (s, 1H), 8.16 (t, 1H, J=5.7 Hz), 7.94 (d, 1H, J=8.1 Hz), 7.84 (d, 1H, J=15.6 Hz), 7.54 (d, 1H, J=8.1 Hz), 7.33 (s, 1H), 7.19 (dd, 1H, J=10.5, 1.8 Hz), 6.61 (d, 1H, J=15.3 Hz), 4.50 (d, 2H, J=5.7 Hz), 3.18 (s, 3H), 2.72 (s, 3H)

ESI [M+H]+: 456

EXAMPLE 69

N-(3-Fluoro-4-methanesulfonylaminobenzyl)-3-(2-methyl-6-trifluoromethylpyridin-3-yl)acrylamide

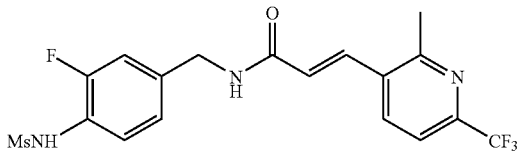

Step 1: Synthesis of N-(3-fluoro-4-methanesulfonylaminobenzyl)-3-(2-methyl-6-trifluoromethylpyridin-3-yl)acrylamide To a suspension of 3-fluoro-4-methansulfonylaminobenzylamine hydrochloride (67 mg, 0.26 mmol) in THF (5 mL) was added N-methylmorpholine (43 μL, 0.39 mmol). After stirring for 5 minutes, 3-(2-methyl-6-trifluoromethylpyridin-3-yl)acrylic acid (60 mg, 0.26 mmol) and 4-(4,6-dimethoxy[1,3,5]triazin-2-yl)-4-methylmorpholinium chloride hydrate (DMTMM, 73 mg, 0.26 mmol) were added. The mixture was stirred at room temperature overnight, concentrated under reduced pressure, and diluted with EtOAc and water. The organic layer was dried over anhydrous magnesium sulfate, filtered, and concentrated under reduced pressure. The crude product was purified by recrystallization from EtOAc/hexane to give N-(3-fluoro-4-methanesulfonylaminobenzyl)-3-(2-methyl-6-trifluoromethylpyridin-3-yl)acrylamide (66 mg, 58.8%) as a solid.

¹H NMR (300 MHz, CDCl₃): δ 7.95~7.88 (m, 2H), 7.56~7.51 (m, 2H), 7.18~7.11 (m, 2H), 6.51 (br s, 1H), 6.41 (d, 1H, J=15.6 Hz), 6.07 (br t, 1H), 4.57 (d, 2H, J=6 Hz), 3.03 (s, 3H), 2.72 (s, 3H)

ESI [M+H]+: 432

EXAMPLE 70

3-(2-Isopropoxy-6-trifluoromethyl-pyridin-3-yl)-N-(3-ethynyl-5-fluoro-4-methanesulfonylamino-benzyl)-acrylamide

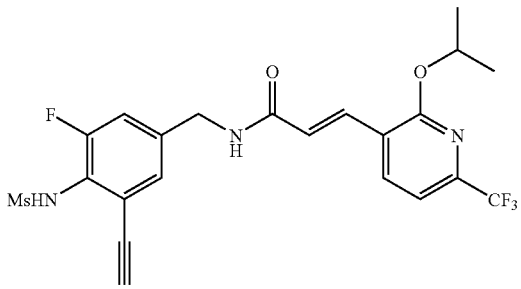

Step 1: Synthesis of 3-(2-isopropoxy-6-trifluoromethyl-pyridin-3-yl)-acrylic acid 60% NaH (24 mg, 3.0 eq) was put into a flask and 2-propanol (30 μl) in DMF (1 ml) was added in syringe, stirred for a while, and finally 3-(2-chloro-6-trifluoromethyl-4-yl-pyridin-3-yl)-acrylic acid (50 mg) was added at room temperature. The reaction mixture was stirred for 18 hrs. After the reaction was completed through the TLC checking, the mixture was diluted with EtOAc, washed with water and brine. The organic layer was dried over anhydrous MgSO₄ and concentrated under reduced pressure to give a crude 3-(2-isopropoxy-6-trifluoromethyl-pyridin-3-yl)-acrylic acid (23 mg, 42%).

¹H NMR (300 MHz, CDCl₃): δ 7.86 (m, 2H), 7.24 (m, 1H), 6.71 (d, 1H, J=15.9 Hz), 5.49 (m, 1H), 1.43 (m, 6H)

Step 2: Synthesis of 3-(2-isopropoxy-6-trifluoromethyl-pyridin-3-yl)-N-(3-ethynyl-5-fluoro-4-methane sulfonylamino-benzyl)-acrylamide N-(4-Aminomethyl-5-ethynyl-2-fluoro-phenyl)-methanesulfonamide HCl salt (23 mg, 0.084 mmol) was reacted with 3-(2-isopropoxy-6-trifluoromethyl-pyridin-3-yl)-acrylic acid (23 mg) to give 3-(2-isopropoxy-6-trifluoromethyl-pyridin-3-yl)-N-(3-ethynyl-5-fluoro-4-methanesulfonylaminobenzyl)-acrylamide (19 mg, 45%) after purification by column chromatography (Hex/EtOAc=3/2).

¹H NMR (300 MHz, CDCl₃): δ 7.81 (m, 1H), 7.75 (d, 1H, J=15.9 Hz), 7.29 (s, 1H), 7.20 (m, 2H), 6.73 (d, 1H, J=15.9 Hz), 6.44 (s, 1H), 6.12 (bs, 1H), 5.48 (m, 1H), 4.53 (d, 2H, J=6.0 Hz), 3.47 (s, 1H), 3.26 (s, 3H), 1.43 (m, 6H)

ESI [M+H]+: 500

EXAMPLE 71

N-(3-Ethynyl-5-fluoro-4-methanesulfonylamino-benzyl)-3-[2-(2-benzyloxycarbonyl-pyrrolidin-1-yl)-6-trifluoromethyl-pyridin-3-yl]-acrylamide

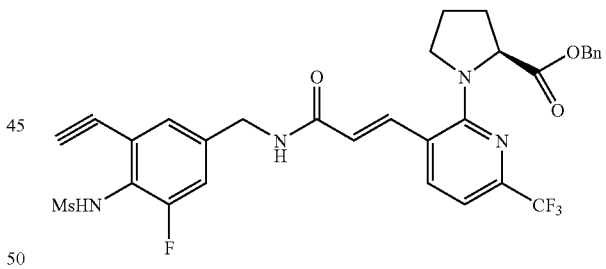

L-Proline benzyl ester hydrochloride (96 mg, 2.0 eq) in DMF was put into a flask and K₂CO₃ (132 mg, 2.0 eq) was added, stirred for a while, and 3-(2-chloro-6-trifluoromethyl-4-yl-pyridin-3-yl)-acrylic acid (50 mg) was added at room temperature. The reaction mixture was stirred for 18 hrs. After the reaction was completed through the TLC checking, the mixture was diluted with EtOAc, washed with 1N HCl solution. The organic layer was dried over anhydrous MgSO₄ and concentrated under reduced pressure to give a crude 6-trifluoromethyl-pyridin-2-yl}-pyrrolidin-2-yl carboxylic acid benzyl ester (45 mg). N-(4-Aminomethyl-5-ethynyl-2-fluoro-phenyl)-methanesulfonamide, HCl salt (30 mg, 0.11 mmol) was reacted with 6-trifluoromethyl-pyridin-2-yl}-pyrrolidin-2-yl-carboxylic acid benzyl ester (45 mg) to give 1-{3-[2-(3-ethynyl-5-fluoro-4-methanesulfonylamino-benzylcarbamoyl)-vinyl]-6-trifluoromethyl-pyridin-2-yl}-pyrrolidin-2-yl-carboxylic acid benzyl ester (3.2 mg, 4.5%) after purification by column chromatography (EtOAc/MeOH=10/1).

¹H NMR (300 MHz, CDCl₃): δ 7.81 (d, 1H, J=15.6 Hz), 7.67 (m, 1H), 7.29 (s, 1H), 7.19 (m, 5H), 6.92 (m, 1H), 6.86 (bs, 1H), 6.40 (m, 2H), 6.09 (d, 1H, J=15.0 Hz), 4.49 (d, 2H, J=5.7 Hz), 4.32 (d, 2H, J=5.7 Hz), 3.48 (s, 1H), 3.26 (s, 3H), 2.38 (m, 2H), 2.25 (m, 2H), 2.02 (m, 3H)

EXAMPLE 72

3-(2-Butylamino-6-trifluoromethyl-pyridin-3-yl)-N-(3-ethynyl-5-fluoro-4-methanesulfonylamino-benzyl)-acrylamide

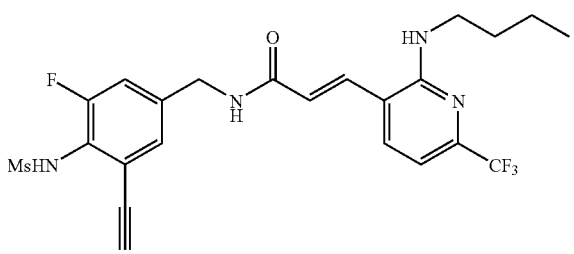

3-(2-Chloro-6-trifluoromethyl-pyridin-3-yl)-N-(3-ethynyl-5-fluoro-4-methanesulfonylamino-benzyl)-acrylamide (30 mg, 0.057 mmol) was reacted with n-butylamine (500 μl) as in example 65 to give the title compound (3.6 mg, 12%) after purification by column chromatography (Hex EtOAc=1/1).

¹H NMR (300 MHz, CDCl₃): δ 7.66 (d, 1H, J=15.3 Hz), 7.57 (d, 1H, J=7.8 Hz), 7.23 (s, 1H), 7.12 (dd, 1H, J=1.8 and 10.8 Hz), 6.89 (d, 1H, J=7.8 Hz), 6.64 (s, 1H), 6.35 (d, 1H, J=15.3 Hz), 6.24 (t, 1H), 5.04 (s, 1H), 4.48 (d, 2H, J=6.0 Hz), 3.50 (m, 2H), 3.46 (s, 1H), 3.27 (s, 3H), 1.61 (m, 2H), 1.36 (m, 2H), 0.95 (t, 3H, J=7.2 Hz)

ESI [M+H]+: 513

EXAMPLE 73

3-(2-Cyclopentylamino-6-trifluoromethyl-pyridin-3-yl)-N-(3-ethynyl-5-fluoro-4-methane sulfonylamino-benzyl)-acrylamide

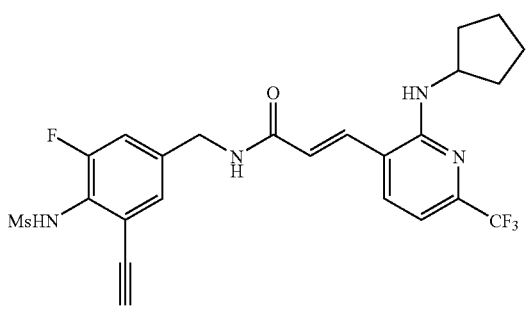

3-(2-Chloro-6-trifluoromethyl-pyridin-3-yl)-N-(3-ethynyl-5-fluoro-4-methanesulfonylamino-benzyl)-acrylamide (30 mg, 0.057 mmol) was reacted with cyclopentylamine (500 μl) as in example 65 to give the title compound (2.5 mg, 8%) after purification by column chromatography (Hex/EtOAc=1/1).

¹H NMR (300 MHz, CDCl₃): δ 7.65 (d, 1H, J=15.0 Hz), 7.58 (d, 1H, J=7.5 Hz), 7.29 (s, 1H), 7.17 (dd, 1H, J=2.1 and 10.8 Hz), 6.90 (d, 1H, J=7.5 Hz), 6.46 (s, 1H), 6.35 (d, 1H, J=15.0 Hz), 6.07 (t, 1H), 4.82 (s, 1H), 4.53 (d, 2H, J=6.3 Hz), 4.41 (m, 1H), 3.49 (s, 1H), 3.27 (s, 3H), 2.17 (m, 2H), 1.70-1.30 (m, 6H).

ESI [M+H]+: 525

EXAMPLE 74

N-(3-Ethynyl-5-fluoro-4-methanesulfonylamino-benzyl)-3-(2-isobutoxy-6-trifluoromethyl-pyridin-3-yl)-acrylamide

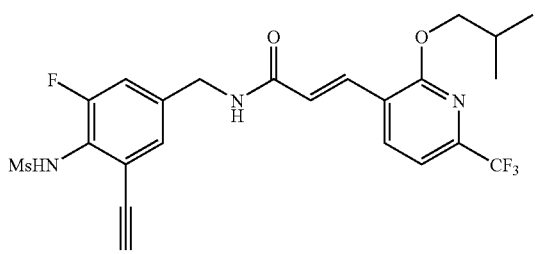

A mixture of 3-(2-chloro-6-trifluoromethyl-pyridin-3-yl)-N-(3-ethynyl-5-fluoro-4-methanesulfonylamino-benzyl)-acrylamide (50 mg, 0.11 mmol), 2-methyl-1-propanol (20 μl, 0.22 mmol) and 60% NaH (13 mg, 0.33 mmol) in DMF was stirred at ambient temperature for 4 hrs. The reaction mixture was diluted with water and then acidified with 2N HCl solution. The aqueous phase was extracted with EtOAc and the combined organic phase was washed with brine, dried over anhydrous MgSO₄ and concentrated under reduced pressure. The resulting residue was purified by column chromatography (Hex EtOAc=1/2) to give the title compound (12 mg, 40%).

¹H NMR (300 MHz, CDCl₃): δ 7.97 (d, 1H, J=7.8 Hz), 7.83 (m, 2H), 7.71 (s, 1H), 7.31 (m, 2H), 7.22 (dd, 1H, J=1.8 and 10.5 Hz), 6.94 (d, 1H, J=15.9 Hz), 4.54 (d, 2H, J=6.0 Hz), 4.22 (d, 2H, J=6.6 Hz), 3.64 (s, 1H), 3.18 (s, 3H), 2.18 (m, 1H), 1.04 (d, 6H, J=6.6 Hz).

ESI [M+H]+: 514

EXAMPLE 75

N-(3-Ethynyl-5-fluoro-4-methanesulfonylamino-benzyl)-3-[2-(2-methoxy-ethoxy)-6-trifluoromethyl-pyridin-3-yl]-acrylamide

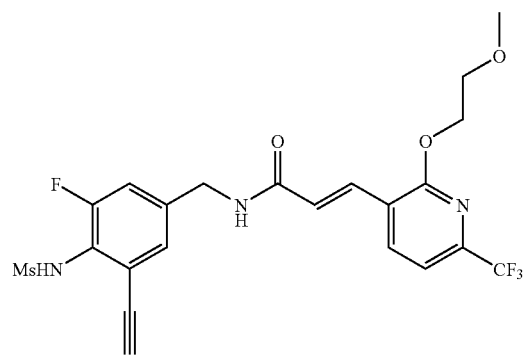

Step 1: 3-[2-(2-Methoxy-ethoxy)-6-trifluoromethyl-pyridin-3-yl]-acrylic acid

The title compound was obtained according to the general procedure described in example 66 (step 1).

3-(2-Chloro-6-trifluoromethyl-pyridin-3-yl)-acrylic acid (86.6 mg, 0.344 mmol) was reacted with methoxyethanol to give 3-[2-(2-methoxy-ethoxy)-6-trifluoromethyl-pyridin-3-yl]-acrylic acid (100 mg, 99%).

$^1$H NMR (300 MHz, CDCl$_3$): δ 7.90 (d, 1H, J=7.5 Hz), 7.88 (d, 1H, J=16.2 Hz), 7.30 (d, 1H, J=7.5 Hz), 4.66-4.63 (m, 2H), 3.86-3.82 (m, 2H), 3.47 (s, 3H).

Step 2: N-(3-Ethynyl-5-fluoro-4-methanesulfonylamino-benzyl)-3-[2-(2-methoxy-ethoxy)-6-trifluoromethyl-pyridin-3-yl]-acrylamide The title compound was obtained according to the general procedure described in example 38 (step 6).

N-(4-Aminomethyl-2-ethynyl-6-fluoro-phenyl)-methanesulfonamide HCl salt (45 mg, 0.156 mmol) was reacted with 3-[2-(2-methoxy-ethoxy)-6-trifluoromethyl-pyridin-3-yl]-acrylic acid (38 mg, 0.13 mmol) to give the title compound (47 mg, 70%).

$^1$H NMR (300 MHz, DMSO-d$^6$): δ 9.44 (s, 1H), 8.85 (t, 1H, J=6.0 Hz), 8.20 (d, 1H, J=7.5 Hz), 7.58 (d, 1H, J=16.8 Hz), 7.54 (d, 1H, J=8.1 Hz), 7.29-7.26 (m, 2H), 6.93 (d, 1H, J=15.9 Hz), 4.54-4.51 (m, 2H), 4.40 (d, 2H, J=6.0 Hz), 3.97 (s, 1H), 3.76-3.73 (m, 2H), 3.31 (s, 3H), 3.07 (s, 3H).

ESI [M+H]+: 516

EXAMPLE 76

3-(2-Butyl-5-chloro-6-trifluoromethyl-pyridin-3-yl)-N-(3-ethynyl-5-fluoro-4-methanesulfonylamino-benzyl)-acrylamide

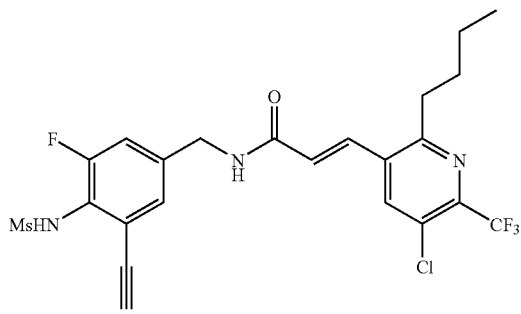

Step 1: 3-(2-Butyl-5-chloro-6-trifluoromethyl-pyridin-3-yl)-acrylic acid

To a suspension of 3-(2-chloro-6-trifluoromethyl-pyridin-3-yl)-acrylic acid (78 mg, 0.31 mmol) in THF (2 mL) was added dropwise 2.5M n-buthyllithium (2 eq) at −78° C. The mixture was stirred for 12 hours at room temperature. The residue was diluted with EtOAc and water. The organic layer was washed with 1N HCl, saturated sodium bicarbonate, and brine, dried over anhydrous magnesium sulfate, filtered and concentrated under reduced pressure. The crude residue was column-chromatographed to give 3-(2-butyl-5-chloro-6-trifluoromethyl-pyridin-3-yl)-acrylic acid (14 mg, 17%).

$^1$H NMR (300 MHz, CDCl$_3$): δ 7.83 (d, 1H, J=16.5 Hz), 7.51 (s, 1H), 6.35 (d, 1H, J=16.5 Hz), 2.79-2.66 (m, 2H), 1.66-1.50 (m, 2H), 1.50-1.44 (m, 2H), 0.98 (t, 3H, J=7.5 Hz),

Step 2: 3-(2-Butyl-5-chloro-6-trifluoromethyl-pyridin-3-yl)-N-(3-ethynyl-5-fluoro-4-methanesulfonylamino-benzyl)-acrylamide The title compound was obtained according to the general procedure described in example 38 (step 6).

N-(4-Aminomethyl-2-ethynyl-6-fluoro-phenyl)-methanesulfonamide, HCl salt (13 mg, 0.044 mmol) was reacted with 3-(2-butyl-5-chloro-6-trifluoromethyl-pyridin-3-yl)-acrylic acid (14 mg, 0.036 mmol) to give the title compound (18 mg, 86%).

$^1$H NMR (300 MHz, DMSO-d$^6$): δ 9.45 (s, 1H), 8.92 (t, 1H, J=6.0 Hz), 7.92 (s, 1H), 7.50 (d, 1H, J=15.6 Hz), 7.30-7.29 (m, 2H), 6.55 (d, 1H, J=15.9 Hz), 4.52 (s, 1H), 4.41 (d, 2H, J=5.7 Hz), 3.02 (s, 3H), 2.80-2.75 (m, 2H), 1.59-1.49 (m, 2H), 0.88 (t 3H, J=7.5 Hz).

ESI [M+H]+: 532

EXAMPLE 77

3-(2-sec-Butoxy-6-trifluoromethyl-pyridin-3-yl)-N-(3-ethynyl-5-fluoro-4-methanesulfonylamino-benzyl)-acrylamide

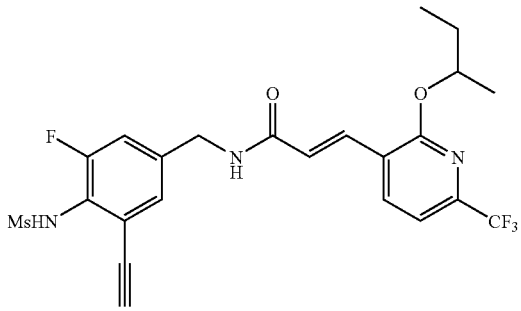

Step 1: 3-(2-sec-Butoxy-6-trifluoromethyl-pyridin-3-yl)-acrylic acid

2-Butanol (70.1 mg, 0.945 mmol) and sodium hydride (70 mg, 1.8 mmol) were added in DMF. The reaction mixture was stirred for 10 mins and then 3-(2-chloro-6-trifluoromethyl-pyridin-3-yl)-acrylic acid (67 mg, 0.266 mmol) was added into the reaction mixture. The reaction mixture was diluted with EtOAc, and washed with water and brine. The organic layer was dried over anhydrous MgSO$_4$ and concentrated under reduced pressure. The resulting residue was purified by column chromatography (Hex/EtOAc=1/1) to give the title product (52 mg).

$^1$H NMR (300 MHz, CDCl$_3$): δ 7.89 (d, 1H, J=7.2), 7.86 (d, 1H, J=3.6 Hz), 7.25 (d, 1H, J=7.8 Hz), 6.72 (d, 1H, J=16.2 Hz), 5.35 (h, 1H, J=6.0 Hz), 1.79 (m, 2H), 1.26 (m, 3H), 1.02 (m, 3H)

Step 2: 3-(2-sec-Butoxy-6-trifluoromethyl-pyridin-3-yl)-N-(3-ethynyl-5-fluoro-4-methanesulfonylamino-benzyl)-acrylamide N-(4-Aminomethyl-2-ethenyl-6-fluoro-phenyl)-methanesulfonamide HCl salt (35 mg, 0.13 mmol) was reacted with 3-(2-sec-butoxy-6-trifluoromethyl-pyridin-3-yl)-acrylic acid (22 mg) to give the title compound (10 mg) after purification by column chromatography (Hex/EtOAc=1/1).

$^1$H NMR (300 MHz, CDCl$_3$): δ 7.82 (d, 1H, J=7.8 Hz), 7.75 (d, 1H, J=15.6 Hz), 7.27 (d, 1H, J=15.9 Hz), 7.21 (m, 3H), 6.73 (d, 1H, J=15.6 Hz), 6.44 (s, 1H), 6.11 (t, 1H), 5.33 (h, 1H, J=6.3 Hz), 4.53 (d, 2H, J=6.3 Hz), 3.48 (s, 1H), 3.26 (s, 3H), 1.37 (d, 3H, H=6.0 Hz), 0.98 (t, 3H, J=7.2 Hz)

ESI [M+H]+: 514

EXAMPLE 78

N-(3-Ethynyl-5-fluoro-4-methanesulfonylamino-benzyl)-3-(2-phenoxy-6-trifluoromethyl-pyridin-3-yl)-acrylamide

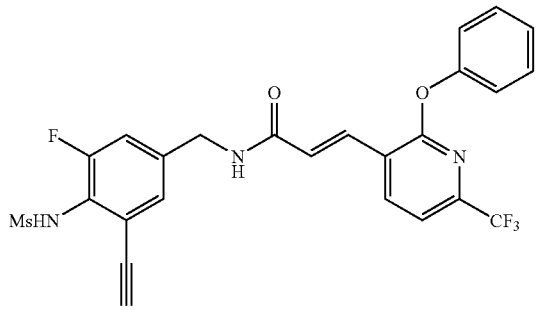

Step 1: 3-(2-Phenoxy-6-trifluoromethyl-pyridin-3-yl)-acrylic acid

Phenol (57 mg, 0.60 mmol) and sodium hydride (32 mg, 0.8 mmol) were added in DMF (15 mL). The reaction mixture was stirred for 10 mins and then 3-(2-chloro-6-trifluoromethyl-pyridin-3-yl)-acrylic acid (70 mg, 0.27 mmol) was added into the reaction mixture. The reaction mixture was diluted with EtOAc, and washed with water and brine. The organic layer was dried over anhydrous $MgSO_4$ and concentrated under reduced pressure. The resulting residue was purified by column chromatography (Hex EtOAc=1/1) to give the title product (15 mg).

$^1$H NMR (300 MHz, $CDCl_3$): δ 8.07 (d, 1H, J=15.9 Hz), 8.04 (d, 1H, J=7.5 Hz), 7.43 (m, 3H), 7.21 (m, 2H), 6.79 (d, 1H, J=15.9 Hz)

Step 2: N-(3-Ethynyl-5-fluoro-4-methanesulfonylamino-benzyl)-3-(2-phenoxy-6-trifluoromethyl-pyridin-3-yl)-acrylamide N-(4-Aminomethyl-2-ethenyl-6-fluoro-phenyl)-methanesulfonamide HCl salt (35 mg, 0.13 mmol) was reacted with 3-(2-phenoxy-6-trifluoromethyl-pyridin-3-yl)-acrylic acid (17 mg) to give the title compound (22 mg, 75%) after purification by column chromatography (Hex/EtOAc=1/1).

$^1$H NMR (300 MHz, $CDCl_3$): δ 7.90 (d, 1H, J=7.5 Hz), 7.80 (d, 1H, J=15.6 Hz), 7.33 (m, 3H), 7.21 (m, 2H), 7.03 (m, 2H), 6.80 (d, 1H, J=15.6 Hz), 6.45 (s, 1H), 6.37 (t, 1H), 4.43 (d, 2H, J=6.0 Hz), 3.32 (s, 1H), 3.22 (s, 3H)

ESI [M+H]+: 534

EXAMPLE 79

3-[2-(Tetrahydro-furan-3-yloxy)-6-trifluoromethyl-pyridin-3-yl]-N-(3-ethynyl-5-fluoro-4-methanesulfonylamino-benzyl)-acrylamide

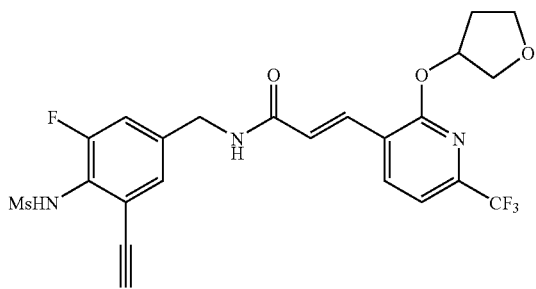

3-(2-Chloro-6-trifluoromethyl-pyridin-3-yl)-N-(3-ethynyl-5-fluoro-4-methanesulfonylamino-benzyl)-acrylamide (50 mg, 0.11 mmol) and 3-hydroxytetrahydrofuran (18 μl, 0.22 mmol) was reacted as in example 72 to give the title compound (23 mg, 21%).

$^1$H NMR (300 MHz, $CDCl_3$): δ 7.85 (d, 1H, J=7.8 Hz), 7.71 (d, 1H, J=15.9 Hz), 7.30 (d, 1H, J=7.8 Hz), 7.29 (s, 1H), 7.18 (dd, 1H, J=2.1 and 10.8 Hz), 6.77 (d, 1H, J=15.9 Hz), 6.51 (s, 1H), 6.41 (t, 1H), 5.74 (m, 1H), 4.52 (d, 2H, J=6.0 Hz), 4.05 (m, 3H), 3.91 (m, 1H), 3.46 (s, 1H), 3.25 (s, 3H), 2.35 (m, 1H), 2.30 (m, 1H).

ESI [M+H]+: 528

EXAMPLE 80

N-(3-Ethynyl-5-fluoro-4-methanesulfonylamino-benzyl)-3-[2-pyrazol-1-yl-6-trifluoromethyl-pyridin-3-yl]-acrylamide

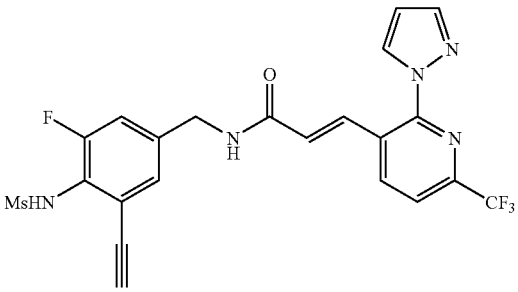

Step 1: 3-(5-Chloro-2-pyrazol-1-yl-6-trifluoromethyl-pyridin-3-yl)-acrylic acid The title compound was obtained according to the general procedure described in example 66 (step 1).

3-(2-Chloro-6-trifluoromethyl-pyridin-3-yl)-acrylic acid (100 mg, 0.397 mmol) was reacted with pyrazole to give 3-(5-chloro-2-pyrazol-1-yl-6-trifluoromethyl-pyridin-3-yl)-acrylic acid (100 mg, 99%).

$^1$H NMR (300 MHz, $CDCl_3$): δ 8.59 (d, 1H, J=15.9 Hz), 8.53 (d, 1H, J=2.7 Hz), 8.16 (d, 1H, J=8.1 Hz), 7.84 (d, 1H, J=0.6 Hz), 7.64 (d, 1H, J=8.1 Hz), 5.52 (d, 1H, J=2.7 Hz), 6.42 (d, 1H, J=15.9 Hz).

Step 2: N-(3-Ethynyl-5-fluoro-4-methanesulfonylamino-benzyl)-3-[2-(2-methoxy-ethoxy)-6-trifluoromethyl-pyridin-3-yl]-acrylamide The title compound was obtained according to the general procedure described in example 38 (step 6).

N-(4-Aminomethyl-2-ethynyl-6-fluoro-phenyl)-methanesulfonamide HCl salt (8.5 mg, 0.029 mmol) was reacted with 3-(5-chloro-2-pyrazol-1-yl-6-trifluoromethyl-pyridin-3-yl)-acrylic acid (7 mg, 0.025 mmol) to give the title compound (9 mg, 70%).

$^1$H NMR (300 MHz, $CDCl_3$): δ 8.47 (d, 1H, J=2.7 Hz), 8.32 (d, 1H, J=15.9 Hz), 8.11 (d, 1H, J=7.8 Hz), 7.80 (d, 1H, J=0.6 Hz), 7.60 (d, 1H, J=7.8 Hz), 7.23 (s, 1H), 7.15-7.11 (m, 1H), 6.59-6.49 (m, 3H), 6.38 (d, 1H, J=15.9 Hz), 4.46 (d, 2H, J=6.0 Hz), 3.44 (s, 1H), 3.24 (s, 3H)

ESI [M+H]+: 534

EXAMPLE 81

N-(3-Fluoro-4-methanesulfonylamino-benzyl)-3-[2-(pyridin-3-yloxy)-6-trifluoromethyl-pyridin-3-yl]-acrylamide

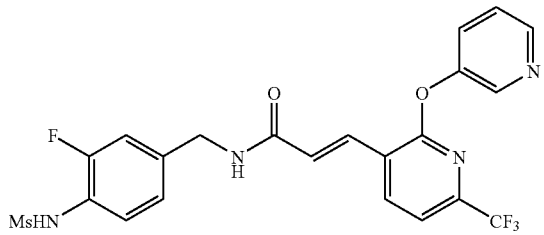

3-(2-Chloro-6-trifluoromethyl-pyridin-3-yl)-N-(3-fluoro-4-methanesulfonylamino-benzyl)-acrylamide (48 mg, 0.11 mmol), 3-hydroxypyridine (97 mg) and potassium carbonate (421 mg) were added in 40 ml DMF. The reaction mixture was stirred overnight. The reaction mixture was extracted with ethyl acetate (30 ml×2) and water (30 ml). A combined organic layer was washed with H$_2$O (30 ml×4) and brine (40 ml), dried with MgSO$_4$, and then concentrated in vacuo. The residue was purified with column chromatography (hexane/ethylacetate=1/4) to yield the title compound (46 mg, 82%).

$^1$H NMR (300 MHz, acetone d$_6$): δ 8.53 (d, 1H, J=2.4 Hz), 8.45 (dd, 1H, J=4.5, 1.2 Hz), 8.31 (d, 1H, J=7.8 Hz), 8.00 (br t, 1H), 7.83 (d, 1H, J=15.9 Hz), 7.71 (m, 1H), 7.60 (d, 1H, J=7.8 Hz), 7.44 (m, 1H), 7.20 (m, 1H), 7.12 (d, 1H, J=15.9 Hz), 4.50 (d, 2H, J=6.0 Hz), 2.98 (s, 3H).

EXAMPLE 82

N-(3-Ethynyl-5-fluoro-4-methanesulfonylamino-benzyl)-3-[2-(4-fluoro-phenoxy)-6-trifluoromethyl-pyridin-3-yl]-acrylamide

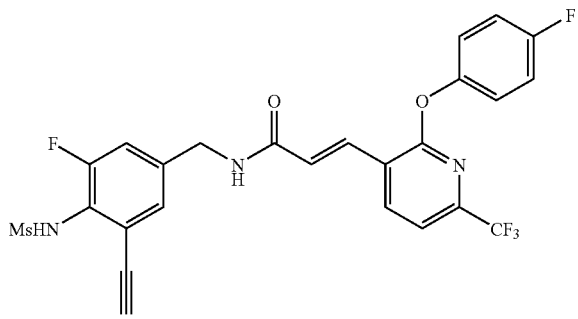

Step 1: 3-[2-(4-Fluoro-phenoxy)-6-trifluoromethyl-pyridin-3-yl]-acrylic acid 4-Fluoro-phenol (116 mg, 1.03 mmol) and sodium hydride (53 mg, 1.3 mmol) were added in DMF (7 mL). The reaction mixture was stirred for 10 mins and then 3-(2-chloro-6-trifluoromethyl-pyridin-3-yl)-acrylic acid (132 mg, 0.52 mmol) was added into the reaction mixture. The reaction mixture was diluted with EtOAc, and washed with water and brine. The organic layer was dried over anhydrous MgSO$_4$ and concentrated under reduced pressure. The resulting residue was purified by column chromatography (Hex EtOAc=1/1) to give the title product (57 mg).

$^1$H NMR (300 MHz, CDCl$_3$): δ 8.00 (d, 1H, J=15.9 Hz), 7.99 (d, 1H, J=7.8 Hz), 7.36 (d, 1H, J=7.8 Hz), 7.08 (m, 3H), 6.73 (d, 1H, J=15.9 Hz)

Step 2: N-(3-Ethynyl-5-fluoro-4-methanesulfonylamino-benzyl)-3-[2-(4-fluoro-phenoxy)-6-trifluoromethyl-pyridin-3-yl]-acrylamide N-(4-Aminomethyl-2-ethenyl-6-fluoro-phenyl)-methanesulfonamide HCl salt (32 mg, 0.13 mmol) was reacted with 3-[2-(4-fluoro-phenoxy-6-trifluoromethyl-pyridin-3-yl)-acrylic acid (25 mg) to give the title compound (42 mg, 67%) after purification by column chromatography (Hex/EtOAc=1/1).

$^1$H NMR (300 MHz, CDCl$_3$): δ 7.90 (d, 1H, J=7.8 Hz), 7.79 (d, 1H, J=15.6 Hz), 7.30 (d, 1H, J=7.5 Hz), 7.19 (s, 1H), 7.03 (m, 4H), 6.79 (d, 1H, J=15.6 Hz), 6.64 (br t, 1H), 6.57 (s, 1H), 4.41 (d, 2H, J=6.0 Hz), 3.37 (s, 1H), 3.16 (s, 3H)

EXAMPLE 83

N-(3-Ethynyl-5-fluoro-4-methansulfonylamino-benzyl)-3-[2-(2-hydroxymethyl-pyrrolidin-1-yl)-6-trifluoromethyl-pyridin-3-yl]-acrylamide

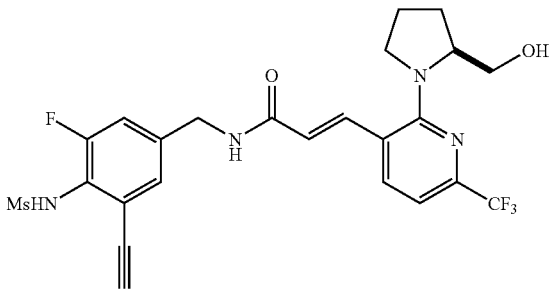

N-(4-Aminomethyl-5-ethynyl-2-fluoro-phenyl)-methanesulfonamide, HCl salt (17 mg, 0.06 mmol) was reacted with 2-(2-hydroxymethyl-pyrrolidin-1-yl)-6-trifluoromethyl-pyridin-3-yl)-acrylic acid (19 mg, 0.06 mmol) to give the title compound (15 mg, 46%) after purification by column chromatography (Hex/EtOAc=1/2).

$^1$H NMR (300 MHz, CDCl$_3$): δ 7.88 (d, 1H, J=15.6 Hz), 7.68 (m, 1H), 7.30 (s, 1H), 7.18 (m, 1H), 7.03 (m, 1H), 6.44 (s, 1H), 6.20 (d, 1H, J=15.0 Hz), 6.05 (bs, 1H), 4.52 (d, 1H, J=6.3 Hz), 3.79 (m, 6H), 3.41 (m, 3H), 3.27 (s, 3H).

EXAMPLE 84

N-(3-Ethynyl-5-fluoro-4-methansulfonylamino-benzyl)-3-[2-(2,2,2-trifluoro-ethoxy)-6-trifluoromethyl-pyridin-3-yl]-acrylamide

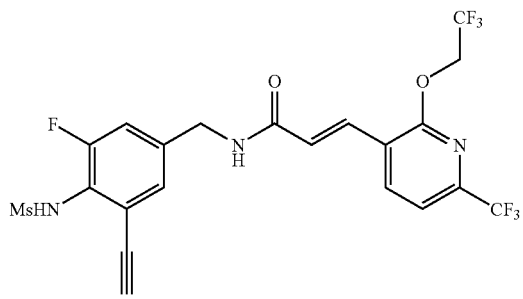

N-(4-Aminomethyl-5-ethynyl-2-fluoro-phenyl)-methanesulfonamide, HCl salt (69 mg, 0.25 mmol) was reacted with 2-(2,2,2-trifluoro-ethoxy)-6-trifluoromethyl-pyridin-3-yl-acrylic acid (78 mg, 0.26 mmol) to give the title compound (73 mg, 54%) after purification by column chromatography (Hex/EtOAc=1:1).

¹H NMR (300 MHz, CDCl₃): δ 7.92 (d, 1H, J=7.5 Hz), 7.73 (d, 1H, J=16.8 Hz), 7.42 (d, 1H, J=7.8 Hz), 7.20 (m, 2H), 6.77 (d, 1H, J=15.6 Hz), 6.41 (s, 1H), 6.03 (bs, 1H), 4.90 (d, 2H, J=8.1 Hz), 4.55 (d, 2H, J=5.7 Hz), 3.89 (s, 1H), 3.26 (s, 3H),

EXAMPLE 85

N-(3-Ethynyl-5-fluoro-4-methanesulfonylamino-benzyl)-3-[2-(3-methoxy-pyrrolidin-1-yl)-4-trifluoromethyl-phenyl]-acrylamide

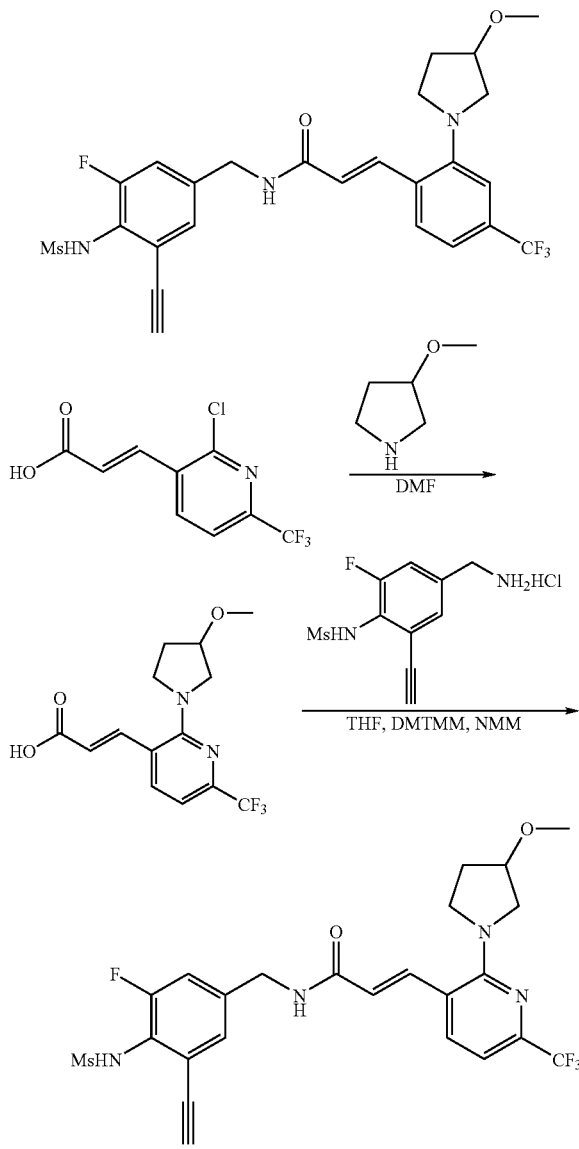

Step 1: Synthesis of 3-[2-(3-methoxy-pyrrolidin-1-yl)-6-trifluoromethyl-pyridin-3-yl]-acrylic acid To a suspension of 3-(2-chloro-6-trifluoromethyl-pyridin-3-yl)-acrylic acid (50 mg, 0.198 mmol) in 3-methoxy-pyrrolidine (40 mg, 0.396 mmol) was added DMF (1.0 ml). The mixture was stirred for 12 hours at room temperature. The reaction mixture was diluted with EtOAc and then washed two times with 1N-HCl and brine, dried over MgSO₄, filtered and concentrated under reduced pressure. The crude residue was chromatographed to yield the 3-[2-(3-methoxy-pyrrolidin-1-yl)-6-trifluoromethyl-pyridin-3-yl]-acrylic acid (59 mg, 98%).

¹H NMR (300 MHz, CDCl₃): δ 8.06 (d, 1H, J=15.9 Hz), 7.71 (d, 1H, J=7.5 Hz), 7.01 (d, 1H, J=7.50 Hz), 6.23 (d, 1H, J=15.9 Hz), 4.05 (t, 1H, J=2.1 Hz), 3.89-3.58 (m, 2H), 3.69-3.58 (m, 2H), 3.37 (s, 3H), 2.18-2.11 (m, 1H), 2.05-1.94 (m, 1H).

Step 2: Synthesis of N-(3-ethynyl-5-fluoro-4-methanesulfonylamino-benzyl)-3-[2-(3-methoxy-pyrrolidin-1-yl)-4-trifluoromethyl-phenyl]-acrylamide N-(4-Aminomethyl-2-ethynyl-6-fluoro-phenyl)-methanesulfonamide, HCl salt (16.6 mg, 0.057 mmol) was reacted with 3-[2-(3-methoxy-pyrrolidin-1-yl)-6-trifluoromethyl-pyridin-3-yl]-acrylic acid (15.2 mg, 0.048 mmol) to give N-(3-ethynyl-5-fluoro-4-methanesulfonylamino-benzyl)-3-[2-(3-methoxy-pyrrolidin-1-yl)-6-trifluoromethyl-pyridin-3-yl]-acrylamide (18 mg, 58%) after purification by recrystallization from n-hexane/EtOAc.

¹H NMR (300 MHz, DMSO): δ 9.45 (s, 1H, br), 8.75 (t, 1H, J=6.0 Hz), 7.83 (d, 1H, J=7.8 Hz), 7.67 (d, 1H, J=15.6 Hz), 7.28 (s, 1H), 7.27 (d, 1H, J=7.8 Hz), 7.13 (d, 1H, J=7.8 Hz), 6.45 (d, 1H, J=15.6 Hz), 4.50 (s, 1H), 4.38 (d, 2H, J=5.7 Hz), 4.00 (d, 1H, J=1.8 Hz), 3.71-3.12 (m, 7H), 3.06 (s, 3H), 2.00-1.92 (m, 2H).

EXAMPLE 86

3-(2-Butoxy-6-trifluoromethyl-pyridin-3-yl)-N-(3-fluoro-4-methanesulfonylamino-benzyl)-propionamide

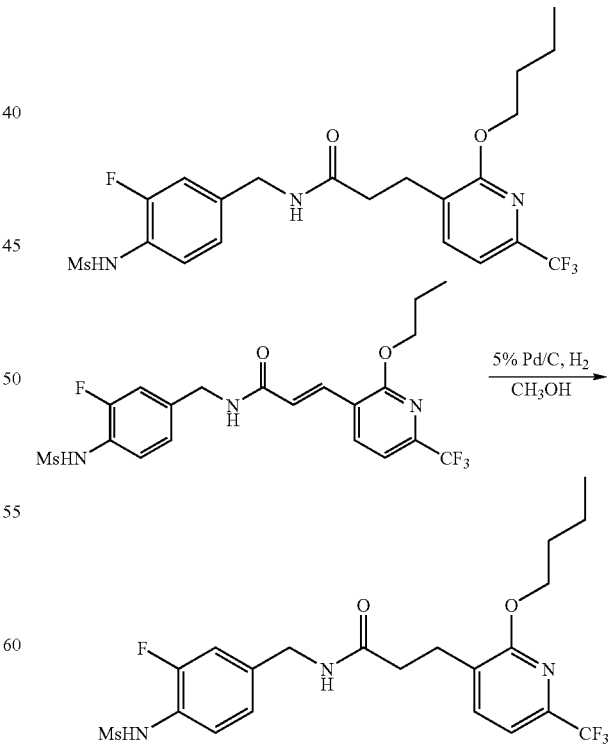

To a suspension of 3-(2-butoxy-6-trifluoromethyl-pyridin-3-yl)-N-(3-fluoro-4-methanesulfonylamino-benzyl)-acrylamide (19.3 mg, 0.039 mmol) in 5% Pd/C (6 mg) was added CH$_3$OH (1.0 ml). The mixture was purged three times with hydrogen gas (50 psi) and shaken for 40 min at room temperature. The reaction mixture was filtered over celite pad and concentrated under reduced pressure. The crude residue was chromatographed to yield the 3-(2-butoxy-6-trifluoromethyl-pyridin-3-yl)-N-(3-fluoro-4-methanesulfonylamino-benzyl)-propionamide (19 mg, 98%).

$^1$H NMR (300 MHz, DMSO): δ 9.49 (s, 1H, br), 8.43 (s, 1H), 7.71 (d, 1H, J=7.5 Hz), 7.35 (d, 1H, J=7.2 Hz), 7.28 (t, 1H, J=8.1 Hz), 6.70 (d, 1H, J=8.4 Hz), 6.96 (d, 1H, J=9.0 Hz), 4.31 (t, 2H, J=3.3 Hz), 4.21 (d, 2H, J=5.7 Hz), 2.87 (s, 3H), 2.85 (t, 2H, J=8.2 Hz), 2.51-2.47 (m, 2H), 1.77-1.68 (m, 2H), 1.50-1.37 (m, 2H), 0.93 (t 3H, J=7.5 Hz).

EXAMPLE 87

N-(3-Fluoro-4-methanesulfonylamino-benzyl)-3-[2-(2,2,2-trifluoro-ethoxy)-6-trifluoromethyl-pyridin-3-yl]-acrylamide

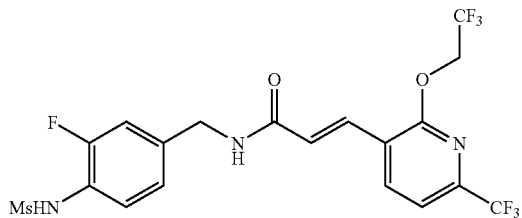

N-(4-Aminomethyl-2-fluoro-phenyl)-methanesulfonamide, HCl salt (41 mg, 0.16 mmol) was reacted with 2-(2,2,2-trifluoro-ethoxy)-6-trifluoromethyl-pyridin-3-yl-acrylic acid (50 mg, 0.16 mmol) to give the title compound (53 mg, 64%) after purification by column chromatography (Hex/EtOAc=1.1).

$^1$H NMR (300 MHz, CDCl$_3$): δ 7.92 (d, 1H, J=8.1 Hz), 7.73 (d, 1H, J=15.3 Hz), 7.55 (t, 1H, J=8.7 Hz), 7.42 (d, 1H, J=7.42 Hz), 7.15 (m, 2H), 6.78 (d, 1H, J=16.2 Hz), 6.50 (bs, 1H), 6.03 (bs, 1H), 4.90 (q, 2H, J=7.8 Hz), 4.57 (d, 2H, J=5.7 Hz), 3.03 (s, 3H),

EXAMPLE 88

3-(2-Butylamino-6-trifluoromethyl-pyridin-3-yl)-N-(3-fluoro-4-methanesulfonylamino-benzyl)-acrylamide

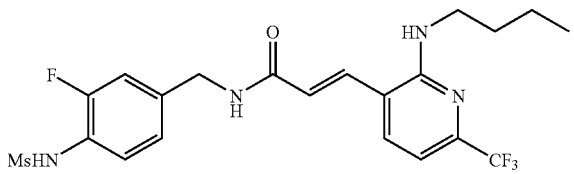

N-(4-Aminomethyl-2-fluoro-phenyl)-methanesulfonamide, HCl salt (53 mg, 0.19 mmol) was reacted with 3-(2-butylamino-6-trifluoromethyl-pyridin-3-yl)-acrylic acid (10 mg, 0.036 mmol) to give the title compound (12 mg, 69%) after purification by column chromatography (Hex/EtOAc=2/3).

$^1$H NMR (300 MHz, CDCl$_3$): δ 7.68 (d, 1H, J=15.0 Hz), 7.57 (d, 1H, J=7.5 Hz), 7.48 (t, 1H, J=8.4 Hz), 7.10 (m, 2H), 6.89 (d, 1H, J=7.5 Hz), 6.80 (s, 1H), 6.37 (d, 1H, J=15.0 Hz), 6.12 (t, 1H, J=6.0 Hz), 6.95 (t, 1H, J=5.4 Hz), 4.54 (d, 2H, J=6.0 Hz), 3.50 (m, 2H), 3.03 (s, 3H), 1.61 (m, 2H), 1.40 (m, 2H), 0.95 (t, 3H, J=7.5 Hz).

EXAMPLE 89

3-(2-Cyclopentylamino-6-trifluoromethyl-pyridin-3-yl)-N-(3-fluoro-4-methanesulfonylamino-benzyl)-acrylamide

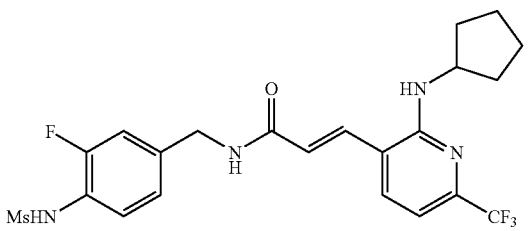

N-(4-Aminomethyl-2-fluoro-phenyl)-methanesulfonamide, HCl salt (53 mg, 0.19 mmol) was reacted with 3-(2-cyclopentylamino-6-trifluoromethyl-pyridin-3-yl)-acrylic acid (10 mg, 0.034 mmol) to give the title compound (6.3 mg, 38%) after purification by column chromatography (Hex/EtOAc=2/3).

$^1$H NMR (300 MHz, CDCl$_3$): δ 7.65 (d, 1H, J=15.3 Hz), 7.56 (m, 2H), 7.13 (m, 2H), 6.89 (d, 1H, J=7.8 Hz), 6.60 (s, 1H), 6.35 (d, 1H, J=15.3 Hz), 6.03 (t, 1H), 4.82 (d, 1H, J=6.3 Hz), 4.56 (d, 2H, J=6.0 Hz), 4.40 (m, 1H), 3.03 (s, 3H), 2.14 (m, 2H), 1.67 (m, 4H), 1.44 (m, 2H).

EXAMPLE 90

N-(3-Fluoro-4-methanesulfonylamino-benzyl)-3-[2-(3-methoxy-pyrrolidin-1-yl)-6-trifluoromethyl-pyridin-3-yl]-acrylamide

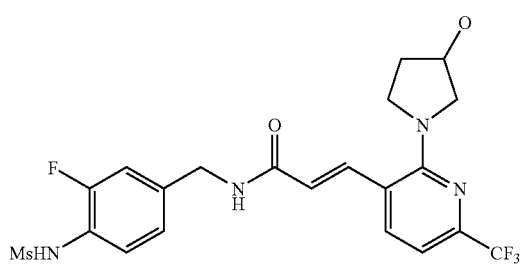

N-(4-Aminomethyl-2-fluoro-phenyl)-methanesulfonamide, HCl salt (14.5 mg, 0.057 mmol) was reacted with 3-[2-(3-methoxy-pyrrolidin-1-yl)-6-trifluoromethyl-pyridin-3-yl]-acrylic acid (15 mg, 0.047 mmol) to give N-(3-fluoro-4-methanesulfonylamino-benzyl)-3-[2-(3-methoxy-pyrrolidin-1-yl)-6-trifluoromethyl-pyridin-3-yl]-acrylamide (22 mg, 76%) after purification by recrystallization from n-hexane/CH$_2$Cl$_2$.

$^1$H NMR (300 MHz, DMSO): δ 9.55 (s, 1H, br), 8.71 (t, 1H, J=57 Hz), 7.81 (d, 1H, J=7.5 Hz), 7.67 (d, 1H, J=15.3 Hz), 7.34 (t, 1H, J=8.4 Hz), 7.21-7.10 (m, 2H), 6.44 (d, 1H, J=15.6 Hz), 4.38 (d, 1H, J=6.0 Hz), 4.01 (s, 1H), 3.71-3.16 (m, 7H), 2.99 (s, 3H), 2.00-1.93 (m, 2H).

EXAMPLE 91

N-(3-Ethynyl-5-fluoro-4-methanesulfonylamino-benzyl)-3-(2-pyrrolidin-1-yl-6-trifluoromethyl-pyridin-3-yl)-propionamide

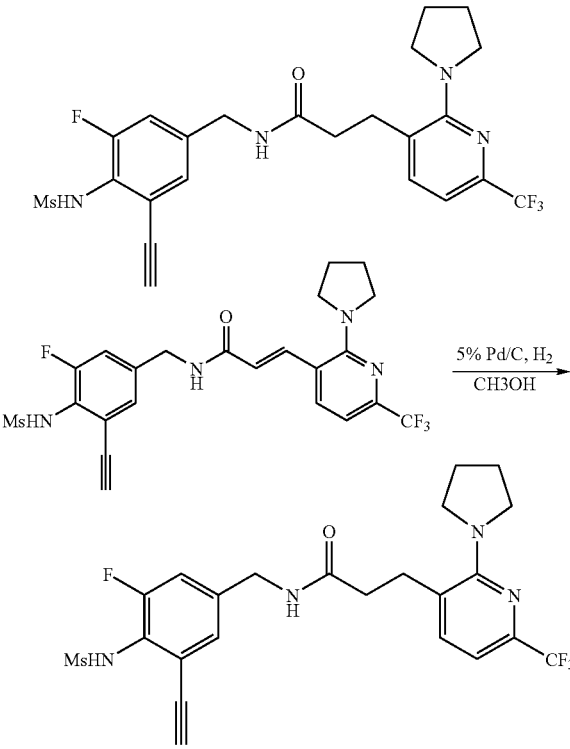

To a suspension of N-(3-ethynyl-5-fluoro-4-methanesulfonylamino-benzyl)-3-(2-pyrrolidin-1-yl-6-trifluoromethyl-pyridin-3-yl)-acrylamide (15 mg, 0.029 mmol) in 5% Pd/C (5 mg) was added CH$_3$OH (1.0 ml). The mixture was purged three times with hydrogen gas (50 psi) and then shaken for 40 min at room temperature. The reaction mixture was filtered over celite pad and concentrated under reduced pressure. The crude residue was chromatographed to yield the N-(3-ethynyl-5-fluoro-4-methanesulfonylamino-benzyl)-3-(2-pyrrolidin-1-yl-6-trifluoromethyl-pyridin-3-yl)-propionamide (15 mg, 98%).

$^1$H NMR (300 MHz, CDCl$_3$): δ 7.33 (d, 1H, J=7.2 Hz), 7.12 (s, 1H), 6.96 (dd, 1H, J=10.5, 1.8 Hz), 6.89 (d, 1H, J=7.8 Hz), 6.39 (s, 1H), 5.78 (s, 1H, br), 4.27 (d, 2H, J=6.0 Hz), 3.89 (s, 1H), 3.50-3.42 (m, 4H), 3.20 (s, 3H), 3.05 (t, 2H, J=7.5 Hz), 2.41 (t, 2H, J=7.5 Hz), 1.91-1.86 (m, 4H).

EXAMPLE 92

3-(2-Cyclopentoxy-6-trifluoromethyl-pyridin-3-yl)-N-(3-ethynyl-5-fluoro-4-methanesulfonylamino-benzyl)-acrylamide

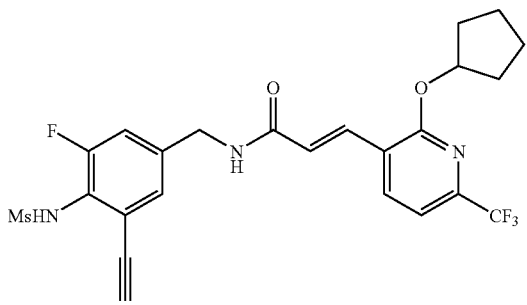

N-(4-Aminomethyl-5-ethynyl-2-fluoro-phenyl)-methanesulfonamide, HCl salt (41 mg, 0.15 mmol) was reacted with 3-(2-cyclopentoxy-6-trifluoromethyl-pyridin-3-yl)-acrylic acid (40 mg, 0.13 mmol) to give the title compound (50 mg, 73%) after purification by column chromatography (Hex/EtOAc=1/2).

$^1$H NMR (300 MHz, CDCl$_3$): δ 7.80 (d, 1H, J=7.5 Hz), 7.74 (d, 1H, J=15.9 Hz), 7.22 (m, 3H), 6.72 (d, 1H, J=15.9 Hz), 6.41 (s, 1H), 6.02 (t, 1H), 5.58 (m, 1H), 4.54 (d, 2H, J=6.0 Hz), 3.48 (s, 1H), 3.26 (s, 3H), 1.82 (m, 8H).

EXAMPLE 93

3-(2-Cyclopropylmethoxy-6-trifluoromethyl-pyridin-3-yl)-N-(3-ethynyl-5-fluoro-4-methanesulfonylamino-benzyl)-acrylamide

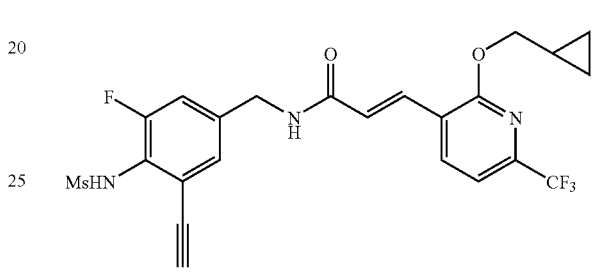

N-(4-Aminomethyl-5-ethynyl-2-fluoro-phenyl)-methanesulfonamide, HCl salt (41 mg, 0.15 mmol) was reacted with 3-(2-cyclopropylmethoxy-6-trifluoromethyl-pyridin-3-yl)-acrylic acid (10 mg, 0.036 mmol) to give the title compound (48 mg, 72%) after crystallization from EtOAc/Hex.

$^1$H NMR (300 MHz, CDCl$_3$): δ 7.81 (m, 2H), 7.26 (m, 3H), 6.80 (d, 1H, J=15.6 Hz), 6.40 (s, 1H), 6.00 (t, 1H), 4.55 (d, 2H, J=6.3 Hz), 4.31 (d, 2H, J=7.5 Hz), 3.48 (s, 1H), 3.27 (s, 3H), 1.39 (m, 1H), 0.63 (m, 2H), 0.40 (m, 2H).

EXAMPLE 94

3-(2-Dimethylamino-6-trifluoromethyl-pyridin-3-yl)-N-(3-ethynyl-5-fluoro-4-methanesulfonylamino-benzyl)-acrylamide

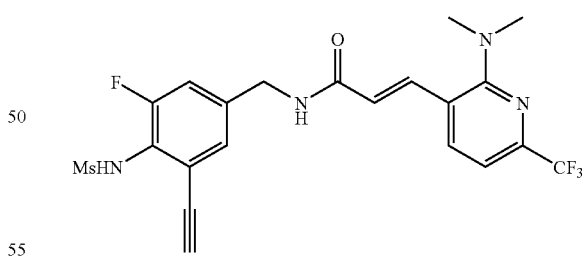

N-(4-Aminomethyl-5-ethynyl-2-fluoro-phenyl)-methanesulfonamide, HCl salt (33 mg, 0.12 mmol) was reacted with 3-(2-dimethylamino-6-trifluoromethyl-pyridin-3-yl)-acrylic acid (26 mg, 0.10 mmol) to give the title compound (42 mg, 87%) after purification by column chromatography (Hex/EtOAc=2/3).

$^1$H NMR (300 MHz, CDCl$_3$): δ 7.77 (d, 1H, J=15.6 Hz), 7.70 (d, 1H, J=7.8 Hz), 7.30 (s, 1H), 7.18 (d, 1H, J=10.8 Hz), 7.10 (d, 1H, J=7.8 Hz), 6.41 (s, 1H), 6.35 (d, 1H, J=15.6 Hz), 5.96 (t, 1H), 4.54 (d, 2H, J=6.0 Hz), 3.46 (s, 1H), 3.27 (s, 3H), 3.01 (s, 6H).

EXAMPLE 95

N-(3-Fluoro-4-methanesulfonylamino-benzyl)-3-[2-(4-ethoxycarbonyl-piperid-1-yl)-6-trifluoromethyl-pyridin-3-yl]-acrylamide

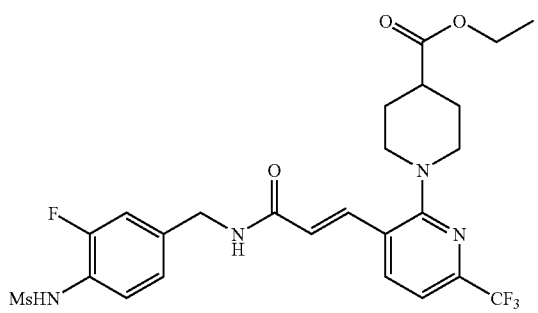

N-(4-Aminomethyl-2-fluoro-phenyl)-methanesulfonamide, HCl salt (60 mg, 0.24 mmol) was reacted with 3-[2-(4-ethoxycarbonyl-piperid-1-yl)-6-trifluoromethyl-pyridin-3-yl]-acrylic acid (50 mg, 0.16 mmol) to give the title compound (34 mg, 25%) after purification by column chromatography (Hex/EtOAc=2/3).

$^1$H NMR (300 MHz, CDCl$_3$): δ 7.74 (d, 1H, J=7.8 Hz), 7.69 (d, 1H, J=15.6 Hz), 7.54 (m, 1H), 7.18 (m, 2H), 6.51 (s, 1H), 6.47 (d, 1H, J=15.9 Hz), 6.04 (bs, 1H), 4.57 (d, 2H, J=6.0 Hz), 4.16 (d, 2H, J=7.2 Hz), 3.72 (m, 2H), 3.03 (s, 3H), 2.99 (m, 2H), 2.50 (m, 1H), 1.96 (m, 4H), 1.28 (t, 3H, J=7.2 Hz)

EXAMPLE 96

N-(3-Ethynyl-5-fluoro-4-methanesulfonylamino-benzyl)-3-(2-benzyloxy 6-trifluoromethyl-pyridin-3-yl)-acrylamide

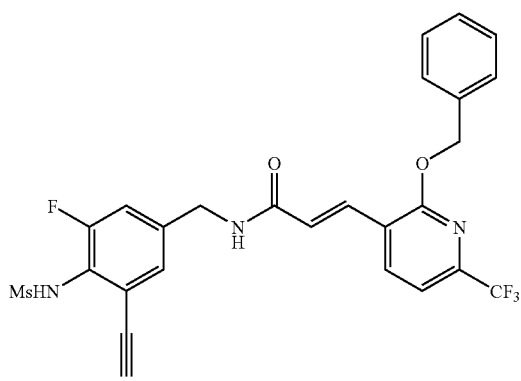

N-(5-Ethynyl-4-aminomethyl-2-fluoro-phenyl)-methanesulfonamide, HCl salt (58 mg, 0.21 mmol) was reacted with 3-(2-benzyloxy 6-trifluoromethyl-pyridin-3-yl)-acrylic acid (87 mg, 0.21 mmol) to give the title compound (75 mg, 66%) after purification by column chromatography (Hex/EtOAc=2/3).

$^1$H NMR (300 MHz, CDCl$_3$): δ 7.83 (m, 1H), 7.75 (d, 1H, J=15.9 Hz), 7.49 (m, 2H), 7.35 (m, 5H), 7.15 (m, 1H), 6.74 (d, 1H, J=15.6 Hz), 6.39 (s, 1H), 5.93 (bs, 1H), 5.54 (s, 2H), 4.51 (d, 2H, J=6.3 Hz), 3.48 (s, 1H), 3.26 (s, 3H)

EXAMPLE 97

N-(3-Cyano-5-fluoro-4-methanesulfonylamino-benzyl)-3-(2-pyrrolidin-1-yl-6-trifluoromethyl-pyridin-3-yl)-acrylamide

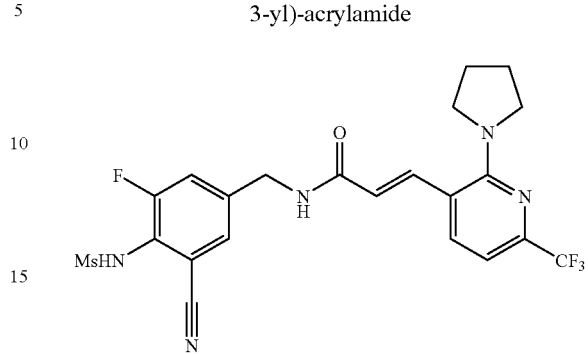

N-(4-Aminomethyl-2-cyano-6-fluoro-phenyl)-methanesulfonamide, HCl salt (33 mg, 0.118 mmol) was reacted with 3-(2-pyrrolidin-1-yl-6-trifluoromethyl-pyridin-3-yl)-acrylic acid (33 mg, 0.118 mmol) to give N-(3-cyano-5-fluoro-4-methanesulfonylamino-benzyl)-3-(2-pyrrolidin-1-yl-6-trifluoromethyl-pyridin-3-yl)-acrylamide (33 mg, 55%) after purification by recrystallization from Et$_2$O.

$^1$H NMR (300 MHz, DMSO): δ 10.07 (s, 1H, br), 8.77 (t, 1H, J=6.0 Hz), 7.82 (d, 1H, J=7.8 Hz), 7.70 (d, 1H, J=15.6 Hz), 7.76-7.60 (m, 2H), 7.10 (d, 1H, J=7.8 Hz), 6.43 (d, 1H, J=15.6 Hz), 4.44 (d, 1H, J=6.0 Hz), 3.51-3.34 (m, 4H), 3.11 (s, 3H), 1.88-1.84 (m, 4H).

EXAMPLE 98

3-(2-Butoxy-6-trifluoromethyl-pyridin-3-yl)-N-(3-cyano-5-fluoro-4-methanesulfonylamino-benzyl)-acrylamide

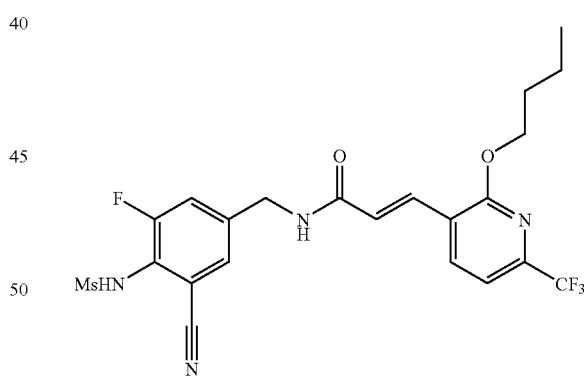

N-(4-Aminomethyl-2-cyano-6-fluoro-phenyl)-methanesulfonamide, HCl salt (33 mg, 0.118 mmol) was reacted with 3-(2-butoxy-6-trifluoromethyl-pyridin-3-yl)-acrylic acid (34 mg, 0.118 mmol) to give 3-(2-butoxy-6-trifluoromethyl-pyridin-3-yl)-N-(3-cyano-5-fluoro-4-methanesulfonylamino-benzyl)-acrylamide (32 mg, 53%) after purification by recrystallization from Et$_2$O.

$^1$H NMR (300 MHz, DMSO): δ 10.07 (s, 1H, br), 8.90 (t, 1H, J=6.0 Hz), 8.18 (d, 1H, J=7.5 Hz), 7.76-7.51 (m, 4H), 6.93 (d, 1H, J=15.9 Hz), 4.45 (d, 2H, J=5.4 Hz), 4.40 (t 2H, J=6.3 Hz), 3.10 (s, 3H), 1.83-1.73 (m, 2H), 1.47-1.40 (m, 2H), 0.94 (t 3H, J=7.5 Hz).

EXAMPLE 99

N-(3-Cyano-5-fluoro-4-methanesulfonylamino-benzyl)-3-[2-(2-methoxy-ethoxy)-6-trifluoromethyl-pyridin-3-yl]-acrylamide

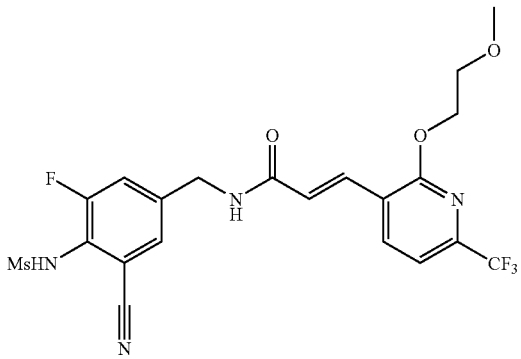

N-(4-Aminomethyl-2-cyano-6-fluoro-phenyl)-methanesulfonamide, HCl salt (33 mg, 0.118 mmol) was reacted with 3-[2-(2-methoxy-ethoxy)-6-trifluoromethyl-pyridin-3-yl]-acrylic acid (34 mg, 0.118 mmol) to give N-(3-cyano-5-fluoro-4-methanesulfonylamino-benzyl)-3-[2-(2-methoxy-ethoxy)-6-trifluoromethyl-pyridin-3-yl]-acrylamide (38 mg, 62%) after purification by recrystallization from $Et_2O$.

$^1$H NMR (300 MHz, DMSO): δ 10.08 (s, 1H, br), 8.89 (t, 1H, J=5.4 Hz), 8.20 (d, 1H, J=7.5 Hz), 7.64-7.53 (m, 3H), 6.93 (d, 1H, J=15.9 Hz), 4.54-4.44 (m, 4H), 3.74 (t, 2H, J=4.5 Hz), 3.31 (s, 3H), 3.09 (m, 4H).

EXAMPLE 100

N-(3-Ethynyl-5-fluoro-4-methanesulfonylamino-benzyl)-3-(2-isopropylamino-6-trifluoromethyl-pyridin-3-yl)-acrylamide

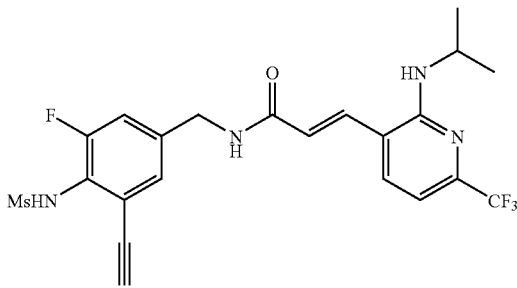

N-(4-Aminomethyl-5-ethynyl-2-fluoro-phenyl)-methanesulfonamide, HCl salt (58 mg, 0.21 mmol) was reacted with 3-(2-isopropylamino-6-trifluoromethyl-pyridin-3-yl)-acrylic acid (48 mg, 0.18 mmol) to give the title compound (40 mg, 45%) after purification by column chromatography (Hex/EtOAc=3/5).

$^1$H NMR (300 MHz, DMSO-d6+CDCl$_3$): δ 8.40 (bs, 1H), 8.20 (t, 1H, J=5.7 Hz), 7.59 (m, 2H), 7.32 (s, 1H), 7.19 (dd, 1H, J=2.1 and 10.5 Hz), 6.88 (d, 1H, J=7.8 Hz), 6.53 (d, 1H, J=15.3 Hz), 5.01 (d, 1H, J=7.2 Hz), 4.48 (d, 2H, J=6.0 Hz), 4.33 (m, 1H), 3.48 (s, 1H), 3.17 (s, 3H), 1.25 (d, 6H, J=6.3 Hz).

ESI [M+H]+: 499

EXAMPLE 101

N-(3-Cyano-5-fluoro-4-methanesulfonylamino-benzyl)-3-[2-(2-methoxy-ethylamino)-6-trifluoromethyl-pyridin-3-yl]-acrylamide

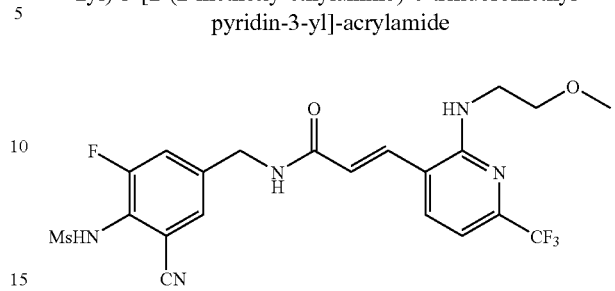

N-(4-Aminomethyl-5-cyano-2-fluoro-phenyl)-methanesulfonamide, HCl salt (168 mg, 0.60 mmol) was reacted with 3-[2-(2-methoxy-ethylamino)-6-trifluoromethyl-pyridin-3-yl]-acrylic acid (145 mg, 0.50 mmol) to give the title compound (189 mg, 73%) after crystallization from MeOH/EtOAc/Hex.

$^1$H NMR (300 MHz, DMSO-d6+CDCl$_3$): δ 9.90 (bs, 1H), 8.63 (t, 1H, J=6.0 Hz), 7.64 (d, 1H, J=7.8 Hz), 7.58 (d, 1H, J=15.3 Hz), 7.45 (s, 1H), 7.43 (dd, 1H, J=1.8 and 10.2 Hz), 6.83 (d, 1H, J=7.8 Hz), 6.24 (t, 1H, J=5.1 Hz), 6.52 (d, 1H, J=15.3 Hz), 4.42 (d, 2H, J=6.0 Hz), 3.52 (m, 4H), 3.27 (s, 3H), 3.04 (s, 3H).

EXAMPLE 102

N-(3-Cyano-5-fluoro-4-methanesulfonylamino-benzyl)-3-(2-dimethylamino-6-trifluoromethyl-pyridin-3-yl)-acrylamide

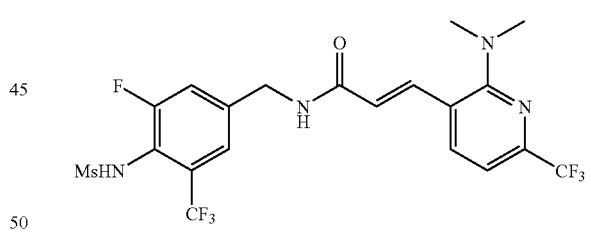

N-(4-Aminomethyl-6-cyano-2-fluoro-phenyl)-methanesulfonamide, HCl salt (130 mg, 0.46 mmol) was reacted with a mixture (120 mg) of 3-(2-dimethylamino-6-trifluoromethyl-pyridin-3-yl)-acrylic acid and 3-(2-morpholin-4-yl-6-trifluoromethyl-pyridin-3-yl)-acrylic acid to give N-(3-cyano-5-fluoro-4-methanesulfonylamino-benzyl)-3-(2-dimethylamino-6-trifluoromethyl-pyridin-3-yl)-acrylamide (59 mg) after purification by column chromatography (Hex/EtOAc=1/1) followed by recrystallization from EtOAc/hexane.

$^1$H NMR (300 MHz, CDCl$_3$): δ 7.78 (d, 1H, J=15 Hz), 7.71 (d, 1H, J=7.2 Hz), 7.49~7.42 (m, 2H), 7.11 (d, 1H, J=7.8 Hz), 6.39~6.34 (m, 2H), 6.05 (m, 1H), 4.59 (d, 2H, J=6.3 Hz), 3.33 (s, 3H), 3.02 (s, 6H)

EXAMPLE 103

N-(3-Cyano-5-fluoro-4-methanesulfonylamino-benzyl)-3-(2-morpholin-4-yl-6-trifluoromethyl-pyridin-3-yl)-acrylamide

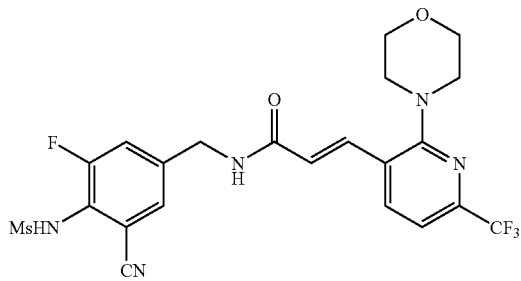

N-(4-Aminomethyl-6-cyano-2-fluoro-phenyl)-methanesulfonamide, HCl salt (130 mg, 0.46 mmol) was reacted with a mixture (120 mg) of 3-(2-dimethylamino-6-trifluoromethyl-pyridin-3-yl)-acrylic acid and 3-(2-morpholin-4-yl-6-trifluoromethyl-pyridin-3-yl)-acrylic acid to give N-(3-cyano-5-fluoro-4-methanesulfonylamino-benzyl)-3-(2-morpholin-4-yl-6-trifluoromethyl-pyridin-3-yl)-acrylamide (7 mg) after purification by column chromatography (Hex/EtOAc=1/1) followed by recrystallization from EtOAc/hexane.

$^1$H NMR (300 MHz, CDCl$_3$): δ 7.81 (d, 1H, J=7.5 Hz), 7.72 (d, 1H, J=15.6 Hz), 7.42~7.38 (m, 2H), 7.23 (d, 1H, J=7.8 Hz), 6.75 (t, 1H, J=6 Hz), 6.55 (d, 1H, J=15.3 Hz), 4.56 (d, 2H, J=6 Hz), 3.85~3.82 (m, 4H), 3.35~3.32 (m, 4H), 3.23 (s, 3H)

EXAMPLE 104

3-[2-(Tetrahydro-furan-3-yloxy)-6-trifluoromethyl-pyridin-3-yl]-N-(3-fluoro-4-methanesulfonylamino-benzyl)-acrylamide

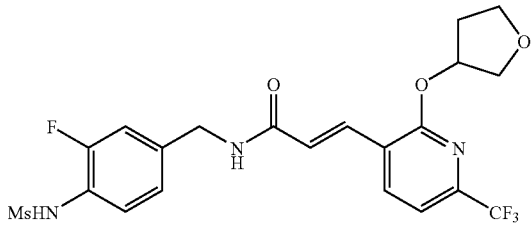

N-(4-Aminomethyl-2-fluoro-phenyl)-methanesulfonamide, HCl salt (76 mg, 0.30 mmol) was reacted with 3-[2-(tetrahydro-furan-3-yloxy)-6-trifluoromethyl-pyridin-3-yl]-acrylic acid (60 mg, 0.20 mmol) to give the title compound (70 mg, 70%) after purification by column chromatography (Hex/EtOAc=1/2).

$^1$H NMR (300 MHz, CDCl$_3$): δ 7.84 (d, 1H, J=7.8 Hz), 7.71 (d, 1H, J=15.9 Hz), 7.51 (t, 1H, J=8.4 Hz), 7.30 (d, 1H, J=7.8 Hz), 7.13 (m, 2H), 6.79 (d, 1H, J=15.9 Hz), 6.73 (s, 1H), 6.46 (t, 1H, J=6.0 Hz), 5.76 (m, 1H), 4.54 (d, 2H, J=6.0 Hz), 4.05 (m, 2H), 3.91 (m, 2H), 3.02 (s, 3H), 2.35 (m, 1H), 2.20 (m, 1H).

EXAMPLE 105

N-(3-Cyano-5-fluoro-4-methanesulfonylamino-benzyl)-3-(2-phenoxy-6-trifluoromethyl-pyridin-3-yl)-acrylamide

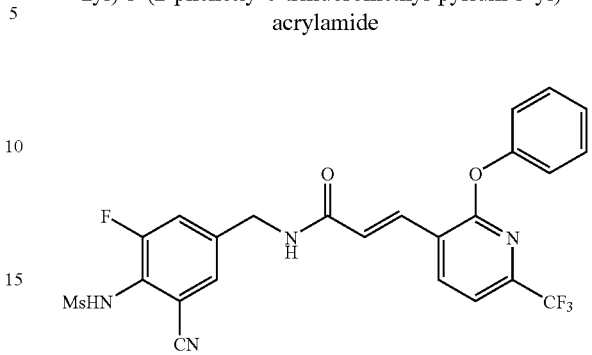

N-(4-Aminomethyl-2-fluoro-6-cyano-phenyl)-methanesulfonamide, HCl salt (48.5 mg, 0.173 mmol) was reacted with NMM (0.07 ml), DMTMM (55 mg) and 3-(2-phenoxy-6-trifluoromethyl-pyridin-3-yl)-acrylic acid (50 mg, 0.16 mmol) to give the title compound (66 mg, 76%) after purification by column chromatography (Hex/EtOAc=2/3).

$^1$H NMR (300 MHz, CD$_3$OD): δ 8.20 (d, 1H, J=7.5 Hz), 7.83 (d, 1H, J=16.2 Hz), 7.45 (m, 4H), 7.15 (m, 2H), 6.99 (d, 1H, J=15.9 Hz), 4.47 (s, 2H), 3.05 (s, 3H)

EXAMPLE 106

3-(2-sec-Butoxy-6-trifluoromethyl-pyridin-3-yl)-N-(3-cyano-5-fluoro-4-methane sulfonylamino-benzyl)-acrylamide

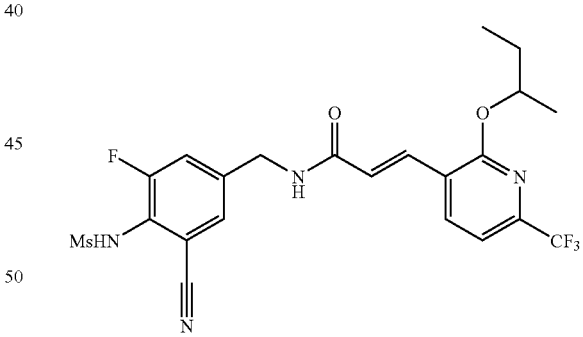

N-(4-Aminomethyl-2-fluoro-6-cyano-phenyl)-methanesulfonamide, HCl salt (46.1 mg, 0.165 mmol) was reacted with NMM (0.2 ml), DMTMM (60.1 mg) and 3-(2-sec-butoxy-6-trifluoromethyl-pyridin-3-yl)-acrylic acid (43 mg, 0.15 mmol) to give the title compound (57 mg, 75%) after purification by column chromatography (Hex/EtOAc=1/2).

$^1$H NMR (300 MHz, CD$_3$OD): δ 8.02 (d, 1H, J=7.8 Hz), 7.69 (d, 1H, J=15.9 Hz), 7.52 (m, 1H), 7.47 (dd, 1H, J=0.75 and 9.9 Hz), 7.30 (d, 1H, J=7.8 Hz), 6.87 (d, 1H, J=15.9 Hz), m, 2H), 5.27 (m, 1H), 4.89 (s, 1H), 3.07 (s, 3H), 1.33 (d, 3H, J=6.0 Hz), 0.95 (t, 3H, J=7.5 Hz)

ESI [M+H]+: 515

EXAMPLE 107

N-(3-Ethynyl-5-fluoro-4-methanesulfonylamino-benzyl)-3-(2-phenyl-6-trifluoromethyl-pyridin-3-yl)-acrylamide

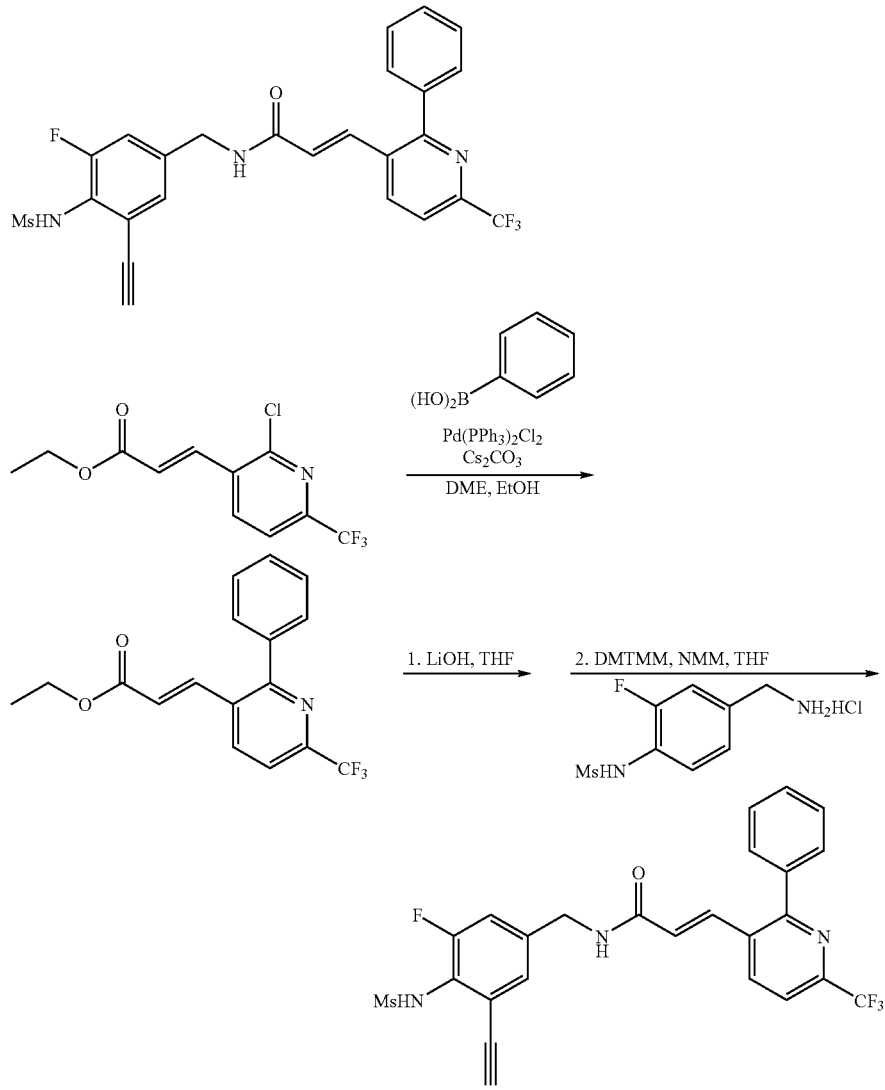

Step 1: Synthesis of 3-(2-phenyl-6-trifluoromethyl-pyridin-3-yl)-acrylic acid ethyl ester Microwave vial was charged with 3-(2-chloro-6-trifluoromethyl-pyridin-3-yl)-acrylic acid ethyl ester (100 mg, 0.376 mmol), phenylboronic acid (2 eq), $Cs_2CO_3$ (3 eq), $Pd(PPh_3)_2Cl_2$ (0.08 eq), DME (1 ml), and ethanol (0.25 ml). The vial was irradiated in microwave synthesizer at 140° C. for 20 min. The contents of the vial were filtered through a celite pad, which was washed out thoroughly with methanol. The filtrate was evaporated, and the residue was purified by column chromatography to give 3-(2-phenyl-6-trifluoromethyl-pyridin-3-yl)-acrylic acid ethyl ester (96 mg, 80%).

$^1$H NMR (300 MHz, $CDCl_3$): δ 8.07 (d, 1H, J=7.5 Hz), 7.73 (d, 1H, J=16.2 Hz), 7.64 (d, 1H, J=8.1 Hz), 7.57-7.53 (m, 2H), 7.47-7.43 (m, 3H), 6.45 (d, 1H, J=16.3 Hz), 4.21 (q, 2H, J=7.2 Hz), 1.26 (t, 3H, J=7.2 Hz).

Step 2: Synthesis of N-(3-ethylnyl-5-fluoro-4-methanesulfonylamino-benzyl)-3-(2-phenyl-6-trifluoromethyl-pyridin-3-yl)-acrylamide To a suspension of 3-(2-phenyl-6-trifluoromethyl-pyridin-3-yl)-acrylic acid ethyl ester (20 mg, 0.062 mmol) in THF (1 ml) was added an aqueous solution of 0.5 N-LiOH (0.3 ml), and the mixture was stirred for 3 hours at room temperature. The resulting residue was dissolved in $H_2O$ and then washed three times with EtOAc, acidified with 1N HCl to pH 1~2. The solution was extracted three times with methylene chloride and then dried over anhyd. $Na_2SO_4$ and concentrated in vacuo to give 3-(2-phenyl-6-trifluoromethyl-pyridin-3-yl)-acrylic acid (19 mg, 96%). To a suspension of N-(4-aminomethyl-2-ethynyl-6-fluoro-phenyl)-methanesulfonamide, HCl salt (21 mg, 0.074 mmol) in THF (3 mL) was added N-methylmorpholine (0.015 ml, 0.148 mmol). The mixture was stirred for 5 minutes, to which were added 3-(2-phenyl-6-trifluoromethyl-pyridin-3-yl)-acrylic acid (19 mg, 0.065- mmol) and 4-(4,6-dimethoxy[1,3,5]triazin-2-yl)-4-methyl-morpholinium chloride hydrate (DMTMM, 19 mg, 0.068 mmol). The mixture was stirred overnight at room temperature and was concentrated under reduced pressure. The residue was diluted with EtOAc and water. The organic layer was washed with saturated sodium bicarbonate, 1N HCl and brine, dried over anhydrous magnesium sulfate, filtered, and concentrated under reduced pressure. The crude residue was purified by recrystallization from Et$_2$O to give N-(3-ethynyl-5-fluoro-4-methane sulfonylamino-benzyl)-3-(2-phenyl-6-trifluoromethyl-pyridin-3-yl)-acrylamide (18 mg, 56%).

$^1$H NMR (300 MHz, DMSO): δ 9.46 (s, 1H, br), 8.85 (t, 1H, J=5.7 Hz), 8.39 (d, 1H, J=8.1 Hz), 7.98 (d, 1H, J=8.1 Hz), 7.61-7.54 (m, 5H), 7.45 (d, 1H, J=15.9 Hz), 7.26 (m, 2H), 6.84 (d, 1H, J=15.9 Hz), 4.52 (s, 1H), 4.36 (d, 2H, J=5.7 Hz), 3.06 (s, 3H).

EXAMPLE 108

N-(3-Fluoro-4-methanesulfonylamino-benzyl)-3-(2-isopropoxy-6-trifluoromethyl-pyridin-3-yl)-acrylamide

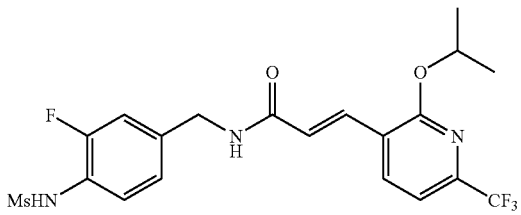

N-(4-Aminomethyl-2-fluoro-phenyl)-methanesulfonamide, HCl salt (46 mg, 0.18 mmol) was reacted with 3-(2-isopropoxy-6-trifluoromethyl-pyridin-3-yl)-acrylic acid (50 mg, 0.18 mmol) to give the title compound (34 mg, 25%) after purification by column chromatography (Hex/EtOAc=2/1).

$^1$H NMR (300 MHz, CDCl$_3$): δ 7.81 (d, 1H, J=7.8 Hz), 7.76 (d, 1H, J=15.6 Hz), 7.54 (m, 1H), 7.19 (m, 3H), 6.72 (d, 1H, J=15.6 Hz), 6.51 (s, 1H), 6.03 (bs, 1H), 5.48 (septet, 1H, J=6.0 Hz), 4.57 (d, 2H, J=6.3 Hz), 3.03 (s, 3H), 1.41 (d, 6H, J=7.2 Hz).

EXAMPLE 109

N-(3-Cyano-5-fluoro-4-methanesulfonylamino-benzyl)-3-(2-isopropoxy-6-trifluoromethyl-pyridin-3-yl)-acrylamide

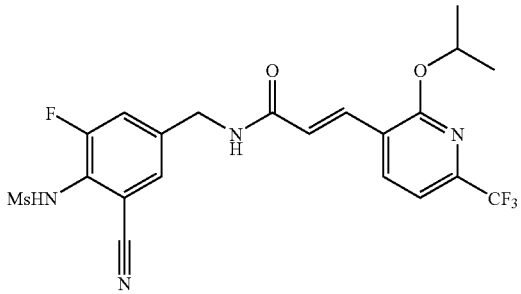

N-(4-Aminomethyl-6-cyano-2-fluoro-phenyl)-methanesulfonamide, HCl salt (51 mg, 0.18 mmol) was reacted with 3-(2-isopropoxy-6-trifluoromethyl-pyridin-3-yl)-acrylic acid (50 mg, 0.18 mmol) to give the title compound (44 mg, 51%) after purification by column chromatography (Hex/EtOAc=1/1). $^1$H NMR (300 MHz, DMSO-d$_6$): δ 10.08 (bs, 1H), 8.90 (m, 1H), 8.177 (d, 1H, J=7.8 Hz), 7.56 (m, 4H), 7.35 (septet, 1H, J=6.0 Hz), 4.44 (d, 2H, J=5.7 Hz), 3.08 (s, 3H), 1.38 (d, 6H, J=6.0 Hz)

EXAMPLE 110

AT-(3-Ethynyl-5-fluoro-4-methansulfonylamino-benzyl)-3-[2-(4-ethoxycarbonyl-piperid-1-yl)-6-trifluoromethyl-pyridin-3-yl]-acrylamide

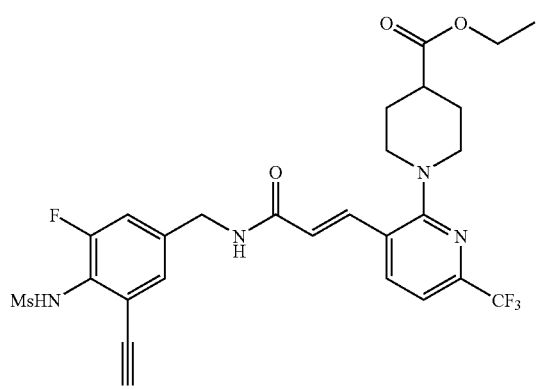

N-(4-Aminomethyl-5-ethynyl-2-fluoro-phenyl)-methanesulfonamide, HCl salt (75 mg, 0.27 mmol) was reacted with 3-[2-(4-ethoxycarbonyl-piperid-1-yl)-6-trifluoromethyl-pyridin-3-yl]-acrylic acid (100 mg, 0.27 mmol) to give the title compound (111 mg, 69%) after purification by column chromatography (Hex/EtOAc=2/3).

$^1$H NMR (300 MHz, CDCl$_3$): δ 7.72 (m, 2H), 7.31 (bs, 1H), 7.19 (m, 2H), 6.45 (d, 2H, J=15.6 Hz), 6.41 (bs, 1H), 6.00 (bs, 1H), 4.54 (d, 2H, J=6.3 Hz), 4.15 (q, 2H, J=7.2 Hz), 3.71 (m, 2H), 3.49 (s, 1H), 3.27 (s, 3H), 3.01 (m, 2H), 2.51 (m, 1H), 1.96 (m, 4H), 1.27 (t, 3H, J=7.2 Hz)

EXAMPLE 111

N-(3-Cyano-5-fluoro-4-methanesulfonylamino-benzyl)-3-[2-(4-ethoxycarbonyl-piperid-1-yl)-6-trifluoromethyl-pyridin-3-yl]-acrylamide

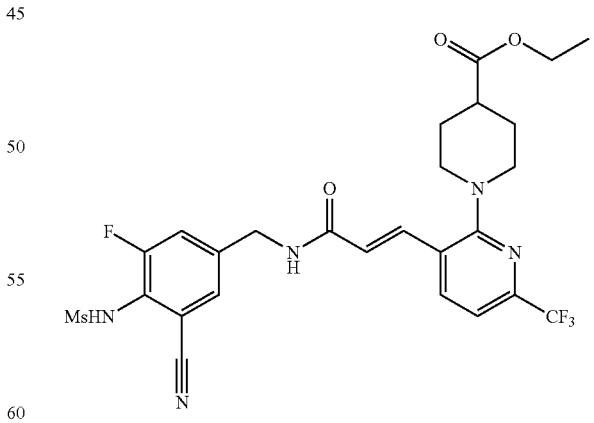

N-(4-Aminomethyl-5-cyano-2-fluoro-phenyl)-methanesulfonamide, HCl salt (39 mg, 0.14 mmol) was reacted with 3-[2-(4-ethoxycarbonyl-piperid-1-yl)-6-trifluoromethyl-pyridin-3-yl]-acrylic acid (52 mg, 0.14 mmol) to give the title compound (63 mg, 75%) after purification by column chromatography (Hex/EtOAc=1/2).

¹H NMR (300 MHz, CDCl₃): δ 7.77 (m, 1H), 7.70 (d, 1H, J=15.0 Hz), 7.46 (m, 2H), 7.21 (m, 1H), 6.50 (d, 1H, J=15.6 Hz), 6.44 (bs, 1H), 4.59 (d, 2H, J=6.6 Hz), 4.16 (q, 2H, J=7.2 Hz), 3.72 (m, 2H), 3.32 (s, 3H), 3.02 (m, 2H), 2.52 (m, 1H), 1.96 (m, 4H), 1.28 (t, 3H, J=7.2 Hz)

EXAMPLE 112

3-(2-Benzyloxy-6-trifluoromethyl-pyridin-3-yl)-N-(3-fluoro-4-methanesulfonylamino-benzyl)-acrylamide

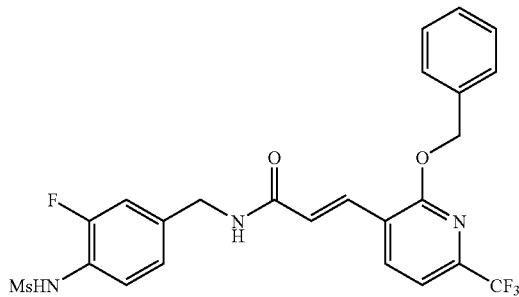

N-(4-Aminomethyl-2-fluoro-phenyl)-methanesulfonamide, HCl salt (21 mg, 0.083 mmol) was reacted with 3-(2-benzyloxy-6-trifluoromethyl-pyridin-3-yl)-acrylic acid (35 mg, 0.083 mmol) to give the title compound (18 mg, 41%) after purification by column chromatography (Hex/EtOAc=1/1).

¹H NMR (300 MHz, CDCl₃): δ 7.84 (m, 1H), 7.76 (d, 1H, J=15.9 Hz), 7.49 (m, 3H), 7.35 (m, 4H), 7.12 (m, 2H), 6.74 (d, 1H, J=15.6 Hz), 6.46 (s, 1H), 5.92 (bs, 1H), 5.54 (s, 2H), 4.54 (d, 2H, J=6.3 Hz), 3.02 (s, 3H)

EXAMPLE 113

N-(3-Ethynyl-5-fluoro-4-methanesulfonylamino-benzyl)-3-(2-phenylamino-6-trifluoromethyl-pyridin-3-yl)-acrylamide

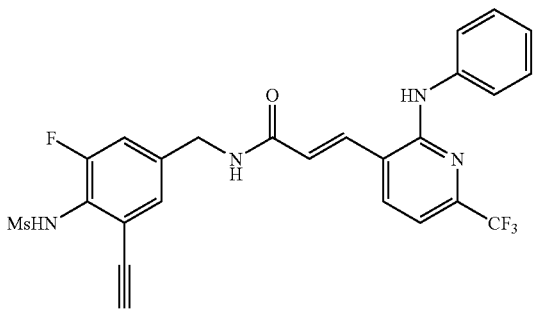

N-(4-Aminomethyl-5-ethynyl-2-fluoro-phenyl)-methanesulfonamide, HCl salt (31 mg, 0.11 mmol) was reacted with 3-(2-phenylamino-6-trifluoromethyl-pyridin-3-yl)-acrylic acid (19 mg, 0.06 mmol) to give the title compound (10 mg, 17%) after purification by column chromatography (Hex/EtOAc=1/2).

¹H NMR (300 MHz, CDCl₃): δ 7.57 (d, 1H, J=16.2 Hz), 7.43 (m, 5H), 7.23 (m, 3H), 7.06 (m, 1H), 6.49 (d, 1H, J=15.9 Hz), 6.45 (bs, 1H), 6.29 (bs, 1H), 4.34 (d, 2H, J=6.6 Hz), 3.46 (s, 1H), 3.31 (s, 3H),

EXAMPLE 114

N-(3-Ethynyl-5-fluoro-4-methansulfonylamino-benzyl)-3-[2-(3-ethoxycarbonyl-piperid-1-yl)-6-trifluoromethyl-pyridin-3-yl]-acrylamide

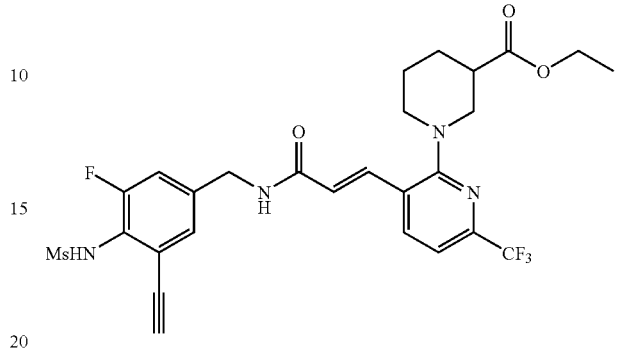

N-(5-Ethynyl-4-aminomethyl-2-fluoro-phenyl)-methanesulfonamide, HCl salt (75 mg, 0.27 mmol) was reacted with 3-[2-(3-ethoxycarbonyl-piperid-1-yl)-6-trifluoromethyl-pyridin-3-yl]-acrylic acid (100 mg, 0.27 mmol) to give the title compound (75 mg, 46%) after purification by column chromatography (Hex/EtOAc=4/5).

¹H NMR (300 MHz, CDCl₃): δ 7.79 (d, 1H, J=7.2 Hz), 7.67 (d, 1H, J=16.2 Hz), 7.32 (bs, 1H), 7.21 (m, 2H), 6.82 (bs, 1H), 6.54 (d, 1H, J=16.2 Hz), 6.39 (s, 1H), 4.54 (t, 2H, J=6.6 Hz), 4.10 (m, 2H), 3.48 (s, 1H), 3.43 (m, 4H), 3.26 (s, 3H), 3.19 (m, 2H), 2.75 (m, 1H), 1.92 (m, 2H), 1.24 (t, 3H, J=7.2 Hz)

EXAMPLE 115

N-(3-Cyano-5-fluoro-4-methansulfonylamino-benzyl)-3-[2-(3-ethoxycarbonyl-piperid-1-yl)-6-trifluoromethyl-pyridin-3-yl]-acrylamide

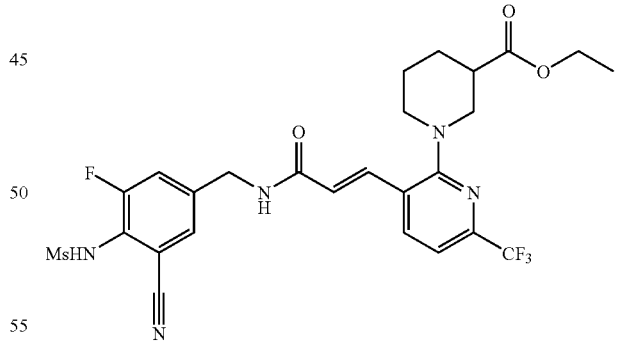

N-(4-Aminomethyl-3-cyano-5-fluoro-phenyl)-methanesulfonamide, HCl salt (23 mg, 0.081 mmol) was reacted with 3-[2-(3-ethoxycarbonyl-piperid-1-yl)-6-trifluoromethyl-pyridin-3-yl]-acrylic acid (30 mg, 0.081 mmol) to give the title compound (35 mg, 72%) after purification by column chromatography (Hex/EtOAc=1/2).

¹H NMR (300 MHz, DMSO-d₆): δ 10.10 (bs, 1H), 8.85 (m, 1H), 8.03 (d, 1H, J=7.5 Hz), 7.63 (m, 2H), 7.43 (m, 2H), 6.76

(d, 1H, J=16.2 Hz), 4.45 (d, 2H, J=5.7 Hz), 4.03 (q, 2H, J=6.9 Hz), 3.72 (m, 1H), 3.09 (s, 3H), 2.94 (m, 4H), 1.81 (m, 4H), 1.12 (t, 3H, J=7.2 Hz)

EXAMPLE 116

N-(3-Ethynyl-5-fluoro-4-methanesulfonylamino-benzyl)-3-(2-piperaz-1-yl-6-trifluoromethyl-pyridin-3-yl)-acrylamide, HCl salt

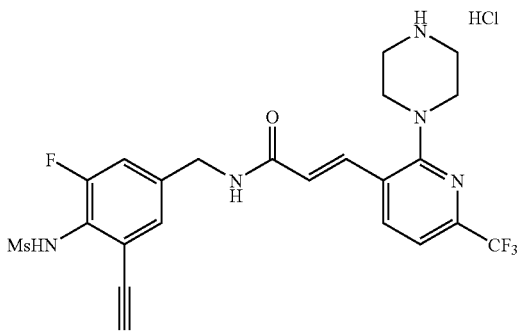

N-(4-Aminomethyl-5-ethynyl-2-fluoro-phenyl)-methanesulfonamide, HCl salt (192 mg, 0.70 mmol) was reacted with 3-(2-piperaz-1-yl-6-trifluoromethyl-pyridin-3-yl)-acrylic acid (230 mg, 0.57 mmol) to give N-(3-Ethynyl-5-fluoro-4-methanesulfonylamino-benzyl)-3-[2-(4-Boc-piperaz-1-yl-6-trifluoromethyl-pyridin-3-yl)-acrylamide. The acrylamide was treated with 4M HCl in dioxane to give the title compound (90 mg, 28%) after purification using MeOH.

$^1$H NMR (300 MHz, DMSO-d6+CDCl$_3$): δ 9.57 (bs, 2H), 9.08 (s, 1H), 8.75 (t, 1H, J=5.7 Hz), 7.86 (d, 1H, J=7.8 Hz), 7.49 (d, 1H, J=15.9 Hz), 7.30 (d, 1H, J=7.8 Hz), 7.23 (s, 1H), 7.12 (dd, 1H, J=2.1 and 10.2 Hz), 6.75 (d, 1H, J=15.9 Hz), 4.37 (d, 2H, J=5.7 Hz), 3.68 (s, 1H), 3.51 (m, 4H), 3.25 (m, 4H), 3.03 (s, 3H).

EXAMPLE 117

3-(2-sec-Butylamino-6-trifluoromethyl-pyridin-3-yl)-N-(3-ethynyl-5-fluoro-4-methanesulfonylamino-benzyl)-acrylamide

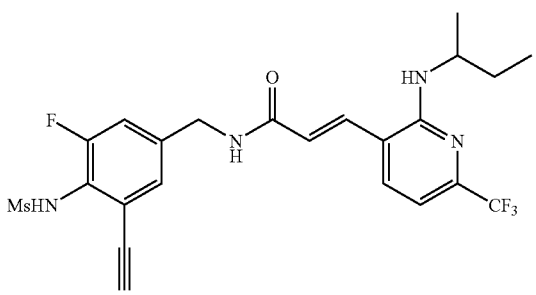

N-(4-Aminomethyl-5-ethynyl-2-fluoro-phenyl)-methanesulfonamide, HCl salt (84 mg, 0.30 mmol) was reacted with 3-(2-sec-butylamino-6-trifluoromethyl-pyridin-3-yl)-acrylic acid (70 mg, 0.24 mmol) to give the title compound (75 mg, 63%) after purification by column chromatography (Hex/EtOAc=1/1).

$^1$H NMR (300 MHz, DMSO-d6+CDCl$_3$): δ 9.40 (bs, 1H), 8.71 (t, 1H), 7.74 (d, 1H, J=7.8 Hz), 7.64 (d, 1H, J=15.3 Hz), 7.26 (m, 2H), 6.87 (d, 1H, J=7.8 Hz), 6.68 (d, 1H, J=8.1 Hz), 6.59 (d, 1H, J=15.3 Hz), 4.39 (d, 2H, J=6.0 Hz), 4.38 (s, 1H), 4.09 (m, 1H), 3.05 (s, 3H), 1.55 (m, 2H), 1.14 (d, 3H, J=6.6 Hz), 0.86 (t, 3H, J=7.2 Hz).

ESI [M+H]+: 514

EXAMPLE 118

N-(3-Cyano-5-fluoro-4-methanesulfonylamino-benzyl)-3-[2-(3-methyl-butoxy)-6-trifluoromethyl-pyridin-3-yl]-acrylamide

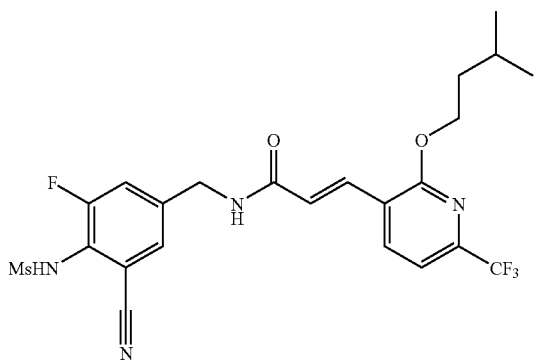

N-(4-Aminomethyl-2-cyano-6-fluoro-phenyl)-methanesulfonamide, HCl salt (17.3 mg, 0.062 mmol) was reacted with 3-[2-(3-methyl-butoxy)-6-trifluoromethyl-pyridin-3-yl]-acrylic acid (15.7 mg, 0.052 mmol) to give N-(3-cyano-5-fluoro-4-methanesulfonylamino-benzyl)-3-(2-phenyl-6-trifluoromethyl-pyridin-3-yl)-acrylamide (22 mg, 80%) after purification by chromatography (Hex/EtOAc=1/2).

$^1$H NMR (300 MHz, DMSO): δ 10.08 (s, 1H, br), 8.83 (t, 1H, J=5.7 Hz), 8.12 (d, 1H, J=7.5 Hz), 7.59-7.45 (m, 4H), 6.86 (d, 1H, J=16.2 Hz), 4.49-4.35 (m, 4H), 3.02 (s, 3H), 1.73-1.60 (m, 3H), 0.87 (d, 6H, J=6.0 Hz).

EXAMPLE 119

N-(3-Ethynyl-5-fluoro-4-methanesulfonylamino-benzyl)-3-(2-thien-3-yl-6-trifluoromethyl-pyridin-3-yl)-acrylamide

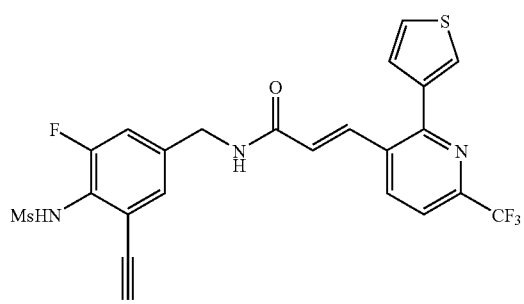

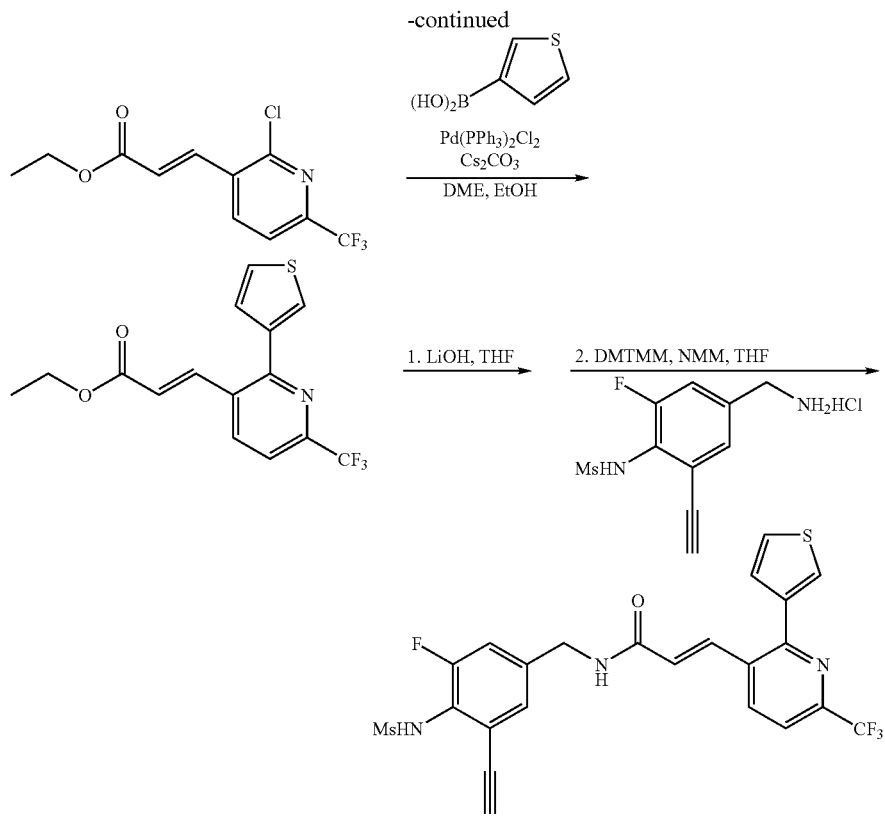

Step 1: Synthesis of 3-(2-thien-3-yl-6-trifluoromethyl-pyridin-3-yl)-acrylic acid ethyl ester 3-(2-Thien-3-yl-6-trifluoromethyl-pyridin-3-yl)-acrylic acid ethyl ester was obtained according to the general procedure described in Example 107 (step 1).

3-(2-Chloro-6-trifluoromethyl-pyridin-3-yl)-acrylic acid ethyl ester (100 mg, 0.357 mmol) was reacted with 3-thienyl boronic acid (2 eq) to give 3-(2-thien-3-yl-6-trifluoromethyl-pyridin-3-yl)-acrylic acid ethyl ester (80 mg, 68%).

$^1$H NMR (300 MHz, CDCl$_3$): δ 7.99 (d 1H, J=6.0 Hz), 7.91 (d, 1H, J=16.5 Hz), 7.61 (dd, 1H, J=2.7, 1.2 Hz), 7.57 (d, 1H, J=8.1 Hz), 7.49 (dd, 1H, J=4.8, 1.2 Hz), 7.39 (dd, 1H, J=5.4, 3.0 Hz), 6.43 (d, 1H, J=15.9 Hz), 4.24 (q, 2H, J=7.2 Hz), 1.30 (t, 3H, J=7.2 Hz).

Step 2: Synthesis of N-(3-ethynyl-5-fluoro-4-methanesulfonylamino-benzyl)-3-(2-thien-3-yl-6-trifluoromethyl-pyridin-3-yl)-acrylamide N-(3-Ethynyl-5-fluoro-4-methanesulfonylamino-benzyl)-3-(2-thiophen-3-yl-6-trifluoromethyl-pyridin-3-yl)-acrylamide was obtained according to the general procedure described in Example 107 (step 2).

N-(4-Aminomethyl-2-ethynyl-6-fluoro-phenyl)-methanesulfonamide, HCl salt (19 mg, 0.068 mmol) was reacted with 3-(2-thien-3-yl-6-trifluoromethyl-pyridin-3-yl)-acrylic acid (17 mg, 0.057 mmol) to give N-(3-ethynyl-5-fluoro-4-methanesulfonylamino-benzyl)-3-(2-thien-3-yl-6-trifluoromethyl-pyridin-3-yl)-acrylamide (12 mg, 34%).

$^1$H NMR (300 MHz, DMSO): δ 9.39 (s, 1H, br), 8.80 (t, 1H, J=6.0 Hz), 8.26 (d, 1H, J=8.1 Hz), 7.86 (d, 1H, J=8.4 Hz), 7.76 (d, 1H, J=2.4 Hz), 7.66 (dd, 1H, J=4.8, 2.7 Hz), 7.56 (d, 1H, J=15.6 Hz), 7.35 (d, 1H, J=5.4 Hz), 7.23 (s, 1H), 7.22 (d, 1H, J=7.5 Hz), 6.75 (d, 1H, J=15.6 Hz), 4.45 (s, 1H), 4.33 (d, 2H, J=5.4 Hz), 3.00 (s, 3H).

EXAMPLE 120

N-(3-Ethynyl-5-fluoro-4-methanesulfonylamino-benzyl)-3-[2-(3-fluoro-phenyl)-6-trifluoromethyl-pyridin-3-yl]-acrylamide

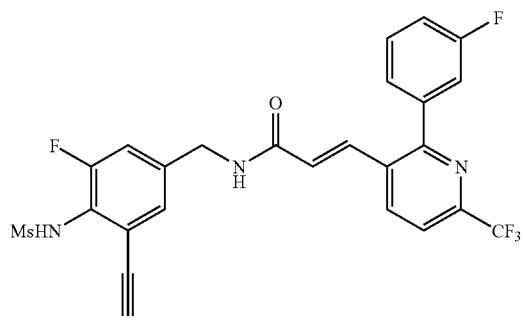

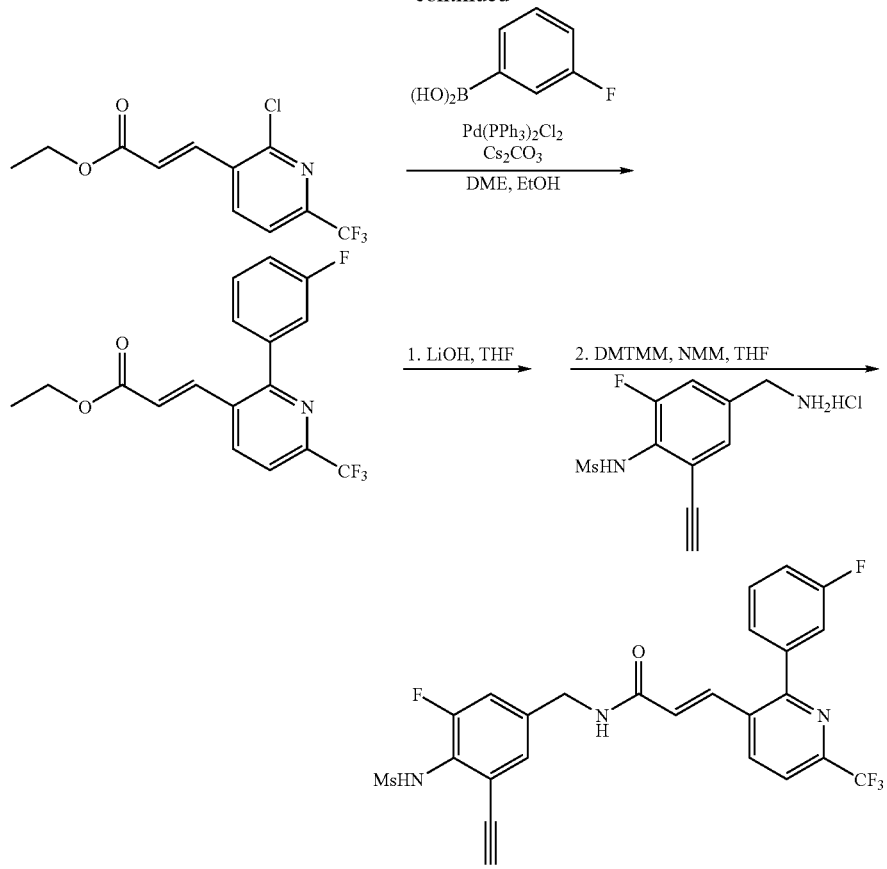

Step 1: Synthesis of 3-[2-(3-fluoro-phenyl)-6-trifluoromethyl-pyridin-3-yl]-acrylic acid ethyl ester 3-[2-(3-Fluoro-phenyl)-6-trifluoromethyl-pyridin-3-yl]-acrylic acid ethyl ester was obtained according to the general procedure described in Example 107 (step 1).

3-(2-Chloro-6-trifluoromethyl-pyridin-3-yl)-acrylic acid ethyl ester (110 mg, 0.393 mmol) was reacted with 3-fluorophenyl boronic acid (2 eq) to give 3-[2-(3-fluoro-phenyl)-6-trifluoromethyl-pyridin-3-yl]-acrylic acid ethyl ester (70 mg, 53%).

$^1$H NMR (300 MHz, CDCl$_3$): δ 8.13 (d, 1H, J=8.1 Hz), 7.76 (d, 1H, J=15.6 Hz), 7.72 (d, 1H, J=8.4 Hz), 7.51-7.43 (m, 1H), 7.38-7.33 (m, 2H), 7.27-7.16 (m, 1H), 6.50 (d, 1H, J=15.6 Hz), 4.26 (q, 2H, J=7.2 Hz), 1.30 (t, 3H, J=7.2 Hz).

Step 2: Synthesis of N-(3-ethynyl-5-fluoro-4-methanesulfonylamino-benzyl)-3-[2-(3-fluoro-phenyl)-6-trifluoromethyl-pyridin-3-yl]-acrylamide N-(3-Ethynyl-5-fluoro-4-methanesulfonylamino-benzyl)-3-[2-(3-fluoro-phenyl)-6-trifluoromethyl-pyridin-3-yl]-acrylamide was obtained according to the general procedure described in Example 107 (step 2).

N-(4-Aminomethyl-2-ethynyl-6-fluoro-phenyl)-methanesulfonamide, HCl salt (71.45 mg, 0.255 mmol) was reacted with 3-[2-(3-fluoro-phenyl)-6-trifluoromethyl-pyridin-3-yl]-acrylic acid (53 mg, 0.170 mmol) to give N-(3-ethynyl-5-fluoro-4-methanesulfonylamino-benzyl)-3-[2-(3-fluoro-phenyl)-6-trifluoromethyl-pyridin-3-yl]-acrylamide (52 mg, 57%).

$^1$H NMR (300 MHz, DMSO): δ 9.45 (s, 1H, br), 8.86 (t, 1H, J=6.0 Hz), 8.40 (d, 1H, J=8.1 Hz), 8.01 (d, 1H, J=8.1 Hz), 7.63-7.56 (m, 1H), 7.45-7.35 (m, 4H), 7.27 (s, 1H), 7.26 (d, 1H, J=8.7 Hz), 6.83 (d, 1H, J=15.9 Hz), 4.51 (s, 1H), 4.36 (d, 2H, J=6.0 Hz), 3.06 (s, 3H).

EXAMPLE 121

N-(3-Fluoro-4-methanesulfonylamino-benzyl)-3-(2-isopropylamino-6-trifluoromethyl-pyridin-3-yl)-acrylamide

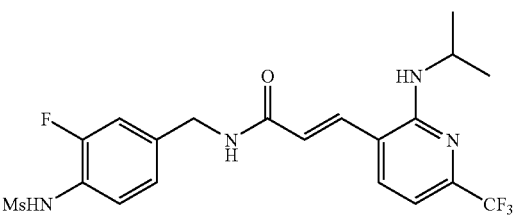

N-(4-Aminomethyl-2-fluoro-phenyl)-methanesulfonamide, HCl salt (95 mg, 0.37 mmol) was reacted with 3-(2-isopropylamino-6-trifluoromethyl-pyridin-3-yl)-acrylic acid (84 mg, 0.31 mmol) to give the title compound (125 mg, 84%) after purification by crystallization from methylene chloride.

¹H NMR (300 MHz, DMSO-d6): δ 9.55 (bs, 1H), 8.72 (t, 1H, J=5.7 Hz), 7.78 (d, 1H, J=7.5 Hz), 7.63 (d, 1H, J=15.6 Hz), 7.34 (t, 1H, J=8.4 Hz), 7.20 (dd, 1H, J=2.1 and 11.4 Hz), 7.13 (d, 1H, J=8.4 Hz), 6.96 (d, 1H, J=7.5 Hz), 6.82 (d, 1H, J=7.5 Hz), 6.61 (d, 1H, J=15.6 Hz), 4.39 (d, 2H, J=5.7 Hz), 4.21 (m, 1H), 3.00 (s, 3H), 1.18 (d, 6H, J=6.6 Hz).

EXAMPLE 122

N-(3-Cyano-5-fluoro-4-methanesulfonylamino-benzyl)-3-(2-isopropylamino-6-trifluoromethyl-pyridin-3-yl)-acrylamide

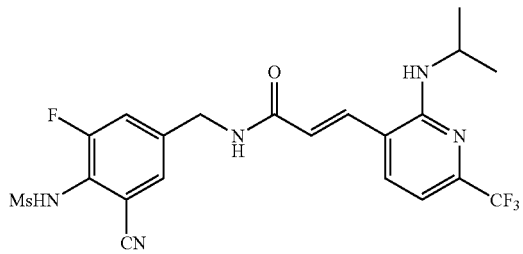

N-(4-Aminomethyl-5-cyano-2-fluoro-phenyl)-methanesulfonamide, HCl salt (104 mg, 0.37 mmol) was reacted with 3-(2-isopropylamino-6-trifluoromethyl-pyridin-3-yl)-acrylic acid (84 mg, 0.31 mmol) to give the title compound (115 mg, 74%) after purification by crystallization from methylene chloride.

¹H NMR (300 MHz, DMSO-d6): δ 10.1 (bs, 1H), 8.79 (t, 1H, J=5.7 Hz), 7.80 (d, 1H, J=7.5 Hz), 7.63 (m, 2H), 6.96 (d, 1H, J=7.5 Hz), 6.82 (d, 1H, J=7.5 Hz), 6.61 (d, 1H, J=15.6 Hz), 4.39 (d, 2H, J=5.7 Hz), 4.21 (m, 1H), 3.10 (s, 3H), 1.18 (d, 6H, J=6.6 Hz).

ESI [M+H]+: 500

EXAMPLE 123

3-(2-sec-Butylamino-6-trifluoromethyl-pyridin-3-yl)-N-(3-fluoro-4-methanesulfonylamino-benzyl)-acrylamide

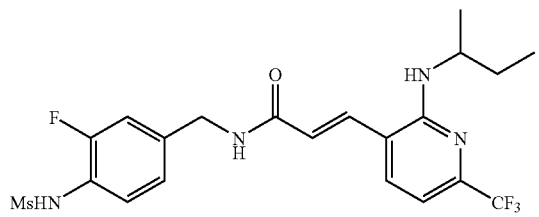

N-(4-Aminomethyl-2-fluoro-phenyl)-methanesulfonamide, HCl salt (325 mg, 1.27 mmol) was reacted with 3-(2-sec-butylamino-6-trifluoromethyl-pyridin-3-yl)-acrylic acid (306 mg, 1.06 mmol) to give the title compound (490 mg, 95%) after purification by crystallization from ether.

¹H NMR (300 MHz, DMSO-d6): δ 9.55 (bs, 1H), 8.70 (t, 1H, J=6.0 Hz), 7.77 (d, 1H, J=7.8 Hz), 7.64 (d, 1H, J=15.3 Hz), 7.35 (t, 1H, J=8.4 Hz), 7.21 (dd, 1H, J=1.5 and 11.4 Hz), 7.13 (d, 1H, J=8.4 Hz), 6.94 (d, 1H, J=7.5 Hz), 6.74 (d, 1H, J=7.8 Hz), 6.63 (d, 1H, J=15.3 Hz), 4.40 (d, 2H, J=6.0 Hz), 4.07 (m, 1H), 3.00 (s, 3H), 1.55 (m, 2H), 1.14 (d, 3H, J=6.6 Hz), 0.86 (t, 3H, J=7.5 Hz).

ESI [M+H]+: 489

EXAMPLE 124

3-(2-sec-Butylamino-6-trifluoromethyl-pyridin-3-yl)-N-(3-cyano-5-fluoro-4-methane sulfonylamino-benzyl)-acrylamide

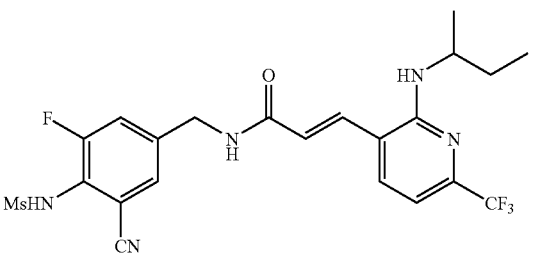

N-(4-Aminomethyl-5-cyano-2-fluoro-phenyl)-methanesulfonamide, HCl salt (104 mg, 0.37 mmol) was reacted with 3-(2-sec-butylamino-6-trifluoromethyl-pyridin-3-yl)-acrylic acid (100 mg, 0.34 mmol) to give the title compound (130 mg, 74%) after purification by crystallization from ether.

¹H NMR (300 MHz, DMSO-d6): δ 10.1 (bs, 1H), 8.77 (t, 1H, J=6.0 Hz), 7.80 (d, 1H, J=7.2 Hz), 7.63 (m, 3H), 6.94 (d, 1H, J=7.8 Hz), 6.76 (d, 1H, J=7.8 Hz), 6.62 (d, 1H, J=15.6 Hz), 4.55 (d, 2H, J=6.0 Hz), 4.07 (m, 1H), 3.09 (s, 3H), 1.55 (m, 2H), 1.14 (d, 3H, J=6.6 Hz), 0.85 (t, 3H, J=7.5 Hz).

ESI [M+H]+: 514

EXAMPLE 125

N-(3-Ethynyl-5-fluoro-4-methanesulfonylamino-benzyl)-3-[2-(3-methoxy-phenyl)-6-trifluoromethyl-pyridin-3-yl]-acrylamide

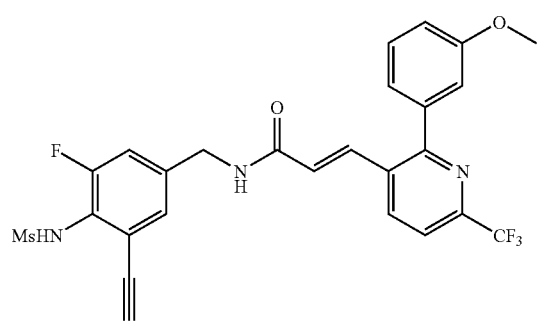

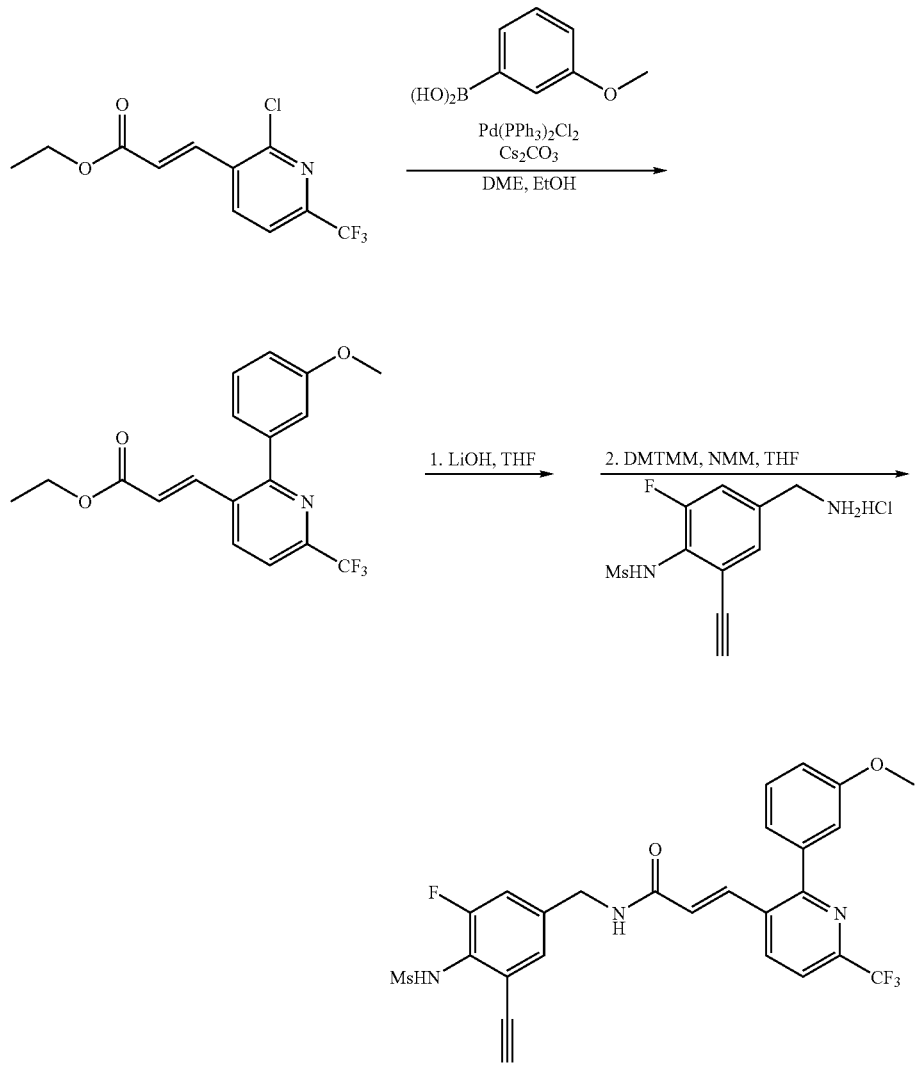

Step 1: Synthesis of 3-[2-(3-methoxy-phenyl)-6-trifluoromethyl-pyridin-3-yl]-acrylic acid ethyl ester 3-[2-(3-Methoxy-phenyl)-6-trifluoromethyl-pyridin-3-yl]-acrylic acid ethyl ester was obtained according to the general procedure described in Example 107 (step 1).

3-(2-Chloro-6-trifluoromethyl-pyridin-3-yl)-acrylic acid ethyl ester (103 mg, 0.368 mmol) was reacted with 3-methoxy phenyl boronic acid (2 eq) to give 3-[2-(3-methoxy-phenyl)-6-trifluoromethyl-pyridin-3-yl]-acrylic acid ethyl ester (70 mg, 54%).

$^1$H NMR (300 MHz, CDCl$_3$): δ 8.09 (d, 1H, J=8.4 Hz), 7.79 (d, 1H, J=15.9 Hz), 7.68 (d, 1H, J=7.8 Hz), 7.39 (dd, 1H, J=7.2, 1.5 Hz), 7.51-7.12 (m, 2H), 7.04-7.00 (m, 1H), 6.47 (d, 1H, J=15.9 Hz), 4.25 (q, 2H, J=7.2 Hz), 3.85 (s, 3H), 1.31 (t, 3H, J=7.2 Hz).

Step 2: Synthesis of N-(3-ethynyl-5-fluoro-4-methanesulfonylamino-benzyl)-3-[2-(3-methoxy-phenyl)-6-trifluoromethyl-pyridin-3-yl]-acrylamide N-(3-Ethynyl-5-fluoro-4-methanesulfonylamino-benzyl)-3-[2-(3-methoxy-phenyl)-6-trifluoromethyl-pyridin-3-yl]-acrylamide was obtained according to the general procedure described in Example 107 (step 2).

N-(4-Aminomethyl-2-ethynyl-6-fluoro-phenyl)-methanesulfonamide, HCl salt (15.6 mg, 0.056 mmol) was reacted with 3-[2-(3-methoxy-phenyl)-6-trifluoromethyl-pyridin-3-yl]-acrylic acid (15 mg, 0.046 mmol) to give N-(3-ethynyl-5-fluoro-4-methanesulfonylamino-benzyl)-3-[2-(3-methoxy-phenyl)-6-trifluoromethyl-pyridin-3-yl]-acrylamide (15 mg, 60%).

$^1$H NMR (300 MHz, DMSO): δ 9.44 (s, 1H, br), 8.84 (t, 1H, J=6.0 Hz), 8.37 (d, 1H, J=8.1 Hz), 7.97 (d, 1H, J=8.1 Hz), 7.47 (d, 1H, J=15.9 Hz), 7.46 (t, 1H, J=7.8 Hz), 7.27 (s, 1H), 7.25 (d, 1H, J=8.1 Hz), 7.11 (dd, 2H, J=3.0, 2.4 Hz), 7.07 (dd, 1H, J=5.1, 1.8 Hz), 6.82 (d, 1H, J=15.9 Hz), 4.51 (s, 1H), 4.37 (d, 2H, J=5.7 Hz), 3.79 (s, 3H), 3.06 (s, 3H).

EXAMPLE 126

N-(3-Ethynyl-5-fluoro-4-methanesulfonylamino-benzyl)-3-(2-pyridin-3-yl-6-trifluoromethyl-pyridin-3-yl)-acrylamide

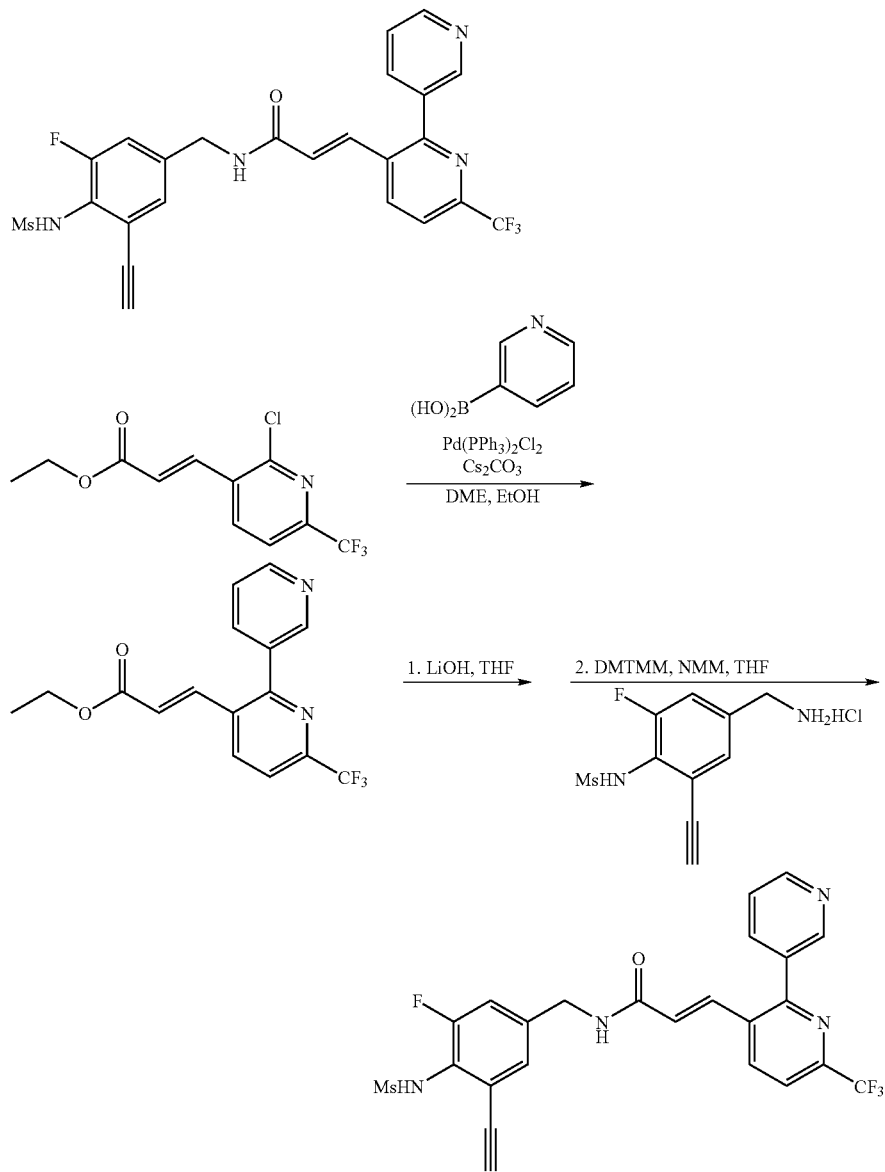

Step 1: Synthesis of 3-(2-pyridin-3-yl-6-trifluoromethyl-pyridin-3-yl)-acrylic acid ethyl ester 3-(2-Pyridin-3-yl-6-trifluoromethyl-pyridin-3-yl)-acrylic acid ethyl ester was obtained according to the general procedure described in Example 107 (step 1).

3-(2-Chloro-6-trifluoromethyl-pyridin-3-yl)-acrylic acid ethyl ester (103 mg, 0.368 mmol) was reacted with 3-pyridine boronic acid (2 eq) to give 3-(2-pyridin-3-yl-6-trifluoromethyl-pyridin-3-yl)-acrylic acid ethyl ester (60 mg, 50%).

$^1$H NMR (300 MHz, CDCl$_3$): δ 8.84 (d, 1H, J=1.8 Hz), 8.74 (d, 1H, J=4.8 Hz), 8.14 (d, 1H, J=8.1 Hz), 7.79 (dd, 1H, J=6.3, 1.8 Hz), 7.75 (d, 1H, J=7.8 Hz), 7.72 (d, 1H, J=15.9 Hz), 7.46 (dd, 1H, J=4.8, 3.0 Hz), 6.54 (d, 1H, J=15.9 Hz), 4.26 (q, 2H, J=7.2 Hz), 1.32 (t, 3H, J=7.2 Hz).

Step 2: N-(3-Ethynyl-5-fluoro-4-methanesulfonylamino-benzyl)-3-(2-pyridin-3-yl-6-trifluoromethyl-pyridin-3-yl)-acrylamide N-(3-Ethynyl-5-fluoro-4-methanesulfonylamino-benzyl)-3-(2-pyridin-3-yl-6-trifluoromethyl-pyridin-3-yl)-acrylamide was obtained according to the general procedure described in Example 107 (step 2).-

N-(4-Aminomethyl-2-ethynyl-6-fluoro-phenyl)-methanesulfonamide, HCl salt (68 mg, 0.24 mmol) was reacted with 3-(2-pyridin-3-yl-6-trifluoromethyl-pyridin-3-yl)-acrylic acid (60 mg, 0.20 mmol) to give N-(3-ethynyl-5-fluoro-4-methanesulfonylamino-benzyl)-3-(2-pyridin-3-yl-6-trifluoromethyl-pyridin-3-yl)-acrylamide (60 mg, 58%).

$^1$H NMR (300 MHz, CDCl$_3$): δ 8.81 (d, 1H, J=2.4 Hz), 8.69 (dd, 1H, J=3.6, 1.5 Hz), 8.11 (d, 1H, J=8.1 Hz), 7.97 (dd, 1H, J=4.2, 1.2 Hz), 7.72 (d, 1H, J=8.4 Hz), 7.69 (d, 1H, J=15.6 Hz), 7.44 (dd, 1H, J=7.8, 5.1 Hz), 7.72 (dd, 1H, J=9.0, 1.8 Hz), 6.53 (d, 1H, J=15.6 Hz), 6.45 (t, 1H, J=5.7 Hz), 4.46 (d, 2H, J=6.3 Hz), 3.50 (s, 1H), 3.24 (s, 3H).

EXAMPLE 127

N-(3-Fluoro-4-methanesulfonylamino-benzyl)-3-(2-phenylamino-6-trifluoromethyl-pyridin-3-yl)-acrylamide

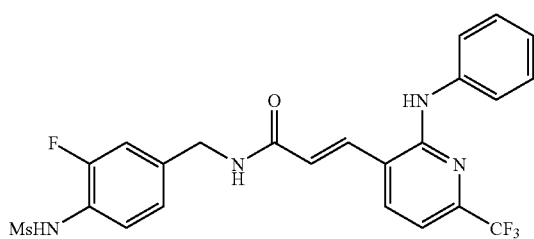

N-(4-Aminomethyl-3-fluoro-phenyl)-methanesulfonamide, HCl salt (74 mg, 0.29 mmol) was reacted with 3-(2-phenylamino-6-trifluoromethyl-pyridin-3-yl)-acrylic acid (90 mg, 0.29 mmol) to give the title compound (100 mg, 67%) after purification by column chromatography (Hex/EtOAc=2/3).

$^1$H NMR (300 MHz, DMSO-d$_6$): δ 9.57 (s, 1H), 8.80 (m, 1H), 8.02 (d, 1H, J=7.8 Hz), 7.80 (d, 1H, J=15.9 Hz), 7.63 (m, 2H), 7.29 (m, 6H), 6.98 (m, 1H), 6.73 (d, 1H, J=15.6 Hz), 4.41 (d, 2H, J=5.1 Hz), 2.99 (s, 3H),

EXAMPLE 128

N-(3-Cyano-5-fluoro-4-methanesulfonylamino-benzyl)-3-(2-phenylamino-6-trifluoromethyl-pyridin-3-yl)-acrylamide

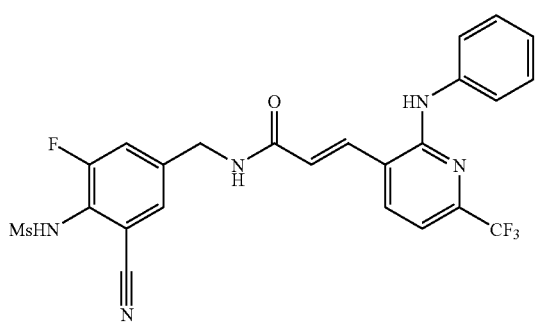

N-(4-Aminomethyl-2-cyano-6-fluoro-phenyl)-methanesulfonamide, HCl salt (81 mg, 0.29 mmol) was reacted with 3-(2-phenylamino-6-trifluoromethyl-pyridin-3-yl)-acrylic acid (90 mg, 0.29 mmol) to give the title compound (95 mg, 61%) after purification by column chromatography (Hex/EtOAc=1/3).

$^1$H NMR (300 MHz, DMSO-d$_6$): δ 10.09 (s, 1H), 9.01 (s, 1H), 8.88 (m, 1H), 8.04 (d, 1H, J=7.5 Hz), 7.82 (m, 1H), 7.64 (m, 4H), 7.29 (m, 3H), 6.98 (m, 1H), 6.74 (d, 1H, J=15.6 Hz), 4.48 (d, 2H, J=6.0 Hz), 3.10 (s, 3H),

EXAMPLE 129

3-(2-sec-Butylamino-6-trifluoromethyl-pyridin-3-yl)-N-(3,5-difluoro-4-methanesulfonylamino-benzyl)-acrylamide

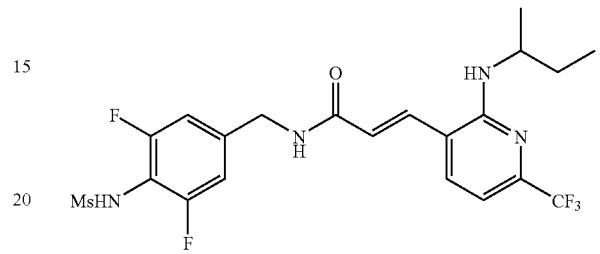

N-(4-Aminomethyl-2,6-difluoro-phenyl)-methanesulfonamide, HCl salt (86 mg, 0.32 mmol) was reacted with 3-(2-sec-butylamino-6-trifluoromethyl-pyridin-3-yl)-acrylic acid (90 mg, 0.31 mmol) to give the title compound (106 mg, 68%) after purification by crystallization from ether.

$^1$H NMR (300 MHz, DMSO-d6): δ 8.76 (t, 1H, J=6.0 Hz), 7.79 (d, 1H, J=7.5 Hz), 7.65 (d, 1H, J=15.3 Hz), 7.11 (d, 2H, J=8.4 Hz), 6.95 (d, 1H, J=7.8 Hz), 6.78 (d, 1H, J=7.8 Hz), 6.62 (d, 1H, J=15.3 Hz), 4.41 (d, 2H, J=6.0 Hz), 4.07 (m, 1H), 3.03 (s, 3H), 1.55 (m, 2H), 1.14 (d, 3H, J=6.6 Hz), 0.86 (t, 3H, J=7.5 Hz).

EXAMPLE 130

3-(2-sec-Butylamino-6-trifluoromethyl-pyridin-3-yl)-N-(3-fluoro-4-methanesulfonylamino-5-methyl-benzyl)-acrylamide

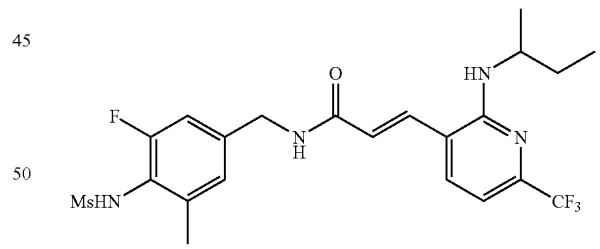

N-(4-Aminomethyl-2-fluoro-6-methyl-phenyl)-methanesulfonamide, HCl salt (99 mg, 0.37 mmol) was reacted with 3-(2-sec-butylamino-6-trifluoromethyl-pyridin-3-yl)-acrylic acid (100 mg, 0.34 mmol) to give the title compound (140 mg, 82%) after purification by crystallization from ether.

$^1$H NMR (300 MHz, DMSO-d6): δ 10.1 (bs, 1H), 8.64 (t, 1H, J=5.7 Hz), 7.75 (d, 1H, J=7.5 Hz), 7.63 (d, 1H, J=15.3 Hz), 7.16 (m, 2H), 6.94 (d, 1H, J=7.2 Hz), 6.76 (d, 1H, J=7.8 Hz), 6.62 (d, 1H, J=15.3 Hz), 4.40 (d, 2H, J=5.7 Hz), 4.06 (m, 1H), 2.97 (s, 3H), 2.20 (d, 3H, J=2.4 Hz), 1.55 (m, 2H), 1.14 (d, 3H, J=6.6 Hz), 0.85 (t, 3H, J=7.5 Hz).

ESI [M+H]+: 503

EXAMPLE 131

N-(3-Fluoro-4-methanesulfonylamino-5-methyl-benzyl)-3-(2-piperid-1-yl-6-trifluoromethyl-pyridinyl-3-yl)-acrylamide

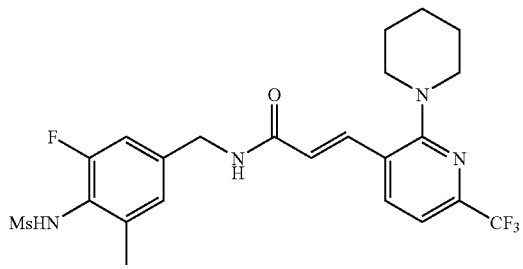

N-(4-Aminomethyl-2-fluoro-6-methyl-phenyl)-methanesulfonamide, HCl salt (50 mg, 0.19 mmol) was reacted with 3-(2-piperid-1-yl-6-trifluoromethyl-pyridin-3-yl)-acrylic acid (56 mg, 0.19 mmol) to give N-(3-fluoro-4-methanesulfonylamino-5-methyl-benzyl)-3-(2-piperid-1-yl-6-trifluoromethyl-pyridinyl-3-yl)-acrylamide (66 mg, 69%) after purification by recrystallization from EtOAc/hexane.

$^1$H NMR (300 MHz, DMSO-$d_6$): δ 9.26 (s, 1 H), 8.72 (t, 1 H, J=5.7 Hz), 7.97 (d, 1 H, J=7.8 Hz), 7.46~7.37 (m, 2 H), 7.22~7.10 (m, 2 H), 6.74 (d, 1H, J=15.6 Hz), 4.41 (d, 2H, J=5.7 Hz), 3.20~3.17 (m, 4 H), 2.98 (s, 3 H), 2.21 (d, 3 H, J=2.1 Hz), 1.62 (br, 6 H)

EXAMPLE 132

N-(3-Fluoro-4-methanesulfonylamino-benzyl)-3-(2-phenoxy-6-trifluoromethyl-pyridin-3-yl)-acrylamide

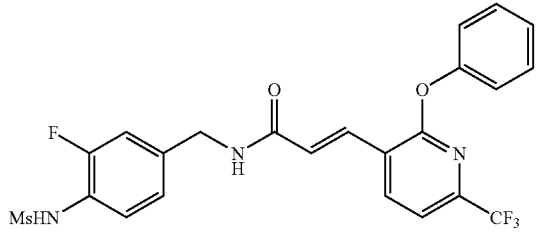

N-(4-Aminomethyl-2-fluoro-phenyl)-methanesulfonamide, HCl salt (41.7 mg, 0.162 mmol) was reacted with NMM (0.07 ml), DMTMM (44.7 mg) and 3-(2-phenoxy-6-trifluoromethyl-pyridin-3-yl)-acrylic acid (45 mg, 0.15 mmol) to give the title compound (63 mg, 85%) after purification by column chromatography (Hex/EtOAc=2/3).

$^1$H NMR (300 MHz, CDCl$_3$): δ 7.96 (d, 1H, J=7.8 Hz), 7.86 (d, 1H, J=15.6 Hz), 7.53 (t, 1H, J=7.8 Hz), 7.39 (m, 3H), 7.15 (m, 4H), 6.87 (d, 1H, J=15.6 Hz), 6.53 (s, 1H), 6.13 (t, 1H), 4.56 (d, 2H, J=6.0 Hz), 3.01 (s, 3H)

EXAMPLE 133

N-(3-Fluoro-4-methanesulfonylamino-5-vinyl-benzyl)-3-(2-phenoxy-6-trifluoromethyl-pyridin-3-yl)-acrylamide

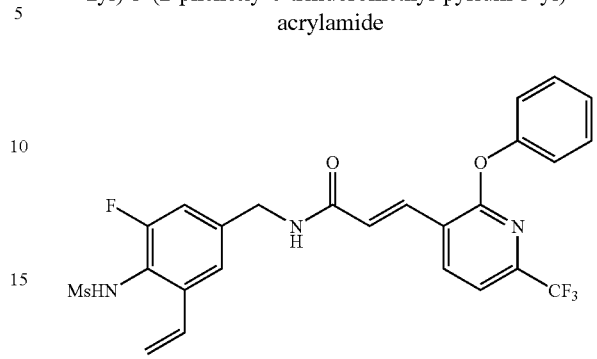

N-(4-Aminomethyl-2-fluoro-6-vinyl-phenyl)-methanesulfonamide, HCl salt (85 mg, 0.302 mmol) was reacted with NMM (0.1 ml), DMTMM (83.7 mg) and 3-(2-phenoxy-6-trifluoromethyl-pyridin-3-yl)-acrylic acid (69 mg, 0.245 mmol) to give the title compound (69 mg, 53%) after purification by column chromatography (Hex EtOAc=2/3).

$^1$H NMR (300 MHz, CDCl$_3$): δ 7.96 (d, 1H, J=8.1 Hz), 7.87 (d, 1H, J=15.6 Hz), 7.40 (m, 3H), 7.17 (m, 2H), 7.10 (m, 2H), 6.88 (d, 1H, J=15.6 Hz), 6.20 (t, 1H), 6.09 (m, 1H), 5.80 (dd, 1H, J=3.6 and 17.4 Hz), 5.46 (d, 1H, J=11.1 Hz), 4.57 (d, 2H, J=6.0 Hz), 3.37 (s, 1H), 3.07 (s, 3H).

EXAMPLE 134

N-(3-Ethynyl-5-fluoro-4-methanesulfonylamino-benzyl)-3-[2-(pyridin-3-yloxy)-6-trifluoromethyl-pyridin-3-yl]-acrylamide

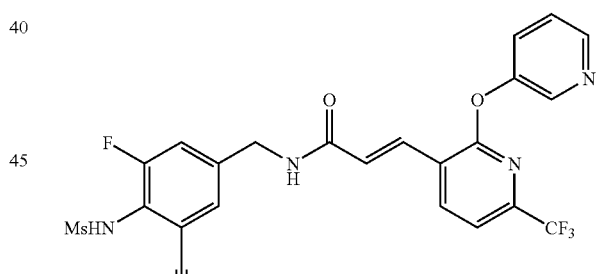

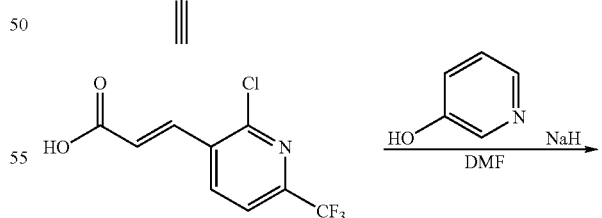

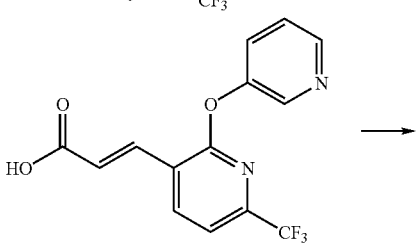

-continued

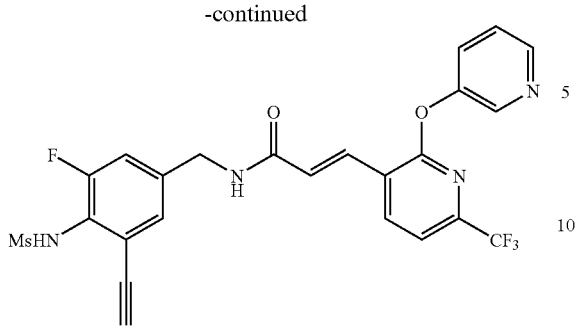

Step 1: 3-[2-(Pyridin-3-yloxy)-4-trifluoromethyl-phenyl]-acrylic acid

3-Hydroxypyridine (69.1 mg) and sodiumhydride (65 mg, 1.6 mmol) were added in THF. 3-(2-Chloro-6-trifluoromethyl-pyridin-3-yl)-acrylic acid (156 mg, 0.620 mmol) was added the reaction mixture. The reaction mixture was purified to yield the title compound (15 mg) after purification by column chromatography (Hex/EtOAc=1/4).

$^1$H NMR (300 MHz, CD$_3$OD): δ 8.48 (m, 1H), 8.32 (d, 1H, J=7.8 Hz), 8.03 (s, 1H), 7.93 (d, 1H, J=16.2 Hz), 7.73 (m, 1H), 7.51 (m, 1H), 7.21 (m, 1H), 6.79 (d, 1H, J=16.2 Hz).

Step 2: N-(3-Ethynyl-5-fluoro-4-methanesulfonylamino-benzyl)-3-[2-(pyridin-3-yloxy)-6-trifluoromethyl-pyridin-3-yl]-acrylamide N-(4-Aminomethyl-2-fluoro-6-ethynyl-phenyl)-methanesulfonamide, HCl salt (50.5 mg, 0.198 mmol) was reacted with NMM (0.08 ml), DMTMM (57.8 mg) and 3-[2-(pyridin-3-yloxy)-4-trifluoromethyl-phenyl]-acrylic acid (40.5 mg) to give the title compound (29 mg) after purification by column chromatography (Hex/EtOAc=1/4).

$^1$H NMR (300 MHz, CD$_3$OD): δ 8.52 (d, 1H, J=2.7 Hz), 8.45 (md, 1H), 8.30 (d, 1H, J=7.2 Hz), 7.88 (d, 1H, J=15.9 Hz), 7.77 (m, 1H), 7.55 (m, 2H), 7.33 (s, 1H), 7.21 (dd, 1H, J=1.2 and 10.2 Hz), 7.02 (d, 1H, J=15.9 Hz), 4.49 (s, 2H), 3.31 (s, 1H), 3.11 (s, 3H).

EXAMPLE 135

N-(3-Ethynyl-5-fluoro-4-methanesulfonylamino-benzyl)-3-[2-(4-fluoro-pyridin-3-yl)-6-trifluoromethyl-pyridin-3-yl]-acrylamide

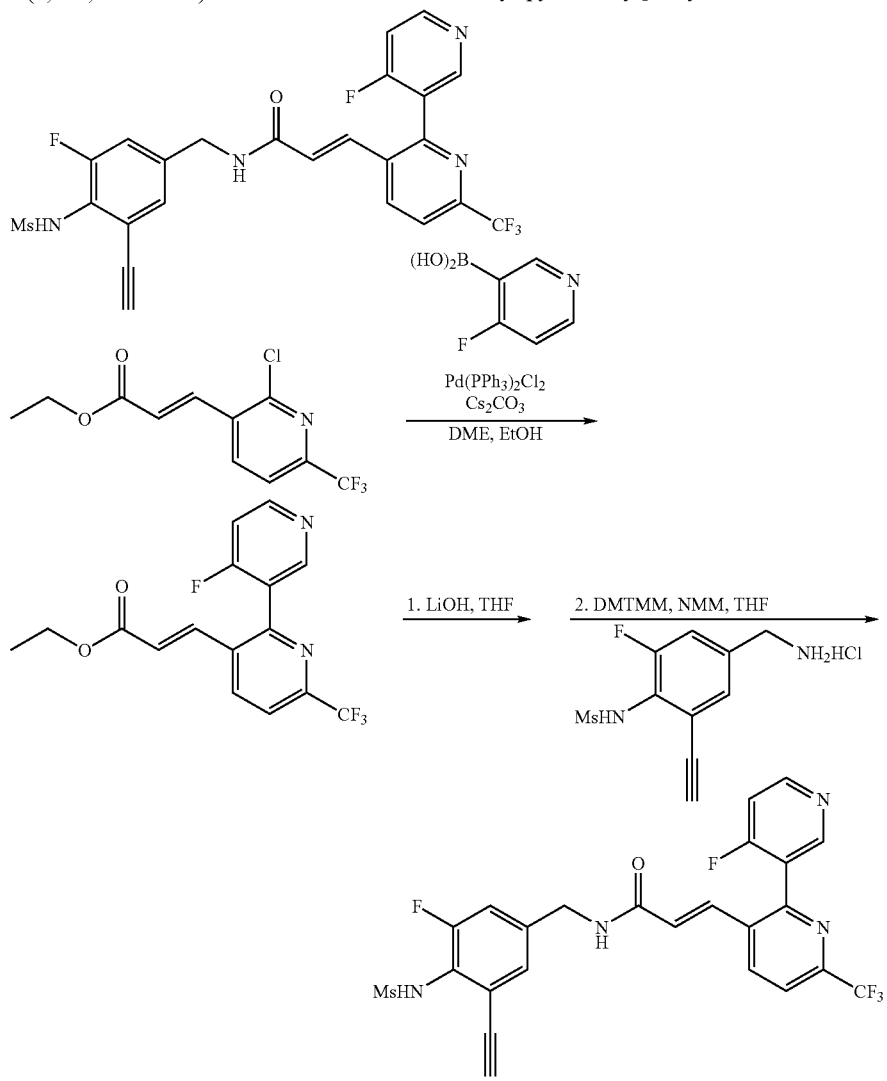

Step 1: Synthesis of 3-[2-(4-fluoro-pyridin-3-yl)-6-trifluoromethyl-pyridin-3-yl]-acrylic acid ethyl ester 3-[2-(4-Fluoro-pyridin-3-yl)-6-trifluoromethyl-pyridin-3-yl]-acrylic acid ethyl ester was obtained according to the general procedure described in Example 107 (step 1).

3-(2-Chloro-6-trifluoromethyl-pyridin-3-yl)-acrylic acid ethyl ester (110 mg, 0.393 mmol) was reacted with 2-fluoro-5-pyridine boronic acid (2 eq) to give 3-[2-(4-fluoro-pyridin-3-yl)-6-trifluoromethyl-pyridin-3-yl]-acrylic acid ethyl ester (40 mg, 30%).

$^1$H NMR (300 MHz, CDCl$_3$): δ 8.45 (d, 1H, J=2.4 Hz), 8.16-8.08 (m, 2H), 7.76 (d, 1H, J=8.4 Hz), 7.70 (d, 1H, J=15.9 Hz), 7.11 (dd, 1H, J=5.4, 3.0 Hz), 6.55 (d, 1H, J=15.9 Hz), 4.27 (q, 2H, J=7.2 Hz), 1.33 (t, 3H, J=7.2 Hz).

Step 2: N-(3-Ethynyl-5-fluoro-4-methanesulfonylamino-benzyl)-3-[2-(4-fluoro-pyridin-3-yl)-6-trifluoromethyl-pyridin-3-yl]-acrylamide N-(3-Ethynyl-5-fluoro-4-methanesulfonylamino-benzyl)-3-(4'-fluoro-6-trifluoromethyl-[2,3']bipyridinyl-3-yl)-acrylamide was obtained according to the general procedure described in Example 107 (step 2).

N-(4-Aminomethyl-2-ethynyl-6-fluoro-phenyl)-methanesulfonamide, HCl salt (29.5 mg, 0.107 mmol) was reacted with 3-[2-(4-fluoro-pyridin-3-yl)-6-trifluoromethyl-pyridin-3-yl]-acrylic acid (22 mg, 0.070 mmol) to give N-(3-ethynyl-5-fluoro-4-methanesulfonylamino-benzyl)-3-[2-(4-fluoro-pyridin-3-yl)-6-trifluoromethyl-pyridin-3-yl]-acrylamide (14 mg, 39%).

$^1$H NMR (300 MHz, DMSO): δ 9.46 (s, 1H, br), 8.88 (t, 1H, J=6.0 Hz), 8.43 (d, 1H, J=8.1 Hz), 8.41 (s, 1H), 8.23-8.16 (m, 1H), 8.04 (d, 1H, J=8.1 Hz), 7.42 (d, 1H, J=15.6 Hz), 7.41 (d, 1H, J=2.7 Hz), 7.28 (s, 1H), 7.26 (d, 1H, J=4.8 Hz), 6.83 (d, 1H, J=15.6 Hz), 4.52 (s, 1H), 4.37 (d, 2H, J=5.7 Hz), 3.06 (s, 3H).

EXAMPLE 136

N-(3-Cyano-5-fluoro-4-methanesulfonylamino-benzyl)-3-[2-(3-fluoro-phenyl)-6-trifluoromethyl-pyridin-3-yl]-acrylamide

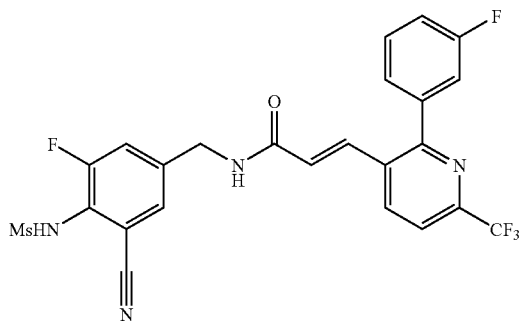

N-(4-Aminomethyl-2-cyano-6-fluoro-phenyl)-methanesulfonamide, HCl salt (18 mg, 0.065 mmol) was reacted with 3-[2-(3-fluoro-phenyl)-6-trifluoromethyl-pyridin-3-yl]-acrylic acid (17 mg, 0.054 mmol) to give N-(3-cyano-5-fluoro-4-methanesulfonylamino-benzyl)-3-[2-(3-fluoro-phenyl)-6-trifluoromethyl-pyridin-3-yl]-acrylamide (21 mg, 62%) after purification by recrystallization from n-hexane/EtOAc.

$^1$H NMR (300 MHz, DMSO): δ 8.90 (t, 1H, J=6.0 Hz), 8.41 (d, 1H, J=8.1 Hz), 8.02 (d, 1H, J=8.1 Hz), 7.62-7.57 (m, 3H), 7.45-7.35 (m, 4H), 6.83 (d, 1H, J=15.6 Hz), 4.42 (d, 2H, J=6.0 Hz), 3.06 (s, 3H).

EXAMPLES 137 AND 138 ARE MISSING

EXAMPLE 139

N-(3-Ethynyl-5-fluoro-4-methanesulfonylamino-benzyl)-3-(2-phenylthio-6-trifluoromethyl-pyridin-3-yl)-acrylamide

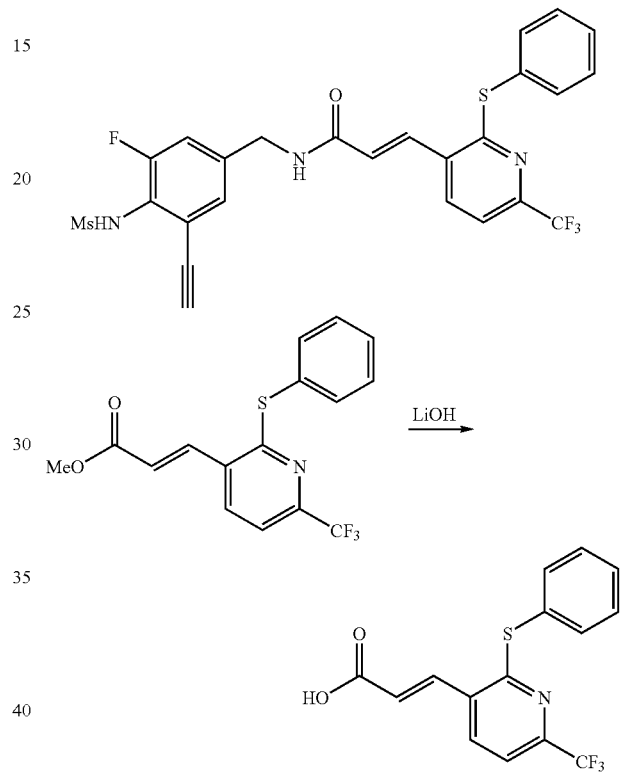

Step 1: 3-(2-phenylthio-6-trifluoromethyl-pyridin-3-yl)-acrylic acid 3-(2-phenylthio-6-trifluoromethyl-pyridin-3-yl)-acrylic acid methyl ester (80 mg) was hydrolyzed with 1 M LiOH solution (3 mmol) at room temperature to yield the title compound (63 mg)

$^1$H NMR (300 MHz, CDCl$_3$): δ 8.13 (d, 1H, J=15.6 Hz), 7.81 (m, 1H), 7.53 (m, 2H), 7.38 (m, 3H), 6.48 (d, 1H, J=15.9 Hz).

Step 2: N-(3-Ethynyl-5-fluoro-4-methanesulfonylamino-benzyl)-3-(2-phenylthio-6-trifluoromethyl-pyridin-3-yl)-acrylamide N-(4-Aminomethyl-2-fluoro-6-ethynyl-phenyl)-methanesulfonamide, HCl salt (43 mg, 0.154 mmol) was reacted with NMM (0.1 ml), DMTMM (46 mg) and 3-(2-phenylthio-6-trifluoromethyl-pyridin-3-yl)-acrylic acid (41 mg, 0.126 mmol) to give the title compound (25.6 mg, 37%) after purification by column chromatography (Hex/EtOAc=1/2).

$^1$H NMR (300 MHz, CDCl$_3$): δ 7.88 (d, 1H, J=15.6 Hz), 7.76 (d, 1H, J=8.1 Hz), 7.48 (m, 2H), 7.32 (m, 4H), 7.21 (s,

1H), 7.08 (d, 1H, J=10.5 Hz), 6.45 (d, 1H, J=15.3 Hz), 6.43 (s, 1H), 4.44 (d, 2H, J=6.3 Hz), 3.40 (s, 1H), 3.20 (s, 3H)

EXAMPLE 140

N-(3-fluoro-4-methanesulfonylamino-benzyl)-3-(2-phenylthio-6-trifluoromethyl-pyridin-3-yl)-acrylamide

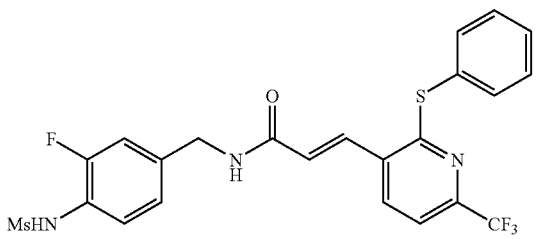

N-(4-Aminomethyl-2-fluoro-phenyl)-methanesulfonamide, HCl salt (21 mg, 0.082 mmol) was reacted with NMM (0.1 ml), DMTMM (26 mg) and 3-(2-phenylthio-6-trifluoromethyl-pyridin-3-yl)-acrylic acid (21 mg) to give the title compound (18 mg, 53%) after purification by column chromatography (Hex/EtOAc=1/2).

$^1$H NMR (300 MHz, CDCl$_3$): 7.88 (d, 1H, J=15.6 Hz), 7.76 (d, 1H, J=7.8 Hz), 7.48 (m, 2H), 7.32 (m, 4H), 7.11 (s, 1H), 6.91 (m, 2H), 6.43 (d, 1H, J=15.3 Hz), 6.42 (s, 1H), 4.52 (d, 2H, J=6.3 Hz), 3.00 (s, 3H)

EXAMPLE 141

N-(3-Fluoro-4-methanesulfonylamino-benzyl)-3-(2-phenethyl-6-trifluoromethyl-pyridin-3-yl)-acrylamide

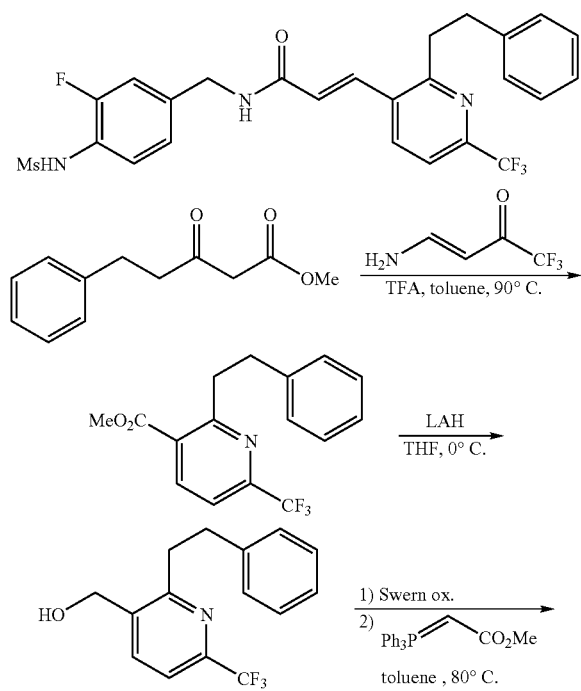

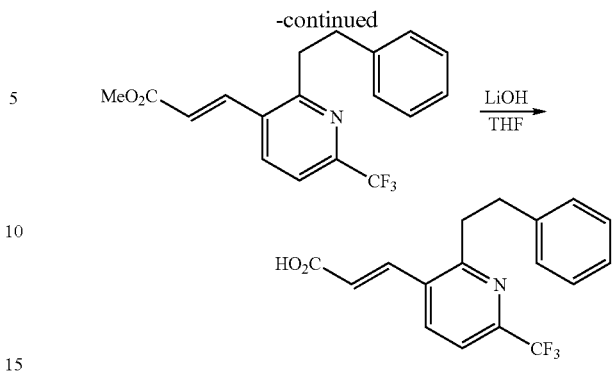

Step 1: 2-phenethyl-4-trifluoromethyl-nicotinic acid, methyl ester

To a solution of β-ketoester (2.43 g, 17.5 mmol) in toluene (30 mL) were added 4-amino-1,1,1-trifluorobuten-2-one (3.60 g, 17.5 mmol) and trifluoroacetic acid (1.30 mL, 17.5 mmol), and the resulting mixture was stirred at 90° C. for 60 hrs. To this mixture was washed with aqueous 20% Na$_2$CO$_3$ and dried over MgSO$_4$, filtered, and concentrated under reduced pressure. The crude residue was purified by column chromatography (Hex/EtOAc=10:1) to give 2-phenethyl-4-trifluoromethyl-nicotinic acid, methyl ester (1.84 g, 41%).

$^1$H NMR (300 MHz, CDCl$_3$): δ 8.30 (d, 1H, J=8.1 Hz), 7.59 (d, 1H, J=8.1 Hz), 7.24 (m, 5H), 3.92 (s, 3H), 3.53 (m, 1H), 3.07 (m, 1H).

Step 2: 2-phenethyl-4-trifluoromethyl-pyridin-3-yl methyl alcohol

To a suspension of 2-phenethyl-4-trifluoromethyl-nicotinic acid, methyl ester (1.84 g, 5.95 mmol) in THF (50 mL) was added dropwise 1.0M LiAlH$_4$ (6.0 ml, 6.0 mmol) at 0° C. After stirring at 0° C. for 1 hr, the reaction was quenched by adding 10% sodium potassium tartarate (50 mL) and the resulting mixture was vigorously stirred for 1 hr. Two phases were separated and the aqueous phase was extracted with ether. The combined organic layer was washed with brine, dried over anhyd. MgSO$_4$, filtered and concentrated under reduced pressure. The crude residue was purified by column chromatography (Hex/EtOAc=10:1) to give alcohol product (1.55 g, 93%).

$^1$H NMR (300 MHz, CDCl$_3$): δ 7.87 (d, 1H, J=8.1 Hz), 7.54 (d, 1H, J=8.1 Hz), 7.20 (m, 5H), 5.59 (d, 2H, J=5.4 Hz), 3.11 (s, 4H).

Step 3: 3-(2-phenethyl-6-trifluoromethyl-pyridin-3-yl)-acrylic acid, methyl ester To a solution of oxalyl chloride (540 mL, 6.06 mmol) in CH$_2$Cl$_2$ (30 mL) at −78° C. was added dropwise DMSO (860 mL, 12.2 mmol) and the resulting solution was stirred for 5 min at −78° C. A solution of the alcohol prepared in the above step 2 (1.55 g, 5.51 mmol) in CH$_2$Cl$_2$ (10 mL) was added dropwise to the reaction mixture. After stirring at −78° C. for 30 min, the reaction was quenched by adding triethylamine (3.84 mL, 27.6 mmol) and the resulting mixture was warmed up to room temperature. Water (40 mL) was added to the reaction mixture and two phases were separated. The aqueous phase was extracted with CH$_2$Cl$_2$. The combined organic layer was washed with brine, dried over anhyd. MgSO$_4$, filtered and concentrated under reduced pressure to afford aldehyde product, which was used without further purification.

To a solution of the aldehyde product prepared above in toluene (20 mL) was added methyl(triphenylphosphoranylidene)acetate (1.77 g, 5.51 mmol), and the resulting mixture was heated at 90° C. for 3 hrs. The reaction mixture was diluted with EtOAc, and washed with water and brine. The organic layer was dried over anhydrous MgSO$_4$ and concentrated under reduced pressure. The resulting residue was purified by column chromatography (Hex/EtOAc=10/1) to give 3-(2-phenethyl-6-trifluoromethyl-pyridin-3-yl)-acrylic acid, methyl ester (1.46 g, 79% over 2 steps).

$^1$H NMR (300 MHz, CDCl$_3$): δ 7.88 (d, 1H, J=7.8 Hz), 7.79 (d, 1H, J=15.9 Hz), 7.54 (d, 1H, J=7.8 Hz), 7.20 (m, 5H), 6.30 (d, 1H, J=15.9 Hz), 3.82 (s, 3H), 3.29 (m, 2H), 3.07 (m, 2H).

Step 4: 3-(2-phenethyl-6-trifluoromethyl-pyridin-3-yl)-acrylic acid

To a suspension of compound 3-(2-phenethyl-6-trifluoromethyl-pyridin-3-yl)-acrylic acid, methyl ester (1.46 g, 4.35 mmol) in THF (3 ml) was added a solution of 1 N-LiOH (6.0 ml), and the mixture was stirred for 3 hours at room temperature. The resulting residue was dissolved in H$_2$O and then washed with EtOAc, acidified with 1N HCl to pH 1~2. The solution was extracted three times with methylene chloride and then dried over anhyd. MgSO$_4$ and concentrated in vacuo to give 3-(2-phenethyl-6-trifluoromethyl-pyridin-3-yl)-acrylic acid (1.37 g, 98%).

$^1$H NMR (300 MHz, CDCl$_3$): δ 7.91 (m, 2H), 7.58 (d, 1H, J=7.8 Hz), 7.20 (m, 5H), 6.31 (d, 1H, J=15.9 Hz), 3.31 (m, 2H), 3.09 (m, 2H).

Step 5: synthesis of N-(3-Fluoro-4-methanesulfonylamino-benzyl)-3-(2-phenethyl-6-trifluoromethyl-pyridin-3-yl)-acrylamide N-(4-Aminomethyl-2-fluoro-phenyl)-methanesulfonamide, HCl salt (153 mg, 0.60 mmol) was reacted with 3-(2-phenethyl-6-trifluoromethyl-pyridin-3-yl)-acrylic acid (160 mg, 0.50 mmol) to give N-(3-fluoro-4-methanesulfonylamino-benzyl)-3-(2-phenethyl-6-trifluoromethyl-pyridin-3-yl)-acrylamide (174 mg, 67%) after purification by crystallization from Hex/EtOAc.

$^1$H NMR (300 MHz, DMSO-d6+CDCl$_3$): δ 8.70 (bs, 1H), 7.91 (m, 2H), 7.82 (d, 1H, J=15.3 Hz), 7.54 (d, 1H, J=8.1 Hz), 7.46 (t, 1H, J=8.1 Hz), 7.20 (m, 7H), 6.51 (d, 1H, J=15.3 Hz), 4.50 (d, 2H, J=5.7 Hz), 3.29 (m, 2H), 3.08 (m, 2H), 3.00 (s, 3H).

ESI [M+H]+: 528

EXAMPLE 142

N-(3-Ethynyl-5-fluoro-4-methanesulfonylamino-benzyl)-3-(2-phenethyl-6-trifluoromethyl-pyridin-3-yl)-acrylamide

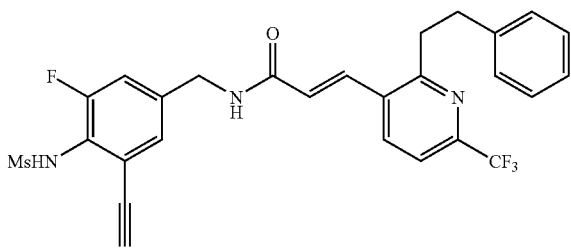

N-(4-Aminomethyl-6-ethynyl-2-fluoro-phenyl)-methanesulfonamide, HCl salt (167 mg, 0.60 mmol) was reacted with 3-(2-phenethyl-6-trifluoromethyl-pyridin-3-yl)-acrylic acid (160 mg, 0.50 mmol) to give the title compound (175 mg, 64%) after purification by crystallization from Hex/EtOAc.

$^1$H NMR (300 MHz, DMSO-d6+CDCl$_3$): δ 8.20 (bs, 1H), 8.11 (t, 1H), 7.92 (d, 1H, J=8.1 Hz), 7.72 (d, 1H, J=15.3 Hz), 7.55 (d, 1H, J=8.1 Hz), 7.33 (s, 1H), 7.20 (m, 6H), 6.52 (d, 1H, J=15.3 Hz), 4.49 (d, 2H, J=6.0 Hz), 3.47 (s, 1H), 3.29 (m, 2H), 3.18 (s, 3H), 3.08 (m, 2H).

ESI [M+H]+: 546

EXAMPLE 143

3-(2-Butyl-6-trifluoromethyl-pyridin-3-yl)-N-(3-fluoro-4-methane sulfonylamino-benzyl)-acrylamide

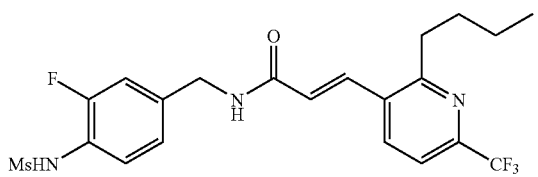

N-(4-Aminomethyl-2-fluoro-phenyl)-methanesulfonamide, HCl salt (153 mg, 0.60 mmol) was reacted with 3-(2-butyl-6-trifluoromethyl-pyridin-3-yl)-acrylic acid (137 mg, 0.50 mmol) similarly prepared as above to give the title compound (160 mg, 68%) after purification by crystallization from Hex/EtOAc.

$^1$H NMR (300 MHz, DMSO-d6): δ 9.50 (bs, 1H), 8.84 (t, 1H, J=5.7 Hz), 8.16 (d, 1H, J=7.8 Hz), 7.79 (d, 1H, J=8.1 Hz), 7.72 (d, 1H, J=15.3 Hz), 7.35 (t, 1H, J=8.1 Hz), 7.16 (m, 2H), 6.74 (d, 1H, J=15.3 Hz), 4.40 (d, 2H, J=6.3 Hz), 2.99 (s, 3H), 2.94 (m, 2H), 1.60 (m, 2H), 1.35 (m, 2H), 0.90 (t, 3H, J=7.2 Hz).

EXAMPLE 144

3-(2-Butyl-6-trifluoromethyl-pyridin-3-yl)-N-(3-ethynyl-5-fluoro-4-methanesulfonylamino-benzyl)-acrylamide

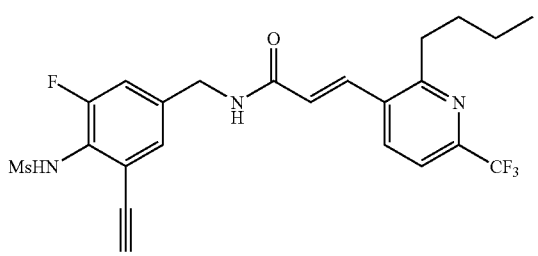

N-(4-Aminomethyl-6-ethynyl-2-fluoro-phenyl)-methanesulfonamide, HCl salt (167 mg, 0.60 mmol) was reacted with 3-(2-butyl-6-trifluoromethyl-pyridin-3-yl)-acrylic acid (137 mg, 0.50 mmol) to give the title compound (158 mg, 64%) after purification by crystallization from Hex/EtOAc.

$^1$H NMR (300 MHz, DMSO-d6): δ 9.46 (bs, 1H), 8.88 (t, 1H, J=5.7 Hz), 8.18 (d, 1H, J=7.8 Hz), 7.79 (d, 1H, J=8.4 Hz), 7.71 (d, 1H, J=15.6 Hz), 7.29 (m, 2H), 6.74 (d, 1H, J=15.6 Hz), 4.52 (s, 1H), 4.40 (d, 2H, J=5.7 Hz), 3.06 (s, 3H), 2.94 (m, 2H), 1.60 (m, 2H), 1.35 (m, 2H), 0.90 (t, 3H, J=6.9 Hz).

ESI [M+H]+: 498

EXAMPLE 145

N-(3-Ethynyl-5-fluoro-4-methanesulfonylamino-benzyl)-3-(2-ethynyl-6-trifluoromethyl-pyridin-3-yl)-acrylamide

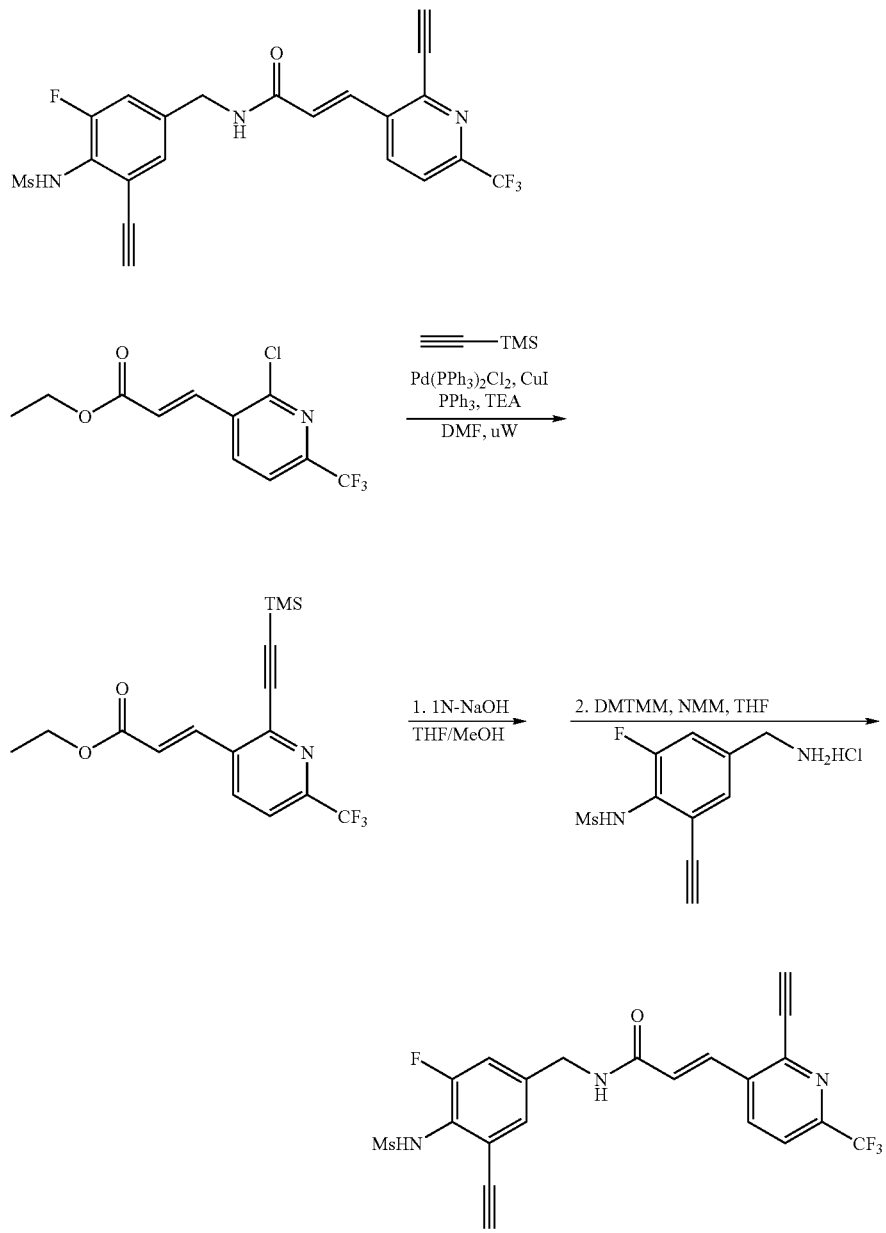

Step 1: Synthesis of 3-(6-trifluoromethyl-2-trimethylsilanylethynyl-pyridin-3-yl)-acrylic acid ethyl ester Microwave vial was charged with 3-(2-chloro-6-trifluoromethyl-pyridin-3-yl)-acrylic acid ethyl ester (103 mg, 0.368 mmol), Pd(PPh$_3$)$_2$Cl$_2$ (0.06 eq), CuI (0.06 eq), PPh$_3$ (0.2 eq), Et$_3$N (15 eq), (trimethylsilyl)acetylene and DMF (0.25 ml). The vial was irradiated in microwave synthesizer at 120° C. for 25 min. The contents of the vial were filtered through a Celite pad, which was washed out thoroughly with EtOAc. The filtrate was evaporated, and the residue was purified by column chromatography to 3-(6-trifluoromethyl-2-trimethylsilanylethynyl-pyridin-3-yl)-acrylic acid ethyl ester (58 mg, 46%).

$^1$H NMR (300 MHz, CDCl$_3$): δ 8.08 (d, 1H, J=16.4 Hz), 8.0 (d, 1H, J=8.1 Hz), 6.55 (d, 1H, J=8.1 Hz), 6.54 (d, 1H, J=16.4 Hz), 4.25 (q, 2H, J=7.2 Hz), 1.30 (t, 3H, J=7.2 Hz), 0.27 (s, 9H).

Step 2: Synthesis of N-(3-ethynyl-5-fluoro-4-methanesulfonylamino-benzyl)-3-(2-ethynyl-6-trifluoromethyl-pyridin-3-yl)-acrylamide To a suspension of 3-(6-trifluoromethyl-2-trimethylsilanylethynyl-pyridin-3-yl)-acrylic acid ethyl ester (68 mg, 0.169 mmol) in THF (1 ml) and CH$_3$OH (0.5 ml) was added a solution of 1N-NaOH (0.5 ml) and the mixture was stirred for 50 min at room temperature. The resulting residue was dissolved in H$_2$O and then washed three times with EtOAc, acidified with 1N HCl to pH 1~2. The solution was extracted three times with methylene chloride and then dried over anhyd. Na$_2$SO$_4$ and concentrated in vacuo to give 3-(2-ethynyl-6-trifluoromethyl-pyridin-3-yl)-acrylic acid (48 mg, 99%). To a suspension of N-(4-aminomethyl-2-ethynyl-6-fluoro-phenyl)-methanesulfonamide, HCl salt (83 mg, 0.298 mmol) in THF (3 mL) was added N-methylmorpholine (0.066 ml, 0.597 mmol). The mixture was stirred for 5 minutes, to which were added 3-(2-ethynyl-6-trifluoromethyl-pyridin-3-yl)-acrylic acid (48 mg, 0.065 mmol) and 4-(4,6-dimethoxy[1,3,5]triazin-2-yl)-4-methylmorpholinium chloride hydrate (DMTMM, 71.4 mg, 0.258 mmol). The mixture was stirred overnight at room temperature and was concentrated under reduced pressure. The residue was diluted with EtOAc and water. The organic layer was washed with saturated sodium bicarbonate, 1N HCl and brine, dried over anhydrous magnesium sulfate, filtered, and concentrated under reduced pressure. The crude residue was purified by recrystallization from CH$_2$Cl$_2$ to give N-(3-ethynyl-5-fluoro-4-methanesulfonylamino-benzyl)-3-(2-ethynyl-6-trifluoromethyl-pyridin-3-yl)-acrylamide (30 mg, 32%).

$^1$H NMR (300 MHz, DMSO): δ 9.46 (s, 1H, br), 8.94 (t, 1H, J=5.4 Hz), 8.39 (d, 1H, J=8.4 Hz), 8.00 (d, 1H, J=8.4 Hz), 7.83 (d, 1H, J=15.9 Hz), 7.30 (s, 1H), 7.28 (d, 1H, J=7.8 Hz), 6.97 (d, 1H, J=15.9 Hz), 4.94 (s, 1H), 4.51 (s, 1H), 4.41 (d, 2H, J=5.7 Hz), 3.06 (s, 3H).

EXAMPLE 146

Missing

EXAMPLE 147

N-(3-Fluoro-4-methanesulfonylamino-benzyl)-3-(2-isobutyl-6-trifluoromethyl-pyridin-3-yl)-acrylamide

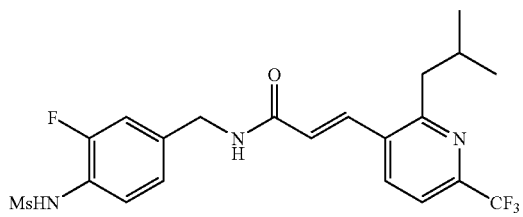

N-(4-Aminomethyl-2-fluoro-phenyl)-methanesulfonamide, HCl salt (153 mg, 0.60 mmol) was reacted with 3-(2-isobutyl-6-trifluoromethyl-pyridin-3-yl)-acrylic acid (137 mg, 0.50 mmol) similarly prepared as above to give the title compound (151 mg, 64%) after purification by crystallization from Hex EtOAc.

$^1$H NMR (300 MHz, DMSO-d6): δ 9.55 (bs, 1H), 8.83 (t, 1H), 8.17 (d, 1H, J=8.1 Hz), 7.79 (d, 1H, J=7.8 Hz), 7.72 (d, 1H, J=15.3 Hz), 7.35 (t, 1H, J=8.4 Hz), 7.16 (m, 2H), 6.74 (d, 1H, J=15.3 Hz), 4.40 (d, 2H, J=5.7 Hz), 3.00 (s, 3H), 2.83 (d, 2H, J=6.9 Hz), 2.01 (m, 1H), 0.89 (t, 6H, J=6.6 Hz).

EXAMPLE 148

N-(3-Ethynyl-5-fluoro-4-methanesulfonylamino-benzyl)-3-(2-isobutyl-6-trifluoromethyl-pyridin-3-yl)-acrylamide

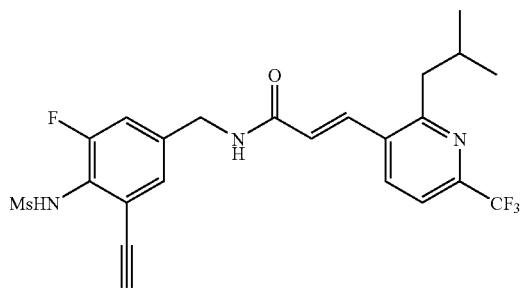

N-(4-Aminomethyl-6-ethynyl-2-fluoro-phenyl)-methanesulfonamide, HCl salt (167 mg, 0.60 mmol) was reacted with 3-(2-isobutyl-6-trifluoromethyl-pyridin-3-yl)-acrylic acid (137 mg, 0.50 mmol) to give the title compound (153 mg, 62%) after purification by crystallization from Hex/EtOAc.

$^1$H NMR (300 MHz, DMSO-d6): δ 9.46 (bs, 1H), 8.86 (t, 1H, J=5.7 Hz), 8.19 (d, 1H, J=8.1 Hz), 7.79 (d, 1H, J=8.1 Hz), 7.72 (d, 1H, J=15.3 Hz), 7.29 (m, 2H), 6.74 (d, 1H, J=15.3 Hz), 4.50 (s, 1H), 4.41 (d, 2H, J=5.7 Hz), 3.07 (s, 3H), 2.83 (d, 2H, J=7.2 Hz), 2.01 (m, 1H), 0.89 (t, 6H, J=6.6 Hz).
ESI [M+H]+: 498

EXAMPLE 149

(R)—N-[1-(3-Fluoro-4-methane sulfonylamino-phenyl)-ethyl]-3-(2-phenylamino-6-trifluoromethyl-pyridin-3-yl)-acrylamide

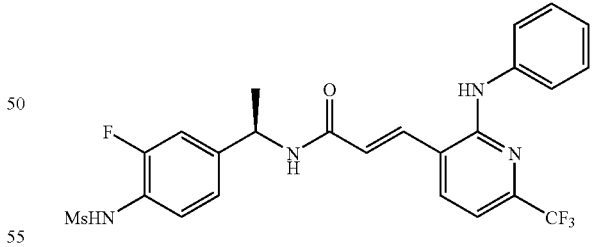

(R)—N-[4-(1-Amino-ethyl)-2-fluoro-phenyl]-methanesulfonamide, HCl salt (78 mg, 0.29 mmol) was reacted with 3-(2-phenylamino-6-trifluoromethyl-pyridin-3-yl)-acrylic acid (90 mg, 0.29 mmol) to give the title compound (120 mg, 80%) after purification by column chromatography (Hex/EtOAc=1/1).

$^1$H NMR (300 MHz, DMSO-d$_6$): δ 8.34 (d, 1H, J=8.1 Hz), 8.12 (s, 1H), 7.72 (m, 5H), 7.40 (m, 1H), 7.29 (m, 2H), 7.15 (m, 3H), 7.01 (m, 1H), 6.66 (d, 1H, J=15.6 Hz), 5.16 (q, 1H, J=6.6 Hz), 2.93 (s, 3H), 1.51 (d, 3H, J=6.9 Hz)

EXAMPLE 150
3-(2-Ethyl-6-trifluoromethyl-pyridin-3-yl)-N-(3-ethynyl-5-fluoro-4-methanesulfonylamino-benzyl)-acrylamide
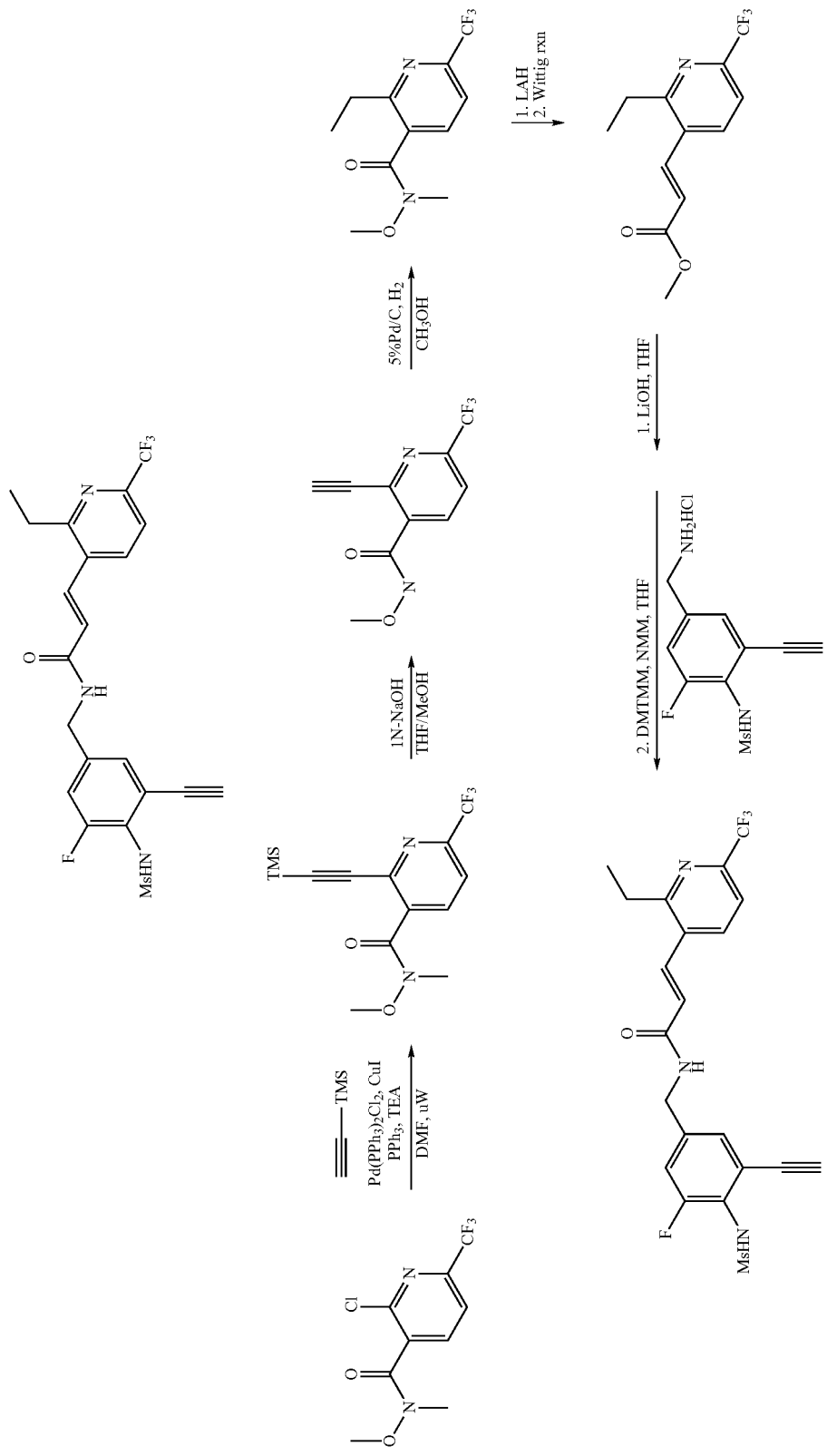

Step 1: Synthesis of N-methoxy-N-methyl-6-trifluoromethyl-2-trimethylsilanylethynyl-nicotinamide N-Methoxy-N-methyl-6-trifluoromethyl-2-trimethylsilanylethynyl-nicotinamide was obtained according to the general procedure described in Example 145 (step 1).

2-Chloro-N-methoxy-N-methyl-6-trifluoromethyl-nicotinamide (1.2 g, 4.52 mmol) was reacted with (trimethylsilyl)acetylene (0.689 ml, 4.97 mmol) to give N-methoxy-N-methyl-6-trifluoromethyl-2-trimethylsilanylethynyl-nicotinamide (896 mg, 60%).

$^1$H NMR (300 MHz, CDCl$_3$): δ 7.83 (d, 1H, J=7.8 Hz), 7.66 (d, 1H, J=7.8 Hz), 3.51 (s, 3H), 3.39 (s, 3H), 0.26 (s, 9H).

Step 2: Synthesis of 2-ethynyl-N-methoxy-N-methyl-6-trifluoromethyl-nicotinamide To a suspension of N-methoxy-N-methyl-6-trifluoromethyl-2-trimethylsilanylethynyl-nicotinamide (148 g, 0.449 mmol) in THF (1 ml) and CH$_3$OH (0.5 ml) was added a solution of 1N-NaOH (0.5 ml) and the mixture was stirred for 50 min at room temperature. The resulting residue was dissolved in H$_2$O and then washed three times with EtOAc, acidified with 1N HCl to pH 1~2. The solution was extracted three times with methylene chloride and then dried over anhyd. Na$_2$SO$_4$ and concentrated in vacuo to give 2-ethynyl-N-methoxy-N-methyl-6-trifluoromethyl-nicotinamide (116 mg, 99%).

$^1$H NMR (300 MHz, CDCl$_3$): δ 7.82 (d, 1H, J=7.8 Hz), 7.65 (d, 1H, J=7.8 Hz), 3.69 (s, 3H), 3.45 (s, 3H).

Step 3: Synthesis of 2-ethyl-N-methoxy-N-methyl-6-trifluoromethyl-nicotinamide To a suspension of 2-ethynyl-N-methoxy-N-methyl-6-trifluoromethyl-nicotinamide (145 mg, 0.561 mmol) in 5% Pd/C (30 mg) was added CH$_3$OH (4 ml). The mixture was purged three times with hydrogen gas (50 psi) and shaken for 2 hours at room temperature. The reaction mixture was filtered over a pad of Celite and concentrated under reduced pressure. The crude residue was chromatographed to yield the 2-ethyl-N-methoxy-N-methyl-6-trifluoromethyl-nicotinamide (112 mg, 76%).

$^1$H NMR (300 MHz, CDCl$_3$): δ 7.75 (d, 1H, J=7.8 Hz), 7.54 (d, 1H, J=7.8 Hz), 3.43 (s, 3H), 3.39 (s, 3H), 2.89 (q, 2H, J=7.5 Hz), 1.33 (t, 3H, J=7.5 Hz).

Step 4: 3-(2-Ethyl-6-trifluoromethyl-pyridin-3-yl)-acrylic acid methyl ester To a cooled (−78° C.) solution of 2-ethyl-N-methoxy-N-methyl-6-trifluoromethyl-nicotinamide (113 mg, 0.43 mmol) in THF (4 mL) was added lithium aluminum hydride (1M LAH in THF, 0.22 mL). The mixture was stirred for 15 minutes, and then warmed to −10° C. After additional stirring for 30 minutes, the mixture was quenched with saturated potassium hydrogen sulfate solution (1 mL) and extracted with diethyl ether. The organic layer was dried over anhydrous magnesium sulfate, filtered, and concentrated under reduced pressure to give 2-ethyl-6-trifluoromethyl-pyridine-3-carbaldehyde quantitatively as oil. The crude product was used directly in the following reaction.

To a solution of 2-ethyl-6-trifluoromethyl-pyridine-3-carbaldehyde in toluene (10 mL) was added methyl(triphenylphosphoranylidene)acetate (172 mg, 0.516 mmol). The mixture was heated at 110° C. for overnight cooled to room temperature, and diluted with EtOAc and water. The organic layer was dried over anhydrous magnesium sulfate, filtered, and concentrated under reduced pressure. The crude residue was purified by column chromatography (EtOAc/hexanes=1/4) to yield the 3-(2-ethyl-6-trifluoromethyl-pyridin-3-yl)-acrylic acid methyl ester (89 mg, 80%).

$^1$H NMR (300 MHz, CDCl$_3$): δ 7.95 (d, 1H, J=15.9 Hz), 7.94 (d, 1H, J=7.8 Hz), 7.54 (d, 1H, J=8.1 Hz), 6.44 (d, 1H, J=15.9 Hz), 3.85 (s, 3H), 3.02 (q, 2H, J=7.5 Hz), 1.31 (t, 3H, J=7.5 Hz).

Step 5: 3-(2-Ethyl-6-trifluoromethyl-pyridin-3-yl)-N-(3-ethynyl-5-fluoro-4-methanesulfonylamino-benzyl)-acrylamide 3-(2-Ethyl-6-trifluoromethyl-pyridin-3-yl)-N-(3-ethynyl-5-fluoro-4-methanesulfonylamino-benzyl)-acrylamide was obtained according to the general procedure described in Example 107 (Step 2).

N-(4-Aminomethyl-2-ethynyl-6-fluoro-phenyl)-methanesulfonamide, HCl salt (74 mg, 0.263 mmol) was reacted with 3-(2-ethyl-6-trifluoromethyl-pyridin-3-yl)-acrylic acid (43 mg, 0.175 mmol) to give 3-(2-ethyl-6-trifluoromethyl-pyridin-3-yl)-N-(3-ethynyl-5-fluoro-4-methanesulfonylamino-benzyl)-acrylamide (45 mg, 37%).

$^1$H NMR (300 MHz, DMSO): δ 9.45 (s, 1H, br), 8.87 (t, 1H, J=6.0 Hz), 8.18 (d, 1H, J=8.1 Hz), 7.79 (d, 1H, J=8.1 Hz), 7.71 (d, 1H, J=15.6 Hz), 7.30 (s, 1H), 7.28 (d, 1H, J=8.4 Hz), 6.74 (d, 1H, J=15.6 Hz), 4.51 (s, 1H), 4.40 (d, 2H, J=5.7 Hz), 3.00 (s, 3H), 2.96 (q, 2H, J=7.5 Hz), 1.21 (t, 3H, J=7.5 Hz).

EXAMPLE 151

N-(3-Fluoro-4-methanesulfonylamino-benzyl)-3-[2-(2-methyl-butyl)-6-trifluoromethyl-pyridin-3-yl]-acrylamide

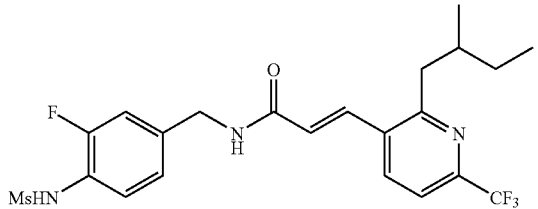

N-(4-Aminomethyl-2-fluoro-phenyl)-methanesulfonamide, HCl salt (153 mg, 0.60 mmol) was reacted with 3-[2-(2-methyl-butyl)-6-trifluoromethyl-pyridin-3-yl]-acrylic acid (144 mg, 0.50 mmol) similarly prepared as above to give the title compound (176 mg, 72%) after purification by column chromatography (Hex/EtOAc=2/3).

$^1$H NMR (300 MHz, DMSO-d6): δ 9.55 (bs, 1H), 8.83 (t, 1H), 8.17 (d, 1H, J=8.1 Hz), 7.79 (d, 1H, J=7.8 Hz), 7.72 (d, 1H, J=15.3 Hz), 7.35 (t, 1H, J=8.4 Hz), 7.16 (m, 2H), 6.74 (d, 1H, J=15.3 Hz), 4.40 (d, 2H, J=5.7 Hz), 3.00 (s, 3H), 2.97 (m, 1H), 2.70 (m, 1H), 1.80 (m, 1H), 1.30 (m, 2H), 0.87 (t, 3H, J=7.2 Hz), 0.81 (d, 3H, J=6.6 Hz).

EXAMPLE 152

N-(3-Ethynyl-5-fluoro-4-methanesulfonylamino-benzyl)-3-[2-(2-methyl-butyl)-6-trifluoromethyl-pyridin-3-yl]-acrylamide

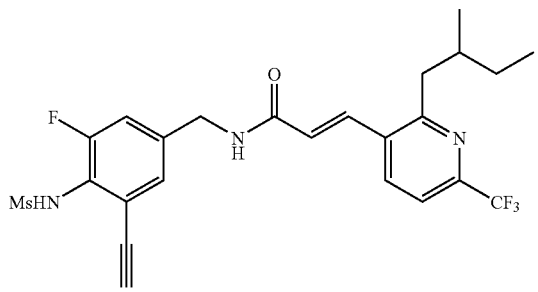

N-(4-Aminomethyl-6-ethynyl-2-fluoro-phenyl)-methane-sulfonamide, HCl salt (167 mg, 0.60 mmol) was reacted with 3-[2-(2-methyl-butyl)-6-trifluoromethyl-pyridin-3-yl]-acrylic acid (144 mg, 0.50 mmol) to give the title compound (175 mg, 68%) after purification by column chromatography (Hex/EtOAc=2/3).

$^1$H NMR (300 MHz, DMSO-d6): δ 9.45 (bs, 1H), 8.85 (t, 1H, J=5.7 Hz), 8.19 (d, 1H, J=8.4 Hz), 7.79 (d, 1H, J=8.1 Hz), 7.72 (d, 1H, J=15.6 Hz), 7.28 (m, 2H), 6.74 (d, 1H, J=15.6 Hz), 4.52 (s, 1H), 4.41 (d, 2H, J=6.0 Hz), 3.07 (s, 3H), 2.97 (m, 1H), 2.70 (m, 1H), 1.80 (m, 1H), 1.30 (m, 2H), 0.87 (t, 3H, J=7.2 Hz), 0.81 (d, 3H, J=6.6 Hz).

ESI [M+H]+: 512

EXAMPLE 153

N-(3-Ethynyl-5-fluoro-4-methanesulfonylamino-benzyl)-3-[2-(3-methoxy-prop-1-ynyl)-6-trifluorom-ethyl-pyridin-3-yl]-acrylamide

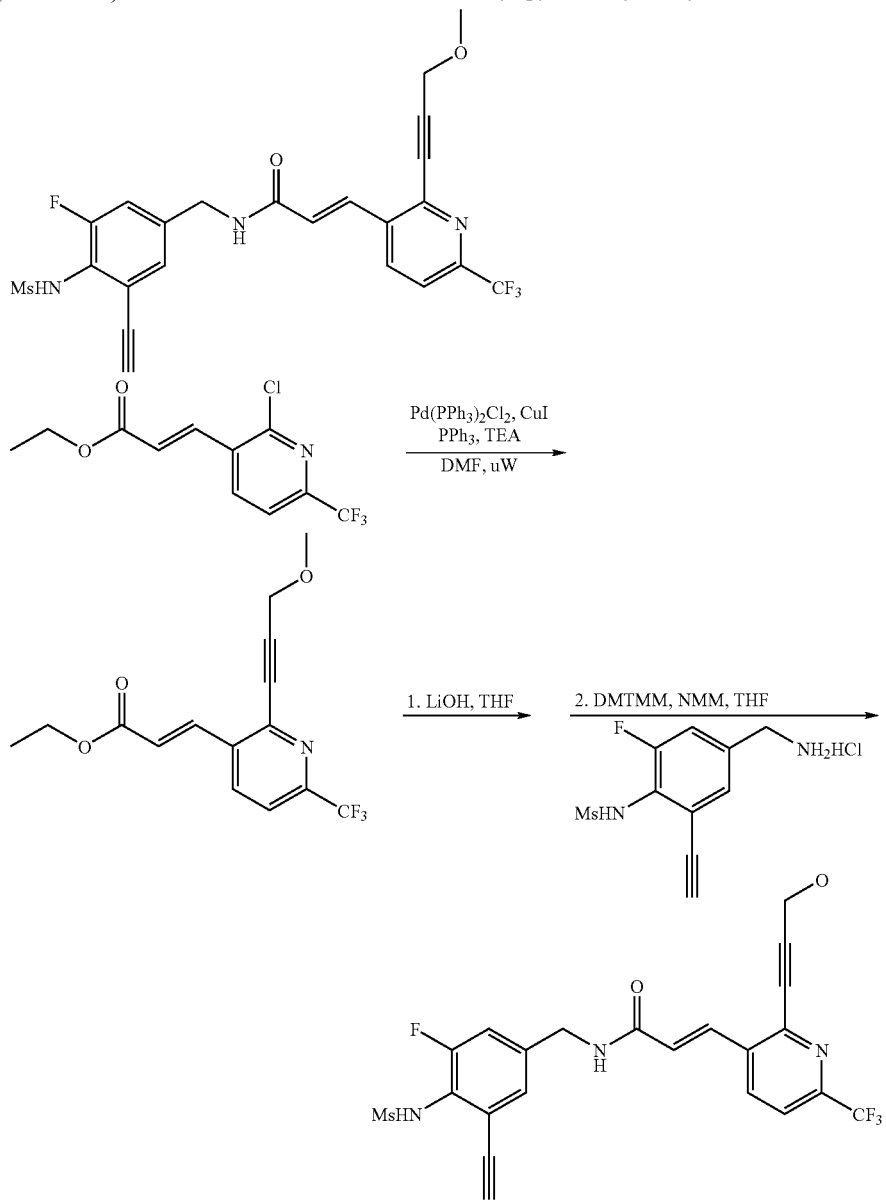

Step 1: Synthesis of N-methoxy-N-methyl-6-trifluoromethyl-2-trimethylsilanylethynyl-nicotinamide N-Methoxy-N-methyl-6-trifluoromethyl-2-trimethylsilanylethynyl-nicotinamide was obtained according to the general procedure described in Example 145 (step 1).

2-Chloro-N-methoxy-N-methyl-6-trifluoromethyl-nicotinamide (128 mg, 0.457 mmol) was reacted with 3-methoxy-propyne (0.042 mg, 0.504 mmol) to give 3-[2-(3-methoxy-prop-1-ynyl)-6-trifluoromethyl-pyridin-3-yl]-acrylic acid ethyl ester (89 mg, 62%).

$^1$H NMR (300 MHz, CDCl$_3$): δ 8.11 (d, 1H, J=16.2 Hz), 8.08 (d, 1H, J=9.0 Hz), 7.66 (d, 1H, J=9.0 Hz), 6.60 (d, 1H, J=16.2 Hz), 4.44 (s, 2H), 4.30 (d, 2H, J=7.2 Hz), 3.53 (s, 3H), 1.36 (t, 3H, J=7.2 Hz).

Step 2: N-(3-Ethynyl-5-fluoro-4-methanesulfonylamino-benzyl)-3-[2-(3-methoxy-prop-1-ynyl)-6-trifluoromethyl-pyridin-3-yl]-acrylamide N-(3-Ethynyl-5-fluoro-4-methanesulfonylamino-benzyl)-3-[2-(3-methoxy-prop-1-ynyl)-6-trifluoromethyl-pyridin-3-yl]-acrylamide was obtained according to the general procedure described in Example 107 (Step 2).

N-(4-Aminomethyl-2-ethynyl-6-fluoro-phenyl)-methanesulfonamide, HCl salt (59 mg, 0.21 mmol) was reacted with 3-[2-(3-methoxy-prop-1-ynyl)-6-trifluoromethyl-pyridin-3-yl]-acrylic acid (40 mg, 0.14 mmol) to give N-(3-ethynyl-5-fluoro-4-methanesulfonylamino-benzyl)-3-[2-(3-methoxy-prop-1-ynyl)-6-trifluoromethyl-pyridin-3-yl]-acrylamide (35 mg, 33%).

$^1$H NMR (300 MHz, CDCl$_3$): δ 8.04 (d, 1H, J=7.2 Hz), 8.00 (d, 1H, J=16.5 Hz), 7.62 (d, 1H, J=8.1 Hz), 7.22 (s, 1H), 7.09 (dd, 1H, J=10.8, 1.8 Hz), 6.73 (d, 1H, J=15.9 Hz), 6.68 (d, 1H, J=5.7 Hz), 6.61 (s, 1H), 4.47 (d, 2H, J=5.7 Hz), 4.40 (s, 2H), 3.47 (s, 3H), 3.24 (s, 3H).

EXAMPLE 154

N-(3-Fluoro-4-methanesulfonylamino-benzyl)-3-[2-(3-methoxy-prop-1-ynyl)-6-trifluoromethyl-pyridin-3-yl]-acrylamide

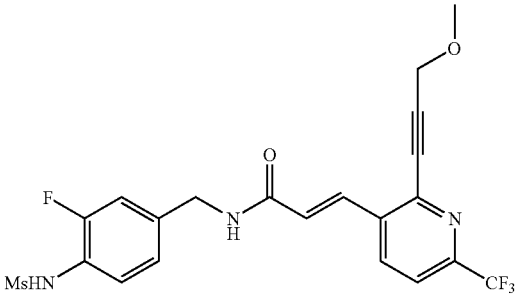

N-(4-Aminomethyl-2-fluoro-phenyl)-methanesulfonamide, HCl salt (19.1 mg, 0.075 mmol) was reacted with 3-[2-(3-methoxy-prop-1-ynyl)-6-trifluoromethyl-pyridin-3-yl]-acrylic acid (18 mg, 0.063 mmol) to give N-(3-fluoro-4-methanesulfonylamino-benzyl)-3-[2-(3-methoxy-prop-1-ynyl)-6-trifluoromethyl-pyridin-3-yl]-acrylamide (35 mg, 33%).

$^1$H NMR (300 MHz, CDCl$_3$): δ 8.04 (d, 1H, J=16.2 Hz), 8.01 (d, 1H, J=7.2 Hz), 7.63 (d, 1H, J=8.1 Hz), 7.52 (t, 1H, J=8.1 Hz), 7.17-7.11 (m, 2H), 6.73 (d, 1H, J=15.6 Hz), 6.56 (s, 1H), 6.22 (t, 1H, J=6.0 Hz), 4.56 (d, 2H, J=6.0 Hz), 4.42 (s, 2H), 3.48 (s, 3H), 3.03 (s, 3H).

EXAMPLE 155

N-(3-Ethynyl-5-fluoro-4-methanesulfonylamino-benzyl)-3-[2-(3-methoxy-propyl)-6-trifluoromethyl-pyridin-3-yl]-acrylamide

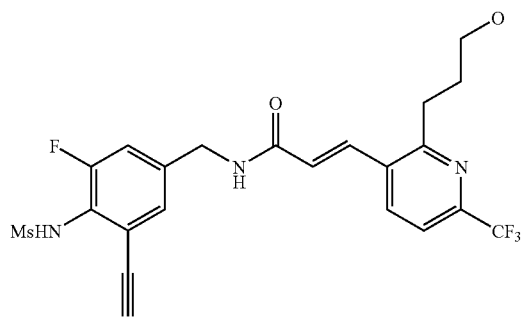

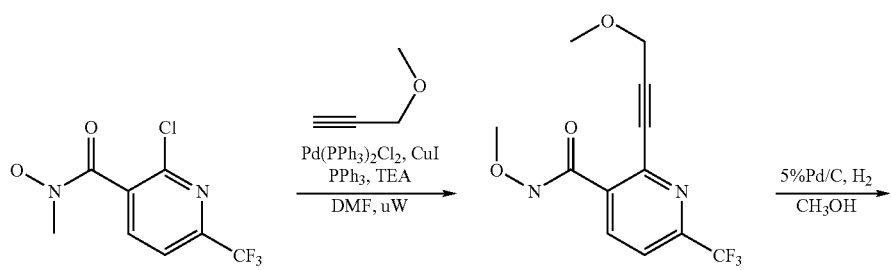

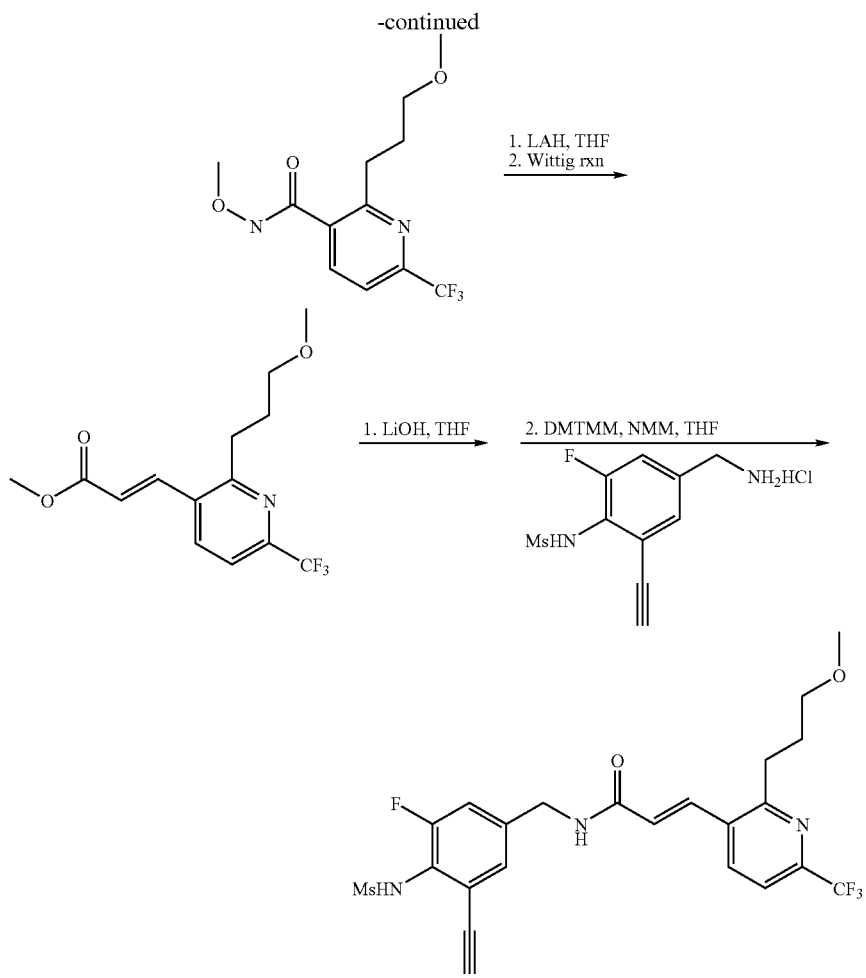

Step 1: Synthesis of N-methoxy-2-(3-methoxy-prop-1-ynyl)-N-methyl-6-trifluoromethyl-nicotinamide N-Methoxy-2-(3-methoxy-prop-1-ynyl)-N-methyl-6-trifluoromethyl-nicotinamide was obtained according to the general procedure described in Example 145 (step 1).

2-Chloro-N-methoxy-N-methyl-6-trifluoromethyl-nicotinamide (1000 mg, 3.72 mmol) was reacted with 3-methoxypropyne (0.345 ml, 4.09 mmol) to give N-methoxy-2-(3-methoxy-prop-1-ynyl)-N-methyl-6-trifluoromethyl-nicotinamide (247 mg, 22%).

$^1$H NMR (300 MHz, CDCl$_3$): δ 7.87 (d, 1H, J=7.8 Hz), 7.68 (d, 1H, J=7.8 Hz), 4.35 (s, 3H), 3.51 (s, 3H), 3.44 (s, 3H), 3.41 (s, 3H).

Step 2: Synthesis of N-methoxy-2-(3-methoxy-propyl)-N-methyl-6-trifluoromethyl-nicotinamide To a suspension of N-methoxy-2-(3-methoxy-prop-1-ynyl)-N-methyl-6-trifluoromethyl-nicotinamide (247 mg, 0.817 mmol) in 5% Pd/C (50 mg) was added CH$_3$OH (6 ml). The mixture was purged three times with hydrogen gas (50 psi) and shaken for 2 hours at room temperature. The reaction mixture was filtered over a pad of Celite and concentrated under reduced pressure. The crude residue was chromatographed to yield the N-methoxy-2-(3-methoxy-propyl)-N-methyl-6-trifluoromethyl-nicotinamide (160 mg, 64%).

$^1$H NMR (300 MHz, CDCl$_3$): δ 7.74 (d, 1H, J=7.8 Hz), 7.68 (d, 1H, J=7.8 Hz), 3.46-3.34 (m, 8H), 3.32 (s, 3H), 2.93 (t, 2H, J=7.8 Hz), 2.12-2.03 (m, 2H)

Step 3: Synthesis of 3-[2-(3-methoxy-propyl)-6-trifluoromethyl-pyridin-3-yl]-acrylic acid methyl ester 3-[2-(3-Methoxy-propyl)-6-trifluoromethyl-pyridin-3-yl]-acrylic acid methyl ester was obtained according to the general procedure described in Example 150 (step 4).

N-Methoxy-2-(3-methoxy-propyl)-N-methyl-6-trifluoromethyl-nicotinamide (156 mg, 0.509 mmol) was reacted with 1M-LAH in THF solution to give 2-(3-methoxy-propyl)-6-trifluoromethyl-pyridine-3-carbaldehyde quantitatively as oil. The crude product was used directly in the following reaction. 2-(3-Methoxy-propyl)-6-trifluoromethyl-pyridine-3-carbaldehyde was reacted with methyl (triphenylphosphoranylidene)acetate (204 mg, 0.61 mmol) to give 3-[2-(3-methoxy-propyl)-6-trifluoromethyl-pyridin-3-yl]-acrylic acid methyl ester (124 mg, 80%).

$^1$H NMR (300 MHz, CDCl$_3$): δ 7.98 (d, 1H, J=15.9 Hz), 7.93 (d, 1H, J=7.8 Hz), 7.53 (d, 1H, J=7.8 Hz), 6.43 (d, 1H, J=15.9 Hz), 3.84 (s, 3H), 3.43 (t, 2H, J=6.0 Hz), 3.33 (s, 3H), 3.09-3.04 (m, 2H), 2.09-1.99 (m, 2H).

Step 4: Synthesis of N-(3-ethynyl-5-fluoro-4-methanesulfonylamino-benzyl)-3-[2-(3-methoxy-propyl)-6-trifluoromethyl-pyridin-3-yl]-acrylamide.

N-(3-Ethynyl-5-fluoro-4-methanesulfonylamino-benzyl)-3-[2-(3-methoxy-propyl)-6-trifluoromethyl-pyridin-3-yl]-acrylamide was obtained according to the general procedure described in Example 107 (Step 2).
N-(4-Aminomethyl-2-ethynyl-6-fluoro-phenyl)-methanesulfonamide, HCl salt (57.9 mg, 0.207 mmol) was reacted with 3-[2-(3-methoxy-propyl)-6-trifluoromethyl-pyridin-3-yl]-acrylic acid (40 mg, 0.138 mmol) to give N-(3-ethynyl-5-fluoro-4-methanesulfonylamino-benzyl)-3-[2-(3-methoxy-propyl)-6-trifluoromethyl-pyridin-3-yl]-acrylamide (18 mg, 17%).
$^1$H NMR (300 MHz, CDCl$_3$): δ 7.92 (d, 1H, J=15.9 Hz), 7.90 (d, 1H, J=8.1 Hz), 7.52 (d, 1H, J=8.1 Hz), 7.27 (d, 1H, J=5.4 Hz), 7.16 (dd, 1H, J=9.0, 1.8 Hz), 6.48 (d, 1H, J=11.7 Hz), 6.41-6.36 (m, 2H), 4.51 (d, 2H, J=5.7 Hz), 3.47-3.42 (m, 3H), 3.31 (s, 3H), 3.26 (s, 3H), 3.09-3.04 (m, 2H), 2.07-1.98 (m, 2H).

EXAMPLE 156
N-(3-Fluoro-4-methanesulfonylamino-benzyl)-3-[2-(3-methoxy-propyl)-6-trifluoromethyl-pyridin-3-yl]-acrylamide N-(3-Fluoro-4-methanesulfonylamino-benzyl)-3-[2-(3-methoxy-propyl)-6-trifluoromethyl-pyridin-3-yl]-acrylamide was obtained according to the general procedure described in Example 107 (Step 2).

N-(4-Aminomethyl-2-fluoro-phenyl)-methanesulfonamide, HCl salt (21 mg, 0.083 mmol) was reacted with 3-[2-(3-methoxy-propyl)-6-trifluoromethyl-pyridin-3-yl]-acrylic acid (20 mg, 0.096 mmol) to give N-(3-fluoro-4-methanesulfonylamino-benzyl)-3-[2-(3-methoxy-propyl)-6-trifluoromethyl-pyridin-3-yl]-acrylamide (18 mg, 17%).

$^1$H NMR (300 MHz, CDCl$_3$): δ 7.93 (d, 1H, J=15.0 Hz), 7.89 (d, 1H, J=7.4 Hz), 7.55-7.49 (m, 2H), 7.17-7.10 (m, 2H), 6.59 (s, 1H), 6.43 (d, 1H, J=15.6 Hz), 6.27 (t, 1H, J=6.0 Hz), 4.55 (d, 2H, J=6.0 Hz), 3.44 (t, 2H, J=2.0 Hz), 3.31 (s, 3H), 3.09-3.04 (m, 2H), 3.02 (s, 3H), 2.07-1.98 (m, 2H).

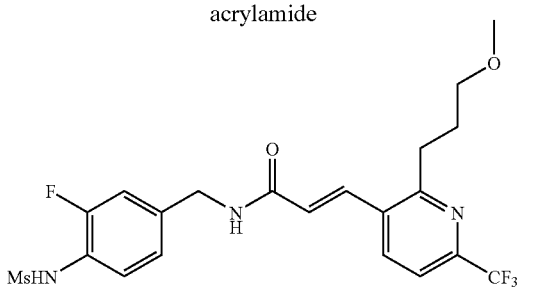

EXAMPLE 157

N-(3-Ethynyl-5-fluoro-4-methanesulfonylamino-benzyl)-3-(2-styryl-6-trifluoromethyl-pyridin-3-yl)-acrylamide

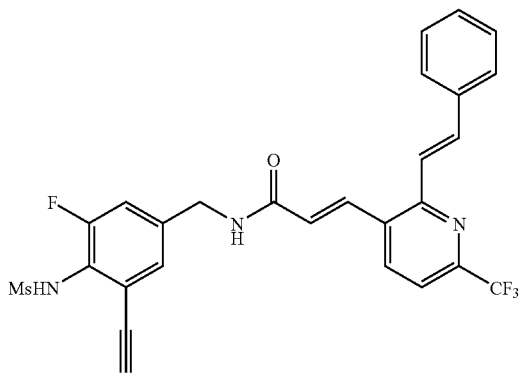

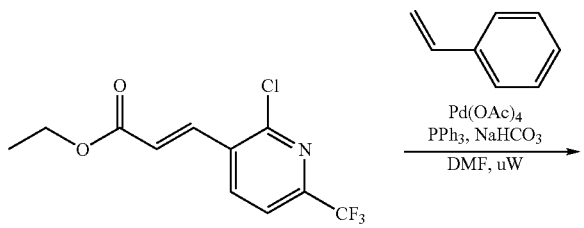

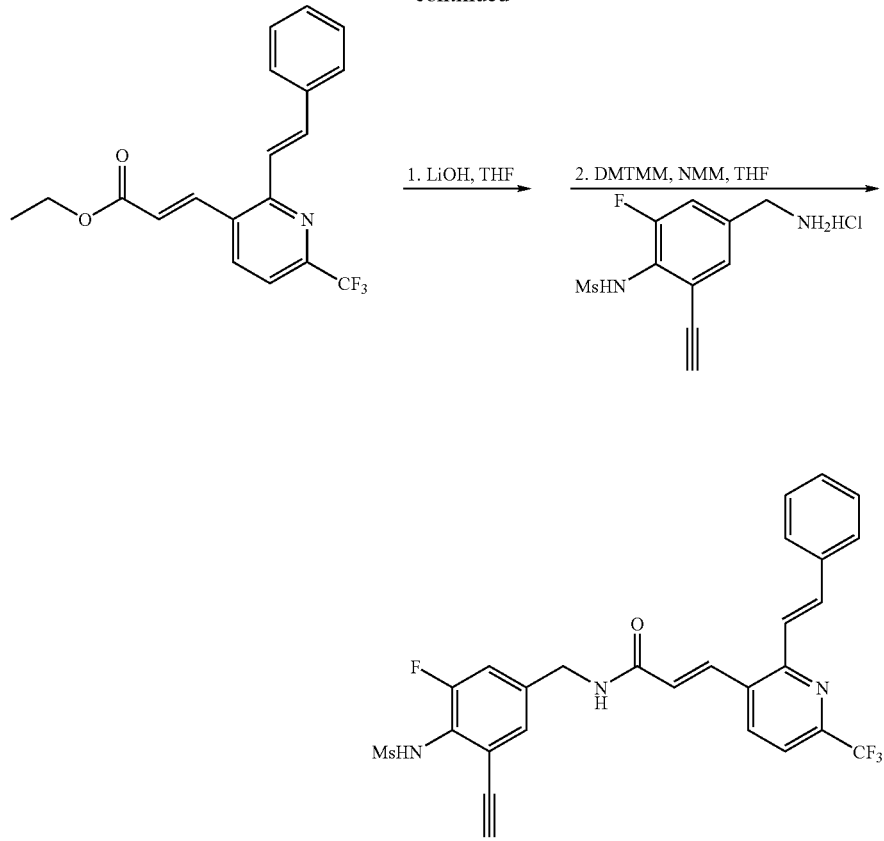

Step 1: Synthesis of 3-(2-styryl-6-trifluoromethyl-pyridin-3-yl)-acrylic acid ethyl ester Microwave vial was charged with 3-(2-chloro-6-trifluoromethyl-pyridin-3-yl)-acrylic acid ethyl ester (100 mg, 0.357 mmol), Pd(OAc)$_4$ (0.05 eq), NaHCO$_3$ (2 eq), PPh$_3$ (0.5 eq), stylene (5 eq) and DMF (1 ml). The vial was irradiated in microwave synthesizer at 135° C. for 3 hours. The contents of the vial were filtered through a Celite pad, which was washed out thoroughly with EtOAc. The filtrate was evaporated, and the residue was purified by column chromatography to 3-(2-styryl-6-trifluoromethyl-pyridin-3-yl)-acrylic acid ethyl ester (37 mg, 20%).

$^1$H NMR (300 MHz, CDCl$_3$): δ 8.10 (d, 1H, J=15.6 Hz), 7.95 (d, 1H, J=15.6 Hz), 7.93 (d, 1H, J=7.8 Hz), 7.63 (d, 1H, J=7.2 Hz), 7.52 (d, 1H, J=7.8 Hz), 7.43-7.34 (m, 5H), 6.45 (d, 1H, J=15.9 Hz), 4.32 (q, 2H, J=7.2 Hz), 1.36 (t, 3H, J=7.2 Hz).

Step 2: Synthesis of N-(3-ethynyl-5-fluoro-4-methanesulfonylamino-benzyl)-3-(2-styryl-6-trifluoromethyl-pyridin-3-yl)-acrylamide N-(4-Aminomethyl-2-ethynyl-6-fluoro-phenyl)-methanesulfonamide, HCl salt (36 mg, 0.127 mmol) was reacted with 3-(2-styryl-6-trifluoromethyl-pyridin-3-yl)-acrylic acid (37 mg, 0.115 mmol) to give N-(3-ethynyl-5-fluoro-4-methanesulfonylamino-benzyl)-3-(2-styryl-6-trifluoromethyl-pyridin-3-yl)-acrylamide (38 mg, 55%).

$^1$H NMR (300 MHz, DMSO): δ 9.45 (s, 1H, br), 8.91 (t, 1H, J=6.0 Hz), 8.23 (d, 1H, J=8.1 Hz), 7.97 (d, 1H, J=15.9 Hz), 7.82-7.74 (m, 4H), 7.61 (d, 1H, J=15.9 Hz), 7.46-7.29 (m, 5H), 6.75 (d, 1H, J=15.6 Hz), 4.51 (s, 1H), 4.42 (d, 2H, J=5.7 Hz), 3.07 (s, 3H).

EXAMPLE 158

N-(3-Fluoro-4-methanesulfonylamino-benzyl)-3-[2-(N-methyl-N-propyl-amino)-6-trifluoromethyl-pyridin-3-yl]-acrylamide

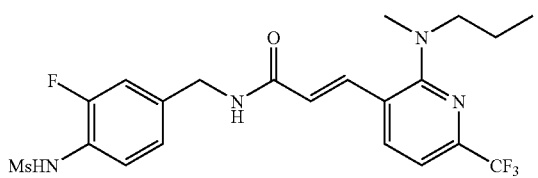

N-(4-Aminomethyl-2-fluoro-phenyl)-methanesulfonamide, HCl salt (53 mg, 0.21 mmol) was reacted with 3-[2-(methyl-propyl-amino)-6-trifluoromethyl-pyridin-3-yl]-acrylic acid (50 mg, 0.18 mmol) to give the title compound (62 mg, 71%) after purification by column chromatography (Hex/EtOAc=2/3).

$^1$H NMR (300 MHz, DMSO-d6): δ 9.56 (bs, 1H), 8.75 (t, 1H), 8.17 (d, 1H), 7.92 (d, 1H, J=7.2 Hz), 7.49 (d, 1H, J=15.6 Hz), 7.20 (m, 4H), 6.63 (d, 1H, J=15.6 Hz), 4.39 (d, 2H, J=5.1 Hz), 3.21 (m, 2H), 3.00 (s, 3H), 2.91 (s, 3H), 1.63 (m, 2H), 0.81 (t, 3H, J=4.8 Hz).

EXAMPLE 159

N-(3-Ethynyl-5-fluoro-4-methanesulfonylamino-benzyl)-3-[2-(N-methyl-N-propyl-amino)-6-trifluoromethyl-pyridin-3-yl]-acrylamide

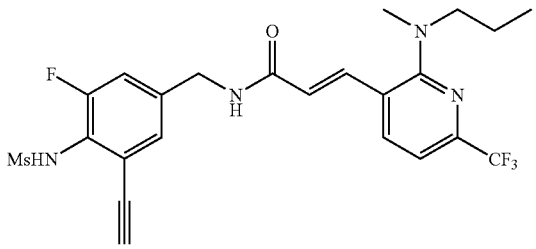

N-(4-Aminomethyl-6-ethynyl-2-fluoro-phenyl)-methanesulfonamide, HCl salt (93 mg, 0.33 mmol) was reacted with 3-[2-(methyl-propyl-amino)-6-trifluoromethyl-pyridin-3-yl]-acrylic acid (80 mg, 0.28 mmol) to give the title compound (96 mg, 57%) after purification by column chromatography (Hex/EtOAc=2/3).

$^1$H NMR (300 MHz, DMSO-d6): δ 9.46 (bs, 1H), 8.78 (t, 1H, J=5.3 Hz), 7.93 (d, 1H, J=7.5 Hz), 7.49 (d, 1H, J=15.6 Hz), 7.28 (m, 3H), 6.63 (d, 1H, J=15.6 Hz), 4.51 (s, 1H), 4.40 (d, 2H, J=5.7 Hz), 3.21 (m, 2H), 3.07 (s, 3H), 2.91 (s, 3H), 1.63 (m, 2H), 0.81 (t, 3H, J=7.5 Hz).

EXAMPLE 161

N-(3-Ethynyl-5-fluoro-4-methanesulfonylamino-benzyl)-3-(2-ethoxymethyl-6-trifluoromethyl-pyridin-3-yl)-acrylamide

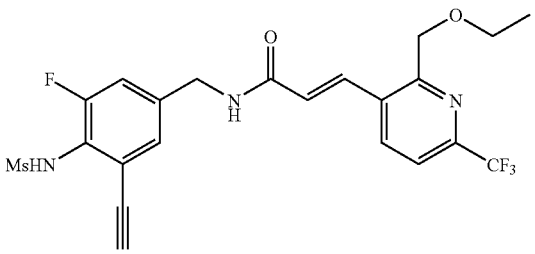

N-(4-Aminomethyl-6-ethynyl-2-fluoro-phenyl)-methanesulfonamide, HCl salt (140 mg, 0.50 mmol) was reacted with 3-(2-ethoxymethyl-6-trifluoromethyl-pyridin-3-yl)-acrylic acid (125 mg, 0.45 mmol) to give the title compound (141 mg, 63%) after purification by column chromatography (Hex/EtOAc=1/2).

$^1$H NMR (300 MHz, DMSO-d6+CDCl$_3$): δ 8.41 (s, 1H), 8.20 (t, 1H), 8.01 (d, 1H, J=7.8 Hz), 7.94 (d, 1H, J=15.6 Hz), 7.61 (d, 1H, J=8.1 Hz), 7.27 (s, 1H), 7.14 (d, 1H, J=10.2 Hz), 6.51 (d, 1H, J=15.6 Hz), 4.71 (s, 2H), 4.4 (d, 2H, J=5.7 Hz), 3.60 (q, 2H, J=6.9 Hz), 3.11 (s, 3H), 1.19 (t, 3H, J=6.9 Hz).

EXAMPLE 160

N-(3-Fluoro-4-methanesulfonylamino-benzyl)-3-(2-ethoxymethyl-6-trifluoromethyl-pyridin-3-yl)-acrylamide

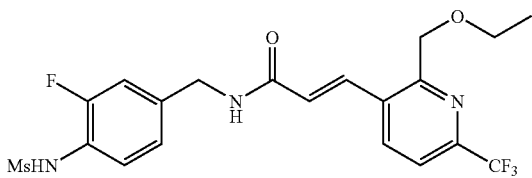

N-(4-Aminomethyl-2-fluoro-phenyl)-methanesulfonamide, HCl salt (53 mg, 0.21 mmol) was reacted with 3-(2-ethoxymethyl-6-trifluoromethyl-pyridin-3-yl)-acrylic acid (52 mg, 0.19 mmol) similarly prepared as above to give the title compound (53 mg, 59%) after purification by column chromatography (Hex/EtOAc=1/2).

$^1$H NMR (300 MHz, DMSO-d6+CDCl$_3$): δ 8.03 (m, 2H), 7.86 (t, 1H), 7.65 (d, 1H, J=7.8 Hz), 7.46 (t, 1H, J=7.8 Hz), 7.13 (m, 2H), 6.64 (d, 1H, J=15.3 Hz), 4.77 (s, 2H), 4.52 (d, 2H, J=5.7 Hz), 3.66 (q, 2H, J=6.9 Hz), 3.01 (s, 3H), 1.25 (t, 3H, J=6.9 Hz).

EXAMPLE 162

3-(2-sec-Butoxy-6-trifluoromethyl-pyridin-3-yl)-N-(4-methane sulfonylamino-3-methyl-benzyl)-acrylamide

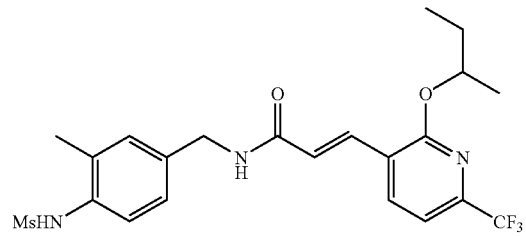

N-(4-Aminomethyl-2-methyl-phenyl)-methanesulfonamide, HCl salt (43 mg, 0.156 mmol) was reacted with NMM (0.1 ml), DMTMM (44 mg) and 3-(2-sec-butoxy-6-trifluoromethyl-pyridin-3-yl)-acrylic acid (42 mg) to give the title compound (52.7 mg, 75%) after purification by column chromatography (Hex/EtOAc=2/3).

$^1$H NMR (300 MHz, CDCl$_3$): δ 7.80 (d, 1H, J=7.8 Hz), 7.75 (d, 1H, J=16.2 Hz), 7.41 (d, 2H, J=8.1 Hz), 7.21 (m, 3H), 6.70 (d, 2H, J=15.6 Hz), 6.19 (s, 1H), 5.95 (t, 1H), 4.53 (d, 2H, J=6.0 Hz), 3.02 (s, 3H), 2.32 (s, 3H), 1.75 (m, 2H), 1.36 (d, 3H, J=6.0 Hz), 0.97 (t, 3H, J=7.2 Hz).

EXAMPLE 163

N-(3-Cyano-5-fluoro-4-methanesulfonylamino-benzyl)-3-(2-isobutyl-6-trifluoromethyl-pyridin-3-yl)-acrylamide

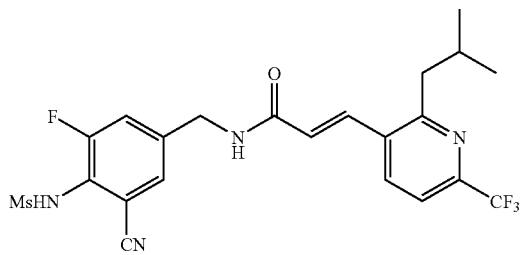

N-(4-Aminomethyl-6-cyano-2-fluoro-phenyl)-methanesulfonamide, HCl salt (101 mg, 0.36 mmol) was reacted with 3-(2-isobutyl-6-trifluoromethyl-pyridin-3-yl)-acrylic acid (82 mg, 0.30 mmol) to give the title compound (102 mg, 68%) after purification by crystallization from methylene chloride.

$^1$H NMR (300 MHz, DMSO-d6): δ 8.78 (t, 1H), 8.04 (d, 1H, J=8.4 Hz), 7.81 (m, 2H), 7.60 (d, 1H, J=7.8 Hz), 7.53 (s, 1H), 7.47 (d, 1H, J=10.2 Hz), 6.67 (d, 1H, J=15.6 Hz), 4.51 (d, 2H, J=5.4 Hz), 3.12 (s, 3H), 2.86 (d, 2H, J=7.5 Hz), 2.15 (m, 1H), 0.93 (d, 6H, J=6.6 Hz).

EXAMPLE 164

N-(3-Fluoro-4-methanesulfonylamino-5-methyl-benzyl)-3-(2-isobutyl-6-trifluoromethyl-pyridin-3-yl)-acrylamide

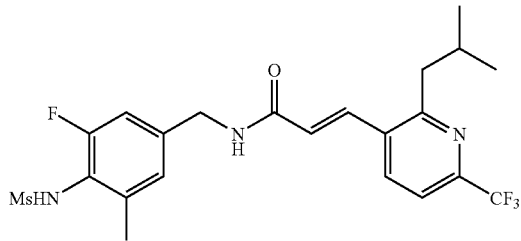

N-(4-Aminomethyl-2-fluoro-6-methyl-phenyl)-methanesulfonamide, HCl salt (89 mg, 0.33 mmol) was reacted with 3-(2-isobutyl-6-trifluoromethyl-pyridin-3-yl)-acrylic acid (82 mg, 0.30 mmol) to give the title compound (116 mg, 79%) after purification by column chromatography (Hex/EtOAc=1/2).

$^1$H NMR (300 MHz, DMSO-d6): δ 9.30 (bs, 1H), 8.78 (t, 1H), 8.15 (d, 1H, J=8.4 Hz), 7.79 (d, 1H, J=8.1 Hz), 7.70 (d, 1H, J=15.6 Hz), 7.13 (m, 2H), 6.74 (d, 1H, J=15.6 Hz), 4.42 (d, 2H, J=5.7 Hz), 2.97 (s, 3H), 2.82 (d, 2H, J=7.2 Hz), 2.20 (d, 3H, J=2.1 Hz), 2.10 (m, 1H), 0.88 (d, 6H, J=6.6 Hz).

ESI [M+H]+: 488

EXAMPLE 165

(R)—N-[1-(3-Fluoro-4-methanesulfonylamino-phenyl)-ethyl]-3-[2-(methyl-phenylamino)-6-trifluoromethyl-pyridin-3-yl]-acrylamide

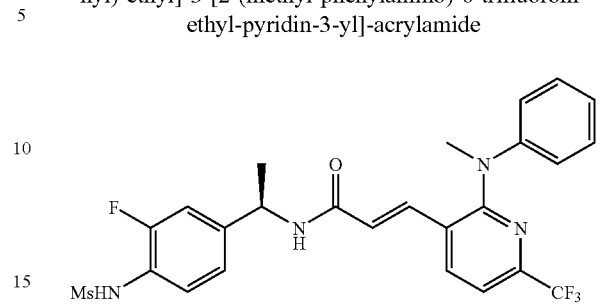

(R)—N-[4-(1-Amino-ethyl)-2-fluoro-phenyl]-methanesulfonamide, HCl salt (46 mg, 0.17 mmol) was reacted with 2-methyl-phenylamino-6-trifluoromethyl-pyridin-3-yl-acrylic acid (55 mg, 0.17 mmol) to give the title compound (45 mg, 49%) after purification by column chromatography (Hex/EtOAc=3/2).

$^1$H NMR (300 MHz, CDCl$_3$): δ 7.66 (m, 1H), 7.53 (m, 1H), 7.23 (m, 4H), 7.03 (m, 4H), 6.89 (d, 1H, J=15.9 Hz), 6.47 (bs, 1H), 6.03 (d, 1H, J=16.2 Hz), 5.16 (d, 1H, J=7.5 Hz), 5.00 (q, 1H, J=7.2 Hz), 3.53 (s, 3H), 3.04 (s, 3H), 1.40 (d, 3H, J=6.9 Hz)

EXAMPLE 166

N-(3-Ethynyl-5-fluoro-4-methanesulfonylamino-benzyl)-3-[2-(methyl-phenylamino)-6-trifluoromethyl-pyridin-3-yl]-acrylamide

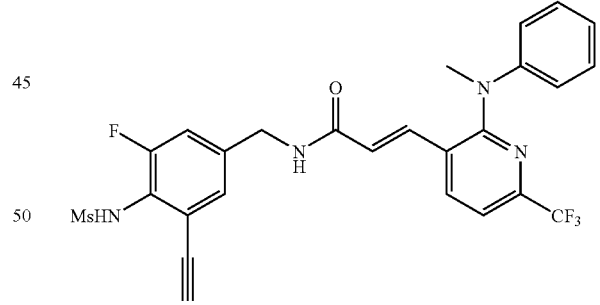

N-(4-Aminomethyl-6-ethynyl-2-fluoro-phenyl)-methanesulfonamide, HCl salt (47 mg, 0.17 mmol) was reacted with 3-(2-methyl-phenylamino-6-trifluoromethyl-pyridin-3-yl)-acrylic acid (55 mg, 0.17 mmol) to give the title compound (30 mg, 32%) after purification by column chromatography (Hex/EtOAc=1:1).

$^1$H NMR (300 MHz, CDCl$_3$): δ 7.65 (m, 1H), 7.20 (m, 4H), 7.00 (m, 5H), 6.43 (bs, 1H), 6.02 (d, 1H, J=16.2 Hz), 5.31 (bs, 1H), 4.32 (d, 2H, J=6.0 Hz), 3.52 (s, 3H), 3.48 (s, 1H), 3.29 (s, 3H)

ESI [M+H]+: 547

EXAMPLE 167

N-(4-methanesulfonylamino-3-methyl-benzyl)-3-[2-(methyl-phenylamino)-6-trifluoromethyl-pyridin-3-yl]-acrylamide

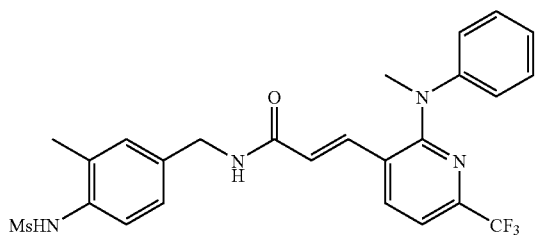

N-(4-Aminomethyl-3-methyl-phenyl)-methanesulfonamide, HCl salt (46 mg, 0.17 mmol) was reacted with 3-(2-methyl-phenylamino-6-trifluoromethyl-pyridin-3-yl)-acrylic acid (55 mg, 0.17 mmol) to give the title compound (32 mg, 36%) after purification by column chromatography (Hex/EtOAc=2/3).

$^1$H NMR (300 MHz, CDCl$_3$): δ 7.66 (m, 1H), 7.42 (m, 1H), 7.08 (m, 9H), 6.18 (bs, 1H), 6.05 (d, 1H, J=16.2 Hz), 5.25 (bs, 1H), 4.31 (d, 2H, J=5.7 Hz), 3.51 (s, 3H), 3.04 (s, 3H), 2.33 (s, 3H)

EXAMPLE 168

3-(2-Butoxy-6-trifluoromethyl-pyridin-3-yl)-N-(3-fluoro-4-methane sulfonylamino-5-trifluoromethyl-benzyl)-acrylamide

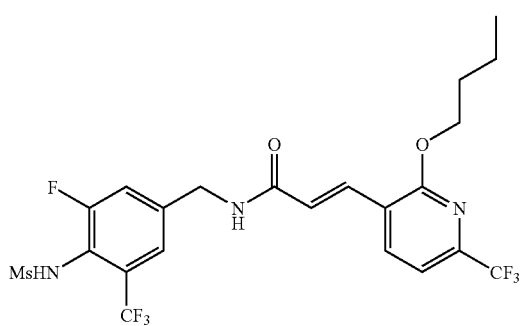

N-(4-Aminomethyl-2-fluoro-6-trifluoromethyl-phenyl)-methanesulfonamide, HCl salt (68 mg, 0.21 mmol) was reacted with 3-(2-butoxy-6-trifluoromethyl-pyridin-3-yl)-acrylic acid (51 mg, 0.17 mmol) to give 3-(2-butoxy-6-trifluoromethyl-pyridin-3-yl)-N-(3-fluoro-4-methanesulfonylamino-5-trifluoromethyl-benzyl)-acrylamide (80 mg, 68%).

$^1$H NMR (300 MHz, CDCl$_3$): δ 7.82 (d, 1H, J=7.5 Hz), 7.76 (d, 1H, J=15.9 Hz), 7.40-7.23 (m, 3H), 6.76 (d, 1H, J=15.6 Hz), 6.37-6.34 (m, 2H), 4.57 (d, 2H, J=6.0 Hz), 4.48-4.44 (m, 2H), 3.27 (s, 3H), 1.83-1.76 (m, 2H), 1.51-1.44 (m, 2H), 0.97 (t 3H, J=7.5 Hz).

EXAMPLE 169

(R)-3-(2-Butoxy-6-trifluoromethyl-pyridin-3-yl)-N-[1-(3-fluoro-4-methanesulfonylamino-phenyl)-ethyl]-acrylamide

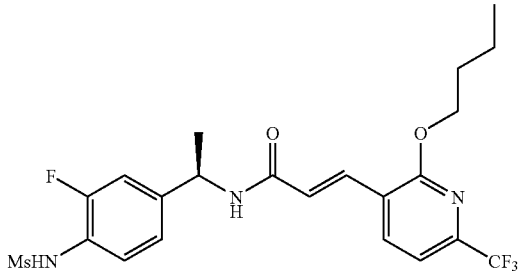

(R)—N-[4-(1-Amino-ethyl)-2-fluoro-phenyl]-methanesulfonamide, HCl salt (57 mg, 0.21 mmol) was reacted with 3-(2-butoxy-6-trifluoromethyl-pyridin-3-yl)-acrylic acid (51 mg, 0.17 mmol) to give (R)-3-(2-butoxy-6-trifluoromethyl-pyridin-3-yl)-N-[1-(3-fluoro-4-methanesulfonylamino-phenyl)-ethyl]-acrylamide (57 mg, 54%).

$^1$H NMR (300 MHz, CDCl$_3$): δ 7.80 (d, 1H, J=7.5 Hz), 7.73 (d, 1H, J=15.6 Hz), 7.24 (d, 1H, J=8.4 Hz), 7.16 (d, 2H, J=9.6 Hz), 6.69 (d, 1H, J=15.9 Hz), 6.53 (s, 1H), 5.87 (d, 1H, J=7.5 Hz), 5.24-5.19 (m, 1H), 4.46 (t, 2H, J=6.9 Hz), 3.02 (s, 3H), 1.86-1.76 (m, 2H), 1.56-1.45 (m, 5H), 0.9 (t 3H, J=7.5 Hz).

EXAMPLE 170

3-(2-Butoxy-6-trifluoromethyl-pyridin-3-yl)-N-(4-methane sulfonylamino-3-methyl-benzyl)-acrylamide

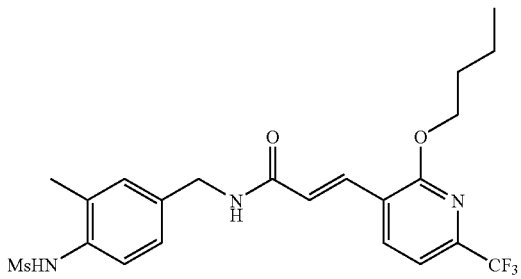

N-(4-Aminomethyl-2-methyl-phenyl)-methanesulfonamide, HCl salt (58 mg, 0.21 mmol) was reacted with 3-(2-butoxy-6-trifluoromethyl-pyridin-3-yl)-acrylic acid (51 mg, 0.17 mmol) to give 3-(2-butoxy-6-trifluoromethyl-pyridin-3-yl)-N-(4-methanesulfonylamino-3-methyl-benzyl)-acrylamide (58 mg, 57%).

$^1$H NMR (300 MHz, CDCl$_3$): δ 7.76 (d, 1H, J=9.9 Hz), 7.71 (d, 1H, J=16.5 Hz), 7.35 (dd, 1H, J=5.7, 2.4 Hz), 7.21-7.11 (m, 3H), 6.68 (dd, 1H, J=13.4, 2.7 Hz), 6.28 (s, 1H), 6.00 (s, 1H), 4.49-4.38 (m, 4H), 2.96 (s, 3H), 2.26 (s, 3H), 1.79-1.74 (m, 2H), 1.47-1.40 (m, 2H), 0.92 (t, 3H, J=7.2 Hz).

EXAMPLE 171

3-(2-Ethylthio-6-trifluoromethyl-pyridin-3-yl)-N-(3-ethynyl-5-fluoro-4-methanesulfonylamino-benzyl)-acrylamide

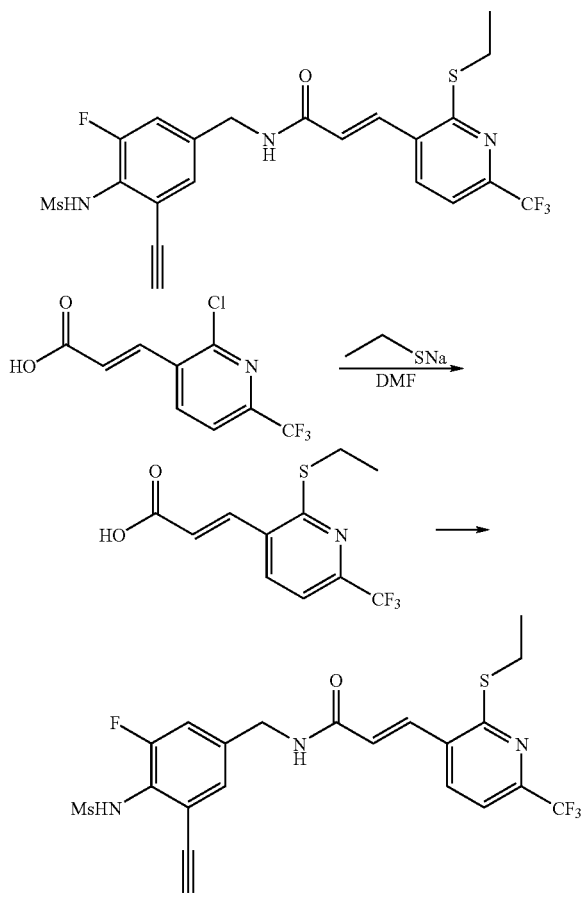

Step 1: 3-(2-Ethylthio-6-trifluoromethyl-pyridin-3-yl)-acrylic acid 3-(2-Chloro-6-trifluoromethyl-pyridin-3-yl)-acrylic acid (214 mg, 0.850 mmol) and sodium methoxide (95 mg, 1.13 mmol) were added in microwave vial. The vial was irradiated in a Biotage synthesizer at 200° C. for 10 min. The reaction mixture was purified to yield the title compound (15 mg) (Hex/EtOAc=5/1).

$^1$H NMR (300 MHz, CDCl$_3$): δ 7.92 (d, 1H), 7.75 (d, 1H), 7.25 (d, 1H), 6.38 (d, 1H), 3.23 (q, 2H), 1.37 (t, 3H).

Step 2: 3-(2-Ethylthio-6-trifluoromethyl-pyridin-3-yl)-N-(3-ethynyl-5-fluoro-4-methanesulfonylamino-benzyl)-acrylamide N-(4-Aminomethyl-2-fluoro-6-ethynyl-phenyl)-methanesulfonamide, HCl salt (67 mg, 0.240 mmol) was reacted with NI (0.2 ml), DMTMM (65 mg) and 3-(2-ethylthio-6-trifluoromethyl-pyridin-3-yl)-acrylic acid (56 mg, 0.200 mmol) to give the title compound (22 mg, 21%) after purification by column chromatography (Hex/EtOAc=2/3).

$^1$H NMR (300 MHz, CDCl$_3$): δ 7.92 (d, 1H, J=7.5 Hz), 7.75 (d, 1H, J=15.3 Hz), 7.50 (d, 1H, J=7.5 Hz), 7.28 (d, 1H, J=7.8 Hz), 7.08 (m, 1H), 6.44 (d, 1H, J=15.6 Hz), 6.37 (t, 1H), 4.44 (d, 2H, J=5.7 Hz), 3.40 (s, 1H), 3.21 (t, 2H, J=7.2 Hz), 3.02 (s, 3H), 1.32 (t, 3H, J=7.2 Hz).

EXAMPLE 172

N-(4-Methanesulfonylamino-3-methyl-benzyl)-3-(2-phenethyl-6-trifluoromethyl-pyridin-3-yl)-acrylamide

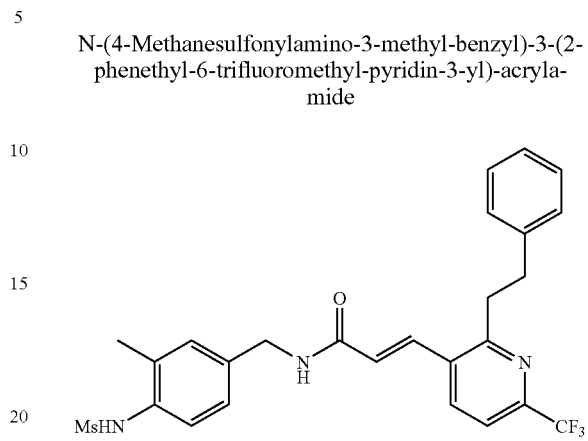

N-(4-Aminomethyl-2-methyl-phenyl)-methanesulfonamide, HCl salt (57.8 mg, 0.210 mmol) was reacted with NMM (0.15 ml), DMTMM (64.8 mg) and 3-(2-phenethyl-6-trifluoromethyl-pyridin-3-yl)-acrylic acid (76 mg, 0.236 mmol) to give the title compound (61.5 mg, 57%) after purification by column chromatography (Hex/EtOAc=1/2).

$^1$H NMR (300 MHz, CDCl$_3$): δ 7.83 (d, 1H, J=8.7 Hz), 7.79 (d, 1H, J=15.6 Hz), 7.51 (d, 1H, J=8.4 Hz), 7.41 (d, 1H, J=8.4 Hz), 7.20 (m, 5H), 6.30 (s, 1H), 6.25 (d, 1H, J=15.3 Hz), 5.99 (t, 1H), 4.51 (d, 2H, J=6.0 Hz), 3.28 (t, 2H, J=8.4 Hz), 3.06 (t, 2H, J=8.4 Hz), 3.01 (s, 3H).

ESI [M+H]+: 518

EXAMPLE 173

N-(3-Fluoro-4-methanesulfonylamino-5-methyl-benzyl)-3-(2-phenethyl-6-trifluoromethyl-pyridin-3-yl)-acrylamide

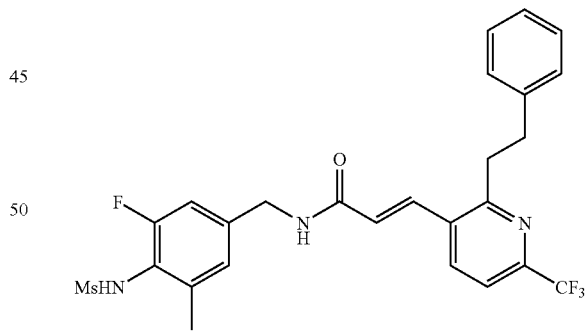

N-(4-Aminomethyl-2-fluoro-6-methyl-phenyl)-methanesulfonamide, HCl salt (56 mg, 0.208 mmol) was reacted with NMM (0.15 ml), DMTMM (62.4 mg) and 3-(2-phenethyl-6-trifluoromethyl-pyridin-3-yl)-acrylic acid (74 mg, 0.230 mmol) to give the title compound (62 mg, 56%) after purification by column chromatography (Hex/EtOAc=2/3).

$^1$H NMR (300 MHz, CDCl$_3$): δ 7.82 (d, 1H, J=8.1 Hz), 7.76 (d, 1H, J=15.6 Hz), 7.50 (d, 1H, J=7.8 Hz), 7.20 (m, 6H), 6.62 (s, 1H), 6.25 (d, 1H, J=15.6 Hz), 6.18 (t, 1H), 4.55 (d, 2H, J=5.4 Hz), 3.26 (t, 2H, J=8.4 Hz), 3.05 (t, 2H, J=8.4 Hz), 3.01 (s, 3H), 2.23 (d, 3H, J=2.1 Hz).

EXAMPLE 174

3-(2-Isobutyl-6-trifluoromethyl-pyridin-3-yl)-N-(4-methane sulfonylamino-3-methyl-benzyl)-acrylamide

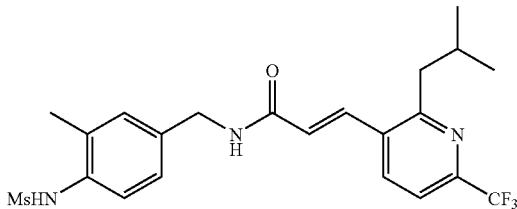

N-(4-Aminomethyl-2-methyl-phenyl)-methanesulfonamide, HCl salt (47 mg, 0.17 mmol) was reacted with 3-(2-isobutyl-6-trifluoromethyl-pyridin-3-yl)-acrylic acid (41 mg, 0.15 mmol) to give the title compound (68 mg, 96%) after purification by column chromatography (Hex/EtOAc=2/3).

$^1$H NMR (300 MHz, DMSO-d6): δ 9.05 (bs, 1H), 8.78 (t, 1H, J=6.0 Hz), 8.16 (d, 1H, J=7.8 Hz), 7.78 (d, 1H, J=8.1 Hz), 7.71 (d, 1H, J=15.6 Hz), 7.17 (m, 3H), 6.74 (d, 1H, J=15.6 Hz), 4.36 (d, 2H, J=5.7 Hz), 2.95 (s, 3H), 2.83 (d, 2H, J=6.9 Hz), 2.29 (s, 3H), 2.10 (m, 1H), 0.89 (d, 6H, J=6.6 Hz).

ESI [M+H]+: 470

EXAMPLE 175

(R)—N-[1-(3-Fluoro-4-methanesulfonylamino-phenyl)-ethyl]-3-(2-isobutyl-6-trifluoromethyl-pyridin-3-yl)-acrylamide

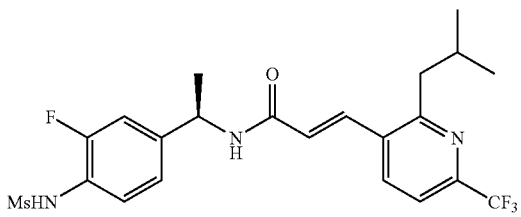

(R)—N-[4-(1-Aminoethyl)-2-fluoro-phenyl]-methanesulfonamide, HCl salt (44 mg, 0.17 mmol) was reacted with 3-(2-isobutyl-6-trifluoromethyl-pyridin-3-yl)-acrylic acid (41 mg, 0.15 mmol) to give the title compound (47 mg, 64%) after purification by column chromatography (Hex/EtOAc=2/3).

$^1$H NMR (300 MHz, DMSO-d6): δ 9.56 (bs, 1H), 8.78 (d, 1H, J=8.1 Hz), 8.16 (d, 1H, J=8.1 Hz), 7.80 (d, 1H, J=8.1 Hz), 7.67 (d, 1H, J=15.6 Hz), 7.17 (m, 3H), 6.74 (d, 1H, J=15.6 Hz), 5.03 (t, 1H, J=7.2 Hz), 3.00 (s, 3H), 2.81 (d, 2H, J=7.2 Hz), 2.01 (m, 1H), 1.41 (d, 3H, J=7.2 Hz), 0.88 (dd, 6H, J=2.1 and 6.6 Hz).

ESI [M+H]+: 488

EXAMPLE 176

3-(2-sec-Butylamino-6-trifluoromethyl-pyridin-3-yl)-N-(4-methane sulfonylamino-3-methyl-benzyl)-acrylamide

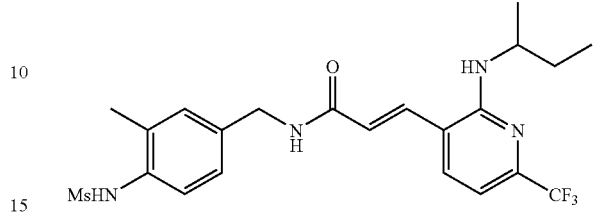

N-(4-Aminomethyl-2-methyl-phenyl)-methanesulfonamide, HCl salt (60 mg, 0.22 mmol) was reacted with 3-(2-sec-butylamino-6-trifluoromethyl-pyridin-3-yl)-acrylic acid (58 mg, 0.20 mmol) to give the title compound (85 mg, 88%) after purification by column chromatography (Hex/EtOAc=2/3).

$^1$H NMR (300 MHz, DMSO-d6): δ 9.04 (bs, 1H), 8.65 (t, 1H, J=6.0 Hz), 7.76 (d, 1H, J=7.8 Hz), 7.63 (d, 1H, J=15.3 Hz), 7.17 (m, 3H), 6.94 (d, 1H, J=7.5 Hz), 6.79 (d, 1H, J=7.5 Hz), 6.61 (d, 1H, J=15.3 Hz), 4.35 (d, 2H, J=5.7 Hz), 4.07 (m, 1H), 2.94 (s, 3H), 2.28 (s, 3H), 1.55 (m, 2H), 1.14 (d, 3H, J=6.6 Hz), 0.85 (t, 3H, J=7.5 Hz).

ESI [M+H]+: 485

EXAMPLE 177

N-(3-Ethynyl-5-fluoro-4-methanesulfonylamino-benzyl)-3-(2-isopropylthio-6-trifluoromethyl-pyridin-3-yl)-acrylamide

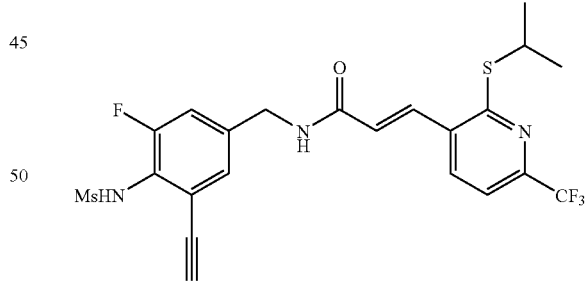

N-(4-Aminomethyl-2-fluoro-6-ethynyl-phenyl)-methanesulfonamide, HCl salt (53 mg, 0.190 mmol) was reacted with NMM (0.15 ml), DMTMM (62 mg) and 3-(2-isopropylthio-6-trifluoromethyl-pyridin-3-yl)-acrylic acid (51 mg, 0.175 mmol) to give the title compound (65 mg, 72%) after purification by column chromatography (Hex/EtOAc=2/3).

$^1$H NMR (300 MHz, CDCl$_3$): δ 7.80 (d, 1H, J=15.9 Hz), 7.74 (d, 1H, J=7.5 Hz), 7.34 (d, 1H, J=8.1 Hz), 7.29 (m, 1H), 7.15 (dd, 1H, J=2.1 and 10.8 Hz), 6.45 (d, 1H, J=15.9 Hz), 6.42 (s, 1H), 6.16 (t, 1H), 4.52 (d, 2H, J=6.3 Hz), 4.14 (m, 1H), 3.48 (s, 1H), 3.27 (s, 3H), 1.43 (d, 6H, J=6.6 Hz).

EXAMPLE 178

N-(3-Fluoro-4-methanesulfonylamino-benzyl)-3-(2-isopropylthio-6-trifluoromethyl-pyridin-3-yl)-acrylamide

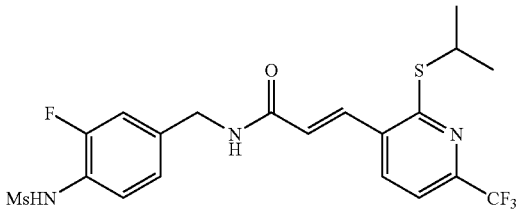

Step 1: 3-(2-Isopropylthio-6-trifluoromethyl-pyridin-3-yl)-acrylic acid 3-(2-Chloro-6-trifluoromethyl-pyridin-3-yl)-acrylic acid (245 mg, 0.974 mmol) was reacted with 2-propanthiol (240 mg, 3.15 mmol) and sodium hydride (143 mg, 3.56 mmol) to afford the title compound (103 mg) after purification by column chromatography (Hex/EtOAc=2.5/1).

$^1$H NMR (300 MHz, CDCl$_3$): δ 7.98 (d, 1H, J=15.9 Hz), 7.82 (d, 1H, J=7.8 Hz), 7.37 (d, 1H, J=8.1 Hz), 6.46 (d, 1H, J=15.6 Hz), 4.13 (m, 1H), 1.44 (d, 6H, J=6.9 Hz).

Step 2: N-(3-Fluoro-4-methanesulfonylamino-benzyl)-3-(2-isopropylthio-6-trifluoromethyl-pyridin-3-yl)-acrylamide N-(4-Aminomethyl-2-fluoro-phenyl)-methanesulfonamide, HCl salt (37 mg, 0.145 mmol) was reacted with NMM (0.15 ml), DMTMM (39 mg) and 3-(2-isopropylthio-6-trifluoromethyl-pyridin-3-yl)-acrylic acid (31 mg, 0.106 mmol) to give the title compound (49 mg, 94%) after purification by column chromatography (Hex/EtOAc=2/3).

$^1$H NMR (300 MHz, CDCl$_3$): δ 7.80 (d, 1H, J=15.6 Hz), 7.72 (d, 1H, J=7.5 Hz), 7.53 (t, 1H, J=8.1 Hz), 7.34 (d, 1H, J=7.5 Hz), 7.16 (d, 1H, J=10.2 Hz), 7.12 (d, 1H, J=8.4 Hz), 6.52 (s, 1H), 6.45 (d, 1H, J=15.6 Hz), 6.10 (t, 1H), 4.55 (d, 2H, J=6.0 Hz), 4.11 (m, 1H), 3.03 (s, 3H), 1.43 (d, 6H, J=6.9 Hz)

EXAMPLE 179

N-(3-Fluoro-4-methanesulfonylamino-benzyl)-3-[2-(3-fluoro-phenyl)-6-trifluoromethyl-pyridin-3-yl]-acrylamide

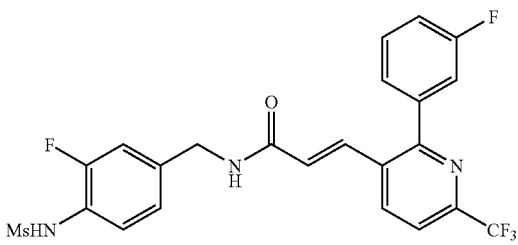

N-(4-Aminomethyl-2-fluoro-phenyl)-methanesulfonamide, HCl salt (49 mg, 0.19 mmol) was reacted with 3-[2-(3-fluoro-phenyl)-6-trifluoromethyl-pyridin-3-yl]-acrylic acid (50 mg, 0.16 mmol) to give N-(3-fluoro-4-methanesulfonylamino-benzyl)-3-[2-(3-fluoro-phenyl)-6-trifluoromethyl-pyridin-3-yl]-acrylamide (58 mg, 71%).

$^1$H NMR (300 MHz, DMSO): δ 9.57 (s, 1H, br), 8.84 (t, 1H, J=5.7 Hz), 8.38 (d, 1H, J=7.8 Hz), 8.02 (d, 1H, J=7.8 Hz), 7.61-7.56 (m, 1H), 7.45-7.31 (m, 5H), 7.18 (d, 1H, J=11.1 Hz), 7.10 (d, 1H, J=8.1 Hz), 6.83 (d, 1H, J=15.6 Hz), 4.36 (d, 2H, J=5.7 Hz), 3.00 (s, 3H).

EXAMPLE 180

N-(3-Fluoro-4-methanesulfonylamino-5-methyl-benzyl)-3-[2-(3-fluoro-phenyl)-6-trifluoromethyl-pyridin-3-yl]-acrylamide

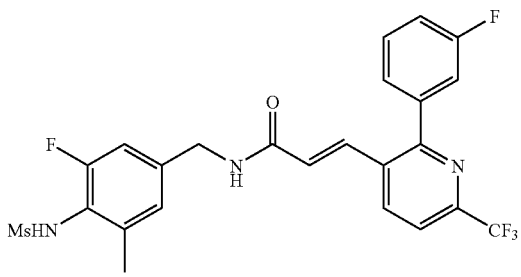

N-(4-Aminomethyl-2-fluoro-6-methyl-phenyl)-methanesulfonamide, HCl salt (51 mg, 0.19 mmol) was reacted with 3-[2-(3-fluoro-phenyl)-6-trifluoromethyl-pyridin-3-yl]-acrylic acid (50 mg, 0.16 mmol) to give N-(3-fluoro-4-methanesulfonylamino-5-methyl-benzyl)-3-[2-(3-fluoro-phenyl)-6-trifluoromethyl-pyridin-3-yl]-acrylamide (47 mg, 56%).

$^1$H NMR (300 MHz, DMSO): δ 9.28 (s, 1H, br), 8.80 (t, 1H, J=6.0 Hz), 8.36 (d, 1H, J=8.4 Hz), 8.01 (d, 1H, J=8.4 Hz), 7.59 (dd, 1H, J=7.8, 5.7 Hz), 7.43-7.34 (m, 4H), 7.19-7.09 (m, 2H), 6.83 (d, 1H, J=15.6 Hz), 4.37 (d, 2H, J=5.4 Hz), 2.98 (s, 3H), 2.20 (s, 3H).

EXAMPLE 181

(R)—N-[1-(3-Fluoro-4-methanesulfonylamino-phenyl)-ethyl]-3-[2-(3-fluoro-phenyl)-6-trifluoromethyl-pyridin-3-yl]-acrylamide

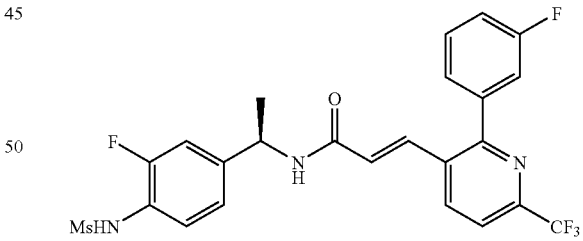

(R)—N-[4-(1-Amino-ethyl)-2-fluoro-phenyl]-methanesulfonamide, HCl salt (51 mg, 0.19 mmol) was reacted with 3-[2-(3-fluoro-phenyl)-6-trifluoromethyl-pyridin-3-yl]-acrylic acid (50 mg, 0.16 mmol) to give (R)—N-[1-(3-fluoro-4-methanesulfonylamino-phenyl)-ethyl]-3-[2-(3-fluoro-phenyl)-6-trifluoromethyl-pyridin-3-yl]-acrylamide (54 mg, 64%).

$^1$H NMR (300 MHz, CDCl$_3$): δ 8.07 (d, 1H, J=8.1 Hz), 7.72 (d, 1H, J=15.3 Hz), 7.70 (d, 1H, J=8.1 Hz), 7.56-7.41 (m, 2H), 7.35-7.30 (m, 2H), 7.19-7.15 (m, 3H), 6.48 (s, 1H), 6.45 (d, 1H, J=15.3 Hz), 5.87 (d, 1H, J=7.5 Hz), 5.20-5.15 (m, 1H), 3.02 (s, 3H), 1.54 (d, 3H, J=7.2 Hz).

EXAMPLE 182

3-[2-(3-Fluoro-phenyl)-6-trifluoromethyl-pyridin-3-yl]-N-(4-methanesulfonylamino-3-methyl-benzyl)-acrylamide

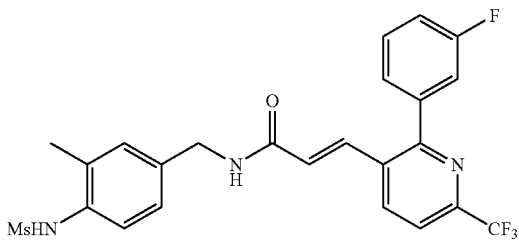

N-(4-Aminomethyl-2-methyl-phenyl)-methanesulfonamide, HCl salt (53 mg, 0.19 mmol) was reacted 3-[2-(3-Fluoro-phenyl)-6-trifluoromethyl-pyridin-3-yl]-acrylic acid (50 mg, 0.16 mmol) to give 3-[2-(3-fluoro-phenyl)-6-trifluoromethyl-pyridin-3-yl]-N-(4-methanesulfonylamino-3-methyl-benzyl)-acrylamide (48 mg, 59%).

$^1$H NMR (300 MHz, CDCl$_3$): δ 8.06 (d, 1H, J=8.1 Hz), 7.75 (d, 1H, J=15.3 Hz), 7.79 (d, 1H, J=8.1 Hz), 7.50-7.33 (m, 3H), 7.26-7.20 (m, 3H), 6.44 (d, 1H, J=15.0 Hz), 6.15 (s, 1H), 5.93 (s, 1H), 4.51 (d, 2H, J=5.7 Hz), 3.03 (s, 3H), 2.31 (s, 3H).

EXAMPLE 183

(R)—N-[1-(3-Fluoro-4-methanesulfonylamino-phenyl)-ethyl]-3-(2-piperid-1-yl-6-trifluoromethyl-pyridin-3-yl)-acrylamide

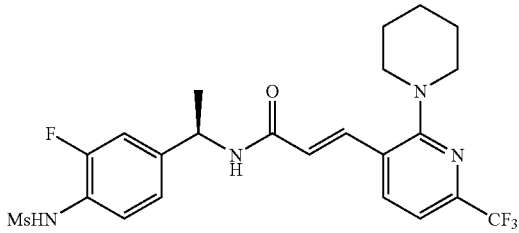

(R)—N-[4-(1-Amino-ethyl)-2-fluoro-phenyl]-methanesulfonamide, HCl salt (54 mg, 0.19 mmol) was reacted with 3-(2-piperid-1-yl-6-trifluoromethyl-pyridin-3-yl)-acrylic acid (50 mg, 0.16 mmol) to give (R)—N-[1-(3-fluoro-4-methanesulfonylamino-phenyl)-ethyl]-3-(2-piperid-1-yl-6-trifluoromethyl-pyridin-3-yl)-acrylamide (54 mg, 64%).

$^1$H NMR (300 MHz, CDCl$_3$): δ 7.71 (d, 1H, J=8.1 Hz), 7.66 (d, 1H, J=15.6 Hz), 7.52 (d, 1H, J=8.1 Hz), 7.17-7.12 (m, 3H), 6.56 (s, 1H), 6.42 (d, 1H, J=15.6 Hz), 5.92 (d, 1H, J=7.5 Hz), 5.24-5.19 (m, 1H), 3.29-3.26 (m, 4H), 3.03 (s, 3H), 1.70-1.64 (m, 6H), 1.54 (d, 3H, J=7.2 Hz).

EXAMPLE 184

N-(4-Methanesulfonylamino-3-methyl-benzyl)-3-(2-piperid-1-yl-6-trifluoromethyl-pyridin-3-yl)-acrylamide

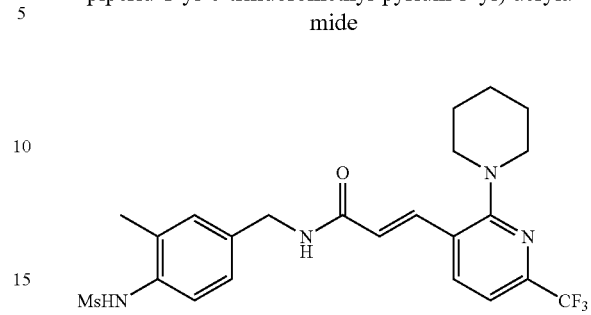

N-(4-Aminomethyl-2-methyl-phenyl)-methanesulfonamide, HCl salt (55 mg, 0.19 mmol) was reacted with 3-(2-piperid-1-yl-6-trifluoromethyl-pyridin-3-yl)-acrylic acid (50 mg, 0.16 mmol) to give 3 N-(4-methanesulfonylamino-3-methyl-benzyl)-3-(2-piperid-1-yl-6-trifluoromethyl-pyridin-3-yl)-acrylamide (33 mg, 40%).

$^1$H NMR (300 MHz, CDCl$_3$): δ 7.72-7.67 (m, 2H), 7.41 (d, 1H, J=8.4 Hz), 7.21-7.12 (m, 3H), 6.43 (d, 1H, J=15.6 Hz), 6.24 (s, 1H), 5.96 (t, 1H, J=5.7 Hz), 4.53 (d, 2H, J=5.7 Hz), 3.30-3.25 (m, 4H), 3.03 (s, 3H), 2.32 (s, 3H), 1.71-1.63 (m, 6H).

EXAMPLE 185

N-(3-Ethynyl-5-fluoro-4-methanesulfonylamino-benzyl)-3-(2-propylthio-6-trifluoromethyl-pyridin-3-yl)-acrylamide

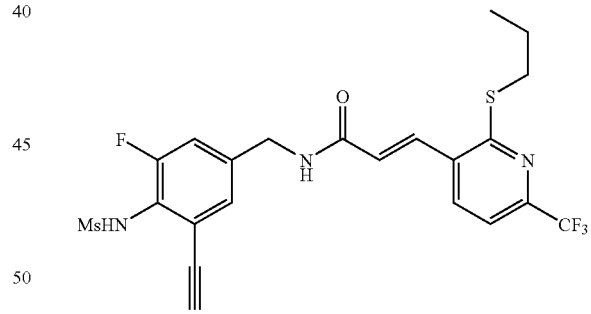

Step 1: Step 1: 3-(2-Propylthio-6-trifluoromethyl-pyridin-3-yl)-acrylic acid 3-(2-Chloro-6-trifluoromethyl-pyridin-3-yl)-acrylic acid (243 mg, 0.966 mmol) was reacted with propanthiol (229 mg, 3.01 mmol) and sodium hydride (145 mg, 3.62 mmol) to afford title compound (115 mg) after purification by column chromatography (Hex EtOAc=2/3).

$^1$H NMR (300 MHz, CDCl$_3$): δ 7.97 (d, 1H, J=15.9 Hz), 7.77 (d, 1H, J=7.8 Hz), 7.32 (d, 1H, J=7.8 Hz), 6.42 (d, 1H, J=15.9 Hz), 3.21 (t, 2H, J=7.2 Hz), 1.73 (m, 2H), 1.00 (t, 3H, J=7.2 Hz).

Step 2: N-(3-Ethynyl-5-fluoro-4-methanesulfonylamino-benzyl)-3-(2-propylthio-6-trifluoromethyl-pyridin-3-yl)-acrylamide N-(4-Aminomethyl-2-fluoro-6-ethynyl-phenyl)-methanesulfonamide, HCl salt (60.2 mg, 0.215 mmol) was reacted with NMM (0.15 ml), DMTMM (70.2 mg) and 3-(2-propylthio-6-trifluoromethyl-pyridin-3-yl)-acrylic acid (58.7 mg, 0.201 mmol) to give the title compound (60 mg, 58%) after purification by column chromatography (Hex/EtOAc=2/3).

$^1$H NMR (300 MHz, CDCl$_3$): δ 7.85 (d, 1H, J=15.6 Hz), 7.74 (d, 1H, J=7.8 Hz), 7.34 (d, 1H, J=8.1 Hz), 7.30 (m, 1H), 7.16 (dd, 1H, J=1.8 and 10.8 Hz), 6.47 (d, 1H, J=15.3 Hz), 6.42 (m, 1H), 6.17 (m, 1H), 4.52 (d, 2H, J=6.0 Hz), 3.48 (s, 1H), 3.26 (s, 3H), 3.23 (q, 2H, J=7.5 Hz), 1.73 (m, 2H), 1.03 (t, 3H, J=7.5 Hz).

EXAMPLE 186

N-(4-Methanesulfonylamino-3-methyl-benzyl)-3-(2-propylthio-6-trifluoromethyl-pyridin-3-yl)-acrylamide

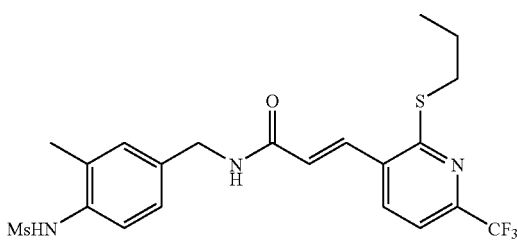

N-(4-Aminomethyl-2-methyl-phenyl)-methanesulfonamide, HCl salt (115.3 mg, 0.420 mmol) was reacted with NMM (0.15 ml), DMTMM (123 mg) and 3-(2-propylthio-6-trifluoromethyl-pyridin-3-yl)-acrylic acid (114.4 mg, 0.393 mmol) to give the title compound (57 mg, 30%) after purification by column chromatography (Hex/EtOAc=2/3).

$^1$H NMR (300 MHz, CDCl$_3$): δ 7.84 (d, 1H, J=15.6 Hz), 7.72 (d, 1H, J=7.8 Hz), 7.41 (d, 1H, J=7.8 Hz), 7.320 (d, 1H, J=7.8 Hz), 7.19 (m, 2H), 6.45 (d, 1H, J=15.6 Hz), 6.22 (m, 1H), 6.03 (m, 1H), 4.52 (d, 2H, J=5.7 Hz), 3.23 (q, 2H, J=6.9 Hz), 3.02 (s, 3H), 1.73 (m, 2H), 1.03 (t, 3H, J=6.9 Hz).

EXAMPLE 187

N-(4-Methanesulfonylamino-3-methyl-benzyl)-3-(2-butylamino-6-trifluoromethyl-pyridin-3-yl)-acrylamide

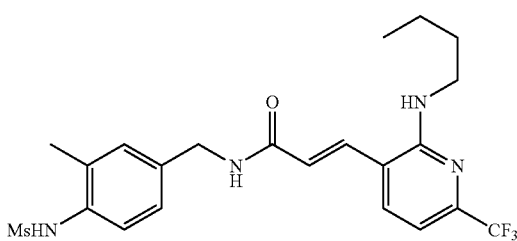

N-(4-Aminomethyl-2-methyl-phenyl)-methanesulfonamide, HCl salt (47 mg, 0.17 mmol) was reacted with 3-(2-butylamino-6-trifluoromethyl-pyridin-3-yl)-acrylic acid (50 mg, 0.17 mmol) to give the title compound (39 mg, 47%) after purification by column chromatography (Hex/EtOAc=1/1).

$^1$H N NMR (300 MHz, CDCl$_3$): δ 7.61 (m, 2H), 7.42 (m, 1H), 7.20 (m, 2H), 6.89 (d, 1H, J=7.5 Hz), 6.33 (d, 1H, J=15.0 Hz), 6.17 (bs, 1H), 5.90 (bs, 1H), 4.80 (bs, 1H), 4.53 (d, 2H, J=57 Hz), 3.50 (m, 2H), 3.03 (s, 3H), 2.32 (s, 3H), 1.49 (m, 4H), 1.40 (m, 2H), 0.96 (t, 3H, J=7.2 Hz)

ESI [N+H]+: 485

EXAMPLE 188

N-(3-Fluoro-4-methanesulfonylamino-5-methyl-benzyl)-3-(2-butylamino-6-trifluoromethyl-pyridin-3-yl)-acrylamide

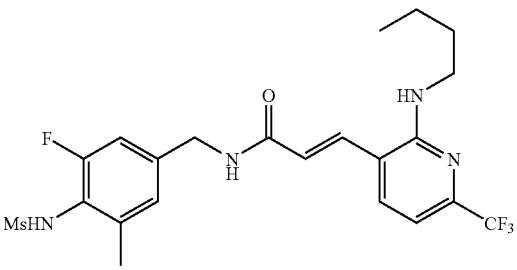

N-(4-Aminomethyl-2-fluoro-6-methyl-phenyl)-methanesulfonamide, HCl salt (56 mg, 0.21 mmol) was reacted with 3-(2-butylamino-6-trifluoromethyl-pyridin-3-yl)-acrylic acid (60 mg, 0.21 mmol) to give the title compound (60 mg, 57%) after purification by column chromatography (Hex/EtOAc=1/1).

$^1$H NMR (300 MHz, CDCl$_3$): δ 7.60 (m, 2H), 7.23 (m, 2H), 6.89 (d, 1H, J=7.8 Hz), 6.33 (d, 1H, J=15.3 Hz), 6.30 (bs, 1H), 6.01 (bs, 1H), 4.84 (bs, 1H), 4.59 (d, 2H, J=6.0 Hz), 3.49 (m, 2H), 3.05 (s, 3H), 2.25 (d, 3H, J=2.1 Hz), 1.60 (m, 2H), 1.39 (m, 2H), 0.95 (t, 3H, J=7.2 Hz)

ESI [M+H]+: 503

EXAMPLE 189

N-(3-Fluoro-4-methanesulfonylamino-5-trifluoromethyl-benzyl)-3-(2-phenethyl-6-trifluoromethyl-pyridin-3-yl)-acrylamide

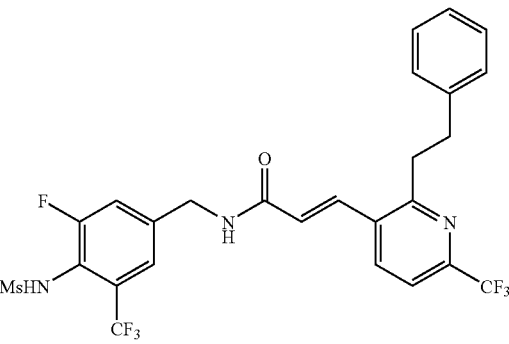

N-(4-Aminomethyl-2-fluoro-6-trifluoromethyl-phenyl)-methanesulfonamide, HCl salt (51.7 mg, 0.160 mmol) was reacted with NMM (0.17 ml), DMTMM (57.2 mg) and 3-(2-phenethyl-6-trifluoromethyl-pyridin-3-yl)-acrylic acid (49.7 mg, 0.154 mmol) to give the title compound (82 mg, 90%) after purification by column chromatography (Hex/EtOAc=2/3).

$^1$H NMR (300 MHz, CDCl$_3$): δ 7.85 (d, 1H, J=8.1 Hz), 7.77 (d, 1H, J=15.3 Hz), 7.53 (d, 1H, J=8.1 Hz), 7.43 (m, 1H), 7.39 (d, 1H, J=9.9 Hz), 7.22 (m, 2H), 7.17 (s, 1H), 7.14 (m, 1H), 6.25 (d, 1H, J=15.3 Hz), 6.18 (s, 1H), 6.08 (t, 1H), 4.58 (d, 2H, J=6.0 Hz), 3.29 (t, 2H, J=8.7 Hz), 3.28 (s, 3H), 3.08 (t, 2H, J=8.7 Hz).

EXAMPLE 190
3-[2-(3-Diethylamino-prop-1-ynyl)-4-trifluoromethyl-phenyl]-N-(3-ethynyl-5-fluoro-4-methanesulfonylamino-benzyl)-acrylamide
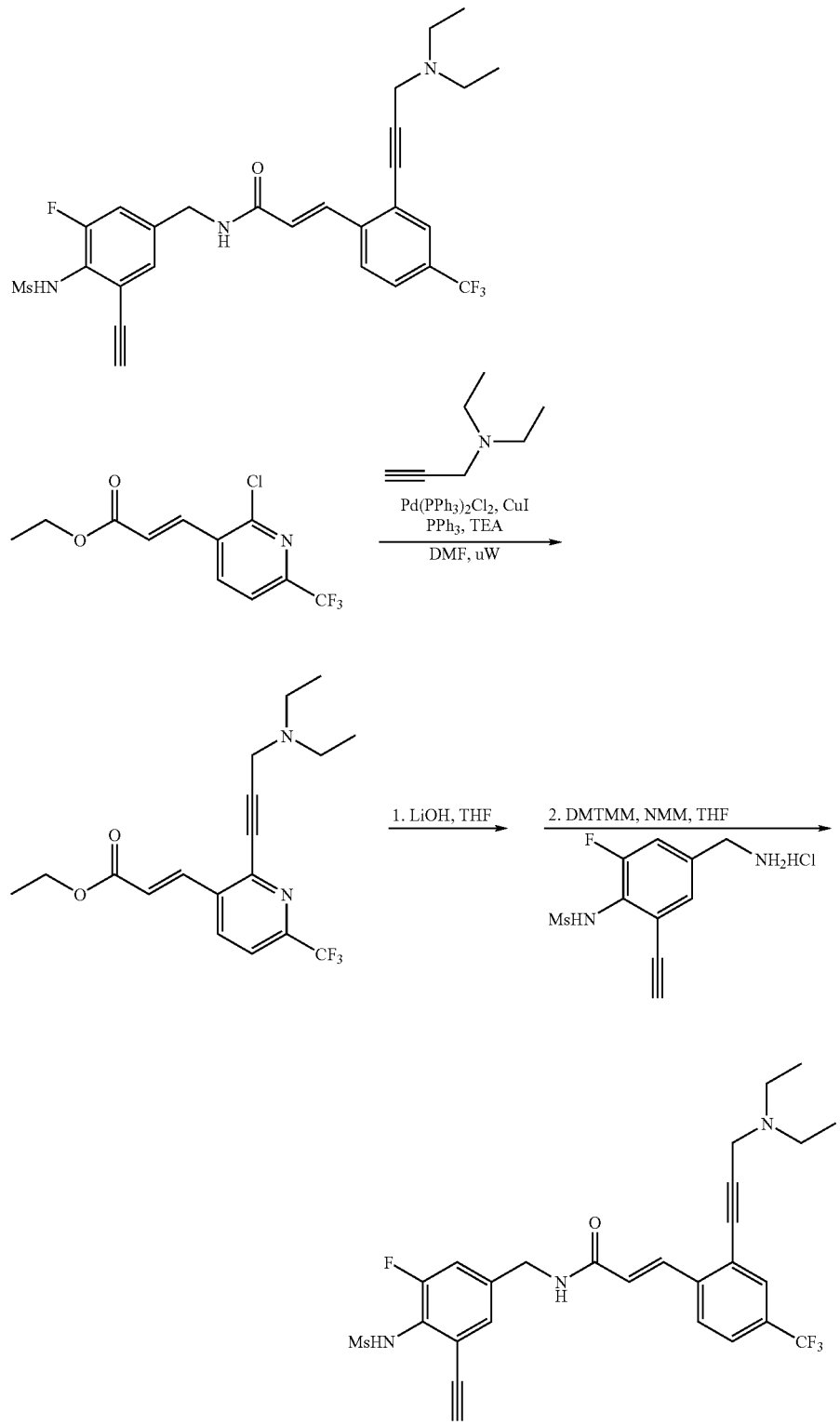

Step 1: Synthesis of 3-[2-(3-diethylamino-prop-1-ynyl)-4-trifluoromethyl-phenyl]-acrylic acid ethyl ester 3-[2-(3-Diethylamino-prop-1-ynyl)-4-trifluoromethyl-phenyl]-acrylic acid ethyl ester was obtained according to the general procedure described in Example 145 (step 1).

2-Chloro-N-methoxy-N-methyl-6-trifluoromethyl-nicotinamide (50 mg, 0.178 mmol) was reacted as described above with diethyl-prop-2-ynyl-amine (2 eq) to give 3-[2-(3-diethylamino-prop-1-ynyl)-4-trifluoromethyl-phenyl]-acrylic acid ethyl ester (30 mg, 47%).

$^1$H NMR (300 MHz, CDCl$_3$): δ 8.14 (d, 1H, J=16.2 Hz), 8.05 (d, 1H, J=8.4 Hz), 7.63 (d, 1H, J=8.4 Hz), 6.57 (d, 1H, J=16.2 Hz), 4.30 (q, 2H, J=7.2 Hz), 3.81 (s, 2H), 2.69 (q, 4H, J=7.2 Hz), 1.35 (t, 3H, J=7.2 Hz), 1.15 (t 6H, J=7.2 Hz).

Step 2: Synthesis of 3-[2-(3-Diethylamino-prop-1-ynyl)-4-trifluoromethyl-phenyl]-N-(3-ethynyl-5-fluoro-4-methanesulfonylamino-benzyl)-acrylamide 3-[2-(3-Diethylamino-prop-1-ynyl)-4-trifluoromethyl-phenyl]-N-(3-ethynyl-5-fluoro-4-methanesulfonylamino-benzyl)-acrylamide was obtained according to the general procedure described in Example 107 (Step 2).

N-(4-Aminomethyl-2-ethynyl-6-fluoro-phenyl)-methanesulfonamide, HCl salt (31 mg, 0.11 mmol) was reacted with 3-[2-(3-diethylamino-prop-1-ynyl)-4-trifluoromethyl-phenyl]-acrylic acid (30 mg, 0.092 mmol) as described above to give 3-[2-(3-diethylamino-prop-1-ynyl)-4-trifluoromethyl-phenyl]-N-(3-ethynyl-5-fluoro-4-methanesulfonylamino-benzyl)-acrylamide (7 mg, 12%).

$^1$H NMR (300 MHz, CDCl$_3$): δ 8.05 (d, 1H, J=15.9 Hz), 8.81 (d, 1H, J=8.1 Hz), 7.61 (d, 1H, J=8.4 Hz), 7.28-7.26 (m, 2H), 7.16 (d, 1H, J=10.2 Hz), 6.70 (d, 1H, J=15.6 Hz), 6.60 (s, 1H), 4.52 (d, 2H, J=6.0 Hz), 3.77 (s, 2H), 3.47 (s, 1H), 3.25 (s, 3H), 2.71 (q, 4H, J=7.2 Hz), 1.13 (t, 6H, J=7.2 Hz).

EXAMPLE 191

3-(2-Benzylamino-6-trifluoromethyl-pyridin-3-yl)-N-(4-methane sulfonylamino-3-methyl-benzyl)-acrylamide

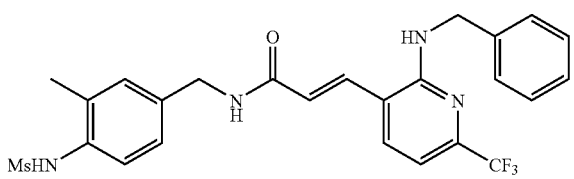

N-(4-Aminomethyl-2-methyl-phenyl)-methanesulfonamide, HCl salt (40 mg, 0.15 mmol) was reacted with 3-(2-benzylamino-6-trifluoromethyl-pyridin-3-yl)-acrylic acid (40 mg, 0.12 mmol) to give the title compound (32 mg, 51%) after purification by column chromatography (Hex/EtOAc=1/2).

$^1$H NMR (300 MHz, DMSO-d6): δ 9.04 (bs, 1H), 8.63 (t, 1H), 7.78 (m, 2H), 7.63 (d, 1H, J=15.9 Hz), 7.25 (m, 8H), 6.99 (d, 1H, J=8.1 Hz), 6.65 (d, 1H, J=15.9 Hz), 4.53 (d, 2H, J=5.1 Hz), 4.35 (d, 2H, J=6.3 Hz), 2.99 (s, 3H), 2.28 (s, 3H).

EXAMPLE 192

3-(2-Butyl-6-trifluoromethyl-pyridin-3-yl)-N-(3-fluoro-4-methane sulfonylamino-5-methyl-benzyl)-acrylamide

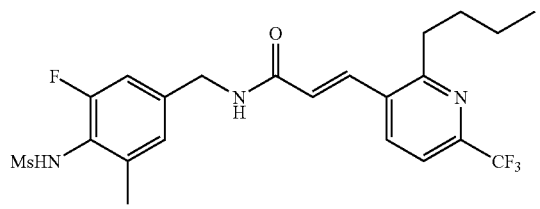

N-(4-Aminomethyl-2-fluoro-6-methyl-phenyl)-methanesulfonamide, HCl salt (65 mg, 0.24 mmol) was reacted with 3-(2-butyl-6-trifluoromethyl-pyridin-3-yl)-acrylic acid (55 mg, 0.20 mmol) to give the title compound (43 mg, 44%) after purification by crystallization from methylene chloride.

$^1$H NMR (300 MHz, DMSO-d6): δ 9.18 (bs, 1H), 8.77 (t, 1H, J=5.7 Hz), 8.14 (d, 1H, J=8.1 Hz), 7.79 (d, 1H, J=8.4 Hz), 7.70 (d, 1H, J=15.6 Hz), 7.16 (m, 2H), 6.74 (d, 1H, J=15.6 Hz), 4.42 (d, 2H, J=5.4 Hz), 2.99 (s, 3H), 2.94 (m, 2H), 2.22 (d, 3H, J=2.7 Hz), 1.62 (m, 2H), 1.35 (m, 2H), 0.91 (t, 3H, J=7.5 Hz).

ESI [M+H]+: 488

EXAMPLE 193

(R)-3-(2-Butyl-6-trifluoromethyl-pyridin-3-yl)-N-[1-(3-fluoro-4-methanesulfonylamino-phenyl)-ethyl]-acrylamide

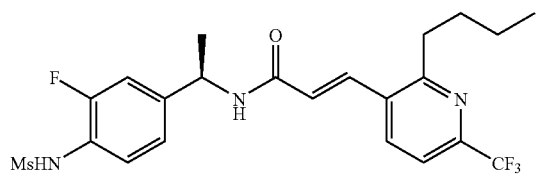

(R)—N-[4-(1-Aminoethyl)-2-fluoro-phenyl]-methanesulfonamide, HCl salt (65 mg, 0.24 mmol) was reacted with 3-(2-butyl-6-trifluoromethyl-pyridin-3-yl)-acrylic acid (55 mg, 0.20 mmol) to give the title compound (49 mg, 50%) after purification by crystallization from methylene chloride.

$^1$H NMR (300 MHz, DMSO-d6): δ 9.54 (bs, 1H), 8.76 (d, 1H, J=7.8 Hz), 8.15 (d, 1H, J=7.8 Hz), 7.80 (d, 1H, J=8.1 Hz), 7.67 (d, 1H, J=15.6 Hz), 7.24 (m, 3H), 6.74 (d, 1H, J=15.6 Hz), 5.04 (t, 1H, J=7.5 Hz), 3.01 (s, 3H), 2.93 (m, 2H), 1.60 (m, 2H), 1.42 (d, 3H, J=7.5 Hz), 1.33 (m, 2H), 0.90 (t, 3H, J=7.2 Hz).

ESI [M+H]+: 488

EXAMPLE 194

3-(2-Butyl-6-trifluoromethyl-pyridin-3-yl)-N-(4-methane sulfonylamino-3-methyl-benzyl)-acrylamide

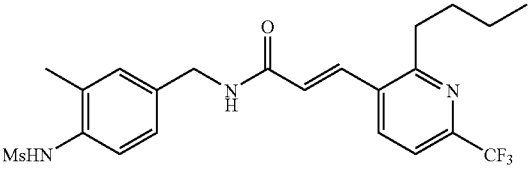

N-(4-Aminomethyl-2-methyl-phenyl)-methanesulfonamide, HCl salt (66 mg, 0.24 mmol) was reacted with 3-(2- butyl-6-trifluoromethyl-pyridin-3-yl)-acrylic acid (55 mg, 0.20 mmol) to give the title compound (69 mg, 73%) after purification by column chromatography (Hex/EtOAc=1/2).

$^1$H NMR (300 MHz, CDCl$_3$) δ 7.97 (d, 1H, J=15.6 Hz), 7.88 (d, 1H, J=8.4 Hz), 7.51 (d, 1H, J=8.4 Hz), 7.44 (d, 1H, J=8.1 Hz), 7.20 (m, 2H), 6.37 (d, 1H, J=15.6 Hz), 6.11 (bs, 1H), 5.92 (t, 1H), 4.55 (d, 2H, J=5.4 Hz), 3.03 (s, 3H), 2.99 (m, 2H), 2.33 (s, 3H), 1.70 (m, 2H), 1.41 (m, 2H), 0.95 (t, 3H, J=7.2 Hz).

ESI [M+H]+: 470

EXAMPLE 195

(R)-3-(2-Benzylamino-6-trifluoromethyl-pyridin-3-yl)-N-[1-(3-fluoro-4-methane sulfonylamino-phenyl)-ethyl]-acrylamide

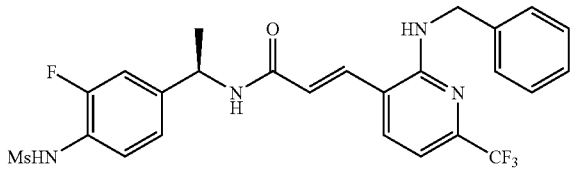

(R)—N-[4-(1-Aminoethyl)-2-fluoro-phenyl]-methanesulfonamide, HCl salt (27 mg, 0.10 mmol) was reacted with 3-(2-benzylamino-6-trifluoromethyl-pyridin-3-yl)-acrylic acid (30 mg, 0.093 mmol) to give the title compound (39 mg, 78%) after purification by column chromatography (Hex/EtOAc=2/3).

$^1$H NMR (300 MHz, DMSO-d6): δ 9.30 (bs, 1H), 8.35 (d, 1H, J=7.8 Hz), 7.64 (m, 2H), 7.27 (m, 8H), 7.01 (t, 1H), 6.89 (d, 1H, J=7.8 Hz), 6.59 (d, 1H, J=15.3 Hz), 5.11 (t, 1H, J=7.5 Hz), 4.63 (d, 2H, J=5.7 Hz), 2.98 (s, 3H), 1.48 (d, 3H, J=6.9 Hz).

ESI [M+H]+: 537

EXAMPLE 196

3-(2-Benzylamino-6-trifluoromethyl-pyridin-3-yl)-N-(3-ethynyl-5-fluoro-4-methanesulfonylamino-benzyl)-acrylamide

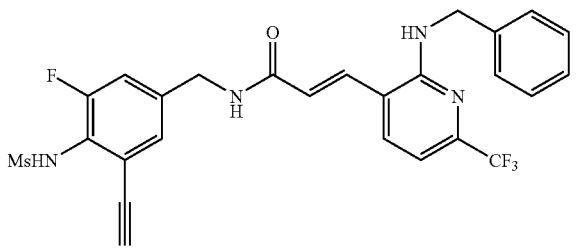

N-(4-Aminomethyl-6-ethynyl-2-fluoro-phenyl)-methanesulfonamide, HCl salt (28 mg, 0.10 mmol) was reacted with 3-(2-benzylamino-6-trifluoromethyl-pyridin-3-yl)-acrylic acid (30 mg, 0.093 mmol) to give the title compound (44 mg, 87%) after purification by column chromatography (Hex/EtOAc=2/3).

$^1$H NMR (300 MHz, DMSO-d6): δ 9.45 (bs, 1H), 8.75 (t, 1H), 7.81 (m, 2H), 7.65 (d, 1H, J=15.3 Hz), 7.27 (m, 7H), 6.99 (d, 1H, J=7.2 Hz), 6.66 (d, 1H, J=15.3 Hz), 4.53 (d, 2H, J=6.0 Hz), 4.48 (s, 1H), 4.39 (d, 2H, J=5.7 Hz), 3.04 (s, 3H).

ESI [M+H]+: 547

EXAMPLE 197

N-(3-Ethynyl-5-fluoro-4-methanesulfonylamino-benzyl)-3-(2-pentyl-6-trifluoromethyl)-pyridin-3-yl-acrylamide

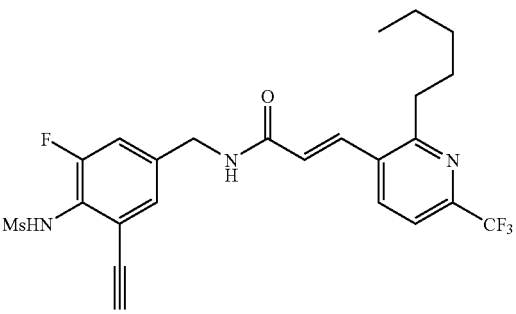

Step 1: 3-(2-Pentyl-6-trifluoromethyl-pyridin-3-yl)-acrylic acid

To a suspension of compound 3-(2-pentyl-6-trifluoromethyl-pyridin-3-yl)-acrylic acid, methyl ester (366 mg, 1.22 mmol) in THF (3 ml) was added a solution of 1 N-LiOH (3.0 ml), and the mixture was stirred for 3 hours at room temperature. The resulting residue was dissolved in H$_2$O and then washed with EtOAc, acidified with 1N HCl to pH 1~2. The solution was extracted three times with methylene chloride and then dried over anhyd. MgSO$_4$ and concentrated in vacuo to give 3-(2-pentyl-6-trifluoromethyl-pyridin-3-yl)-acrylic acid (340 mg, 97%).

$^1$H NMR (300 MHz, CDCl$_3$): δ 8.05 (d, 1H, J=15.9 Hz), 7.98 (d, 1H, J=8.4 Hz), 7.56 (d, 1H, J=8.1 Hz), 6.46 (d, 1H, J=15.6 Hz), 3.00 (t, 2H, J=7.8 Hz), 1.73 (m, 2H), 1.39 (m, 4H), 0.91 (t, 3H, J=7.2 Hz)

Step 2: N-(3-Ethynyl-5-fluoro-4-methanesulfonylamino-benzyl)-3-(2-pentyl-6-trifluoromethyl)-pyridin-3-yl-acrylamide N-(4-Aminomethyl-6-ethynyl-2-fluoro-phenyl)-methanesulfonamide, HCl salt (74 mg, 0.27 mmol) was reacted with 3-(2-pentyl-6-trifluoromethyl-pyridin-3-yl)-acrylic acid (77 mg, 0.27 mmol) to give N-(3-ethynyl-5-fluoro-4-methanesulfonylamino-benzyl)-3-(2-pentyl-6-trifluoromethyl)-pyridin-3-yl-acrylamide (57 mg, 42%) after purification by column chromatography (Hex/EtOAc=1/1)

$^1$H NMR (300 MHz, CDCl$_3$): δ 7.93 (m, 2H), 7.52 (d, 1H, J=8.1 Hz), 7.30 (bs, 1H), 7.17 (m, 1H), 6.39 (d, 1H, J=15.3 Hz), 6.42 (bs, 1H), 6.09 (bs, 1H), 4.54 (d, 2H, J=6.0 Hz), 3.49 (s, 1H), 3.27 (s, 3H), 2.98 (m, 2H), 1.72 (m, 2H), 1.37 (m, 4H), 0.89 (m, 3H).

ESI [M+H]+: 512

EXAMPLE 198

N-(4-Methanesulfonylamino-3-methyl-benzyl)-3-(2-pentyl-6-trifluoromethyl)-pyridin-3-yl-acrylamide

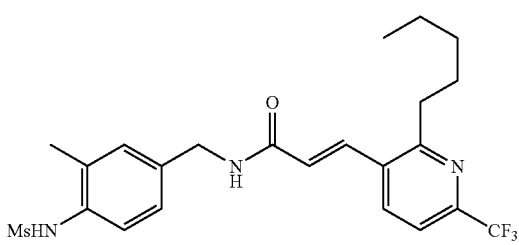

N-(4-Aminomethyl-2-methyl-phenyl)-methanesulfonamide, HCl salt (70 mg, 0.26 mmol) was reacted with 3-(2-pentyl-6-trifluoromethyl-pyridin-3-yl)-acrylic acid (74 mg, 0.26 mmol) to give N-(4-methanesulfonylamino-3-methyl-benzyl)-3-(2-pentyl-6-trifluoromethyl)-pyridin-3-yl-acrylamide (57 mg, 46%) after purification by column chromatography (Hex/EtOAc=3/2)

$^1$H NMR (300 MHz, CDCl$_3$): δ 7.96 (d, 1H, J=15.9 Hz), 7.88 (d, 1H, J=7.8 Hz), 7.47 (m, 2H), 7.22 (m, 2H), 6.37 (d, 1H, J=15.3 Hz), 6.14 (bs, 1H), 5.94 (bs, 1H), 4.55 (d, 2H, J=5.7 Hz), 3.03 (s, 3H), 2.98 (s, 3H), 2.32 (s, 3H), 1.72 (m, 2H), 1.37 (m, 4H), 0.89 (m, 3H).

ESI [M+H]+: 484

EXAMPLE 199

N-(3,5-Difluoro-4-methanesulfonylamino-benzyl)-3-(2-pentyl-6-trifluoromethyl)-pyridin-3-yl-acrylamide

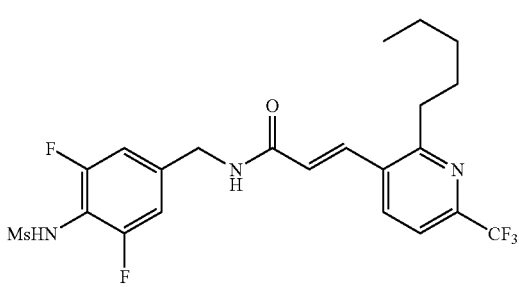

N-(4-Aminomethyl-2,6-difluoro-phenyl)-methanesulfonamide, HCl salt (49 mg, 0.18 mmol) was reacted with 3-(2-pentyl-6-trifluoromethyl-pyridin-3-yl)-acrylic acid (52 mg, 0.18 mmol) to give the title compound (58 mg, 63%) after purification by column chromatography (Hex/EtOAc=1:1)

$^1$H NMR (300 MHz, CDCl$_3$): δ 7.94 (m, 2H), 7.41 (m, 1H), 6.99 (m, 2H), 6.40 (d, 1H, J=15.0 Hz), 6.09 (bs, 1H), 6.06 (bs, 1H), 4.56 (d, 2H, J=6.0 Hz), 3.22 (s, 3H), 2.96 (m, 2H), 1.72 (m, 2H), 1.37 (m, 4H), 0.89 (m, 3H).

ESI [M+H]+: 506

EXAMPLE 200

Synthesis of N-(4-Methanesulfonylamino-3,5-difluoro-benzyl)-3-(2-piperid-1-yl-6-trifluoromethyl-pyridin-3-yl)-acrylamide

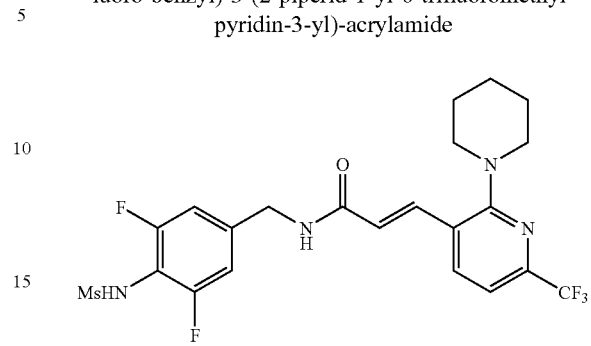

N-(4-Aminomethyl-2,6-difluoro-phenyl)-methanesulfonamide, HCl salt (55 mg, 0.19 mmol) was reacted with 3-(2-piperid-1-yl-6-trifluoromethyl-pyridin-3-yl)-acrylic acid (50 mg, 0.16 mmol) to give 3 N-(4-methanesulfonylamino-3,5-difluoro-benzyl)-3-(2-piperid-1-yl-6-trifluoromethyl-pyridin-3-yl)-acrylamide (35 mg, 41%).

$^1$H NMR (300 MHz, DMSO): δ 9.50 (s, 1H, br), 8.82 (t, 1H, J=6.0 Hz), 7.01 (d, 1H, J=7.8 Hz), 7.45 (d, 1H, J=15.9 Hz), 7.40 (d, 1H, J=7.8 Hz), 7.13 (s, 1H), 7.12 (d, 1H, J=8.7 Hz), 6.75 (d, 1H, J=15.9 Hz), 4.42 (d, 2H, J=6.0 Hz), 3.19 (s, 4H), 3.04 (s, 3H), 1.63 (s, 6H).

EXAMPLE 201

N-(4-Methanesulfonylamino-3,5-difluoro-benzyl)-3-[2-(3-fluoro-phenyl)-6-trifluoromethyl-pyridin-3-yl]-acrylamide

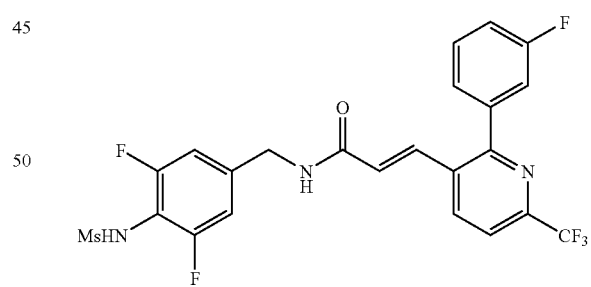

N-(4-Aminomethyl-2,6-difluoro-phenyl)-methanesulfonamide, HCl salt (53 mg, 0.19 mmol) was reacted with 3-[2-(3-fluoro-phenyl)-6-trifluoromethyl-pyridin-3-yl]-acrylic acid (50 mg, 0.16 mmol) to give N-(4-methanesulfonylamino-3,5-difluoro-benzyl)-3-[2-(3-fluoro-phenyl)-6-trifluoromethyl-pyridin-3-yl]-acrylamide (31 mg, 37%).

$^1$H NMR (300 MHz, DMSO): δ 9.50 (s, 1H, br), 8.87 (t, 1H, J=6.0 Hz), 8.40 (d, 1H, J=8.1 Hz), 8.02 (d, 1H, J=8.4 Hz), 7.63-7.56 (m, 2H), 7.46-7.35 (m, 3H), 7.11-7.09 (m, 2H), 6.84 (d, 1H, J=15.6 Hz), 4.39 (d, 2H, J=5.7 Hz), 3.04 (s, 3H).

EXAMPLE 202

N-(3,5-Difluoro-4-methanesulfonylamino-benzyl)-3-(2-butylamino-6-trifluoromethyl)-pyridin-3-yl-acrylamide

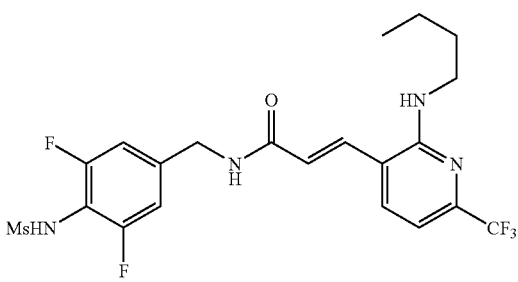

N-(4-Aminomethyl-2,6-difluoro-phenyl)-methane-sulfonamide, HCl salt (47 mg, 0.17 mmol) was reacted with 3-(2-butylamino-6-trifluoromethyl-pyridin-3-yl)-acrylic acid (50 mg, 0.17 mmol) to give the title compound (52 mg, 59%) after purification by column chromatography (Hex/EtOAc=1:1).

$^1$H NMR (300 MHz, CDCl$_3$): δ 7.84 (m, 1H), 7.51 (d, 1H, J=7.8 Hz), 6.79 (m, 1H), 6.47 (bs, 3H), 6.30 (d, 1H, J=15.6 Hz), 4.05 (d, 2H, J=2.1 Hz), 3.50 (m, 2H), 3.32 (s, 3H), 1.65 (m, 2H), 1.26 (m, 2H), 0.95 (m, 3H)

ESI [M+H]+: 507

EXAMPLE 203

N-(3,5-Difluoro-4-methanesulfonylamino-benzyl)-3-(2-phenethyl-6-trifluoromethyl-pyridin-3-yl)-acrylamide

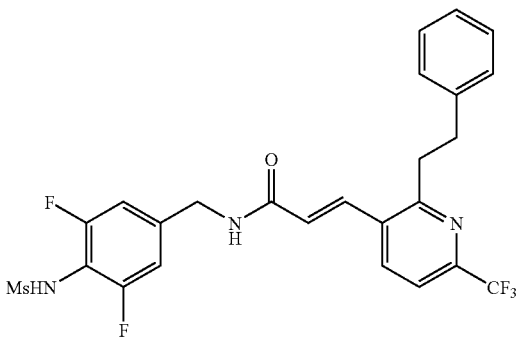

N-(4-Aminomethyl-2,6-difluoro-phenyl)-methane-sulfonamide, HCl salt (107.2 mg, 0.393 mmol) was reacted with NMM (0.20 ml), DMTMM (123 mg) and 3-(2-phenethyl-6-trifluoromethyl-pyridin-3-yl)-acrylic acid (101.3 mg, 0.315 mmol) to give the title compound (99 mg, 58%) after purification by column chromatography (Hex/EtOAc=2/3).

$^1$H NMR (300 MHz, CDCl$_3$): δ 7.86 (d, 1H, J=7.8 Hz), 7.79 (d, 1H, J=15.6 Hz), 7.52 (d, 1H, J=7.8 Hz), 7.17 (m, 4H), 6.91 (d, 2H, J=8.4 Hz), 6.40 (d, 1H, J=15.6 Hz), 6.32 (t, 1H), 6.28 (s, 1H), 4.48 (d, 2H, J=6.0 Hz), 3.27 (t, 2H, J=7.2 Hz), 3.17 (s, 3H), 3.06 (t, 2H, J=7.2 Hz).

ESI [M+H]+: 540

EXAMPLE 204

N-(3,5-Difluoro-4-methanesulfonylamino-benzyl)-3-[2-(2-methoxy-ethylamino)-6-trifluoromethyl-pyridin-3-yl]-acrylamide

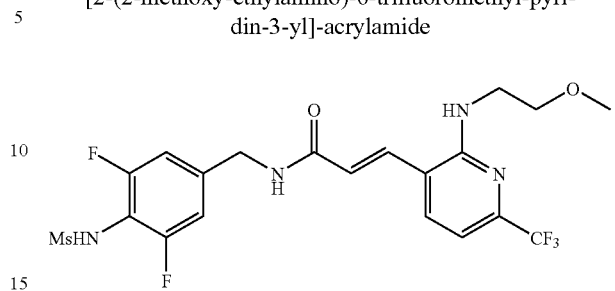

N-(4-Aminomethyl-2,6-difluoro-phenyl)-methane-sulfonamide, HCl salt (100 mg, 0.37 mmol) was reacted with 3-[2-(2-methoxy-ethylamino)-6-trifluoromethyl-pyridin-3-yl]-acrylic acid (102 mg, 0.35 mmol) to give the title compound (107 mg, 60%) after purification by column chromatography (Hex/EtOAc=1/2).

$^1$H NMR (300 MHz, DMSO-d6): 9.52 (bs, 1H), δ 8.76 (t, 1H), 7.81 (d, 1H, J=7.8 Hz), 7.59 (d, 1H, J=15.3 Hz), 7.11 (m, 3H), 6.99 (d, 1H, J=7.8 Hz), 6.64 (d, 1H, J=15.3 Hz), 4.41 (d, 2H, J=6.0 Hz), 3.50 (m, 4H), 3.25 (s, 3H), 3.03 (s, 3H).

ESI [M+H]+: 509

EXAMPLE 205

3-(2-Butyl-6-trifluoromethyl-pyridin-3-yl)-N-(3,5-difluoro-4-methanesulfonylamino-benzyl)-acrylamide

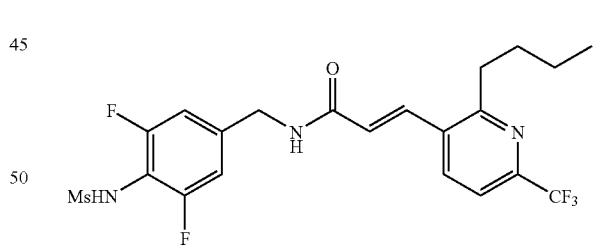

N-(4-Aminomethyl-2,6-difluoro-phenyl)-methane-sulfonamide, HCl salt (100 mg, 0.37 mmol) was reacted with 3-(2-butyl-6-trifluoromethyl-pyridin-3-yl)-acrylic acid (96 mg, 0.35 mmol) to give the title compound (125 mg, 73%) after purification by column chromatography (Hex/EtOAc=2/3).

$^1$H NMR (300 MHz, DMSO-d6): δ 9.50 (bs, 1H), 8.88 (t, 1H), 8.18 (d, 1H, J=7.8 Hz), 7.79 (d, 1H, J=7.8 Hz), 7.72 (d, 1H, J=15.6 Hz), 7.13 (d, 2H, J=8.7 Hz), 6.75 (d, 1H, J=15.6 Hz), 4.43 (d, 2H, J=5.7 Hz), 3.05 (s, 3H), 2.94 (m, 2H), 1.62 (m, 2H), 1.35 (m, 2H), 0.90 (t, 3H, J=7.5 Hz).

ESI [M+H]+: 492

EXAMPLE 206

N-(3-Ethynyl-5-fluoro-4-methanesulfonylamino-benzyl)-3-(2-propyl-6-trifluoromethyl-pyridin-3-yl)-acrylamide

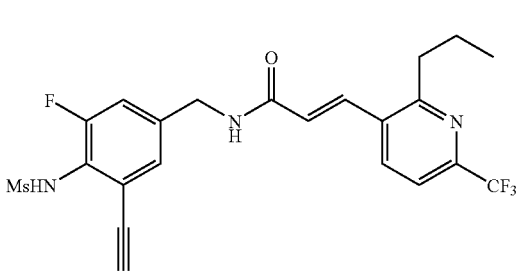

N-(4-Aminomethyl-6-ethynyl-2-fluoro-phenyl)-methanesulfonamide, HCl salt (167 mg, 0.60 mmol) was reacted with 3-(2-propyl-6-trifluoromethyl-pyridin-3-yl)-acrylic acid (30 mg, 0.50 mmol) to give the title compound (211 mg, 87%) after purification by column chromatography (Hex/EtOAc=2/3).

$^1$H NMR (300 MHz, DMSO-d6): δ 9.46 (bs, 1H), 8.87 (t, 1H), 8.18 (d, 1H, J=8.4 Hz), 7.79 (d, 1H, J=8.1 Hz), 7.72 (d, 1H, J=15.6 Hz), 7.13 (m, 2H), 6.75 (d, 1H, J=15.6 Hz), 4.53 (s, 1H), 4.41 (d, 2H, J=6.0 Hz), 3.07 (s, 3H), 2.93 (m, 2H), 1.66 (m, 2H), 0.94 (t, 3H, J=7.5 Hz).

ESI [M+H]+: 484

EXAMPLE 207

N-(3,5-Difluoro-4-methanesulfonylamino-benzyl)-3-(2-propyl-6-trifluoromethyl-pyridin-3-yl)-acrylamide

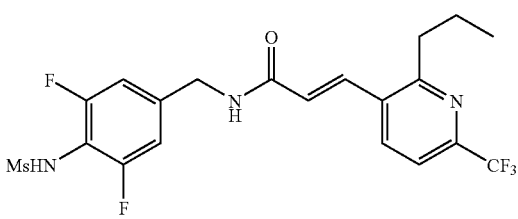

N-(4-Aminomethyl-2,6-difluoro-phenyl)-methanesulfonamide, HCl salt (100 mg, 0.37 mmol) was reacted with 3-(2-propyl-6-trifluoromethyl-pyridin-3-yl)-acrylic acid (90 mg, 0.35 mmol) to give the title compound (134 mg, 80%) after purification by column chromatography (Hex/EtOAc=1/2).

$^1$H NMR (300 MHz, DMSO-d6): δ 9.50 (bs, 1H), 8.88 (t, 1H), 8.18 (d, 1H, J=8.1 Hz), 7.79 (d, 1H, J=8.1 Hz), 7.72 (d, 1H, J=15.6 Hz), 7.13 (d, 2H, J=8.4 Hz), 6.75 (d, 1H, J=15.6 Hz), 4.43 (d, 2H, J=5.7 Hz), 3.05 (s, 3H), 2.92 (m, 2H), 1.67 (m, 2H), 0.93 (t, 3H, J=6.9 Hz).

ESI [M+H]+: 478

EXAMPLE 208

N-(4-Methanesulfonylamino-3-methyl-benzyl)-3-(2-propyl-6-trifluoromethyl-pyridin-3-yl)-acrylamide

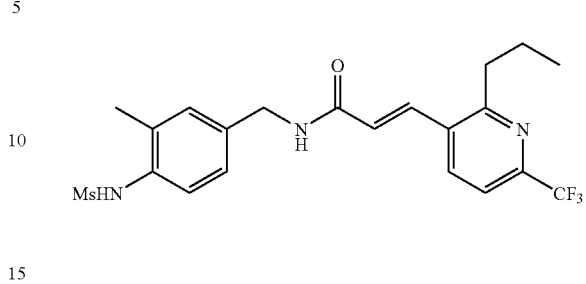

N-(4-Aminomethyl-2-methyl-phenyl)-methanesulfonamide, HCl salt (102 mg, 0.37 mmol) was reacted with 3-(2-propyl-6-trifluoromethyl-pyridin-3-yl)-acrylic acid (90 mg, 0.35 mmol) to give the title compound (120 mg, 75%) after purification by column chromatography (Hex/EtOAc=1/2).

$^1$H NMR (300 MHz, DMSO-d6): δ 9.03 (bs, 1H), 8.77 (t, 1H), 8.15 (d, 1H, J=7.8 Hz), 7.78 (d, 1H, J=8.4 Hz), 7.70 (d, 1H, J=15.6 Hz), 7.18 (m, 3H), 6.74 (d, 1H, J=15.6 Hz), 4.37 (d, 2H, J=6.0 Hz), 2.96 (s, 3H), 2.92 (m, 2H), 2.30 (s, 3H), 1.67 (m, 2H), 0.94 (t, 3H, J=7.5 Hz).

ESI [M+H]+: 456

EXAMPLE 209

(R)-3-(2-Propyl-6-trifluoromethyl-pyridin-3-yl)-N-[1-(3-fluoro-4-methanesulfonylamino-phenyl)-ethyl]-acrylamide

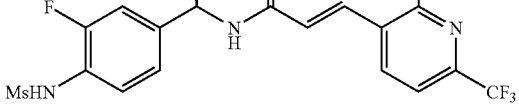

(R)—N-[4-(1-Aminoethyl)-2-fluoro-phenyl]-methanesulfonamide, HCl salt (105 mg, 0.39 mmol) was reacted with 3-(2-propyl-6-trifluoromethyl-pyridin-3-yl)-acrylic acid (90 mg, 0.35 mmol) to give the title compound (151 mg, 91%) after purification by column chromatography (Hex/EtOAc=2/3).

$^1$H NMR (300 MHz, DMSO-d6): δ 9.56 (bs, 1H), 8.77 (d, 1H, J=7.8 Hz), 8.14 (d, 1H, J=8.1 Hz), 7.80 (d, 1H, J=8.4 Hz), 7.66 (d, 1H, J=15.6 Hz), 7.27 (m, 3H), 6.74 (d, 1H, J=15.6 Hz), 5.04 (t, 1H, J=7.5 Hz), 3.00 (s, 3H), 2.91 (m, 2H), 1.67 (m, 2H), 1.41 (d, 3H, J=6.9 Hz), 0.92 (t, 3H, J=7.5 Hz).

ESI [M+H]+: 474

EXAMPLE 210

(R)-3-(2-sec-Butylamino-6-trifluoromethyl-pyridin-3-yl)-N-[1-(3-fluoro-4-methanesulfonylamino-phenyl)-ethyl]-acrylamide

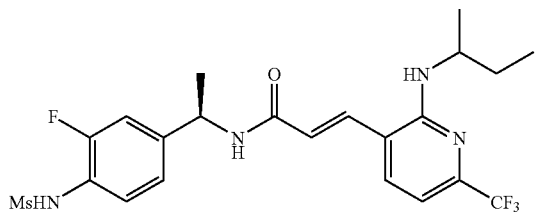

(R)—N-[4-(1-Aminoethyl)-2-fluoro-phenyl]-methanesulfonamide, HCl salt (92 mg, 0.34 mmol) was reacted with 3-(2-sec-Butylamino-6-trifluoromethyl-pyridin-3-yl)-acrylic acid (82 mg, 0.28 mmol) to give the title compound (133 mg, 95%) after purification by crystallization from Hex/EtOAc.

$^1$H NMR (300 MHz, DMSO-d6): δ 9.56 (bs, 1H), 8.64 (d, 1H, J=8.4 Hz), 7.76 (d, 1H, J=7.8 Hz), 7.58 (d, 1H, J=15.6 Hz), 7.25 (m, 3H), 6.94 (d, 1H, J=7.8 Hz), 6.77 (d, 1H, J=7.8 Hz), 6.53 (d, 1H, J=15.6 Hz), 5.03 (t, 1H), 4.06 (m, 1H), 3.00 (s, 3H), 1.55 (m, 2H), 1.40 (d, 3H, J=7.2 Hz), 1.12 (m, 3H), 0.84 (m, 3H).

ESI [M+H]+: 503

EXAMPLE 211

(R)-3-[2-(2-Methyl-butyl)-6-trifluoromethyl-pyridin-3-yl]-N-[1-(3-fluoro-4-methanesulfonylamino-phenyl)-ethyl]-acrylamide

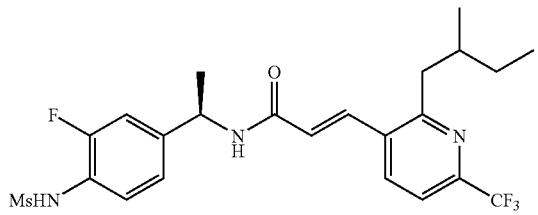

(R)—N-[4-(1-Aminoethyl)-2-fluoro-phenyl]-methanesulfonamide, HCl salt (105 mg, 0.39 mmol) was reacted with 3-[2-(2-methyl-butyl)-6-trifluoromethyl-pyridin-3-yl]-acrylic acid (101 mg, 0.35 mmol) to give the title compound (73 mg, 42%) after purification by crystallization from ether.

$^1$H NMR (300 MHz, DMSO-d6): δ 8.76 (d, 1H, J=8.1 Hz), 8.16 (d, 1H, J=8.4 Hz), 7.78 (d, 1H, J=15.6 Hz), 7.25 (m, 3H), 6.74 (d, 1H, J=15.6 Hz), 5.04 (t, 1H, J=7.5 Hz), 3.01 (s, 3H), 3.00 (m, 1H), 2.70 (m, 1H), 1.92 (m, 1H), 1.41 (d, 3H, J=6.9 Hz), 1.30 (m, 2H), 0.84 (m, 6H).

ESI [M+H]+: 502

EXAMPLE 212

(R)—N-[1-(3-Fluoro-4-methanesulfonylamino-phenyl)-ethyl]-3-[2-(2-methoxy-ethylamino)-6-trifluoromethyl-pyridin-3-yl]-acrylamide

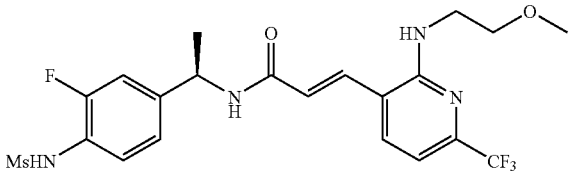

(R)—N-[4-(1-Aminoethyl)-2-fluoro-phenyl]-methanesulfonamide, HCl salt (105 mg, 0.39 mmol) was reacted with 3-[2-(2-methoxy-ethylamino)-6-trifluoromethyl-pyridin-3-yl]-acrylic acid (102 mg, 0.35 mmol) to give the title compound (114 mg, 65%) after purification by crystallization from ether.

$^1$H NMR (300 MHz, DMSO-d6): δ 9.54 (bs, 1H), 8.65 (d, 1H, J=7.8 Hz), 7.78 (d, 1H, J=7.8 Hz), 7.54 (d, 1H, J=15.3 Hz), 7.25 (m, 4H), 6.99 (d, 1H, J=7.8 Hz), 6.64 (d, 1H, J=15.3 Hz), 5.04 (t, 1H, J=6.9 Hz), 3048 (s, 4H), 3.25 (s, 3H), 3.01 (s, 3H), 1.41 (d, 3H, J=6.9 Hz).

EXAMPLE 213

(R)—N-[1-(3-Fluoro-4-methanesulfonylamino-phenyl)-ethyl]-3-(2-butylamino)-6-trifluoromethyl-pyridin-3-yl-acrylamide

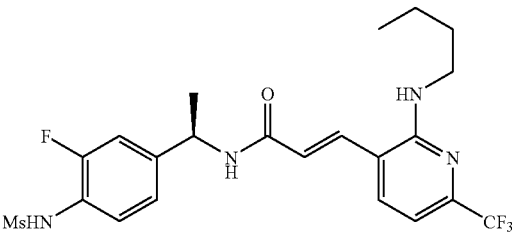

(R)—N-[4-(1-Amino-ethyl)-2-fluoro-phenyl]-methanesulfonamide, HCl salt (103 mg, 0.38 mmol) was reacted with 3-(2-butylamino-6-trifluoromethyl-pyridin-3-yl)-acrylic acid (110 mg, 0.38 mmol) to give the title compound (120 mg, 63%) after purification by column chromatography (Hex/EtOAc=1/1).

$^1$H NMR (300 MHz, DMSO-d6+CDCl$_3$): δ 9.23 (bs, 1H), 8.24 (bs, 1H), 7.56 (m, 3H), 7.41 (m, 1H), 7.17 (m, 2H), 6.86 (d, 1H, J=7.5 Hz), 6.56 (d, 1H, J=15.6 Hz), 5.15 (m, 1H), 3.46 (m, 2H), 2.99 (s, 3H), 1.60 (m, 2H), 1.50 (d, 3H, J=7.2 Hz), 0.94 (m, 3H)

ESI [M+H]+: 503

EXAMPLE 214

N-(3-Fluoro-4-methanesulfonylamino-5-methyl-benzyl)-3-(2-pentyl-6-trifluoromethyl)-pyridin-3-yl-acrylamide

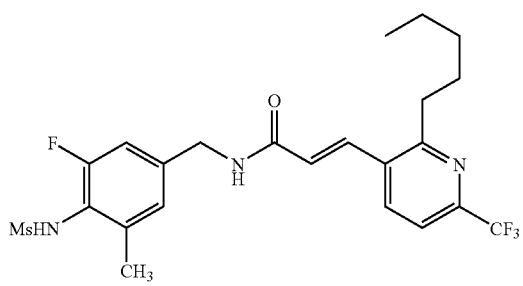

N-(4-Aminomethyl-2-fluoro-6-methyl-phenyl)-methanesulfonamide, HCl salt (52 mg, 0.19 mmol) was reacted with 3-(2-pentyl-6-trifluoromethyl-pyridin-3-yl)-acrylic acid (55 mg, 0.19 mmol) to give the title compound (65 mg, 68%) after purification by column chromatography (Hex/EtOAc=1/1)

$^1$H NMR (300 MHz, CDCl$_3$): δ 7.91 (m, 2H), 7.50 (d, 1H, J=5.8 Hz), 7.25 (m, 2H), 6.36 (d, 1H, J=15.3 Hz), 6.15 (bs, 1H), 6.01 (bs, 1H), 4.61 (d, 2H, J=6.0 Hz), 3.05 (s, 3H), 2.97 (m, 2H), 2.25 (s, 3H), 1.71 (m, 2H), 1.34 (m, 2H), 0.89 (m, 3H).

ESI [M+H]+: 502

EXAMPLE 215

(R)—N-[1-(3-Fluoro-4-methanesulfonylamino-phenyl)-ethyl]-3-(2-pentyl-6-trifluoromethyl)-pyridin-3-yl-acrylamide

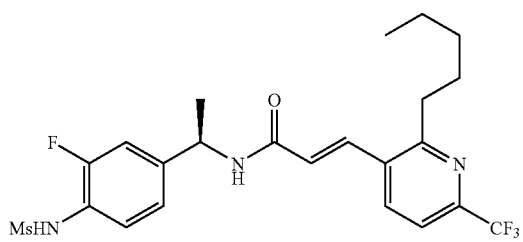

(R)—N-[4-(1-Amino-ethyl)-2-fluoro-phenyl]-methanesulfonamide, HCl salt (54 mg, 0.20 mmol) was reacted with 3-(2-pentyl-6-trifluoromethyl-pyridin-3-yl)-acrylic acid (57 mg, 0.20 mmol) to give the title compound (35 mg, 35%) after purification by column chromatography (Hex/EtOAc=1/1)

$^1$H NMR (300 MHz, CDCl$_3$): δ 7.90 (m, 2H), 7.53 (m, 2H), 6.45 (bs, 1H), 6.37 (d, 1H, J=15.6 Hz), 5.85 (d, 1H, J=7.8 Hz), 5.22 (m, 1H), 3.04 (s, 3H), 2.96 (m, 2H), 1.70 (m, 2H), 1.58 (s, 3H), 1.36 (m, 4H), 0.88 (m, 3H).

ESI [M+H]+: 502

EXAMPLE 216

N-(4-Methanesulfonylamino-3-methyl-benzyl)-3-[2-(propane-1-sulfonyl)-6-trifluoromethyl-pyridin-3-yl]-acrylamide

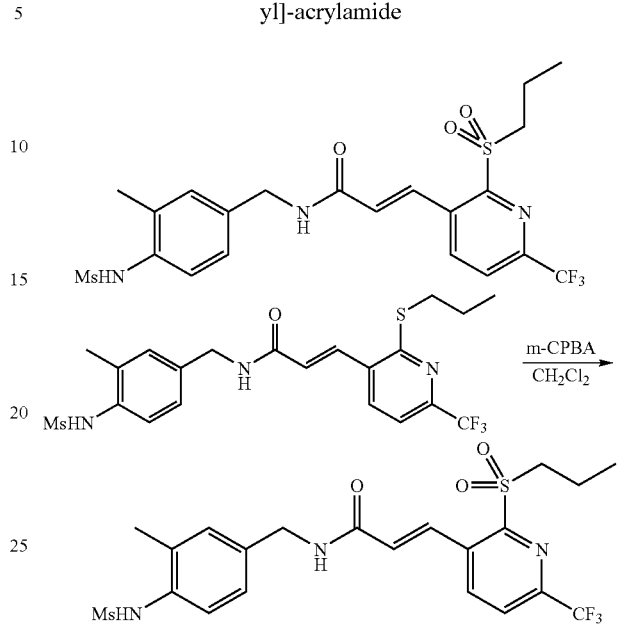

N-(4-Methanesulfonylamino-3-methyl-benzyl)-3-(2-propylthio-6-trifluoromethyl-pyridin-3-yl)-acrylamide (34.9 mg, 0.0715 mmol) was reacted with m-CPBA (60% 43.7 mg) for 3 hrs at room temperature to yield the title compound (31 mg, 83%) after purification by column chromatography (Hex/EtOAc=1/4).

$^1$H NMR (300 MHz, CDCl$_3$): δ 8.24 (d, 1H, J=14.1 Hz), 8.20 (d, 1H, J=8.1 Hz), 7.86 (d, 1H, J=8.1 Hz), 7.33 (d, 1H, J=8.4 Hz), 7.15 (m, 2H), 6.55 (d, 1H, J=15.9 Hz), 6.50 (t, 1H), 6.38 (s, 1H), 4.45 (d, 2H, J=6.0 Hz), 3.62 (m, 2H), 3.00 (s, 3H), 2.68 (s, 3H), 1.94 (m, 2H), 1.11 (t, 3H, J=7.5 Hz)

EXAMPLE 217

N-(3,5-Difluoro-4-methanesulfonylamino-benzyl)-3-(2-isopropylamino-6-trifluoromethyl-pyridin-3-yl)-acrylamide

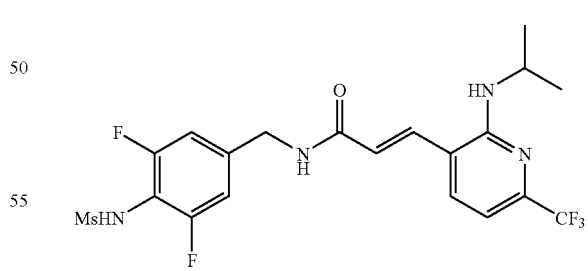

N-(4-Aminomethyl-2,6-difluoro-phenyl)-methanesulfonamide, HCl salt (109 mg, 0.40 mmol) was reacted with 3-(2-isopropylamino-6-trifluoromethyl-pyridin-3-yl)-acrylic acid (82 mg, 0.30 mmol) to give the title compound (109 mg, 74%) after purification by crystallization from ether.

$^1$H NMR (300 MHz, DMSO-d6): δ 9.50 (bs, 1H), 8.76 (t, 1H, J=6.0 Hz), 7.80 (d, 1H, J=7.5 Hz), 7.64 (d, 1H, J=15.6 Hz), 7.13 (d, 2H, J=8.7 Hz), 6.96 (d, 1H, J=7.8 Hz), 6.82 (d,

1H, J=7.5 Hz), 6.62 (d, 1H, J=15.6 Hz), 4.41 (d, 2H, J=6.0 Hz), 4.22 (m, 1H), 3.05 (s, 3H), 1.18 (d, 6H, J=6.3 Hz).
ESI [M+H]+: 493

EXAMPLE 218

(R)—N-[1-(3-Fluoro-4-methanesulfonylamino-phenyl)-ethyl]-3-(2-isopropylamino-6-trifluoromethyl-pyridin-3-yl)-acrylamide

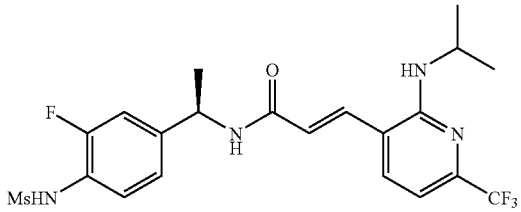

(R)—N-[4-(1-Aminoethyl)-2-fluoro-phenyl]-methanesulfonamide, HCl salt (107 mg, 0.40 mmol) was reacted with 3-(2-isopropylamino-6-trifluoromethyl-pyridin-3-yl)-acrylic acid (82 mg, 0.30 mmol) to give the title compound (137 mg, 93%) after purification by crystallization from ether.

$^1$H NMR (300 MHz, DMSO-d6): δ 9.54 (bs, 1H), 8.65 (d, 1H, J=7.8 Hz), 7.76 (d, 1H, J=7.8 Hz), 7.57 (d, 1H, J=15.3 Hz), 7.25 (m, 3H), 6.96 (d, 1H, J=7.5 Hz), 6.80 (d, 1H, J=7.5 Hz), 6.60 (d, 1H, J=15.3 Hz), 5.03 (t, 1H, J=7.5 Hz), 4.20 (m, 1H), 3.01 (s, 3H), 1.40 (d, 3H, J=6.9 Hz), 1.16 (dd, 6H, J=2.1 and 6.3 Hz).
ESI [M+H]+: 489

EXAMPLE 219

3-(2-Isopropylamino-6-trifluoromethyl-pyridin-3-yl)-N-(4-methane sulfonylamino-3-methyl-benzyl)-acrylamide

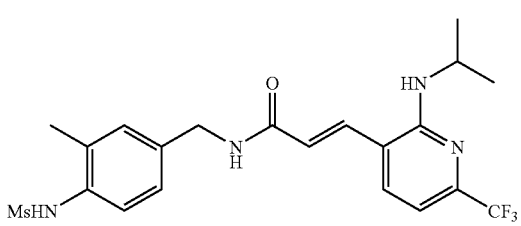

N-(4-Aminomethyl-2-methyl-phenyl)-methanesulfonamide, HCl salt (110 mg, 0.40 mmol) was reacted with 3-(2-isopropylamino-6-trifluoromethyl-pyridin-3-yl)-acrylic acid (82 mg, 0.30 mmol) to give the title compound (92 mg, 65%) after purification by crystallization from Hex/EtOAc.

$^1$H NMR (300 MHz, DMSO-d6): δ 9.00 (bs, 1H), 8.64 (t, 1H), 7.76 (d, 1H, J=7.2 Hz), 7.62 (d, 1H, J=15.3 Hz), 7.18 (m, 3H), 6.95 (d, 1H, J=7.5 Hz), 6.80 (d, 1H, J=7.2 Hz), 6.61 (d, 1H, J=15.3 Hz), 4.45 (d, 2H, J=5.4 Hz), 4.20 (m, 1H), 2.95 (s, 3H), 2.29 (s, 3H), 1.18 (d, 6H, J=5.7 Hz).
ESI [M+H]+: 471

EXAMPLE 220

N-(3-Fluoro-4-methanesulfonylamino-5-methyl-benzyl)-3-(2-isopropylamino-6-trifluoromethyl-pyridin-3-yl)-acrylamide

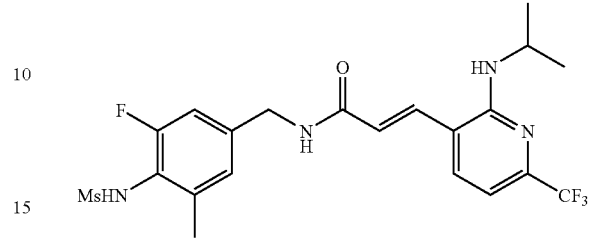

N-(4-Aminomethyl-2-fluoro-6-methyl-phenyl)-methanesulfonamide, HCl salt (71 mg, 0.26 mmol) was reacted with 3-(2-isopropylamino-6-trifluoromethyl-pyridin-3-yl)-acrylic acid (55 mg, 0.20 mmol) to give the title compound (88 mg, 90%) after purification by crystallization from Hex/EtOAc.

$^1$H NMR (300 MHz, DMSO-d6): δ 9.25 (bs, 1H), 8.64 (t, 1H), 7.75 (d, 1H, J=7.5 Hz), 7.62 (d, 1H, J=15.3 Hz), 7.14 (m, 2H), 6.95 (d, 1H, J=6.6 Hz), 6.80 (d, 1H, J=7.5 Hz), 6.62 (d, 1H, J=15.3 Hz), 4.41 (d, 2H, J=5.4 Hz), 4.21 (m, 1H), 2.99 (s, 3H), 2.21 (s, 3H), 1.18 (d, 6H, J=6.3 Hz).
ESI [M+H]+: 489

EXAMPLE 221

N-(3-Ethynyl-5-fluoro-4-methanesulfonylamino-benzyl)-3-(2-propylamino-6-trifluoromethyl-pyridin-3-yl)-acrylamide

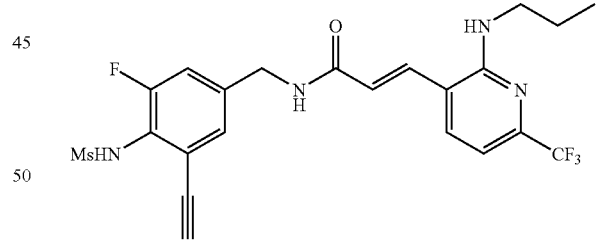

N-(4-Aminomethyl-6-ethynyl-2-fluoro-phenyl)-methanesulfonamide, HCl salt (106 mg, 0.39 mmol) was reacted with 3-(2-propylamino-6-trifluoromethyl-pyridin-3-yl)-acrylic acid (70 mg, 0.26 mmol) to give the title compound (86 mg, 66%) after purification by column chromatography (Hex/EtOAc=1/2).

$^1$H NMR (300 MHz, DMSO-d6): δ 9.45 (bs, 1H), 8.74 (t, 1H, J=5.7 Hz), 7.79 (d, 1H, J=7.5 Hz), 7.60 (d, 1H, J=15.3 Hz), 7.29 (m, 2H), 7.15 (m, 1H), 6.95 (d, 1H, J=7.5 Hz), 6.63 (d, 1H, J=15.3 Hz), 4.52 (s, 1H), 4.39 (d, 2H, J=5.7 Hz), 3.30 (m, 2H), 3.07 (s, 3H), 1.58 (m, 2H), 0.87 (t, 3H, J=7.5 Hz).
ESI [M+H]+: 499

EXAMPLE 222

N-(3,5-Difluoro-4-methanesulfonylamino-benzyl)-3-(2-propylamino-6-trifluoromethyl-pyridin-3-yl)-acrylamide

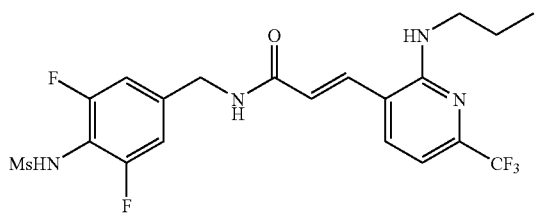

N-(4-Aminomethyl-2,6-difluoro-phenyl)-methanesulfonamide, HCl salt (92 mg, 0.34 mmol) was reacted with 3-(2-propylamino-6-trifluoromethyl-pyridin-3-yl)-acrylic acid (70 mg, 0.26 mmol) to give the title compound (74 mg, 58%) after purification by column chromatography (Hex/EtOAc=1/2).

$^1$H NMR (300 MHz, DMSO-d6): δ 9.49 (bs, 1H), 8.75 (t, 1H, J=6.0 Hz), 7.79 (d, 1H, J=7.5 Hz), 7.60 (d, 1H, J=15.3 Hz), 7.13 (m, 3H), 6.95 (d, 1H, J=7.5 Hz), 6.64 (d, 1H, J=15.3 Hz), 4.41 (d, 2H, J=6.0 Hz), 3.30 (m, 2H), 3.04 (s, 3H), 1.58 (m, 2H), 0.88 (t, 3H, J=7.5 Hz).

ESI [M+H]+: 493

EXAMPLE 223

N-(3-Fluoro-4-methanesulfonylamino-5-methyl-benzyl)-3-(2-propylamino-6-trifluoromethyl-pyridin-3-yl)-acrylamide

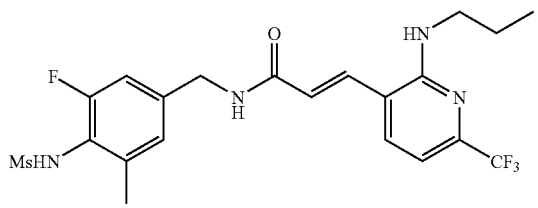

N-(4-Aminomethyl-2-fluoro-6-methyl-phenyl)-methanesulfonamide, HCl salt (91 mg, 0.34 mmol) was reacted with 3-(2-propylamino-6-trifluoromethyl-pyridin-3-yl)-acrylic acid (70 mg, 0.26 mmol) to give the title compound (98 mg, 77%) after purification by crystallization from Hex/EtOAc.

$^1$H NMR (300 MHz, DMSO-d6): δ 9.27 (bs, 1H), 8.64 (t, 1H), 7.75 (d, 1H, J=7.2 Hz), 7.58 (d, 1H, J=15.6 Hz), 7.15 (m, 3H), 6.95 (d, 1H, J=7.8 Hz), 6.63 (d, 1H, J=15.6 Hz), 4.40 (d, 2H, J=5.4 Hz), 3.27 (m, 2H), 2.97 (s, 3H), 2.21 (s, 3H), 1.57 (m, 2H), 0.87 (t, 3H, J=7.2 Hz).

EXAMPLE 224

(R)-N-[1-(3-Fluoro-4-methane sulfonylamino-phenyl)-ethyl]-3-(2-propylamino-6-trifluoromethyl-pyridin-3-yl)-acrylamide

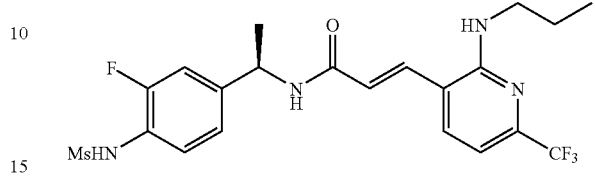

(R)-N-[4-(1-Aminoethyl)-2-fluoro-phenyl]-methanesulfonamide, HCl salt (91 mg, 0.34 mmol) was reacted with 3-(2-propylamino-6-trifluoromethyl-pyridin-3-yl)-acrylic acid (70 mg, 0.26 mmol) to give the title compound (106 mg, 83%) after purification by crystallization from Hex/EtOAc.

$^1$H NMR (300 MHz, DMSO-d6): δ 9.50 (bs, 1H), 8.64 (d, 1H, J=7.5 Hz), 7.76 (d, 1H, J=7.5 Hz), 7.55 (d, 1H, J=15.6 Hz), 7.25 (m, 4H), 6.95 (d, 1H, J=8.1 Hz), 6.63 (d, 1H, J=15.6 Hz), 5.03 (t, 1H, J=7.2 Hz), 3.27 (m, 2H), 3.00 (s, 3H), 1.56 (m, 2H), 1.40 (d, 3H, J=6.6 Hz), 0.86 (t, 3H, J=7.5 Hz).

EXAMPLE 225

N-(4-Methanesulfonylamino-3-methyl-benzyl)-3-(2-propylamino-6-trifluoromethyl-pyridin-3-yl)-acrylamide

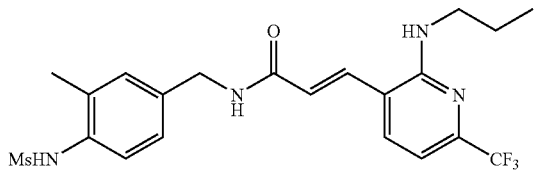

N-(4-Aminomethyl-2-methyl-phenyl)-methanesulfonamide, HCl salt (93 mg, 0.34 mmol) was reacted with 3-(2-propylamino-6-trifluoromethyl-pyridin-3-yl)-acrylic acid (70 mg, 0.26 mmol) to give the title compound (85 mg, 69%) after purification by crystallization from Hex/EtOAc.

$^1$H NMR (300 MHz, DMSO-d6): δ 9.12 (bs, 1H), 8.64 (t, 1H), 7.76 (d, 1H, J=7.8 Hz), 7.58 (d, 1H, J=15.6 Hz), 7.25 (m, 4H), 6.95 (d, 1H, J=7.8 Hz), 6.63 (d, 1H, J=15.6 Hz), 4.36 (d, 2H, J=4.2 Hz), 3.30 (m, 2H), 2.92 (s, 3H), 2.29 (s, 3H), 1.57 (m, 2H), 0.87 (t, 3H, J=7.2 Hz).

EXAMPLE 226

N-(3,5-Difluoro-4-methanesulfonylamino-benzyl)-3-(2-isobutyl-6-trifluoromethyl-pyridin-3-yl)-acrylamide

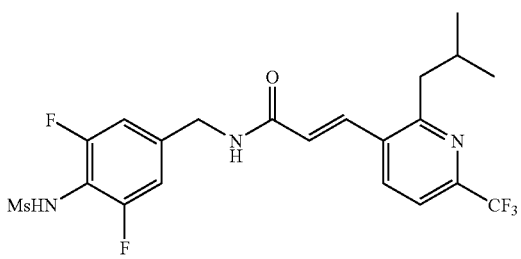

N-(4-Aminomethyl-2,6-difluoro-phenyl)-methanesulfonamide, HCl salt (30 mg, 0.11 mmol) was reacted with 3-(2-isobutyl-6-trifluoromethyl-pyridin-3-yl)-acrylic acid (20 mg, 0.73 mmol) to give the title compound (30 mg, 84%) after purification by column chromatography (Hex/EtOAc=1/2).

$^1$H NMR (300 MHz, DMSO-d6): δ 9.50 (bs, 1H), 8.88 (t, 1H), 8.19 (d, 1H, J=8.1 Hz), 7.80 (d, 1H, J=7.8 Hz), 7.73 (d, 1H, J=15.6 Hz), 7.13 (d, 2H, J=8.7 Hz), 6.75 (d, 1H, J=15.6 Hz), 4.43 (d, 2H, J=5.4 Hz), 3.05 (s, 3H), 2.83 (d, 2H, J=6.9 Hz), 2.01 (m, 1H), 0.88 (t, 3H, J=6.6 Hz).

EXAMPLE 227

(R)—N-[1-(3,5-Difluoro-4-methane sulfonylamino-phenyl)-ethyl]-3-(2-isopropylamino-6-trifluoromethyl-pyridin-3-yl)-acrylamide

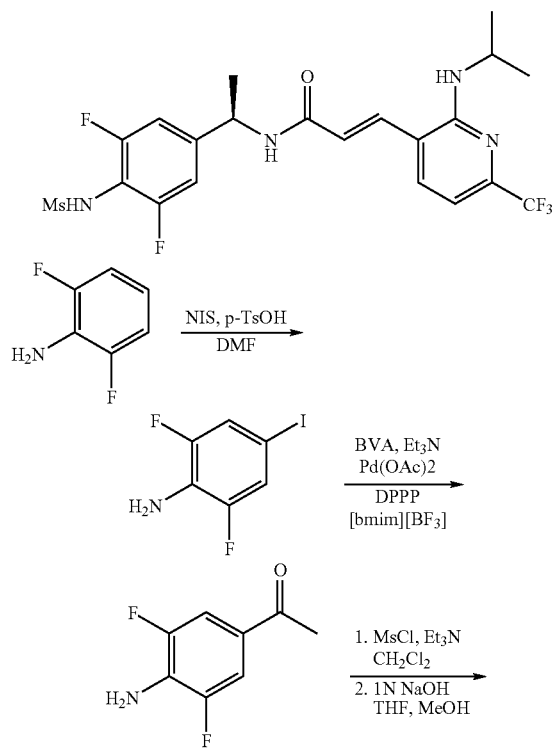

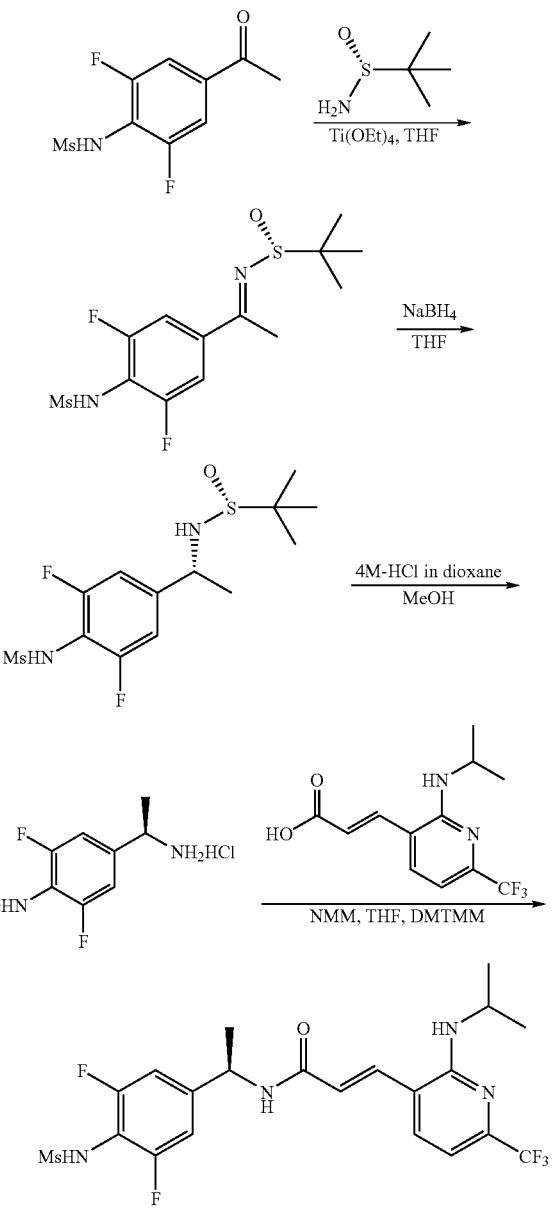

Step 1: Synthesis of 2,6-difluoro-4-iodoaniline

To a solution of 2,6-difluoroaniline (5.0 g, 38.7 mmol) and p-toluenesulfonic acid (1.45 g, 7.62 mmol) in DMF (70 mL) was added dropwise N-iodosuccinimide (9.6 g, 42.7 mmol) dissolved in DMF (50 mL) at 5° C. The mixture was stirred for 2.5 hours at room temperature. The mixture was concentrated under reduced pressure, and then diluted with EtOAc and water. The organic layer was washed with saturated aqueous sodium thiosulfate and brine, dried over anhydrous magnesium sulfate, filtered, and concentrated under reduced pressure. The crude residue was purified by crystallization from EtOAc and hexane to give 2,6-difluoro-4-iodoaniline (9.12 g, 92.4%).

¹H NMR (300 MHz, CDCl₃): δ 7.16 (d, 1H, J=1.8 Hz), 7.14 (d, 1H, J=1.8 Hz), 3.76 (br s, 2H)

Step 2: Synthesis of
1-(4-amino-3,5-difluoro-phenyl)-ethanone

A suspension of 2,6-difluoro-4-iodoaniline (1 g, 3.92 mmol) and Pd(OAc)₂ (0.025 eq), DPPP (0.05 eq) in [bmim][3F3] (6 mL) was stirred for 10 min. After the mixture was degassed three times, butyl vinyl ether (5 eq) and Et₃N (1.2 eq) were injected sequentially. The mixture was stirred for 15 hrs at 115° C. The mixture cooled to room temperature, and then was added 1N-HCl. After the mixture was stirred for 0.5 hour, CH₂Cl₂ was added. The organic layer was washed with brine, dried over anhydrous magnesium sulfate, filtered, and concentrated under reduced pressure. The crude residue was purified by chromatography to give 1-(4-amino-3,5-difluoro-phenyl)-ethanone (300 mg, 45%).

¹H NMR (300 MHz, CDCl₃): δ 7.15 (d, 1H, J=1.2 Hz), 7.13 (d, 1H, J=1.2 Hz), 3.76 (s, 2H, br).

Step 3: Synthesis of
N-(4-acetyl-2,6-difluoro-phenyl)-methane
sulfonamide

To a solution of 1-(4-amino-3,5-difluoro-phenyl)-ethanone (2.35 g, 13.73 mmol) and Et₃N (2 mL) in CH₂Cl₂ (10 mL) was added dropwise MsCl (2.34 mL, 2.34 mmol) at 0° C. The mixture was stirred for 3 hours at room temperature. The mixture was then diluted with EtOAc and 1N-HCl. The organic layer was washed with water and brine, dried over anhydrous magnesium sulfate, filtered, and concentrated under reduced pressure. The crude product was used directly in the following reaction. The crude residue was dissolved in THF (8 mL), after then was added 1N NaOH (4 mL) and CH₃OH (4 mL) to the solution. After stirred for 5 hrs at room temperature, the mixture was diluted with EtOAc and 1N-HCl. The organic layer was washed with water and brine, dried over anhydrous magnesium sulfate, filtered, and concentrated under reduced pressure. The crude residue was purified by chromatography to afford N-(4-acetyl-2,6-difluoro-phenyl)-methanesulfonamide (1.85 g, 54%).

¹H NMR (300 MHz, CDCl₃): δ 7.60 (d, 1H, J=3.3 Hz), 7.56 (d, 1H, J=3.3 Hz), 6.43 (s, 1H), 3.89 (s, 3H), 3.58 (s, 3H).

Step 4: Synthesis of N-{2,6-difluoro-4-[1-(2-methyl-propane-2-sulfinylamino)-ethyl]-phenyl}-methane-sulfonamide To a solution of N-(4-acetyl-2,6-difluoro-phenyl)-methanesulfonamide (1.84 g, 7.38 mmol) and (R)-(+)-2-methyl-2-propanesulfinamide (1.07 g, 8.86 mL) in THF (15 mL) was added dropwise Ti(OEt)₄ (2.61 mL, 12.6 mmol) at room temperature. The mixture was stirred overnight at 90° C. The mixture cooled to room temperature and then was added brine. After the mixture was extracted three times with EtOAc, dried over anhydrous magnesium sulfate, filtered, and concentrated under reduced pressure. The crude residue was purified by chromatography to yield N-{2,6-difluoro-4-[1-(2-methyl-propane-2-sulfinylimino)-ethyl]-phenyl}-methanesulfonamide (2.2 g, 85%). To a solution of N-{2,6-difluoro-4-[1-(2-methyl-propane-2-sulfinylimino)-ethyl]-phenyl}-methanesulfonamide (2.2 g, 6.24 mmol) in THF (20 mL) was added portionwise NaBH₄ (944 mg, 24.9 mmol) dissolved in THF (2 mL) at −48° C. The mixture was stirred for 10 hours at −48° C. room temperature, and then CH₃OH was added dropwise until gas was no longer evolved. The mixture was concentrated under reduced pressure, and then was purified by chromatography to afford N-{2,6-difluoro-4-[1-(2-methyl-propane-2-sulfinylamino)-ethyl]-phenyl}-methanesulfonamide (1.89 g, 50%).

¹H NMR (300 MHz, CDCl₃): δ 7.04 (d, 1H, J=2.4 Hz), 6.99 (d, 1H, J=2.4 Hz), 6.59 (s, 1H), 4.54-4.49 (m, 1H), 3.53 (d, 1H, J=3.6 Hz), 3.20 (s, 3H), 1.50 (d, 3H, 6.6 Hz), 1.23 (s, 9H)

Step 5: Synthesis of (R)—N-[4-(1-amino-ethyl)-2,6-difluoro-phenyl]-methanesulfonamide, HCl salt To a solution of N-{2,6-difluoro-4-[1-(2-methyl-propane-2-sulfinylamino)-ethyl]-phenyl}-methanesulfonamide (789 mg, 2.22 mmol) in CH₃OH (8 mL) was added dropwise 4-M HCl in dioxane (2 ml) at room temperature. The mixture was stirred for 30 mins at room temperature, and then was concentrated under reduced pressure. The crude residue was purified by crystallization form CH₂Cl₂ and Et₂O to give (R)—N-[4-(1-amino-ethyl)-2,6-difluoro-phenyl]-methanesulfonamide, HCl salt (611 g, 96%).

¹H NMR (300 MHz, DMSO): δ 8.73 (s, 3H, br), 7.48 (d, 1H, J=2.7 Hz), 7.43 (d, 1H, J=2.7 Hz), 4.43 (q, 1H, J=3.6 Hz), 3.53 (d, 1H, J=3.6 Hz), 3.07 (s, 3H), 1.51 (d, 3H, 6.9 Hz).

Step 6: Synthesis of (R)—N-[1-(3,5-difluoro-4-methanesulfonylamino-phenyl)-ethyl]-3-(2-isopropylamino-6-trifluoromethyl-pyridin-3-yl)-acrylamide (R)—N-[4-(1-Aminoethyl)-2,6-difluoro-phenyl]-methanesulfonamide, HCl salt (70 mg, 0.24 mmol) was reacted with 3-(2-isopropylamino-6-trifluoromethyl-pyridin-3-yl)-acrylic acid (67 mg, 0.24 mmol) to give the title compound (108 mg, 89%) after purification by crystallization from ether.

¹H NMR (300 MHz, DMSO-d6): δ 9.49 (bs, 1H), 8.68 (d, 1H, J=7.8 Hz), 7.78 (d, 1H, J=7.5 Hz), 7.57 (d, 1H, J=15.3 Hz), 7.17 (d, 2H, J=9.0 Hz), 6.96 (d, 1H, J=7.8 Hz), 6.82 (d, 1H, J=7.5 Hz), 6.62 (d, 1H, J=15.3 Hz), 5.03 (m, 1H), 4.22 (m, 1H), 3.04 (s, 3H), 1.40 (d, 3H, J=6.9 Hz), 1.17 (dd, 6H, J=2.4 and 6.3 Hz).

ESI [M+H]+: 507

EXAMPLE 228

(R)-3-(2-Butyl-6-trifluoromethyl-pyridin-3-yl)-N-[1-(3,5-difluoro-4-methanesulfonylamino-phenyl)-ethyl]-acrylamide

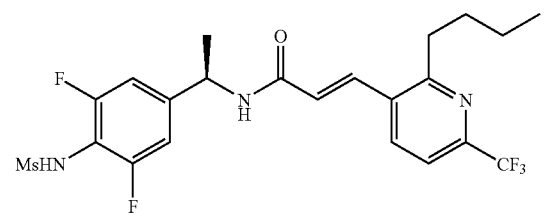

(R)—N-[4-(1-Aminoethyl)-2,6-difluoro-phenyl]-methanesulfonamide, HCl salt (70 mg, 0.24 mmol) was reacted with 3-(2-butyl-6-trifluoromethyl-pyridin-3-yl)-acrylic acid (67 mg, 0.24 mmol) to give the title compound (115 mg, 95%) after purification by crystallization from ether.

¹H NMR (300 MHz, DMSO-d6): δ 9.50 (bs, 1H), 8.80 (d, 1H, J=7.5 Hz), 8.16 (d, 1H, J=8.1 Hz), 7.80 (d, 1H, J=8.4 Hz), 7.67 (d, 1H, J=15.6 Hz), 7.17 (d, 2H, J=8.4 Hz), 6.75 (d, 1H,

J=15.6 Hz), 5.04 (m, 1H), 3.03 (s, 3H), 2.93 (m, 2H), 1.61 (m, 2H), 1.41 (d, 3H, J=6.9 Hz), 1.36 (m, 2H), 0.90 (t, 3H, J=7.2 Hz).

ESI [M+H]+: 506

EXAMPLE 229

(R)—N-[1-(3,5-Difluoro-4-methanesulfonylamino-phenyl)-ethyl]-3-(2-propylamino-6-trifluoromethyl-pyridin-3-yl)-acrylamide

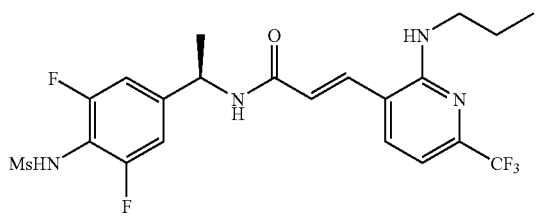

(R)—N-[4-(1-Aminoethyl)-2,6-difluoro-phenyl]-methanesulfonamide, HCl salt (60 mg, 0.21 mmol) was reacted with 3-(2-propylamino-6-trifluoromethyl-pyridin-3-yl)-acrylic acid (56 mg, 0.20 mmol) to give the title compound (95 mg, 95%) after purification by crystallization from ether.

$^1$H NMR (300 MHz, DMSO-d6): δ 9.50 (bs, 1H), 8.68 (d, 1H, J=7.8 Hz), 7.78 (d, 1H, J=7.8 Hz), 7.55 (d, 1H, J=15.3 Hz), 7.16 (m, 3H), 6.96 (d, 1H, J=7.5 Hz), 6.63 (d, 1H, J=15.3 Hz), 5.03 (m, 1H), 3.28 (m, 2H), 3.04 (s, 3H), 1.56 (m, 2H), 1.40 (d, 3H, J=6.5 Hz), 0.87 (t, 3H, J=7.2 Hz).

ESI [M+H]+: 507

EXAMPLE 230

(R)—N-[1-(3,5-Difluoro-4-methanesulfonylamino-phenyl)-ethyl]-3-(2-propyl-6-trifluoromethyl-pyridin-3-yl)-acrylamide

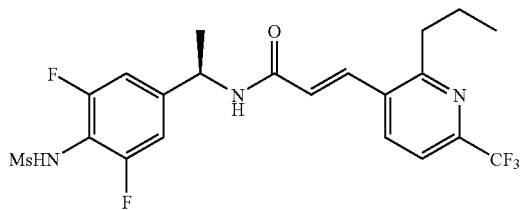

(R)—N-[4-(1-Aminoethyl)-2,6-difluoro-phenyl]-methanesulfonamide, HCl salt (62 mg, 0.22 mmol) was reacted with 3-(2-propyl-6-trifluoromethyl-pyridin-3-yl)-acrylic acid (56 mg, 0.22 mmol) to give the title compound (81 mg, 73%) after purification by crystallization from ether.

$^1$H NMR (300 MHz, DMSO-d6): δ 9.50 (bs, 1H), 8.81 (d, 1H, J=7.8 Hz), 8.16 (d, 1H, J=8.4 Hz), 7.80 (d, 1H, J=7.8 Hz), 7.67 (d, 1H, J=15.6 Hz), 7.18 (d, 2H, J=7.2 Hz), 6.76 (d, 1H, J=15.6 Hz), 5.04 (m, 1H), 3.05 (s, 3H), 2.91 (m, 2H), 1.65 (m, 2H), 1.41 (d, 3H, J=6.9 Hz), 0.92 (t, 3H, J=7.2 Hz).

ESI [M+H]+: 492

EXAMPLE 231

N-(3-Ethynyl-5-fluoro-4-methanesulfonylamino-benzyl)-3-(2-isopropyl-6-trifluoromethyl-pyridin-3-yl)-acrylamide

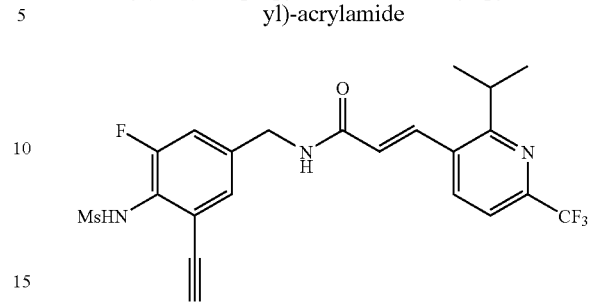

N-(4-Aminomethyl-6-ethynyl-2-fluoro-phenyl)-methanesulfonamide, HCl salt (75 mg, 0.27 mmol) was reacted with 3-(2-isopropyl-6-trifluoromethyl-pyridin-3-yl)-acrylic acid (70 mg, 0.27 mmol) to give N-(3-ethynyl-5-fluoro-4-methanesulfonylamino-benzyl)-3-(2-isopropyl-6-trifluoromethyl-pyridin-3-yl)-acrylamide (54 mg, 42%) after purification by recrystallization (Hex/EtOAc)

$^1$H NMR (300 MHz, CDCl$_3$) δ 8.04 (d, 1H, J=15.6 Hz), 7.85 (d, 1H, J=7.8 Hz), 7.49 (d, 1H, J=8.4 Hz), 7.31 (s, 1H), 7.19 (m, 1H), 6.41 (s, 1H), 6.35 (d, 1H, J=15.6 Hz), 6.02 (bs, 1H), 4.55 (d, 2H, J=5.7 Hz), 3.49 (s, 1H), 3.48 (m, 1H), 3.27 (s, 3H), 1.32 (s, 3H), 1.29 (s, 3H).

ESI [M+H]+: 484

EXAMPLE 232

N-(3,5-Difluoro-4-methanesulfonylamino-benzyl)-3-(2-isopropyl-6-trifluoromethyl-pyridin-3-yl)-acrylamide

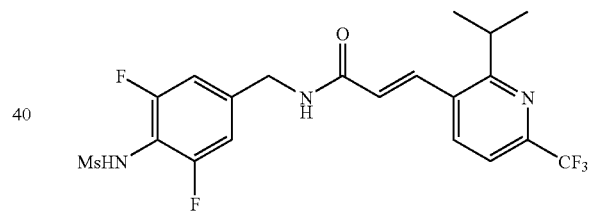

N-(4-Aminomethyl-2,6-difluoro-phenyl)-methanesulfonamide, HCl salt (74 mg, 0.27 mmol) was reacted with 3-(2-isopropyl-6-trifluoromethyl-pyridin-3-yl)-acrylic acid (70 mg, 0.27 mmol) to give the title compound (46 mg, 36%) after purification by recrystallization (Hex/EtOAc)

$^1$H NMR (300 MHz, DMSO-d$_6$): δ 9.60 (s, 1H), 8.89 (t, 1H, J=6.0 Hz), 8.15 (d, 1H, J=8.4 Hz), 7.78 (m, 2H), 7.13 (d, 1H, J=8.4 Hz), 6.72 (d, 1H, J=15.9 Hz), 4.43 (d, 2H, J=5.7 Hz), 3.47 (m, 1H), 3.04 (s, 3H), 1.24 (s, 3H), 1.21 (s, 3H)

EXAMPLE 233

N-(4-methanesulfonylamino-3-methyl-benzyl)-3-(2-isopropyl-6-trifluoromethyl-pyridin-3-yl)-acrylamide

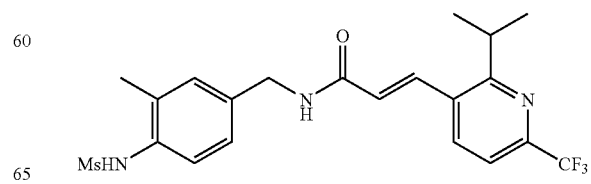

N-(4-Aminomethyl-2-methyl-phenyl)-methanesulfonamide, HCl salt (74 mg, 0.27 mmol) was reacted with 3-(2- isopropyl-6-trifluoromethyl-pyridin-3-yl)-acrylic acid (74 mg, 0.27 mmol) to give the title compound (61 mg, 50%) after purification by recrystallization (Hex/EtOAc)

$^1$H NMR (300 MHz, CDCl$_3$): δ 8.03 (d, 1H, J=15.6 Hz), 7.83 (d, 1H, J=8.1 Hz), 7.45 (m, 2H), 7.22 (s, 1H), 7.19 (s, 1H), 6.34 (d, 1H, J=15.3 Hz), 6.19 (s, 1H), 5.98 (s, 1H), 4.54 (d, 2H, J=6.0 Hz), 3.47 (m, 1H), 3.03 (s, 3H), 2.32 (s, 3H), 1.31 (s, 3H), 1.29 (s, 3H)

EXAMPLE 234

(R)—N-[1-(3-Fluoro-4-methanesulfonylamino-phenyl)-ethyl]-3-(2-isopropyl-6-trifluoromethyl-pyridin-3-yl)-acrylamide

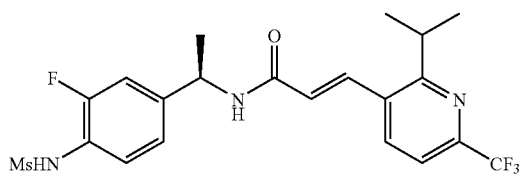

(R)—N-[4-(1-Amino-ethyl)-2-fluoro-phenyl]-methanesulfonamide, HCl salt (73 mg, 0.27 mmol) was reacted with 3-(2-isopropyl-6-trifluoromethyl-pyridin-3-yl)-acrylic acid (70 mg, 0.27 mmol) to give the title compound (69 mg, 54%) after purification by recrystallization (Hex/EtOAc)

$^1$H NMR (300 MHz, CDCl$_3$): δ 8.49 (d, 1H, J=15.6 Hz), 7.83 (d, 1H, J=8.1 Hz), 7.51 (m, 2H), 7.17 (m, 2H), 6.50 (s, 1H), 6.34 (d, 1H, J=15.9 Hz), 5.87 (bs, 1H), 5.21 (bs, 1H), 3.90 (d, 1H, J=5.1 Hz), 3.44 (m, 1H), 3.04 (s, 3H), 1.54 (s, 3H), 1.29 (s, 3H), 1.27 (s, 3H)

ESI [M+H]+: 474

EXAMPLE 235

N-(3,5-Difluoro-4-methanesulfonylamino-benzyl)-3-(2-sec-butyl-6-trifluoromethyl-pyridin-3-yl)-acrylamide

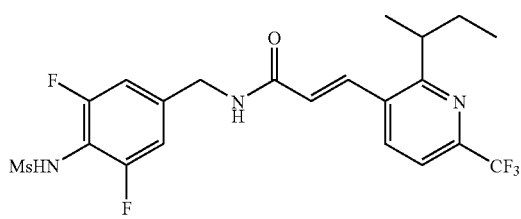

N-(4-Aminomethyl-2,6-difluoro-phenyl)-methanesulfonamide, HCl salt (89 mg, 0.33 mmol) was reacted with 3-(2-sec-butyl-6-trifluoromethyl-pyridin-3-yl)-acrylic acid (89 mg, 0.33 mmol) to give the title compound (33 mg, 20%) after purification by recrystallization (Hex/EtOAc=2:3)

$^1$H NMR (300 MHz, CDCl$_3$): δ 8.05 (d, 1H, J=15.6 Hz), 7.86 (d, 1H, J=7.8 Hz), 7.49 (d, 1H, J=7.8 Hz), 7.00 (d, 2H, J=7.8 Hz), 6.35 (d, 1H, J=15.3 Hz), 6.03 (bs, 2H), 4.57 (d, 2H, J=6.0 Hz), 3.22 (s, 3H), 1.88 (m, 2H), 1.66 (m, 1H), 1.27 (d, 2H, J=6.6 Hz), 0.82 (t, 3H, J=7.5 Hz)

EXAMPLE 236

(R)—N-[1-(3,5-Difluoro-4-methanesulfonylamino-phenyl)-ethyl]-3-(2-phenethyl-6-trifluoromethyl-pyridin-3-yl)-acrylamide

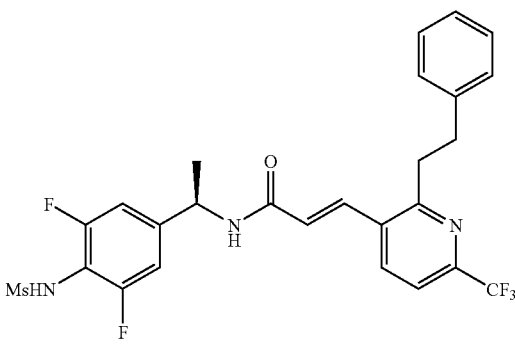

(R)—N-[4-(1-Amino-ethyl)-2,6-difluoro-phenyl]-methanesulfonamide, HCl salt (61.8 mg, 0.215 mmol) was reacted with NMM (0.10 ml), DMTMM (93 mg) and 3-(2-phenethyl-6-trifluoromethyl-pyridin-3-yl)-acrylic acid (67 mg, 0.208 mmol) to give the title compound (98.3 mg, 85%) after purification by column chromatography (Hex/EtOAc=2/3).

$^1$H NMR (300 MHz, CDCl$_3$): δ 7.84 (d, 1H, J=7.8 Hz), 7.76 (d, 1H, J=15.6 Hz), 7.51 (d, 1H, J=7.8 Hz), 7.19 (m, 4H), 6.95 (d, 1H, J=8.1 Hz), 6.48 (s, 1H), 6.27 (d, 1H, J=15.6 Hz), 6.12 (d, 1H), 5.14 (m, 1H), 3.24 (t, 2H, J=6.3 Hz), 3.18 (s, 3H), 3.07 (t, 2H, J=8.4 Hz).

EXAMPLE 237

(R)—N-[1-(3-Fluoro-4-methanesulfonylamino-phenyl)-ethyl]-3-(2-phenethyl-6-trifluoromethyl-pyridin-3-yl)-acrylamide

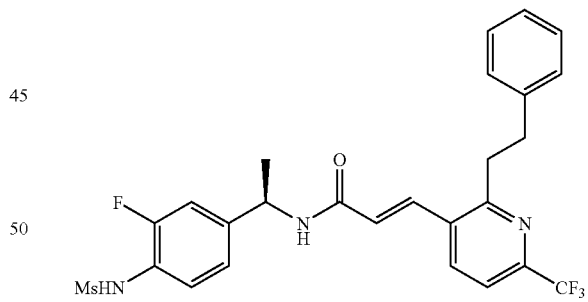

(R)—N-[4-(1-Amino-ethyl)-2-fluoro-phenyl]-methanesulfonamide, HCl salt (61.4 mg, 0.228 mmol) was reacted with NMM (0.10 ml), DMTMM (97 mg) and 3-(2-phenethyl-6-trifluoromethyl-pyridin-3-yl)-acrylic acid (72 mg, 0.224 mmol) to give the title compound (80.8 mg, 67%) after purification by column chromatography (Hex/EtOAc=2/3).

$^1$H NMR (300 MHz, CDCl$_3$): δ 7.83 (d, 1H, J=8.1 Hz), 7.76 (d, 1H, J=15.3 Hz), 7.55 (m, 2H), 7.19 (m, 5H), 6.528 (s, 1H), 6.22 (d, 1H, J=15.3 Hz), 5.83 (d, 1H, J=7.5 Hz), 5.20 (m, 1H J=6.9 Hz), 3.25 (t, 2H, J=7.8 Hz), 3.07 (t, 2H, J=7.8 Hz), 3.02 (s, 3H).

ESI [M+H]+: 554

EXAMPLE 238

(R)-3-(2-Butylamino-6-trifluoromethyl-pyridin-3-yl)-N-[(1R)-(3,5-difluoro-4-methanesulfonylamino-phenyl)-ethyl]-acrylamide

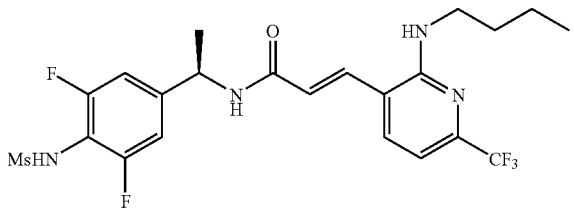

(R)—N-[4-(1-Aminoethyl)-2,6-difluoro-phenyl]-methanesulfonamide, HCl salt (80 mg, 0.28 mmol) was reacted with 3-(2-butylamino-6-trifluoromethyl-pyridin-3-yl)-acrylic acid (96 mg, 0.33 mmol) to give the title compound (140 mg, 96%) after purification by crystallization from ether.

$^1$H NMR (300 MHz, DMSO): δ 9.49 (s, 1H), 8.68 (d, 1H, J=7.2 Hz), 7.77 (d, 1H, J=7.2 Hz), 7.54 (d, 1H, J=15.3 Hz), 7.19-7.12 (m, 3H), 6.95 (d, 1H, J=7.8 Hz), 6.63 (d, 1H, J=15.6 Hz), 5.05-5.01 (m, 1H), 3.34-3.26 (m, 2H), 3.05 (s, 3H), 1.55-1.45 (m, 2H), 1.40 (d, 3H, J=5.7 Hz), 0.88 (t, 3H, J=7.5 Hz).

ESI [M+H]+: 521

EXAMPLE 239

(R)—N-[1-(3,5-Difluoro-4-methanesulfonylamino-phenyl)-ethyl]-3-(2-piperid-1-yl-6-trifluoromethyl-pyridin-3-yl)-acrylamide

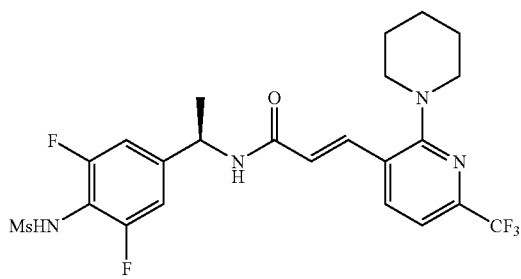

(R)—N-[4-(1-Aminoethyl)-2,6-difluoro-phenyl]-methanesulfonamide, HCl salt (80 mg, 0.28 mmol) was reacted with 3-(2-piperid-1-yl-6-trifluoromethyl-pyridin-3-yl)-acrylic acid (100 mg, 0.33 mmol) to give the title compound (140 mg, 95%) after purification by crystallization from ether.

$^1$H NMR (300 MHz, DMSO): δ 9.95 (s, 1H), 8.68 (d, 1H, J=7.5 Hz), 7.99 (d, 1H, J=7.5 Hz), 7.42 (d, 1H, J=7.2 Hz), 7.41 (d, 1H, J=15.0 Hz), 7.25-7.15 (m, 3H), 6.74 (d, 1H, J=15.6 Hz), 5.06-5.02 (m, 1H), 3.32 (s, 4H, br), 3.05 (s, 3H), 1.61 (s, 5H, br), 1.40 (t, 3H, J=5.1 Hz).

ESI [M+H]+: 533

EXAMPLE 240

(S)-3-(2-Butylamino-6-trifluoromethyl-pyridin-3-yl)-N-[(1S)-(3,5-difluoro-4-methanesulfonylamino-phenyl)-ethyl]-acrylamide

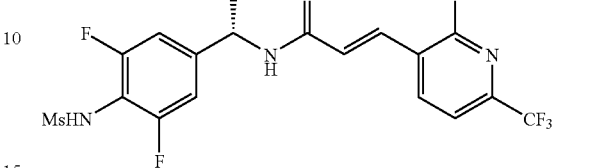

(S)—N-[4-(1-Aminoethyl)-2,6-difluoro-phenyl]-methanesulfonamide, HCl salt (40 mg, 0.14 mmol) was reacted with 3-(2-butylamino-6-trifluoromethyl-pyridin-3-yl)-acrylic acid (48 mg, 0.16 mmol) to give the title compound (57 mg, 80%) after purification by crystallization from ether.

$^1$H NMR (300 MHz, DMSO): δ 9.49 (s, 1H), 8.68 (d, 1H, J=7.5 Hz), 7.77 (d, 1H, J=7.5 Hz), 7.54 (d, 1H, J=15.3 Hz), 7.19-7.14 (m, 3H), 6.95 (d, 1H, J=7.8 Hz), 6.63 (d, 1H, J=15.3 Hz), 5.05-5.00 (m, 1H), 3.34-3.29 (m, 2H), 3.05 (s, 3H), 1.58-1.48 (m, 2H), 1.40 (d, 3H, J=6.9 Hz), 0.88 (t, 3H, J=7.5 Hz).

ESI [M+H]+: 521

EXAMPLE 241

(R)-3-(2-sec-Butyl-6-trifluoromethyl-pyridin-3-yl)-N-1-(4-methane sulfonylamino-3-methyl-benzyl)-acrylamide

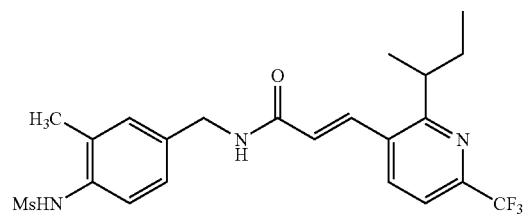

N-(4-Aminomethyl-2-methyl-phenyl)-methanesulfonamide, HCl salt (98 mg, 0.359 mmol) was reacted with NMM (0.10 ml), DMTMM (99 mg) and 3-(2-sec-butyl-6-trifluoromethyl-pyridin-3-yl)-acrylic acid (98 mg, 0.359 mmol) to give the title compound (25 mg, 15%) after purification by column chromatography (Hex EtOAc=1/1).

$^1$H NMR (300 MHz, CDCl$_3$): δ 8.03 (d, 1H, J=15 Hz), 7.84 (d, 1H, J=7.8 Hz), 7.45 (m, 2H), 7.22 (s, 1H), 6.99 (bs, 1H), 6.33 (d, 1H, J=15.3 Hz), 6.20 (s, 1H), 4.54 (d, 2H, J=5.7 Hz), 3.21 (m, 1H), 3.03 (s, 3H), 2.32 (s, 3H), 1.85 (m, 1H), 1.66 (m, 1H), 1.26 (d, 3H, J=6.6 Hz), 0.81 (t, 3H, J=7.2 Hz)

EXAMPLE 242

(R)—N-[1-(3,5-Difluoro-4-methane sulfonylamino-phenyl)-ethyl]-3-(2-isopropyl-6-trifluoromethyl-pyridin-3-yl)-acrylamide

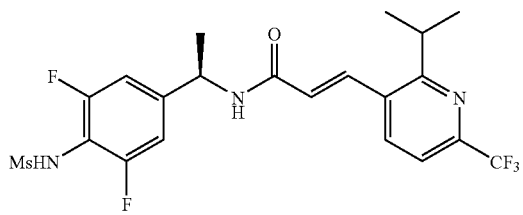

(R)—N-[4-(1-Amino-ethyl)-2,6-difluoro-phenyl]-methanesulfonamide, HCl salt (77 mg, 0.27 mmol) was reacted with NMM (0.10 ml), DMTMM (90 mg) and 3-(2-isopropyl-6-trifluoromethyl-pyridin-3-yl)-acrylic acid (70 mg, 0.27 mmol) to give the title compound (75 mg, 57%) after purification by column chromatography (Hex/EtOAc=1/1).

$^1$H NMR (300 MHz, CDCl$_3$): δ 7.99 (d, 1H, J=15.6 Hz), 7.85 (d, 1H, J=7.8 Hz), 7.49 (d, 1H, J=8.1 Hz), 7.02 (s, 1H), 6.99 (s, 1H), 6.35 (d, 1H, J=15.3 Hz), 6.12 (s, 1H), 5.95 (d, 1H, J=7.2 Hz), 5.19 (m, 1H), 3.44 (m, 1H), 3.22 (s, 3H), 1.53 (d, 3H, J=6.6 Hz), 1.30 (s, 3H), 1.28 (s, 3H)

EXAMPLE 243

(R)-3-(2-sec-Butyl-6-trifluoromethyl-pyridin-3-yl)-N-[1-(3-fluoro-4-methanesulfonylamino-phenyl)-ethyl]-acrylamide

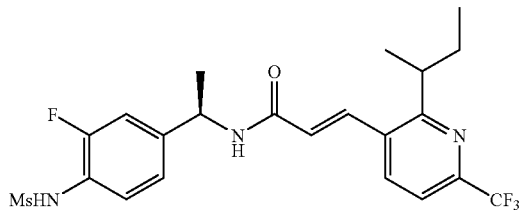

(R)—N-[4-(1-Amino-ethyl)-2-fluoro-phenyl]-methanesulfonamide, HCl salt (69 mg, 0.256 mmol) was reacted with NMM (0.10 ml), DMTMM (85 mg) and 3-(2-sec-butyl-6-trifluoromethyl-pyridin-3-yl)-acrylic acid (70 mg, 0.256 mmol) to give the title compound (40 mg, 32%) after purification by column chromatography (Hex EtOAc=1/1).

$^1$H NMR (300 MHz, CDCl$_3$): δ 8.00 (d, 1H, J=15.3 Hz), 7.84 (d, 1H, J=8.1 Hz), 7.56 (t, 1H, J=7.8 Hz), 7.48 (d, 1H, J=8.1 Hz), 7.19 (s, 1H), 7.16 (s, 1H), 6.46 (s, 1H), 6.32 (d, 1H, J=15.3 Hz), 5.85 (d, 1H, NH), 5.22 (m, 1H), 3.19 (m, 1H), 3.03 (s, 3H), 1.84 (m, 1H), 1.64 (m, 1H), 1.25 (dd, 3H, J=6.6 Hz, 1.2 Hz), 0.80 (m, 3H)

EXAMPLE 244

(R)—N-[1-(3,5-Difluoro-4-methane sulfonylamino-phenyl)-ethyl]-3-(2-ethylamino-6-trifluoromethyl-pyridin-3-yl)-acrylamide

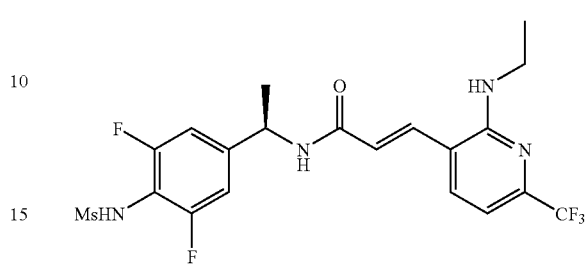

(R)—N-[4-(1-Amino-ethyl)-2,6-difluoro-phenyl]-methanesulfonamide, HCl salt (22 mg, 0.215 mmol) was reacted with NMM (0.10 ml), DMTMM (43 mg) and 3-(2-ethylamino-6-trifluoromethyl-pyridin-3-yl)-acrylic acid (21 mg, 0.081 mmol) to give the title compound (22 mg, 55%) after purification by column chromatography (Hex EtOAc=2/3).

$^1$H NMR (300 MHz, CDCl$_3$): δ 8.02 (d, 1H), 7.92 (d, 1H, J=15.3 Hz), 7.62 (m, 3H), 7.08 (d, 1H, J=7.8 Hz), 6.53 (d, 1H, J=15.3 Hz), 5.20 (m, 1H), 3.20 (m, 2H), 2.99 (s, 3H), 1.56 (m, 2H), 1.49 (d, 3H, J=6.5 Hz), 0.87 (t, 3H, J=7.2 Hz).

EXAMPLE 245

(R)—N-[1-(3,5-Difluoro-4-methanesulfonylamino-phenyl)-ethyl]-3-(2-isobutyl-6-trifluoromethyl-pyridin-3-yl)-acrylamide

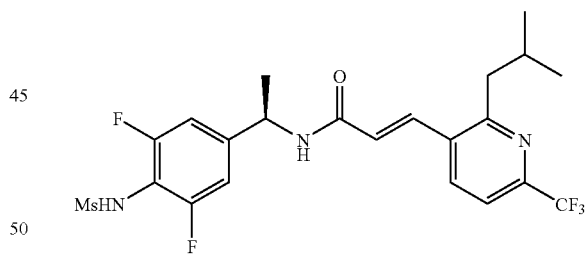

(R)—N-[4-(1-Amino-ethyl)-2,6-difluoro-phenyl]-methanesulfonamide, HCl salt (138 mg, 0.48 mmol) was reacted with NMM (0.11 ml), DMTMM (138 mg, 0.499 mmol) and 3-(2-isopropyl-6-trifluoromethyl-pyridin-3-yl)-acrylic acid (127 mg, 0.467 mmol) to give the title compound (178 mg, 74%) after purification by column chromatography (Hex/EtOAc=1/1).

$^1$H NMR (300 MHz, CDCl$_3$): δ 7.94 (d, 1H, J=4.2 Hz), 7.90 (d, 1H, J=2.7 Hz), 7.49 (d, 1H, J=8.1 Hz), 6.93 (d, 1H, J=8.4 Hz), 6.64 (s, 1H), 6.45 (d, 1H, J=15.3 Hz), 6.35 (d, 1H, J=7.5 Hz), 5.13 (m, 1H), 3.19 (s, 3H), 2.83 (d, 2H, J=7.2 Hz), 2.12 (m, 1H), 1.46 (d, 3H, J=6.9 Hz), 0.90 (d, 6H)

ESI [M−H]−: 504

EXAMPLE 246

N-[1-(3-Fluoro-4-methanesulfonylamino-phenyl)-ethyl]-3-(2-ethylamino)-6-trifluoromethyl-pyridin-3-yl-acrylamide

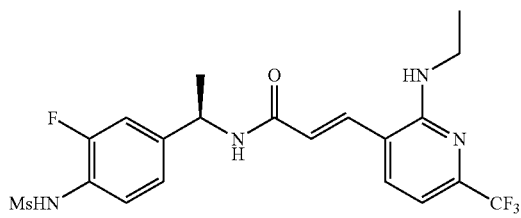

(R)—N-[4-(1-Amino-ethyl)-2-fluoro-phenyl]-methanesulfonamide, HCl salt (145 mg, 0.54 mmol) was reacted with 3-(2-ethylamino-6-trifluoromethyl-pyridin-3-yl)-acrylic acid (140 mg, 0.54 mmol) to give the title compound (113 mg, 41%) after purification by column chromatography (Hex/EtOAc=1.1).

$^1$H NMR (300 MHz, CDCl$_3$): δ 7.58 (m, 3H), 7.18 (s, 1H), 7.14 (m, 1H), 6.90 (d, 1H, J=7.2 Hz), 6.48 (s, 1H), 6.33 (d, 1H, J=15.0 Hz), 5.82 (bs, 1H), 5.21 (m, 1H), 4.78 (bs, 1H), 3.53 (m, 2H), 3.03 (s, 3H), 1.56 (d, 3H, J=5.5 Hz), 1.25 (t, 3H, J=7.5 Hz).

ESI [M−H]−: 473

EXAMPLE 247

N-(4-methanesulfonylamino-3-methyl-benzyl)-3-(2-ethylamino-6-trifluoromethyl)-pyridin-3-yl-acrylamide

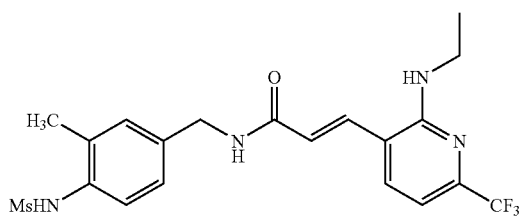

N-(4-Aminomethyl-3-methyl-phenyl)-methanesulfonamide, HCl salt (78 mg, 0.284 mmol) was reacted with 2-ethylamino-6-trifluoromethyl-pyridin-3-yl-acrylic acid (74 mg, 0.284 mmol) to give the title compound (83 mg, 64%) after purification by column chromatography (Hex/EtOAc=2:3).

$^1$H NMR (300 MHz, CDCl$_3$): δ 7.66 (d, 1H, J=14.7 Hz), 7.57 (m, 1H), 7.19 (m, 2H), 6.90 (m, 1H), 6.35 (d, 1H, J=15.3 Hz), 6.30 (s, 1H), 5.96 (s, 1H), 4.86 (s, 1H), 4.53 (d, 2H, J=5.4 Hz), 3.54 (m, 2H), 3.02 (s, 3H), 2.31 (s, 3H), 1.26 (t, 3H, J=6.6 Hz)

ESI [M−H]−: 455

EXAMPLE 248

N-(2,5-Difluoro-4-methanesulfonylamino-benzyl)-3-(2-propylamino-6-trifluoromethyl-pyridin-3-yl)-acrylamide

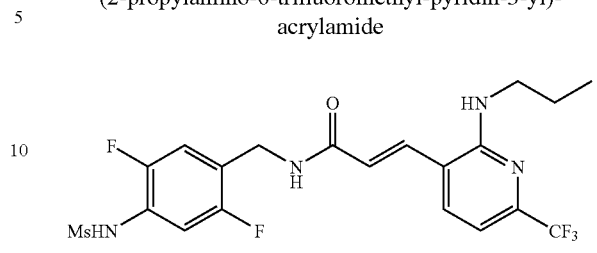

N-(4-Aminomethyl-2,5-difluoro-phenyl)-methanesulfonamide, HCl salt (33 mg, 0.12 mmol) was reacted with 3-(2-propylamino-6-trifluoromethyl-pyridin-3-yl)-acrylic acid (38 mg, 0.14 mmol) to give the title compound (35 mg, 59%) after purification by crystallization from Hex/EtOAc.

$^1$H NMR (300 MHz, DMSO-d6): δ 9.84 (bs, 1H), 8.69 (t, 1H, J=5.7 Hz), 7.77 (d, 1H, J=7.5 Hz), 7.59 (d, 1H, J=15.6 Hz), 7.25 (m, 2H), 7.14 (m, 1H), 6.96 (d, 1H, J=7.5 Hz), 6.62 (d, 1H, J=15.6 Hz), 4.39 (d, 2H, J=5.4 Hz), 3.28 (m, 2H), 3.07 (s, 3H), 1.57 (m, 2H), 0.87 (t, 3H, J=7.2 Hz).

ESI [M−H]−: 491

EXAMPLE 249

3-(2-Ethylamino-6-trifluoromethyl-pyridin-3-yl)-N-(3-ethynyl-5-fluoro-4-methanesulfonylamino-benzyl)-acrylamide

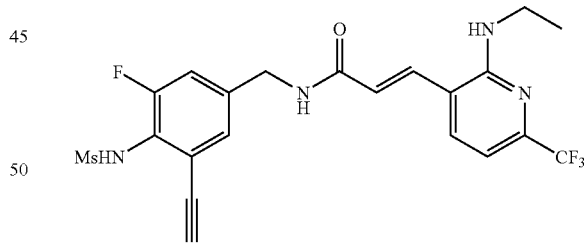

N-(4-Aminomethyl-2-ethynyl-6-fluoro-phenyl)-methanesulfonamide, HCl salt (301 mg, 1.07 mmol) was reacted with 3-(2-ethylamino-6-trifluoromethyl-pyridin-3-yl)-acrylic acid (200 mg, 0.76 mmol) to give the title compound (110 mg, 74%) after purification by recrystallization from diethylether.

$^1$H NMR (300 MHz, DMSO-d$_6$): δ 9.45 (s, 1H), 8.75 (t, 1H, J=6.0 Hz), 7.80 (d, 1H, J=7.5 Hz), 7.59 (d, 1H, J=15.6 Hz), 7.30 (s, 1H), 7.29 (d, 1H, J=9.0 Hz), 7.13 (t, 1H, J=5.1 Hz), 6.96 (d, 1H, J=7.8 Hz), 6.63 (d, 1H, J=15.3 Hz), 4.51 (s, 1H), 4.39 (d, 2H, J=6.0 Hz), 3.41-3.37 (m, 2H), 3.06 (s, 3H), 1.14 (t, 3H, J=6.9 Hz).

ESI [M−H]−: 483

EXAMPLE 250

3-(2-Ethylamino-6-trifluoromethyl-pyridin-3-yl)-N-(3-fluoro-4-methanesulfonylamino-5-vinyl-benzyl)-acrylamide

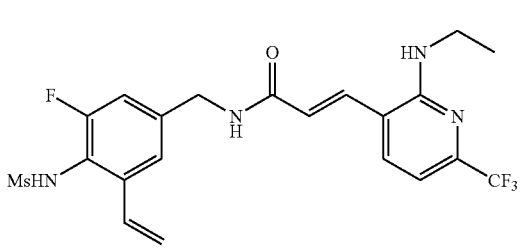

N-(4-Aminomethyl-2-fluoro-6-vinyl-phenyl)-methanesulfonamide, HCl salt (258 mg, 0.92 mmol) was reacted with 3-(2-ethylamino-6-trifluoromethyl-pyridin-3-yl)-acrylic acid (200 mg, 0.76 mmol) to give the title compound (270 mg, 60%) after purification by recrystallization from diethylether.

$^1$H NMR (300 MHz, DMSO-$d_6$): δ 9.32 (s, 1H), 8.74 (t, 1H, J=6.0 Hz), 7.79 (d, 1H, J=7.5 Hz), 7.58 (d, 1H, J=15.3 Hz), 7.50 (s, 1H), 7.18-7.04 (m, 2H), 6.96 (d, 1H, J=7.8 Hz), 6.64 (d, 1H, J=15.6 Hz), 5.86 (d, 1H, J=18.0 Hz), 5.42 (d, 1H, J=11.4 Hz), 4.42 (d, 2H, J=5.7 Hz), 3.50-3.40 (m, 2H), 3.00 (s, 3H), 1.13 (t 3H, J=6.9 Hz).

ESI [M−H]−: 485

EXAMPLE 251

N-(2-Chloro-4-methanesulfonylamino-benzyl)-3-(2-propyl-6-trifluoromethyl-pyridin-3-yl)-acrylamide

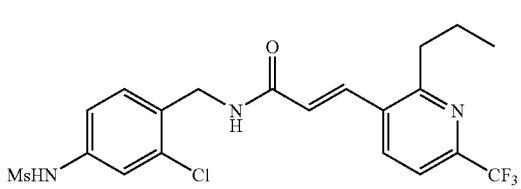

A mixture of N-(4-aminomethyl-3-chloro-phenyl)-methanesulfonamide, HCl salt and N-(4-aminomethyl-phenyl)-methanesulfonamide, HCl salt (80 mg) was reacted with 3-(2-propyl-6-trifluoromethyl-pyridin-3-yl)-acrylic acid (76 mg, 0.28 mmol) to give the title compound (77 mg, 57%) after purification by column chromatography (Hex EtOAc=2/3).

$^1$H NMR (300 MHz, DMSO-d6): δ 9.98 (bs, 1H), 8.76 (t, 1H, J=5.7 Hz), 8.15 (d, 1H, J=7.8 Hz), 7.79 (d, 1H, J=7.8 Hz), 7.70 (d, 1H, J=15.9 Hz), 7.36 (d, 1H, J=8.4 Hz), 7.27 (d, 1H, J=2.4 Hz), 7.17 (dd, 1H, J=8.4 and 2.4 Hz), 6.78 (d, 1H, J=15.9 Hz), 4.43 (d, 2H, J=5.4 Hz), 3.02 (s, 3H), 2.91 (m, 2H), 1.66 (m, 2H), 0.93 (t, 3H, J=7.5 Hz).

ESI [M−H]−: 474

EXAMPLE 252

N-(4-Methanesulfonylamino-benzyl)-3-(2-propyl-6-trifluoromethyl-pyridin-3-yl)-acrylamide

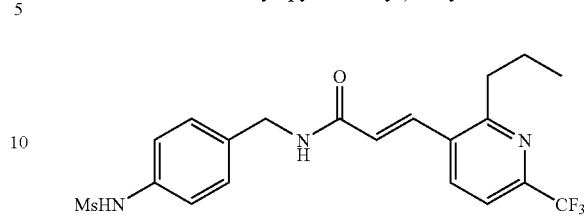

A mixture of N-(4-aminomethyl-3-chloro-phenyl)-methanesulfonamide, HCl salt and N-(4-aminomethyl-phenyl)-methanesulfonamide, HCl salt (80 mg) was reacted with 3-(2-propyl-6-trifluoromethyl-pyridin-3-yl)-acrylic acid (76 mg, 0.28 mmol) to give the title compound (50 mg, 39%) after purification by column chromatography (Hex EtOAc=2/3).

$^1$H NMR (300 MHz, DMSO-d6): δ 9.69 (bs, 1H), 8.77 (t, 1H, J=5.7 Hz), 8.14 (d, 1H, J=7.8 Hz), 7.78 (d, 1H, J=7.8 Hz), 7.71 (d, 1H, J=15.9 Hz), 7.28 (d, 2H, J=8.4 Hz), 7.18 (d, 2H, J=8.4 Hz), 6.73 (d, 1H, J=15.9 Hz), 4.37 (d, 2H, J=5.7 Hz), 3.00 (m, 5H), 1.66 (m, 2H), 0.93 (t, 3H, J=7.5 Hz).

ESI [M−H]−: 440

EXAMPLE 253

N-(3-Chloro-4-methanesulfonylamino-benzyl)-3-(2-propyl-6-trifluoromethyl)-pyridin-3-yl-acrylamide

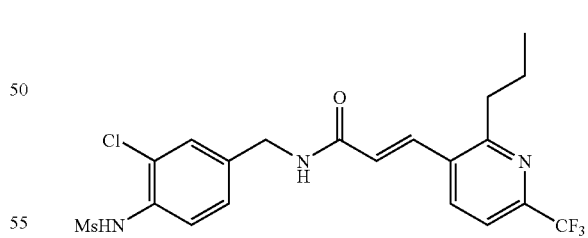

N-(4-Aminomethyl-2-chloro-phenyl)-methanesulfonamide, HCl salt (58 mg, 0.22 mmol) was reacted with 3-(2-propyl-6-trifluoromethyl-pyridin-3-yl)-acrylic acid (60 mg, 0.22 mmol) to give the title compound (65 mg, 62%) after purification by column chromatography (Hex/EtOAc=1:1)

$^1$H NMR (300 MHz, CDCl$_3$): δ 7.98 (m, 1H), 7.89 (m, 1H), 7.46 (m, 4H), 6.38 (d, 1H, J=15.3 Hz), 6.02 (bs, 1H), 4.59 (dd, 2H, J=7.8 Hz, 6.0 Hz), 3.49 (s, 3H), 1.76 (m, 2H), 1.26 (m, 2H), 1.01 (m, 3H).

EXAMPLE 254

N-(3-Chloro-4-methanesulfonylamino-benzyl)-3-(2-propylamino-6-trifluoromethyl)-pyridin-3-yl-acrylamide

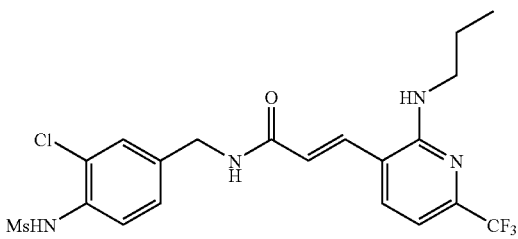

N-(3-Chloro-4-aminomethyl-phenyl)-methanesulfonamide, HCl salt (61 mg, 0.22 mmol) was reacted with 3-(2-propylamino-6-trifluoromethyl-pyridin-3-yl)-acrylic acid (60 mg, 0.22 mmol) to give the title compound (73 mg, 68%) after purification by column chromatography (Hex/EtOAc=1:1).

$^1$H NMR (300 MHz, CDCl$_3$): δ 7.59 (m, 3H), 7.31 (m, 2H), 6.90 (m, 1H), 6.84 (bs, 1H), 6.36 (d, 1H, J=15.0 Hz), 6.13 (bs, 1H), 4.55 (dd, 2H, J=14.1 Hz, 6.3 Hz), 3.48 (s, 3H), 1.65 (m, 4H), 0.97 (t, 3H, J=7.2 Hz).

EXAMPLE 255

N-(2,5-Difluoro-4-methanesulfonylamino-benzyl)-3-(2-ethylamino-6-trifluoromethyl)-pyridin-3-yl-acrylamide

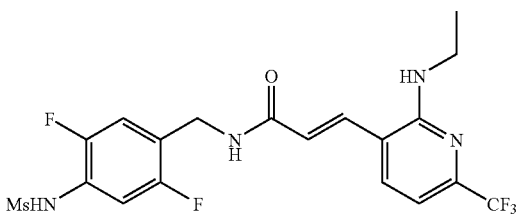

N-(4-Aminomethyl-2,5-difluoro-phenyl)-methanesulfonamide, HCl salt (61 mg, 0.22 mmol) was reacted with 3-(2-ethylamino-6-trifluoromethyl-pyridin-3-y)l-acrylic acid (58 mg, 0.22 mmol) to give the title compound (20 mg, 18%) after purification by column chromatography (Hex/EtOAc=1.1).

$^1$H NMR (300 MHz, CDCl$_3$): δ 8.91 (m, 1H), 8.22 (m, 1H), 7.67 (d, 1H, J=15.3 Hz), 7.57 (d, 1H, J=7.5 Hz), 6.87 (m, 2H), 6.36 (d, 1H, J=15.0 Hz), 6.25 (bs, 1H), 5.01 (bs, 1H), 4.53 (d, 2H, J=6.0 Hz), 3.06 (s, 3H), 3.04 (m, 2H), 1.25 (m, 3H).

ESI [M−H]−: 477

EXAMPLE 256

3-(2-Ethylamino-6-trifluoromethyl-pyridin-3-yl)-N-(3-fluoro-4-methanesulfonylamino-benzyl)-acrylamide

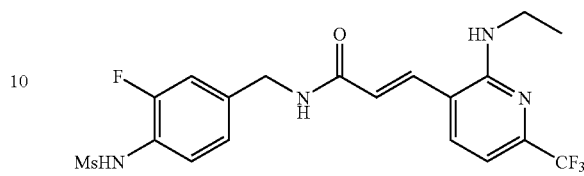

N-(4-Aminomethyl-2-fluoro-phenyl)-methanesulfonamide, HCl salt (117 mg, 0.46 mmol) was reacted with 3-(2-ethylamino-6-trifluoromethyl-pyridin-3-yl)-acrylic acid (100 mg, 0.38 mmol) to give the title compound (118 mg, 56%) after purification by recrystallization from diethylether.

$^1$H NMR (300 MHz, DMSO-d$_6$): δ 9.55 (s, 1H), 8.71 (t, 1H, J=6.0 Hz), 7.78 (d, 1H, J=7.2 Hz), 7.58 (d, 1H, J=15.3 Hz), 7.34 (t, 1H, J=8.1 Hz), 7.21 (dd, 1H, J=11.4, 1.8 Hz), 7.14-7.11 (m, 2H), 6.96 (d, 1H, J=7.5 Hz), 6.63 (d, 1H, J=15.6 Hz), 4.39 (d, 2H, J=5.7 Hz), 3.42-3.37 (m, 2H), 3.00 (s, 3H), 1.14 (t, 3H, J=6.9 Hz).

ESI [M−H]−: 459

EXAMPLE 257

N-(3,5-Difluoro-4-methanesulfonylamino-benzyl)-3-(2-ethylamino-6-trifluoromethyl-pyridin-3-yl)-acrylamide

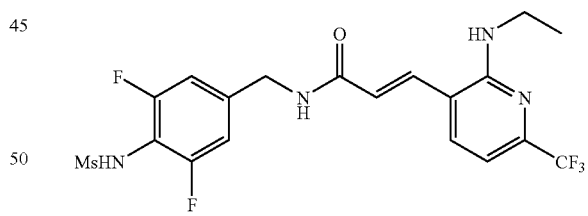

N-(4-Aminomethyl-2,6-difluoro-phenyl)-methanesulfonamide, HCl salt (125 mg, 0.46 mmol) was reacted with 3-(2-ethylamino-6-trifluoromethyl-pyridin-3-yl)-acrylic acid (100 mg, 0.38 mmol) to give the title compound (110 mg, 60%) after purification by recrystallization from diethylether.

$^1$H NMR (300 MHz, DMSO-d$_6$): δ 9.50 (s, 1H), 8.76 (t, 1H, J=6.0 Hz), 7.80 (d, 1H, J=7.8 Hz), 7.59 (d, 1H, J=15.3 Hz), 7.13 (s, 1H), 7.13 (d, 1H, J=8.4 Hz), 6.96 (d, 1H, J=7.5 Hz), 6.64 (d, 1H, J=15.6 Hz), 4.41 (d, 2H, J=6.0 Hz), 3.42-3.35 (m, 2H), 3.04 (s, 3H), 1.14 (t, 3H, J=6.9 Hz).

ESI [M−H]−: 477

EXAMPLE 258

3-(2-Ethylamino-6-trifluoromethyl-pyridin-3-yl)-N-(3-fluoro-4-methanesulfonylamino-5-methyl-benzyl)-acrylamide

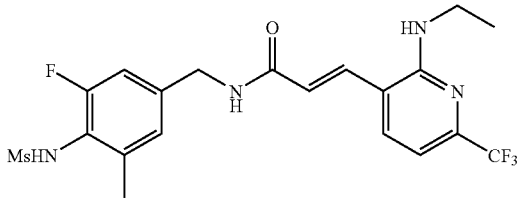

N-(4-Aminomethyl-2-fluoro-6-methyl-phenyl)-methanesulfonamide, HCl salt (124 mg, 0.46 mmol) was reacted with 3-(2-ethylamino-6-trifluoromethyl-pyridin-3-yl)-acrylic acid (100 mg, 0.38 mmol) to give the title compound (230 mg, 62%) after purification by recrystallization from diethylether.

$^1$H NMR (300 MHz, DMSO-$d_6$): δ 9.26 (s, 1H), 8.64 (t, 1H, J=6.0 Hz), 7.75 (d, 1H, J=7.5 Hz), 7.57 (d, 1H, J=15.6 Hz), 7.22-7.17 (m, 1H), 6.96 (d, 1H, J=7.8 Hz), 6.63 (d, 1H, J=15.6 Hz), 4.41 (d, 2H, J=5.4 Hz), 3.42-3.37 (m, 2H), 2.98 (s, 3H), 2.21 (s, 3H), 1.14 (t, 3H, J=6.9 Hz).

ESI [M−H]−: 473

EXAMPLE 259

N-(3-Cyano-5-fluoro-4-methanesulfonylamino-benzyl)-3-(2-ethylamino-6-trifluoromethyl-pyridin-3-yl)-acrylamide

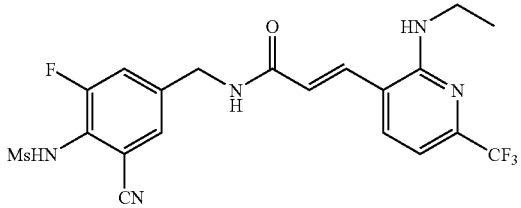

N-(4-Aminomethyl-2-cyano-6-fluoro-phenyl)-methanesulfonamide, HCl salt (129 mg, 0.46 mmol) was reacted with 3-(2-ethylamino-6-trifluoromethyl-pyridin-3-yl)-acrylic acid (100 mg, 0.38 mmol) to give the title compound (113 mg, 54%) after purification by recrystallization from diethylether.

$^1$H NMR (300 MHz, DMSO-$d_6$): δ 10.07 (s, 1H), 8.79 (t, 1H, J=6.0 Hz), 7.80 (d, 1H, J=7.2 Hz), 7.66-7.56 (m, 3H), 7.13 (t, 1H, J=8.1 Hz), 6.97 (d, 1H, J=7.5 Hz), 6.64 (d, 1H, J=15.6 Hz), 4.45 (d, 2H, J=5.7 Hz), 3.42-3.38 (m, 2H), 3.11 (s, 3H), 1.14 (t, 3H, J=6.9 Hz).

EXAMPLE 260

3-(2-Butylamino-6-trifluoromethyl-pyridin-3-yl)-propynoic acid, 3-ethynyl-5-fluoro-4-methanesulfonylamino-benzylamide

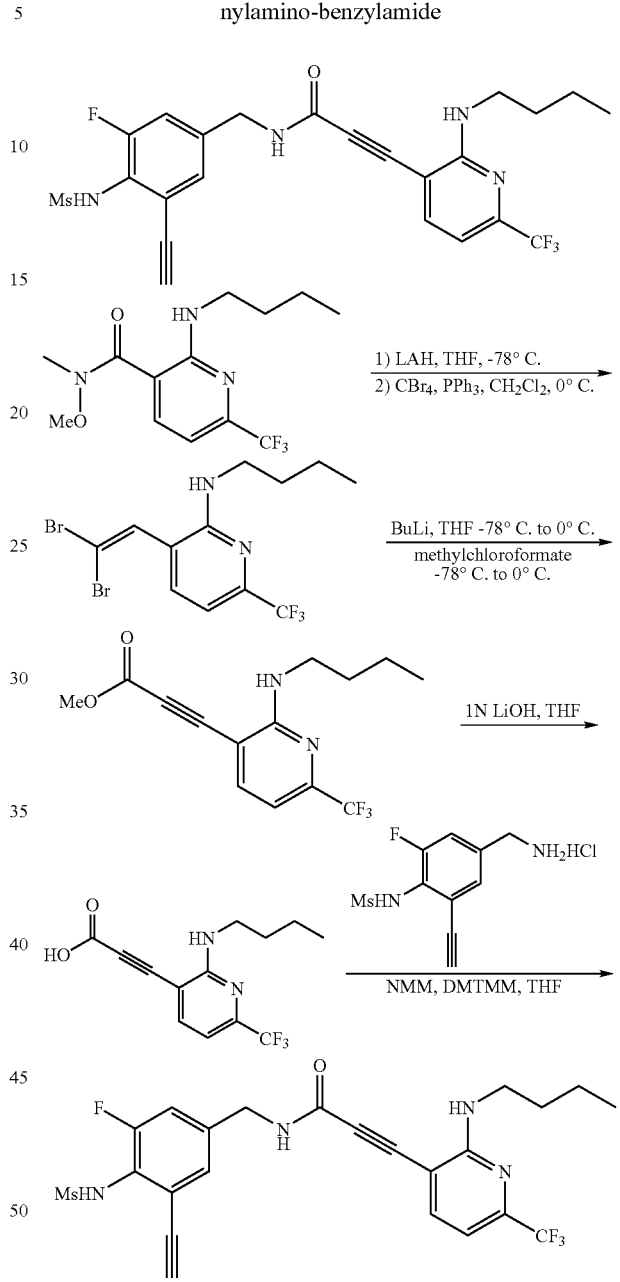

Step 1: Butyl-[3-(2,2-dibromo-vinyl)-6-trifluoromethyl-pyridin-2-yl]-amine

A solution of 2-butylamino-N-methoxy-N-methyl-6-trifluoromethyl-nicotinamide (2.00 g, 6.55 mmol) in THF (50 mL) was cooled to −78° C., to which was added dropwise 1M LiAlH$_4$ in THF (3.3 mL. 3.3 mmol). The resulting mixture was stirred for 1 hr at −78° C. and then slowly warmed to −20° C. for 2 hrs before carefully quenched by adding 10% sodium potassium tartarate followed by EtOAc. After vigorously stirring for 30 min at room temperature, the two phases were separated and the aqueous phase was extracted twice with EtOAc. The combined organic layer was washed with brine, dried over anhydrous magnesium sulfate, filtered, and concentrated under reduced pressure to give the resulting aldehyde.

A solution of carbon tetrabromide (4.35 g, 13.1 mmol) in methylene chloride under nitrogen at 0° C. was treated with triphenylphosphine (6.87 g, 26.2 mmol) and stirred for 1 hr at 0° C. The mixture was treated with the aldehyde obtained above, stirred for 1 hr at 0° C., and then quenched with water. The separated organic phase was washed with brine, dried over anhydrous magnesium sulfate, filtered, and concentrated under reduced pressure. The resulting residue was treated with hexane and the supernatant was collected. The residue was dissolved in methylene chloride and poured into hexane. The supernatant was collected. The procedure was repeated two more times. The combined supernatant was passed through silica gel and then concentrated to give the title compound (1.60 g, 61%).

$^1$H NMR (300 MHz, CDCl$_3$): δ 7.51 (d, 1H, J=7.8 Hz), 7.09 (s, 1H), 6.89 (d, 1H, J=7.8 Hz), 4.40 (bs, 1H), 3.45 (m, 2H), 1.58 (m, 2H), 1.36 (m, 2H), 0.92 (t, 3H, J=7.2 Hz).

Step 2: (2-Butylamino-6-trifluoromethyl-pyridin-3-yl)-propynoic acid methyl ester A solution of butyl-[3-(2,2-dibromo-vinyl)-6-trifluoromethyl-pyridin-2-yl]-amine (1.02 g, 2.54 mmol) in THF under nitrogen at −78° C. was slowly treated with 2.5 M BuLi in hexane (2.0 mL, 5.00 mmol) and then stirred for 30 min at −78° C. and 30 min at −0° C. The mixture was treated with methyl chloroformate (0.235 mL, 3.05 mmol) at −78° C. and warmed to 0° C. for 1 hr. The mixture was diluted with 1:1 mixture of saturated NaHCO$_3$ and NH$_4$Cl solution and the aqueous layer was extracted with ether (×3). The combined organic layer was dried over anhydrous magnesium sulfate, filtered, and concentrated under reduced pressure. The crude residue was purified by chromatography (Hex/EtOAc=10/1) to give the title compound (78 mg, 10%).

$^1$H NMR (300 MHz, CDCl$_3$) δ 7.85 (d, 1 H, J=7.8 Hz), 7.52 (d, 1 H, J=7.8 Hz), 3.78 (m, 2H), 3.64 (s, 3H), 1.48 (m, 2H), 1.26 (m, 2H), 0.82 (t 3H, J=7.5 Hz).

Step 3: (2-Butylamino-6-trifluoromethyl-pyridin-3-yl)-propynoic acid

To a suspension of (2-butylamino-6-trifluoromethyl-pyridin-3-yl)-propynoic acid methyl ester (78 mg, 0.26 mmol) in THF (0.50 ml) was added a solution of 1 N-LiOH (1.0 ml), and the mixture was stirred for 3 hours at room temperature. The reaction mixture was acidified with 1N HCl to pH 1~2. The solution was extracted three times with methylene chloride and then dried over anhyd. Na$_2$SO$_4$ and concentrated in vacuo to the title compound (50 mg, 65%).

$^1$H NMR (300 MHz, DMSO-d6): δ 8.17 (d, 1 H, J=7.8 Hz), 7.80 (d, 1 H, J=7.8 Hz), 3.71 (m, 5H), 1.47 (m, 2H), 1.26 (m, 2H), 0.81 (t, 3H, J=7.2 Hz).

Step 4: 3-(2-Butylamino-6-trifluoromethyl-pyridin-3-yl)-propynoic acid, 3-ethynyl-5-fluoro-4-methanesulfonylamino-benzylamide N-(4-Aminomethyl-2-ethynyl-6-fluoro-phenyl)-methanesulfonamide, HCl salt (80 mg, 0.29 mmol) was reacted with (2-butylamino-6-trifluoromethyl-pyridin-3-yl)-propynoic acid (70 mg, 0.2 4 mmol) to give the title compound (84 mg, 57%) after purification by column chromatography (Hex/EtOAc=2/3).

$^1$H NMR (300 MHz, DMSO-d6): δ 9.46 (m, 2H), 8.38 (d, 1H, J=7.8 Hz), 7.92 (d, 1H, J=7.8 Hz), 7.27 ((m, 2H), 4.53 (s, 1H), 4.36 (d, 2H, J=5.7 Hz), 3.77 (m, 2H), 3.07 (s, 3H), 1.51 (m, 2H), 1.28 (m, 2H), 0.82 (t, 3H, J=7.2 Hz).

EXAMPLE 261

3-(2-Butyl-6-trifluoromethyl-pyridin-3-yl)-propynoic acid 3,5-difluoro-4-methanesulfonylamino-benzylamide

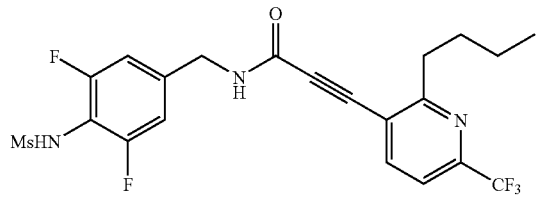

N-(4-Aminomethyl-2,6-difluoro-phenyl)-methanesulfonamide, HCl salt (82 mg, 0.30 mol) was reacted with (2-butyl-6-trifluoromethyl-pyridin-3-yl)-propynoic acid (68 mg, 0.25 mmol) prepared as described in steps 1-3 of example 260 to give the title compound (74 mg, 50%) after purification by crystallization from Hex/EtOAc.

$^1$H NMR (300 MHz, DMSO-d6): δ 9.55 (t, 1H, J=5.7 Hz), 9.50 (bs, 1H), 8.25 (d, 1H, J=8.1 Hz), 7.83 (d, 1H, J=8.1 Hz), 7.13 (d, 2H, J=8.4 Hz), 4.40 (d, 2H, J=6.0 Hz), 3.03 (m, 5H), 1.70 (m, 2H), 1.36 (m, 2H), 0.91 (t, 3H, J=7.2 Hz).

EXAMPLE 262

3-(2-Butyl-6-trifluoromethyl-pyridin-3-yl)-propynoic acid [1-(3,5-difluoro-4-methanesulfonylamino-phenyl)-ethyl]-amide

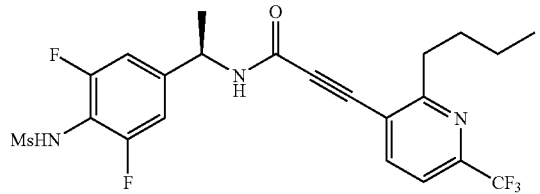

(R)—N-[4-(1-Aminoethyl)-2,6-difluoro-phenyl]-methanesulfonamide, HCl salt (86 mg, 0.30 mol) was reacted with (2-butyl-6-trifluoromethyl-pyridin-3-yl)-propynoic acid (68 mg, 0.25 mmol) to give the title compound (76 mg, 50%) after purification by crystallization from Hex/EtOAc.

$^1$H NMR (300 MHz, DMSO-d6): δ 9.24 (d, 1H), 8.25 (d, 1H, J=8.1 Hz), 7.83 (d, 1H, J=8.1 Hz), 7.19 (d, 2H, J=8.7 Hz), 5.02 (t, 1H), 3.06 (m, 5H), 1.70 (m, 2H), 1.38 (m, 5H), 0.92 (t, 3H, J=7.2 Hz).

ESI [M−H]−: 502

EXAMPLE 263

3-(2-Butyl-6-trifluoromethyl-pyridin-3-yl)-propynoic acid 2-chloro-4-methanesulfonylamino-benzylamide

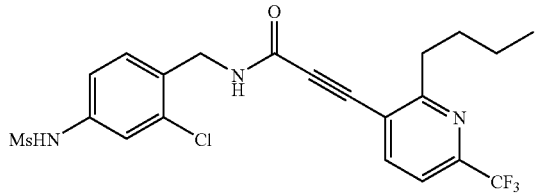

A mixture of N-(4-aminomethyl-3-chloro-phenyl)-methanesulfonamide, HCl salt and N-(4-aminomethyl-phenyl)-methanesulfonamide, HCl salt (80 mg) was reacted with (2-butyl-6-trifluoromethyl-pyridin-3-yl)-propynoic acid (76 mg, 0.28 mmol) to give the title compound (80 mg, 55%) after purification by column chromatography (Hex/EtOAc=2/3).

$^1$H NMR (300 MHz, DMSO-d6): δ 9.99 (bs, 1H), 9.44 (bs, 1H), 8.23 (d, 1H, J=7.8 Hz), 7.82 (d, 1H, J=8.1 Hz), 7.27 (m, 3H), 4.41 (d, 2H, J=6.0 Hz), 3.03 (m, 5H), 1.69 (m, 2H), 1.36 (m, 2H), 0.91 (t, 3H, J=7.2 Hz).

EXAMPLE 264

N-(4-Methanesulfonylamino-benzyl)-3-(2-phenethyl-6-trifluoromethyl-pyridin-3-yl)-acrylamide

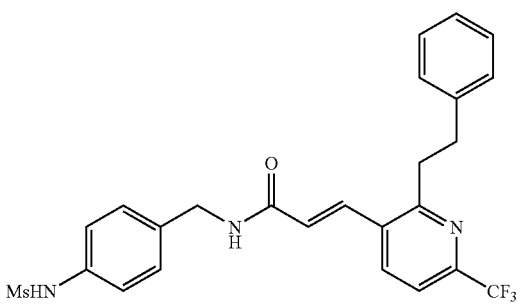

N-[4-(1-Amino-methyl)-phenyl]-methanesulfonamide, HCl salt (111 mg, 0.47 mmol) was reacted with NMM (0.11 ml), DMTMM (138 mg, 0.499 mmol) and 3-(2-phenethyl-6-trifluoromethyl-pyridin-3-yl)-acrylic acid (132 mg, 0.472 mmol) to give the title compound (144 mg) after purification by column chromatography (Hex/EtOAc=1/2).

$^1$H NMR (300 MHz, CDCl$_3$) δ 7.83 (d, 1H, J=8.7 Hz), 7.80 (d, 1H, J=15.6 Hz), 7.49 (d, 1H, J=8.1 Hz), 7.53 (d, 1H, J=7.8 Hz), 7.33 (m, 2H), 7.18 (m, 6H), 6.71 (s, 1H), 6.22 (d, 1H, J=15.3 Hz), 5.99 (m, 1H), 4.54 (d, 2H, J=5.7 Hz), 3.28 (m, 2H), 3.10 (m, 2H), 3.08 (m, 3H)

EXAMPLE 265

3-(2-Isobutyl-6-trifluoromethyl-pyridin-3-yl)-N-(4-methane sulfonylamino-benzyl)-acrylamide

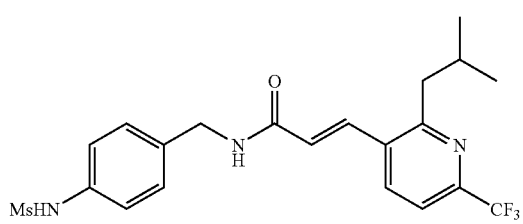

N-[4-(1-Amino-methyl)-phenyl]-methanesulfonamide, HCl salt (117 mg, 0.496 mmol) was reacted with NMM (350 ul), DMTMM (165 mg) and 3-(2-isobutyl-6-trifluoromethyl-pyridin-3-yl)-acrylic acid (116 mg, 0.498 mmol) to give the title compound (92 mg) after purification by column chromatography (Hex/EtOAc=1/2).

$^1$H NMR (300 MHz, CDCl$_3$); δ 7.93 (d, 1H, J=15.6 Hz), 7.90 (d, 1H, J=9.3 Hz), 7.46 (d, 1H, J=8.1 Hz), 7.31 (s, 1H), 7.23 (m, 4H), 6.48 (m, 1H), 6.44 (d, 1H, J=15.3 Hz), 4.51 (d, 2H, J=6.0 Hz), 2.97 (s, 3H), 2.83 (d, J=6.9 Hz), 2.15 (m, 1H), 0.90 (d, 6H)

EXAMPLE 266

3-(2-Butyl-6-trifluoromethyl-pyridin-3-yl)-propynoic acid 4-methanesulfonylamino-benzylamide

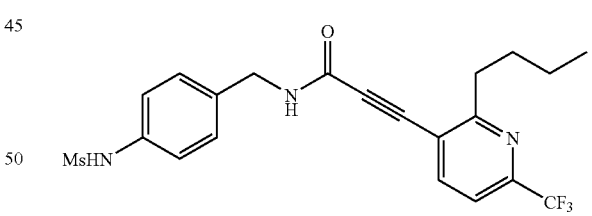

A mixture of N-(4-aminomethyl-3-chloro-phenyl)-methanesulfonamide, HCl salt and N-(4-aminomethyl-phenyl)-methanesulfonamide, HCl salt (80 mg) was reacted with (2-butyl-6-trifluoromethyl-pyridin-3-yl)-propynoic acid (76 mg, 0.28 mmol) to give the title compound (45 mg, 33%) after purification by column chromatography (Hex/EtOAc=2/3).

$^1$H NMR (300 MHz, DMSO-d6): δ 9.72 (bs, 1H), 9.45 (bs, 1H), 8.24 (d, 1H, J=7.8 Hz), 7.83 (d, 1H, J=8.1 Hz), 7.27 (d, 2H, J=8.4 Hz), 7.18 (d, 2H, J=8.4 Hz), 4.34 (d, 2H, J=6.0 Hz), 2.97 (m, 5H), 1.70 (m, 2H), 1.36 (m, 2H), 0.91 (t, 3H, J=7.2 Hz).

ESI [M−H]−: 452

EXAMPLE 267

N-(4-Ethenesulfonylamino-benzyl)-3-(2-isopropylamino-6-trifluoromethyl-pyridin-3-yl)-acrylamide

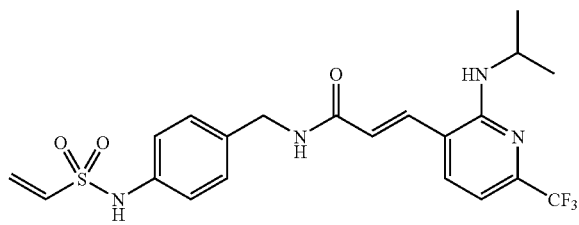

N-[4-(1-Amino-methyl)-phenyl]-ethenesulfonamide, HCl salt (97.8 mg, 0.392 mmol) was reacted with NMM (0.2 ml), DMTMM (121 mg) and 3-(2-isopropylamino-6-trifluoromethyl-pyridin-3-yl)-acrylic acid (97.9 mg) to give the title compound (62 mg) after purification by column chromatography (Hex/EtOAc=2/3).

$^1$H NMR (300 MHz, CDCl$_3$): δ 7.86 (s, 1H), 7.65 (d, 1H, J=15.3 Hz), 7.51 (d, 1H, J=7.8 Hz), 7.11 (d, 2H, J=8.4 Hz), 7.01 (d, 2H, J=6.6 Hz), 6.77 (d, 1H, J=7.8 Hz), 6.46 (m, 1H), 6.40 (d, 1H, J=19.2 Hz), 6.15 (d, 1H, J=16.5 Hz), 5.85 (d, 1H, J=9.6 Hz), 5.00 (d, 1H), 4.43 (d, 2H, J=6.0 Hz), 4.30 (m, 1H), 1.20 (d, 6H)

ESI [M−H]−: 467

EXAMPLE 268

N-(4-Ethenesulfonylamino-benzyl)-3-(2-phenethyl-6-trifluoromethyl-pyridin-3-yl)-acrylamide

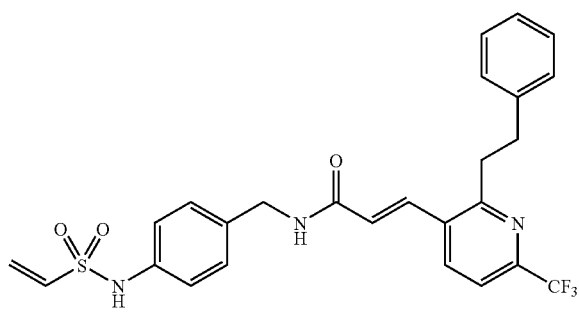

N-[4-(1-Amino-methyl)-phenyl]-ethenesulfonamide, HCl salt (95.5 mg, 0.384 mmol) was reacted with NMM (0.2 ml), DMTMM (116 mg) and 3-(2-phenethyl-6-trifluoromethyl-pyridin-3-yl)-acrylic acid (99.9 mg) to give the title compound (17 mg) after purification by column chromatography (Hex/EtOAc=2/3).

$^1$H NMR (300 MHz, CDCl$_3$): δ 7.83 (s, 1H), 7.80 (d, 1H, J=15.3 Hz), 7.48 (d, 1H, J=8.1 Hz), 7.22 (m, 6H), 6.47 (d, 1H, J=9.9 Hz), 6.30 (d, 1H, J=15.3 Hz), 6.20 (d, 1H, J=16.5 Hz), 5.89 (d, 1H, J=9.6 Hz), 4.47 (d, 2H, J=5.7 Hz), 3.32 (m, 2H), 3.04 (m, 2H)

EXAMPLE 269

N-(4-Ethenesulfonylamino-benzyl)-3-(2-isobutyl-6-trifluoromethyl-pyridin-3-yl)-acrylamide

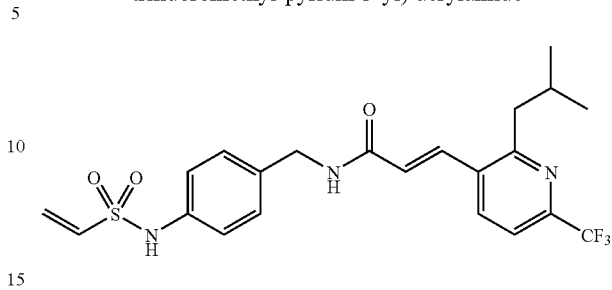

N-[4-(1-Amino-methyl)-phenyl]-ethenesulfonamide, HCl salt (96.6 mg, 0.388 mmol) was reacted with NMM (0.2 ml), DMTMM (124.8 mg) and 3-(2-isobutyl-6-trifluoromethyl-pyridin-3-yl)-acrylic acid (107.2 mg) to give the title compound (19 mg) after purification by column chromatography (Hex/EtOAc=1/1).

$^1$H NMR (300 MHz, CDCl$_3$): δ 7.95 (d, 1H, J=15.6 Hz), 7.88 (d, 1H, J=7.5 Hz), 7.50 (d, 1H, J=8.1 Hz), 7.26 (m, 2H), 7.12 (m, 2H), 6.96 (s, 1H), 6.40 (d, 1H, J=15.6 Hz), 6.27 (d, 1H, J=16.5 Hz), 6.20 (m, 1H), 5.96 (d, 1H, J=9.6 Hz), 4.53 (d, 2H, J=5.7 Hz), 2.86 (d, 1H, J=7.2 Hz), 2.15 (m, 1H), 0.92 (d, 6H, J=6.6 Hz)

EXAMPLE 270

3-(2-Isopropylamino-6-trifluoromethyl-pyridin-3-yl)-N-(4-trifluoromethanesulfonylamino-benzyl)-acrylamide

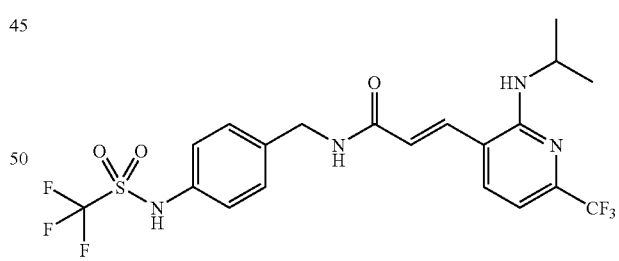

N-[4-(1-Amino-methyl)-phenyl]-trifluoromethanesulfonamide, HCl salt (78.4 mg) was reacted with NMM (0.2 ml), DMTMM (119.8 mg) and 3-(2-isopropylamino-6-trifluoromethyl-pyridin-3-yl)-acrylic acid (70.8 mg) to give the title compound (20 mg) after purification by column chromatography (Hex/EtOAc=1/1).

$^1$H NMR (300 MHz, CDCl$_3$): δ 8.08 (s, 1H), 7.61 (m, 3H), 7.28 (m, 1H), 7.10 (d, 1H, J=8.1 Hz), 6.87 (m, 1H), 6.65 (d, 1H, J=8.4 Hz), 6.32 (d, 1H, J=16.5 Hz), 4.72 (m, 1H) 4.44 (d, 2H, J=8.4 Hz), 4.35 (m, 1H), 1.25 (d, 6H)

ESI [M−H]−: 509

EXAMPLE 271

(Z)-3-(2-propyl-6-trifluoromethyl-pyridin-3-yl)-hex-2-enoic acid 1-(3-chloro-4-methanesulfonylamino-benzylamide

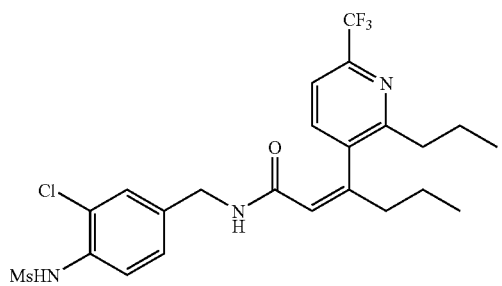

$^1$H NMR (300 MHz, CDCl$_3$): δ 7.58 (d, 1H, J=8.1 Hz), 7.52 (d, 1H, J=8.1 Hz), 7.41 (d, 1H, J=8.1 Hz), 7.25 (m, 1H), 7.10 (m, 1H), 6.73 (s, 1H), 5.76 (s, 1H), 5.63 (t, 1H, J=7.5 Hz), 4.34 (d, 2H, J=6.0 Hz), 3.33 (s, 2H), 3.01 (s, 3H), 2.74 (m, 2H), 2.29 (m, H), 1.74 (m, 2H), 1.10 (t, 1H, J=7.5 Hz), 0.94 (t, 3H, J=7.5 Hz).

EXAMPLE 272

(E)-3-(2-Propyl-6-trifluoromethyl-pyridin-3-yl)-hex-2-enoic acid 1-(3-chloro-4-methanesulfonylamino-benzylamide

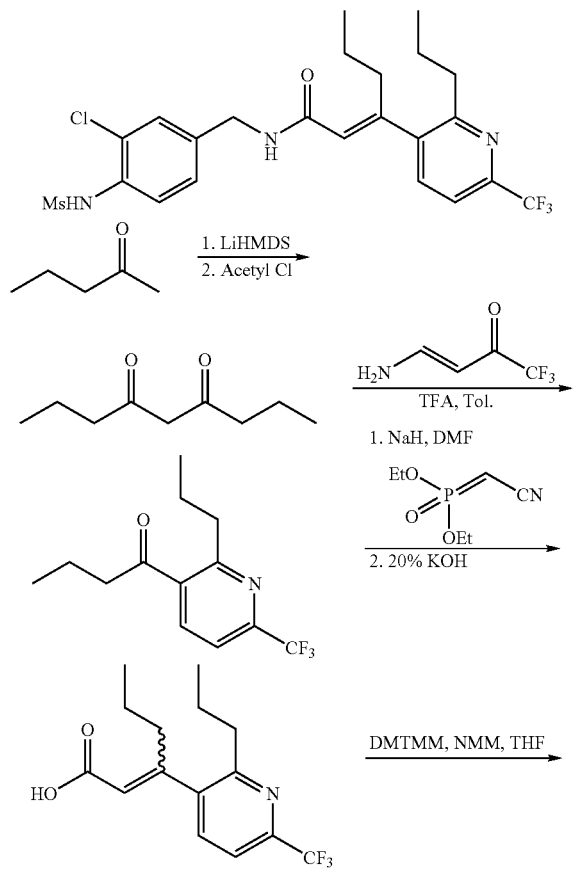

-continued

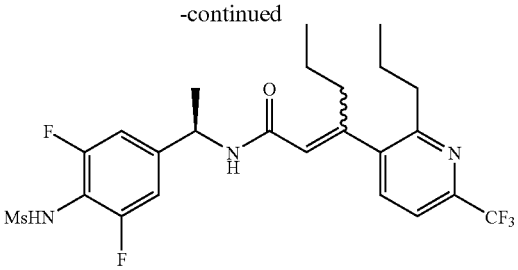

Step 1:
3-Propionyl-2-propyl-6-trifluoromethyl-pyridine

2-Pentanone (1 ml, 9.4 mmol) was dissolved in 15 ml of dry toluene in a two-neck flask, and the solution was cooled to 0° C. under argon. LiHMDS (9.4 ml, 1.0 M in THF, 2.1 mmol) was added via syringe with stirring, and the formed anion was allowed to sit for 1 min before the addition of butyryl chloride (0.49 ml, 4.7 mmol) in one portion with stirring. The flask was then removed from ice bath and allowed to stand for 1 min, and 1M HCl solution was added with stirring. The solution mixture was extracted with EtOAc. The organic mixture was then washed with brine, dried over Na$_2$SO$_4$, and evaporated under reduced pressure. To a solution of the resulting crude residue in toluene (20 ml) was added 4-amino-1,1,1-trifluoro-3-butene-2-one (0.72 g, 4.7 mmol) and trifluoroacetic acid (0.42 ml, 5.64 mmol) and the mixture was stirred under reflux for 24 h. The reaction mixture was washed with aq. 20% Na$_2$CO$_3$ and dried with Na$_2$SO$_4$. After removal of the solvent, the residue was submitted to silica gel column chromatography to give a title compound (0.62 g, 51%).

$^1$H NMR (300 MHz, CDCl$_3$): δ 7.91 (d, 1H, J=8.1 Hz), 7.57 (d, 1H, J=7.8 Hz), 2.90 (m, 4H), 1.76 (m, 4H), 1.00 (m, 4H).

Step 2: 3-(2-Propyl-6-trifluoromethyl-pyridine-3-yl)-hex-2-enoic acid

The solution of 3-propionyl-2-propyl-6-trifluoromethyl-pyridine (0.62 g, 2.39 mmol) and cyanomethyl phosphonic acid diethyl ester (1.1 eq, 2.7 g) in DMF was put into the 50 ml one-neck round bottom flask followed by the portionwise addition of NaH (144 mg, 3.59 mmol). And the mixture was stirred for 18 hours at room temperature. The reaction mixture was quenched with 10 ml ice water. The reaction mixture was extracted with ethylacetate, and then washed 1N HCl solution. And the combined organic layer was dried over MgSO$_4$, filtered and concentrated under reduced pressure. The obtained liquid was hydrolyzed with 20% KOH solution under reflux overnight. After the mixture was washed with EtOAc, the aqueous phase was acidified with c-.HCl and extracted with 50 mL EtOAc three times. The combined organic layer was concentrated under reduced pressure to give crude residue (0.349 g, 49%). The crude residue was used in next step without further purification.

Step 3: (E)-3-(2-Propyl-6-trifluoromethyl-pyridin-3-yl)-hex-2-enoic acid 1-(3-chloro-4-methanesulfonylamino-benzylamide N-(3-Chloro-4-aminomethyl-phenyl)-methanesulfonamide, HCl salt (69 mg, 0.23 mmol) was reacted with 3-(2-propyl-6-trifluoromethyl-pyridin-3-yl)-hex-2-enoic acid (59 mg, 0.23 mmol) to give the title compound (69 mg, 58%) after purification by column chromatography (Hex/EtOAc=1.1).

¹H NMR (300 MHz, CDCl₃): δ 7.58 (d, 1H, J=8.4 Hz), 7.45 (m, 2H), 7.10 (m, 1H), 6.73 (bs, 1H), 5.82 (ts, 1H), 5.75 (bs, 1H), 4.33 (d, 2H, J=6.3 Hz), 3.20 (m, 2H), 3.01 (s, 3H), 2.71 (m, 2H), 1.74 (m, 4H), 0.94 (m, 3H).

ESI [M−H]−: 516

EXAMPLE 273

3-(2-Butyl-6-trifluoromethyl-pyridin-3-yl)-propynoic acid 3-fluoro-4-methanesulfonylamino-5-methyl-benzylamide

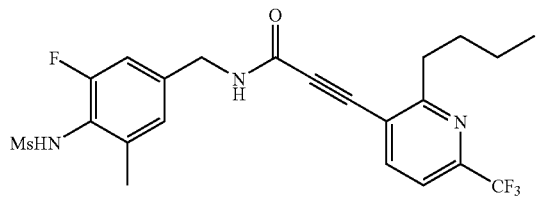

N-(4-Aminomethyl-2-chloro-6-methyl-phenyl)-methanesulfonamide, HCl salt (60 mg, 0.30 mol) was reacted with (2-butyl-6-trifluoromethyl-pyridin-3-yl)-propynoic acid (50 mg, 0.18 mmol) to give the title compound (48 mg, 55%) after purification by crystallization from Hex/EtOAc.

¹H NMR (300 MHz, DMSO-d6): δ 9.46 (t, 1H), 9.18 (bs, 1H), 8.23 (d, 1H, J=7.8 Hz), 7.82 (d, 1H, J=7.8 Hz), 7.17 (m, 2H), 4.39 (d, 2H, J=5.4 Hz), 3.00 (m, 5H), 2.22 (d, 3H), 1.69 (m, 2H), 1.35 (m, 2H), 0.90 (t, 3H, J=7.5 Hz).

EXAMPLE 274

3-(2-Butyl-6-trifluoromethyl-pyridin-3-yl)-propynoic acid [1-(3-fluoro-4-methane sulfonylamino-phenyl)-ethyl]-amide

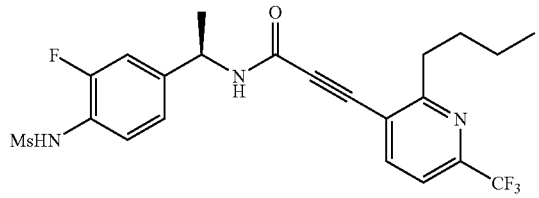

(R)—N-[4-(1-Aminoethyl)-2-fluoro-phenyl]-methanesulfonamide, HCl salt (91 mg, 0.34 mol) was reacted with (2-butyl-6-trifluoromethyl-pyridin-3-yl)-propynoic acid (92 mg, 0.34 mmol) to give the title compound (68 mg, 43%) after purification by column chromatography (Hex/EtOAc=1/1).

¹H NMR (300 MHz, CDCl₃): δ 7.90 (d, 1H, J=7.8 Hz), 7.50 (d, 1H, J=7.8 Hz), 6.97 (m, 2H), 6.77 (t, 3H, J=8.4 Hz), 6.04 (d, 1H, J=7.5 Hz), 5.12 (m, 1H), 3.03 (m, 5H), 1.77 (m, 2H), 1.55 (m, 3H), 1.40 (m, 2H), 0.95 (t, 3H, J=7.2 Hz).

EXAMPLE 275

(Z)-3-(2-Propyl-6-trifluoromethyl-pyridin-3-yl)-hex-2-enoic acid 1-(3,5-difluoro-4-methanesulfonylamino-phenyl)-ethyl]-amide

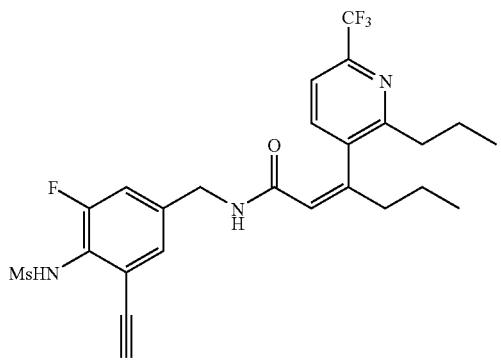

¹H NMR (300 MHz, CDCl₃): δ 7.46 (m, 3H), 7.14 (s, 1H), 6.97 (m, 1H), 6.42 (s, 1H), 5.83 (s, 1H), 5.62 (t, 1H, J=7.5 Hz), 4.32 (d, 2H, J=6.0 Hz), 3.48 (s, 1H), 3.26 (s, 3H), 2.75 (m, 2H), 2.29 (m, 2H), 1.75 (m, 4H), 1.10 (m, 3H), 0.94 (m, 3H).

EXAMPLE 276

(E)-3-(2-Propyl-6-trifluoromethyl-pyridin-3-yl)-hex-2-enoic acid 1-(3-ethynyl-5-fluoro-4-methanesulfonylamino-benzylamide

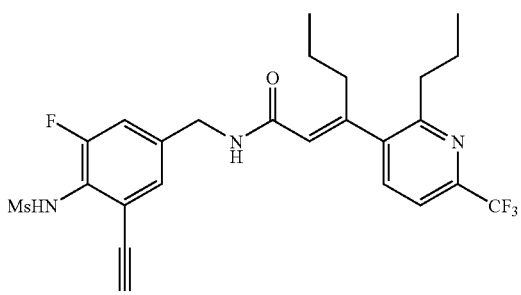

N-(4-Aminomethyl-5-ethynyl-2-fluoro-phenyl)-methanesulfonamide, HCl salt (113 mg, 0.41 mmol) was reacted with 3-(2-Propyl-6-trifluoromethyl-pyridine-3-yl)-hex-2-enoic acid (122 mg, 0.41 mmol) to give (E)-3-(2-propyl-6-trifluoromethyl-pyridin-3-yl)-hex-2-enoic acid 1-(3-ethynyl-5-fluoro-4-methanesulfonylamino-benzylamide (139 mg, 65.3%) after purification by column chromatography (Hex/EtOAc=1:1).

¹H NMR (300 MHz, CDCl₃): δ 7.44 (s, 2H), 7.15 (s, 1H), 6.98 (m, 1H), 6.41 (s, 1H), 5.83 (m, 2H), 4.32 (d, 2H, J=6.0 Hz), 3.49 (s, 1H), 3.27 (s, 3H), 2.71 (m, 2H), 1.74 (m, 4H), 1.26 (m, 2H), 0.95 (m, 6H).

ESI [M−H]−: 524

EXAMPLE 277

(Z)-3-(2-Propyl-6-trifluoromethyl-pyridin-3-yl)-hex-2-enoic acid [1-(3,5-difluoro-4-methanesulfonylamino-phenyl)-ethyl]-amide

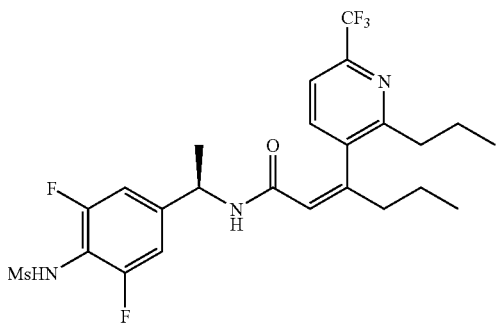

$^1$H NMR (300 MHz, CDCl$_3$): δ 7.44 (m, 2H), 6.82 (s, 1H), 6.79 (s, 1H), 6.14 (s, 1H), 5.62 (t, 1H, J=7.2 Hz), 4.97 (m, 1H), 4.12 (m, 1H), 3.25 (m, 2H), 3.21 (s, 3H), 2.74 (m, 2H), 2.27 (m, 2H), 1.74 (m, 2H), 1.37 (d, 3H, J=7.2 Hz), 1.10 (t, 3H, J=7.8 Hz), 0.95 (t, 3H, J=7.5 Hz).

ESI [M−H]−: 532

EXAMPLE 278

(E)-3-(2-Propyl-6-trifluoromethyl-pyridin-3-yl)-hex-2-enoic acid [1-(3,5-difluoro-4-methanesulfonylamino-phenyl)-ethyl]-amide

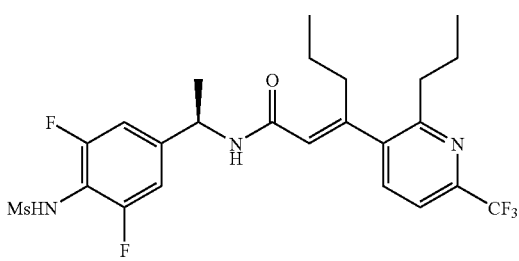

(R)—N-[4-(1-Amino-ethyl)-2,6-difluoro-phenyl]-methanesulfonamide, HCl salt (150 mg, 0.52 mmol) was reacted with 3-(2-Propyl-6-trifluoromethyl-pyridine-3-yl)-hex-2-enoic acid (158 mg, 0.52 mmol) to give (E)-3-(2-propyl-6-trifluoromethyl-pyridin-3-yl)-hex-2-enoic acid 1-(3-ethynyl-5-fluoro-4-methanesulfonylamino-benzylamide (162 mg, 58%) after purification by column chromatography (Hex/EtOAc=1:1)

$^1$H NMR (300 MHz, CDCl$_3$): δ 7.44 (s, 1H), 7.40 (s, 1H), 6.87 (d, 2H, J=8.4 Hz), 6.76 (d, 1H, J=8.4 Hz), 6.06 (s, 1H), 5.80 (t, 1H, J=7.2 Hz), 5.59 (s, 1H), 4.97 (m, 1H), 3.21 (s, 3H), 3.15 (m, 2H), 2.71 (m, 2H), 1.75 (m, 4H), 1.37 (m, 3H), 0.94 (m, 6H).

ESI [M−H]−: 532

EXAMPLE 279

3-(2-Phenethyl-6-trifluoromethyl-pyridin-3-yl)-N-(4-trifluoromethanesulfonylamino-benzyl)-acrylamide

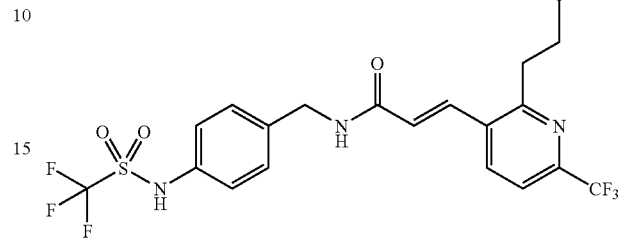

N-[4-(1-Amino-methyl)-phenyl]-trifluoromethanesulfonamide, HCl salt (75 mg) was reacted with NMM (0.2 ml), DMTMM (119 mg) and 3-(2-phenethyl-6-trifluoromethyl-pyridin-3-yl)-acrylic acid (78 mg) to give the title compound (8.5 mg) after purification by column chromatography (Hex/EtOAc=2/3).

$^1$H NMR (300 MHz, CDCl$_3$): δ 7.82 (m, 2H), 7.51 (m, 1H), 7.19 (m, 3H), 6.66 (d, 1H, J=6.6 Hz), 6.18 (d, 1H, J=17.4 Hz), 5.80 (m, 1H) 4.42 (d, 2H, J=5.4 Hz), 3.29 (m, 2H), 3.05 (m, 2H)

EXAMPLE 280

(E)-3-(2-Propyl-6-trifluoromethyl-pyridin-3-yl)-but-2-enoic acid [1-(3,5-difluoro-4-methanesulfonylamino-phenyl)-ethyl]-amide

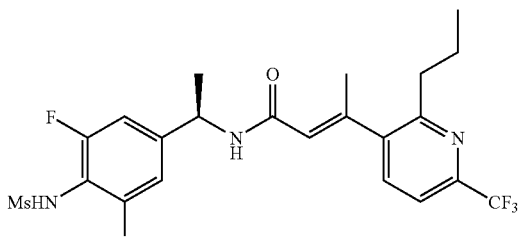

(R)—N-[4-(1-Amino-ethyl)-2,6-difluoro-phenyl]-methanesulfonamide, HCl salt (70 mg, 0.25 mmol) was reacted with 3-(2-propyl-6-trifluoromethyl-pyridine-3-yl)-but-2-enoic acid (67 mg, 0.25 mmol) to give a title compound (32 mg, 24%) after purification by column chromatography (Hex/EtOAc=3:2)

$^1$H NMR (300 MHz, CDCl$_3$): δ 7.45 (bs, 2H), 6.82 (m, 2H), 6.06 (s, 1H), 5.80 (t, 1H, J=7.2 Hz), 5.57 (s, 1H), 4.97 (m, 1H), 3.22 (s, 3H), 2.50 (s, 3H), 1.76 (m, 2H), 1.55 (m, 2H), 1.37 (d, 3H, J=6.9 Hz), 0.93 (t, 3H, J=7.8 Hz).

EXAMPLE 281

N-(3-Ethenyl-5-fluoro-4-methanesulfonylamino-benzyl)-3-(2-morpholin-1-yl-6-trifluoromethyl-pyridin-3-yl)-acrylamide

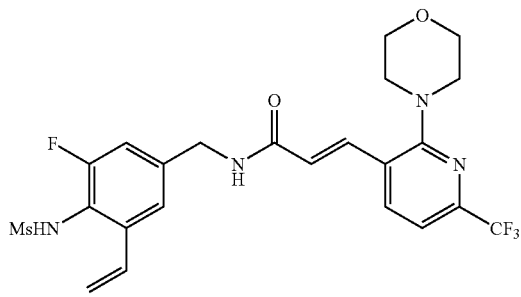

N-[4-(1-Amino-methyl)-2-ethenyl-6-fluoro-phenyl]-methanesulfonamide, HCl salt (70 mg, 0.25 mmol) was reacted with NMM (0.055 ml), DMTMM (83 mg, 0.30 mmol) and 3-(2-morpholin-1-yl-6-trifluoromethyl-pyridin-3-yl)-acrylic acid (76 mg, 0.25 mmol) to give the title compound (95 mg, 74%) after purification by column chromatography (Hex EtOAc=1/1).

$^1$H NMR (300 MHz, DMSO-d6+CDCl$_3$): δ 8.84 (bs, 1H), 8.37 (t, 1H, J=5.7 Hz), 7.76 (d, 1H, J=7.5 Hz), 7.55 (d, 1H, J=15.6 Hz), 7.33 (s, 1H), 7.18 (d, 1H, J=7.5 Hz), 7.10 (dd, 1H, J=17.1 and 10.8 Hz), 7.01 (d, 1H, J=9.3 Hz), 6.61 (d, 1H, J=15.6 Hz), 5.73 (d, 1H, J=17.1 Hz), 5.32 (d, 1H, J=10.8 Hz), 4.42 (d, 2H, J=5.7 Hz), 3.75 (m, 4H), 3.24 (m, 4H), 2.90 (s, 3H).

Experimental Example: Biological Potency Test

1. $^{45}$Ca Influx Test

1) Separation of Spinal Dorsal Root Ganglia (DRG) in Newborn Rats and Primary Culture Thereof Neonatal (2-3 day old or younger than 2-3 day old) SD rats were put in ice for 5 minutes to anesthetize and disinfected with 70% ethanol. DRG of all part of spinal cord were dissected (Wood et al., 1988, J. Neurosci. 8, pp 3208-3220) and collected in DME/F12 medium to which 1.2 g/l sodium bicarbonate and 50 mg/l gentamycin were added. The DRG were incubated sequentially at 37° C. for 30 mins in 200 U/ml collagenase and 2.5 mg/ml trypsin, separately. The ganglia were washed twice with DME/F12 medium supplemented with 10% horse serum, triturated through a fire-polished Pasteur pipette, filtered through Nitex 80 membrane to obtain single cell suspension and the suspension was washed once more. This was subjected to centrifugation, then resuspended in cell culture medium at certain level of cell density. As the cell culture medium, DME/F12 medium supplemented with 10% horse serum was diluted with identical medium conditioned by C6 glioma cells 2 days on a confluent monolayer (1:1), and NGF (Nerve Growth Factor) was added to adjust 200 ng/ml as final concentration. After the cells were grown 2 days in medium where cytosine arabinoside (Ara-C, 100 μM) was added to kill dividing nonneuronal cells, medium was changed to one without Ara-C. The resuspended cells were plated at a density of 1500-2000 neurons/well onto Terasaki plates previously coated with 10 μg/ml poly-D-ornithine.

2) $^{45}$Ca Influx Experiments

DRG nerve cells from the primary culture of 2 days were equilibrated by washing 4 times with HEPES (10 mM, pH 7.4)-buffered Ca$^{2+}$, Mg$^{2+}$-free HBSS (H-HBSS). The solution in each well was removed from the individual well. Medium containing the test compound plus capsaicin (final concentration 0.5 μM) and $^{45}$Ca (final concentration 10 μCi/ml) in H-HBSS was added to each well and incubated at room temperature for 10 mins. Terasaki plates were washed five times with H-HBSS and dried at room temperature. To each well, 0.3% SDS (10 μl) was added to elute $^{45}$Ca. After the addition of scintillation cocktail of into each well, the amount of $^{45}$Ca influx into neuron was measured by counting radioactivity. Antagonistic activities of test compounds against vanilloid receptor were calculated as percent of the inhibition of maximal response of capsaicin at a concentration of 0.5 μM.

TABLE 1

Results of Calcium Influx Test

| Examples | Antagonist Calcium Uptake Test (IC$_{50}$, μM) |
|---|---|
| 1 | 1.3 |
| 2 | 1.3 |
| 3 | 0.52 |
| 4 | 0.22 |
| 5 | 1.5 |
| 6 | 0.30 |
| 7 | 1.0 |
| 8 | 0.42 |
| 9 | 0.40 |
| 10 | 0.28 |
| 11 | 0.29 |
| 12 | 0.26 |
| 13 | 3.5 |
| 14 | >10 |
| 15 | 5.9 |
| 16 | >10 |
| 17 | 0.57 |
| 18 | 0.13 |
| 19 | >10 |
| 20 | >10 |
| 21 | 1.1 |
| 22 | 3.3 |
| 23 | >10 |
| 24 | 0.34 |
| 25 | >10 |
| 26 | 1.1 |
| 27 | 2.9 |
| 28 | 1.6 |
| 29 | >10 |
| 30 | 3.8 |
| 31 | >10 |
| 32 | >10 |
| 33 | 1.0 |
| 34 | >10 |
| 35 | >10 |
| 36 | 0.18 |
| 37 | 0.059 |
| 38 | 0.22 |
| 39 | 1.6 |
| 40 | 0.98 |
| 41 | 1.6 |
| 42 | 0.096 |
| 43 | 9.2 |
| 44 | >10 |
| 45 | 0.51 |
| 47 | 0.96 |
| 49 | 5.4 |
| 50 | >10 |
| 51 | 0.14 |
| 52 | 3.0 |
| 53 | >10 |
| 55 | 1.4 |
| 56 | >10 |
| 57 | >10 |
| 58 | >10 |
| 59 | 0.21 |
| 60 | 2.1 |
| 61 | 4.9 |
| 62 | 0.26 |

TABLE 1-continued

Results of Calcium Influx Test

| Examples | Antagonist Calcium Uptake Test (IC$_{50}$, μM) |
|---|---|
| 63 | 0.56 |
| 64 | 6.5 |
| 65 | 0.089 |
| 66 | 0.25 |
| 67 | 1.0 |
| 68 | 1.3 |
| 69 | 3.2 |
| 70 | 0.13 |
| 71 | >10 |
| 72 | 0.16 |
| 73 | 0.15 |
| 74 | 0.51 |
| 75 | 0.37 |
| 76 | 0.20 |
| 77 | 0.34 |
| 78 | 0.12 |
| 79 | 0.43 |
| 80 | 3.1 |
| 81 | 11.9 |
| 82 | 0.60 |
| 83 | 2.1 |
| 84 | 0.24 |
| 85 | 0.18 |
| 86 | 1.2 |
| 87 | 2.2 |
| 88 | 0.40 |
| 89 | 0.28 |
| 90 | 0.41 |
| 91 | 0.58 |
| 92 | 0.52 |
| 93 | 0.36 |
| 94 | 0.59 |
| 95 | 0.55 |
| 96 | 1.7 |
| 97 | 0.29 |
| 98 | 0.19 |
| 99 | 1.8 |
| 100 | 0.069 |
| 101 | 0.84 |
| 102 | 1.6 |
| 103 | 5.9 |
| 104 | 1.6 |
| 105 | 0.63 |
| 106 | 0.083 |
| 107 | 0.51 |
| 108 | 0.74 |
| 109 | 0.15 |
| 110 | 0.58 |
| 111 | 0.82 |
| 112 | 1.4 |
| 113 | 0.27 |
| 114 | 0.43 |
| 115 | 0.47 |
| 116 | 4.5 |
| 117 | 0.077 |
| 118 | 0.20 |
| 119 | 0.27 |
| 120 | 0.31 |
| 121 | 0.12 |
| 122 | 0.076 |
| 123 | 0.093 |
| 124 | 0.088 |
| 125 | >1 |
| 126 | 4.9 |
| 127 | 0.32 |
| 128 | 0.60 |
| 129 | 0.047 |
| 130 | 0.054 |
| 131 | 1.0 |
| 132 | >3 |
| 133 | 0.28 |
| 134 | 2.6 |
| 135 | 2.3 |
| 136 | 0.90 |
| 139 | 0.34 |
| 140 | 9.7 |
| 141 | 0.18 |
| 142 | 0.035 |
| 143 | 0.20 |
| 144 | 0.033 |
| 145 | 1.9 |
| 147 | 0.22 |
| 148 | 0.051 |
| 149 | 0.25 |
| 150 | 0.21 |
| 151 | 0.15 |
| 152 | 0.043 |
| 153 | 1.1 |
| 154 | 2.1 |
| 155 | 0.78 |
| 156 | 2.2 |
| 157 | 0.45 |
| 158 | 0.48 |
| 159 | 0.27 |
| 160 | 2.4 |
| 161 | 0.55 |
| 162 | 0.12 |
| 163 | 0.15 |
| 164 | 0.083 |
| 165 | 0.16 |
| 166 | 0.069 |
| 167 | 0.12 |
| 168 | 1.8 |
| 169 | 0.17 |
| 170 | 0.34 |
| 171 | 0.18 |
| 172 | 0.069 |
| 173 | 0.20 |
| 174 | 0.070 |
| 175 | 0.024 |
| 176 | 0.057 |
| 177 | 0.20 |
| 178 | 0.92 |
| 179 | 0.78 |
| 180 | 0.46 |
| 181 | 0.27 |
| 182 | 0.40 |
| 183 | 0.22 |
| 184 | 0.23 |
| 185 | 0.28 |
| 186 | 0.51 |
| 187 | 0.075 |
| 188 | 0.087 |
| 189 | 0.40 |
| 190 | 2.3 |
| 191 | 0.22 |
| 192 | 0.090 |
| 193 | 0.042 |
| 194 | 0.076 |
| 195 | 0.067 |
| 196 | 0.076 |
| 197 | 0.065 |
| 198 | 0.054 |
| 199 | 0.092 |
| 200 | 0.58 |
| 201 | 0.42 |
| 202 | 0.035 |
| 203 | 0.12 |
| 204 | 0.17 |
| 205 | 0.086 |
| 206 | 0.040 |
| 207 | 0.14 |
| 208 | 0.049 |
| 209 | 0.087 |
| 210 | 0.022 |
| 211 | 0.062 |

TABLE 1-continued

Results of Calcium Influx Test

| Examples | Antagonist Calcium Uptake Test ($IC_{50}$, µM) |
|---|---|
| 212 | 0.11 |
| 213 | 0.028 |
| 214 | 0.098 |
| 215 | 0.054 |
| 216 | 2.0 |
| 217 | 0.13 |
| 218 | 0.046 |
| 219 | 0.073 |
| 220 | 0.071 |
| 221 | 0.023 |
| 222 | 0.049 |
| 223 | 0.055 |
| 224 | 0.016 |
| 225 | 0.052 |
| 226 | 0.085 |
| 227 | 0.019 |
| 228 | 0.012 |
| 229 | 0.015 |
| 230 | 0.062 |
| 231 | 0.076 |
| 232 | 0.19 |
| 233 | 0.080 |
| 234 | 0.041 |
| 235 | 0.19 |
| 236 | 0.049 |
| 237 | 0.096 |
| 238 | 0.045 |
| 239 | 0.12 |
| 240 | 0.20 |
| 241 | 0.034 |
| 242 | 0.025 |
| 243 | 0.041 |
| 244 | 0.067 |
| 245 | 0.024 |
| 246 | 0.010 |
| 247 | 0.013 |
| 248 | 0.12 |
| 249 | 0.025 |
| 250 | 0.032 |
| 251 | 0.70 |
| 252 | 0.33 |
| 253 | 0.50 |
| 254 | 0.15 |
| 255 | 0.13 |
| 256 | 0.068 |
| 257 | 0.056 |
| 258 | 0.021 |
| 259 | 0.19 |
| 260 | 0.81 |
| 261 | 0.35 |
| 262 | 0.15 |
| 263 | 4.7 |
| 264 | 0.34 |
| 265 | 0.77 |
| 266 | 1.4 |
| 267 | 0.45 |
| 268 | 2.9 |
| 269 | 1.4 |
| 270 | >10 |
| 271 | 1.3 |
| 272 | 0.74 |
| 273 | 0.84 |
| 274 | 1.2 |
| 275 | 0.31 |
| 276 | 0.24 |
| 277 | 0.32 |
| 278 | 0.16 |
| 279 | 3.9 |
| 280 | 3.0 |
| 281 | 0.22 |

2. Analgesic Activity Test: Mouse Writhing Test by Inducing with Phenyl-p-Quinone Male ICR mice (mean body weight 25 g) were maintained in a controlled lighting environment (12 h on/12 h off) for experiment. Animals received an intraperitoneal injection of 0.3 ml of the chemical irritant phenyl-p-quinone (dissolved in saline containing 5% ethanol to be a dose of 4.5 mg/kg) and 6 mins later, the number of abdominal constrictions was counted in the subsequent 6 mins period. Animals (10 animals/group) received 0.2 ml of test compounds solution in vehicle of ethanol/Tween 80/saline (10/10/80) intraperitoneally 30 min before the injection of phenyl-p-quinone. In the case of oral administration, 0.2 ml of test compounds solution in vehicle of ethanol/Tween 80/saline (5/5/90) were administered 54 min prior to the 0.2 ml of 0.02% phenyl-p-quinone injection. A reduction in the number of writhes responding to the test drug compound relative to the number responding in saline control group was considered to be indicative of an analgesic effect. Analgesic effect was calculated by % inhibition equation (% inhibition=(C−T)/C×100), wherein C and T represent the number of writhes in control and compound-treated group, respectively. Most examples of the present invention having good in vitro activities, were tested at various doses (ranging from 0.1 to 3 mg/kg) and all compounds tested in vivo showed analgesic effects from 12 to 70% inhibition at each dose, respectively.

3. Metabolic Stability and PK Study

1) Metabolic Stability Test

Diluted sample (final 5 µg/mL in 0.1 M potassium phosphate buffer, pH 7.4) was pre-incubated with cofactors (glucose-6-phosphate 3.3 mM, NADPH 1.3 mM, $MgCl_2$ 0.16 mM, glucose-6-phosphate dehydrogenase 0.4 U/mL final) and enzyme reaction was initiated with the addition of human intestinal (1 mg/mL protein) or rat liver microsomes (0.5 mg/mL protein). Reaction was terminated with 2× volume of cold acetonitrile after 1 min (initial point) or 30 min (reacted sample) incubation. In case of human intestinal microsomes, 2 hr reaction time was employed. Reaction mixture was undergone extraction in shaking bath over 20 min, after which resultant supernatant was separated by centrifugation. Area of parent compound peak was analyzed in the supernatant using HPLC-UV method and the extent of metabolism was shown as the decreased compound peak area (%) from initial point.

Metabolic stabilities of compounds with a CF3-pyridinyl partial structure according to the present invention, were generally better than the corresponding tert-butyl phenyl-containing compounds, which were at least in part disclosed in the art, e.g. in WO 06/101318. The details of the metabolic stability data obtained are presented in Table 2.

2) PK Study

Pharmacokinetics of compounds in rats were analyzed using the following experiment. Rats were fasted overnight prior to administration and until approximately 4 hours after administration. Rats were given a single oral administration of compound at same dose. Administration volume was 10 ml/kg. Blood samples were collected from the retro-orbital sinus at various times over the following 7 hrs. Immediately after each collection, plasmas were separated from blood cells by centrifugation and stored at −20° C. until the analysis was performed. The plasma samples were analyzed using a reverse phase high-performance chromatography (HPLC) method.

As shown in Table 3, PK profile of compounds with a $CF_3$-pyridinyl partial structure according to the present invention, were generally better than the corresponding tert-butyl phenyl-containing compounds, which were at least in part disclosed in the art, e.g. in WO 06/101318. Substantial increases in absorption and apparent half-life were observed by the replacement of tert-butyl phenyl to CF3 pyridinyl.

TABLE 2

Results of metabolic stability test

| Ex # | Structure | IC50 | Stability RLM[c] | HIM[d] |
|---|---|---|---|---|
| Ex 22[a] | 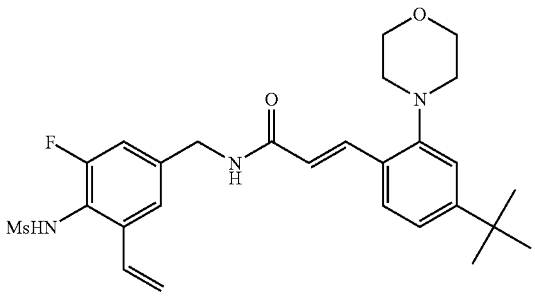 | 0.25 | 48.7 | 100 |
| Ex 27[a] | 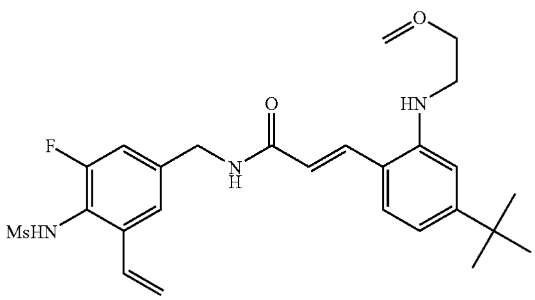 | 0.076 | 19.8 | 80.5 |
| Ex 34[a] | 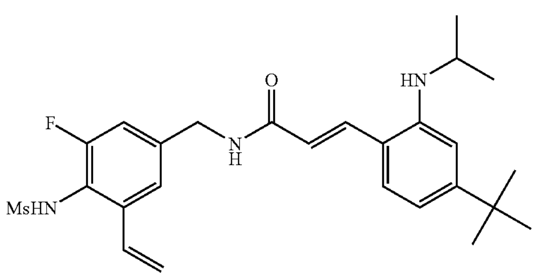 | 0.17 | 24.2 | 28.1 |
| Ex 23[a] | 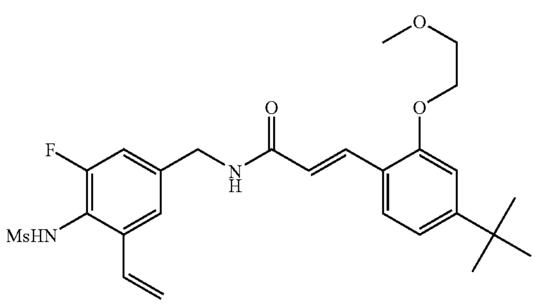 | 0.067 | 60.7 | 93.9 |
| Ex 28[a] | 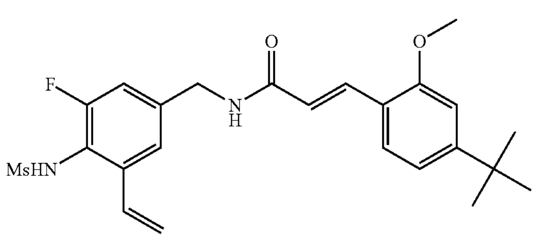 | 0.073 | 49.1 | 93.0 |

TABLE 2-continued
Results of metabolic stability test
| Ex # | Structure | IC50 | Stability RLM[c] | HIM[d] |
|---|---|---|---|---|
| None | 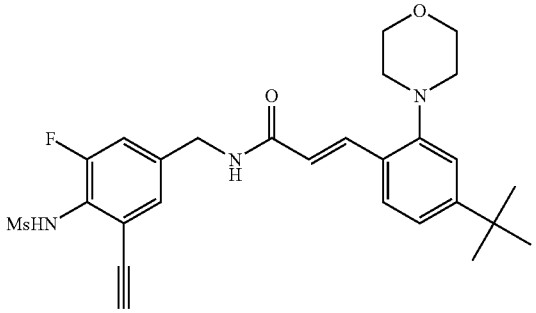 | 0.86 | 12.8 | 54.0 |
| Ex 1[b] | 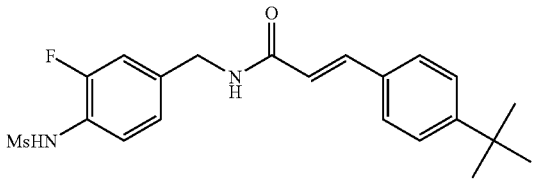 | 0.49 | 42.4 | 38.7 |
| Ex 2[b] | 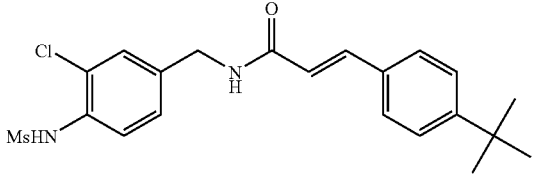 | 0.26 | 48.0 | 30.9 |
| Ex 4[b] | 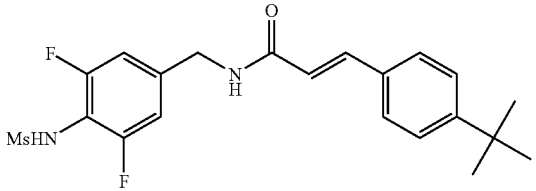 | 0.31 | 27.8 | 20.1 |
| Ex 9[b] | 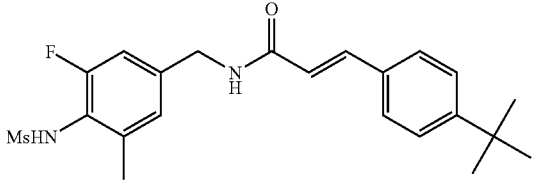 | 0.36 | 39.0 | 50.1 |
| Ex 281 | 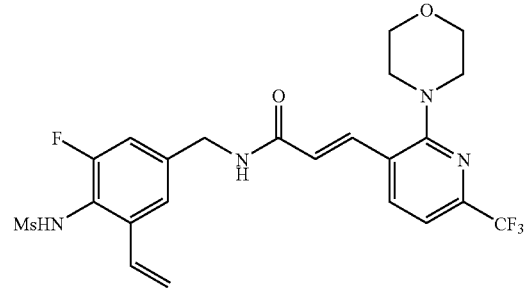 | 0.22 | 0.5 | 0 |

TABLE 2-continued

Results of metabolic stability test

| Ex # | Structure | IC50 | Stability RLM[c] | HIM[d] |
|---|---|---|---|---|
| Ex 65 | | 0.089 | 15.3 | 14.0 |
| Ex 100 | | 0.069 | 3.4 | 0 |
| Ex 75 | | 0.37 | 17.0 | 17.0 |
| Ex 42 | | 0.096 | 17.1 | 17.1 |
| Ex 12 | | 0.26 | 11.7 | 12.0 |

TABLE 2-continued

Results of metabolic stability test

| Ex # | Structure | IC50 | Stability RLM[c] | HIM[d] |
|---|---|---|---|---|
| Ex 45 | | 0.51 | 10 | 8.0 |
| Ex 253 | | 0.50 | 0 | 3.2 |
| Ex 222 | | 0.049 | 0 | 0 |
| Ex 188 | | 0.087 | 2.7 | 1.6 |

[a]Example number in WO 06/101,318
[b]Example number in WO 06/101,321
[c]% metabolized in rat liver microsomes
[d]% metabolized in human intestinal microsomes

TABLE 3

Results of PK study

| Ex # | Structure | IC50 | Cmax (µg/ml) | Tmax (hour) | AUCpo (µg hr ml-1) | T$_{1/2}$ (hr) |
|---|---|---|---|---|---|---|
| Ex 22[a] | 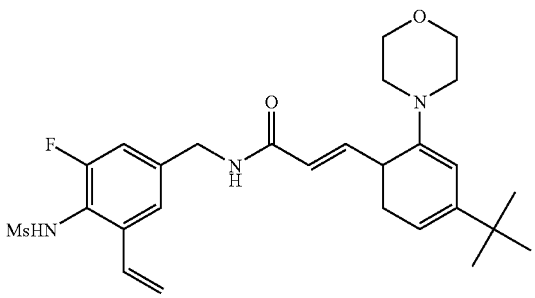 | 0.25 | <0.100 | ∴[e] | ∴[e] | ∴[e] |
| None | 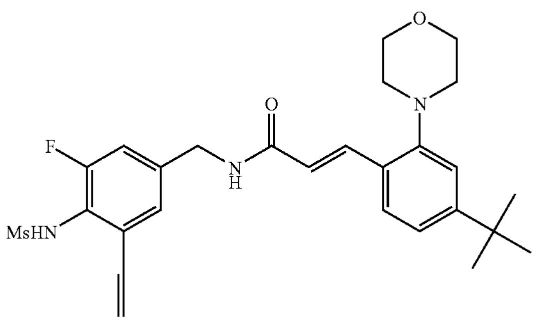 | 0.86 | 0.334 | 2.000 | 0.706 | 0.932 |
| Ex 34[a] | 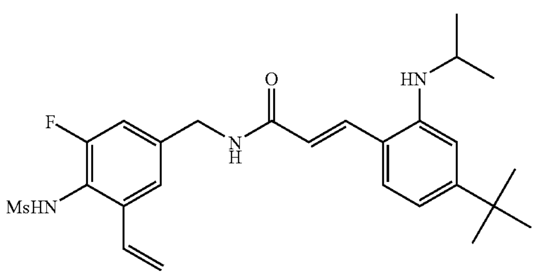 | 0.17 | <0.100 | ∴[e] | ∴[e] | ∴[e] |
| Ex 16[a] | | 0.047 | <0.100 | ∴[e] | ∴[e] | ∴[e] |
| Ex 16[a] | | 0.047 | <0.100 | −e | −e | −e |

TABLE 3-continued

Results of PK study

| Ex # | Structure | IC50 | Cmax (μg/ml) | Tmax (hour) | AUCpo (μg hr ml-1) | T$_{1/2}$ (hr) |
| --- | --- | --- | --- | --- | --- | --- |
| Ex 281 | 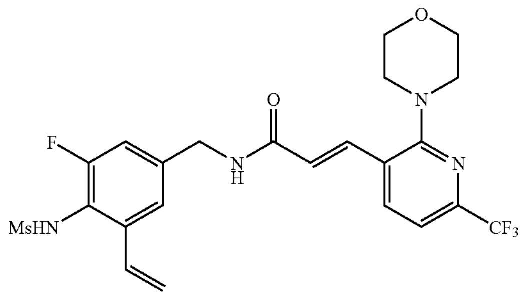 | 0.22 | 0.215 | 2.00 | 0.654 | 1.261 |
| Ex 12 | 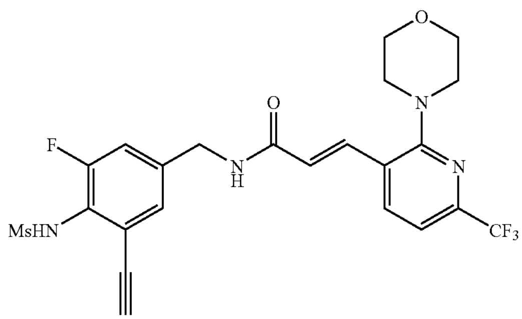 | 0.26 | 0.723 | 2.375 | 3.237 | 1.702 |
| Ex 100 | 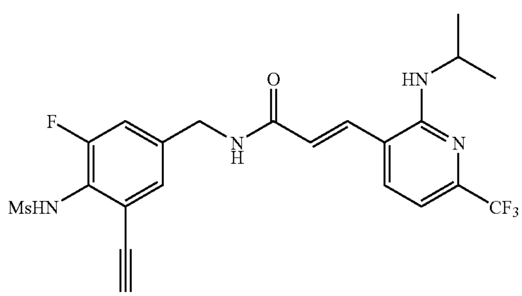 | 0.069 | 2.533 | 3.000 | 17.378 | 3.211 |
| Ex 57 | 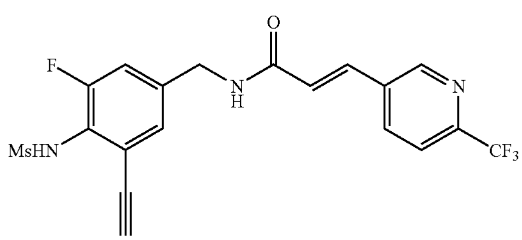 | >10 | 2.205 | 0.833 | 56.524 | 3.951 |
| Ex 206 | 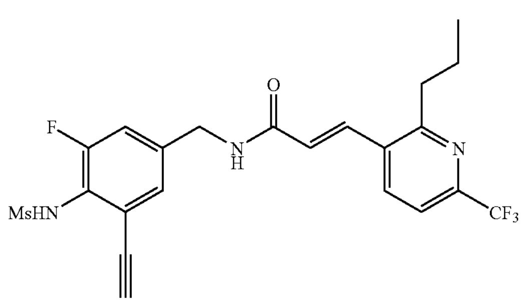 | 0.040 | 5.497 | 3.500 | 25.928 | 1.423 |

$^a$Example number in WO 06/101,318
$^e$This value could not be determined due to low plasma concentration (detection limit 0.1000 μg/ml).

INDUSTRIAL APPLICABILITY

As explained above, the compound according to the present invention is useful to prevent or to treat pain, inflammatory disease of the joints, neuropathies, HIV-related neuropathy, nerve injury, neurodegeneration, stroke, urinary bladder hypersensitivity including urinary incontinence, cystitis, stomach duodenal ulcer, irritable bowel syndrome (IBS) and inflammatory bowel disease (IBD), fecal urgency, gastroesophageal reflux disease (GERD), Crohn's disease, asthma, chronic obstructive pulmonary disease, cough, neurotic/allergic/inflammatory skin disease, psoriasis, pruritus, prurigo, irritation of skin, eye or mucous membrane, hyperacusis, tinnitus, vestibular hypersensitivity, episodic vertigo, cardiac diseases such as myocardial ischemia, hair growth-related disorders such as effluvium, alopecia, rhinitis, and pancreatitis.

More specifically, the compound according to the present invention is useful to preventing and treating of pain, which is or which is associated with a condition selected from the group consisting of osteoarthritis, rheumatoid arthritis, ankylosing spondylitis, diabetic neuropathic pain, post-operative pain, dental pain, non-inflammatory musculo skeletal pain (including fibromyalgia, myofascial pain syndrome and back pain), migraine, and other types of headaches.

The invention claimed is:

1. A compound of the formula (I), an isomer, or a pharmaceutically acceptable salt thereof:

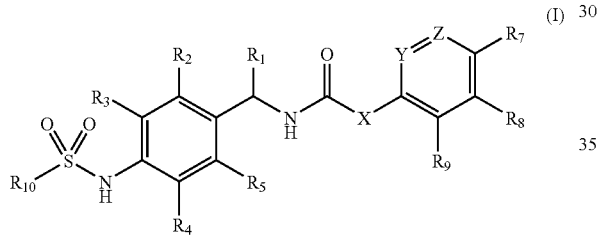

wherein,
—X is $CR_{11}=CR_{12}$, or $C\equiv C$; wherein, $R_{11}$ and $R_{12}$, if present, are independently hydrogen, halogen, or C1-C5 alkyl;
—Z is N;
—Y is $CR_6$;
$R_1$ is hydrogen, halogen, or C1-C5 alkyl;
$R_2$, $R_3$, $R_4$, and $R_5$ are independently hydrogen, halogen, nitro, cyano, C1-C5 alkyl, C1-C5 alkoxy, halo (C1-C5) alkyl, C2-C5 alkenyl, C2-C5 alkynyl, carboxy, C1-C5 alkoxycarbonyl, or C1-C5 alkylthio;
$R_6$ is hydroxy, halogen, nitro, carboxy, C1-C10 alkyl, C1-C10 alkoxy, C2-C10 alkenyl, C2-C10 alkynyl, C1-C10 alkylthio, C1-C10 alkylsulfonyl, C1-C10 alkylcarbonyl, C1-C10 alkoxycarbonyl, C2-C10 alkenyloxy, C1-C5 alkoxy (C1-C5) alkoxy, C1-C5 alkoxy (C1-C5) alkoxy (C1-C5) alkyl, piperidyl, piperazinyl, C1-C5 alkoxy (C1-C5) alkylamino, C1-C10 alkylamino, di(C1-C10 alkyl)amino, C3-C8 cycloalkyl, C3-C3 cycloalkylamino, C3-C8 cycloalkoxy, C3-C8 oxacycloalkyloxy, N—(C1-C5) alkoxy (C1-C5) alkyl-N—(C1-C5) alkylamino, N—(C3-C8) cycloalkyl-N—(C1-C5) alkylamino, N-aryl-N—(C1-C5) alkylamino, aryl, arylamino, arylthio, heteroaryl, heteroarylamino, aryloxy, heteroaryloxy, pyrrolidinyl, or morpholinyl,
$R_8$, and $R_9$ are independently hydrogen, hydroxy, halogen, nitro, carboxy, C1-C10 alkyl, C1-C10 alkoxy, C2-C10 alkenyl, C2-C10 alkynyl, C1-C10 alkylthio, C1-C10 alkylsulfonyl, C1-C10 alkylcarbonyl, C1-C10 alkoxycarbonyl, C2-C10 alkenyloxy, C1-C5 alkoxy (C1-C5) alkoxy, C1-C5 alkoxy (C1-C5) alkoxy (C1-C5) alkyl, piperidyl, piperazinyl, C1-C5 alkoxy (C1-C5) alkylamino, C1-C10 alkylamino, di(C1-C10 alkyl)amino, C3-C8 cycloalkyl, C3-C8 cycloalkylamino, C3-C8 cycloalkoxy, C3-C8 oxacycloalkyloxy, N—(C1-C5) alkoxy (C1-C5) alkyl-N—(C1-C5) alkylamino, N—(C3-C8) cycloalkyl-N—(C1-C5) alkylamino, N-aryl-N—(C1-C5) alkylamino, aryl, arylamino, arylthio, heteroaryl, heteroarylamino, aryloxy, heteroaryloxy, pyrrolidinyl, or morpholinyl, wherein,
each alkyl, alkenyl and alkynyl, alone or as a part of an alkoxy, alkylsulfonyl, alkylcarbonyl, alkylamino, or alkenyloxy may be independently unsubstituted or substituted with one or more substituents selected from among halogen, hydroxyl, unsubstituted or halo-substituted (C1-C5) alkoxy, (C3-C8), cycloalkyl which may be unsubstituted or substituted with one or two halogen radicals and/or methyl groups, unsubstituted or halo-substituted (C1-C5) alkylamino, phenyl which may be unsubstituted or substituted with one or more substituents selected from halogen, unsubstituted C1-C3 alkyl, or halo (C1-C3) alkyl, or unsubstituted or halo-substituted di(C1-C5) alkylamino,
each aryl or heteroaryl, alone or as a part of an arylamino, aryloxy, heteroarylamino, or heteroaryloxy, may be independently unsubstituted or substituted with one or more substituents selected from halogen, unsubstituted C1-C5 alkyl, unsubstituted C1-C5 alkoxy, or halo (C1-C5) alkyl,
each cycloalkyl, alone or as a part of a cycloalkoxy or cycloalkylamino may be unsubstituted or substituted with one or more unsubstituted or halo-substituted C1-C3 alkyl groups, hydroxymethyl, hydroxy, methoxy, or amino, and
each piperazinyl, piperidyl, morpholinyl, and pyrrolidinyl may be unsubstituted or substituted with one or more unsubstituted or halo-substituted C1-C3 alkyl groups, hydroxy(C1-C3)alkyl, C1-C3 alkoxy, (C1-C3)alkoxycarbonyl, or hydroxyl;

$R_7$ is halo(C1-C5)alkyl;
and
$R_{10}$ is C1-C5 alkyl, halo (C1-C5) alkyl, or C2-C5 alkenyl.

2. A compound of the formula (I), an isomer, or a pharmaceutically acceptable salt thereof:

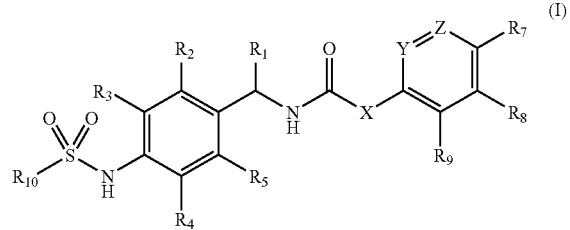

wherein,
—X is $CR_{11}=CR_{12}$ or $C\equiv C$; wherein, $R_{11}$ and $R_{12}$, if present, are independently hydrogen, halogen, or C1-C5 alkyl;
—Z is N;
—Y is $CR_6$;
$R_1$ is hydrogen, halogen, or C1-C5 alkyl;

$R_2$, $R_3$, $R_4$, and $R_5$ are independently hydrogen, halogen, nitro, cyano, C1-C5 alkyl, C1-C5 alkoxy, halo (C1-C5) alkyl, C2-C5 alkenyl, C2-C5 alkynyl, carboxy, C1-C5 alkoxycarbonyl, or C1-C5 alkylthio;

$R_6$ is hydroxy, halogen, nitro, carboxy, C1-C10 alkyl, C1-C10 alkoxy, C2-C10 alkenyl, C2-C10 alkynyl, C1-C10 alkylthio, C1-C10 alkylsulfonyl, C1-C10 alkylcarbonyl, C1-C10 alkoxycarbonyl, C2-C10 alkenyloxy, C1-C5 alkoxy (C1-C5) alkoxy, C1-C5 alkoxy (C1-C5) alkoxy (C1-C5) alkyl, piperidyl, C1-C5 alkoxy (C1-C5) alkylamino, C1-C10 alkylamino, di(C1-C10 alkyl)amino, C3-C8 cycloalkyl, C3-C8 cycloalkylamino, C3-C8 cycloalkoxy, C3-C8 oxacycloalkyloxy, N—(C1-C5) alkoxy (C1-C5) alkyl-N—(C1-C5) alkylamino, N—(C3-C8) cycloalkyl-N—(C1-C5) alkylamino, N-aryl-N—(C1-C5) alkylamino, aryl, arylamino, thienyl, heteroarylamino, aryloxy, pyrrolidinyl, or morpholinyl, provided that R6 is not a hydroxyl-substituted alkylamino;

$R_8$ and $R_9$ are independently hydrogen, hydroxy, halogen, nitro, carboxy, C1-C10 alkyl, C1-C10 alkoxy, C2-C10 alkenyl, C2-C10 alkynyl, C1-C10 alkylthio, C1-C10 alkylsulfonyl, C1-C10 alkylcarbonyl, C1-C10 alkoxycarbonyl, C2-C10 alkenyloxy, C1-C5 alkoxy (C1-C5) alkoxy, C1-C5 alkoxy (C1-C5) alkoxy (C1-C5) alkyl, piperidyl, piperazinyl, C1-C5 alkoxy (C1-C5) alkylamino, C1-C10 alkylamino, di(C1-C10 alkyl)amino, C3-C8 cycloalkyl, C3-C8 cycloalkylamino, C3-C8 cycloalkoxy, C3-C8 oxacycloalkyloxy, N—(C1-C5) alkoxy (C1-C5) alkyl-N—(C1-C5) alkylamino, N—(C3-C8) cycloalkyl-N—(C1-C5) alkylamino, N-aryl-N—(C1-C5) alkylamino, aryl, arylamino, arylthio, heteroaryl, heteroarylamino, aryloxy, heteroaryloxy, pyrrolidinyl, or morpholinyl, wherein, each alkyl, alkenyl and alkynyl, alone or as a part of an alkoxy, alkylsulfonyl, alkylcarbonyl, alkylamino, or alkenyloxy may be independently unsubstituted or substituted with one or more substituents selected from among halogen, hydroxyl, unsubstituted or halo-substituted (C1-C5) alkoxy, (C3-C8), cycloalkyl which may be unsubstituted or substituted with one or two halogen radicals and/or methyl groups, unsubstituted or halo-substituted (C1-C5) alkylamino, phenyl which may be unsubstituted or substituted with one or more substituents selected from halogen, unsubstituted C1-C3 alkyl, or halo (C1-C3) alkyl, or unsubstituted or halo-substituted di(C1-C5) alkylamino, each aryl or heteroaryl, alone or as a part of an arylamino, aryloxy, heteroarylamino, or heteroaryloxy, may be independently unsubstituted or substituted with one or more substituents selected from halogen, unsubstituted C1-C5 alkyl, unsubstituted C1-C5 alkoxy, or halo (C1-C5) alkyl, each cycloalkyl, alone or as a part of a cycloalkoxy or cycloalkylamino may be unsubstituted or substituted with one or more unsubstituted or halo-substituted C1-C3 alkyl groups, hydroxymethyl, hydroxy, methoxy, or amino, and each piperidyl, and morpholinyl, may be unsubstituted or substituted with one or more unsubstituted or halo-substituted C1-C3 alkyl groups, hydroxy(C1-C3) alkyl, C1-C3 alkoxy, (C1-C3)alkoxycarbonyl, or hydroxyl;

$R_7$ is halo(C1-C5)alkyl; and $R_{10}$ is C1-C5 alkyl, halo (C1-C5) alkyl, or C2-C5 alkenyl.

3. The compound of claim 1 or 2, an isomer, or a pharmaceutically acceptable salt thereof;

wherein

X is —CH=CH—, —C(CH$_3$)=CH—, —CH=C(CH$_3$)—, —C(CH$_3$)=C(CH$_3$)—, —C(C$_2$H$_5$)=CH—, —CH=C(C$_2$H$_5$)—, —CF=CH—, —CH=CF—, or C≡C;

$R_1$ is hydrogen, fluoro, methyl, or ethyl;

$R_2$, $R_3$, $R_4$, and $R_5$ are independently hydrogen, fluoro, chloro, bromo, nitro, cyano, methyl, ethyl, ethenyl, ethynyl, trifluoromethyl, methoxy, ethoxy, or methoxycarbonyl;

$R_6$ is hydroxy, fluoro, bromo, chloro, hydroxymethyl, C1-C6 alkyl, C1-C6 alkoxy, C2-C6 alkenyl, C2-C6 alkynyl, halo (C1-C6) alkyl, halo (C1-C6) alkoxy, C2-C6 alkenyloxy, C1-C5 alkoxy (C1-C5) alkoxy, C1-C5 alkoxy (C1-C5) alkoxy (C1-C5) alkyl, di(C1-C6 alkyl)amino, C1-C6 alkylamino, C1-C3 alkoxy (C1-C5) alkylamino, C3-C6 cycloalkyl which may be unsubstituted or substituted with one or more methyl groups, C3-C6 cycloalkylamino which may be unsubstituted or substituted with one or more methyl groups, C3-C6 cycloalkoxy, C3-C6 oxacycloalkoxy, N—(C1-C2) alkoxy (C1-C3) alkyl-N—(C1-C3) alkylamino, N—(C3-C6) cycloalkyl-N—(C1-C3) alkylamino, piperidyl, pyrrolidinyl, halophenyl, phenyl, phenoxy, phenylamino, halophenoxy, morpholinyl; C1-C2 alkoxy (C1-C3) alkyl, phenyl(C1-C3)alkyl, phenyl(C2-C3)alkenyl, C1-C3 alkoxyalkynyl, di(C1-C3)alkylaminoalkynyl, (C1-C3) alkoxyphenyl, thienyl, (C3-C6) cycloalkyl (C1-C3) alkoxy, phenyl (C1-C3) alkoxy, C1-C5 alkylthio, phenyl (C1-C3) alkylamino, arylamino, N-phenyl-N—(C1-C3) alkylamino, (C1-C3) alkoxycarbonyl, or piperidyl;

$R_7$ is halo (C1-C5) alkyl;

$R_8$ and $R_9$ are independently hydrogen, halogen, or trifluoromethyl; and $R_{10}$ is C1-C5 alkyl, halo (C1-C5) alkyl, or C2-C5 alkenyl.

4. The compound of claim 1 or 2, an isomer, or a pharmaceutically acceptable salt thereof;

wherein,

X is CR$_{11}$=CR$_{12}$, wherein, $R_{11}$ and $R_{12}$, are independently hydrogen, halogen, or C1-C3 alkyl;

$R_1$ is hydrogen or C1-C3 alkyl;

$R_2$, $R_3$, $R_4$, and $R_5$ are independently hydrogen, halogen, nitro, cyano, methyl, ethyl, ethenyl, ethynyl, trifluoromethyl, methoxy, ethoxy, or methoxycarbonyl;

$R_6$ is hydroxy, halogen, nitro, carboxy, C1-C5 alkyl, C1-C5 alkoxy, hydroxy (C1-C5) alkyl, C2-C5 alkenyl, C2-C5 alkynyl, halo (C1-C5) alkyl, halo (C1-C5) alkoxy, C1-C5 alkylthio, C1-C5 alkylsulfonyl, C1-C5 alkylcarbonyl, C1-C5 alkoxycarbonyl, C2-C5 alkenyloxy, C1-C5 alkoxy (C1-C5) alkoxy, C1-C5 alkoxy (C1-C5) alkoxy (C1-C5) alkyl, piperidyl, C1-C5 alkoxy (C1-C5) alkylamino, C1-C7 alkylamino, di(C1-C3 alkyl)amino, C3-C6 cycloalkyl which may be unsubstituted or substituted with one or more methyl groups, pyrrolidinyl, phenyl, or morpholinyl, wherein the phenyl may be unsubstituted or substituted with one or more substituents selected from halogen, C1-C5 alkyl, and halo (C1-C5) alkyl $R_8$ and $R_9$ are independently hydrogen, hydroxy, halogen, nitro, carboxy, C1-C5 alkyl, C1-C5 alkoxy, hydroxy (C1-C5) alkyl, C2-C5 alkenyl, C2-C5 alkynyl, halo (C1-C5) alkyl, halo (C1C5) alkoxy, C1-C5 alkylthio, C1-C5 alkylsulfonyl, C1-C5 alkylcarbonyl, C1-C5 alkoxycarbonyl, C2-C5 alkenyloxy, C1-C5 alkoxy (C1-C5)

alkoxy, C1-C5 alkoxy (C1-C5) alkoxy (C1-C5) alkyl, C1-C3 alkylpiperazinyl, piperidyl, C1-C5 alkoxy (C1-C5) alkylamino, C1-C7 alkylamino, di(C1-C3 alkyl) amino, C3-C6 cycloalkyl which may be unsubstituted or substituted with one or more methyl groups, pyrrolidinyl, phenyl, or morpholinyl, wherein the phenyl may be unsubstituted or substituted with one or more substituents selected from halogen, C1-C5 alkyl, and halo (C1-C5) alkyl;

$R_7$ is halo(C1-C4)alkyl;

and $R_{10}$ is C1-C3 alkyl or C2-C3 alkenyl.

5. The compound of claim 1, an isomer, or a pharmaceutically acceptable salt thereof; wherein $R_7$ is trifluoromethyl.

6. The compound of claim 1, an isomer, or a pharmaceutically acceptable salt thereof; wherein $R_7$ is $CF_2Cl$ or $CF_2CF_3$.

7. A compound of the formula (III), an isomer, or a pharmaceutically acceptable salt thereof;

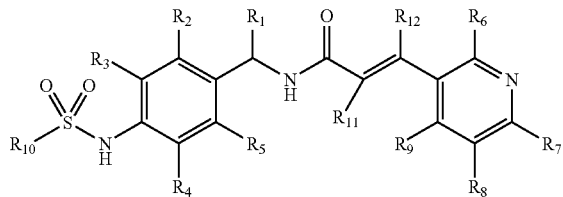

(III)

wherein, $R_1$ is hydrogen, halogen or C1-C5 alkyl;

$R_2$, $R_3$, $R_4$, and $R_5$ are independently hydrogen, halogen, nitro, cyano, C1-C5 alkyl, C1-C5 alkoxy, halo (C1-C5) alkyl, C2-CC5 alkenyl, C2-C5 alkynyl, carboxy, C1-C5 alkoxycarbonyl, or C1-C5 alkylthio;

$R_6$ is hydroxy, halogen, nitro, carboxy, C1-C10 alkyl, C1-C10 alkoxy, C2-C10 alkenyl, C2-C10 alkynyl, C1-C10 alkylthio, C1-C10 alkylsulfonyl, C1-C10 alkylcarbonyl, C1-C10 alkoxycarbonyl, C2-C10 alkenyloxy, C1-C5 alkoxy (C1-C5) alkoxy, C1-C5 alkoxy (C1-C5) alkoxy (C1-C5) alkyl, piperidyl, piperazinyl, C1-C5 alkoxy (C1-C5) alkylamino, C1-C10 alkylamino, di(C1-C10 alkyl)amino, C3-C8 cycloalkyl, C3-C8 cycloalkylamino, C3-C8 cycloalkoxy, C3-C8 oxacycloalkyl-oxy, N—(C1-C5)alkoxy (C1-C5) alkyl-N—(C1-C5) alkylamino, N—(C3-C8)cycloalkyl-N—(C1-C5) alkylamino, N-aryl-N—(C1-C5) alkylamino, aryl, arylamino, arylthio, heteroaryl, heteroarylamino, aryloxy, heteroaryloxy, pyrrolidinyl, or morpholinyl;

$R_8$ and $R_9$ are independently hydrogen, hydroxy, halogen, nitro, carboxy, C1-C10 alkyl, C1-C10 alkoxy, C2-C10 alkenyl, C2-C10 alkynyl, C1-C10 alkylthio, C1-C10 alkylsulfonyl, C1-C10 alkylcarbonyl, C1-C10 alkoxycarbonyl, C2-C10 alkenyloxy, C1-C5 alkoxy (C1-C5) alkoxy, C1-C5 alkoxy (C1-C5) alkoxy (C1-C5) alkyl, piperidyl, piperazinyl, C1-C5 alkoxy (C1-C5) alkylamino, C1-C10 alkylamino, di(C1-C10 alkyl)amino, C3-C8 cycloalkyl, C3-C8 cycloalkylamino, C3-C8 cycloalkoxy, C3-C8 oxacycloalkyl-oxy, N—(C1-C5) alkoxy (C1-C5) alkyl-N—(C1-C5) alkylamino, N—(C3C8)cycloalkyl-N—(C1-C5) alkylamino, N-aryl-N—(C1-C5) alkylamino, aryl, arylamino, arylthio, heteroaryl, heteroarylamino, aryloxy, heteroaryloxy, pyrrolidinyl, or morpholinyl, wherein, each alkyl, alkenyl and alkynyl, alone or as a part of an alkoxy, alkylsulfonyl, alkylcarbonyl, alkylamino, or alkenyloxy may be independently unsubstituted or substituted with one or more substituents selected from among halogen, hydroxyl, unsubstituted or halo-substituted (C1-C5) alkoxy, (C3-C8) cycloalkyl which may be unsubstituted or substituted with one or two halogen radicals and/or methyl groups, unsubstituted or halo-substituted (C1-C5) alkylamino, phenyl which may be unsubstituted or substituted with one or more substituents selected from halogen, unsubstituted C1-C3 alkyl, or halo (C1-C3) alkyl, or unsubstituted or halo-substituted di(C1-C5) alkylamino, each aryl or heteroaryl, alone or as a part of an arylamino, aryloxy, heteroaryloxy, or heteroarylamino, may be independently unsubstituted or substituted with one or more substituents selected from halogen, unsubstituted C1-C5 alkyl, unsubstituted C1-C5 alkoxy, or halo (C1-C5) alkyl, each cycloalkyl, alone or as a part of a cycloalkoxy or cycloalkylamino may be unsubstituted or substituted with one or more unsubstituted or halo-substituted C1-C3 alkyl groups, hydroxymethyl, hydroxy, methoxy, or amino, and each piperazinyl, piperidyl, morpholinyl and pyrrolidinyl may be unsubstituted or substituted with one or more unsubstituted or halo-substituted C1-C3 alkyl groups, hydroxy(C1-C3)alkyl, C1-C3 alkoxy, (C1-C3)alkoxycarbonyl, or hydroxyl;

$R_7$ is halo(C1-C5)alkyl;

$R_{10}$ is C1-C5 alkyl, halo (C1-C5) alkyl, or C2-C5 alkenyl; and $R_{11}$ and $R_{12}$ are independently hydrogen, C1-C5 alkyl, or halogen.

8. The compound of claim 2 or 7, an isomer, or a pharmaceutically acceptable salt thereof;

wherein, $R_1$ is hydrogen, methyl, or ethyl;

$R_2$, $R_3$, $R_4$, and $R_5$ are independently hydrogen, fluoro, chloro, bromo, nitro, cyano, methyl, ethyl, ethenyl, ethynyl, trifluoromethyl, methoxy, ethoxy, or methoxycarbonyl;

$R_6$ is hydroxy, fluoro, bromo, chloro, hydroxymethyl, C1-C5 alkyl, C1-C5 alkoxy, C2-C5 alkenyl, C2-C5 alkynyl, halo (C1-C5) alkyl, halo (C1-C5) alkoxy, C2-C5 alkenyloxy, C1-C5 alkoxy (C1-C5) alkoxy, C1-C5 alkoxy (C1-C5) alkoxy (C1-C5) alkyl, di(C1-C3 alkyl)amino, C1-C3 alkylpiperazinyl, piperidyl, pyrrolidinyl, halophenyl, phenyl, or morpholinyl;

$R_7$ is halo (C1-C4) alkyl;

$R_8$ and $R_9$ are independently hydrogen, halogen, or trifluoromethyl;

$R_{10}$ is C1-C5 alkyl, halo (C1-C5) alkyl, or C2-C5 alkenyl; and $R_{11}$ and $R_{12}$, if present, are independently hydrogen, or methyl.

9. The compound of claim 1, an isomer, or a pharmaceutically acceptable salt thereof;

wherein, $R_1$, $R_2$, and $R_5$ are hydrogen;

$R_3$ is hydrogen, fluoro, chloro, cyano, methyl, ethenyl, ethynyl, or trifluoromethyl;

$R_4$ is hydrogen, fluoro, chloro, cyano, methyl, ethyl, or trifluoromethyl;

$R_6$ is hydroxy, fluoro, bromo, chloro, methyl, hydroxymethyl, methoxy, trifluoromethyl, diethylamino, piperidyl, pyrrolidinyl, trifluorophenyl, phenyl, or morpholinyl;
$R_7$ is trifluoromethyl;
$R_8$ is hydrogen;
$R_{11}$ and $R_{12}$, if present, are hydrogen;
$R_9$ is hydrogen or trifluoromethyl; and
$R_{10}$ is methyl.

10. The compound of formula III according to claim 7, an isomer, or a pharmaceutically acceptable salt thereof;
wherein,
$R_1$, $R_2$, and $R_5$ are hydrogen;
$R_3$ is hydrogen, fluoro, chloro, cyano, methyl, ethenyl, ethynyl, or trifluoromethyl;
$R_4$ is hydrogen, fluoro, chloro, cyano, methyl, ethyl, or trifluoromethyl;
$R_6$ is hydroxy, fluoro, bromo, chloro, methyl, propyl, butyl, pentyl, hydroxymethyl, methoxy, ethoxy, propoxy, butoxy, pentoxy, methoxymethoxy, methoxyethoxy, methoxypropoxy, trifluoromethyl, diethylamino, methoxymethylamino, methoxyethylamino, methoxypropylamino, cyclobutylamino, cyclopentylamino, cyclohexylamino, ethylamino, propylamino, butylamino, pentylamino, N,N-dimethylamino, N-methyl-N-ethylamino N,N diethylamino, N-methyl-N-propylamino, N-ethyl-N-propylamino, N,N-dipropylamino, N methyl-N-butylamino, N-ethyl-N-butylamino, N-methyl-N-methoxymethylamino, N-methyl-N methoxyethylamino, N-methyl-N-methoxypropylamino, N-methyl-N-cyclobutylamino, N methyl-N-cyclopentylamino, N-methyl-N-cyclohexylamino, phenoxy, halophenoxy, piperidyl, pyrrolidinyl, trifluorophenyl, phenyl, or morpholinyl;
$R_7$ is trifluoromethyl;
$R_8$ is hydrogen;
$R_{11}$ and $R_{12}$ are hydrogen;
$R_9$ is hydrogen or trifluoromethyl; and
$R_{10}$ is methyl.

11. The compound of formula III according to claim 7, an isomer, or a pharmaceutically acceptable salt thereof;
wherein,
$R_1$ is hydrogen or methyl;
$R_2$ is hydrogen;
$R_3$ is hydrogen, fluoro, chloro, bromo, cyano, methyl, ethyl, ethenyl, ethynyl, or trifluoromethyl;
$R_4$ and $R_5$ are independently hydrogen, fluoro, chloro, cyano, methyl, ethyl, or trifluoromethyl;
$R_6$ is fluoro, chloro, bromo, methyl, n-butyl, methoxy, n-butyloxy, isobutyloxy, sec-butyloxy, methoxyethoxy, methoxyethylamino, diethylamino, n-butylamino, cyclopentylamino, phenoxy, N-pyrrolidinyl, N-piperidyl, or N-morpholinyl;
$R_7$ is trifluoromethyl;
$R_8$ is hydrogen;
$R_{11}$ and $R_{12}$ are hydrogen;
$R_9$ is hydrogen or trifluoromethyl; and
$R_{10}$ is methyl.

12. The compound of formula III according to claim 7, an isomer, or a pharmaceutically acceptable salt thereof;
wherein,
$R_1$ is hydrogen or methyl;
$R_2$ is hydrogen;
$R_3$ is hydrogen, ethenyl, or ethynyl;
$R_4$ is hydrogen or fluoro;
$R_5$ is hydrogen;
$R_6$ is hydroxy, fluoro, bromo, chloro, methyl, propyl, butyl, pentyl, hydroxymethyl, methoxy, ethoxy, propoxy, butoxy, pentoxy, methoxymethoxy, methoxyethoxy, methoxypropoxy, ethoxyethoxy, trifluoromethyl, N,N-dimethylamino, N-methyl-N-ethylamino N,N-diethylamino, N-methyl-N-propylamino, N-ethyl-N-propylamino, N,N-dipropylamino, N-methyl-N-butylamino, N-ethyl-N-butylamino, methoxymethylamino, methoxyethylamino, methoxypropylamino, N-methyl-N-methoxymethylamino, N-methyl-N-methoxyethylamino, N-methyl-N-methoxypropylamino, cyclobutylamino, cyclopentylamino, cyclohexylamino, N-methyl-N-cyclobutylamino, N-methyl-N-cyclopentylamino, N-methyl-N-cyclohexylamino, ethylamino, propylamino, butylamino, pentylamino, phenoxy, halophenoxy, N-piperidyl, N-pyrrolidinyl, trifluorophenyl, phenyl, or N-morpholinyl;
$R_7$ is trifluoromethyl;
$R_8$ is hydrogen;
$R_9$ is hydrogen or trifluoromethyl;
$R_{10}$ is methyl; and
$R_{11}$ and $R_{12}$ are hydrogen.

13. The compound of formula III according to claim 7, an isomer, or a pharmaceutically acceptable salt thereof;
wherein,
$R_1$ is hydrogen;
$R_2$ is hydrogen;
$R_3$ is hydrogen, ethenyl, or ethynyl;
$R_4$ is hydrogen or fluoro;
$R_5$ is hydrogen;
$R_6$ is bromo, chloro, n-butyl, methoxy, isobutyloxy, sec-butyloxy, methoxyethoxy, diethylamino, N-pyrrolidinyl, N-piperidyl, N-morpholinyl, cyclopentylamino, n-butylamino, phenoxy, n-butyloxy, methoxyethylamino;
$R_7$ is trifluoromethyl;
$R_8$ is hydrogen;
$R_9$ is hydrogen or trifluoromethyl;
$R_{10}$ is methyl; and
$R_{11}$ and $R_{12}$ are hydrogen.

14. The compound of formula III according to claim 7, an isomer, or a pharmaceutically acceptable salt thereof;
wherein,
$R_1$ is hydrogen or methyl;
$R_2$ is hydrogen;
$R_3$ is hydrogen, fluoro, methyl, ethyl, cyano, ethenyl, ethynyl, or trifluoromethyl;
$R_4$ is hydrogen, fluoro, chloro, or methyl;
$R_5$ is hydrogen;
$R_6$ is fluoro, chloro, bromo, methyl, ethyl, propyl, butyl, pentyl, trifluoromethyl, ethoxymethyl, methoxypropyl, phenylethyl, phenylethenyl, ethynyl, methoxypropynyl, diethylaminopropynyl, phenyl, halophenyl, methoxyphenyl, thienyl, pyridinyl, halopyridinyl, methoxy, ethoxy, propoxy, butoxy, pentoxy, trifluoroethoxy, cyclopentoxy, cyclopropylmethoxy, methoxyethoxy, tetrahydropyranyloxy, phenoxy, halophenoxy, benzyloxy, pyridinyloxy, ethylthio, propylthio, butylthio, pentylthio, ethylamino, propylamino, butylamino, pentylamino, methoxyethylamino, ethoxyethylamino, methoxypropylamino, cyclobutylamino, cyclopentylamino, cyclohexylamino, benzylamino, phenylamino, N,N-dimethylamino, N-methyl-N-propylamino, N-ethyl-N-propylamino, N,N-dipropylamino, N-methyl-N-butylamino, N-ethyl-N-butylamino, N-ethyl-N-phenylamino, N-methyl-N-phenylamino, N-pyrrolidinyl, methoxy N-pyrrolidinyl, hydroxymethyl N-pyrrolidinyl, N-piperidyl, ethoxycarbonyl N-piperidyl, piperazinyl, or N-morpholinyl;
$R_7$ is trifluoromethyl;
$R_8$ is hydrogen;
$R_9$ is hydrogen or trifluoromethyl;
$R_{10}$ is methyl; and
$R_{11}$ and $R_{12}$ are hydrogen.

15. The compound of formula III according to claim 7, an isomer, or a pharmaceutically acceptable salt thereof;
wherein,
$R_1$ is hydrogen or methyl;
$R_2$ is hydrogen;
$R_3$ is hydrogen, fluoro, chloro, bromo, cyano, methyl, ethyl, ethenyl, ethynyl, or trifluoromethyl;
$R_4$ and $R_5$ are independently hydrogen, fluoro, chloro, cyano, methyl, or ethyl;
$R_6$ is n-propyl, isopropyl, n-butyl, isobutyl, sec-butyl, 2-methylbutyl, 3-methylbutyl, n-pentyl, 2-phenylethyl, n-butoxy, isobutoxy, sec-butoxy, ethylamino, n-propylamino, isopropylamino, n-butylamino, isobutylamino, sec-butylamino, methoxyethylamino, ethoxyethylamino, benzylamino, phenylamino, N-ethyl-N-phenylamino, or N-methyl-N-phenylamino;
$R_7$ is trifluoromethyl;
$R_8$ is hydrogen or chloro;
$R_9$ is hydrogen or trifluoromethyl;
$R_{10}$ is methyl; and
$R_{11}$ and $R_{12}$ are hydrogen.

16. The compound of formula III according to claim 7, an isomer, or a pharmaceutically acceptable salt thereof;
wherein,
$R_1$ is hydrogen or methyl;
$R_2$ is hydrogen;
$R_4$ is hydrogen, fluoro, chloro, or methyl;
$R_3$ is hydrogen, fluoro, methyl, cyano, ethenyl, ethynyl, or trifluoromethyl;
$R_5$ is hydrogen;
$R_6$ is ethyl, n-propyl, isopropyl, n-butyl, isobutyl, sec-butyl, 2-methylbutyl, 3-methylbutyl, n-pentyl, ethoxymethyl, 2-phenylethyl, phenylethenyl, phenyl, fluorophenyl, thienyl, n-propoxy, isopropoxy, n-butoxy, isobutoxy, sec-butoxy, 3-metylbutoxy, 2,2,2-trifluoroethoxy, cyclopentoxy, cyclopropylmethoxy, phenoxy, ethylthio, propylthio, isopropylthio, phenylthio, ethylamino, n-propylamino isopropylamino, n-butylamino, isobutylamino, sec-butylamino, methoxymethylamino, methoxyethylamino, ethoxyethylamino, cyclopentylamino, benzylamino, phenylamino, N-ethyl-N-phenylamino, N-methyl-N-phenylamino, N-methyl-N-propylamino, N-pyrrolidinyl, methoxy N-pyrrolidinyl, N-piperidyl, or ethoxycarbonyl N-piperidyl;
$R_7$ is trifluoromethyl;
$R_8$ is hydrogen or chloro;
$R_9$ is hydrogen or trifluoromethyl;
$R_{10}$ is methyl; and
$R_{11}$ and $R_{12}$ are hydrogen.

17. The compound of formula III according to claim 7, an isomer, or a pharmaceutically acceptable salt thereof;
wherein,
$R_1$ is hydrogen or methyl;
$R_2$ is hydrogen;
$R_3$ is hydrogen, fluoro, methyl, cyano, ethenyl, or ethynyl;
$R_4$ is hydrogen, fluoro, or methyl;
$R_5$ is hydrogen;
$R_6$ is n-propyl, isopropyl, n-butyl, isobutyl, sec-butyl, 2-methylbutyl, 3-methylbutyl, n-pentyl, 2-phenylethyl, n-butoxy, isobutoxy, sec-butoxy, ethylamino, n-propylamino, isopropylamino, n-butylamino, isobutylamino, sec-butylamino, methoxyethylamino, ethoxyethylamino, benzylamino, N-ethyl-N-phenylamino, or N-methyl-N-phenylamino;
$R_7$ is trifluoromethyl;
$R_8$ and $R_9$ are hydrogen;
$R_{10}$ is methyl; and
$R_{11}$ and $R_{12}$ are hydrogen.

18. The compound of claim 9, wherein $R_7$ is $CF_2Cl$ or $CF_2CF_3$ instead of $CF_3$.

19. The compound of formula III according to claim 7, an isomer, or a pharmaceutically acceptable salt thereof;
wherein,
$R_1$ is hydrogen or methyl;
$R_2$ is hydrogen;
$R_3$ is hydrogen, fluoro, chloro, methyl, cyano, ethenyl, or ethynyl;
$R_4$ is hydrogen;
$R_5$ is fluoro, chloro, or methyl;
$R_6$ is ethyl, n-propyl, isopropyl, n-butyl, isobutyl, sec-butyl, 2-methylbutyl, 3-methylbutyl, n-pentyl, ethoxymethyl, 2-phenylethyl, phenylethenyl, phenyl, fluorophenyl, thienyl, n-propoxy, isopropoxy, n-butoxy, isobutoxy, sec-butoxy, 3-metylbutoxy, 2,2,2-trifluoroethoxy, cyclopentoxy, cyclopropylmethoxy, phenoxy, ethylthio, propylthio, isopropylthio, ethylamino, n-propylamino isopropylamino, n-butylamino, isobutylamino, sec-butylamino, methoxymethylamino, methoxyethylamino, ethoxyethylamino, cyclopentylamino, benzylamino, phenylamino, N-ethyl-N-phenylamino, N-methyl-N-phenylamino, N-methyl-N-propylamino, N-pyrrolidinyl, N-piperidyl, or ethoxycarbonyl N-piperidyl;
$R_7$ is halo(C1-C3)alkyl;
$R_8$ and $R_9$ are independently hydrogen, halogen or trifluoromethyl;
$R_{10}$ is methyl; and
$R_{11}$ and $R_{12}$ are hydrogen.

20. The compound of formula III according to claim 7, an isomer, or a pharmaceutically acceptable salt thereof;
wherein,
$R_1$ is hydrogen or methyl;
$R_2$ is hydrogen;
$R_3$ is hydrogen, fluoro, chloro, methyl, cyano, ethenyl, or ethynyl;
$R_4$ is hydrogen;
$R_5$ is fluoro;
$R_6$ is n-propyl, isopropyl, n-butyl, isobutyl, sec-butyl, 2-methylbutyl, 3-methylbutyl, n-pentyl, 2-phenylethyl, n-butoxy, isobutoxy, sec-butoxy, ethylamino, n-propylamino, isopropylamino, n-butylamino, isobutylamino, sec-butylamino, methoxyethylamino, ethoxyethylamino, benzylamino, N-ethyl-N-phenylamino, or N-methyl-N-phenylamino;
$R_7$ is trifluoromethyl;
$R_8$ is hydrogen or chloro;
$R_9$ is hydrogen;
$R_{10}$ is methyl; and
$R_{11}$ and $R_{12}$ are hydrogen.

21. The compound according to claim 2 or 7, an isomer, or a pharmaceutically acceptable salt thereof, and having the formula IV formula IV wherein,
R$_1$ is hydrogen, methyl, or ethyl;
R$_{12}$ is hydrogen or propyl;
R$_6$ is C2-C6 alkyl, di (C1-C6 alkyl)amino, C1-C6 alkoxy, 2,2,2-trifluoro(C1-C3)alkoxy, C1-C3 alkoxy (C1-C5) alkylamino, C1-C6 alkylamino, C3-C6 cycloalkylamino, phenoxy, phenylamino, phenyl(C1-C3)alkylamino, phenyl(C1-C3)alkyl, N-phenyl-N—(C1-C5) alkylamino, methoxy-N-pyrrolidinyl, or C1-C6 alkylthio;
R$_7$ is CF$_3$, CF$_2$Cl, or CF$_2$CF$_3$; and
R$_8$ and R$_9$ are independently hydrogen, CF$_3$, or halogen.

22. The compound of formula IV, according to claim 21, an isomer, or a pharmaceutically acceptable salt thereof, wherein,
R$_1$ is hydrogen or methyl;
R$_6$ is C2-C5 alkyl, C1-C4 alkylamino, methoxy, or methoxyethylamino;
R$_7$ is CF$_3$;
R$_8$ and R$_9$ are all hydrogen; and
R$_{12}$ is hydrogen.

23. The compound of claim 1, 2, or 7, an isomer, or a pharmaceutically acceptable salt thereof, and having the formula V formula V wherein,
R$_1$ is hydrogen, methyl or ethyl;
R$_3$ is hydrogen, fluoro, or chloro;
R$_6$ is C2-C6 alkyl, di (C1-C6 alkyl)amino, C1-C6 alkoxy, 2,2,2-trifluoro(C1-C3)alkoxy, C1-C3 alkoxy (C1-C5) alkylamino, C1-C6 alkylamino, C3-C6 cycloalkylamino, phenoxy, phenylamino, phenyl(C1-C3)alkylamino, phenyl(C1-C3)alkyl, or N-phenyl-N—(C1-C5) alkylamino;
R$_7$ is CF$_3$, CF$_2$Cl, or CF$_2$CF$_3$;
R$_8$ and R$_9$ are independently hydrogen, CF$_3$, or halogen; and
R$_{12}$ is hydrogen or propyl.

24. The compound of formula V, according to claim 23, an isomer, or a pharmaceutically acceptable salt thereof, wherein,
R$_1$ is hydrogen or methyl;
R$_3$ is hydrogen or fluoro;
R$_6$ is C2-C5 alkyl, C1-C4 alkylamino, methoxy, or methoxyethylamino;
R$_7$ is CF$_3$;
R$_8$ and R$_9$ are all hydrogen; and
R$_{12}$ is hydrogen.

25. The compound of claim 1, 2, or 7, an isomer, or a pharmaceutically acceptable salt thereof, and having the formula VI, an isomer or a pharmaceutically acceptable formular VI wherein,
W is hydrogen or fluoro;
X is —CR$_{11}$=CR$_{12}$— or —C≡C—;
R$_1$ is selected from hydrogen and C1-C3 alkyl;
R$_6$ is hydroxy, halogen, nitro, carboxy, C1-C10 alkyl, C1-C10 alkoxy, C2-C10 alkenyl, C2-C10 alkynyl, C1-C10 alkylthio, C1-C10 alkylsulfonyl, C1-C10 alkylcarbonyl, C1-C10 alkoxycarbonyl, C2-C10 alkenyloxy, C1-C5 alkoxy (C1-C5) alkoxy, C1-C5 alkoxy (C1-C5) alkoxy (C1-C5) alkyl, piperidyl, C1-C5 alkoxy (C1C5) alkylamino, C1-C10 alkylamino, di(C1-C10 alkyl) amino, C3-C8 cycloalkyl, C3C8 cycloalkylamino, C3-C8 cycloalkoxy, C3-C8 oxacycloalkyl-oxy, N—(C1C5)alkoxy (C1-C5) alkyl-N—(C1-C5) alkylamino, N—(C3-C8)cycloalkyl-N—(C1-C5) alkylamino, N-aryl-N—(C1-C5) alkylamino, aryl, arylamino, heteroaryl, heteroarylamino, aryloxy, pyrrolidinyl, or morpholinyl;
R$_{11}$ and R$_{12}$, if present, are independently selected from hydrogen and propyl;
R$_7$ is CF$_3$, CF$_2$Cl, or CF$_2$CF$_3$;
R$_8$ and R$_9$ are independently selected from hydrogen, halogen, or CF$_3$;
wherein,
each alkyl, alkenyl and alkynyl, alone or as a part of an alkoxy, alkylsulfonyl, alkylcarbonyl, alkylamino, or alkenyloxy may be independently unsubstituted or substituted with one or more substituents selected from among halogen, hydroxyl, unsubstituted or halo-substituted (C1-C5) alkoxy, (C3-C8) cycloalkyl which may be unsubstituted or substituted with one or two halogen radicals and/or methyl groups, unsubstituted or halo-substituted (C1-C5) alkylamino, phenyl which may be unsubstituted or substituted with one or more substituents selected from halogen, unsubstituted C1-C3 alkyl, or halo (C1-C3) alkyl, or unsubstituted or halo-substituted di(C1-C5) alkylamino,
each aryl or heteroaryl, alone or as a part of an arylamino, aryloxy, heteroaryloxy, or heteroarylamino, may be independently unsubstituted or substituted with one or more substituents selected from halogen, unsubstituted C1-C5 alkyl, unsubstituted C1-C5 alkoxy, or halo (C1-C5) alkyl,
each cycloalkyl, alone or as a part of a cycloalkoxy or cycloalkylamino may be unsubstituted or substituted with one or more unsubstituted or halo-substituted C1-C3 alkyl groups, hydroxymethyl, hydroxy, methoxy, or amino, and each piperidyl, or morpholinyl may be unsubstituted or substituted with one or more unsubstituted or halo-substituted C1-C3 alkyl groups, hydroxy(C1-C3)alkyl, C1-C3 alkoxy, (C1-C3)alkoxycarbonyl, or hydroxyl.

26. The compound of claim 25, an isomer, or a pharmaceutically acceptable salt thereof, wherein $R_8$ and $R_9$ are both hydrogen.

27. The compound of claim 25 or 26, an isomer, or a pharmaceutically acceptable salt thereof, wherein X is —CH=CH—.

28. The compound of claim 25, an isomer, or a pharmaceutically acceptable salt thereof, wherein X is —CH=CH—, and W, $R_8$, and $R_9$ are all hydrogen.

29. The compound of claim 25, an isomer, or a pharmaceutically acceptable salt thereof, wherein,
$R_6$ is selected from C2-C6 alkyl, di (C1-C6 alkyl)amino, 2,2,2-trifluoro(C1-C3)alkoxy, C1-C3 alkoxy (C1-C5) alkylamino, C1-C6 alkylamino, C3-C6 cycloalkylamino, phenyl, phenylamino, phenyl(C1-C3)alkylamino, phenyl(C1-C3)alkyl, or N-phenyl-N—(C1-C5) alkylamino, wherein each phenyl can be substituted with one or more halogens; and
$R_7$ is $CF_3$.

30. The compound of claim 25, an isomer, or a pharmaceutically acceptable salt thereof, wherein,
$R_6$ is selected from C2-C5 alkyl, C1-C4 alkylamino, or methoxyethylamino;
$R_7$ is $CF_3$; and
$R_{12}$ is hydrogen.

31. The compound of claim 25, an isomer, or a pharmaceutically acceptable salt thereof, wherein,
$R_6$ is —NH—(C1-C4) alkyl, or linear or branched C2-C5 alkyl; and
$R_7$ is $CF_3$.

32. The compound of claim 21, wherein $R_1$ is hydrogen or methyl.

33. The compound of claim 1, wherein if $R_1$ is methyl or ethyl, then the atom to which $R_1$ is attached is in (R)-configuration.

34. The compound of claim 1, 2, or 7, an isomer, or a pharmaceutically acceptable salt thereof, wherein the compound is selected from the group consisting of;
3-(2-Diethylamino-6-trifluoromethyl-pyridin-3-yl)-N-(3-ethynyl-5-fluoro-4-methanesulfonylamino-benzyl)-acrylamide,
3-(2-Chloro-6-trifluoromethyl-pyridin-3-yl)-N-(3-ethynyl-5-fluoro-4-methanesulfonylamino-benzyl)-acrylamide,
N-(3-Ethynyl-5-fluoro-4-methanesulfonylamino-benzyl)-3-(2-methoxy-6-trifluoromethyl-pyridin -3-yl)-acrylamide,
N-(3-Fluoro-4-methanesulfonylamino-benzyl)-3-[2-(2-methoxy-ethylamino)-6-trifluoromethyl -pyridin-3-yl]-acrylamide,
3-(2-Diethylamino-6-trifluoromethyl-pyridin-3-yl)-N-(3-fluoro-4-methanesulfonylamino -benzyl)-acrylamide,
N-(3-Fluoro-4-methanesulfonylamino-benzyl)-3-(2-pyrrolidin-1-yl-6-trifluoromethyl-pyridin-3-yl)-acrylamide,
N-(3-Fluoro-4-methanesulfonylamino-benzyl)-3-(2-methoxy-6-trifluoromethyl-pyridin-3-yl) -acrylamide,
N-(3-Fluoro-4-methanesulfonylamino-benzyl)-3-[2-(2-hydroxy-ethylamino)-6-trifluoromethyl -pyridin-3-yl]-acrylamide,
N-(3-Ethynyl-5-fluoro-4-methanesulfonylamino-benzyl)-3-(2-pyrrolidin-1-yl-6-trifluoromethyl -pyridin-3-yl)-acrylamide,
3-(2-Butoxy-6-trifluoromethyl-pyridin-3-yl)-N-(3-fluoro-4-methanesulfonylamino-benzyl) -acrylamide,
N-(3-Ethynyl-5-fluoro-4-methanesulfonylamino-benzyl)-3-[2-(2-methoxy-ethylamino)-6-trifluoromethyl-pyridin-3-yl]-acrylamide,
3-(2-Butoxy-6-trifluoromethyl-pyridin-3-yl)-N-(3-ethynyl-5-fluoro-4-methanesulfonylamino -benzyl)-acrylamide,
N-(3-Ethynyl-5-fluoro-4-methanesulfonylamino-benzyl)-3-(2-methyl-6-trifluoromethyl-pyridin -3-yl)-acrylamide,
N-(3-Fluoro-4-methanesulfonylamino-benzyl)-3-(2-methyl-6-trifluoromethyl-pyridin-3-yl) -acrylamide,
3-(2-Butylamino-6-trifluoromethyl-pyridin-3-yl)-N-(3-ethynyl-5-fluoro-4-methanesulfonylamino-benzyl)-acrylamide,
3-(2-Cyclopentylamino-6-trifluoromethyl-pyridin-3-yl)-N-(3-ethynyl-5-fluoro-4-methanesulfonylamino-benzyl)-acrylamide,
N-(3-Ethynyl-5-fluoro-4-methanesulfonylamino-benzyl)-3-[2-(2-methoxy-ethoxy)-6-trifluoromethyl-pyridin-3-yl]-acrylamide,
3-(2-Butyl-5-chloro-6-trifluoromethyl-pyridin-3-yl)-N-(3-ethynyl-5-fluoro-4-methanesulfonylamino-benzyl)-acrylamide,
3-(2-sec-Butoxy-6-trifluoromethyl-pyridin-3-yl)-N-(3-ethynyl-5-fluoro-4-methanesulfonylamino-benzyl)-acrylamide,
N-(3-Ethynyl-5-fluoro-4-methanesulfonylamino-benzyl)-3-(2-phenoxy-6-trifluoromethyl -pyridin-3-yl)-acrylamide,
3-(2-Isopropyloxy-6-trifluoromethyl-pyridin-3-yl)-N-(3-ethynyl-5-fluoro-4-methanesulfonylamino-benzyl)-acrylamide,
N-(3-Ethynyl-5-fluoro-4-methanesulfonylamino-benzyl)-3-(2-isobutoxy-6-trifluoromethyl -pyridin-3-yl)-acrylamide,
3-[2-(tetrahydro-furan-3-yloxy)-6-trifluoromethyl-pyridin-3-yl]-N-(3-ethynyl-5-fluoro-4-methanesulfony-lamino-benzyl)-acrylamide,
N-(3-Ethynyl-5-fluoro-4-methanesulfonylamino-benzyl)-3-[2-(4-fluoro-phenoxy)-6-trifluoromethyl-pyridin-3-yl]-acrylamide
N-(3-Fluoro-4-methanesulfonylamino-benzyl)-3-(2-morpholin-4-yl-6-trifluoromethyl-pyridin-3-yl)-acrylamide,
N-(4-Methanesulfonylamino-3-vinyl-benzyl)-3-(2-morpholin-4-yl-6-trifluoromethyl-pyridin-3-yl)-acrylamide,
N-(3-Chloro-4-methanesulfonylamino-benzyl)-3-(2-morpholin-4-yl-6-trifluoromethyl-pyridin-3-yl)-acrylamide,
N-(3-Fluoro-4-methanesulfonylamino-5-methyl-benzyl)-3-(2-morpholin-4-yl-6-trifluoromethyl -pyridin-3-yl)-acrylamide,
N-(3-Ethynyl-5-fluoro-4-methanesulfonylamino-benzyl)-3-(2-morpholin-4-yl-6-trifluoromethyl -pyridin-3-yl)-acrylamide,
N-(3,5-Difluoro-4-methanesulfonylamino-benzyl)-3-(2-morpholin-4-yl-6-trifluoromethyl -pyridin-3-yl)-acrylamide,
N-(3-Ethynyl-5-fluoro-4-methanesulfonylamino-benzyl)-3-(2-piperid-1-yl-6-trifluoromethyl -pyridin-3-yl)-acrylamide, N-(3-Fluoro-4-methanesulfonylamino-benzyl)-3-(2-piperid-1-yl-6-trifluoromethyl-pyridin-3-yl)-acrylamide,
N-(3-Ethynyl-5-fluoro-4-methanesulfonylamino-benzyl)-3-[2-(2,2,2-trifluoro-ethoxy)-6-trifluoromethyl-pyridin-3-yl]-acrylamide,
N-(3-Ethynyl-5-fluoro-4-methanesulfonylamino-benzyl)-3-[2-(2-(3-methoxy-pyrrolidin-1-yl)-6-trifluoromethyl-pyridin-3-yl]-acrylamide,
3-(2-Butylamino-6-trifluoromethyl-pyridin-3-yl)-N-(3-fluoro-4-methanesulfonylamino-benzyl)-acrylamide,
3-(2-Cyclopentylamino-6-trifluoromethyl-pyridin-3-yl)-N-(3-fluoro-4-methanesulfonylamino-benzyl)-acrylamide,
N-(3-Fluoro-4-methanesulfonylamino-benzyl)-3-[2-(3-methoxy-pyrrolidin-1-yl)-6-trifluoromethyl-pyridin-3-yl]-acrylamide,
3-(2-Cyclopropylmethoxy-6-trifluoromethyl-pyridin-3-yl)-N-(3-ethynyl-5-fluoro-4-methanesulfonylamino-benzyl)-acrylamide,
N-(3-Cyano-5-fluoro-4-methanesulfonylamino-benzyl)-3-(2-pyrrolidin-1-yl-6-trifluoromethyl-pyridin-3-yl)-acrylamide,
3-(2-Butoxy-6-trifluoromethyl-pyridin-3-yl)-N-(3-cyano-5-fluoro-4-methanesulfonylamino-benzyl)-acrylamide,
N-(3-Ethynyl-5-fluoro-4-methanesulfonylamino-benzyl)-3-(2-isopropylamino-6-trifluoromethyl-pyridin-3-yl)-acrylamide,
3-(2-sec-Butoxy-6-trifluoromethyl-pyridin-3-yl)-N-(3-cyano-5-fluoro-4-methanesulfonylamino-benzyl)-acrylamide,
N-(3-Ethynyl-5-fluoro-4-methanesulfonylamino-benzyl)-3-(2-phenyl-6-trifluoromethyl-pyridin-3-yl)-acrylamide,
N-(3-Cyano-5-fluoro-4-methanesulfonylamino-benzyl)-3-(2-isopropoxy-6-trifluoromethyl-pyridin-3-yl)-acrylamide,
N-(3-Ethynyl-5-fluoro-4-methanesulfonylamino-benzyl)-3-(2-phenylamino-6-trifluoromethyl-pyridin-3-yl)-acrylamide,
N-(3-Ethynyl-5-fluoro-4-methansulfonylamino-benzyl)-3-[2-(3-ethoxycarbony-piperid-1-yl)-6-trifluoromethyl-pyridin-3-yl]-acrylamide,
N-(3-Cyano-5-fluoro-4-methansulfonylamino-benzyl)-3-[2-(3-ethoxycarbony-piperid-1-yl)-6-trifluoromethyl-pyridin-3-yl]-acrylamide,
3-(2-sec-Butylamino-6-trifluoromethyl-pyridin-3-yl)-N-(3-ethynyl-5-fluoro-4-methanesulfonylamino-benzyl)-acrylamide,
N-(3-Cyano-5-fluoro-4-methanesulfonylamino-benzyl)-3-[2-(3-methyl-butoxy)-6-trifluoromethyl-pyridin-3-yl]-acrylamide,
N-(3-Ethynyl-5-fluoro-4-methanesulfonylamino-benzyl)-3-(2-thien-3-yl-6-trifluoromethyl-pyridin-3-yl)-acrylamide,
N-(3-Ethynyl-5-fluoro-4-methanesulfonylamino-benzyl)-3-[2-(3-fluoro-phenyl)-6-trifluoromethyl-pyridin-3-yl]-acrylamide,
N-(3-Fluoro-4-methanesulfonylamino-benzyl)-3-(2-isopropylamino-6-trifluoromethyl-pyridin-3-yl)-acrylamide,
N-(3-Cyano-5-fluoro-4-methanesulfonylamino-benzyl)-3-(2-isopropylamino-6-trifluoromethyl-pyridin-3-yl)-acrylamide,
3-(2-sec-Butylamino-6-trifluoromethyl-pyridin-3-yl)-N-(3-fluoro-4-methanesulfonylamino-benzyl)-acrylamide,
3-(2-sec-Butylamino-6-trifluoromethyl-pyridin-3-yl)-N-(3-cyano-5-fluoro-4-methanesulfonylamino-benzyl)-acrylamide,
N-(3-Fluoro-4-methanesulfonylamino-benzyl)-3-(2-phenylamino-6-trifluoromethyl-pyridin-3-yl)-acrylamide,
3-(2-sec-Butylamino-6-trifluoromethyl-pyridin-3-yl)-N-(3,5-difluoro-4-methanesulfonylamino-benzyl)-acrylamide,
3-(2-sec-Butylamino-6-trifluoromethyl-pyridin-3-yl)-N-(3-fluoro-4-methanesulfonylamino-5-methyl-benzyl)-acrylamide,
N-(3-Fluoro-4-methanesulfonylamino-5-vinyl-benzyl)-3-(2-phenoxy-6-trifluoromethyl-pyridin-3-yl)-acrylamide,
N-(3-Ethynyl-5-fluoro-4-methanesulfonylamino-benzyl)-3-(2-phenylthio-6-trifluoromethyl-pyridin-3-yl)-acrylamide,
N-(3-Fluoro-4-methanesulfonylamino-benzyl)-3-(2-phenethyl-6-trifluoromethyl-pyridin-3-yl)-acrylamide,
N-(3-Ethynyl-5-fluoro-4-methanesulfonylamino-benzyl)-3-(2-phenethyl-6-trifluoromethyl-pyridin-3-yl)-acrylamide,
3-(2-Butyl-6-trifluoromethyl-pyridin-3-yl)-N-(3-fluoro-4-methanesulfonylamino-benzyl)-acrylamide,
3-(2-Butyl-6-trifluoromethyl-pyridin-3-yl)-N-(3-ethynyl-5-fluoro-4-methanesulfonylamino-benzyl)-acrylamide,
N-(3-Fluoro-4-methanesulfonylamino-benzyl)-3-(2-isobutyl-6-trifluoromethyl-pyridin-3-yl)-acrylamide,
N-(3-Ethynyl-5-fluoro-4-methanesulfonylamino-benzyl)-3-(2-isobutyl-6-trifluoromethyl-pyridin-3-yl)-acrylamide,
(R)—N-[1-(3-Fluoro-4-methanesulfonylamino-phenyl)-ethyl]-3-(2-phenylamino-6-trifluoromethyl-pyridin-3-yl)-acrylamide,
3-(2-Ethyl-6-trifluoromethyl-pyridin-3-yl)-N-(3-ethynyl-5-fluoro-4-methanesulfonylamino-benzyl)-acrylamide,
N-(3-Fluoro-4-methanesulfonylamino-benzyl)-3-[2-(2-methyl-butyl)-6-trifluoromethyl-pyridin-3-yl]-acrylamide,
N-(3-Ethynyl-5-fluoro-4-methanesulfonylamino-benzyl)-3-[2-(2-methyl-butyl)-6-trifluoromethyl-pyridin-3-yl]-acrylamide,
N-(3-Ethynyl-5-fluoro-4-methanesulfonylamino-benzyl)-3-(2-styryl-6-trifluoromethyl-pyridin-3-yl)-acrylamide,
N-(3-Fluoro-4-methanesulfonylamino-benzyl)-3-[2-(methyl-propyl-amino)-6-trifluoromethyl-pyridin-3-yl]-acrylamide,
N-(3-Ethynyl-5-fluoro-4-methanesulfonylamino-benzyl)-3-[2-(methyl-propyl-amino)-6-trifluoromethyl-pyridin-3-yl]-acrylamide,
3-(2-sec-Butoxy-6-trifluoromethyl-pyridin-3-yl)-N-(4-methanesulfonylamino-3-methyl-benzyl)-acrylamide,
N-(3-Cyano-5-fluoro-4-methanesulfonylamino-benzyl)-3-(2-isobutyl-6-trifluoromethyl-pyridin-3-yl)-acrylamide,
N-(3-Fluoro-4-methanesulfonylamino-5-methyl-benzyl)-3-(2-isobutyl-6-trifluoromethyl-pyridin-3-yl)-acrylamide,
(R)—N-[1-(3-Fluoro-4-methanesulfonylamino-phenyl)-ethyl]-3-[2-(methyl-phenyl-amino)-6-trifluoromethyl-pyridin-3-yl]-acrylamide,
N-(3-Ethynyl-5-fluoro-4-methanesulfonylamino-benzyl)-3-[2-(methyl-phenyl-amino)-6-trifluoromethyl-pyridin-3-yl]-acrylamide, N-(4-Methanesulfonylamino-3-methyl-benzyl)-3-[2-(methyl-phenyl-amino)-6-trifluoromethyl -pyridin-3-yl]-acrylamide, (R)-3-(2-Butoxy-6-trifluoromethyl-pyridin-3-yl)-N-[1-(3-fluoro-4-methanesulfonylamino -phenyl)-ethyl]-acrylamide, 3-(2-Butoxy-6-trifluoromethyl-pyridin-3-yl)-N-(4-methanesulfonylamino-3-methyl-benzyl) -acrylamide, 3-(2-Ethylthio-6-trifluoromethyl-pyridin-3-yl)-N-(3-ethynyl-5-fluoro-4-methanesulfonylamino -benzyl)-acrylamide, N-(4-Methanesulfonylamino-3-methyl-benzyl)-3-(2-phenethyl-6-trifluoromethyl-pyridin-3-yl) -acrylamide, N-(3-Fluoro-4-methanesulfonylamino-5-methyl-benzyl)-3-(2-phenethyl-6-trifluoromethyl -pyridin-3-yl)-acrylamide, 3-(2-Isobutyl-6-trifluoromethyl-pyridin-3-yl)-N-(4-methanesulfonylamino-3-methyl-benzyl) -acrylamide, (R)—N-[1-(3-Fluoro-4-methanesulfonylamino-phenyl)-ethyl]-3-(2-isobutyl-6-trifluoromethyl -pyridin-3-yl)-acrylamide, 3-(2-sec-Butylamino-6-trifluoromethyl-pyridin-3-yl)-N-(4-methanesulfonylamino-3-methyl -benzyl)-acrylamide, N-(3-Ethynyl-5-fluoro-4-methanesulfonylamino-benzyl)-3-(2-isopropylthio-6-trifluoromethyl -pyridin-3-yl)-acrylamide, N-(3-Fluoro-4-methanesulfonylamino-5-methyl-benzyl)-3-[2-(3-fluoro-phenyl)-6-trifluoromethyl-pyridin-3-yl]-acrylamide, (R)—N-[1-(3-Fluoro-4-methanesulfonylamino-phenyl)-ethyl]-3-[2-(3-fluoro-phenyl)-6-trifluoromethyl-pyridin-3-yl]-acrylamide, 3-[2-(3-Fluoro-phenyl)-6-trifluoromethyl-pyridin-3-yl]-N-(4-methane sulfonylamino-3-methyl -benzyl)-acrylamide, (R)—N-[1-(3-Fluoro-4-methanesulfonylamino-phenyl)-ethyl]-3-[2-piperid-1-yl--6-trifluoromethyl-pyridin-3-yl]-acrylamide, N-(4-Methanesulfonylamino-3-methyl-benzyl)-3-[2-piperid-1-yl --6-trifluoromethyl-pyridin-3-yl]-acrylamide, N-(3-Ethynyl-5-fluoro-4-methanesulfonylamino-benzyl)-3-(2-propylthio-6-trifluoromethyl -pyridin-3-yl)-acrylamide, N-(4-Methanesulfonylamino-3-methyl-benzyl)-3-(2-propylthio-6-trifluoromethyl-pyridin-3-yl) -acrylamide, 3-(2-Butylamino-6-trifluoromethyl-pyridin-3-yl)-N-(4-methanesulfonylamino-3-methyl-benzyl) -acrylamide, 3-(2-Butylamino-6-trifluoromethyl-pyridin-3-yl)-N-(3-fluoro-4-methanesulfonylamino-5-methyl-benzyl)-acrylamide, N-(3-Fluoro-4-methanesulfonylamino-5-trifluoromethyl-benzyl)-3-(2-phenethyl-6-trifluoromethyl-pyridin-3-yl)-acrylamide, 3-(2-Benzylamino-6-trifluoromethyl-pyridin-3-yl)-N-(4-methanesulfonylamino-3-methyl -benzyl)-acrylamide, 3-(2-Butyl-6-trifluoromethyl-pyridin-3-yl)-N-(3-fluoro-4-methanesulfonylamino-5-methyl -benzyl)-acrylamide, (R)-3-(2-Butyl-6-trifluoromethyl-pyridin-3-yl)-N-[1-(3-fluoro-4-methanesulfonylamino-phenyl) -ethyl]-acrylamide, 3-(2-Butyl-6-trifluoromethyl-pyridin-3-yl)-N-(4-methanesulfonylamino-3-methyl-benzyl) -acrylamide, (R)-3-(2-Benzylamino-6-trifluoromethyl-pyridin-3-yl)-N-[1-(3-fluoro-4-methanesulfonylamino -phenyl)-ethyl]-acrylamide, 3-(2-Benzylamino-6-trifluoromethyl-pyridin-3-yl)-N-(3-ethynyl -5-fluoro-4-methanesulfonylamino-benzyl)-acrylamide, N-(3-Ethynyl-5-fluoro-4-methanesulfonylamino-benzyl)-3-(2-pentyl-6-trifluoromethyl-pyridin -3-yl)-acrylamide, N-(4-Methanesulfonylamino-3-methyl-benzyl)-3-(2-pentyl-6-trifluoromethyl-pyridin-3-yl) -acrylamide, N-(3,5-Difluoro-4-methanesulfonylamino-benzyl)-3-(2-pentyl-6-trifluoromethyl-pyridin-3-yl) -acrylamide, N-(3,5-Difluoro-4-methanesulfonylamino-benzyl)-3-[2-(3-fluoro-phenyl)-6-trifluoromethyl -pyridin-3-yl]-acrylamide, 3-(2-Butylamino-6-trifluoromethyl-pyridin-3-yl)-N-(3,5-difluoro-4-methanesulfonylamino -benzyl)-acrylamide, N-(3,5-Difluoro-4-methanesulfonylamino-benzyl)-3-(2-phenethyl-6-trifluoromethyl-pyridin-3-yl)-acrylamide, N-(3,5-Difluoro-4-methanesulfonylamino-benzyl)-3-[2-(2-methoxy-ethylamino)-6-trifluoromethyl-pyridin-3-yl]-acrylamide, 3-(2-Butyl-6-trifluoromethyl-pyridin-3-yl)-N-(3,5-difluoro-4-methanesulfonylamino-benzyl) -acrylamide, N-(3-Ethynyl-5-fluoro-4-methanesulfonylamino-benzyl)-3-(2-propyl-6-trifluoromethyl-pyridin -3-yl)-acrylamide, N-(3,5-Difluoro-4-methanesulfonylamino-benzyl)-3-(2-propyl-6-trifluoromethyl-pyridin-3-yl) -acrylamide, N-(4-Methanesulfonylamino-3-methyl-benzyl)-3-(2-propyl-6-trifluoromethyl-pyridin-3-yl) -acrylamide, (R)—N-[1-(3-Fluoro-4-methanesulfonylamino-phenyl)-ethyl]-3-(2-propyl-6-trifluoromethyl -pyridin-3-yl)-acrylamide, (R)-3-(2-sec-Butylamino-6-trifluoromethyl-pyridin-3-yl)-N-[1-(3-fluoro-4-methanesulfonylamino-phenyl)-ethyl]-acrylamide, (R)—N-[1-(3-Fluoro-4-methanesulfonylamino-phenyl)-ethyl]-3-[2-(2-methyl-butyl)-6-trifluoromethyl-pyridin-3-yl]-acrylamide, (R)—N-[1-(3-Fluoro-4-methanesulfonylamino-phenyl)-ethyl]-3-[2-(2-methoxy-ethylamino)-6-trifluoromethyl-pyridin-3-yl]-acrylamide, (R)-3-(2-Butylamino-6-trifluoromethyl-pyridin-3-yl)-N-[1-(3-fluoro-4-methanesulfonylamino -phenyl)-ethyl]-acrylamide, N-(3-Fluoro-4-methanesulfonylamino-5-methyl-benzyl)-3-(2-pentyl-6-trifluoromethyl-pyridin-3-yl)-acrylamide, (R)—N-[1-(3-Fluoro-4-methanesulfonylamino-phenyl)-ethyl]-3-(2-pentyl-6-trifluoromethyl -pyridin-3-yl)-acrylamide, N-(3,5-Difluoro-4-methanesulfonylamino-benzyl)-3-(2-isopropylamino-6-trifluoromethyl -pyridin-3-yl)-acrylamide, (R)—N-[1-(3-Fluoro-4-methanesulfonylamino-phenyl)-ethyl]-3-(2-isopropylamino-6-trifluoromethyl-pyridin-3-yl)-acrylamide, 3-(2-Isopropylamino-6-trifluoromethyl-pyridin-3-yl)-N-(4-methanesulfonylamino-3-methyl -benzyl)-acrylamide, N-(3-Fluoro-4-methanesulfonylamino-5-methyl-benzyl)-3-(2-isopropylamino-6-trifluoromethyl -pyridin-3-yl)-acrylamide, N-(3-Ethynyl-5-fluoro-4-methanesulfonylamino-benzyl)-3-(2-propylamino-6-trifluoromethyl -pyridin-3-yl)-acrylamide, N-(3,5-Difluoro-4-methanesulfonylamino-benzyl)-3-(2-propylamino-6-trifluoromethyl-pyridin -3-yl)-acrylamide, N-(3-Fluoro-4-methanesulfonylamino-5-methyl-benzyl)-3-(2-propylamino-6-trifluoromethyl -pyridin-3-yl)-acrylamide, (R)—N-[1-(3-Fluoro-4-methanesulfonylamino-phenyl)-ethyl]-3-(2-propylamino-6-trifluoromethyl-pyridin-3-yl)-acrylamide, N-(4-Methanesulfonylamino-3-methyl-benzyl)-3-(2-propylamino-6-trifluoromethyl-pyridin-3-yl)-acrylamide, N-(3,5-Difluoro-4-methanesulfonylamino-benzyl)-3-(2-isobutyl-6-trifluoromethyl-pyridin-3-yl) -acrylamide, (R)—N-[1-(3,5-Difluoro-4-methane sulfonylamino-phenyl)-ethyl]-3-(2-isopropylamino-6-trifluoromethyl-pyridin-3-yl)-acrylamide, (R)-3-(2-Butyl-6-trifluoromethyl-pyridin-3-yl)-N-[1-(3,5-difluoro-4-methanesulfonylamino -phenyl)-ethyl]-acrylamide, (R)—N-[1-(3,5-Difluoro-4-methane sulfonylamino-phenyl)-ethyl]-3-(2-propylamino-6-trifluoromethyl-pyridin-3-yl)-acrylamide, (R)—N-[1-(3,5-Difluoro-4-methane sulfonylamino-phenyl)-ethyl]-3-(2-propyl-6-trifluoromethyl -pyridin-3-yl)-acrylamide, N-(3-Ethynyl-5-fluoro-4-methanesulfonylamino-benzyl)-3-(2-isopropyl-6-trifluoromethyl -pyridin-3-yl)-acrylamide, N-(3,5-Difluoro-4-methanesulfonylamino-benzyl)-3-(2-isopropyl-6-trifluoromethyl-pyridin-3-yl)-acrylamide, 3-(2-Isopropyl-6-trifluoromethyl-pyridin-3-yl)-N-(4-methanesulfonylamino-3-methyl-benzyl) -acrylamide, (R)—N-[1-(3-Fluoro-4-methanesulfonylamino-phenyl)-ethyl]-3-(2-isopropyl-6-trifluoromethyl -pyridin-3-yl)-acrylamide, 3-(2-sec-Butyl-6-trifluoromethyl-pyridin-3-yl)-N-(3,5-difluoro -4-methanesulfonylamino -benzyl)-acrylamide, (R)—N-[1-(3,5-Difluoro-4-methane sulfonylamino-phenyl)-ethyl]-3-(2-phenethyl-6-trifluoromethyl-pyridin-3-yl)-acrylamide, (R)—N-[1-(3-Fluoro-4-methanesulfonylamino-phenyl)-ethyl]-3-(2-phenethyl-6-trifluoromethyl -pyridin-3-yl)-acrylamide, (R)-3-(2-Butylamino-6-trifluoromethyl-pyridin-3-yl)-N-[1-(3,5-difluoro-4-methanesulfonylamino-phenyl)-ethyl]-acrylamide, (R)—N-[1-(3,5-Difluoro-4-methane sulfonylamino-phenyl)-ethyl]-3-(2-piperid-1-yl-6-trifluoromethyl-pyridin-3-yl)-acrylamide, (S)-3-(2-Butylamino-6-trifluoromethyl-pyridin-3-yl)-N-[1-(3,5-difluoro-4-methanesulfonylamino-phenyl)-ethyl]-acrylamide, (R)-3-(2-sec-Butyl-6-trifluoromethyl-pyridin-3-yl)-N-1-(4-methanesulfonylamino-3-methyl -benzyl)-acrylamide, (R)—N-[1-(3,5-Difluoro-4-methanesulfonylamino-phenyl)-ethyl]-3-(2-isopropyl-6-trifluoromethyl-pyridin-3-yl)-acrylamide, (R)-3-(2-sec-Butyl-6-trifluoromethyl-pyridin-3-yl)-N-[1-(3-fluoro-4-methanesulfonylamino -phenyl)-ethyl]-acrylamide, and (R)—N-[1-(3,5-Difluoro-4-methanesulfonylamino-phenyl)-ethyl]-3-(2-ethylamino-6-trifluoromethyl-pyridin-3-yl)-acrylamide.

35. The compound of claim 34, an isomer, or a pharmaceutically acceptable sal thereof, wherein the compound is selected from the group consisting of;

3-(2-Diethylamino-6-trifluoromethyl-pyridin-3-yl)-N-(3-ethynyl-5-fluoro-4-methanesulfonylamino-benzyl)-acrylamide, N-(3-Ethynyl-5-fluoro-4-methanesulfonylamino-benzyl)-3-(2-methoxy-6-trifluoromethyl -pyridin-3-yl)-acrylamide, N-(3-Fluoro-4-methanesulfonylamino-benzyl)-3-[2-(2-methoxy -ethylamino)-6-trifluoromethyl -pyridin-3-yl]-acrylamide, 3-(2-Diethylamino-6-trifluoromethyl-pyridin-3-yl)-N-(3-fluoro-4-methanesulfonylamino -benzyl)-acrylamide, N-(3-Ethynyl-5-fluoro-4-methanesulfonylamino-benzyl)-3-(2-pyrrolidin-l-yl-6-trifluoromethyl -pyridin-3-yl)-acrylamide, 3-(2-Butoxy-6-trifluoromethyl-pyridin-3-yl)-N-(3-fluoro-4-methanesulfonylamino-benzyl) -acrylamide, N-(3-Ethynyl-5-fluoro-4-methanesulfonylamino-benzyl)-3-[2-(2-methoxy-ethylamino)-6-trifluoromethyl-pyridin-3-yl]-acrylamide, 3-(2-Butoxy-6-trifluoromethyl-pyridin-3-yl)-N-(3-ethynyl-5-fluoro-4-methanesulfonylamino -benzyl)-acrylamide, 3-(2-Butylamino-6-trifluoromethyl-pyridin-3-yl)-N-(3-ethynyl-5-fluoro-4-methanesulfonylamino-benzyl)-acrylamide, 3-(2-Cyclopentylamino-6-trifluoromethyl-pyridin-3-yl)-N-(3-ethynyl-5-fluoro-4-methanesulfonylamino-benzyl)-acrylamide, N-(3-Ethynyl-5-fluoro-4-methanesulfonylamino-benzyl)-3-[2-(2-methoxy-ethoxy)-6-trifluoromethyl-pyridin-3-yl]-acrylamide, 3-(2-Butyl-5-chloro-6-trifluoromethyl-pyridin-3-yl)-N-(3-ethynyl-5-fluoro-4-methanesulfonylamino-benzyl)-acrylamide, 3-(2-sec-Butoxy-6-trifluoromethyl-pyridin-3-yl)-N-(3-ethynyl-5-fluoro-4-methanesulfonylamino-benzyl)-acrylamide, N-(3-Ethynyl-5-fluoro-4-methanesulfonylamino-benzyl)-3-(2-phenoxy-6-trifluoromethyl -pyridin-3-yl)-acrylamide, 3-(2-Isopropyloxy-6-trifluoromethyl-pyridin-3-yl)-N-(3-ethynyl -5-fluoro-4-methanesulfonylamino-benzyl)-acrylamide, N-(3-Ethynyl-5-fluoro-4-methanesulfonylamino-benzyl)-3-(2-isobutoxy-6-trifluoromethyl -pyridin-3-yl)-acrylamide, 3-[2-(Tetrahydro-furan-3-yloxy)-6-trifluoromethyl-pyridin-3-yl]-N-(3-ethynyl-5-fluoro-4-methanesulfonylamino-benzyl)-acrylamide N-(3-Ethynyl-5-fluoro-4-methanesulfonylamino-benzyl)-3-[2-(4-fluoro-phenoxy)-6-trifluoromethyl-pyridin-3-yl]-acrylamide N-(4-Methanesulfonylamino-3-vinyl-benzyl)-3-(2-morpholin-4-yl -6-trifluoromethyl-pyridin-3-y1)-acrylamide, N-(3-Fluoro-4-methanesulfonylamino-5-methyl-benzyl)-3-(2-morpholin-4-yl-6-trifluoromethyl -pyridin-3-yl)-acrylamide, N-(3-Ethynyl-5-fluoro-4-methanesulfonylamino-benzyl)-3-(2-morpholin-4-yl-6-trifluoromethyl -pyridin-3-yl)-acrylamide, and N-(3-Ethynyl-5-fluoro-4-methanesulfonylamino-benzyl)-3-(2-piperid-1-yl-6-trifluoromethyl -pyridin-3-yl)-acrylamide.

36. The compound of claim 34, an isomer, a racemic mixture or a pharmaceutically acceptable salt thereof, wherein the compound is selected from the group consisting of;

N-(3-Ethynyl-5-fluoro-4-methanesulfonylamino-benzyl)-3-(2-isopropylamino-6-trifluoromethyl-pyridin-3-yl)-acrylamide,
3-(2-sec-Butoxy-6-trifluoromethyl-pyridin-3-yl)-N-(3-cyano-5-fluoro-4-methanesulfonylamino-benzyl)-acrylamide,
3-(2-sec-Butylamino-6-trifluoromethyl-pyridin-3-yl)-N-(3-ethynyl-5-fluoro-4-methanesulfonylamino-benzyl)-acrylamide,
N-(3-Cyano-5-fluoro-4-methanesulfonylamino-benzyl)-3-(2-isopropylamino-6-trifluoromethyl-pyridin-3-yl)-acrylamide,
3-(2-sec-Butylamino-6-trifluoromethyl-pyridin-3-yl)-N-(3-fluoro-4-methanesulfonylamino-benzyl)-acrylamide,
3-(2-sec-Butylamino-6-trifluoromethyl-pyridin-3-yl)-N-(3-cyano-5-fluoro-4-methanesulfonylamino-benzyl)-acrylamide,
3-(2-sec-Butylamino-6-trifluoromethyl-pyridin-3-yl)-N-(3,5-difluoro-4-methanesulfonylamino-benzyl)-acrylamide,
3-(2-sec-Butylamino-6-trifluoromethyl-pyridin-3-yl)-N-(3-fluoro-4-methanesulfonylamino-5-methyl-benzyl)-acrylamide,
N-(3-Ethynyl-5-fluoro-4-methanesulfonylamino-benzyl)-3-(2-phenethyl-6-trifluoromethyl-pyridin-3-yl)-acrylamide,
3-(2-Butyl-6-trifluoromethyl-pyridin-3-yl)-N-(3-ethynyl-5-fluoro-4-methanesulfonylamino-benzyl)-acrylamide,
N-(3-Ethynyl-5-fluoro-4-methanesulfonylamino-benzyl)-3-(2-isobutyl-6-trifluoromethyl-pyridin-3-yl)-acrylamide,
N-(3-Ethynyl-5-fluoro-4-methanesulfonylamino-benzyl)-3-[2-(2-methyl-butyl)-6-trifluoromethyl-pyridin-3-yl]-acrylamide,
N-(3-Fluoro-4-methanesulfonylamino-5-methyl-benzyl)-3-(2-isobutyl-6-trifluoromethyl-pyridin-3-yl)-acrylamide,
N-(3-Ethynyl-5-fluoro-4-methanesulfonylamino-benzyl)-3-[2-(methyl-phenyl-amino)-6-trifluoromethyl-pyridin-3-yl]-acrylamide,
N-(4-Methanesulfonylamino-3-methyl-benzyl)-3-(2-phenethyl-6-trifluoromethyl-pyridin-3-yl)-acrylamide,
3-(2-Isobutyl-6-trifluoromethyl-pyridin-3-yl)-N-(4-methanesulfonylamino-3-methyl-benzyl)-acrylamide,
(R)-N-[1-(3-Fluoro-4-methanesulfonylamino-phenyl)-ethyl]-3-(2-isobutyl-6-trifluoromethyl-pyridin-3-yl)-acrylamide,
3-(2-sec-Butylamino-6-trifluoromethyl-pyridin-3-yl)-N-(4-methanesulfonylamino-3-methyl-benzyl)-acrylamide,
3-(2-Butylamino-6-trifluoromethyl-pyridin-3-yl)-N-(4-methanesulfonylamino-3-methyl-benzyl)-acrylamide,
3-(2-Butylamino-6-trifluoromethyl-pyridin-3-yl)-N-(3-fluoro-4-methanesulfonylamino-5-methyl-benzyl)-acrylamide,
3-(2-Butyl-6-trifluoromethyl-pyridin-3-yl)-N-(3-fluoro-4-methanesulfonylamino-5-methyl-benzyl)-acrylamide,
(R)-3-(2-Butyl-6-trifluoromethyl-pyridin-3-yl)-N-[1-(3-fluoro-4-methanesulfonylamino-phenyl)-ethyl]-acrylamide,
3-(2-Butyl-6-trifluoromethyl-pyridin-3-yl)-N-(4-methanesulfonylamino-3-methyl-benzyl)-acrylamide,
(R)-3-(2-Benzylamino-6-trifluoromethyl-pyridin-3-yl)-N-[1-(3-fluoro-4-methanesulfonylamino-phenyl)-ethyl]-acrylamide,
3-(2-Benzylamino-6-trifluoromethyl-pyridin-3-yl)-N-(3-ethynyl-5-fluoro-4-methanesulfonylamino-benzyl)-acrylamide,
N-(3-Ethynyl-5-fluoro-4-methanesulfonylamino-benzyl)-3-(2-pentyl-6-trifluoromethyl-pyridin-3-yl)-acrylamide,
N-(4-Methanesulfonylamino-3-methyl-benzyl)-3-(2-pentyl-6-trifluoromethyl-pyridin-3-yl)-acrylamide,
N-(3,5-Difluoro-4-methanesulfonylamino-benzyl)-3-(2-pentyl-6-trifluoromethyl-pyridin-3-yl)-acrylamide,
m3-(2-Butylamino-6-trifluoromethyl-pyridin-3-yl)-N-(3,5-difluoro-4-methanesulfonylamino-benzyl)-acrylamide,
N-(3,5-Difluoro-4-methanesulfonylamino-benzyl)-3-(2-phenethyl-6-trifluoromethyl-pyridin-3-y1)-acrylamide,
N-(3,5-Difluoro-4-methanesulfonylamino-benzyl)-3-[2-(2-methoxy-ethylamino)-6-trifluoromethyl-pyridin-3-yl]-acrylamide,
3-(2-Butyl-6-trifluoromethyl-pyridin-3-yl)-N-(3,5-difluoro-4-methanesulfonylamino-benzyl)-acrylamide,
N-(3-Ethynyl-5-fluoro-4-methanesulfonylamino-benzyl)-3-(2-propyl-6-trifluoromethyl-pyridin-3-yl)-acrylamide,
N-(3,5-Difluoro-4-methanesulfonylamino-benzyl)-3-(2-propyl-6-trifluoromethyl-pyridin-3-yl)-acrylamide,
N-(4-Methanesulfonylamino-3-methyl-benzyl)-3-(2-propyl-6-trifluoromethyl-pyridin-3-yl)-acrylamide,
(R)—N-[1-(3-Fluoro-4-methanesulfonylamino-phenyl)-ethyl]-3-(2-propyl-6-trifluoromethyl-pyridin-3-yl)-acrylamide,
3-(2-sec-Butylamino-6-trifluoromethyl-pyridin-3-yl)-N-[1-(3-fluoro-4-methanesulfonylamino-phenyl)-ethyl]-acrylamide,
(R)—N-[1-(3-Fluoro-4-methanesulfonylamino-phenyl)-ethyl]-3-[2-(2-methyl-butyl)-6-trifluoromethyl-pyridin-3-yl]-acrylamide,
(R)-3-(2-Butylamino-6-trifluoromethyl-pyridin-3-yl)-N-[1-(3-fluoro-4-methanesulfonylamino-phenyl)-ethyl]-acrylamide,
N-(3-Fluoro-4-methanesulfonylamino-5-methyl-benzyl)-3-(2-pentyl-6-trifluoromethyl-pyridin-3-y1)-acrylamide,
(R)—N-[1-(3-Fluoro-4-methanesulfonylamino-phenyl)-ethyl]-3-(2-pentyl-6-trifluoromethyl-pyridin-3-yl)-acrylamide,
(R)—N-[1-(3-Fluoro-4-methanesulfonylamino-phenyl)-ethyl]-3-(2-isopropylamino-6-trifluoromethyl-pyridin-3-yl)-acrylamide,
3-(2-Isopropylamino-6-trifluoromethyl-pyridin-3-yl)-N-(4-methanesulfonylamino-3-methyl-benzyl)-acrylamide,
N-(3-Fluoro-4-methanesulfonylamino-5-methyl-benzyl)-3-(2-isopropylamino-6-trifluoromethyl-pyridin-3-yl)-acrylamide,
N-(3-Ethynyl-5-fluoro-4-methanesulfonylamino-benzyl)-3-(2-propylamino-6-trifluoromethyl-pyridin-3-yl)-acrylamide,
N-(3,5-Difluoro-4-methanesulfonylamino-benzyl)-3-(2-propylamino-6-trifluoromethyl-pyridin-3-yl)-acrylamide, N-(3-Fluoro-4-methanesulfonylamino-5-methyl-benzyl)-3-(2-propylamino-6-trifluoromethyl -pyridin-3-yl)-acrylamide,
(R)—N-[1-(3-Fluoro-4-methanesulfonylamino-phenyl)-ethyl]-3-(2-propylamino-6-trifluoromethyl-pyridin-3-yl)-acrylamide,
N-(4-Methanesulfonylamino-3-methyl-benzyl)-3-(2-propylamino-6-trifluoromethyl-pyridin-3-y1)-acrylamide,
(R)—N-[1-(3,5-Difluoro-4-methanesulfonylamino-phenyl)-ethyl]-3-(2-isopropylamino-6-trifluoromethyl-pyridin-3-yl)-acrylamide,
(R)-3-(2-Butyl-6-trifluoromethyl-pyridin-3-yl)-N-[1-(3,5-difluoro-4-methanesulfonylamino -phenyl)-ethyl]-acrylamide,
(R)—N-[1-(3,5-Difluoro-4-methanesulfonylamino-phenyl)-ethyl]-3-(2-propylamino-6-trifluoromethyl-pyridin-3-yl)-acrylamide,
(R)—N-[1-(3,5-Difluoro-4-methanesulfonylamino-phenyl)-ethyl]-3-(2-propyl-6-trifluoromethyl -pyridin-3-yl)-acrylamide,
N-(3-Ethynyl-5-fluoro-4-methanesulfonylamino-benzyl)-3-(2-isopropyl-6-trifluoromethyl -pyridin-3-yl)-acrylamide,
3-(2-Isopropyl-6-trifluoromethyl-pyridin-3-yl)-N-(4-methanesulfonylamino-3-methyl-benzyl) -acrylamide,
(R)—N-[1-(3-Fluoro-4-methanesulfonylamino-phenyl)-ethyl]-3-(2-isopropyl-6-trifluoromethyl -pyridin-3-yl)-acrylamide,
(R)—N-[1-(3,5-Difluoro-4-methanesulfonylamino-phenyl)-ethyl]-3-(2-phenethyl-6-trifluoromethyl-pyridin-3-yl)-acrylamide,
(R)-3-(2-Butylamino-6-trifluoromethyl-pyridin-3-yl)-N-[1-(3,5-difluoro-4-methanesulfonylamino-phenyl)-ethyl]-acrylamide,
(R)-3-(2-sec-Butyl-6-trifluoromethyl-pyridin-3-yl)-N-1-(4-methanesulfonylamino-3-methyl -benzyl)-acrylamide,
(R)—N-[1-(3,5-Difluoro-4-methanesulfonylamino-phenyl)-ethyl]-3-(2-isopropyl-6-trifluoromethyl-pyridin-3-yl)- acrylamide,
(R)-3-(2-sec-Butyl-6-trifluoromethyl-pyridin-3-yl)-N-[1-(3-fluoro-4-methanesulfonylamino -phenyl)-ethyl]-acrylamide, and
(R)—N-[1-(3,5-Difluoro-4-methanesulfonylamino-phenyl)-ethyl]-3-(2-ethylamino-6-trifluoromethyl-pyridin-3-yl)-acrylamide.

37. The compound of claim 1, 2, or 7, an isomer, or a pharmaceutically acceptable salt thereof, wherein the compound is selected from the group consisting of;
(R)—N-[1-(3,5-Difluoro-4-methanesulfonylamino-phenyl)-ethyl]-3-(2-isobutyl-6-trifluoromethyl -pyridin-3-yl)-acrylamide,
(R)-3-(2-Ethylamino-6-trifluoromethyl-pyridin-3-yl)-N-[1-(3-fluoro-4-methanesulfonylamino -phenyl)-ethyl]-acrylamide,
3-(2-Ethylamino-6-trifluoromethyl-pyridin-3-yl)-N-1-(4-methanesulfonylamino-3-methyl -benzyl)-acrylamide,
N-(2,5-Difluoro-4-methanesulfonylamino-benzyl)-3-(2-propylamino-6-trifluoromethyl-pyridin -3-yl)-acrylamide,
3-(2-Ethylamino-6-trifluoromethyl-pyridin-3-yl)-N-(3-ethynyl-5-fluoro-4-methanesulfonylamino-benzyl)-acrylamide,
3-(2-Ethylamino-6-trifluoromethyl-pyridin-3-yl)-N-(3-ethenyl-5-fluoro-4-methanesulfonylamino-benzyl)-acrylamide,
N-(4-Methanesulfonylamino-benzyl)-3-(2-propyl-6-trifluoromethyl -pyridin-3-yl)-acrylamide,
N-(3-Chloro-4-methanesulfonylamino-benzyl)-3-(2-propyl-6-trifluoromethyl-pyridin-3-yl) -acrylamide,
N-(3-Chloro-4-methanesulfonylamino-benzyl)-3-(2-propylamino-6-trifluoromethyl-pyridin-3-y1)-acrylamide,
N-(2,5-Difluoro-4-methanesulfonylamino-benzyl)-3-(2-ethylamino-6-trifluoromethyl-pyridin-3-y1)-acrylamide,
N-(3-Fluoro-4-methanesulfonylamino-benzyl)-3-(2-ethylamino-6-trifluoromethyl-pyridin-3-yl) -acrylamide,
N-(3,5-Difluoro-4-methanesulfonylamino-benzyl)-3-(2-ethylamino-6-trifluoromethyl-pyridin-3-y1)-acrylamide,
N-(3-Fluoro-4-methanesulfonylamino-5-methyl-benzyl)-3-(2-ethylamino-6-trifluoromethyl -pyridin-3-yl)-acrylamide,
N-(3-Cano-5-fluoro-4-methanesulfonylamino-benzyl)-3-(2-ethylamino-6-trifluoromethyl -pyridin-3-yl)-acrylamide,
3-(2-Butyl-6-trifluoromethyl-pyridin-3-yl)-propynoic acid 3,5-difluoro-4-methanesulfonylamino-benzylamide,
3-(2-Butyl-6-trifluoromethyl-pyridin-3-yl)-propynoic acid [1-(3,5-difluoro-4-methanesulfonylamino-phenyl)-ethyl]-amide,
N-(4-Methanesulfonylamino-benzyl)-3-(2-phenethyl-6-trifluoromethyl -pyridin-3-yl)-acrylamide,
N-(4-Ethenesulfonylamino-benzyl)-3-(2-isoproylamino-6-trifluoromethyl-pyridin-3-yl) -acrylamide,
(Z)-3-(2-propyl-6-trifluoromethyl-pyridin-3-yl)-hex-2-enoic acid 3-ethynyl-5-fluoro-4-methanesulfonylamino-benzylamide,
(E)-3-(2-propyl-6-trifluoromethyl-pyridin-3-yl)-hex-2-enoic acid 3-ethynyl-5-fluoro-4-methanesulfonylamino-benzylamide,
(Z)-3-(2-propyl-6-trifluoromethyl-pyridin-3-yl)-hex-2-enoic acid [1-(3,5-difluoro-4-methanesulfonylamino-phenyl)-ethyl]-amide,
(E)-3-(2-propyl-6-trifluoromethyl-pyridin-3-yl)-hex-2-enoic acid [1-(3,5-difluoro-4-methanesulfonylamino-phenyl)-ethyl]-amide, and
N-(3-Ethenyl-5-fluoro-4-methanesulfonylamino-benzyl)-3-(2-morpholin-l-yl-6-trifluoromethyl pyridin-3-yl)-acrylamide.

38. The compound of claim 37, an isomer, or a pharmaceutically acceptable salt thereof, wherein the compound is selected from the group consisting of;
(R)-N-[1-(3,5-Difluoro-4-methanesulfonylamino-phenyl)-ethyl]-3-(2-isobutyl-6-trifluoromethyl -pyridin-3-yl)-acrylamide,
(R)-3-(2-Ethylamino-6-trifluoromethyl-pyridin-3-yl)-N-[1-(3-fluoro-4-methanesulfonylamino -phenyl)-ethyl]-acrylamide,
3-(2-Ethylamino-6-trifluoromethyl-pyridin-3-yl)-N-1-(4-methanesulfonylamino-3-methyl -benzyl)-acrylamide,
N-(2,5-Difluoro-4-methanesulfonylamino-benzyl)-3-(2-propylamino-6-trifluoromethyl-pyridin -3-yl)-acrylamide,
3-(2-Ethylamino-6-trifluoromethyl-pyridin-3-yl)-N-(3-ethynyl-5-fluoro-4-methanesulfonylamino-benzyl)-acrylamide,
3-(2-Ethylamino-6-trifluoromethyl-pyridin-3-yl)-N-(3-ethenyl -5-fluoro-4-methanesulfonylamino-benzyl)-acrylamide,
N-(3-Chloro-4-methanesulfonylamino-benzyl)-3-(2-propylamino-6-trifluoromethyl-pyridin-3-y1)-acrylamide, N-(2,5-Difluoro-4-methanesulfonylamino-benzyl)-3-(2-ethylamino-6-trifluoromethyl-pyridin-3-y1)-acrylamide, N-(3-Fluoro-4-methanesulfonylamino-benzyl)-3-(2-ethylamino-6-trifluoromethyl-pyridin-3-yl)-acrylamide, N-(3,5-Difluoro-4-methanesulfonylamino-benzyl)-3-(2-ethylamino-6-trifluoromethyl-pyridin-3-y1)-acrylamide, N-(3-Fluoro-4-methanesulfonylamino-5-methyl-benzyl)-3-(2-ethylamino-6-trifluoromethyl -pyridin-3-yl)-acrylamide, 3-(2-Butyl-6-trifluoromethyl-pyridin-3-yl)-propynoic acid [1-(3,5-difluoro-4-methanesulfonylamino-phenyl)-ethyl]-amide, and (E)-3-(2-propyl-6-trifluoromethyl-pyridin-3-yl)-hex-2-enoic acid [1-(3,5-difluoro-4-methanesulfonylamino-phenyl)-ethyl]-amide.

39. A pharmaceutical composition comprising the compound of claim 1, an isomer, or a pharmaceutically acceptable salt thereof, as an active ingredient and a pharmaceutically acceptable carrier.

40. The pharmaceutical composition of claim 39 that is for oral administration.

41. A method for treating pain associated with the pathological stimulation and/or aberrant expression of vanilloid receptors, wherein said method comprises administering to a patient in need thereof, a therapeutically effective amount of a pharmaceutical composition comprising the compound of claim 1, an isomer, or a pharmaceutically acceptable salt thereof; and a pharmaceutically acceptable carrier.

42. The method of claim 41 wherein the pain is associated with a condition selected from the group consisting of osteoarthritis, rheumatoid arthritis, ankylosing spondylitis, diabetic neuropathic pain, post-operative pain, dental pain, non-inflammatory musculoskeletal pain, migraine and other types of headaches.

43. A process for preparing a compound represented by the formula (III)

(III)

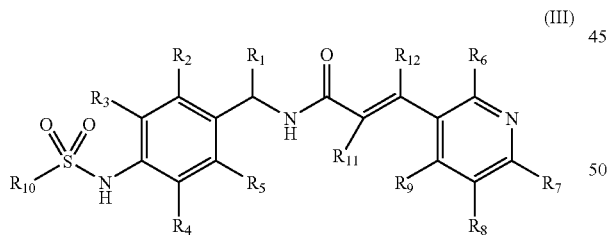

which comprises reacting a compound represented by the formula (IIIa);

(IIIa)

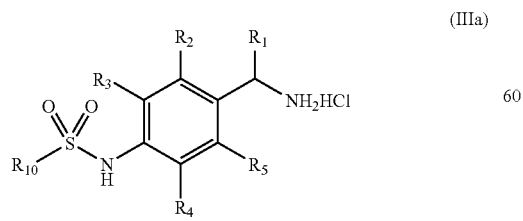

with a compound represented by the formula (IIIb);

(IIIb)

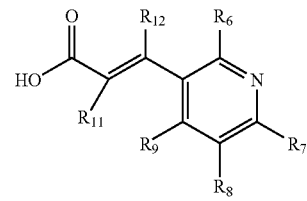

wherein, $R_1$ is hydrogen, halogen or C1-C5 alkyl;

$R_2$, $R_3$, $R_4$, and $R_5$ are independently hydrogen, halogen, nitro, cyano, C1-C5 alkyl, C1C5 alkoxy, halo (C1-C5) alkyl, C2-C5 alkenyl, C2-C5 alkynyl, carboxy, C1-C5 alkoxycarbonyl, or C1-C5 alkylthio;

$R_6$ is hydroxy, halogen, nitro, carboxy, C1-C10 alkyl, C1-C10 alkoxy, C2-C10 alkenyl, C2-C10 alkynyl, C1-C10 alkylthio, C1-C10 alkylsulfonyl, C1-C10 alkylcarbonyl, C1-C10 alkoxycarbonyl, C2-C10 alkenyloxy, C1-C5 alkoxy (C1-C5) alkoxy, C1-C5 alkoxy (C1C5) alkoxy (C1-C5) alkyl, piperidyl, piperazinyl, C1-C5 alkoxy (C1-C5) alkylamino, C1C10 alkylamino, di(C1-C10 alkyl)amino, C3-C8 cycloalkyl, C3-C8 cycloalkylamino, C3C8 cycloalkoxy, C3-C8 oxacycloalkyl-oxy, N—(C1-C5)alkoxy (C1-C5) alkyl-N—(C1-C5) alkylamino, N—(C3-C8)cycloalkyl-N—(C1-C5) alkylamino, N-aryl-N—(C1-C5) alkylamino, aryl, arylamino, arylthio, heteroaryl, heteroarylamino, aryloxy, heteroaryloxy, pyrrolidinyl, or morpholinyl;

$R_8$ and $R_9$ are independently hydrogen, hydroxy, halogen, nitro, carboxy, C1-C10 alkyl, C1-C10 alkoxy, C2-C10 alkenyl, C2-C10 alkynyl, C1-C10 alkylthio, C1-C10 alkylsulfonyl, C1-C10 alkylcarbonyl, C1-C10 alkoxycarbonyl, C2-C10 alkenyloxy, C1-C5 alkoxy (C1-C5) alkoxy, C1-C5 alkoxy (C1-C5) alkoxy (C1-C5) alkyl, piperidyl, piperazinyl, C1-C5 alkoxy (C1-C5) alkylamino, C1-C10 alkylamino, di(C1-C10 alkyl)amino, C3-C8 cycloalkyl, C3-C8 cycloalkylamino, C3-C8 cycloalkoxy, C3-C8 oxacycloalkyl-oxy, N—(C1-C5) alkoxy (C1-C5) alkyl-N—(C1-C5) alkylamino, N—(C3C8)cycloalkyl-N—(C1-C5) alkylamino, N-aryl-N—(C1-C5) alkylamino, aryl, arylamino, arylthio, heteroaryl, heteroarylamino, aryloxy, heteroaryloxy, pyrrolidinyl, or morpholinyl, wherein, each alkyl, alkenyl and alkynyl, alone or as a part of an alkoxy, alkylsulfonyl, alkylcarbonyl, alkylamino, or alkenyloxy may be independently unsubstituted or substituted with one or more substituents selected from among halogen, hydroxyl, unsubstituted or halo-substituted (C1-C5) alkoxy, (C3-C8) cycloalkyl which may be unsubstituted or substituted with one or two halogen radicals and/or methyl groups, unsubstituted or halo-substituted (C1-C5) alkylamino, phenyl which may be unsubstituted or substituted with one or more substituents selected from halogen, unsubstituted C1-C3 alkyl, or halo (C1-C3) alkyl, or unsubstituted or halo-substituted di(C1-C5) alkylamino, each aryl or heteroaryl, alone or as a part of an arylamino, aryloxy, heteroaryloxy, or heteroarylamino, may be independently unsubstituted or substituted with one or more substituents selected from halogen, unsubstituted C1-C5 alkyl, unsubstituted C1-C5 alkoxy, or halo (C1-C5) alkyl, each cycloalkyl, alone or as a part of a cycloalkoxy or cycloalkylamino may be unsubstituted or substituted with one or more unsubstituted or halo-substituted C1-C3 alkyl groups, hydroxymethyl, hydroxy, methoxy, or amino, and each piperazinyl, piperidyl, morpholinyl and pyrrolidinyl may be unsubstituted or substituted with one or more unsubstituted or halo-substituted C1-C3 alkyl groups, hydroxy(C1-C3)alkyl, C1-C3 alkoxy, (C1-C3)alkoxycarbonyl, or hydroxyl;

$R_7$ is halo(C1-C5)alkyl;

$R_{10}$ is C1-C5 alkyl, halo (C1-C5) alkyl, or C2-C5 alkenyl; and $R_{11}$ and $R_{12}$ are independently hydrogen, C1-C5 alkyl, or halogen.

44. The process according to claim 43, wherein the reaction is conducted in the presence of a coupling agent selected from the group consisting of DCC (N,N-dicycicohexylcarbodidimide), EDCI { 1 -(3 -dimethylaminopropyl)-3 -ethylcarbodidimide hydrochloride (EDCI)}, and DMTMM {4-(4,6-dimethoxy-1,3,5-triazin-2-yl)-4-methylmorpholinium chloride}.

45. The method of claim 42 wherein the non-inflammatory musculoskeletal pain is selected from fibromyalgia, myofascial pain syndrome and back pain.

* * * * *

UNITED STATES PATENT AND TRADEMARK OFFICE
CERTIFICATE OF CORRECTION

PATENT NO. : 7,858,621 B2  
APPLICATION NO. : 11/829531  
DATED : December 28, 2010  
INVENTOR(S) : Kim et al.

Page 1 of 1

It is certified that error appears in the above-identified patent and that said Letters Patent is hereby corrected as shown below:

IN THE CLAIMS:

Claim 4, at Column 270, Line 65: Delete "halo (C1C5) alkoxy" and insert --halo (C1-C5) alkoxy--

Claim 25, at Column 278, Line 31: Delete "alkoxy (C1C5) alkylamino" and insert --alkoxy (C1-C5) alkylamino--

Claim 34, at Column 281, Line 7: Delete "3-[2-2(3-methoxy-pyrrolidin-1-yl)" and insert --3-[2-(3-methoxy-pyrrolidin-1-yl)--

Claim 35, at Column 286, Line 2: Delete "acceptable sal thereof," and insert --acceptable salt thereof--

Claim 36, at Column 288, Line 16: Delete "m3-(2-Butylamino-6-trifluoromethyl-pyridin-3-yl)" and insert --3-(2-Butylamino-6-trifluoromethyl-pyridin-3-yl)--

Claim 43, at Column 292, Line 17: Delete "C1C5 alkoxy" and insert --C1-C5 alkoxy--

Claim 43, at Column 292, Line 24: Delete "alkoxy (C1C5) alkoxy" and insert --alkoxy (C1-C5) alkoxy--

Claim 43, at Column 292, Line 28: Delete "C3C8 cycloalkoxy," and insert --C3-C8 cycloalkoxy,--

Claim 43, at Column 292, Line 45: Delete "N-(C3C8)cycloalky-N-(C-5)" and insert --N-(C3-C8)cycloalky-N-(C-5)--

Signed and Sealed this  
Twenty-second Day of March, 2011

David J. Kappos  
*Director of the United States Patent and Trademark Office*